(12) United States Patent
Sato

(10) Patent No.: US 11,676,684 B2
(45) Date of Patent: Jun. 13, 2023

(54) ARTIFICIAL INTELLIGENCE MODEL FOR PREDICTING ACTIONS OF TEST SUBSTANCE IN HUMANS

(71) Applicant: Karydo TherapeutiX, Inc., Tokyo (JP)

(72) Inventor: Narutoku Sato, Kyoto (JP)

(73) Assignee: Karydo Therapeutix, Inc., Tokyo (JP)

( * ) Notice: Subject to any disclaimer, the term of this patent is extended or adjusted under 35 U.S.C. 154(b) by 9 days.

(21) Appl. No.: 16/623,604

(22) PCT Filed: May 31, 2019

(86) PCT No.: PCT/JP2019/021735
§ 371 (c)(1),
(2) Date: Dec. 17, 2019

(87) PCT Pub. No.: WO2020/021857
PCT Pub. Date: Jan. 30, 2020

(65) Prior Publication Data
US 2021/0327543 A1 Oct. 21, 2021

(30) Foreign Application Priority Data
Jul. 27, 2018 (JP) .............................. JP2018-141890

(51) Int. Cl.
*G16C 20/70* (2019.01)
*G16B 40/20* (2019.01)
(Continued)

(52) U.S. Cl.
CPC ............. *G16B 40/20* (2019.02); *G01N 33/15* (2013.01); *G06N 20/10* (2019.01); *G16C 20/70* (2019.02)

(58) Field of Classification Search
CPC ........ G16B 40/20; G16B 20/00; G01N 33/15; G01N 33/50; G06N 20/10; G16C 20/70; G16H 20/10; G16H 50/50; C12Q 1/6869
See application file for complete search history.

(56) References Cited

U.S. PATENT DOCUMENTS

2004/0193019 A1* 9/2004 Wei ..................... G16H 50/70
 600/300
2010/0145896 A1 6/2010 Yuta
(Continued)

FOREIGN PATENT DOCUMENTS

JP 2004-514879 A 5/2004
JP 2014-095931 A 5/2014
(Continued)

OTHER PUBLICATIONS

Providing a "Treasure Chest of Drug Repositioning", Karydo Therapeutix, Inc. Dec. 7, 2017.
(Continued)

*Primary Examiner* — Tarun Sinha
*Assistant Examiner* — Yossef Korang-Beheshti
(74) *Attorney, Agent, or Firm* — Morgan, Lewis & Bockius LLP

(57) ABSTRACT

Actions, such as effects and adverse-events, of a test substance in humans are predicted by using an artificial intelligence model trained by a method for training an artificial intelligence model, the method including inputting into the artificial intelligence model a set of first training data and second training data or a set of the second training data to train the artificial intelligence model.

18 Claims, 155 Drawing Sheets

(51) Int. Cl.
  *G06N 20/10* (2019.01)
  *G01N 33/15* (2006.01)

(56) References Cited

U.S. PATENT DOCUMENTS

| | | | |
|---|---|---|---|
| 2015/0278451 | A1 | 10/2015 | Kitano et al. |
| 2015/0371009 | A1 | 12/2015 | Chen |
| 2019/0172588 | A1* | 6/2019 | Tran ............ G16H 15/00 |
| 2019/0272924 | A1 | 9/2019 | Sato |
| 2019/0325991 | A1* | 10/2019 | Ishii ............ A61K 49/0008 |
| 2020/0387831 | A1 | 12/2020 | Oono et al. |
| 2021/0074434 | A1* | 3/2021 | Clancy ............ G16H 50/50 |
| 2021/0327543 | A1 | 10/2021 | Sato et al. |

FOREIGN PATENT DOCUMENTS

| | | | | |
|---|---|---|---|---|
| JP | 2015-507470 | A | | 3/2015 |
| JP | 6232689 | B2 | | 11/2017 |
| JP | 2019-502988 | A | | 1/2019 |
| JP | 6559850 | B1 | | 8/2019 |
| WO | 02/10746 | A2 | | 2/2002 |
| WO | 2009/025045 | A1 | | 2/2009 |
| WO | WO-2009114591 | A | * 9/2009 | ............ G06F 19/707 |
| WO | WO-2011127150 | A2 | * 10/2011 | ............ C12Q 1/6809 |
| WO | 2013/071099 | A1 | | 5/2013 |
| WO | 2016/208776 | A1 | | 12/2016 |
| WO | 2017/094899 | A1 | | 6/2017 |
| WO | 2018/124293 | A1 | | 7/2018 |
| WO | 2021/075574 | A1 | | 4/2021 |
| WO | 2021/145434 | A1 | | 7/2021 |
| WO | 2021/145436 | A1 | | 7/2021 |

OTHER PUBLICATIONS

Drug side effects, AI identification, University of Tokyo, enhancing development efficiency, Nikkei Business Daily, Feb. 10, 2017.
Gao et al., "Machine Learning-based Prediction of Seizure-inducing Action as an Adverse Drug Effect," Yakugaku Zasshi, 138: 809-813 (2018) (see English abstract).
Structure-Activity Forum 2018, "Use of big data and AI strategy in drug discovery," Jun. 15, 2018, pp. 1-11.
Wang et al., "Drug Repositioning by Kernal-Based Integration of Molecular Structure, Molecular Activity, and Phenotype Data," PLOS One, 8 (11): e78518 (2013).
Zhang et al., "Exploring the Relationship Between Drug Side-Effects and Therapeutic Indications," AMIA Annual Symposium Proceedings Archive, Nov. 16, 2013, pp. 1568-1577.
Adachi et al., "A Method to Predict New Uses of Existing Drugs Using Machine Learning and to Evaluate Their Reliability," IEICE Technical Report, 115 (513): 1-4 (2016).
Pushpakom et al., "Drug repurposing: progress, challenges and recommendations," Nature Reviews Drug Discovery, 18: 41-58 (2019).
Perwitasari et al., "siRNA Genome Screening Approaches to Therapeutic Drug Repositioning," Pharmaceuticals, 6: 124-160 (2013).
Kozawa et al., "Predicting Human Clinical Outcomes Using Mouse Multi-Organ Transcriptome," iScience 23, 100791, (2020).
Li et al., "A New Method for Computational Drug Repositioning Using Drug Pairwise Similarity," Proceedings (IEEE Int Conf Bioinformatics Biomed), 1-4 (2012).
Office Action dated Nov. 13, 2018 for JP patent application No. 2018-141890.
Office Action dated Mar. 12, 2019 for JP patent application No. 2018-141890.
International Search Report issued in corresponding International Patent Application No. PCT/JP2019/021735 dated Sep. 3, 2019.
Extended European Search Report issued in corresponding European Patent Application No. 19816189.5 dated Apr. 4, 2022.
Nugent et al., "Computational drug repositioning based on side-effects mined from social media," PeerJ Computer Science (2016).
Extended European Search Report issued in corresponding European Patent Application No. 20877483.6 dated Nov. 9, 2022.

* cited by examiner

[Fig. 1]
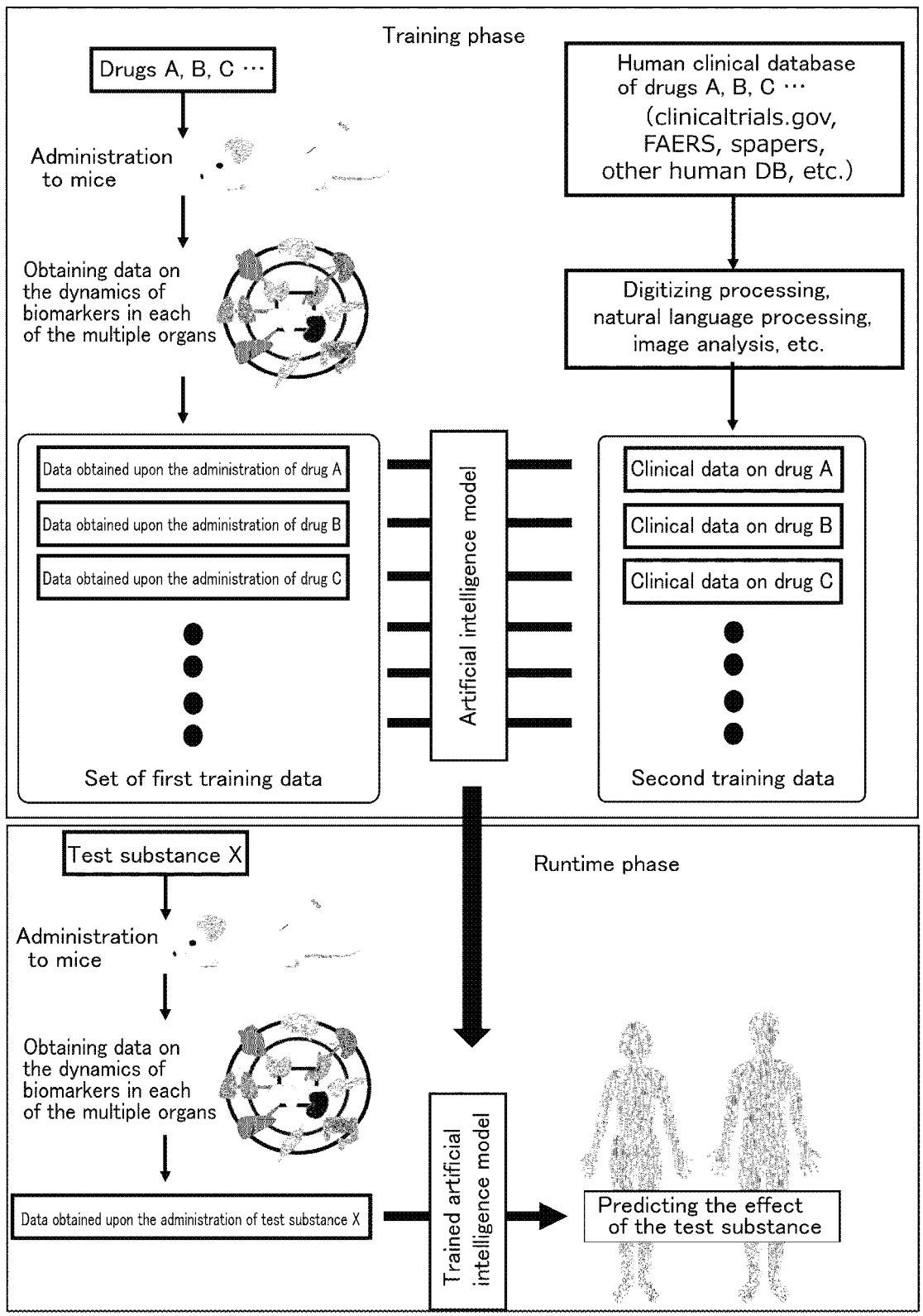

[Fig. 2]
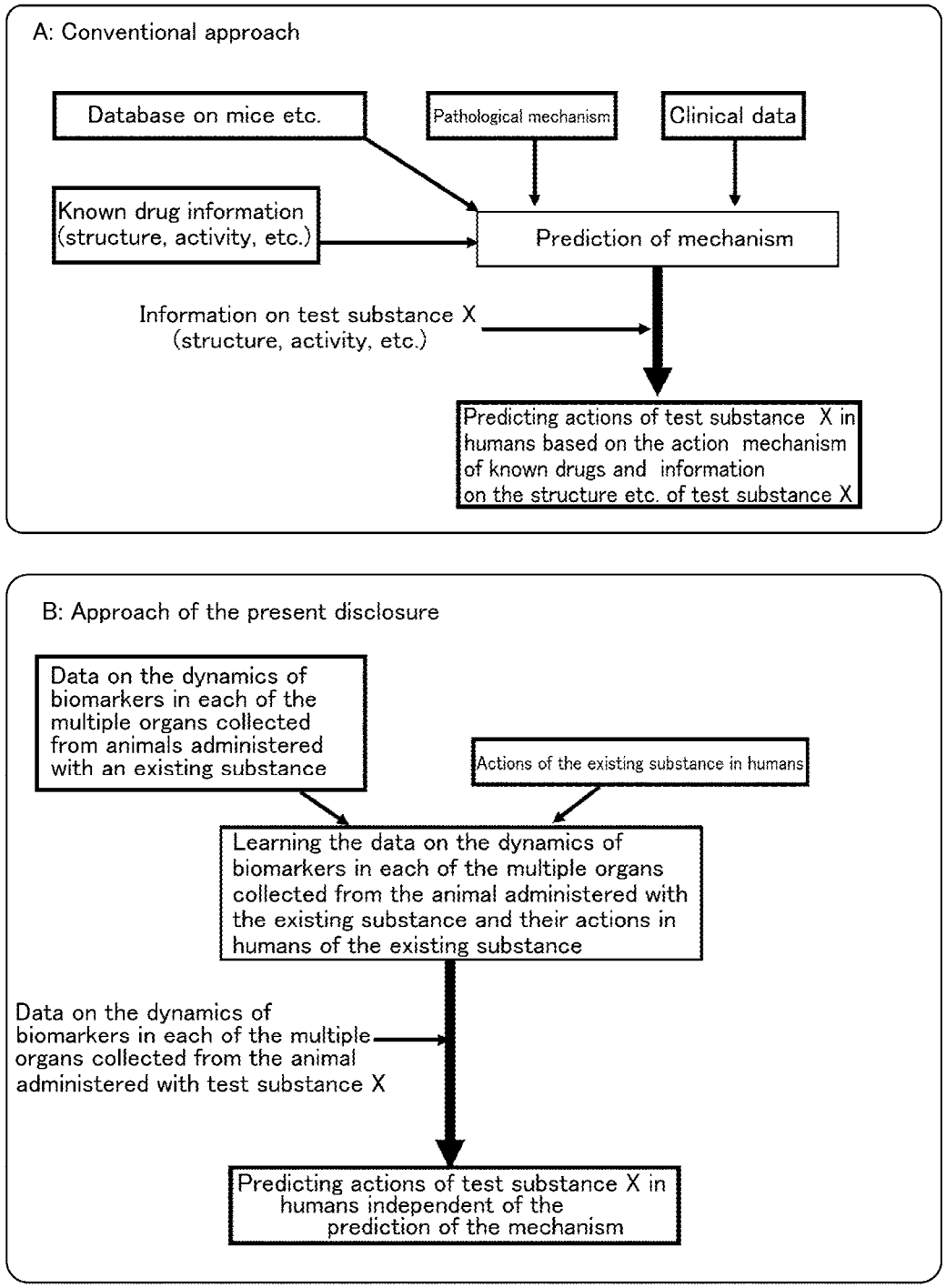

[Fig. 3-1]

| Name of Side Effect | Actual | Predicted | Difference |
|---|---|---|---|
| Abasia | 3 | 3 | 0 |
| Abdominal abscess | 4 | 4 | 0 |
| Abdominal adhesions | 3 | 4 | 1 |
| Abdominal cavity drainage | 4 | 4 | 0 |
| Abdominal compartment syndrome | 4 | 3 | 1 |
| Abdominal discomfort | 3 | 3 | 0 |
| Abdominal hernia | 3 | 3 | 0 |
| Abdominal infection | 4 | 4 | 0 |
| Abdominal lymphadenopathy | 4 | 4 | 0 |
| Abdominal mass | 4 | 4 | 0 |
| Abdominal neoplasm | 4 | 4 | 0 |
| Abdominal operation | 3 | 4 | 1 |
| Abdominal pain | 3 | 3 | 0 |
| Abdominal pain lower | 3 | 3 | 0 |
| Abdominal pain upper | 3 | 3 | 0 |
| Abdominal rebound tenderness | 4 | 4 | 0 |
| Abdominal rigidity | 4 | 3 | 1 |
| Abdominal sepsis | 4 | 3 | 1 |
| Abdominal symptom | 4 | 4 | 0 |
| Abdominal tenderness | 3 | 3 | 0 |
| Abdominal wall abscess | 4 | 3 | 1 |
| Abdominal wall disorder | 4 | 4 | 0 |
| Abdominal wall haemorrhage | 4 | 4 | 0 |
| Abdominal wall wound | 4 | 4 | 0 |
| Abdominal wound dehiscence | 3 | 3 | 0 |
| Abnormal behaviour | 3 | 3 | 0 |
| Abnormal dreams | 3 | 4 | 1 |
| Abnormal faeces | 3 | 4 | 1 |
| Abnormal loss of weight | 4 | 4 | 0 |
| Abnormal precordial movement | 4 | 4 | 0 |
| Abnormal sleep-related event | 3 | 4 | 1 |
| Abnormal weight gain | 3 | 3 | 0 |
| Abortion | 3 | 4 | 1 |
| Abortion induced | 3 | 4 | 1 |
| Abortion missed | 3 | 4 | 1 |
| Abortion spontaneous | 3 | 4 | 1 |
| Abscess | 3 | 3 | 0 |
| Abscess drainage | 3 | 4 | 1 |
| Abscess fungal | 4 | 4 | 0 |
| Abscess intestinal | 4 | 4 | 0 |
| Abscess jaw | 3 | 4 | 1 |
| Abscess limb | 4 | 3 | 1 |
| Abscess neck | 4 | 4 | 0 |
| Abscess of eyelid | 3 | 4 | 1 |
| Abscess oral | 4 | 4 | 0 |
| Abulia | 3 | 4 | 1 |
| Acanthosis nigricans | 3 | 4 | 1 |
| Accelerated hypertension | 4 | 4 | 0 |
| Accident | 3 | 4 | 1 |
| Accidental death | 4 | 4 | 0 |
| Accidental exposure to product | 3 | 4 | 1 |
| Accidental exposure to product by child | 3 | 4 | 1 |
| Accidental overdose | 3 | 3 | 0 |
| Accidental underdose | 4 | 4 | 0 |
| Accommodation disorder | 4 | 3 | 1 |
| Acetonaemia | 4 | 4 | 0 |
| Acidosis | 3 | 3 | 0 |
| Acinetobacter infection | 4 | 4 | 0 |
| Acinic cell carcinoma of salivary gland | 4 | 4 | 0 |
| Acne | 3 | 3 | 0 |
| Acne cystic | 3 | 4 | 1 |
| Acne pustular | 4 | 4 | 0 |
| Acoustic stimulation tests abnormal | 4 | 4 | 0 |
| Acquired aminoaciduria | 4 | 4 | 0 |
| Acquired cystic kidney disease | 3 | 4 | 1 |
| Acquired diaphragmatic eventration | 4 | 3 | 1 |
| Acquired epidermolysis bullosa | 4 | 4 | 0 |
| Acquired gene mutation | 4 | 4 | 0 |
| Acquired tracheo-oesophageal fistula | 4 | 4 | 0 |
| ACTH-producing pituitary tumour | 4 | 4 | 0 |
| Actinic keratosis | 4 | 4 | 0 |
| Actinomycosis | 4 | 4 | 0 |
| Action tremor | 3 | 4 | 1 |
| Activated partial thromboplastin time abnormal | 4 | 4 | 0 |
| Activated partial thromboplastin time prolonged | 4 | 3 | 1 |

[Fig. 3-2]

| | | | |
|---|---|---|---|
| Activated partial thromboplastin time ratio increased | 3 | 3 | 0 |
| Activation syndrome | 3 | 4 | 1 |
| Activities of daily living impaired | 3 | 3 | 0 |
| Acute abdomen | 3 | 4 | 1 |
| Acute biphenotypic leukaemia | 4 | 4 | 0 |
| Acute coronary syndrome | 3 | 3 | 0 |
| Acute febrile neutrophilic dermatosis | 3 | 3 | 0 |
| Acute focal bacterial nephritis | 4 | 4 | 0 |
| Acute generalised exanthematous pustulosis | 3 | 4 | 1 |
| Acute graft versus host disease | 3 | 4 | 1 |
| Acute hepatic failure | 3 | 3 | 0 |
| Acute hepatitis B | 4 | 4 | 0 |
| Acute left ventricular failure | 4 | 3 | 1 |
| Acute leukaemia | 4 | 4 | 0 |
| Acute lung injury | 4 | 4 | 0 |
| Acute lymphocytic leukaemia | 3 | 4 | 1 |
| Acute lymphocytic leukaemia recurrent | 3 | 4 | 1 |
| Acute monocytic leukaemia | 4 | 4 | 0 |
| Acute motor axonal neuropathy | 4 | 4 | 0 |
| Acute myeloid leukaemia | 3 | 3 | 0 |
| Acute myeloid leukaemia recurrent | 4 | 4 | 0 |
| Acute myelomonocytic leukaemia | 4 | 4 | 0 |
| Acute myocardial infarction | 3 | 3 | 0 |
| Acute prerenal failure | 4 | 4 | 0 |
| Acute promyelocytic leukaemia | 4 | 4 | 0 |
| Acute psychosis | 3 | 3 | 0 |
| Acute pulmonary oedema | 4 | 3 | 1 |
| Acute respiratory distress syndrome | 3 | 3 | 0 |
| Acute respiratory failure | 3 | 3 | 0 |
| Acute right ventricular failure | 3 | 4 | 1 |
| Acute sinusitis | 4 | 4 | 0 |
| Acute stress disorder | 4 | 4 | 0 |
| Acute vestibular syndrome | 4 | 4 | 0 |
| Adenocarcinoma | 4 | 4 | 0 |
| Adenocarcinoma gastric | 4 | 3 | 1 |
| Adenocarcinoma of colon | 4 | 4 | 0 |
| Adenocarcinoma of the cervix | 4 | 3 | 1 |

| | | | |
|---|---|---|---|
| Adenocarcinoma pancreas | 4 | 4 | 0 |
| Adenoid cystic carcinoma | 4 | 4 | 0 |
| Adenoidal disorder | 4 | 4 | 0 |
| Adenosquamous cell lung cancer stage IV | 4 | 4 | 0 |
| Adenoviral hepatitis | 4 | 4 | 0 |
| Adenovirus infection | 4 | 4 | 0 |
| Adenovirus test positive | 4 | 4 | 0 |
| Adhesion | 4 | 3 | 1 |
| Adipomastia | 3 | 4 | 1 |
| Adjusted calcium | 4 | 4 | 0 |
| Adjusted calcium increased | 4 | 4 | 0 |
| Adjustment disorder | 3 | 4 | 1 |
| Administration related reaction | 4 | 4 | 0 |
| Administration site extravasation | 3 | 4 | 1 |
| Administration site haemorrhage | 4 | 4 | 0 |
| Administration site inflammation | 4 | 4 | 0 |
| Administration site pain | 4 | 4 | 0 |
| Administration site reaction | 4 | 4 | 0 |
| Adrenal disorder | 4 | 3 | 1 |
| Adrenal insufficiency | 3 | 3 | 0 |
| Adrenal mass | 3 | 4 | 1 |
| Adrenal neoplasm | 4 | 4 | 0 |
| Adrenal suppression | 4 | 4 | 0 |
| Adrenocortical carcinoma | 4 | 4 | 0 |
| Adrenocortical insufficiency acute | 4 | 4 | 0 |
| Adult T-cell lymphoma/leukaemia | 4 | 4 | 0 |
| Adverse drug reaction | 3 | 3 | 0 |
| Adverse event | 3 | 3 | 0 |
| Adverse reaction | 3 | 4 | 1 |
| Aerophagia | 3 | 4 | 1 |
| Aesthesioneuroblastoma | 4 | 4 | 0 |
| Affect lability | 3 | 3 | 0 |
| Affective disorder | 3 | 3 | 0 |
| Ageusia | 3 | 3 | 0 |
| Aggression | 3 | 3 | 0 |
| Agitated depression | 3 | 4 | 1 |
| Agitation | 3 | 3 | 0 |
| Agitation neonatal | 3 | 4 | 1 |
| Agnosia | 3 | 4 | 1 |

[Fig. 3-3]

| | | | | | | | |
|---|---|---|---|---|---|---|---|
| Agoraphobia | 4 | 4 | 0 | Amnestic disorder | 4 | 4 | 0 |
| Agranulocytosis | 3 | 3 | 0 | Amniotic cavity infection | 3 | 4 | 1 |
| Airway complication of anaesthesia | 4 | 4 | 0 | Amputation | 4 | 3 | 1 |
| Akathisia | 3 | 4 | 1 | Amylase decreased | 4 | 3 | 1 |
| Akinesia | 3 | 4 | 1 | Amylase increased | 4 | 3 | 1 |
| Alanine aminotransferase abnormal | 4 | 4 | 0 | Amyloidosis | 4 | 4 | 0 |
| Alanine aminotransferase increased | 3 | 3 | 0 | Amyotrophic lateral sclerosis | 4 | 4 | 0 |
| Albumin urine present | 4 | 4 | 0 | Anaemia | 3 | 3 | 0 |
| Albuminuria | 4 | 4 | 0 | Anaemia folate deficiency | 4 | 4 | 0 |
| Alcohol abuse | 3 | 4 | 1 | Anaemia macrocytic | 3 | 3 | 0 |
| Alcohol detoxification | 4 | 4 | 0 | Anaemia of chronic disease | 4 | 4 | 0 |
| Alcohol interaction | 4 | 4 | 0 | Anaemia of pregnancy | 3 | 4 | 1 |
| Alcohol poisoning | 3 | 4 | 1 | Anaesthesia | 4 | 4 | 0 |
| Alcohol use | 3 | 3 | 0 | Anal atresia | 3 | 4 | 1 |
| Alcohol withdrawal syndrome | 4 | 4 | 0 | Anal cancer | 4 | 4 | 0 |
| Alcoholic liver disease | 4 | 4 | 0 | Anal fissure | 4 | 3 | 1 |
| Alcoholism | 3 | 4 | 1 | Anal fistula | 3 | 4 | 1 |
| Alkalosis | 4 | 4 | 0 | Anal haemorrhage | 3 | 4 | 1 |
| Allergic hepatitis | 4 | 4 | 0 | Anal incontinence | 3 | 3 | 0 |
| Allergic myocarditis | 4 | 4 | 0 | Anal inflammation | 4 | 4 | 0 |
| Allergy to chemicals | 3 | 4 | 1 | Anal injury | 4 | 4 | 0 |
| Allergy to metals | 3 | 4 | 1 | Anal pruritus | 4 | 4 | 0 |
| Alopecia | 3 | 3 | 0 | Anal stenosis | 4 | 4 | 0 |
| Alopecia areata | 3 | 4 | 1 | Anal ulcer | 4 | 3 | 1 |
| Alpha 1 foetoprotein increased | 4 | 4 | 0 | Anal ulcer haemorrhage | 4 | 4 | 0 |
| Alpha haemolytic streptococcal infection | 4 | 4 | 0 | Anaphylactic reaction | 3 | 3 | 0 |
| | | | | Anaphylactic shock | 4 | 3 | 1 |
| Altered state of consciousness | 3 | 3 | 0 | Anaphylactoid reaction | 4 | 4 | 0 |
| Alveolar bone resorption | 4 | 4 | 0 | Anaplastic large-cell lymphoma | 3 | 4 | 1 |
| Alveolar lung disease | 4 | 4 | 0 | Anaplastic lymphoma kinase gene mutation | 4 | 4 | 0 |
| Alveolar soft part sarcoma | 4 | 4 | 0 | | | | |
| Alveolitis allergic | 3 | 4 | 1 | Anaplastic thyroid cancer | 4 | 4 | 0 |
| Amaurosis | 3 | 3 | 0 | Anastomotic complication | 4 | 4 | 0 |
| Amblyopia | 3 | 4 | 1 | Anastomotic haemorrhage | 4 | 4 | 0 |
| Ameloblastoma | 4 | 4 | 0 | Anastomotic leak | 4 | 4 | 0 |
| Amenorrhoea | 3 | 3 | 0 | Anastomotic stenosis | 4 | 4 | 0 |
| Amino acid metabolism disorder | 3 | 4 | 1 | Anastomotic ulcer haemorrhage | 3 | 4 | 1 |
| Ammonia abnormal | 3 | 4 | 1 | Androgen deficiency | 4 | 4 | 0 |
| Ammonia increased | 3 | 4 | 1 | Anembryonic gestation | 3 | 4 | 1 |
| Amnesia | 3 | 3 | 0 | Aneurysm | 3 | 4 | 1 |

[Fig. 3-4]

| | | | | | | | |
|---|---|---|---|---|---|---|---|
| Anger | 3 | 3 | 0 | Antipsychotic drug level above therapeutic | 3 | 4 | 1 |
| Angina unstable | 3 | 3 | 0 | Antipsychotic drug level below therapeutic | 3 | 4 | 1 |
| Angioedema | 3 | 3 | 0 | | | | |
| Angioimmunoblastic T-cell lymphoma | 4 | 4 | 0 | Antipsychotic drug level decreased | 3 | 4 | 1 |
| Angiolipoma | 4 | 4 | 0 | Antipsychotic drug level increased | 3 | 4 | 1 |
| Angiopathy | 4 | 3 | 1 | Antisocial behaviour | 3 | 4 | 1 |
| Angiosarcoma | 4 | 4 | 0 | Anuria | 3 | 3 | 0 |
| Anhedonia | 3 | 4 | 1 | Anxiety | 3 | 3 | 0 |
| Animal bite | 4 | 4 | 0 | Anxiety disorder | 3 | 4 | 1 |
| Anion gap | 3 | 4 | 1 | Aorta hypoplasia | 4 | 4 | 0 |
| Anion gap increased | 3 | 3 | 0 | Aortic aneurysm | 4 | 3 | 1 |
| Anisocytosis | 4 | 3 | 1 | Aortic aneurysm rupture | 4 | 4 | 0 |
| Ankle fracture | 3 | 4 | 1 | Aortic arteriosclerosis | 3 | 3 | 0 |
| Ankylosing spondylitis | 3 | 4 | 1 | Aortic dilatation | 3 | 4 | 1 |
| Anorectal disorder | 3 | 4 | 1 | Aortic disorder | 4 | 4 | 0 |
| Anorexia nervosa | 4 | 3 | 1 | Aortic dissection | 4 | 4 | 0 |
| Anosmia | 4 | 4 | 0 | Aortic embolus | 4 | 3 | 1 |
| Anosognosia | 3 | 4 | 1 | Aortic injury | 4 | 4 | 0 |
| Anoxia | 4 | 4 | 0 | Aortic occlusion | 4 | 3 | 1 |
| Anterograde amnesia | 3 | 4 | 1 | Aortic rupture | 3 | 4 | 1 |
| Anti-ganglioside antibody positive | 3 | 4 | 1 | Aortic stenosis | 4 | 4 | 0 |
| Anti-Muellerian hormone level decreased | 4 | 4 | 0 | Aortic thrombosis | 4 | 4 | 0 |
| | | | | Aortic valve calcification | 4 | 4 | 0 |
| Antibody test abnormal | 4 | 4 | 0 | Aortic valve disease | 4 | 4 | 0 |
| Anticholinergic syndrome | 3 | 4 | 1 | Aortic valve incompetence | 3 | 3 | 0 |
| Anticonvulsant drug level abnormal | 3 | 4 | 1 | Aortic valve replacement | 4 | 4 | 0 |
| Anticonvulsant drug level decreased | 4 | 4 | 0 | Aortic valve sclerosis | 4 | 4 | 0 |
| Anticonvulsant drug level increased | 4 | 4 | 0 | Aortic valve stenosis | 4 | 4 | 0 |
| Antidepressant drug level increased | 3 | 4 | 1 | Aortitis | 4 | 4 | 0 |
| Antidiuretic hormone abnormality | 3 | 4 | 1 | Aorto-oesophageal fistula | 4 | 4 | 0 |
| Antineutrophil cytoplasmic antibody decreased | 4 | 4 | 0 | Apallic syndrome | 4 | 4 | 0 |
| | | | | Apathy | 3 | 3 | 0 |
| Antineutrophil cytoplasmic antibody increased | 4 | 4 | 0 | Apgar score low | 3 | 4 | 1 |
| | | | | Aphagia | 4 | 4 | 0 |
| Antineutrophil cytoplasmic antibody positive | 4 | 4 | 0 | Aphasia | 3 | 3 | 0 |
| | | | | Aphonia | 4 | 4 | 0 |
| Antinuclear antibody increased | 4 | 4 | 0 | Aphthous stomatitis | 4 | 4 | 0 |
| Antinuclear antibody positive | 4 | 4 | 0 | Aphthous ulcer | 3 | 4 | 1 |
| Antiphospholipid antibodies positive | 3 | 4 | 1 | | | | |
| Antipsychotic drug level | 3 | 4 | 1 | Aplasia | 4 | 4 | 0 |

[Fig. 3-5]

| | | | | | | | |
|---|---|---|---|---|---|---|---|
| Aplasia pure red cell | 4 | 3 | 1 | Artery dissection | 4 | 4 | 0 |
| Aplastic anaemia | 4 | 4 | 0 | Arthritis | 3 | 3 | 0 |
| Apnoea | 3 | 3 | 0 | Arthritis bacterial | 4 | 4 | 0 |
| Apnoea neonatal | 4 | 4 | 0 | Arthritis infective | 3 | 4 | 1 |
| Apnoeic attack | 3 | 4 | 1 | Arthropathy | 3 | 3 | 0 |
| Apparent death | 4 | 4 | 0 | Arthropod bite | 4 | 3 | 1 |
| Apparent life threatening event | 4 | 4 | 0 | Ascites | 3 | 3 | 0 |
| Appendicectomy | 4 | 4 | 0 | Aspartate aminotransferase abnormal | 4 | 4 | 0 |
| Appendicitis | 3 | 3 | 0 | | | | |
| Appendicitis perforated | 3 | 3 | 0 | Aspartate aminotransferase decreased | 4 | 4 | 0 |
| Appetite disorder | 3 | 3 | 0 | | | | |
| Application site dermatitis | 4 | 4 | 0 | Asperger's disorder | 3 | 4 | 1 |
| Application site discolouration | 3 | 4 | 1 | Aspergilloma | 4 | 4 | 0 |
| Application site discomfort | 4 | 4 | 0 | Aspergillus infection | 4 | 4 | 0 |
| Application site erythema | 4 | 4 | 0 | Asphyxia | 3 | 3 | 0 |
| Application site extravasation | 4 | 4 | 0 | Aspiration | 3 | 3 | 0 |
| Application site haemorrhage | 4 | 4 | 0 | Aspiration pleural cavity | 3 | 4 | 1 |
| Application site pain | 4 | 4 | 0 | Asterixis | 3 | 4 | 1 |
| Application site pruritus | 4 | 4 | 0 | Asthenopia | 3 | 4 | 1 |
| Application site pustules | 4 | 4 | 0 | Asthma | 3 | 3 | 0 |
| Application site rash | 4 | 3 | 1 | Asthmatic crisis | 4 | 4 | 0 |
| Apraxia | 3 | 4 | 1 | Astigmatism | 3 | 4 | 1 |
| Aptyalism | 3 | 4 | 1 | Astringent therapy | 4 | 4 | 0 |
| Areflexia | 4 | 4 | 0 | Ataxia | 3 | 3 | 0 |
| Arm amputation | 4 | 4 | 0 | Atelectasis | 3 | 3 | 0 |
| Arrested labour | 3 | 4 | 1 | Atonic seizures | 4 | 3 | 1 |
| Arrhythmia | 3 | 3 | 0 | Atrial flutter | 3 | 3 | 0 |
| Arterial disorder | 4 | 4 | 0 | Atrial septal defect | 3 | 3 | 0 |
| Arterial haemorrhage | 4 | 4 | 0 | Atrial septal defect acquired | 4 | 4 | 0 |
| Arterial injury | 4 | 4 | 0 | Atrial tachycardia | 4 | 4 | 0 |
| Arterial insufficiency | 4 | 4 | 0 | Atrial thrombosis | 4 | 4 | 0 |
| Arterial occlusive disease | 4 | 4 | 0 | Atrioventricular block | 3 | 3 | 0 |
| Arterial stenosis | 4 | 4 | 0 | Atrioventricular block complete | 3 | 3 | 0 |
| Arterial thrombosis | 4 | 4 | 0 | Atrioventricular block first degree | 3 | 3 | 0 |
| Arterioenteric fistula | 4 | 4 | 0 | Atrioventricular block second degree | 3 | 4 | 1 |
| Arteriosclerosis | 3 | 3 | 0 | Atrophic glossitis | 4 | 4 | 0 |
| Arteriosclerosis coronary artery | 3 | 3 | 0 | Atrophy | 4 | 4 | 0 |
| Arteriosclerotic retinopathy | 4 | 4 | 0 | Attention deficit/hyperactivity disorder | 3 | 3 | 0 |
| Arteriospasm coronary | 4 | 4 | 0 | | | | |
| Arteritis | 4 | 4 | 0 | Atypical femur fracture | 4 | 4 | 0 |

[Fig. 3-6]

| | | | | | | | |
|---|---|---|---|---|---|---|---|
| Atypical fracture | 4 | 4 | 0 | Bacterial pericarditis | 4 | 4 | 0 |
| Atypical pneumonia | 4 | 3 | 1 | Bacterial pyelonephritis | 4 | 4 | 0 |
| Atypical teratoid/rhabdoid tumour of CNS | 4 | 4 | 0 | Bacterial sepsis | 4 | 4 | 0 |
| Audiogram abnormal | 4 | 4 | 0 | Bacterial test | 4 | 3 | 1 |
| Auditory disorder | 4 | 4 | 0 | Bacterial test positive | 3 | 3 | 0 |
| Aura | 4 | 4 | 0 | Bacterial translocation | 4 | 3 | 1 |
| Auricular swelling | 4 | 4 | 0 | Bacterial vaginosis | 3 | 4 | 1 |
| Autism | 3 | 4 | 1 | Bacteriuria | 4 | 4 | 0 |
| Autism spectrum disorder | 3 | 3 | 0 | Balanoposthitis | 4 | 3 | 1 |
| Autoantibody positive | 4 | 4 | 0 | Bandaemia | 4 | 4 | 0 |
| Autoimmune colitis | 4 | 4 | 0 | Bankruptcy | 3 | 4 | 1 |
| Autoimmune disorder | 3 | 4 | 1 | Barrett's oesophagus | 4 | 4 | 0 |
| Autoimmune haemolytic anaemia | 4 | 4 | 0 | Bartonella test positive | 4 | 4 | 0 |
| Autoimmune hepatitis | 3 | 4 | 1 | Basal cell carcinoma | 4 | 4 | 0 |
| Autoimmune hypothyroidism | 4 | 4 | 0 | Basal ganglia haemorrhage | 4 | 4 | 0 |
| Autoimmune nephritis | 4 | 4 | 0 | Basedow's disease | 3 | 4 | 1 |
| Autoimmune pancreatitis | 4 | 4 | 0 | Baseline foetal heart rate variability disorder | 3 | 4 | 1 |
| Autoimmune thyroiditis | 3 | 4 | 1 | Basilar artery occlusion | 3 | 4 | 1 |
| Autoinflammatory disease | 4 | 4 | 0 | Basophil count decreased | 4 | 4 | 0 |
| Autonomic nervous system imbalance | 3 | 4 | 1 | Basophil count increased | 3 | 4 | 1 |
| | | | | Bed rest | 4 | 4 | 0 |
| Autonomic neuropathy | 4 | 4 | 0 | Bedridden | 3 | 3 | 0 |
| Aversion | 3 | 4 | 1 | Behavioral addiction | 3 | 4 | 1 |
| Axillary mass | 3 | 4 | 1 | Behavioural and psychiatric symptoms of dementia | 4 | 4 | 0 |
| Axillary pain | 4 | 4 | 0 | | | | |
| Axillary vein thrombosis | 4 | 4 | 0 | Benign breast neoplasm | 4 | 4 | 0 |
| Axonal neuropathy | 4 | 3 | 1 | Benign ethnic neutropenia | 4 | 4 | 0 |
| Azoospermia | 4 | 4 | 0 | Benign intracranial hypertension | 4 | 4 | 0 |
| Azotaemia | 4 | 3 | 1 | Benign lung neoplasm | 4 | 4 | 0 |
| B-cell lymphoma | 4 | 3 | 1 | Benign neoplasm of bladder | 4 | 4 | 0 |
| B-cell lymphoma recurrent | 4 | 3 | 1 | Benign prostatic hyperplasia | 4 | 4 | 0 |
| B-cell lymphoma refractory | 4 | 4 | 0 | Beta 2 microglobulin increased | 4 | 4 | 0 |
| B-lymphocyte count decreased | 4 | 4 | 0 | Beta haemolytic streptococcal infection | 4 | 4 | 0 |
| Bacillus infection | 4 | 4 | 0 | | | | |
| Bacillus test positive | 4 | 4 | 0 | Bicytopenia | 3 | 3 | 0 |
| Back disorder | 3 | 3 | 0 | Bile duct adenocarcinoma | 4 | 4 | 0 |
| Back injury | 3 | 4 | 1 | Bile duct cancer | 4 | 4 | 0 |
| Bacteraemia | 4 | 3 | 1 | Bile duct obstruction | 3 | 3 | 0 |
| Bacterial infection | 3 | 3 | 0 | Bile duct stenosis | 3 | 4 | 1 |

[Fig. 3-7]

| | | | | | | | |
|---|---|---|---|---|---|---|---|
| Bile duct stone | 3 | 4 | 1 | Blast cells present | 4 | 4 | 0 |
| Biliary ascites | 4 | 4 | 0 | Blastic plasmacytoid dendritic cell neoplasia | 4 | 4 | 0 |
| Biliary cancer metastatic | 4 | 3 | 1 | Blepharophimosis | 4 | 4 | 0 |
| Biliary cirrhosis primary | 4 | 4 | 0 | Blepharospasm | 3 | 4 | 1 |
| Biliary colic | 3 | 4 | 1 | Blindness | 3 | 3 | 0 |
| Biliary cyst | 4 | 4 | 0 | Blindness transient | 3 | 3 | 0 |
| Biliary sepsis | 4 | 4 | 0 | Blindness unilateral | 4 | 4 | 0 |
| Biliary tract disorder | 3 | 4 | 1 | Blister | 3 | 3 | 0 |
| Biliary tract infection | 4 | 4 | 0 | Blister rupture | 4 | 4 | 0 |
| Bilirubin conjugated increased | 4 | 3 | 1 | Blood 1,25-dihydroxycholecalciferol increased | 4 | 4 | 0 |
| Bilirubin urine present | 4 | 4 | 0 | Blood 25-hydroxycholecalciferol decreased | 3 | 4 | 1 |
| Bilirubinuria | 3 | 4 | 1 | Blood albumin abnormal | 4 | 4 | 0 |
| Biloma | 4 | 4 | 0 | Blood albumin decreased | 3 | 3 | 0 |
| Binge eating | 3 | 4 | 1 | Blood albumin increased | 3 | 4 | 1 |
| Bipolar disorder | 3 | 4 | 1 | Blood alcohol increased | 4 | 4 | 0 |
| Bipolar I disorder | 3 | 4 | 1 | Blood alkaline phosphatase | 4 | 4 | 0 |
| Bipolar II disorder | 3 | 4 | 1 | Blood alkaline phosphatase abnormal | 4 | 4 | 0 |
| BK virus infection | 4 | 4 | 0 | Blood alkaline phosphatase decreased | 4 | 3 | 1 |
| Bladder cancer | 3 | 4 | 1 | Blood alkaline phosphatase increased | 3 | 3 | 0 |
| Bladder cancer recurrent | 4 | 4 | 0 | Blood aluminium decreased | 3 | 4 | 1 |
| Bladder catheterisation | 4 | 4 | 0 | Blood beta-D-glucan increased | 4 | 4 | 0 |
| Bladder dilatation | 4 | 4 | 0 | Blood bicarbonate decreased | 3 | 3 | 0 |
| Bladder discomfort | 4 | 4 | 0 | Blood bicarbonate increased | 3 | 3 | 0 |
| Bladder disorder | 3 | 4 | 1 | Blood bilirubin abnormal | 3 | 4 | 1 |
| Bladder diverticulum | 4 | 4 | 0 | Blood bilirubin decreased | 3 | 4 | 1 |
| Bladder dysfunction | 4 | 4 | 0 | Blood bilirubin increased | 3 | 3 | 0 |
| Bladder hypertrophy | 4 | 4 | 0 | Blood calcium abnormal | 3 | 4 | 1 |
| Bladder irrigation | 3 | 4 | 1 | Blood calcium decreased | 3 | 3 | 0 |
| Bladder irritation | 4 | 4 | 0 | Blood calcium increased | 4 | 4 | 0 |
| Bladder neoplasm | 3 | 4 | 1 | Blood chloride abnormal | 4 | 4 | 0 |
| Bladder obstruction | 4 | 4 | 0 | Blood chloride decreased | 3 | 3 | 0 |
| Bladder outlet obstruction | 4 | 4 | 0 | Blood chloride increased | 3 | 3 | 0 |
| Bladder pain | 4 | 4 | 0 | Blood cholesterol | 3 | 4 | 1 |
| Bladder perforation | 4 | 4 | 0 | Blood cholesterol abnormal | 4 | 4 | 0 |
| Bladder spasm | 4 | 3 | 1 | Blood cholesterol decreased | 3 | 4 | 1 |
| Bladder sphincter atony | 4 | 4 | 0 | Blood cholesterol increased | 3 | 3 | 0 |
| Bladder transitional cell carcinoma | 4 | 4 | 0 | | | | |
| Bladder transitional cell carcinoma recurrent | 4 | 4 | 0 | | | | |
| Blast cell count increased | 4 | 4 | 0 | | | | |

[Fig. 3-8]

| | | | | | | | |
|---|---|---|---|---|---|---|---|
| Blood chromogranin A increased | 4 | 4 | 0 | Blood insulin abnormal | 3 | 4 | 1 |
| Blood copper decreased | 3 | 4 | 1 | Blood insulin increased | 3 | 4 | 1 |
| Blood copper increased | 3 | 4 | 1 | Blood iron decreased | 3 | 3 | 0 |
| Blood corticotrophin increased | 4 | 4 | 0 | Blood iron increased | 3 | 4 | 1 |
| Blood cortisol decreased | 4 | 4 | 0 | Blood ketone body | 4 | 4 | 0 |
| Blood count abnormal | 3 | 3 | 0 | Blood ketone body increased | 4 | 4 | 0 |
| Blood creatine abnormal | 4 | 3 | 1 | Blood lactate dehydrogenase | 4 | 4 | 0 |
| Blood creatine decreased | 4 | 4 | 0 | Blood lactate dehydrogenase abnormal | 3 | 4 | 1 |
| Blood creatine increased | 4 | 3 | 1 | | | | |
| Blood creatine phosphokinase abnormal | 3 | 4 | 1 | Blood lactate dehydrogenase decreased | 4 | 4 | 0 |
| Blood creatine phosphokinase decreased | 3 | 4 | 1 | Blood lactate dehydrogenase increased | 3 | 3 | 0 |
| Blood creatine phosphokinase increased | 3 | 3 | 0 | Blood lactic acid increased | 3 | 3 | 0 |
| | | | | Blood luteinising hormone increased | 4 | 4 | 0 |
| Blood creatine phosphokinase MB increased | 3 | 3 | 0 | Blood magnesium abnormal | 4 | 4 | 0 |
| | | | | Blood magnesium decreased | 3 | 3 | 0 |
| Blood creatinine abnormal | 4 | 4 | 0 | Blood magnesium increased | 4 | 3 | 1 |
| Blood creatinine decreased | 3 | 3 | 0 | Blood osmolarity decreased | 4 | 3 | 1 |
| Blood creatinine increased | 3 | 3 | 0 | Blood osmolarity increased | 4 | 4 | 0 |
| Blood culture positive | 4 | 4 | 0 | Blood parathyroid hormone decreased | 4 | 4 | 0 |
| Blood disorder | 3 | 3 | 0 | | | | |
| Blood electrolytes abnormal | 4 | 3 | 1 | Blood parathyroid hormone increased | 4 | 4 | 0 |
| Blood electrolytes decreased | 4 | 4 | 0 | | | | |
| Blood electrolytes increased | 4 | 4 | 0 | Blood pH decreased | 4 | 4 | 0 |
| Blood fibrinogen increased | 3 | 3 | 0 | Blood phosphorus decreased | 3 | 3 | 0 |
| Blood folate decreased | 3 | 4 | 1 | Blood phosphorus increased | 4 | 3 | 1 |
| Blood follicle stimulating hormone abnormal | 4 | 4 | 0 | Blood potassium | 4 | 4 | 0 |
| | | | | Blood potassium abnormal | 4 | 4 | 0 |
| Blood follicle stimulating hormone increased | 4 | 4 | 0 | Blood potassium decreased | 3 | 3 | 0 |
| | | | | Blood potassium increased | 4 | 3 | 1 |
| Blood gases | 4 | 4 | 0 | Blood pressure abnormal | 3 | 3 | 0 |
| Blood gases abnormal | 3 | 4 | 1 | Blood pressure ambulatory decreased | 4 | 4 | 0 |
| Blood glucose | 4 | 4 | 0 | | | | |
| Blood glucose abnormal | 3 | 3 | 0 | Blood pressure ambulatory increased | 4 | 4 | 0 |
| Blood glucose fluctuation | 3 | 4 | 1 | Blood pressure decreased | 3 | 3 | 0 |
| Blood growth hormone decreased | 4 | 4 | 0 | Blood pressure diastolic decreased | 4 | 3 | 1 |
| Blood growth hormone releasing hormone increased | 4 | 4 | 0 | Blood pressure diastolic increased | 3 | 4 | 1 |
| | | | | Blood pressure fluctuation | 3 | 3 | 0 |
| Blood hyposmosis | 3 | 4 | 1 | Blood pressure immeasurable | 4 | 3 | 1 |
| Blood immunoglobulin G decreased | 3 | 4 | 1 | | | | |

[Fig. 3-9]

| | | | | | | | |
|---|---|---|---|---|---|---|---|
| Blood pressure inadequately controlled | 4 | 4 | 0 | Body mass index increased | 3 | 4 | 1 |
| Blood pressure increased | 3 | 3 | 0 | Body temperature abnormal | 3 | 4 | 1 |
| Blood pressure measurement | 4 | 4 | 0 | Body temperature decreased | 3 | 3 | 0 |
| Blood pressure orthostatic decreased | 4 | 4 | 0 | Body temperature fluctuation | 3 | 4 | 1 |
| Blood pressure systolic decreased | 3 | 3 | 0 | Body temperature increased | 3 | 3 | 0 |
| Blood pressure systolic increased | 3 | 3 | 0 | Bone cancer | 3 | 4 | 1 |
| Blood prolactin abnormal | 3 | 4 | 1 | Bone cyst | 4 | 4 | 0 |
| Blood prolactin decreased | 3 | 4 | 1 | Bone density abnormal | 4 | 4 | 0 |
| Blood prolactin increased | 3 | 4 | 1 | Bone density decreased | 4 | 4 | 0 |
| Blood sodium | 4 | 4 | 0 | Bone development abnormal | 3 | 4 | 1 |
| Blood sodium abnormal | 4 | 4 | 0 | Bone disorder | 3 | 4 | 1 |
| Blood sodium decreased | 3 | 3 | 0 | Bone erosion | 4 | 4 | 0 |
| Blood sodium increased | 3 | 3 | 0 | Bone formation increased | 4 | 4 | 0 |
| Blood stem cell transplant failure | 4 | 4 | 0 | Bone giant cell tumour malignant | 4 | 4 | 0 |
| Blood test abnormal | 3 | 3 | 0 | Bone infarction | 4 | 4 | 0 |
| Blood testosterone decreased | 3 | 4 | 1 | Bone lesion | 4 | 4 | 0 |
| Blood testosterone increased | 3 | 4 | 1 | Bone loss | 4 | 4 | 0 |
| Blood thyroid stimulating hormone abnormal | 4 | 4 | 0 | Bone marrow disorder | 3 | 4 | 1 |
| Blood thyroid stimulating hormone decreased | 3 | 4 | 1 | Bone marrow failure | 4 | 3 | 1 |
| | | | | Bone marrow infiltration | 4 | 4 | 0 |
| | | | | Bone marrow oedema | 4 | 4 | 0 |
| Blood thyroid stimulating hormone increased | 3 | 4 | 1 | Bone marrow toxicity | 4 | 3 | 1 |
| | | | | Bone marrow transplant rejection | 4 | 4 | 0 |
| Blood triglycerides abnormal | 3 | 4 | 1 | Bone marrow tumour cell infiltration | 4 | 4 | 0 |
| Blood triglycerides increased | 3 | 3 | 0 | Bone neoplasm | 4 | 4 | 0 |
| Blood urea abnormal | 4 | 4 | 0 | Bone pain | 3 | 3 | 0 |
| Blood urea decreased | 3 | 4 | 1 | Bone scan abnormal | 4 | 4 | 0 |
| Blood urea increased | 3 | 3 | 0 | Bone tuberculosis | 4 | 4 | 0 |
| Blood urea nitrogen/creatinine ratio increased | 4 | 4 | 0 | Borderline personality disorder | 3 | 4 | 1 |
| | | | | Borderline serous tumour of ovary | 4 | 4 | 0 |
| | | | | Bowel movement irregularity | 3 | 4 | 1 |
| Blood uric acid decreased | 4 | 4 | 0 | Brachial plexopathy | 3 | 4 | 1 |
| Blood uric acid increased | 3 | 3 | 0 | Brachial plexus injury | 4 | 4 | 0 |
| Blood urine present | 3 | 3 | 0 | Brachiocephalic vein thrombosis | 4 | 4 | 0 |
| Blue toe syndrome | 4 | 4 | 0 | Bradyarrhythmia | 3 | 4 | 1 |
| Blunted affect | 3 | 4 | 1 | Bradycardia | 3 | 3 | 0 |
| Body dysmorphic disorder | 3 | 4 | 1 | Bradycardia neonatal | 3 | 4 | 1 |
| Body height below normal | 4 | 4 | 0 | Bradykinesia | 3 | 3 | 0 |
| Body height decreased | 3 | 3 | 0 | Bradyphrenia | 3 | 3 | 0 |
| Body mass index | 4 | 4 | 0 | Bradypnoea | 4 | 4 | 0 |

[Fig. 3-10]

| | | | |
|---|---|---|---|
| Brain abscess | 4 | 4 | 0 |
| Brain cancer metastatic | 4 | 4 | 0 |
| Brain compression | 4 | 4 | 0 |
| Brain contusion | 3 | 4 | 1 |
| Brain death | 4 | 3 | 1 |
| Brain herniation | 4 | 4 | 0 |
| Brain hypoxia | 4 | 4 | 0 |
| Brain injury | 3 | 3 | 0 |
| Brain mass | 4 | 4 | 0 |
| Brain natriuretic peptide abnormal | 4 | 4 | 0 |
| Brain natriuretic peptide increased | 4 | 3 | 1 |
| Brain neoplasm | 3 | 3 | 0 |
| Brain neoplasm benign | 3 | 4 | 1 |
| Brain neoplasm malignant | 4 | 4 | 0 |
| Brain oedema | 3 | 3 | 0 |
| Brain operation | 3 | 4 | 1 |
| Brain stem haemorrhage | 4 | 4 | 0 |
| Brain stem infarction | 4 | 4 | 0 |
| BRCA2 gene mutation | 4 | 4 | 0 |
| Breakthrough pain | 4 | 4 | 0 |
| Breast abscess | 4 | 3 | 1 |
| Breast calcifications | 4 | 4 | 0 |
| Breast cancer | 3 | 3 | 0 |
| Breast cancer female | 4 | 4 | 0 |
| Breast cancer metastatic | 3 | 3 | 0 |
| Breast cancer recurrent | 4 | 4 | 0 |
| Breast cancer stage IV | 4 | 4 | 0 |
| Breast cyst | 4 | 4 | 0 |
| Breast discharge | 3 | 4 | 1 |
| Breast discolouration | 3 | 4 | 1 |
| Breast discomfort | 3 | 4 | 1 |
| Breast disorder | 4 | 4 | 0 |
| Breast enlargement | 3 | 4 | 1 |
| Breast feeding | 3 | 4 | 1 |
| Breast mass | 3 | 3 | 0 |
| Breast neoplasm | 4 | 4 | 0 |
| Breast pain | 3 | 4 | 1 |
| Breast tenderness | 3 | 4 | 1 |
| Breath odour | 3 | 4 | 1 |
| Breath sounds abnormal | 4 | 4 | 0 |

| | | | |
|---|---|---|---|
| Breathing-related sleep disorder | 4 | 4 | 0 |
| Breech presentation | 3 | 4 | 1 |
| Bronchial carcinoma | 4 | 4 | 0 |
| Bronchial disorder | 4 | 3 | 1 |
| Bronchial fistula | 4 | 4 | 0 |
| Bronchial haemorrhage | 4 | 4 | 0 |
| Bronchial hyperreactivity | 4 | 4 | 0 |
| Bronchial injury | 4 | 4 | 0 |
| Bronchial metaplasia | 4 | 4 | 0 |
| Bronchial obstruction | 4 | 4 | 0 |
| Bronchiectasis | 4 | 4 | 0 |
| Bronchiolitis | 4 | 3 | 1 |
| Bronchitis | 3 | 3 | 0 |
| Bronchitis chronic | 4 | 4 | 0 |
| Bronchopleural fistula | 4 | 4 | 0 |
| Bronchopneumonia | 4 | 3 | 1 |
| Bronchopneumopathy | 4 | 4 | 0 |
| Bronchopulmonary aspergillosis | 4 | 4 | 0 |
| Bronchopulmonary dysplasia | 3 | 4 | 1 |
| Bronchoscopy | 4 | 4 | 0 |
| Bronchoscopy abnormal | 4 | 4 | 0 |
| Bronchospasm | 4 | 3 | 1 |
| Bronchostenosis | 4 | 4 | 0 |
| Brown-Sequard syndrome | 4 | 4 | 0 |
| Brugada syndrome | 4 | 3 | 1 |
| Bruxism | 3 | 4 | 1 |
| Buccal mucosal roughening | 4 | 4 | 0 |
| Budd-Chiari syndrome | 4 | 3 | 1 |
| Bulbar palsy | 3 | 4 | 1 |
| Bulimia nervosa | 3 | 4 | 1 |
| Bullous lung disease | 4 | 4 | 0 |
| Bundle branch block | 3 | 4 | 1 |
| Bundle branch block bilateral | 4 | 4 | 0 |
| Bundle branch block left | 3 | 3 | 0 |
| Bundle branch block right | 3 | 3 | 0 |
| Burkholderia infection | 4 | 4 | 0 |
| Burkitt's lymphoma | 4 | 4 | 0 |
| Burn oesophageal | 4 | 4 | 0 |
| Burning mouth syndrome | 4 | 4 | 0 |
| Burning sensation | 3 | 3 | 0 |

[Fig. 3-11]

| | | | | | | | |
|---|---|---|---|---|---|---|---|
| Burnout syndrome | 4 | 4 | 0 | Cardiac failure chronic | 4 | 3 | 1 |
| Burns second degree | 4 | 3 | 1 | Cardiac failure congestive | 3 | 3 | 0 |
| Bursa disorder | 4 | 4 | 0 | Cardiac flutter | 3 | 4 | 1 |
| Bursitis | 3 | 4 | 1 | Cardiac function test abnormal | 4 | 4 | 0 |
| Bursitis infective staphylococcal | 4 | 4 | 0 | Cardiac hypertrophy | 4 | 4 | 0 |
| C-reactive protein abnormal | 4 | 4 | 0 | Cardiac index decreased | 4 | 4 | 0 |
| C-reactive protein decreased | 3 | 4 | 1 | Cardiac murmur | 3 | 3 | 0 |
| C-reactive protein increased | 3 | 3 | 0 | Cardiac myxoma | 4 | 4 | 0 |
| Cachexia | 3 | 3 | 0 | Cardiac neoplasm malignant | 4 | 4 | 0 |
| Caesarean section | 3 | 3 | 0 | Cardiac operation | 3 | 4 | 1 |
| Cafe au lait spots | 4 | 4 | 0 | Cardiac output decreased | 3 | 4 | 1 |
| Calcinosis | 4 | 4 | 0 | Cardiac pacemaker insertion | 3 | 4 | 1 |
| Calciphylaxis | 4 | 4 | 0 | Cardiac perforation | 4 | 4 | 0 |
| Calcium ionised decreased | 4 | 4 | 0 | Cardiac pseudoaneurysm | 4 | 4 | 0 |
| Calculus ureteric | 4 | 4 | 0 | Cardiac septal defect | 3 | 4 | 1 |
| Calculus urinary | 4 | 4 | 0 | Cardiac septal hypertrophy | 3 | 4 | 1 |
| Campylobacter infection | 4 | 4 | 0 | Cardiac tamponade | 4 | 3 | 1 |
| Campylobacter test positive | 4 | 4 | 0 | Cardiac telemetry | 4 | 4 | 0 |
| Cancer pain | 4 | 4 | 0 | Cardiac valve disease | 4 | 4 | 0 |
| Candida infection | 3 | 3 | 0 | Cardiac ventricular thrombosis | 3 | 3 | 0 |
| Candida retinitis | 4 | 4 | 0 | Cardio-respiratory arrest | 3 | 3 | 0 |
| Candida sepsis | 4 | 4 | 0 | Cardio-respiratory distress | 4 | 4 | 0 |
| Candida test positive | 4 | 4 | 0 | Cardiogenic shock | 3 | 3 | 0 |
| Capillaritis | 4 | 4 | 0 | Cardiomegaly | 3 | 3 | 0 |
| Capillary fragility | 4 | 4 | 0 | Cardiomyopathy | 3 | 3 | 0 |
| Capillary leak syndrome | 4 | 4 | 0 | Cardiomyopathy acute | 4 | 4 | 0 |
| Capillary nail refill test abnormal | 3 | 4 | 1 | Cardioplegia | 4 | 4 | 0 |
| Carbohydrate antigen 125 increased | 4 | 4 | 0 | Cardiopulmonary failure | 3 | 3 | 0 |
| Carbohydrate antigen 27.29 increased | 4 | 4 | 0 | Cardiotoxicity | 3 | 3 | 0 |
| | | | | Cardiovascular disorder | 3 | 3 | 0 |
| Carbon dioxide decreased | 3 | 4 | 1 | Cardiovascular insufficiency | 3 | 3 | 0 |
| Carbon dioxide increased | 3 | 4 | 1 | Cardioversion | 3 | 4 | 1 |
| Carcinoembryonic antigen increased | 4 | 4 | 0 | Carditis | 3 | 4 | 1 |
| Carcinoid syndrome | 4 | 4 | 0 | Carnitine deficiency | 3 | 4 | 1 |
| Carcinoma in situ | 4 | 4 | 0 | Carotid artery disease | 4 | 4 | 0 |
| Cardiac amyloidosis | 4 | 4 | 0 | Carotid artery dissection | 4 | 4 | 0 |
| Cardiac cirrhosis | 3 | 4 | 1 | Carotid artery occlusion | 4 | 4 | 0 |
| Cardiac death | 4 | 3 | 1 | Carotid artery perforation | 4 | 4 | 0 |
| Cardiac disorder | 3 | 3 | 0 | Carotid artery stenosis | 4 | 4 | 0 |
| Cardiac failure acute | 3 | 3 | 0 | Carotid artery thrombosis | 4 | 4 | 0 |

[Fig. 3-12]

| | | | | | | | |
|---|---|---|---|---|---|---|---|
| Carotidynia | 4 | 4 | 0 | Cerebral artery thrombosis | 4 | 4 | 0 |
| Carpal tunnel syndrome | 3 | 4 | 1 | Cerebral ataxia | 4 | 4 | 0 |
| Castleman's disease | 4 | 4 | 0 | Cerebral atrophy | 3 | 3 | 0 |
| Cataplexy | 3 | 4 | 1 | Cerebral calcification | 3 | 4 | 1 |
| Cataract cortical | 3 | 4 | 1 | Cerebral disorder | 3 | 3 | 0 |
| Cataract subcapsular | 4 | 4 | 0 | Cerebral haemangioma | 4 | 4 | 0 |
| Cataract traumatic | 3 | 4 | 1 | Cerebral haematoma | 4 | 4 | 0 |
| Catatonia | 3 | 4 | 1 | Cerebral haemorrhage | 3 | 3 | 0 |
| Catheter placement | 4 | 4 | 0 | Cerebral infarction | 3 | 3 | 0 |
| Catheter site discharge | 4 | 4 | 0 | Cerebral ischaemia | 4 | 3 | 1 |
| Catheter site erythema | 4 | 4 | 0 | Cerebral palsy | 4 | 4 | 0 |
| Catheter site haemorrhage | 4 | 4 | 0 | Cerebral salt-wasting syndrome | 4 | 4 | 0 |
| Catheter site infection | 4 | 3 | 1 | Cerebral small vessel ischaemic disease | 3 | 4 | 1 |
| Catheter site inflammation | 3 | 4 | 1 | | | | |
| Catheter site pain | 4 | 4 | 0 | Cerebral thrombosis | 4 | 3 | 1 |
| Catheter site pruritus | 4 | 4 | 0 | Cerebral vasoconstriction | 3 | 4 | 1 |
| Catheter site swelling | 4 | 4 | 0 | Cerebral venous thrombosis | 4 | 3 | 1 |
| Cauda equina syndrome | 4 | 4 | 0 | Cerebral ventricle dilatation | 3 | 4 | 1 |
| CD4 lymphocytes abnormal | 4 | 4 | 0 | Cerebrospinal fluid leakage | 4 | 4 | 0 |
| CD4 lymphocytes decreased | 4 | 4 | 0 | Cerebrovascular disorder | 3 | 3 | 0 |
| Cell death | 3 | 4 | 1 | Cerebrovascular stenosis | 3 | 4 | 1 |
| Cellulitis | 3 | 3 | 0 | Ceruloplasmin decreased | 3 | 4 | 1 |
| Cellulitis orbital | 4 | 4 | 0 | Cerumen impaction | 4 | 3 | 1 |
| Cellulitis staphylococcal | 4 | 4 | 0 | Cervical cord compression | 4 | 4 | 0 |
| Central nervous system haemorrhage | 4 | 4 | 0 | Cervical dysplasia | 3 | 4 | 1 |
| Central nervous system infection | 4 | 3 | 1 | Cervical myelopathy | 4 | 4 | 0 |
| Central nervous system lesion | 3 | 3 | 0 | Cervical spinal stenosis | 3 | 4 | 1 |
| Central nervous system leukaemia | 4 | 4 | 0 | Cervical vertebral fracture | 4 | 3 | 1 |
| Central nervous system lymphoma | 4 | 4 | 0 | Cervix cancer metastatic | 4 | 4 | 0 |
| Central nervous system mass | 4 | 4 | 0 | Cervix carcinoma | 4 | 4 | 0 |
| Central nervous system necrosis | 4 | 4 | 0 | Cervix carcinoma recurrent | 4 | 4 | 0 |
| Central obesity | 4 | 3 | 1 | Cervix carcinoma stage II | 4 | 4 | 0 |
| Central venous catheterisation | 4 | 4 | 0 | Cervix carcinoma stage IV | 4 | 4 | 0 |
| Cephalo-pelvic disproportion | 3 | 4 | 1 | Cervix disorder | 4 | 4 | 0 |
| Cerebellar atrophy | 4 | 3 | 1 | Cervix haemorrhage uterine | 4 | 4 | 0 |
| Cerebellar syndrome | 3 | 4 | 1 | Cervix neoplasm | 4 | 3 | 1 |
| Cerebral arteriosclerosis | 3 | 4 | 1 | Change of bowel habit | 4 | 4 | 0 |
| Cerebral artery embolism | 4 | 4 | 0 | Chapped lips | 3 | 4 | 1 |
| Cerebral artery occlusion | 4 | 4 | 0 | Charles Bonnet syndrome | 4 | 4 | 0 |
| Cerebral artery stenosis | 4 | 4 | 0 | Cheilitis | 4 | 3 | 1 |

[Fig. 3-13]

| | | | | | | | |
|---|---|---|---|---|---|---|---|
| Chemical burn of skin | 4 | 4 | 0 | Chorioretinal atrophy | 3 | 4 | 1 |
| Chemical cystitis | 4 | 4 | 0 | Chorioretinopathy | 3 | 4 | 1 |
| Chemical eye injury | 4 | 4 | 0 | Choroid plexus carcinoma | 4 | 4 | 0 |
| Chemical peritonitis | 4 | 4 | 0 | Choroidal haemorrhage | 4 | 4 | 0 |
| Chemical poisoning | 4 | 4 | 0 | Chromaturia | 3 | 3 | 0 |
| Chemotherapeutic drug level increased | 4 | 4 | 0 | Chromosomal deletion | 4 | 4 | 0 |
| | | | | Chronic gastritis | 4 | 4 | 0 |
| Chemotherapy | 4 | 3 | 1 | Chronic hepatic failure | 4 | 4 | 0 |
| Chest discomfort | 3 | 3 | 0 | Chronic hepatitis | 4 | 4 | 0 |
| Chest injury | 3 | 3 | 0 | Chronic hepatitis B | 4 | 4 | 0 |
| Chest X-ray abnormal | 4 | 4 | 0 | Chronic hepatitis C | 3 | 3 | 0 |
| Cheyne-Stokes respiration | 4 | 4 | 0 | Chronic kidney disease | 3 | 3 | 0 |
| Chikungunya virus infection | 4 | 4 | 0 | Chronic lymphocytic leukaemia | 3 | 3 | 0 |
| Child-Pugh-Turcotte score increased | 4 | 4 | 0 | Chronic myeloid leukaemia | 4 | 4 | 0 |
| Choking | 3 | 3 | 0 | Chronic myelomonocytic leukaemia | 4 | 4 | 0 |
| Choking sensation | 3 | 3 | 0 | Chronic obstructive pulmonary disease | 3 | 3 | 0 |
| Cholangiocarcinoma | 4 | 4 | 0 | | | | |
| Cholangitis | 4 | 4 | 0 | Chronic sinusitis | 4 | 4 | 0 |
| Cholangitis acute | 4 | 4 | 0 | Chylothorax | 4 | 4 | 0 |
| Cholangitis sclerosing | 3 | 4 | 1 | Chyluria | 4 | 4 | 0 |
| Cholecystectomy | 3 | 3 | 0 | Circadian rhythm sleep disorder | 3 | 4 | 1 |
| Cholecystitis | 3 | 3 | 0 | Circulatory collapse | 3 | 3 | 0 |
| Cholecystitis acute | 3 | 3 | 0 | Circumstance or information capable of leading to medication error | 3 | 3 | 0 |
| Cholecystitis chronic | 3 | 4 | 1 | | | | |
| Cholecystitis infective | 4 | 4 | 0 | Citrobacter test positive | 4 | 4 | 0 |
| Cholecystocholangitis | 4 | 4 | 0 | Claudication of jaw muscles | 4 | 4 | 0 |
| Cholelithiasis | 3 | 3 | 0 | Clavicle fracture | 3 | 4 | 1 |
| Cholelithiasis obstructive | 4 | 4 | 0 | Cleft palate | 3 | 4 | 1 |
| Cholelithotomy | 4 | 4 | 0 | Clonic convulsion | 4 | 4 | 0 |
| Cholestasis | 3 | 4 | 1 | Clonus | 3 | 4 | 1 |
| Cholestasis of pregnancy | 3 | 4 | 1 | Clostridial infection | 4 | 4 | 0 |
| Choluria | 4 | 4 | 0 | Clostridial sepsis | 4 | 4 | 0 |
| Chondrocalcinosis pyrophosphate | 4 | 4 | 0 | Clostridium bacteraemia | 4 | 4 | 0 |
| Chondromalacia | 4 | 4 | 0 | Clostridium colitis | 4 | 4 | 0 |
| Chondropathy | 3 | 3 | 0 | Clostridium difficile colitis | 3 | 3 | 0 |
| Chondrosarcoma | 4 | 4 | 0 | Clostridium difficile infection | 3 | 3 | 0 |
| Chondrosarcoma metastatic | 4 | 4 | 0 | Clostridium difficile sepsis | 4 | 4 | 0 |
| Chorea | 3 | 4 | 1 | Clostridium test positive | 3 | 4 | 1 |
| Choreoathetosis | 3 | 4 | 1 | Clumsiness | 3 | 4 | 1 |
| Choriocarcinoma | 4 | 4 | 0 | CNS germinoma | 4 | 4 | 0 |

[Fig. 3-14]

| | | | | | | | |
|---|---|---|---|---|---|---|---|
| Coagulation factor deficiency | 4 | 4 | 0 | Complication associated with device | 3 | 3 | 0 |
| Coagulation factor increased | 4 | 4 | 0 | Composite lymphoma | 4 | 4 | 0 |
| Coagulation factor V level decreased | 4 | 4 | 0 | Compression fracture | 4 | 3 | 1 |
| Coagulation factor VII level decreased | 4 | 4 | 0 | Compulsions | 3 | 4 | 1 |
| Coagulation factor X level decreased | 4 | 4 | 0 | Compulsive hoarding | 4 | 4 | 0 |
| Coagulation time prolonged | 4 | 4 | 0 | Compulsive sexual behaviour | 3 | 4 | 1 |
| Coagulopathy | 3 | 3 | 0 | Compulsive shopping | 3 | 4 | 1 |
| Coarctation of the aorta | 4 | 4 | 0 | Computerised tomogram abdomen abnormal | 4 | 3 | 1 |
| Coccydynia | 4 | 4 | 0 | Computerised tomogram abnormal | 4 | 4 | 0 |
| Coeliac disease | 4 | 4 | 0 | Computerised tomogram thorax abnormal | 4 | 3 | 1 |
| Cognitive disorder | 3 | 3 | 0 | | | | |
| Cogwheel rigidity | 3 | 4 | 1 | Concomitant disease aggravated | 4 | 4 | 0 |
| Cold sweat | 3 | 3 | 0 | Concomitant disease progression | 4 | 4 | 0 |
| Colectomy | 4 | 4 | 0 | Concussion | 3 | 4 | 1 |
| Colitis ischaemic | 3 | 3 | 0 | Condition aggravated | 3 | 3 | 0 |
| Colitis microscopic | 3 | 4 | 1 | Conduct disorder | 3 | 4 | 1 |
| Colitis ulcerative | 3 | 3 | 0 | Conduction disorder | 3 | 3 | 0 |
| Coloboma | 3 | 4 | 1 | Confabulation | 3 | 4 | 1 |
| Colon cancer | 3 | 3 | 0 | Confusional arousal | 3 | 4 | 1 |
| Colon cancer metastatic | 4 | 3 | 1 | Confusional state | 3 | 3 | 0 |
| Colonic abscess | 4 | 4 | 0 | Congenital anomaly | 3 | 3 | 0 |
| Colonic fistula | 4 | 4 | 0 | Congenital heart valve disorder | 3 | 4 | 1 |
| Colonic pseudo-obstruction | 4 | 4 | 0 | Congenital pulmonary artery anomaly | 3 | 4 | 1 |
| Colonoscopy | 3 | 4 | 1 | | | | |
| Colony stimulating factor therapy | 4 | 4 | 0 | Congenital skin dimples | 3 | 4 | 1 |
| Colorectal adenocarcinoma | 4 | 4 | 0 | Congenital torticollis | 3 | 4 | 1 |
| Colorectal cancer | 4 | 4 | 0 | Congenital umbilical hernia | 3 | 4 | 1 |
| Colostomy | 4 | 4 | 0 | Congestive cardiomyopathy | 3 | 3 | 0 |
| Colour blindness | 4 | 4 | 0 | Conjunctival haemorrhage | 3 | 3 | 0 |
| Coma | 3 | 3 | 0 | Conjunctival hyperaemia | 3 | 4 | 1 |
| Coma hepatic | 4 | 4 | 0 | Conjunctival oedema | 4 | 4 | 0 |
| Coma scale abnormal | 3 | 3 | 0 | Conjunctivitis | 3 | 3 | 0 |
| Comminuted fracture | 4 | 4 | 0 | Consciousness fluctuating | 3 | 4 | 1 |
| Communication disorder | 3 | 3 | 0 | Constipation | 3 | 3 | 0 |
| Compartment syndrome | 3 | 4 | 1 | Continuous haemodiafiltration | 4 | 3 | 1 |
| Complement factor C3 decreased | 4 | 4 | 0 | Continuous positive airway pressure | 3 | 4 | 1 |
| Complement factor C4 decreased | 4 | 4 | 0 | Contraindicated drug administered | 3 | 3 | 0 |
| Completed suicide | 3 | 3 | 0 | Contraindicated product administered | 3 | 3 | 0 |
| Complex partial seizures | 3 | 4 | 1 | | | | |
| Complex regional pain syndrome | 3 | 4 | 1 | | | | |

[Fig. 3-15]

| | | | | | | | |
|---|---|---|---|---|---|---|---|
| Contraindication to medical treatment | 4 | 4 | 0 | Cryoglobulinaemia | 4 | 4 | 0 |
| Contrast media allergy | 4 | 4 | 0 | Cryptococcosis | 4 | 4 | 0 |
| Contusion | 3 | 3 | 0 | Cryptococcus test positive | 4 | 4 | 0 |
| Conversion disorder | 3 | 4 | 1 | Cryptorchism | 4 | 3 | 1 |
| Convulsion | 3 | 3 | 0 | Crystal nephropathy | 4 | 4 | 0 |
| Convulsive threshold lowered | 4 | 4 | 0 | CSF immunoglobulin decreased | 3 | 4 | 1 |
| Coombs test positive | 4 | 4 | 0 | CSF lymphocyte count increased | 4 | 4 | 0 |
| Coordination abnormal | 3 | 3 | 0 | CSF pressure increased | 4 | 4 | 0 |
| Corneal degeneration | 4 | 4 | 0 | CSF protein increased | 3 | 3 | 0 |
| Corneal disorder | 4 | 4 | 0 | CSF test abnormal | 4 | 4 | 0 |
| Corneal infection | 4 | 4 | 0 | Culture positive | 4 | 3 | 1 |
| Corneal reflex decreased | 4 | 4 | 0 | Culture urine positive | 4 | 4 | 0 |
| Corneal transplant | 4 | 4 | 0 | Cushing's syndrome | 3 | 4 | 1 |
| Coronary arterial stent insertion | 4 | 4 | 0 | Cushingoid | 4 | 4 | 0 |
| Coronary artery bypass | 3 | 4 | 1 | Cutaneous calcification | 4 | 4 | 0 |
| Coronary artery disease | 3 | 3 | 0 | Cutaneous lupus erythematosus | 3 | 4 | 1 |
| Coronary artery embolism | 3 | 3 | 0 | Cutaneous symptom | 3 | 4 | 1 |
| Coronary artery occlusion | 3 | 4 | 1 | Cutaneous vasculitis | 3 | 4 | 1 |
| Coronary artery restenosis | 4 | 4 | 0 | Cyanopsia | 4 | 4 | 0 |
| Coronary artery stenosis | 4 | 3 | 1 | Cyanosis | 3 | 3 | 0 |
| Coronary artery surgery | 3 | 4 | 1 | Cyanosis neonatal | 3 | 4 | 1 |
| Coronary artery thrombosis | 4 | 4 | 0 | Cyclothymic disorder | 3 | 3 | 0 |
| Coronary vascular graft occlusion | 4 | 4 | 0 | CYP2D6 polymorphism | 4 | 4 | 0 |
| Corrective lens user | 4 | 4 | 0 | Cyst | 4 | 4 | 0 |
| Costochondritis | 3 | 4 | 1 | Cystitis | 3 | 3 | 0 |
| Cotard's syndrome | 4 | 4 | 0 | Cystitis escherichia | 4 | 4 | 0 |
| Cranial nerve disorder | 3 | 4 | 1 | Cystitis haemorrhagic | 4 | 4 | 0 |
| Cranial nerve paralysis | 4 | 4 | 0 | Cystitis interstitial | 4 | 4 | 0 |
| Craniocerebral injury | 3 | 4 | 1 | Cystitis klebsiella | 4 | 4 | 0 |
| Craniosynostosis | 4 | 4 | 0 | Cystitis noninfective | 3 | 3 | 0 |
| Creatinine renal clearance decreased | 4 | 4 | 0 | Cystitis radiation | 4 | 4 | 0 |
| Creatinine urine decreased | 4 | 4 | 0 | Cystoid macular oedema | 4 | 4 | 0 |
| Crepitations | 3 | 4 | 1 | Cytogenetic abnormality | 3 | 4 | 1 |
| Creutzfeldt-Jakob disease | 3 | 4 | 1 | Cytokine release syndrome | 3 | 4 | 1 |
| Crime | 4 | 4 | 0 | Cytomegalovirus chorioretinitis | 4 | 4 | 0 |
| Critical illness polyneuropathy | 4 | 4 | 0 | Cytomegalovirus colitis | 3 | 4 | 1 |
| Crohn's disease | 3 | 3 | 0 | Cytomegalovirus duodenitis | 4 | 4 | 0 |
| Cross sensitivity reaction | 4 | 4 | 0 | Cytomegalovirus enterocolitis | 4 | 4 | 0 |
| Crying | 3 | 3 | 0 | Cytomegalovirus infection | 4 | 4 | 0 |

[Fig. 3-16]

| | | | | | | | |
|---|---|---|---|---|---|---|---|
| Cytomegalovirus mucocutaneous ulcer | 4 | 4 | 0 | Delusional disorder, somatic type | 4 | 4 | 0 |
| Cytomegalovirus oesophagitis | 4 | 4 | 0 | Delusional disorder, unspecified type | 3 | 4 | 1 |
| Cytomegalovirus test positive | 4 | 3 | 1 | Delusional perception | 3 | 4 | 1 |
| Cytomegalovirus viraemia | 4 | 4 | 0 | Dementia | 3 | 3 | 0 |
| Cytopenia | 3 | 3 | 0 | Dementia Alzheimer's type | 3 | 4 | 1 |
| Dacryostenosis acquired | 4 | 4 | 0 | Dementia with Lewy bodies | 3 | 4 | 1 |
| Deafness | 3 | 3 | 0 | Demyelination | 4 | 3 | 1 |
| Deafness bilateral | 4 | 4 | 0 | Dengue fever | 4 | 4 | 0 |
| Deafness congenital | 4 | 4 | 0 | Dental caries | 3 | 3 | 0 |
| Deafness neurosensory | 4 | 3 | 1 | Dental fistula | 4 | 4 | 0 |
| Deafness transitory | 4 | 4 | 0 | Dental operation | 4 | 4 | 0 |
| Deafness unilateral | 4 | 4 | 0 | Dental plaque | 3 | 4 | 1 |
| Death of relative | 4 | 4 | 0 | Dependence | 3 | 3 | 0 |
| Debridement | 3 | 4 | 1 | Dependent personality disorder | 4 | 4 | 0 |
| Decorticate posture | 4 | 4 | 0 | Depersonalisation | 4 | 4 | 0 |
| Decreased activity | 3 | 3 | 0 | Depressed level of consciousness | 3 | 3 | 0 |
| Decreased eye contact | 3 | 4 | 1 | Depressed mood | 3 | 3 | 0 |
| Decreased immune responsiveness | 4 | 4 | 0 | Depression suicidal | 3 | 4 | 1 |
| Decreased interest | 3 | 4 | 1 | Depressive symptom | 3 | 3 | 0 |
| Decreased vibratory sense | 4 | 4 | 0 | Derailment | 4 | 4 | 0 |
| Decubitus ulcer | 3 | 3 | 0 | Derealisation | 3 | 4 | 1 |
| Deep brain stimulation | 4 | 4 | 0 | Dermal cyst | 4 | 4 | 0 |
| Deep vein thrombosis | 3 | 3 | 0 | Dermatillomania | 3 | 4 | 1 |
| Deep vein thrombosis postoperative | 4 | 4 | 0 | Dermatitis | 3 | 3 | 0 |
| Defaecation urgency | 3 | 4 | 1 | Dermatitis acneiform | 4 | 4 | 0 |
| Defect conduction intraventricular | 4 | 3 | 1 | Dermatitis allergic | 3 | 4 | 1 |
| Deficiency of bile secretion | 4 | 4 | 0 | Dermatitis atopic | 3 | 4 | 1 |
| Deformity | 3 | 3 | 0 | Dermatitis bullous | 3 | 3 | 0 |
| Deformity thorax | 4 | 4 | 0 | Dermatitis contact | 3 | 4 | 1 |
| Dehydration | 3 | 3 | 0 | Dermatitis diaper | 4 | 4 | 0 |
| Delirium | 3 | 3 | 0 | Dermatitis exfoliative | 3 | 4 | 1 |
| Delirium febrile | 4 | 4 | 0 | Dermatitis infected | 4 | 4 | 0 |
| Delirium tremens | 3 | 4 | 1 | Dermatitis psoriasiform | 4 | 4 | 0 |
| Delusion | 3 | 3 | 0 | Dermatofibrosarcoma protuberans | 3 | 4 | 1 |
| Delusion of grandeur | 3 | 4 | 1 | Dermatophytosis | 4 | 4 | 0 |
| Delusion of reference | 3 | 4 | 1 | Dermo-hypodermitis | 4 | 4 | 0 |
| Delusion of replacement | 3 | 4 | 1 | Desmoplastic small round cell tumour | 4 | 4 | 0 |
| Delusional disorder, erotomanic type | 3 | 4 | 1 | Detachment of retinal pigment epithelium | 3 | 4 | 1 |
| Delusional disorder, persecutory type | 4 | 4 | 0 | Detoxification | 3 | 4 | 1 |

[Fig. 3-17]

| | | | | | | | |
|---|---|---|---|---|---|---|---|
| Detrusor sphincter dyssynergia | 4 | 4 | 0 | Diabetic retinopathy | 3 | 4 | 1 |
| Developmental hip dysplasia | 3 | 4 | 1 | Diabetic ulcer | 4 | 4 | 0 |
| Device adhesion issue | 3 | 4 | 1 | Dialysis | 3 | 3 | 0 |
| Device alarm issue | 4 | 4 | 0 | Diaphragm neoplasm | 4 | 4 | 0 |
| Device breakage | 4 | 4 | 0 | Diaphragmatic hernia | 4 | 4 | 0 |
| Device damage | 4 | 4 | 0 | Diaphragmatic paralysis | 4 | 4 | 0 |
| Device defective | 4 | 4 | 0 | Diaphragmatic rupture | 4 | 4 | 0 |
| Device dependence | 4 | 4 | 0 | Diaphragmatic spasm | 4 | 4 | 0 |
| Device difficult to use | 3 | 4 | 1 | Diarrhoea haemorrhagic | 3 | 4 | 1 |
| Device dislocation | 4 | 3 | 1 | Diarrhoea infectious | 4 | 4 | 0 |
| Device infusion issue | 4 | 4 | 0 | Diarrhoea neonatal | 3 | 4 | 1 |
| Device interaction | 4 | 4 | 0 | Diastolic dysfunction | 3 | 3 | 0 |
| Device intolerance | 4 | 4 | 0 | Diet refusal | 3 | 4 | 1 |
| Device issue | 4 | 3 | 1 | Differential white blood cell count abnormal | 3 | 3 | 0 |
| Device kink | 4 | 4 | 0 | Diffuse alopecia | 4 | 4 | 0 |
| Device lead damage | 4 | 4 | 0 | Diffuse alveolar damage | 4 | 4 | 0 |
| Device leakage | 3 | 3 | 0 | Diffuse large B-cell lymphoma | 4 | 3 | 1 |
| Device malfunction | 3 | 3 | 0 | Diffuse large B-cell lymphoma recurrent | 4 | 4 | 0 |
| Device material opacification | 4 | 4 | 0 | Diffuse large B-cell lymphoma refractory | 4 | 4 | 0 |
| Device occlusion | 4 | 3 | 1 | Diffuse large B-cell lymphoma stage III | 4 | 4 | 0 |
| Device physical property issue | 3 | 4 | 1 | Dilatation ventricular | 3 | 3 | 0 |
| Device related infection | 3 | 4 | 1 | Diplegia | 3 | 4 | 1 |
| Device related sepsis | 4 | 4 | 0 | Diplopia | 3 | 3 | 0 |
| Device related thrombosis | 4 | 4 | 0 | Disability | 3 | 4 | 1 |
| Device use error | 3 | 4 | 1 | Discomfort | 3 | 3 | 0 |
| Device use issue | 3 | 4 | 1 | Disease complication | 3 | 3 | 0 |
| Dextrocardia | 3 | 4 | 1 | Disease prodromal stage | 4 | 4 | 0 |
| Diabetes insipidus | 3 | 3 | 0 | Disease progression | 3 | 3 | 0 |
| Diabetes mellitus | 3 | 3 | 0 | Disease recurrence | 3 | 3 | 0 |
| Diabetes mellitus inadequate control | 3 | 3 | 0 | Disinhibition | 3 | 3 | 0 |
| Diabetic coma | 3 | 4 | 1 | Disorganised speech | 3 | 4 | 1 |
| Diabetic complication | 4 | 3 | 1 | Disorientation | 3 | 3 | 0 |
| Diabetic dyslipidaemia | 3 | 4 | 1 | Disruptive mood dysregulation disorder | 3 | 4 | 1 |
| Diabetic foot | 4 | 4 | 0 | | | | |
| Diabetic hyperglycaemic coma | 3 | 4 | 1 | Disseminated intravascular coagulation | 3 | 3 | 0 |
| Diabetic hyperosmolar coma | 3 | 3 | 0 | | | | |
| Diabetic ketoacidosis | 3 | 3 | 0 | | | | |
| Diabetic ketosis | 4 | 4 | 0 | | | | |
| Diabetic metabolic decompensation | 4 | 4 | 0 | | | | |
| Diabetic nephropathy | 4 | 4 | 0 | | | | |
| Diabetic neuropathy | 3 | 4 | 1 | | | | |

[Fig. 3-18]

| | | | |
|---|---|---|---|
| Disseminated intravascular coagulation in newborn | 3 | 4 | 1 |
| Disseminated tuberculosis | 4 | 4 | 0 |
| Dissociation | 3 | 4 | 1 |
| Dissociative disorder | 3 | 4 | 1 |
| Dissociative identity disorder | 3 | 4 | 1 |
| Distal intestinal obstruction syndrome | 4 | 4 | 0 |
| Distractibility | 3 | 4 | 1 |
| Distributive shock | 3 | 4 | 1 |
| Disturbance in attention | 3 | 3 | 0 |
| Disturbance in sexual arousal | 3 | 4 | 1 |
| Disturbance in social behaviour | 3 | 4 | 1 |
| Diverticular perforation | 3 | 4 | 1 |
| Diverticulitis | 3 | 3 | 0 |
| Diverticulitis intestinal haemorrhagic | 4 | 4 | 0 |
| Diverticulum intestinal | 4 | 4 | 0 |
| Divorced | 3 | 4 | 1 |
| Dizziness postural | 3 | 3 | 0 |
| Drain placement | 4 | 4 | 0 |
| Dreamy state | 4 | 4 | 0 |
| Drooling | 3 | 4 | 1 |
| Drop attacks | 4 | 3 | 1 |
| Drowning | 3 | 4 | 1 |
| Drug-disease interaction | 3 | 3 | 0 |
| Drug-induced liver injury | 3 | 3 | 0 |
| Drug abuse | 3 | 3 | 0 |
| Drug administered at inappropriate site | 3 | 4 | 1 |
| Drug administered to patient of inappropriate age | 3 | 3 | 0 |
| Drug administration error | 3 | 3 | 0 |
| Drug clearance decreased | 4 | 4 | 0 |
| Drug dependence | 3 | 4 | 1 |
| Drug dispensed to wrong patient | 4 | 4 | 0 |
| Drug dispensing error | 3 | 3 | 0 |
| Drug dose titration not performed | 4 | 4 | 0 |
| Drug effect decreased | 3 | 3 | 0 |
| Drug effect incomplete | 3 | 3 | 0 |
| Drug effect increased | 3 | 4 | 1 |

| | | | |
|---|---|---|---|
| Drug effect variable | 4 | 4 | 0 |
| Drug eruption | 3 | 3 | 0 |
| Drug hypersensitivity | 3 | 3 | 0 |
| Drug ineffective for unapproved indication | 3 | 3 | 0 |
| Drug interaction | 3 | 3 | 0 |
| Drug intolerance | 3 | 3 | 0 |
| Drug level above therapeutic | 3 | 3 | 0 |
| Drug level below therapeutic | 3 | 4 | 1 |
| Drug level changed | 4 | 4 | 0 |
| Drug level decreased | 3 | 4 | 1 |
| Drug level fluctuating | 4 | 4 | 0 |
| Drug level increased | 3 | 3 | 0 |
| Drug monitoring procedure incorrectly performed | 3 | 3 | 0 |
| Drug monitoring procedure not performed | 3 | 4 | 1 |
| Drug prescribing error | 3 | 3 | 0 |
| Drug reaction with eosinophilia and systemic symptoms | 3 | 3 | 0 |
| Drug resistance | 3 | 3 | 0 |
| Drug screen false positive | 3 | 4 | 1 |
| Drug screen negative | 4 | 4 | 0 |
| Drug screen positive | 3 | 4 | 1 |
| Drug therapy | 4 | 4 | 0 |
| Drug titration error | 4 | 4 | 0 |
| Drug tolerance | 3 | 4 | 1 |
| Drug tolerance decreased | 4 | 3 | 1 |
| Drug use disorder | 3 | 4 | 1 |
| Drug withdrawal convulsions | 4 | 4 | 0 |
| Drug withdrawal syndrome | 3 | 3 | 0 |
| Drug withdrawal syndrome neonatal | 3 | 4 | 1 |
| Dry age-related macular degeneration | 4 | 4 | 0 |
| Dry eye | 3 | 4 | 1 |
| Dry gangrene | 4 | 4 | 0 |
| Dry mouth | 3 | 3 | 0 |
| Dry skin | 3 | 3 | 0 |
| Dry throat | 3 | 3 | 0 |
| Ductal adenocarcinoma of pancreas | 4 | 4 | 0 |

[Fig. 3-19]

| | | | | | | | |
|---|---|---|---|---|---|---|---|
| Duodenal obstruction | 4 | 4 | 0 | Ear haemorrhage | 4 | 4 | 0 |
| Duodenal perforation | 4 | 4 | 0 | Ear infection | 3 | 3 | 0 |
| Duodenal stenosis | 4 | 4 | 0 | Ear malformation | 4 | 4 | 0 |
| Duodenal ulcer | 3 | 3 | 0 | Ear neoplasm | 4 | 4 | 0 |
| Duodenal ulcer haemorrhage | 4 | 4 | 0 | Ear pain | 3 | 3 | 0 |
| Duodenal ulcer perforation | 4 | 4 | 0 | Ear pruritus | 3 | 4 | 1 |
| Duodenitis | 3 | 4 | 1 | Eastern Cooperative Oncology Group performance status improved | 4 | 4 | 0 |
| Duodenitis haemorrhagic | 4 | 4 | 0 |
| Dysaesthesia | 4 | 4 | 0 | Eastern Cooperative Oncology Group performance status worsened | 4 | 4 | 0 |
| Dysarthria | 3 | 3 | 0 |
| Dysbacteriosis | 3 | 4 | 1 | Eating disorder | 3 | 3 | 0 |
| Dyscalculia | 4 | 4 | 0 | Ecchymosis | 3 | 4 | 1 |
| Dyschezia | 3 | 4 | 1 | Eccrine carcinoma | 4 | 4 | 0 |
| Dysentery | 3 | 4 | 1 | Eccrine squamous syringometaplasia | 4 | 4 | 0 |
| Dysgeusia | 3 | 3 | 0 | ECG signs of myocardial ischaemia | 3 | 4 | 1 |
| Dysgraphia | 3 | 3 | 0 | Echocardiogram abnormal | 4 | 3 | 1 |
| Dyshidrotic eczema | 4 | 4 | 0 | Echolalia | 3 | 4 | 1 |
| Dyskinesia | 3 | 3 | 0 | Economic problem | 3 | 4 | 1 |
| Dyslalia | 3 | 4 | 1 | Ecthyma | 4 | 4 | 0 |
| Dyslexia | 4 | 4 | 0 | Ectopic ACTH syndrome | 4 | 4 | 0 |
| Dyslipidaemia | 3 | 3 | 0 | Ectopic pregnancy | 3 | 4 | 1 |
| Dysmenorrhoea | 3 | 4 | 1 | Eczema | 3 | 3 | 0 |
| Dysmetria | 4 | 4 | 0 | Eczema asteatotic | 4 | 4 | 0 |
| Dyspareunia | 4 | 4 | 0 | Eczema eyelids | 4 | 4 | 0 |
| Dysphagia | 3 | 3 | 0 | Edentulous | 4 | 4 | 0 |
| Dysphemia | 3 | 3 | 0 | Educational problem | 3 | 4 | 1 |
| Dysphonia | 3 | 3 | 0 | Effusion | 4 | 4 | 0 |
| Dysphoria | 3 | 4 | 1 | EGFR gene mutation | 4 | 4 | 0 |
| Dysplasia | 4 | 4 | 0 | Egocentrism | 3 | 4 | 1 |
| Dyspnoea at rest | 4 | 4 | 0 | Ejaculation delayed | 4 | 4 | 0 |
| Dyspnoea exertional | 3 | 3 | 0 | Ejaculation disorder | 3 | 4 | 1 |
| Dyspnoea paroxysmal nocturnal | 4 | 4 | 0 | Ejaculation failure | 3 | 4 | 1 |
| Dyspraxia | 3 | 4 | 1 | Ejection fraction | 4 | 4 | 0 |
| Dysprosody | 4 | 4 | 0 | Ejection fraction abnormal | 4 | 4 | 0 |
| Dysstasia | 3 | 3 | 0 | Ejection fraction decreased | 3 | 3 | 0 |
| Dystonia | 3 | 4 | 1 | Elective surgery | 4 | 4 | 0 |
| Dystrophic calcification | 3 | 4 | 1 | Electrocardiogram abnormal | 3 | 3 | 0 |
| Dysuria | 3 | 3 | 0 | Electrocardiogram change | 3 | 4 | 1 |
| Ear discomfort | 3 | 4 | 1 | Electrocardiogram high voltage | 3 | 4 | 1 |
| Ear disorder | 4 | 4 | 0 | Electrocardiogram J wave | 4 | 4 | 0 |

[Fig. 3-20]

| | | | | | | | |
|---|---|---|---|---|---|---|---|
| Electrocardiogram low voltage | 3 | 4 | 1 | Emotional poverty | 3 | 4 | 1 |
| Electrocardiogram PR prolongation | 3 | 4 | 1 | Emphysema | 3 | 3 | 0 |
| Electrocardiogram PR shortened | 3 | 4 | 1 | Emphysematous cholecystitis | 4 | 4 | 0 |
| Electrocardiogram Q wave abnormal | 4 | 4 | 0 | Emphysematous pyelonephritis | 4 | 4 | 0 |
| Electrocardiogram QRS complex abnormal | 3 | 4 | 1 | Empyema | 3 | 3 | 0 |
| | | | | Encephalitis | 3 | 3 | 0 |
| Electrocardiogram QRS complex prolonged | 3 | 4 | 1 | Encephalitis autoimmune | 3 | 3 | 0 |
| | | | | Encephalitis brain stem | 4 | 4 | 0 |
| Electrocardiogram QT interval abnormal | 3 | 3 | 0 | Encephalitis cytomegalovirus | 4 | 4 | 0 |
| | | | | Encephalitis viral | 4 | 4 | 0 |
| Electrocardiogram QT prolonged | 3 | 3 | 0 | Encephalomalacia | 3 | 4 | 1 |
| Electrocardiogram repolarisation abnormality | 3 | 4 | 1 | Encephalopathy | 3 | 3 | 0 |
| | | | | Encopresis | 4 | 4 | 0 |
| Electrocardiogram ST-T change | 4 | 4 | 0 | End stage renal disease | 3 | 3 | 0 |
| Electrocardiogram ST-T segment abnormal | 4 | 4 | 0 | Endocarditis | 4 | 3 | 1 |
| | | | | Endocarditis bacterial | 4 | 4 | 0 |
| Electrocardiogram ST segment abnormal | 3 | 4 | 1 | Endocarditis noninfective | 4 | 4 | 0 |
| | | | | Endocrine disorder | 3 | 4 | 1 |
| Electrocardiogram ST segment depression | 3 | 3 | 0 | Endocrine toxicity | 4 | 4 | 0 |
| | | | | Endodontic procedure | 3 | 4 | 1 |
| Electrocardiogram ST segment elevation | 3 | 3 | 0 | Endometrial adenocarcinoma | 4 | 3 | 1 |
| | | | | Endometrial atrophy | 4 | 4 | 0 |
| Electrocardiogram T wave abnormal | 3 | 3 | 0 | Endometrial cancer | 4 | 3 | 1 |
| Electrocardiogram T wave amplitude decreased | 4 | 3 | 1 | Endometrial cancer stage IV | 4 | 4 | 0 |
| | | | | Endometrial disorder | 4 | 4 | 0 |
| Electrocardiogram T wave inversion | 3 | 3 | 0 | Endometrial hyperplasia | 3 | 4 | 1 |
| Electrocardiogram T wave peaked | 4 | 4 | 0 | Endometrial stromal sarcoma | 4 | 4 | 0 |
| Electroconvulsive therapy | 3 | 4 | 1 | Endometriosis | 3 | 4 | 1 |
| Electroencephalogram abnormal | 3 | 4 | 1 | Endothelial dysfunction | 4 | 4 | 0 |
| Electrolyte imbalance | 3 | 3 | 0 | Endotracheal intubation | 3 | 4 | 1 |
| Electrophoresis protein | 3 | 4 | 1 | Energy increased | 3 | 4 | 1 |
| Embedded device | 4 | 4 | 0 | Enteritis | 4 | 4 | 0 |
| Embolic cerebral infarction | 4 | 4 | 0 | Enteritis infectious | 4 | 3 | 1 |
| Embolic stroke | 4 | 4 | 0 | Enteritis necroticans | 4 | 4 | 0 |
| Embolism | 3 | 3 | 0 | Enterobacter bacteraemia | 4 | 4 | 0 |
| Embolism arterial | 4 | 4 | 0 | Enterobacter infection | 4 | 4 | 0 |
| Embolism venous | 3 | 3 | 0 | Enterobacter sepsis | 4 | 4 | 0 |
| Embryonal rhabdomyosarcoma | 4 | 4 | 0 | Enterobacter test positive | 4 | 4 | 0 |
| Emergency care | 3 | 4 | 1 | Enterococcal bacteraemia | 4 | 4 | 0 |
| Emotional disorder | 3 | 3 | 0 | Enterococcal infection | 4 | 3 | 1 |
| Emotional distress | 3 | 3 | 0 | | | | |

[Fig. 3-21]

| | | | | | | | |
|---|---|---|---|---|---|---|---|
| Enterococcal sepsis | 4 | 4 | 0 | Epstein-Barr virus associated lymphoproliferative disorder | 4 | 4 | 0 |
| Enterococcus test positive | 4 | 4 | 0 | Epstein-Barr virus infection | 3 | 3 | 0 |
| Enterocolitis | 4 | 4 | 0 | Epstein-Barr virus test positive | 4 | 4 | 0 |
| Enterocolitis bacterial | 4 | 4 | 0 | Erectile dysfunction | 3 | 3 | 0 |
| Enterocolitis haemorrhagic | 4 | 4 | 0 | Erection increased | 3 | 4 | 1 |
| Enterocolitis infectious | 4 | 4 | 0 | Erosive duodenitis | 4 | 4 | 0 |
| Enterocolonic fistula | 4 | 4 | 0 | Erosive oesophagitis | 4 | 4 | 0 |
| Enterocutaneous fistula | 4 | 3 | 1 | Erotomanic delusion | 3 | 4 | 1 |
| Enteropathy-associated T-cell lymphoma | 4 | 4 | 0 | Eructation | 3 | 4 | 1 |
| Enterovesical fistula | 4 | 4 | 0 | Erysipelas | 3 | 4 | 1 |
| Enterovirus test positive | 4 | 4 | 0 | Erythema dyschromicum perstans | 4 | 4 | 0 |
| Enthesopathy | 4 | 4 | 0 | Erythema multiforme | 3 | 3 | 0 |
| Enuresis | 3 | 3 | 0 | Erythema nodosum | 4 | 4 | 0 |
| Enzyme abnormality | 4 | 4 | 0 | Erythema of eyelid | 3 | 4 | 1 |
| Eosinopenia | 4 | 4 | 0 | Erythroblast count increased | 4 | 4 | 0 |
| Eosinophil count abnormal | 3 | 4 | 1 | Erythropenia | 4 | 4 | 0 |
| Eosinophil count decreased | 3 | 3 | 0 | Erythrosis | 3 | 4 | 1 |
| Eosinophil count increased | 3 | 4 | 1 | Eschar | 4 | 4 | 0 |
| Eosinophil percentage decreased | 4 | 4 | 0 | Escherichia bacteraemia | 4 | 3 | 1 |
| Eosinophil percentage increased | 3 | 4 | 1 | Escherichia infection | 3 | 3 | 0 |
| Eosinophilia | 3 | 3 | 0 | Escherichia sepsis | 4 | 4 | 0 |
| Eosinophilic colitis | 4 | 4 | 0 | Escherichia test positive | 4 | 3 | 1 |
| Eosinophilic granulomatosis with polyangiitis | 3 | 4 | 1 | Escherichia urinary tract infection | 4 | 3 | 1 |
| Eosinophilic myocarditis | 3 | 4 | 1 | Essential hypertension | 3 | 4 | 1 |
| Eosinophilic pneumonia | 4 | 3 | 1 | Essential thrombocythaemia | 4 | 4 | 0 |
| Ependymoma | 4 | 4 | 0 | Euglycaemic diabetic ketoacidosis | 4 | 4 | 0 |
| Epidermal necrosis | 4 | 4 | 0 | Euphoric mood | 3 | 3 | 0 |
| Epigastric discomfort | 3 | 3 | 0 | Evans syndrome | 4 | 4 | 0 |
| Epiglottic oedema | 4 | 4 | 0 | Ewing's sarcoma | 4 | 4 | 0 |
| Epiglottitis | 4 | 3 | 1 | Exaggerated startle response | 3 | 4 | 1 |
| Epilepsy | 3 | 3 | 0 | Excessive eye blinking | 3 | 4 | 1 |
| Epiphyses premature fusion | 4 | 4 | 0 | Excessive masturbation | 4 | 4 | 0 |
| Epiphysiolysis | 4 | 4 | 0 | Excoriation | 4 | 4 | 0 |
| Episcleritis | 4 | 4 | 0 | Executive dysfunction | 3 | 4 | 1 |
| Epistaxis | 3 | 3 | 0 | Exercise lack of | 3 | 4 | 1 |
| Epithelioid mesothelioma | 4 | 4 | 0 | Exercise tolerance decreased | 3 | 3 | 0 |
| Epstein-Barr virus antibody positive | 3 | 4 | 1 | Exfoliative rash | 4 | 4 | 0 |
| | | | | Exophthalmos | 3 | 4 | 1 |
| | | | | Exostosis | 3 | 4 | 1 |

[Fig. 3-22]

| | | | | | | | |
|---|---|---|---|---|---|---|---|
| Expired product administered | 3 | 4 | 1 | Eyelid ptosis | 3 | 3 | 0 |
| Exposed bone in jaw | 4 | 4 | 0 | Eyelids pruritus | 4 | 4 | 0 |
| Exposure during breast feeding | 3 | 4 | 1 | Face injury | 3 | 4 | 1 |
| Exposure during pregnancy | 3 | 3 | 0 | Face oedema | 3 | 3 | 0 |
| Exposure to radiation | 4 | 4 | 0 | Facial asymmetry | 3 | 4 | 1 |
| Exposure via body fluid | 3 | 4 | 1 | Facial bones fracture | 4 | 3 | 1 |
| Exposure via father | 3 | 4 | 1 | Facial nerve disorder | 4 | 4 | 0 |
| Exposure via ingestion | 3 | 4 | 1 | Facial pain | 3 | 4 | 1 |
| Exposure via inhalation | 4 | 4 | 0 | Facial paralysis | 3 | 4 | 1 |
| External counterpulsation | 4 | 4 | 0 | Facial paresis | 4 | 4 | 0 |
| External ear cellulitis | 3 | 4 | 1 | Facial spasm | 3 | 4 | 1 |
| Extra dose administered | 3 | 3 | 0 | Facial wasting | 4 | 4 | 0 |
| Extradural abscess | 4 | 4 | 0 | Factor V Leiden mutation | 4 | 4 | 0 |
| Extragonadal primary germ cell tumour | 4 | 4 | 0 | Factor VIII deficiency | 4 | 4 | 0 |
| Extramammary Paget's disease | 4 | 4 | 0 | Faecal incontinence | 3 | 3 | 0 |
| Extraocular muscle paresis | 3 | 4 | 1 | Faecal volume increased | 4 | 3 | 1 |
| Extrapulmonary tuberculosis | 4 | 4 | 0 | Faecal vomiting | 4 | 3 | 1 |
| Extrapyramidal disorder | 3 | 4 | 1 | Faecaloma | 3 | 3 | 0 |
| Extraskeletal ossification | 4 | 4 | 0 | Faecaluria | 4 | 4 | 0 |
| Extrasystoles | 3 | 4 | 1 | Faeces discoloured | 3 | 4 | 1 |
| Extravasation | 4 | 4 | 0 | Faeces hard | 4 | 4 | 0 |
| Extremity necrosis | 4 | 4 | 0 | Faeces soft | 4 | 3 | 1 |
| Eye allergy | 4 | 4 | 0 | Failure to anastomose | 4 | 4 | 0 |
| Eye colour change | 4 | 4 | 0 | Failure to thrive | 3 | 3 | 0 |
| Eye contusion | 3 | 4 | 1 | False positive investigation result | 3 | 3 | 0 |
| Eye discharge | 3 | 4 | 1 | Familial haemophagocytic lymphohistiocytosis | 4 | 4 | 0 |
| Eye disorder | 3 | 3 | 0 | Family stress | 3 | 4 | 1 |
| Eye haemorrhage | 3 | 3 | 0 | Fanconi syndrome | 4 | 4 | 0 |
| Eye inflammation | 4 | 4 | 0 | Fanconi syndrome acquired | 4 | 4 | 0 |
| Eye irritation | 3 | 4 | 1 | Fat embolism | 4 | 4 | 0 |
| Eye movement disorder | 3 | 3 | 0 | Fat necrosis | 4 | 4 | 0 |
| Eye oedema | 4 | 3 | 1 | Fat tissue increased | 3 | 4 | 1 |
| Eye operation | 4 | 4 | 0 | Fear | 3 | 3 | 0 |
| Eye pain | 3 | 3 | 0 | Fear of animals | 3 | 4 | 1 |
| Eye pruritus | 3 | 4 | 1 | Fear of death | 3 | 4 | 1 |
| Eye swelling | 3 | 3 | 0 | Fear of disease | 3 | 4 | 1 |
| Eyelid bleeding | 3 | 4 | 1 | Fear of eating | 4 | 4 | 0 |
| Eyelid infection | 3 | 4 | 1 | Fear of falling | 4 | 4 | 0 |
| Eyelid oedema | 3 | 3 | 0 | Fear of injection | 3 | 4 | 1 |

[Fig. 3-23]

| | | | | | | | | |
|---|---|---|---|---|---|---|---|---|
| Febrile bone marrow aplasia | 4 | 4 | 0 | Flavivirus infection | 3 | 4 | 1 |
| Febrile infection | 3 | 4 | 1 | Flight of ideas | 3 | 4 | 1 |
| Febrile neutropenia | 3 | 3 | 0 | Floppy infant | 4 | 4 | 0 |
| Feeding disorder | 3 | 3 | 0 | Floppy iris syndrome | 3 | 4 | 1 |
| Feeding disorder neonatal | 3 | 4 | 1 | Fluid imbalance | 4 | 4 | 0 |
| Feeding tube complication | 4 | 4 | 0 | Fluid intake reduced | 3 | 4 | 1 |
| Feeling abnormal | 3 | 3 | 0 | Fluid intake restriction | 4 | 3 | 1 |
| Feeling cold | 3 | 3 | 0 | Fluid overload | 3 | 3 | 0 |
| Feeling drunk | 4 | 3 | 1 | Fluid replacement | 3 | 4 | 1 |
| Feeling guilty | 3 | 4 | 1 | Fluid retention | 3 | 3 | 0 |
| Feeling hot | 3 | 3 | 0 | Flushing | 3 | 3 | 0 |
| Feeling jittery | 3 | 3 | 0 | Foaming at mouth | 4 | 4 | 0 |
| Feeling of body temperature change | 4 | 4 | 0 | Focal dyscognitive seizures | 3 | 4 | 1 |
| Feeling of despair | 3 | 4 | 1 | Focal nodular hyperplasia | 4 | 4 | 0 |
| Feeling of relaxation | 3 | 4 | 1 | Foetal death | 3 | 4 | 1 |
| Feelings of worthlessness | 3 | 4 | 1 | Foetal distress syndrome | 3 | 4 | 1 |
| Female genital tract fistula | 4 | 4 | 0 | Foetal exposure during pregnancy | 3 | 3 | 0 |
| Female sexual arousal disorder | 3 | 4 | 1 | Foetal growth restriction | 3 | 4 | 1 |
| Femoral artery aneurysm | 4 | 4 | 0 | Foetal heart rate abnormal | 3 | 4 | 1 |
| Femoral artery occlusion | 4 | 4 | 0 | Foetal heart rate decreased | 3 | 4 | 1 |
| Femoral neck fracture | 3 | 3 | 0 | Foetal heart rate disorder | 4 | 4 | 0 |
| Femur fracture | 3 | 3 | 0 | Foetal malposition | 3 | 4 | 1 |
| Fibrin D dimer increased | 3 | 3 | 0 | Foetal monitoring abnormal | 4 | 4 | 0 |
| Fibrin degradation products increased | 4 | 4 | 0 | Folate deficiency | 4 | 4 | 0 |
| | | | | Follicular thyroid cancer | 4 | 4 | 0 |
| Fibroma | 4 | 4 | 0 | Folliculitis | 3 | 3 | 0 |
| Fibromyalgia | 3 | 4 | 1 | Food allergy | 4 | 4 | 0 |
| Fibrosis | 3 | 3 | 0 | Food aversion | 3 | 4 | 1 |
| Fibula fracture | 4 | 4 | 0 | Food craving | 3 | 3 | 0 |
| Fine motor delay | 4 | 4 | 0 | Food interaction | 3 | 4 | 1 |
| Fine motor skill dysfunction | 3 | 4 | 1 | Food intolerance | 4 | 4 | 0 |
| Finger amputation | 4 | 4 | 0 | Food poisoning | 3 | 4 | 1 |
| Fistula | 4 | 3 | 1 | Foot amputation | 4 | 4 | 0 |
| Fistula discharge | 4 | 4 | 0 | Foot deformity | 4 | 4 | 0 |
| Fistula of small intestine | 4 | 4 | 0 | Foot fracture | 4 | 4 | 0 |
| Flagellate dermatitis | 4 | 4 | 0 | Foot operation | 3 | 4 | 1 |
| Flank pain | 4 | 4 | 0 | Forced expiratory volume decreased | 4 | 4 | 0 |
| Flashback | 3 | 4 | 1 | Forearm fracture | 4 | 3 | 1 |
| Flat affect | 3 | 3 | 0 | Foreign body | 3 | 4 | 1 |
| Flatulence | 3 | 3 | 0 | Foreign body aspiration | 4 | 4 | 0 |

[Fig. 3-24]

| | | | | | | | | |
|---|---|---|---|---|---|---|---|---|
| Formication | 3 | 3 | 0 | | Gamma-glutamyltransferase abnormal | 4 | 4 | 0 |
| Fracture | 3 | 3 | 0 | | Gamma-glutamyltransferase increased | 3 | 3 | 0 |
| Fracture displacement | 4 | 4 | 0 | | | | | |
| Fracture nonunion | 4 | 4 | 0 | | | | | |
| Fracture pain | 4 | 4 | 0 | | Gangrene | 3 | 4 | 1 |
| Fractured coccyx | 4 | 4 | 0 | | Gangrene neonatal | 3 | 4 | 1 |
| Fractured sacrum | 4 | 3 | 1 | | Gas gangrene | 4 | 4 | 0 |
| Freezing phenomenon | 4 | 4 | 0 | | Gastrectomy | 3 | 4 | 1 |
| Frequent bowel movements | 4 | 4 | 0 | | Gastric banding | 3 | 4 | 1 |
| Frontotemporal dementia | 3 | 3 | 0 | | Gastric bypass | 3 | 4 | 1 |
| Frustration | 3 | 4 | 1 | | Gastric cancer | 3 | 3 | 0 |
| Frustration tolerance decreased | 3 | 4 | 1 | | Gastric dilatation | 4 | 3 | 1 |
| Full blood count abnormal | 4 | 3 | 1 | | Gastric disorder | 3 | 3 | 0 |
| Full blood count decreased | 3 | 4 | 1 | | Gastric haemorrhage | 4 | 4 | 0 |
| Full blood count increased | 4 | 4 | 0 | | Gastric hypomotility | 4 | 4 | 0 |
| Fulminant type 1 diabetes mellitus | 3 | 4 | 1 | | Gastric infection | 3 | 3 | 0 |
| Functional gastrointestinal disorder | 3 | 3 | 0 | | Gastric mucosal lesion | 4 | 4 | 0 |
| Fundoscopy abnormal | 4 | 4 | 0 | | Gastric perforation | 4 | 3 | 1 |
| Fungaemia | 4 | 4 | 0 | | Gastric pH decreased | 4 | 4 | 0 |
| Fungal infection | 3 | 3 | 0 | | Gastric polyps | 4 | 4 | 0 |
| Fungal oesophagitis | 3 | 4 | 1 | | Gastric ulcer | 3 | 3 | 0 |
| Fungal skin infection | 3 | 3 | 0 | | Gastric ulcer haemorrhage | 3 | 3 | 0 |
| Fungal test positive | 4 | 4 | 0 | | Gastric ulcer perforation | 4 | 4 | 0 |
| Furuncle | 3 | 3 | 0 | | Gastric volvulus | 4 | 4 | 0 |
| Fusarium infection | 4 | 4 | 0 | | Gastritis | 3 | 3 | 0 |
| Gait disturbance | 3 | 3 | 0 | | Gastritis erosive | 4 | 3 | 1 |
| Gait inability | 3 | 3 | 0 | | Gastritis haemorrhagic | 4 | 4 | 0 |
| Galactorrhoea | 3 | 4 | 1 | | Gastroduodenal ulcer | 4 | 4 | 0 |
| Gallbladder cancer | 4 | 4 | 0 | | Gastroduodenitis | 4 | 4 | 0 |
| Gallbladder cancer metastatic | 4 | 4 | 0 | | Gastroenteritis | 3 | 3 | 0 |
| Gallbladder cancer stage III | 4 | 4 | 0 | | Gastroenteritis clostridial | 4 | 4 | 0 |
| Gallbladder cancer stage IV | 4 | 4 | 0 | | Gastroenteritis eosinophilic | 4 | 4 | 0 |
| Gallbladder disorder | 3 | 3 | 0 | | Gastroenteritis Escherichia coli | 4 | 4 | 0 |
| Gallbladder enlargement | 4 | 4 | 0 | | Gastroenteritis norovirus | 4 | 4 | 0 |
| Gallbladder operation | 4 | 4 | 0 | | Gastroenteritis proteus | 4 | 4 | 0 |
| Gallbladder perforation | 4 | 3 | 1 | | Gastroenteritis radiation | 4 | 4 | 0 |
| Gallbladder polyp | 4 | 4 | 0 | | Gastroenteritis viral | 4 | 3 | 1 |
| Gambling | 3 | 4 | 1 | | Gastrointestinal anastomotic leak | 4 | 4 | 0 |
| Gambling disorder | 3 | 4 | 1 | | Gastrointestinal carcinoma | 4 | 4 | 0 |

[Fig. 3-25]

| | | | | | | | |
|---|---|---|---|---|---|---|---|
| Gastrointestinal complication associated with device | 4 | 3 | 1 | General physical health deterioration | 3 | 3 | 0 |
| Gastrointestinal disorder | 3 | 3 | 0 | General symptom | 4 | 4 | 0 |
| Gastrointestinal fistula | 3 | 4 | 1 | Generalised anxiety disorder | 3 | 4 | 1 |
| Gastrointestinal fungal infection | 4 | 4 | 0 | Generalised erythema | 4 | 4 | 0 |
| Gastrointestinal haemorrhage | 3 | 3 | 0 | Generalised oedema | 3 | 3 | 0 |
| Gastrointestinal hypermotility | 4 | 4 | 0 | Generalised tonic-clonic seizure | 3 | 3 | 0 |
| Gastrointestinal hypomotility | 3 | 3 | 0 | Genital abscess | 4 | 4 | 0 |
| Gastrointestinal infection | 4 | 3 | 1 | Genital burning sensation | 4 | 4 | 0 |
| Gastrointestinal inflammation | 4 | 4 | 0 | Genital discomfort | 4 | 4 | 0 |
| Gastrointestinal injury | 4 | 4 | 0 | Genital haemorrhage | 3 | 4 | 1 |
| Gastrointestinal ischaemia | 4 | 4 | 0 | Genital herpes | 4 | 4 | 0 |
| Gastrointestinal motility disorder | 3 | 3 | 0 | Genital infection | 4 | 4 | 0 |
| Gastrointestinal mucocoele | 4 | 4 | 0 | Genital infection fungal | 4 | 4 | 0 |
| Gastrointestinal mucosal disorder | 4 | 4 | 0 | Genital pain | 3 | 4 | 1 |
| Gastrointestinal necrosis | 4 | 3 | 1 | Genital paraesthesia | 4 | 4 | 0 |
| Gastrointestinal obstruction | 4 | 3 | 1 | Genital rash | 3 | 4 | 1 |
| Gastrointestinal oedema | 4 | 4 | 0 | Genito-pelvic pain/penetration disorder | 4 | 4 | 0 |
| Gastrointestinal pain | 3 | 3 | 0 | Genitourinary symptom | 4 | 4 | 0 |
| Gastrointestinal perforation | 4 | 4 | 0 | Germ cell cancer | 4 | 4 | 0 |
| Gastrointestinal polyp haemorrhage | 4 | 4 | 0 | Germ cell cancer metastatic | 4 | 4 | 0 |
| Gastrointestinal sounds abnormal | 4 | 3 | 1 | Germ cell neoplasm | 4 | 4 | 0 |
| Gastrointestinal stoma complication | 4 | 4 | 0 | Gestational diabetes | 3 | 3 | 0 |
| Gastrointestinal toxicity | 4 | 4 | 0 | Gestational hypertension | 3 | 4 | 1 |
| Gastrointestinal tube insertion | 3 | 3 | 0 | Gestational trophoblastic tumour | 4 | 4 | 0 |
| Gastrointestinal ulcer | 4 | 4 | 0 | Gilbert's syndrome | 4 | 4 | 0 |
| Gastrointestinal ulcer haemorrhage | 4 | 4 | 0 | Gingival abscess | 4 | 4 | 0 |
| Gastrointestinal viral infection | 3 | 4 | 1 | Gingival bleeding | 3 | 3 | 0 |
| Gastrointestinal wall thickening | 4 | 4 | 0 | Gingival disorder | 4 | 4 | 0 |
| Gastrooesophageal cancer | 4 | 4 | 0 | Gingival erosion | 4 | 4 | 0 |
| Gastrooesophageal reflux disease | 3 | 3 | 0 | Gingival hypertrophy | 3 | 4 | 1 |
| Gastrooesophageal sphincter insufficiency | 4 | 3 | 1 | Gingival oedema | 4 | 4 | 0 |
| Gastropleural fistula | 4 | 4 | 0 | Gingival pain | 3 | 3 | 0 |
| Gastroptosis | 4 | 4 | 0 | Gingival swelling | 3 | 4 | 1 |
| Gastrostomy | 3 | 4 | 1 | Gingival ulceration | 4 | 4 | 0 |
| Gastrostomy tube site complication | 4 | 4 | 0 | Gingivitis | 3 | 4 | 1 |
| Gaze palsy | 3 | 4 | 1 | Gingivitis ulcerative | 4 | 4 | 0 |
| Gene mutation | 4 | 4 | 0 | Glaucoma | 3 | 3 | 0 |
| General physical condition abnormal | 3 | 3 | 0 | Glaucomatous optic disc atrophy | 3 | 4 | 1 |
| | | | | Glioblastoma multiforme | 3 | 4 | 1 |

[Fig. 3-26]

| | | | | | | | |
|---|---|---|---|---|---|---|---|
| Glioma | 4 | 4 | 0 | Grimacing | 3 | 4 | 1 |
| Gliosis | 4 | 4 | 0 | Grip strength decreased | 3 | 3 | 0 |
| Globulin abnormal | 4 | 4 | 0 | Groin abscess | 4 | 4 | 0 |
| Globulins decreased | 3 | 4 | 1 | Groin infection | 4 | 4 | 0 |
| Globulins increased | 4 | 4 | 0 | Groin pain | 4 | 4 | 0 |
| Glomerular filtration rate abnormal | 4 | 4 | 0 | Gross motor delay | 4 | 4 | 0 |
| Glomerular filtration rate decreased | 3 | 3 | 0 | Growth accelerated | 3 | 4 | 1 |
| Glomerular filtration rate increased | 4 | 3 | 1 | Growth hormone deficiency | 4 | 4 | 0 |
| Glomerulonephritis | 4 | 4 | 0 | Growth retardation | 4 | 4 | 0 |
| Glomerulonephritis membranous | 4 | 4 | 0 | Grunting | 4 | 4 | 0 |
| Glossitis | 4 | 4 | 0 | Guillain-Barre syndrome | 3 | 3 | 0 |
| Glossodynia | 3 | 4 | 1 | Gun shot wound | 3 | 4 | 1 |
| Glossopharyngeal nerve disorder | 4 | 3 | 1 | Gynaecomastia | 3 | 4 | 1 |
| Glossoptosis | 3 | 4 | 1 | Haemangioma | 3 | 4 | 1 |
| Glucose tolerance impaired | 3 | 3 | 0 | Haemangioma congenital | 3 | 4 | 1 |
| Glucose tolerance increased | 4 | 4 | 0 | Haemangioma of bone | 3 | 4 | 1 |
| Glucose urine | 4 | 4 | 0 | Haemangioma of liver | 4 | 3 | 1 |
| Glucose urine present | 3 | 4 | 1 | Haemangiopericytoma | 4 | 4 | 0 |
| Glutamate dehydrogenase increased | 4 | 4 | 0 | Haemarthrosis | 3 | 4 | 1 |
| Glycosuria | 3 | 3 | 0 | Haematemesis | 3 | 3 | 0 |
| Glycosylated haemoglobin increased | 3 | 3 | 0 | Haematinuria | 4 | 4 | 0 |
| Goitre | 4 | 3 | 1 | Haematochezia | 3 | 3 | 0 |
| Gout | 4 | 4 | 0 | Haematocrit abnormal | 4 | 3 | 1 |
| Graft complication | 4 | 4 | 0 | Haematocrit decreased | 3 | 3 | 0 |
| Graft infection | 4 | 4 | 0 | Haematocrit increased | 3 | 4 | 1 |
| Graft versus host disease | 4 | 4 | 0 | Haematological malignancy | 4 | 4 | 0 |
| Graft versus host disease in gastrointestinal tract | 4 | 4 | 0 | Haematology test abnormal | 4 | 3 | 1 |
| | | | | Haematoma | 3 | 3 | 0 |
| Graft versus host disease in lung | 4 | 4 | 0 | Haematoma infection | 4 | 4 | 0 |
| Grandiosity | 3 | 4 | 1 | Haematopoietic neoplasm | 4 | 4 | 0 |
| Granulocyte count | 4 | 4 | 0 | Haematopoietic stem cell mobilisation | 4 | 4 | 0 |
| Granulocyte count decreased | 4 | 4 | 0 | | | | |
| Granulocyte count increased | 4 | 4 | 0 | Haematotoxicity | 4 | 3 | 1 |
| Granulocytes abnormal | 4 | 3 | 1 | Haematuria | 3 | 3 | 0 |
| Granulocytopenia | 3 | 3 | 0 | Haemoconcentration | 4 | 4 | 0 |
| Granulocytosis | 4 | 4 | 0 | Haemodialysis | 3 | 3 | 0 |
| Granuloma | 4 | 3 | 1 | Haemodialysis complication | 4 | 4 | 0 |
| Granuloma annulare | 3 | 4 | 1 | Haemodynamic instability | 4 | 3 | 1 |
| Granuloma skin | 4 | 4 | 0 | Haemofiltration | 3 | 4 | 1 |
| Granulomatous pneumonitis | 4 | 4 | 0 | Haemoglobin | 4 | 4 | 0 |

[Fig. 3-27]

| | | | | | | | |
|---|---|---|---|---|---|---|---|
| Haemoglobin abnormal | 3 | 3 | 0 | Hand-foot-and-mouth disease | 4 | 4 | 0 |
| Haemoglobin decreased | 3 | 3 | 0 | Hand fracture | 3 | 3 | 0 |
| Haemoglobin increased | 3 | 3 | 0 | Hangover | 3 | 4 | 1 |
| Haemoglobin urine present | 3 | 4 | 1 | Haptoglobin decreased | 4 | 4 | 0 |
| Haemolysis | 3 | 4 | 1 | Hashimoto's encephalopathy | 4 | 4 | 0 |
| Haemolytic anaemia | 3 | 4 | 1 | Head and neck cancer | 3 | 3 | 0 |
| Haemolytic icteroanaemia | 4 | 4 | 0 | Head and neck cancer metastatic | 4 | 4 | 0 |
| Haemolytic uraemic syndrome | 4 | 4 | 0 | Head circumference abnormal | 4 | 4 | 0 |
| Haemophilia | 4 | 4 | 0 | Head discomfort | 3 | 3 | 0 |
| Haemophilus infection | 3 | 4 | 1 | Head injury | 3 | 3 | 0 |
| Haemoptysis | 3 | 3 | 0 | Head titubation | 4 | 4 | 0 |
| Haemorrhage | 3 | 3 | 0 | Hearing aid user | 4 | 4 | 0 |
| Haemorrhage in pregnancy | 3 | 4 | 1 | Hearing impaired | 4 | 4 | 0 |
| Haemorrhage intracranial | 4 | 4 | 0 | Heart block congenital | 3 | 4 | 1 |
| Haemorrhage subcutaneous | 4 | 4 | 0 | Heart disease congenital | 4 | 4 | 0 |
| Haemorrhage urinary tract | 3 | 4 | 1 | Heart injury | 4 | 4 | 0 |
| Haemorrhagic anaemia | 3 | 3 | 0 | Heart rate abnormal | 3 | 4 | 1 |
| Haemorrhagic diathesis | 4 | 4 | 0 | Heart rate decreased | 3 | 3 | 0 |
| Haemorrhagic disorder | 4 | 4 | 0 | Heart rate increased | 3 | 3 | 0 |
| Haemorrhagic fever with renal syndrome | 4 | 4 | 0 | Heart rate irregular | 3 | 3 | 0 |
| | | | | Heart sounds abnormal | 3 | 4 | 1 |
| Haemorrhagic stroke | 4 | 4 | 0 | Heart valve incompetence | 3 | 4 | 1 |
| Haemorrhagic transformation stroke | 4 | 4 | 0 | Heat exhaustion | 3 | 4 | 1 |
| Haemorrhagic tumour necrosis | 4 | 4 | 0 | Heat stroke | 3 | 3 | 0 |
| Haemorrhagic vasculitis | 4 | 4 | 0 | Helicobacter gastritis | 4 | 4 | 0 |
| Haemorrhoid operation | 3 | 4 | 1 | Helicobacter test positive | 3 | 4 | 1 |
| Haemorrhoidal haemorrhage | 4 | 4 | 0 | HELLP syndrome | 3 | 4 | 1 |
| Haemorrhoids | 4 | 3 | 1 | Helplessness | 3 | 4 | 1 |
| Haemothorax | 4 | 4 | 0 | Hemianopia | 4 | 4 | 0 |
| Hair colour changes | 4 | 3 | 1 | Hemianopia homonymous | 4 | 4 | 0 |
| Hair disorder | 4 | 4 | 0 | Hemiparesis | 3 | 3 | 0 |
| Hair follicle tumour benign | 4 | 4 | 0 | Hemiplegia | 3 | 4 | 1 |
| Hair growth abnormal | 3 | 4 | 1 | Hemivertebra | 3 | 4 | 1 |
| Hair injury | 4 | 4 | 0 | Henoch-Schonlein purpura | 3 | 4 | 1 |
| Hair texture abnormal | 3 | 3 | 0 | Heparin-induced thrombocytopenia | 4 | 4 | 0 |
| Hallucination | 3 | 3 | 0 | Hepatectomy | 4 | 4 | 0 |
| Hallucination, auditory | 3 | 4 | 1 | Hepatic angiosarcoma | 4 | 4 | 0 |
| Hallucination, tactile | 3 | 4 | 1 | Hepatic artery thrombosis | 4 | 4 | 0 |
| Hallucination, visual | 3 | 3 | 0 | Hepatic cancer | 4 | 3 | 1 |
| Hallucinations, mixed | 3 | 3 | 0 | Hepatic cancer metastatic | 4 | 4 | 0 |

[Fig. 3-28]

| | | | | | | | |
|---|---|---|---|---|---|---|---|
| Hepatic candidiasis | 4 | 4 | 0 | Hepatocellular injury | 3 | 4 | 1 |
| Hepatic cirrhosis | 3 | 3 | 0 | Hepatomegaly | 3 | 3 | 0 |
| Hepatic congestion | 3 | 4 | 1 | Hepatorenal failure | 4 | 4 | 0 |
| Hepatic cyst | 4 | 3 | 1 | Hepatorenal syndrome | 4 | 4 | 0 |
| Hepatic encephalopathy | 3 | 3 | 0 | Hepatosplenic candidiasis | 4 | 4 | 0 |
| Hepatic enzyme abnormal | 4 | 4 | 0 | Hepatosplenomegaly | 4 | 4 | 0 |
| Hepatic failure | 3 | 3 | 0 | Hepatotoxicity | 3 | 3 | 0 |
| Hepatic fibrosis | 3 | 3 | 0 | Hereditary angioedema | 4 | 4 | 0 |
| Hepatic haematoma | 4 | 4 | 0 | Hernia | 3 | 4 | 1 |
| Hepatic haemorrhage | 4 | 4 | 0 | Hernia obstructive | 3 | 4 | 1 |
| Hepatic infarction | 4 | 4 | 0 | Hernia repair | 3 | 4 | 1 |
| Hepatic lesion | 4 | 4 | 0 | Herpes ophthalmic | 4 | 4 | 0 |
| Hepatic mass | 4 | 4 | 0 | Herpes simplex | 3 | 3 | 0 |
| Hepatic necrosis | 4 | 3 | 1 | Herpes simplex DNA test positive | 4 | 4 | 0 |
| Hepatic neoplasm | 4 | 4 | 0 | Herpes simplex encephalitis | 4 | 4 | 0 |
| Hepatic pain | 3 | 4 | 1 | Herpes simplex oesophagitis | 4 | 4 | 0 |
| Hepatic rupture | 3 | 4 | 1 | Herpes virus infection | 4 | 4 | 0 |
| Hepatic steatosis | 3 | 3 | 0 | Herpes zoster | 3 | 3 | 0 |
| Hepatic vein occlusion | 4 | 4 | 0 | Herpes zoster disseminated | 4 | 4 | 0 |
| Hepatic vein thrombosis | 4 | 4 | 0 | Herpes zoster meningoencephalitis | 4 | 4 | 0 |
| Hepatitis | 4 | 3 | 1 | Hiatus hernia | 3 | 3 | 0 |
| Hepatitis A antibody | 4 | 4 | 0 | Hiccups | 3 | 3 | 0 |
| Hepatitis A virus test positive | 4 | 4 | 0 | Hidradenitis | 3 | 4 | 1 |
| Hepatitis acute | 4 | 3 | 1 | High arched palate | 3 | 4 | 1 |
| Hepatitis B | 3 | 3 | 0 | High density lipoprotein abnormal | 3 | 4 | 1 |
| Hepatitis B DNA increased | 4 | 4 | 0 | High density lipoprotein decreased | 3 | 4 | 1 |
| Hepatitis B reactivation | 4 | 4 | 0 | High density lipoprotein increased | 4 | 4 | 0 |
| Hepatitis B surface antigen | 4 | 4 | 0 | Hilar lymphadenopathy | 4 | 4 | 0 |
| Hepatitis B virus test positive | 3 | 4 | 1 | Hip arthroplasty | 3 | 4 | 1 |
| Hepatitis C | 3 | 3 | 0 | Hip fracture | 3 | 3 | 0 |
| Hepatitis cholestatic | 4 | 3 | 1 | Hip surgery | 3 | 4 | 1 |
| Hepatitis E | 4 | 4 | 0 | Hirsutism | 4 | 4 | 0 |
| Hepatitis fulminant | 4 | 4 | 0 | Histiocytic necrotising lymphadenitis | 4 | 4 | 0 |
| Hepatitis toxic | 3 | 4 | 1 | Histiocytosis haematophagic | 4 | 4 | 0 |
| Hepatitis viral | 4 | 3 | 1 | Histoplasmosis | 4 | 4 | 0 |
| Hepato-lenticular degeneration | 4 | 4 | 0 | Histoplasmosis disseminated | 4 | 4 | 0 |
| Hepatobiliary cancer | 4 | 4 | 0 | Hodgkin's disease | 3 | 3 | 0 |
| Hepatobiliary disease | 4 | 4 | 0 | Hodgkin's disease recurrent | 4 | 4 | 0 |
| Hepatoblastoma recurrent | 4 | 4 | 0 | Hodgkin's disease stage III | 4 | 4 | 0 |
| Hepatocellular carcinoma | 4 | 4 | 0 | Homicidal ideation | 3 | 4 | 1 |

[Fig. 3-29]

| | | | | | | | |
|---|---|---|---|---|---|---|---|
| Homicide | 4 | 4 | 0 | Hypercholesterolaemia | 3 | 3 | 0 |
| Homosexuality | 3 | 4 | 1 | Hypercoagulation | 4 | 4 | 0 |
| Hormone level abnormal | 3 | 4 | 1 | Hypercreatininaemia | 4 | 4 | 0 |
| Hormone replacement therapy | 3 | 4 | 1 | Hyperdynamic left ventricle | 4 | 4 | 0 |
| Horner's syndrome | 4 | 4 | 0 | Hyperemesis gravidarum | 3 | 4 | 1 |
| Hospice care | 4 | 4 | 0 | Hypereosinophilic syndrome | 4 | 4 | 0 |
| Hospitalisation | 3 | 4 | 1 | Hyperferritinaemia | 4 | 4 | 0 |
| Hostility | 3 | 3 | 0 | Hypergammaglobulinaemia | 4 | 4 | 0 |
| Hot flush | 3 | 3 | 0 | Hypergammaglobulinaemia benign monoclonal | 4 | 4 | 0 |
| Human chorionic gonadotropin decreased | 4 | 4 | 0 | Hyperglobulinaemia | 4 | 4 | 0 |
| Human chorionic gonadotropin increased | 4 | 4 | 0 | Hyperglycaemia | 3 | 3 | 0 |
| | | | | Hyperglycaemic hyperosmolar nonketotic syndrome | 4 | 4 | 0 |
| Human herpesvirus 6 infection | 4 | 4 | 0 | | | | |
| Human herpesvirus 8 infection | 4 | 4 | 0 | Hyperglycaemic seizure | 3 | 4 | 1 |
| Human rhinovirus test | 4 | 4 | 0 | Hyperkalaemia | 3 | 3 | 0 |
| Humerus fracture | 4 | 3 | 1 | Hyperkeratosis | 4 | 4 | 0 |
| Hunger | 3 | 4 | 1 | Hyperkinesia | 3 | 3 | 0 |
| Hungry bone syndrome | 4 | 4 | 0 | Hyperlactacidaemia | 4 | 4 | 0 |
| Huntington's disease | 4 | 4 | 0 | Hyperleukocytosis | 4 | 3 | 1 |
| Hydrocele | 4 | 4 | 0 | Hyperlipidaemia | 3 | 3 | 0 |
| Hydrocephalus | 3 | 3 | 0 | Hypermagnesaemia | 4 | 4 | 0 |
| Hydronephrosis | 3 | 3 | 0 | Hypermetropia | 4 | 4 | 0 |
| Hydroureter | 4 | 4 | 0 | Hypernatraemia | 3 | 3 | 0 |
| Hyperactive pharyngeal reflex | 4 | 4 | 0 | Hyperosmolar hyperglycaemic state | 3 | 4 | 1 |
| Hyperacusis | 3 | 4 | 1 | Hyperosmolar state | 3 | 3 | 0 |
| Hyperadrenalism | 4 | 4 | 0 | Hyperparathyroidism | 4 | 4 | 0 |
| Hyperadrenocorticism | 4 | 4 | 0 | Hyperparathyroidism secondary | 4 | 4 | 0 |
| Hyperaemia | 4 | 4 | 0 | Hyperphagia | 3 | 4 | 1 |
| Hyperaesthesia | 3 | 4 | 1 | Hyperphosphataemia | 4 | 4 | 0 |
| Hyperaldosteronism | 4 | 4 | 0 | Hyperplasia | 4 | 4 | 0 |
| Hyperammonaemia | 3 | 3 | 0 | Hyperprolactinaemia | 3 | 4 | 1 |
| Hyperammonaemic encephalopathy | 3 | 3 | 0 | Hyperpyrexia | 3 | 3 | 0 |
| Hyperbilirubinaemia | 3 | 4 | 1 | Hyperreflexia | 3 | 3 | 0 |
| Hyperbilirubinaemia neonatal | 3 | 3 | 0 | Hypersensitivity | 3 | 3 | 0 |
| Hypercalcaemia | 3 | 3 | 0 | Hypersensitivity vasculitis | 3 | 3 | 0 |
| Hypercalcaemia of malignancy | 4 | 4 | 0 | Hypersexuality | 3 | 4 | 1 |
| Hypercapnia | 4 | 3 | 1 | Hypersomnia | 3 | 3 | 0 |
| Hyperchloraemia | 4 | 4 | 0 | Hypersplenism | 3 | 4 | 1 |
| Hyperchlorhydria | 4 | 4 | 0 | Hypertensive crisis | 3 | 3 | 0 |

[Fig. 3-30]

| | | | | | | | |
|---|---|---|---|---|---|---|---|
| Hypertensive heart disease | 4 | 3 | 1 | Hypophosphatasia | 4 | 4 | 0 |
| Hypertensive nephropathy | 4 | 4 | 0 | Hypophysitis | 4 | 4 | 0 |
| Hyperthermia | 3 | 3 | 0 | Hypopituitarism | 4 | 3 | 1 |
| Hyperthermia malignant | 3 | 4 | 1 | Hypopnoea | 4 | 3 | 1 |
| Hyperthyroidism | 3 | 3 | 0 | Hypoproteinaemia | 4 | 4 | 0 |
| Hypertonia | 3 | 4 | 1 | Hyporeflexia | 4 | 3 | 1 |
| Hypertonic bladder | 3 | 4 | 1 | Hyporesponsive to stimuli | 3 | 4 | 1 |
| Hypertransaminasaemia | 3 | 4 | 1 | Hyposideraemia | 4 | 4 | 0 |
| Hypertriglyceridaemia | 3 | 3 | 0 | Hypospadias | 3 | 4 | 1 |
| Hypertrophic cardiomyopathy | 4 | 4 | 0 | Hypothalamo-pituitary disorder | 3 | 4 | 1 |
| Hypertrophy | 3 | 3 | 0 | Hypothermia | 3 | 3 | 0 |
| Hyperuricaemia | 4 | 3 | 1 | Hypothyroidism | 3 | 3 | 0 |
| Hyperventilation | 3 | 4 | 1 | Hypotonia | 3 | 3 | 0 |
| Hypoacusis | 3 | 3 | 0 | Hypotonia neonatal | 3 | 4 | 1 |
| Hypoaesthesia | 3 | 3 | 0 | Hypouricaemia | 4 | 4 | 0 |
| Hypoaesthesia oral | 3 | 3 | 0 | Hypoventilation | 3 | 3 | 0 |
| Hypoaesthesia teeth | 4 | 4 | 0 | Hypovitaminosis | 4 | 4 | 0 |
| Hypoalbuminaemia | 3 | 3 | 0 | Hypovolaemia | 4 | 3 | 1 |
| Hypoaldosteronism | 4 | 4 | 0 | Hypovolaemic shock | 3 | 3 | 0 |
| Hypocalcaemia | 3 | 3 | 0 | Hypoxia | 3 | 3 | 0 |
| Hypocarnitinaemia | 3 | 4 | 1 | Hypoxic-ischaemic encephalopathy | 3 | 3 | 0 |
| Hypochloraemia | 4 | 3 | 1 | Hysterectomy | 3 | 3 | 0 |
| Hypofibrinogenaemia | 4 | 4 | 0 | Iatrogenic injury | 3 | 3 | 0 |
| Hypogammaglobulinaemia | 3 | 3 | 0 | Ideas of reference | 3 | 4 | 1 |
| Hypogeusia | 4 | 4 | 0 | Idiosyncratic drug reaction | 4 | 4 | 0 |
| Hypoglycaemia | 3 | 3 | 0 | IgA nephropathy | 4 | 4 | 0 |
| Hypoglycaemia neonatal | 3 | 4 | 1 | IIIrd nerve paralysis | 4 | 4 | 0 |
| Hypoglycaemic coma | 4 | 4 | 0 | Ileectomy | 4 | 4 | 0 |
| Hypokalaemia | 3 | 3 | 0 | Ileostomy | 4 | 4 | 0 |
| Hypokinesia | 3 | 3 | 0 | Ileostomy closure | 4 | 4 | 0 |
| Hypomagnesaemia | 3 | 4 | 1 | Ileus | 3 | 3 | 0 |
| Hypomania | 3 | 4 | 1 | Ileus paralytic | 3 | 3 | 0 |
| Hypomenorrhoea | 3 | 4 | 1 | Iliac artery occlusion | 4 | 4 | 0 |
| Hyponatraemia | 3 | 3 | 0 | Ill-defined disorder | 3 | 4 | 1 |
| Hyponatraemic coma | 4 | 4 | 0 | Illness anxiety disorder | 4 | 4 | 0 |
| Hyponatraemic seizure | 4 | 4 | 0 | Illogical thinking | 4 | 4 | 0 |
| Hypoparathyroidism | 4 | 4 | 0 | Illusion | 3 | 4 | 1 |
| Hypoperfusion | 3 | 4 | 1 | Immobile | 3 | 3 | 0 |
| Hypophagia | 3 | 3 | 0 | Immobilisation prolonged | 4 | 4 | 0 |
| Hypophosphataemia | 3 | 4 | 1 | | | | |

[Fig. 3-31]

| | | | | | | | | |
|---|---|---|---|---|---|---|---|---|
| Immune reconstitution inflammatory syndrome | 4 | 4 | 0 | Inappropriate schedule of drug administration | 3 | 3 | 0 |
| Immune system disorder | 4 | 4 | 0 | Incarcerated umbilical hernia | 4 | 4 | 0 |
| Immune thrombocytopenic purpura | 3 | 4 | 1 | Incision site cellulitis | 4 | 4 | 0 |
| Immunoblastic lymphoma | 4 | 4 | 0 | Incisional hernia | 4 | 4 | 0 |
| Immunodeficiency | 3 | 4 | 1 | Incoherent | 3 | 3 | 0 |
| Immunodeficiency congenital | 4 | 4 | 0 | Incontinence | 3 | 3 | 0 |
| Immunoglobulins decreased | 4 | 3 | 1 | Incorrect dosage administered | 4 | 4 | 0 |
| Immunosuppressant drug level decreased | 4 | 4 | 0 | Incorrect dose administered | 3 | 3 | 0 |
| Immunosuppressant drug level increased | 3 | 4 | 1 | Incorrect drug administration duration | 3 | 3 | 0 |
| Immunosuppression | 4 | 3 | 1 | Incorrect drug administration rate | 4 | 4 | 0 |
| Impaired driving ability | 3 | 3 | 0 | Incorrect product storage | 4 | 3 | 1 |
| Impaired fasting glucose | 4 | 4 | 0 | Incorrect route of drug administration | 3 | 3 | 0 |
| Impaired gastric emptying | 4 | 3 | 1 | Increased appetite | 3 | 3 | 0 |
| Impaired healing | 3 | 3 | 0 | Increased bronchial secretion | 4 | 3 | 1 |
| Impaired insulin secretion | 3 | 4 | 1 | Increased upper airway secretion | 4 | 4 | 0 |
| Impaired quality of life | 3 | 4 | 1 | Increased viscosity of bronchial secretion | 4 | 4 | 0 |
| Impaired self-care | 3 | 3 | 0 | Increased viscosity of upper respiratory secretion | 4 | 4 | 0 |
| Impaired work ability | 3 | 4 | 1 | | | | |
| Impatience | 3 | 4 | 1 | Indifference | 3 | 4 | 1 |
| Imperforate hymen | 3 | 4 | 1 | Induced labour | 3 | 4 | 1 |
| Implant site extravasation | 3 | 4 | 1 | Induration | 4 | 4 | 0 |
| Implant site infection | 3 | 4 | 1 | Infantile apnoea | 3 | 4 | 1 |
| Implant site pain | 3 | 4 | 1 | Infantile haemangioma | 3 | 4 | 1 |
| Implant site pruritus | 3 | 4 | 1 | Infantile vomiting | 3 | 4 | 1 |
| Implant site swelling | 3 | 4 | 1 | Infarction | 3 | 4 | 1 |
| Implantable defibrillator insertion | 4 | 4 | 0 | Infected bite | 3 | 4 | 1 |
| Imprisonment | 3 | 4 | 1 | Infected dermal cyst | 4 | 4 | 0 |
| Impulse-control disorder | 3 | 4 | 1 | Infected fistula | 3 | 4 | 1 |
| Impulsive behaviour | 3 | 3 | 0 | Infected lymphocele | 4 | 4 | 0 |
| In vitro fertilisation | 3 | 4 | 1 | Infected seroma | 3 | 4 | 1 |
| Inability to afford medication | 3 | 4 | 1 | Infected skin ulcer | 4 | 4 | 0 |
| Inadequate analgesia | 4 | 4 | 0 | Infection | 3 | 3 | 0 |
| Inadequate diet | 4 | 3 | 1 | Infection reactivation | 4 | 4 | 0 |
| Inappropriate affect | 3 | 4 | 1 | Infectious colitis | 3 | 4 | 1 |
| Inappropriate antidiuretic hormone secretion | 3 | 3 | 0 | Infectious pleural effusion | 4 | 3 | 1 |
| | | | | Infective aortitis | 4 | 4 | 0 |

[Fig. 3-32]

| | | | | | | | |
|---|---|---|---|---|---|---|---|
| Infective exacerbation of chronic obstructive airways disease | 4 | 4 | 0 | Injection site haemorrhage | 3 | 3 | 0 |
| Infective myositis | 4 | 4 | 0 | Injection site hypoaesthesia | 3 | 4 | 1 |
| Infective pulmonary exacerbation of cystic fibrosis | 3 | 4 | 1 | Injection site induration | 4 | 4 | 0 |
| | | | | Injection site injury | 4 | 4 | 0 |
| | | | | Injection site irritation | 4 | 4 | 0 |
| Infective spondylitis | 4 | 4 | 0 | Injection site mass | 3 | 4 | 1 |
| Infertility female | 4 | 4 | 0 | Injection site necrosis | 3 | 4 | 1 |
| Infestation | 4 | 4 | 0 | Injection site nodule | 4 | 4 | 0 |
| Inflammation | 3 | 3 | 0 | Injection site paraesthesia | 4 | 4 | 0 |
| Inflammatory bowel disease | 3 | 4 | 1 | Injection site phlebitis | 4 | 4 | 0 |
| Inflammatory marker increased | 4 | 3 | 1 | Injection site pruritus | 3 | 3 | 0 |
| Inflammatory pseudotumour | 4 | 4 | 0 | Injection site pustule | 4 | 4 | 0 |
| Influenza | 3 | 3 | 0 | Injection site rash | 3 | 4 | 1 |
| Influenza A virus test positive | 4 | 3 | 1 | Injection site reaction | 3 | 4 | 1 |
| Influenza B virus test positive | 4 | 4 | 0 | Injection site scar | 4 | 4 | 0 |
| Influenza immunisation | 3 | 4 | 1 | Injection site streaking | 4 | 4 | 0 |
| Infrequent bowel movements | 4 | 4 | 0 | Injection site swelling | 3 | 3 | 0 |
| Infusion related reaction | 4 | 4 | 0 | Injection site urticaria | 3 | 4 | 1 |
| Infusion site discolouration | 4 | 4 | 0 | Injection site vesicles | 4 | 4 | 0 |
| Infusion site erythema | 4 | 4 | 0 | Injection site warmth | 4 | 4 | 0 |
| Infusion site extravasation | 4 | 4 | 0 | Injury | 3 | 3 | 0 |
| Infusion site haematoma | 4 | 4 | 0 | Injury associated with device | 3 | 4 | 1 |
| Infusion site necrosis | 4 | 4 | 0 | Inspiratory capacity decreased | 3 | 4 | 1 |
| Infusion site pain | 4 | 4 | 0 | Insulin resistance | 3 | 4 | 1 |
| Infusion site phlebitis | 4 | 4 | 0 | Insulin resistant diabetes | 4 | 4 | 0 |
| Infusion site pruritus | 3 | 4 | 1 | Insulinoma | 4 | 4 | 0 |
| Infusion site reaction | 4 | 4 | 0 | Intellectual disability | 3 | 3 | 0 |
| Infusion site swelling | 4 | 4 | 0 | Intensive care | 4 | 4 | 0 |
| Ingrowing nail | 3 | 4 | 1 | Intention tremor | 4 | 4 | 0 |
| Inguinal hernia | 3 | 4 | 1 | Intentional device misuse | 4 | 4 | 0 |
| Inhibitory drug interaction | 3 | 4 | 1 | Intentional dose omission | 4 | 4 | 0 |
| Initial insomnia | 3 | 3 | 0 | Intentional overdose | 3 | 4 | 1 |
| Injection related reaction | 4 | 4 | 0 | Intentional product misuse | 3 | 3 | 0 |
| Injection site bruising | 3 | 3 | 0 | Intentional product use issue | 3 | 3 | 0 |
| Injection site dermatitis | 4 | 4 | 0 | Intentional self-injury | 3 | 4 | 1 |
| Injection site discolouration | 3 | 3 | 0 | Intentional underdose | 4 | 4 | 0 |
| Injection site discomfort | 4 | 4 | 0 | Intercepted drug dispensing error | 4 | 4 | 0 |
| Injection site erythema | 3 | 3 | 0 | Intercepted medication error | 4 | 4 | 0 |
| Injection site extravasation | 3 | 4 | 1 | Intercepted product selection error | 4 | 4 | 0 |
| Injection site haematoma | 3 | 4 | 1 | Intermittent claudication | 4 | 4 | 0 |

[Fig. 3-33]

| | | | |
|---|---|---|---|
| Internal haemorrhage | 3 | 4 | 1 |
| Internal hernia | 4 | 4 | 0 |
| International normalised ratio abnormal | 3 | 3 | 0 |
| International normalised ratio decreased | 4 | 4 | 0 |
| International normalised ratio increased | 3 | 3 | 0 |
| Intervertebral disc compression | 3 | 4 | 1 |
| Intervertebral disc degeneration | 3 | 3 | 0 |
| Intervertebral disc disorder | 3 | 4 | 1 |
| Intervertebral disc operation | 3 | 4 | 1 |
| Intervertebral disc protrusion | 3 | 4 | 1 |
| Intervertebral disc space narrowing | 3 | 4 | 1 |
| Intervertebral discitis | 4 | 4 | 0 |
| Intestinal atresia | 3 | 4 | 1 |
| Intestinal dilatation | 3 | 3 | 0 |
| Intestinal fistula | 4 | 3 | 1 |
| Intestinal haematoma | 4 | 4 | 0 |
| Intestinal haemorrhage | 4 | 3 | 1 |
| Intestinal infarction | 4 | 3 | 1 |
| Intestinal ischaemia | 3 | 3 | 0 |
| Intestinal mass | 3 | 4 | 1 |
| Intestinal obstruction | 3 | 3 | 0 |
| Intestinal operation | 3 | 4 | 1 |
| Intestinal perforation | 3 | 3 | 0 |
| Intestinal polyp | 4 | 4 | 0 |
| Intestinal polypectomy | 4 | 4 | 0 |
| Intestinal pseudo-obstruction | 3 | 4 | 1 |
| Intestinal resection | 4 | 4 | 0 |
| Intestinal transit time increased | 4 | 4 | 0 |
| Intestinal tuberculosis | 4 | 4 | 0 |
| Intestinal ulcer | 4 | 4 | 0 |
| Intestinal villi atrophy | 4 | 4 | 0 |
| Intra-abdominal haemorrhage | 4 | 4 | 0 |
| Intra-abdominal pressure increased | 4 | 4 | 0 |
| Intracardiac thrombus | 3 | 3 | 0 |
| Intracranial aneurysm | 3 | 4 | 1 |
| Intracranial germ cell tumour | 4 | 4 | 0 |
| Intracranial haematoma | 3 | 4 | 1 |

| | | | |
|---|---|---|---|
| Intracranial pressure increased | 3 | 4 | 1 |
| Intracranial tumour haemorrhage | 4 | 4 | 0 |
| Intracranial venous sinus thrombosis | 4 | 4 | 0 |
| Intraductal papillary mucinous neoplasm | 4 | 4 | 0 |
| Intraductal papilloma of breast | 4 | 4 | 0 |
| Intraductal proliferative breast lesion | 4 | 4 | 0 |
| Intraocular melanoma | 4 | 4 | 0 |
| Intraocular pressure increased | 4 | 4 | 0 |
| Intravascular haemolysis | 4 | 4 | 0 |
| Intrusive thoughts | 3 | 4 | 1 |
| Intussusception | 4 | 4 | 0 |
| Invasive breast carcinoma | 4 | 4 | 0 |
| Invasive ductal breast carcinoma | 3 | 3 | 0 |
| Invasive lobular breast carcinoma | 4 | 4 | 0 |
| Invasive papillary breast carcinoma | 4 | 4 | 0 |
| Investigation | 3 | 4 | 1 |
| Investigation abnormal | 4 | 4 | 0 |
| Iridocyclitis | 4 | 4 | 0 |
| Iris adhesions | 4 | 4 | 0 |
| Iris coloboma | 3 | 4 | 1 |
| Iritis | 4 | 4 | 0 |
| Iron binding capacity total decreased | 4 | 4 | 0 |
| Iron deficiency | 4 | 3 | 1 |
| Iron deficiency anaemia | 3 | 3 | 0 |
| Irregular breathing | 3 | 4 | 1 |
| Irritability | 3 | 3 | 0 |
| Irritable bowel syndrome | 3 | 4 | 1 |
| Ischaemia | 3 | 3 | 0 |
| Ischaemic cardiomyopathy | 4 | 3 | 1 |
| Ischaemic cerebral infarction | 4 | 4 | 0 |
| Ischaemic hepatitis | 4 | 3 | 1 |
| Ischaemic limb pain | 4 | 4 | 0 |
| Ischaemic stroke | 3 | 3 | 0 |
| Jaundice | 3 | 3 | 0 |
| Jaundice cholestatic | 4 | 4 | 0 |
| Jaundice neonatal | 3 | 4 | 1 |
| Jaw disorder | 3 | 4 | 1 |
| Jaw fracture | 4 | 4 | 0 |
| JC virus test positive | 4 | 4 | 0 |

[Fig. 3-34]

| | | | |
|---|---|---|---|
| Jejunal perforation | 4 | 3 | 1 |
| Jejunal ulcer | 4 | 4 | 0 |
| Job dissatisfaction | 4 | 4 | 0 |
| Joint ankylosis | 3 | 4 | 1 |
| Joint crepitation | 4 | 4 | 0 |
| Joint deposit | 4 | 4 | 0 |
| Joint dislocation | 3 | 3 | 0 |
| Joint effusion | 3 | 4 | 1 |
| Joint hyperextension | 3 | 4 | 1 |
| Joint injury | 3 | 3 | 0 |
| Joint range of motion decreased | 3 | 4 | 1 |
| Joint stiffness | 3 | 3 | 0 |
| Joint swelling | 3 | 3 | 0 |
| Judgement impaired | 3 | 4 | 1 |
| Jugular vein occlusion | 4 | 4 | 0 |
| Jugular vein thrombosis | 4 | 4 | 0 |
| Juvenile chronic myelomonocytic leukaemia | 4 | 4 | 0 |
| Kaposi's sarcoma | 4 | 4 | 0 |
| Keratitis | 3 | 4 | 1 |
| Keratoconus | 3 | 4 | 1 |
| Kernicterus | 4 | 4 | 0 |
| Ketoacidosis | 3 | 3 | 0 |
| Ketonuria | 4 | 3 | 1 |
| Ketosis | 4 | 3 | 1 |
| Ketosis-prone diabetes mellitus | 3 | 4 | 1 |
| Kidney duplex | 4 | 4 | 0 |
| Kidney fibrosis | 3 | 3 | 0 |
| Kidney infection | 3 | 3 | 0 |
| Kidney malformation | 3 | 4 | 1 |
| Kidney rupture | 4 | 4 | 0 |
| Klebsiella bacteraemia | 4 | 4 | 0 |
| Klebsiella infection | 4 | 3 | 1 |
| Klebsiella sepsis | 4 | 4 | 0 |
| Klebsiella test positive | 4 | 4 | 0 |
| Kleptomania | 3 | 4 | 1 |
| Klinefelter's syndrome | 4 | 4 | 0 |
| Knee arthroplasty | 3 | 4 | 1 |
| Knee operation | 3 | 4 | 1 |
| Kussmaul respiration | 4 | 4 | 0 |

| | | | |
|---|---|---|---|
| Kyphosis | 4 | 4 | 0 |
| Labelled drug-disease interaction medication error | 4 | 4 | 0 |
| Labelled drug-drug interaction medication error | 3 | 3 | 0 |
| Labile blood pressure | 4 | 4 | 0 |
| Laboratory test abnormal | 3 | 3 | 0 |
| Laboratory test interference | 3 | 4 | 1 |
| Laboratory test normal | 4 | 4 | 0 |
| Labyrinthitis | 3 | 4 | 1 |
| Laceration | 3 | 3 | 0 |
| Lack of spontaneous speech | 4 | 4 | 0 |
| Lacrimation increased | 3 | 4 | 1 |
| Lactation disorder | 3 | 4 | 1 |
| Lactic acidosis | 3 | 3 | 0 |
| Lactobacillus infection | 4 | 3 | 1 |
| Lacunar infarction | 4 | 3 | 1 |
| Langerhans' cell histiocytosis | 4 | 4 | 0 |
| Language disorder | 3 | 3 | 0 |
| Large cell lung cancer stage IV | 4 | 4 | 0 |
| Large for dates baby | 3 | 4 | 1 |
| Large intestinal haemorrhage | 4 | 4 | 0 |
| Large intestinal obstruction | 4 | 3 | 1 |
| Large intestinal stenosis | 4 | 4 | 0 |
| Large intestinal ulcer | 4 | 4 | 0 |
| Large intestinal ulcer perforation | 4 | 4 | 0 |
| Large intestine perforation | 3 | 3 | 0 |
| Large intestine polyp | 3 | 4 | 1 |
| Laryngeal cancer | 4 | 3 | 1 |
| Laryngeal cancer stage 0 | 4 | 4 | 0 |
| Laryngeal cancer stage IV | 4 | 4 | 0 |
| Laryngeal disorder | 4 | 4 | 0 |
| Laryngeal necrosis | 4 | 4 | 0 |
| Laryngeal oedema | 4 | 4 | 0 |
| Laryngeal pain | 4 | 4 | 0 |
| Laryngeal squamous cell carcinoma | 4 | 4 | 0 |
| Laryngeal stenosis | 4 | 4 | 0 |
| Laryngitis | 3 | 4 | 1 |
| Laryngomalacia | 3 | 4 | 1 |
| Laryngoscopy abnormal | 4 | 4 | 0 |

[Fig. 3-35]

| | | | | | | | |
|---|---|---|---|---|---|---|---|
| Laryngospasm | 3 | 4 | 1 | Limb mass | 4 | 4 | 0 |
| Laser therapy | 3 | 4 | 1 | Limb operation | 3 | 4 | 1 |
| Laziness | 4 | 4 | 0 | Lip and/or oral cavity cancer | 4 | 4 | 0 |
| Learning disorder | 3 | 4 | 1 | Lip disorder | 3 | 4 | 1 |
| Left atrial dilatation | 3 | 3 | 0 | Lip dry | 4 | 4 | 0 |
| Left atrial enlargement | 4 | 4 | 0 | Lip erosion | 3 | 4 | 1 |
| Left ventricular dilatation | 4 | 3 | 1 | Lip infection | 4 | 4 | 0 |
| Left ventricular dysfunction | 3 | 3 | 0 | Lip oedema | 4 | 4 | 0 |
| Left ventricular end-diastolic pressure increased | 3 | 4 | 1 | Lip squamous cell carcinoma | 4 | 4 | 0 |
| | | | | Lip swelling | 3 | 3 | 0 |
| Left ventricular failure | 3 | 3 | 0 | Lip ulceration | 4 | 4 | 0 |
| Left ventricular hypertrophy | 3 | 3 | 0 | Lipase increased | 3 | 3 | 0 |
| Leg amputation | 3 | 4 | 1 | Lipid metabolism disorder | 3 | 4 | 1 |
| Leiomyosarcoma | 4 | 3 | 1 | Lipids abnormal | 3 | 4 | 1 |
| Leiomyosarcoma recurrent | 4 | 4 | 0 | Lipids increased | 3 | 3 | 0 |
| Lemierre syndrome | 4 | 4 | 0 | Lipoma | 4 | 4 | 0 |
| Leptotrichia infection | 4 | 4 | 0 | Lipomatosis | 4 | 4 | 0 |
| Leriche syndrome | 4 | 4 | 0 | Liposarcoma | 4 | 4 | 0 |
| Lethargy | 3 | 3 | 0 | Liposarcoma metastatic | 4 | 4 | 0 |
| Leukaemia | 4 | 3 | 1 | Lisfranc fracture | 3 | 4 | 1 |
| Leukaemoid reaction | 4 | 4 | 0 | Listless | 4 | 4 | 0 |
| Leukocytosis | 3 | 3 | 0 | Live birth | 3 | 3 | 0 |
| Leukoencephalopathy | 4 | 3 | 1 | Livedo reticularis | 3 | 4 | 1 |
| Leukopenia | 3 | 3 | 0 | Liver abscess | 4 | 3 | 1 |
| Lhermitte's sign | 4 | 4 | 0 | Liver carcinoma ruptured | 4 | 4 | 0 |
| Libido decreased | 3 | 3 | 0 | Liver disorder | 3 | 3 | 0 |
| Libido disorder | 3 | 4 | 1 | Liver function test abnormal | 3 | 3 | 0 |
| Libido increased | 3 | 4 | 1 | Liver function test decreased | 4 | 4 | 0 |
| Lichen planus | 4 | 4 | 0 | Liver function test increased | 3 | 3 | 0 |
| Lichenoid keratosis | 4 | 4 | 0 | Liver injury | 3 | 3 | 0 |
| Life support | 3 | 4 | 1 | Liver tenderness | 4 | 4 | 0 |
| Ligament injury | 3 | 4 | 1 | Liver transplant | 4 | 4 | 0 |
| Ligament rupture | 3 | 4 | 1 | Liver transplant rejection | 4 | 4 | 0 |
| Ligament sprain | 4 | 4 | 0 | Living in residential institution | 3 | 4 | 1 |
| Light chain analysis increased | 4 | 4 | 0 | Lobar pneumonia | 4 | 3 | 1 |
| Limb amputation | 4 | 4 | 0 | Local swelling | 4 | 3 | 1 |
| Limb asymmetry | 3 | 4 | 1 | Localised infection | 3 | 3 | 0 |
| Limb deformity | 4 | 4 | 0 | Localised intraabdominal fluid collection | 3 | 3 | 0 |
| Limb discomfort | 3 | 3 | 0 | | | | |
| Limb injury | 3 | 3 | 0 | Localised oedema | 3 | 3 | 0 |

[Fig. 3-36]

| | | | |
|---|---|---|---|
| Locked-in syndrome | 3 | 4 | 1 |
| Locomotive syndrome | 4 | 4 | 0 |
| Logorrhoea | 3 | 4 | 1 |
| Long QT syndrome | 3 | 4 | 1 |
| Loose tooth | 4 | 4 | 0 |
| Loss of consciousness | 3 | 3 | 0 |
| Loss of control of legs | 4 | 4 | 0 |
| Loss of employment | 3 | 4 | 1 |
| Loss of libido | 3 | 3 | 0 |
| Loss of personal independence in daily activities | 3 | 4 | 1 |
| Low birth weight baby | 3 | 3 | 0 |
| Low cardiac output syndrome | 4 | 4 | 0 |
| Low density lipoprotein | 3 | 4 | 1 |
| Low density lipoprotein decreased | 4 | 4 | 0 |
| Low density lipoprotein increased | 4 | 4 | 0 |
| Lower gastrointestinal haemorrhage | 3 | 4 | 1 |
| Lower limb fracture | 3 | 4 | 1 |
| Lower respiratory tract infection | 3 | 3 | 0 |
| Lower urinary tract symptoms | 4 | 4 | 0 |
| Lumbar radiculopathy | 4 | 4 | 0 |
| Lumbar spinal stenosis | 4 | 4 | 0 |
| Lumbar vertebral fracture | 4 | 3 | 1 |
| Lumbosacral plexus injury | 4 | 4 | 0 |
| Lung abscess | 4 | 3 | 1 |
| Lung adenocarcinoma | 4 | 4 | 0 |
| Lung adenocarcinoma metastatic | 4 | 4 | 0 |
| Lung adenocarcinoma recurrent | 4 | 4 | 0 |
| Lung adenocarcinoma stage III | 4 | 4 | 0 |
| Lung adenocarcinoma stage IV | 4 | 4 | 0 |
| Lung cancer metastatic | 4 | 3 | 1 |
| Lung carcinoma cell type unspecified recurrent | 4 | 3 | 1 |
| Lung carcinoma cell type unspecified stage I | 4 | 4 | 0 |
| Lung carcinoma cell type unspecified stage III | 4 | 4 | 0 |
| Lung carcinoma cell type unspecified stage IV | 4 | 3 | 1 |
| Lung consolidation | 3 | 3 | 0 |

| | | | |
|---|---|---|---|
| Lung cyst | 4 | 4 | 0 |
| Lung disorder | 3 | 3 | 0 |
| Lung infection | 3 | 3 | 0 |
| Lung infiltration | 3 | 3 | 0 |
| Lung lobectomy | 4 | 4 | 0 |
| Lung neoplasm | 4 | 3 | 1 |
| Lung neoplasm malignant | 3 | 3 | 0 |
| Lung operation | 3 | 4 | 1 |
| Lung perforation | 4 | 4 | 0 |
| Lung squamous cell carcinoma metastatic | 4 | 4 | 0 |
| Lung squamous cell carcinoma recurrent | 4 | 4 | 0 |
| Lung squamous cell carcinoma stage III | 4 | 4 | 0 |
| Lupus-like syndrome | 3 | 4 | 1 |
| Lymph gland infection | 4 | 4 | 0 |
| Lymph node pain | 4 | 4 | 0 |
| Lymph node palpable | 4 | 4 | 0 |
| Lymph node tuberculosis | 4 | 4 | 0 |
| Lymphadenectomy | 4 | 4 | 0 |
| Lymphadenitis | 4 | 4 | 0 |
| Lymphadenitis bacterial | 3 | 4 | 1 |
| Lymphadenopathy | 3 | 3 | 0 |
| Lymphadenopathy mediastinal | 4 | 3 | 1 |
| Lymphangioma | 4 | 4 | 0 |
| Lymphangiosis carcinomatosa | 4 | 4 | 0 |
| Lymphatic disorder | 4 | 4 | 0 |
| Lymphocele | 4 | 4 | 0 |
| Lymphocyte count abnormal | 4 | 4 | 0 |
| Lymphocyte count decreased | 3 | 3 | 0 |
| Lymphocyte count increased | 3 | 3 | 0 |
| Lymphocyte morphology abnormal | 4 | 4 | 0 |
| Lymphocyte percentage decreased | 3 | 4 | 1 |
| Lymphocyte percentage increased | 4 | 4 | 0 |
| Lymphocytic hypophysitis | 4 | 4 | 0 |
| Lymphocytosis | 3 | 3 | 0 |
| Lymphoedema | 3 | 4 | 1 |
| Lymphoid tissue hyperplasia | 3 | 4 | 1 |
| Lymphoma | 3 | 3 | 0 |

[Fig. 3-37]

| | | | | | | | |
|---|---|---|---|---|---|---|---|
| Lymphopenia | 3 | 3 | 0 | Mantle cell lymphoma recurrent | 4 | 4 | 0 |
| Lymphoproliferative disorder | 4 | 4 | 0 | Marasmus | 4 | 4 | 0 |
| Lymphorrhoea | 4 | 4 | 0 | Marchiafava-Bignami disease | 4 | 4 | 0 |
| Lymphostasis | 4 | 4 | 0 | Marrow hyperplasia | 4 | 3 | 1 |
| Macrocephaly | 4 | 4 | 0 | Masked facies | 3 | 4 | 1 |
| Macrocytosis | 3 | 4 | 1 | Mass | 3 | 3 | 0 |
| Macular degeneration | 3 | 4 | 1 | Mass excision | 4 | 4 | 0 |
| Macular oedema | 4 | 4 | 0 | Mast cell activation syndrome | 4 | 4 | 0 |
| Macular pigmentation | 4 | 4 | 0 | Mastication disorder | 3 | 3 | 0 |
| Macule | 3 | 4 | 1 | Masticatory pain | 4 | 4 | 0 |
| Maculopathy | 3 | 3 | 0 | Mastitis | 3 | 3 | 0 |
| Madarosis | 4 | 4 | 0 | Mastocytosis | 4 | 4 | 0 |
| Magnesium deficiency | 4 | 4 | 0 | Mastoiditis | 4 | 4 | 0 |
| Magnesium metabolism disorder | 3 | 4 | 1 | Maternal death affecting foetus | 4 | 4 | 0 |
| Major depression | 3 | 4 | 1 | Maternal drugs affecting foetus | 3 | 3 | 0 |
| Malabsorption | 3 | 3 | 0 | Maternal exposure before pregnancy | 3 | 4 | 1 |
| Malaise | 3 | 3 | 0 | Maternal exposure during pregnancy | 3 | 3 | 0 |
| Malignant ascites | 4 | 4 | 0 | Maternal exposure timing unspecified | 3 | 4 | 1 |
| Malignant bowel obstruction | 4 | 4 | 0 | | | | |
| Malignant catatonia | 3 | 4 | 1 | Mean arterial pressure decreased | 4 | 4 | 0 |
| Malignant fibrous histiocytoma | 4 | 4 | 0 | Mean cell haemoglobin concentration decreased | 3 | 4 | 1 |
| Malignant melanoma | 4 | 3 | 1 | | | | |
| Malignant melanoma of sites other than skin | 4 | 4 | 0 | Mean cell haemoglobin concentration increased | 4 | 4 | 0 |
| Malignant mesenchymoma | 4 | 4 | 0 | Mean cell haemoglobin decreased | 3 | 4 | 1 |
| Malignant neoplasm of pleura | 4 | 4 | 0 | Mean cell haemoglobin increased | 4 | 4 | 0 |
| Malignant neoplasm of renal pelvis | 4 | 4 | 0 | Mean cell volume abnormal | 4 | 4 | 0 |
| Malignant neoplasm of spinal cord | 3 | 4 | 1 | Mean cell volume decreased | 3 | 4 | 1 |
| Malignant neoplasm of unknown primary site | 4 | 4 | 0 | Mean cell volume increased | 3 | 3 | 0 |
| | | | | Mean platelet volume decreased | 3 | 4 | 1 |
| Malignant neoplasm progression | 3 | 3 | 0 | Mean platelet volume increased | 3 | 4 | 1 |
| Malignant peritoneal neoplasm | 4 | 4 | 0 | Mechanical ileus | 4 | 4 | 0 |
| Malignant pituitary tumour | 4 | 4 | 0 | Mechanical ventilation | 4 | 4 | 0 |
| Malignant pleural effusion | 4 | 4 | 0 | Meconium aspiration syndrome | 3 | 4 | 1 |
| Malignant transformation | 4 | 4 | 0 | Mediastinal disorder | 4 | 4 | 0 |
| Mallory-Weiss syndrome | 3 | 4 | 1 | Mediastinal mass | 4 | 4 | 0 |
| Malnutrition | 3 | 3 | 0 | Mediastinal shift | 4 | 4 | 0 |
| Malocclusion | 4 | 4 | 0 | Mediastinitis | 4 | 4 | 0 |
| Mania | 3 | 3 | 0 | Medical device complication | 4 | 4 | 0 |
| Mantle cell lymphoma | 4 | 4 | 0 | Medical device site dryness | 4 | 4 | 0 |

[Fig. 3-38]

| | | | | | | | |
|---|---|---|---|---|---|---|---|
| Medical device site infection | 3 | 4 | 1 | Merycism | 4 | 4 | 0 |
| Medical device site joint pain | 4 | 4 | 0 | Mesenteric abscess | 4 | 4 | 0 |
| Medical device site oedema | 4 | 4 | 0 | Mesenteric arterial occlusion | 4 | 4 | 0 |
| Medical procedure | 4 | 4 | 0 | Mesenteric artery thrombosis | 4 | 4 | 0 |
| Medication error | 3 | 3 | 0 | Mesenteric panniculitis | 3 | 4 | 1 |
| Medication monitoring error | 3 | 4 | 1 | Mesenteric vascular insufficiency | 4 | 4 | 0 |
| Medication residue present | 3 | 4 | 1 | Mesenteric vein thrombosis | 4 | 4 | 0 |
| Medulloblastoma recurrent | 4 | 4 | 0 | Metabolic acidosis | 3 | 3 | 0 |
| Megacolon | 3 | 3 | 0 | Metabolic alkalosis | 4 | 4 | 0 |
| Meige's syndrome | 3 | 4 | 1 | Metabolic disorder | 3 | 3 | 0 |
| Melaena | 3 | 3 | 0 | Metabolic encephalopathy | 4 | 3 | 1 |
| Melanocytic naevus | 4 | 3 | 1 | Metabolic function test abnormal | 3 | 4 | 1 |
| Melanoderma | 3 | 4 | 1 | Metabolic surgery | 3 | 4 | 1 |
| Melanoma recurrent | 4 | 4 | 0 | Metabolic syndrome | 3 | 4 | 1 |
| Melanosis | 4 | 4 | 0 | Metamorphopsia | 4 | 4 | 0 |
| MELAS syndrome | 4 | 4 | 0 | Metaplastic breast carcinoma | 4 | 4 | 0 |
| Mendelson's syndrome | 4 | 4 | 0 | Metapneumovirus infection | 4 | 3 | 1 |
| Meningeal neoplasm | 4 | 4 | 0 | Metastases to abdominal cavity | 4 | 4 | 0 |
| Meningioma | 4 | 3 | 1 | Metastases to abdominal wall | 4 | 4 | 0 |
| Meningioma benign | 4 | 4 | 0 | Metastases to adrenals | 4 | 4 | 0 |
| Meningitis | 3 | 3 | 0 | Metastases to bladder | 4 | 4 | 0 |
| Meningitis aseptic | 4 | 4 | 0 | Metastases to bone | 4 | 3 | 1 |
| Meningitis bacterial | 4 | 3 | 1 | Metastases to bone marrow | 4 | 4 | 0 |
| Meningitis cryptococcal | 4 | 4 | 0 | Metastases to breast | 4 | 4 | 0 |
| Meningitis fungal | 4 | 4 | 0 | Metastases to central nervous system | 3 | 3 | 0 |
| Meningitis pneumococcal | 4 | 4 | 0 | | | | |
| Meningitis tuberculous | 4 | 4 | 0 | Metastases to eye | 4 | 4 | 0 |
| Meningitis viral | 4 | 4 | 0 | Metastases to gallbladder | 4 | 4 | 0 |
| Meningoencephalitis herpetic | 4 | 4 | 0 | Metastases to gastrointestinal tract | 4 | 4 | 0 |
| Meningoencephalitis viral | 4 | 4 | 0 | Metastases to heart | 4 | 4 | 0 |
| Meniscus injury | 3 | 4 | 1 | Metastases to kidney | 4 | 4 | 0 |
| Menopause | 4 | 4 | 0 | Metastases to liver | 3 | 3 | 0 |
| Menorrhagia | 3 | 3 | 0 | Metastases to lung | 4 | 3 | 1 |
| Menstrual disorder | 3 | 4 | 1 | Metastases to lymph nodes | 3 | 3 | 0 |
| Menstruation delayed | 3 | 4 | 1 | Metastases to meninges | 4 | 4 | 0 |
| Menstruation irregular | 3 | 4 | 1 | Metastases to neck | 4 | 4 | 0 |
| Mental disability | 3 | 4 | 1 | Metastases to nervous system | 4 | 4 | 0 |
| Mental disorder | 3 | 3 | 0 | Metastases to ovary | 4 | 4 | 0 |
| Mental fatigue | 3 | 4 | 1 | Metastases to pancreas | 4 | 4 | 0 |
| Mental impairment | 3 | 3 | 0 | Metastases to pelvis | 4 | 4 | 0 |

[Fig. 3-39]

| | | | | | | | |
|---|---|---|---|---|---|---|---|
| Metastases to peritoneum | 4 | 4 | 0 | Mitral valve calcification | 4 | 4 | 0 |
| Metastases to pleura | 4 | 4 | 0 | Mitral valve disease | 4 | 4 | 0 |
| Metastases to retroperitoneum | 4 | 4 | 0 | Mitral valve incompetence | 3 | 3 | 0 |
| Metastases to skin | 4 | 4 | 0 | Mitral valve sclerosis | 3 | 4 | 1 |
| Metastases to soft tissue | 4 | 4 | 0 | Mixed hepatocellular cholangiocarcinoma | 4 | 4 | 0 |
| Metastases to spine | 4 | 3 | 1 | Mixed liver injury | 4 | 4 | 0 |
| Metastases to stomach | 4 | 4 | 0 | Moaning | 3 | 4 | 1 |
| Metastases to the mediastinum | 4 | 4 | 0 | Mobility decreased | 3 | 3 | 0 |
| Metastases to thorax | 4 | 4 | 0 | Monocyte count decreased | 3 | 3 | 0 |
| Metastases to thyroid | 4 | 4 | 0 | Monocyte count increased | 3 | 3 | 0 |
| Metastases to uterus | 4 | 4 | 0 | Monocyte percentage increased | 3 | 4 | 1 |
| Metastasis | 4 | 3 | 1 | Monocytopenia | 4 | 4 | 0 |
| Metastatic carcinoma of the bladder | 4 | 4 | 0 | Monocytosis | 3 | 4 | 1 |
| Metastatic gastric cancer | 4 | 4 | 0 | Mononeuropathy | 4 | 4 | 0 |
| Metastatic malignant melanoma | 4 | 3 | 1 | Monoparesis | 4 | 4 | 0 |
| Metastatic neoplasm | 4 | 3 | 1 | Monoplegia | 3 | 4 | 1 |
| Metastatic squamous cell carcinoma | 4 | 4 | 0 | Mood altered | 3 | 3 | 0 |
| Metatarsalgia | 4 | 4 | 0 | Mood disorder due to a general medical condition | 3 | 4 | 1 |
| Methaemoglobinaemia | 4 | 4 | 0 | Mood swings | 3 | 3 | 0 |
| Metrorrhagia | 4 | 4 | 0 | Moraxella infection | 4 | 4 | 0 |
| Microalbuminuria | 4 | 4 | 0 | Morbid thoughts | 3 | 4 | 1 |
| Microangiopathic haemolytic anaemia | 4 | 4 | 0 | Morganella test positive | 4 | 4 | 0 |
| Microangiopathy | 4 | 4 | 0 | Morose | 3 | 4 | 1 |
| Microcephaly | 3 | 4 | 1 | Motion sickness | 4 | 3 | 1 |
| Micrococcus test positive | 3 | 4 | 1 | Motor developmental delay | 4 | 4 | 0 |
| Microcytic anaemia | 3 | 4 | 1 | Motor dysfunction | 3 | 3 | 0 |
| Microgenia | 4 | 4 | 0 | Mouth haemorrhage | 4 | 4 | 0 |
| Microphthalmos | 3 | 4 | 1 | Mouth swelling | 4 | 4 | 0 |
| Microsporidia infection | 4 | 4 | 0 | Mouth ulceration | 3 | 4 | 1 |
| Microvascular coronary artery disease | 4 | 4 | 0 | Movement disorder | 3 | 3 | 0 |
| Micturition disorder | 3 | 3 | 0 | Mucinous breast carcinoma | 4 | 4 | 0 |
| Micturition urgency | 3 | 3 | 0 | Mucoepidermoid carcinoma | 4 | 4 | 0 |
| Middle insomnia | 3 | 4 | 1 | Mucoepidermoid carcinoma of salivary gland | 4 | 4 | 0 |
| Migraine | 3 | 3 | 0 | Mucosa vesicle | 4 | 4 | 0 |
| Migraine with aura | 3 | 4 | 1 | Mucosal discolouration | 3 | 4 | 1 |
| Milia | 4 | 4 | 0 | Mucosal dryness | 3 | 4 | 1 |
| Mineral metabolism disorder | 4 | 4 | 0 | Mucosal haemorrhage | 4 | 4 | 0 |
| Miosis | 3 | 3 | 0 | | | | |

[Fig. 3-40]

| | | | | | | | |
|---|---|---|---|---|---|---|---|
| Mucosal hyperaemia | 4 | 4 | 0 | Musculoskeletal discomfort | 3 | 3 | 0 |
| Mucosal infection | 4 | 4 | 0 | Musculoskeletal disorder | 4 | 3 | 1 |
| Mucosal inflammation | 3 | 4 | 1 | Musculoskeletal injury | 4 | 4 | 0 |
| Mucosal membrane hyperplasia | 4 | 4 | 0 | Musculoskeletal pain | 3 | 3 | 0 |
| Mucosal necrosis | 4 | 4 | 0 | Musculoskeletal stiffness | 3 | 3 | 0 |
| Mucosal pain | 4 | 4 | 0 | Mutism | 3 | 3 | 0 |
| Mucosal toxicity | 4 | 4 | 0 | Myasthenia gravis crisis | 4 | 4 | 0 |
| Mucosal ulceration | 3 | 4 | 1 | Myasthenic syndrome | 4 | 4 | 0 |
| Mucous membrane disorder | 3 | 4 | 1 | Mycobacterium avium complex infection | 4 | 4 | 0 |
| Mucous stools | 4 | 4 | 0 | Mycosis fungoides | 4 | 4 | 0 |
| Multi-organ disorder | 4 | 3 | 1 | Mydriasis | 3 | 3 | 0 |
| Multi-organ failure | 3 | 3 | 0 | Myelitis | 4 | 4 | 0 |
| Multifocal motor neuropathy | 4 | 4 | 0 | Myelodysplastic syndrome | 4 | 3 | 1 |
| Multiple-drug resistance | 3 | 4 | 1 | Myelofibrosis | 4 | 4 | 0 |
| Multiple congenital abnormalities | 3 | 4 | 1 | Myeloid leukaemia | 4 | 4 | 0 |
| Multiple drug therapy | 3 | 3 | 0 | Myeloid maturation arrest | 4 | 3 | 1 |
| Multiple fractures | 3 | 3 | 0 | Myeloma cast nephropathy | 4 | 4 | 0 |
| Multiple injuries | 4 | 4 | 0 | Myelopathy | 4 | 4 | 0 |
| Multiple organ dysfunction syndrome | 3 | 3 | 0 | Myeloproliferative disorder | 4 | 3 | 1 |
| Multiple pregnancy | 4 | 4 | 0 | Myeloproliferative neoplasm | 4 | 4 | 0 |
| Multiple sclerosis | 3 | 4 | 1 | Myocardial fibrosis | 3 | 3 | 0 |
| Multiple sclerosis relapse | 3 | 4 | 1 | Myocardial haemorrhage | 4 | 4 | 0 |
| Muscle abscess | 4 | 4 | 0 | Myocardial ischaemia | 3 | 3 | 0 |
| Muscle atrophy | 4 | 3 | 1 | Myocardial necrosis marker increased | 4 | 3 | 1 |
| Muscle contractions involuntary | 3 | 4 | 1 | | | | |
| Muscle contracture | 3 | 4 | 1 | | | | |
| Muscle disorder | 3 | 3 | 0 | Myocarditis | 3 | 3 | 0 |
| Muscle enzyme increased | 4 | 4 | 0 | Myoclonic epilepsy | 3 | 4 | 1 |
| Muscle fibrosis | 4 | 4 | 0 | Myoclonus | 3 | 3 | 0 |
| Muscle haemorrhage | 4 | 4 | 0 | Myofascial pain syndrome | 3 | 4 | 1 |
| Muscle injury | 3 | 4 | 1 | Myoglobin blood increased | 4 | 4 | 0 |
| Muscle mass | 3 | 4 | 1 | Myoglobin urine present | 3 | 4 | 1 |
| Muscle necrosis | 4 | 3 | 1 | Myoglobinaemia | 4 | 4 | 0 |
| Muscle rigidity | 3 | 4 | 1 | Myoglobinuria | 4 | 4 | 0 |
| Muscle spasticity | 3 | 3 | 0 | Myopathy | 3 | 3 | 0 |
| Muscle strain | 3 | 4 | 1 | Myopia | 3 | 4 | 1 |
| Muscle tightness | 3 | 3 | 0 | Myositis | 3 | 3 | 0 |
| Muscle twitching | 3 | 3 | 0 | Myotonia | 3 | 4 | 1 |
| Muscular weakness | 3 | 3 | 0 | Myxoedema | 4 | 4 | 0 |
| Musculoskeletal chest pain | 4 | 3 | 1 | | | | |

[Fig. 3-41]

| | | | |
|---|---|---|---|
| N-terminal prohormone brain natriuretic peptide increased | 3 | 3 | 0 |
| Naevus flammeus | 3 | 4 | 1 |
| Nail bed infection | 4 | 4 | 0 |
| Nail discolouration | 4 | 4 | 0 |
| Nail disorder | 4 | 3 | 1 |
| Nail picking | 3 | 4 | 1 |
| Nail pigmentation | 4 | 4 | 0 |
| Nail toxicity | 4 | 4 | 0 |
| Narcolepsy | 3 | 4 | 1 |
| Nasal cavity cancer | 3 | 4 | 1 |
| Nasal congestion | 3 | 3 | 0 |
| Nasal discomfort | 4 | 4 | 0 |
| Nasal disorder | 3 | 4 | 1 |
| Nasal dryness | 4 | 4 | 0 |
| Nasal injury | 4 | 4 | 0 |
| Nasal mucosal disorder | 4 | 4 | 0 |
| Nasal necrosis | 4 | 4 | 0 |
| Nasal obstruction | 4 | 4 | 0 |
| Nasal oedema | 3 | 4 | 1 |
| Nasal operation | 4 | 4 | 0 |
| Nasal septum deviation | 4 | 4 | 0 |
| Nasal turbinate abnormality | 4 | 4 | 0 |
| Nasal turbinate hypertrophy | 4 | 4 | 0 |
| Nasal ulcer | 4 | 4 | 0 |
| Nasopharyngeal cancer | 4 | 4 | 0 |
| Nasopharyngitis | 3 | 3 | 0 |
| Natural killer-cell lymphoblastic lymphoma | 4 | 4 | 0 |
| Near drowning | 3 | 4 | 1 |
| Neck pain | 3 | 3 | 0 |
| Neck surgery | 3 | 4 | 1 |
| Necrosis | 3 | 3 | 0 |
| Necrosis ischaemic | 4 | 3 | 1 |
| Necrotising colitis | 4 | 3 | 1 |
| Necrotising fasciitis | 4 | 3 | 1 |
| Necrotising myositis | 4 | 4 | 0 |
| Necrotising retinitis | 4 | 4 | 0 |
| Needle issue | 3 | 3 | 0 |
| Negative thoughts | 3 | 4 | 1 |

| | | | |
|---|---|---|---|
| Negativism | 3 | 4 | 1 |
| Neglect of personal appearance | 3 | 4 | 1 |
| Neonatal aspiration | 3 | 4 | 1 |
| Neonatal disorder | 4 | 3 | 1 |
| Neonatal pneumonia | 4 | 4 | 0 |
| Neonatal respiratory distress syndrome | 3 | 3 | 0 |
| Neonatal tachycardia | 3 | 4 | 1 |
| Neonatal tachypnoea | 3 | 4 | 1 |
| Neoplasm | 4 | 3 | 1 |
| Neoplasm malignant | 3 | 3 | 0 |
| Neoplasm of orbit | 4 | 4 | 0 |
| Neoplasm progression | 4 | 4 | 0 |
| Neoplasm recurrence | 4 | 4 | 0 |
| Neoplasm skin | 4 | 4 | 0 |
| Neovascular age-related macular degeneration | 4 | 4 | 0 |
| Nephrectomy | 4 | 4 | 0 |
| Nephritis | 4 | 3 | 1 |
| Nephrogenic diabetes insipidus | 3 | 4 | 1 |
| Nephrolithiasis | 3 | 3 | 0 |
| Nephropathy | 4 | 3 | 1 |
| Nephropathy toxic | 4 | 3 | 1 |
| Nephrosclerosis | 4 | 3 | 1 |
| Nephrotic syndrome | 3 | 3 | 0 |
| Nerve block | 4 | 4 | 0 |
| Nerve compression | 3 | 4 | 1 |
| Nerve conduction studies abnormal | 4 | 4 | 0 |
| Nerve injury | 3 | 3 | 0 |
| Nerve root compression | 3 | 4 | 1 |
| Nervous system disorder | 3 | 3 | 0 |
| Nervousness | 3 | 4 | 1 |
| Neural tube defect | 3 | 4 | 1 |
| Neuralgia | 3 | 3 | 0 |
| Neuralgic amyotrophy | 4 | 4 | 0 |
| Neuritis | 4 | 3 | 1 |
| Neuroblastoma | 4 | 4 | 0 |
| Neuroblastoma recurrent | 4 | 4 | 0 |
| Neurodegenerative disorder | 4 | 4 | 0 |
| Neuroendocrine breast tumour | 4 | 4 | 0 |

[Fig. 3-42]

| | | | | | | | |
|---|---|---|---|---|---|---|---|
| Neuroendocrine carcinoma | 4 | 3 | 1 | No adverse event | 3 | 3 | 0 |
| Neuroendocrine carcinoma metastatic | 4 | 4 | 0 | No therapeutic response | 3 | 3 | 0 |
| | | | | Nocardiosis | 4 | 4 | 0 |
| Neuroendocrine carcinoma of the skin | 4 | 4 | 0 | Nocturia | 3 | 3 | 0 |
| | | | | Nodal arrhythmia | 4 | 4 | 0 |
| Neuroendocrine tumour | 4 | 4 | 0 | Nodal rhythm | 4 | 4 | 0 |
| Neurofibromatosis | 4 | 4 | 0 | Nodule | 3 | 3 | 0 |
| Neurogenic bladder | 3 | 3 | 0 | Non-alcoholic fatty liver | 3 | 4 | 1 |
| Neuroleptic-induced deficit syndrome | 3 | 4 | 1 | Non-alcoholic steatohepatitis | 3 | 4 | 1 |
| | | | | Non-cardiac chest pain | 3 | 3 | 0 |
| Neuroleptic malignant syndrome | 3 | 4 | 1 | Non-cardiogenic pulmonary oedema | 3 | 4 | 1 |
| Neurological decompensation | 3 | 3 | 0 | Non-high-density lipoprotein cholesterol increased | 4 | 4 | 0 |
| Neurological examination abnormal | 4 | 4 | 0 | | | | |
| Neurological symptom | 3 | 3 | 0 | Non-Hodgkin's lymphoma | 3 | 3 | 0 |
| Neuromyopathy | 3 | 3 | 0 | Non-Hodgkin's lymphoma recurrent | 4 | 4 | 0 |
| Neurone-specific enolase increased | 4 | 4 | 0 | Non-renal cell carcinoma of kidney | 4 | 4 | 0 |
| Neuropathy peripheral | 3 | 3 | 0 | Non-small cell lung cancer | 4 | 4 | 0 |
| Neurosensory hypoacusis | 4 | 4 | 0 | Non-small cell lung cancer metastatic | 4 | 4 | 0 |
| Neurosis | 4 | 4 | 0 | Non-small cell lung cancer recurrent | 4 | 4 | 0 |
| Neurotoxicity | 3 | 3 | 0 | Non-small cell lung cancer stage I | 4 | 4 | 0 |
| Neutropenia | 3 | 3 | 0 | Non-small cell lung cancer stage II | 4 | 4 | 0 |
| Neutropenic colitis | 4 | 4 | 0 | Non-small cell lung cancer stage IIIB | 4 | 4 | 0 |
| Neutropenic infection | 4 | 4 | 0 | Non-small cell lung cancer stage IV | 4 | 4 | 0 |
| Neutropenic sepsis | 3 | 3 | 0 | Nonspecific reaction | 3 | 3 | 0 |
| Neutrophil count | 4 | 3 | 1 | Noonan syndrome | 3 | 4 | 1 |
| Neutrophil count abnormal | 4 | 3 | 1 | Normal newborn | 3 | 3 | 0 |
| Neutrophil count decreased | 3 | 3 | 0 | Normochromic normocytic anaemia | 4 | 3 | 1 |
| Neutrophil count increased | 3 | 3 | 0 | Normocytic anaemia | 4 | 4 | 0 |
| Neutrophil morphology abnormal | 4 | 4 | 0 | Nuchal rigidity | 3 | 4 | 1 |
| Neutrophil percentage decreased | 4 | 4 | 0 | Nuclear magnetic resonance imaging abnormal | 3 | 4 | 1 |
| Neutrophil percentage increased | 3 | 4 | 1 | | | | |
| Neutrophilia | 3 | 3 | 0 | Nuclear magnetic resonance imaging spinal abnormal | 3 | 4 | 1 |
| Nicotine dependence | 3 | 4 | 1 | | | | |
| Niemann-Pick disease | 4 | 4 | 0 | Numb chin syndrome | 4 | 4 | 0 |
| Night sweats | 3 | 3 | 0 | Nutritional condition abnormal | 3 | 4 | 1 |
| Nightmare | 3 | 4 | 1 | Nystagmus | 3 | 3 | 0 |
| NIH stroke scale score increased | 3 | 4 | 1 | Obesity | 3 | 4 | 1 |
| Nikolsky's sign | 3 | 4 | 1 | Obliterative bronchiolitis | 4 | 4 | 0 |
| Nipple pain | 4 | 4 | 0 | Obsessive-compulsive disorder | 3 | 4 | 1 |
| Nitrite urine present | 4 | 3 | 1 | | | | |

[Fig. 3-43]

| | | | |
|---|---|---|---|
| Obsessive-compulsive personality disorder | 3 | 4 | 1 |
| Obsessive-compulsive symptom | 3 | 4 | 1 |
| Obsessive thoughts | 3 | 4 | 1 |
| Obstruction | 4 | 4 | 0 |
| Obstruction gastric | 4 | 4 | 0 |
| Obstructive airways disorder | 3 | 4 | 1 |
| Obstructive uropathy | 4 | 4 | 0 |
| Occipital neuralgia | 4 | 4 | 0 |
| Occult blood positive | 4 | 4 | 0 |
| Occupational exposure to product | 4 | 3 | 1 |
| Occupational exposure to toxic agent | 4 | 4 | 0 |
| Ocular hyperaemia | 3 | 3 | 0 |
| Ocular hypertension | 4 | 4 | 0 |
| Ocular icterus | 3 | 4 | 1 |
| Ocular toxicity | 4 | 4 | 0 |
| Oculogyric crisis | 3 | 4 | 1 |
| Odynophagia | 4 | 3 | 1 |
| Oedema | 3 | 3 | 0 |
| Oedema due to cardiac disease | 4 | 4 | 0 |
| Oedema mucosal | 3 | 4 | 1 |
| Oedema peripheral | 3 | 3 | 0 |
| Oesophageal achalasia | 4 | 4 | 0 |
| Oesophageal adenocarcinoma | 4 | 4 | 0 |
| Oesophageal cancer metastatic | 3 | 4 | 1 |
| Oesophageal candidiasis | 4 | 4 | 0 |
| Oesophageal carcinoma | 3 | 3 | 0 |
| Oesophageal carcinoma recurrent | 4 | 4 | 0 |
| Oesophageal disorder | 3 | 3 | 0 |
| Oesophageal fistula | 4 | 4 | 0 |
| Oesophageal haemorrhage | 4 | 4 | 0 |
| Oesophageal infection | 4 | 4 | 0 |
| Oesophageal obstruction | 4 | 4 | 0 |
| Oesophageal oedema | 4 | 3 | 1 |
| Oesophageal pain | 4 | 4 | 0 |
| Oesophageal perforation | 4 | 3 | 1 |
| Oesophageal rupture | 4 | 3 | 1 |
| Oesophageal spasm | 4 | 4 | 0 |
| Oesophageal squamous cell carcinoma | 4 | 4 | 0 |
| Oesophageal squamous cell carcinoma metastatic | 4 | 4 | 0 |
| Oesophageal stenosis | 4 | 3 | 1 |
| Oesophageal stent insertion | 4 | 4 | 0 |
| Oesophageal ulcer | 3 | 3 | 0 |
| Oesophageal ulcer haemorrhage | 4 | 4 | 0 |
| Oesophageal varices haemorrhage | 4 | 4 | 0 |
| Oesophagitis | 3 | 3 | 0 |
| Oesophagitis bacterial | 4 | 4 | 0 |
| Oesophagitis ulcerative | 4 | 3 | 1 |
| Oesophagobronchial fistula | 4 | 4 | 0 |
| Oesophagogastroduodenoscopy | 3 | 4 | 1 |
| Oesophagopleural fistula | 4 | 4 | 0 |
| Oligomenorrhoea | 3 | 4 | 1 |
| Oligospermia | 4 | 4 | 0 |
| Oliguria | 3 | 3 | 0 |
| On and off phenomenon | 4 | 4 | 0 |
| Oncologic complication | 4 | 4 | 0 |
| Onychoclasis | 4 | 4 | 0 |
| Onycholysis | 4 | 4 | 0 |
| Onychomadesis | 3 | 4 | 1 |
| Onychomycosis | 3 | 4 | 1 |
| Onychophagia | 3 | 4 | 1 |
| Ophthalmic vein thrombosis | 3 | 4 | 1 |
| Ophthalmoplegia | 3 | 4 | 1 |
| Opportunistic infection | 4 | 4 | 0 |
| Oppositional defiant disorder | 3 | 4 | 1 |
| Optic nerve disorder | 4 | 3 | 1 |
| Optic neuritis | 3 | 4 | 1 |
| Oral administration complication | 4 | 4 | 0 |
| Oral candidiasis | 3 | 3 | 0 |
| Oral cavity fistula | 4 | 4 | 0 |
| Oral discomfort | 4 | 3 | 1 |
| Oral disorder | 4 | 3 | 1 |
| Oral fungal infection | 3 | 4 | 1 |
| Oral herpes | 3 | 4 | 1 |
| Oral infection | 4 | 3 | 1 |
| Oral lichen planus | 4 | 4 | 0 |
| Oral mucosa erosion | 3 | 4 | 1 |
| Oral mucosal blistering | 4 | 4 | 0 |

[Fig. 3-44]

| | | | | | | | |
|---|---|---|---|---|---|---|---|
| Oral mucosal erythema | 3 | 4 | 1 | Osteosclerosis | 3 | 4 | 1 |
| Oral mucosal exfoliation | 4 | 4 | 0 | Otitis externa | 3 | 3 | 0 |
| Oral neoplasm | 4 | 4 | 0 | Otitis media | 3 | 3 | 0 |
| Oral pain | 3 | 3 | 0 | Otitis media chronic | 3 | 4 | 1 |
| Oral pruritus | 3 | 4 | 1 | Otorrhoea | 4 | 4 | 0 |
| Oral surgery | 3 | 4 | 1 | Ototoxicity | 4 | 4 | 0 |
| Orbital oedema | 4 | 4 | 0 | Ovarian abscess | 4 | 4 | 0 |
| Orchitis | 4 | 4 | 0 | Ovarian adhesion | 3 | 4 | 1 |
| Organ failure | 4 | 3 | 1 | Ovarian cancer | 4 | 3 | 1 |
| Organic brain syndrome | 4 | 4 | 0 | Ovarian cancer metastatic | 4 | 4 | 0 |
| Organising pneumonia | 3 | 4 | 1 | Ovarian cancer recurrent | 4 | 4 | 0 |
| Orgasm abnormal | 3 | 4 | 1 | Ovarian cancer stage I | 3 | 4 | 1 |
| Oromandibular dystonia | 3 | 4 | 1 | Ovarian cancer stage III | 4 | 4 | 0 |
| Oropharyngeal cancer | 4 | 4 | 0 | Ovarian cancer stage IV | 4 | 4 | 0 |
| Oropharyngeal candidiasis | 4 | 4 | 0 | Ovarian cyst | 3 | 3 | 0 |
| Oropharyngeal pain | 3 | 3 | 0 | Ovarian disorder | 4 | 4 | 0 |
| Oropharyngeal swelling | 4 | 4 | 0 | Ovarian enlargement | 4 | 4 | 0 |
| Orthopaedic procedure | 3 | 4 | 1 | Ovarian epithelial cancer | 4 | 4 | 0 |
| Orthopnoea | 4 | 3 | 1 | Ovarian failure | 4 | 3 | 1 |
| Orthostatic hypertension | 3 | 4 | 1 | Ovarian germ cell endodermal sinus tumour | 4 | 4 | 0 |
| Orthostatic hypotension | 3 | 3 | 0 | Ovarian germ cell teratoma | 4 | 3 | 1 |
| Orthostatic intolerance | 3 | 4 | 1 | Ovarian neoplasm | 4 | 4 | 0 |
| Osmotic demyelination syndrome | 4 | 4 | 0 | Ovarian vein thrombosis | 4 | 4 | 0 |
| Osteitis | 4 | 4 | 0 | Overdose | 3 | 3 | 0 |
| Osteoarthritis | 3 | 3 | 0 | Overweight | 4 | 4 | 0 |
| Osteocalcin increased | 4 | 4 | 0 | Oxygen consumption increased | 3 | 4 | 1 |
| Osteochondroma | 4 | 4 | 0 | Oxygen saturation | 3 | 4 | 1 |
| Osteochondrosis | 3 | 4 | 1 | Oxygen saturation decreased | 3 | 3 | 0 |
| Osteolysis | 4 | 4 | 0 | Packed red blood cell transfusion | 4 | 4 | 0 |
| Osteomalacia | 4 | 4 | 0 | Pain in jaw | 3 | 4 | 1 |
| Osteomyelitis | 3 | 3 | 0 | Pain management | 3 | 4 | 1 |
| Osteonecrosis | 3 | 3 | 0 | Pain of skin | 4 | 3 | 1 |
| Osteonecrosis of jaw | 4 | 4 | 0 | Pain threshold decreased | 4 | 4 | 0 |
| Osteopenia | 4 | 4 | 0 | Painful erection | 4 | 4 | 0 |
| Osteoporosis | 3 | 3 | 0 | Painful respiration | 3 | 4 | 1 |
| Osteoporotic fracture | 4 | 4 | 0 | Palatal disorder | 4 | 4 | 0 |
| Osteoradionecrosis | 4 | 4 | 0 | Palliative care | 4 | 4 | 0 |
| Osteosarcoma | 4 | 4 | 0 | Pallor | 3 | 3 | 0 |
| Osteosarcoma metastatic | 4 | 4 | 0 | | | | |
| Osteosarcoma recurrent | 4 | 4 | 0 | | | | |

[Fig. 3-45]

| | | | |
|---|---|---|---|
| Palmar-plantar erythrodysaesthesia syndrome | 3 | 4 | 1 |
| Palmar erythema | 3 | 4 | 1 |
| Palpable purpura | 3 | 4 | 1 |
| Palpitations | 3 | 3 | 0 |
| Pancreas infection | 4 | 4 | 0 |
| Pancreatic abscess | 4 | 4 | 0 |
| Pancreatic carcinoma | 4 | 3 | 1 |
| Pancreatic carcinoma metastatic | 4 | 4 | 0 |
| Pancreatic cyst | 4 | 4 | 0 |
| Pancreatic cyst rupture | 4 | 4 | 0 |
| Pancreatic disorder | 3 | 4 | 1 |
| Pancreatic enzymes increased | 4 | 4 | 0 |
| Pancreatic leak | 4 | 4 | 0 |
| Pancreatic mass | 4 | 4 | 0 |
| Pancreatic neoplasm | 4 | 4 | 0 |
| Pancreatitis | 3 | 3 | 0 |
| Pancreatitis acute | 3 | 3 | 0 |
| Pancreatitis chronic | 3 | 4 | 1 |
| Pancreatitis necrotising | 4 | 4 | 0 |
| Pancreatitis relapsing | 4 | 4 | 0 |
| Pancytopenia | 3 | 3 | 0 |
| Panic attack | 3 | 3 | 0 |
| Panic disorder | 3 | 4 | 1 |
| Panic reaction | 3 | 3 | 0 |
| Panniculitis | 4 | 4 | 0 |
| Pantoea agglomerans infection | 4 | 4 | 0 |
| Papillary thyroid cancer | 4 | 4 | 0 |
| Papilloedema | 4 | 4 | 0 |
| Papilloma | 4 | 4 | 0 |
| Papule | 3 | 3 | 0 |
| Paradoxical drug reaction | 3 | 4 | 1 |
| Paradoxical pressor response | 4 | 4 | 0 |
| Paraesthesia | 3 | 3 | 0 |
| Paraesthesia oral | 4 | 4 | 0 |
| Parainfluenzae virus infection | 4 | 4 | 0 |
| Paralysis | 3 | 4 | 1 |
| Paranasal sinus discomfort | 4 | 4 | 0 |
| Paranasal sinus hypersecretion | 3 | 4 | 1 |

| | | | |
|---|---|---|---|
| Paraneoplastic neurological syndrome | 4 | 4 | 0 |
| Paraneoplastic syndrome | 3 | 4 | 1 |
| Paranoia | 3 | 3 | 0 |
| Paranoid personality disorder | 3 | 4 | 1 |
| Paraparesis | 4 | 4 | 0 |
| Paraphilia | 3 | 4 | 1 |
| Paraplegia | 4 | 4 | 0 |
| Parasitic gastroenteritis | 4 | 4 | 0 |
| Parathyroid tumour | 4 | 4 | 0 |
| Parathyroid tumour benign | 3 | 4 | 1 |
| Paratracheal lymphadenopathy | 4 | 4 | 0 |
| Parent-child problem | 3 | 4 | 1 |
| Paresis | 4 | 4 | 0 |
| Parkinson's disease | 3 | 3 | 0 |
| Parkinson's disease psychosis | 4 | 4 | 0 |
| Parkinsonian crisis | 4 | 4 | 0 |
| Parkinsonian gait | 3 | 4 | 1 |
| Parkinsonian rest tremor | 3 | 4 | 1 |
| Parkinsonism | 3 | 4 | 1 |
| Paronychia | 4 | 4 | 0 |
| Parosmia | 3 | 4 | 1 |
| Parotitis | 4 | 3 | 1 |
| Partial seizures | 3 | 3 | 0 |
| Partial seizures with secondary generalisation | 3 | 4 | 1 |
| Parvovirus B19 test positive | 4 | 4 | 0 |
| Parvovirus infection | 4 | 4 | 0 |
| Patella fracture | 4 | 4 | 0 |
| Patellofemoral pain syndrome | 4 | 4 | 0 |
| Patent ductus arteriosus | 3 | 4 | 1 |
| Pathogen resistance | 3 | 4 | 1 |
| Pathological fracture | 4 | 4 | 0 |
| Pathological gambling | 3 | 4 | 1 |
| Patient restraint | 4 | 3 | 1 |
| PCO2 decreased | 3 | 3 | 0 |
| PCO2 increased | 3 | 4 | 1 |
| Pedal pulse abnormal | 4 | 4 | 0 |
| Pelvic abscess | 4 | 4 | 0 |
| Pelvic congestion | 4 | 4 | 0 |

[Fig. 3-46]

| | | | |
|---|---|---|---|
| Pelvic fluid collection | 3 | 4 | 1 |
| Pelvic haematoma | 4 | 4 | 0 |
| Pelvic infection | 4 | 4 | 0 |
| Pelvic inflammatory disease | 4 | 4 | 0 |
| Pelvic mass | 4 | 4 | 0 |
| Pelvic neoplasm | 4 | 4 | 0 |
| Pelvic pain | 4 | 4 | 0 |
| Pelvic venous thrombosis | 4 | 3 | 1 |
| Pemphigoid | 4 | 4 | 0 |
| Pemphigus | 4 | 4 | 0 |
| Penile pain | 4 | 3 | 1 |
| Penile squamous cell carcinoma | 4 | 4 | 0 |
| Penile vein thrombosis | 4 | 4 | 0 |
| Penis disorder | 3 | 4 | 1 |
| Peptic ulcer | 4 | 4 | 0 |
| Peptic ulcer perforation | 4 | 4 | 0 |
| Percussion test | 4 | 4 | 0 |
| Percussion test abnormal | 4 | 4 | 0 |
| Percutaneous coronary intervention | 4 | 4 | 0 |
| Perforated ulcer | 4 | 4 | 0 |
| Perforation | 4 | 4 | 0 |
| Perforation bile duct | 4 | 4 | 0 |
| Performance status decreased | 3 | 4 | 1 |
| Perianal erythema | 4 | 4 | 0 |
| Pericardial disease | 4 | 4 | 0 |
| Pericardial drainage | 4 | 4 | 0 |
| Pericardial effusion | 3 | 3 | 0 |
| Pericardial effusion malignant | 4 | 4 | 0 |
| Pericardial neoplasm | 4 | 4 | 0 |
| Pericarditis | 3 | 3 | 0 |
| Pericarditis constrictive | 4 | 4 | 0 |
| Pericarditis infective | 4 | 4 | 0 |
| Pericarditis tuberculous | 4 | 4 | 0 |
| Perihepatic abscess | 4 | 4 | 0 |
| Perinatal depression | 3 | 4 | 1 |
| Perineal pain | 4 | 4 | 0 |
| Periodic limb movement disorder | 3 | 4 | 1 |
| Periodontal destruction | 4 | 4 | 0 |
| Periodontal disease | 3 | 4 | 1 |
| Periodontitis | 3 | 4 | 1 |
| Periorbital cellulitis | 4 | 4 | 0 |
| Periorbital haematoma | 3 | 4 | 1 |
| Periorbital oedema | 4 | 4 | 0 |
| Peripancreatic fluid collection | 4 | 4 | 0 |
| Peripheral arterial occlusive disease | 3 | 4 | 1 |
| Peripheral artery occlusion | 4 | 4 | 0 |
| Peripheral artery stenosis | 4 | 4 | 0 |
| Peripheral artery thrombosis | 3 | 4 | 1 |
| Peripheral circulatory failure | 4 | 4 | 0 |
| Peripheral coldness | 3 | 4 | 1 |
| Peripheral embolism | 4 | 4 | 0 |
| Peripheral ischaemia | 3 | 4 | 1 |
| Peripheral motor neuropathy | 4 | 4 | 0 |
| Peripheral nerve destruction | 4 | 4 | 0 |
| Peripheral nerve infection | 4 | 4 | 0 |
| Peripheral primitive neuroectodermal bone tumour | 4 | 4 | 0 |
| Peripheral sensorimotor neuropathy | 4 | 4 | 0 |
| Peripheral sensory neuropathy | 4 | 4 | 0 |
| Peripheral T-cell lymphoma unspecified | 4 | 4 | 0 |
| Peripheral vascular disorder | 3 | 4 | 1 |
| Peripheral venous disease | 3 | 4 | 1 |
| Perirectal abscess | 4 | 4 | 0 |
| Peritoneal abscess | 3 | 4 | 1 |
| Peritoneal carcinoma metastatic | 4 | 4 | 0 |
| Peritoneal disorder | 4 | 4 | 0 |
| Peritoneal gliomatosis | 4 | 4 | 0 |
| Peritoneal haemorrhage | 3 | 4 | 1 |
| Peritoneal lesion | 4 | 4 | 0 |
| Peritonitis | 3 | 3 | 0 |
| Peritonitis bacterial | 4 | 4 | 0 |
| Peritumoural oedema | 4 | 4 | 0 |
| Peroneal nerve palsy | 4 | 4 | 0 |
| Persecutory delusion | 3 | 4 | 1 |
| Perseveration | 3 | 4 | 1 |
| Persistent depressive disorder | 3 | 4 | 1 |
| Persistent foetal circulation | 3 | 4 | 1 |
| Personality change | 3 | 3 | 0 |
| Personality disorder | 3 | 3 | 0 |

[Fig. 3-47]

| | | | | | | | |
|---|---|---|---|---|---|---|---|
| Petechiae | 3 | 3 | 0 | Placental disorder | 3 | 4 | 1 |
| Petit mal epilepsy | 3 | 3 | 0 | Plagiocephaly | 3 | 4 | 1 |
| Phaeochromocytoma | 4 | 4 | 0 | Plantar erythema | 4 | 4 | 0 |
| Phantom pain | 4 | 4 | 0 | Plasma cell leukaemia | 4 | 4 | 0 |
| Pharyngeal abscess | 4 | 4 | 0 | Plasma cell myeloma | 3 | 3 | 0 |
| Pharyngeal cancer | 4 | 4 | 0 | Plasma cell myeloma recurrent | 3 | 4 | 1 |
| Pharyngeal disorder | 3 | 3 | 0 | Plasma cells increased | 4 | 4 | 0 |
| Pharyngeal erythema | 3 | 4 | 1 | Plasma exchange | 3 | 4 | 1 |
| Pharyngeal fistula | 4 | 4 | 0 | Plasmacytoma | 4 | 4 | 0 |
| Pharyngeal haemorrhage | 4 | 4 | 0 | Plasmacytosis | 4 | 4 | 0 |
| Pharyngeal hypoaesthesia | 3 | 4 | 1 | Plasmapheresis | 3 | 4 | 1 |
| Pharyngeal inflammation | 4 | 4 | 0 | Plastic surgery | 4 | 4 | 0 |
| Pharyngeal lesion | 4 | 4 | 0 | Platelet count abnormal | 4 | 4 | 0 |
| Pharyngeal necrosis | 4 | 4 | 0 | Platelet count decreased | 3 | 3 | 0 |
| Pharyngeal operation | 3 | 4 | 1 | Platelet count increased | 3 | 3 | 0 |
| Pharyngeal stenosis | 4 | 4 | 0 | Platelet disorder | 4 | 3 | 1 |
| Pharyngeal ulceration | 4 | 4 | 0 | Platelet morphology abnormal | 4 | 4 | 0 |
| Pharyngitis | 3 | 3 | 0 | Platelet production decreased | 4 | 4 | 0 |
| Pharyngitis streptococcal | 3 | 3 | 0 | Platelet toxicity | 4 | 4 | 0 |
| Pharyngotonsillitis | 4 | 4 | 0 | Platelet transfusion | 4 | 4 | 0 |
| Phimosis | 3 | 4 | 1 | Pleural disorder | 4 | 4 | 0 |
| Phlebitis | 3 | 4 | 1 | Pleural effusion | 3 | 3 | 0 |
| Phobia | 4 | 3 | 1 | Pleural fibrosis | 4 | 4 | 0 |
| Phobic avoidance | 3 | 4 | 1 | Pleural infection | 4 | 4 | 0 |
| Phonophobia | 3 | 4 | 1 | Pleural infection bacterial | 4 | 4 | 0 |
| Photophobia | 3 | 3 | 0 | Pleural mesothelioma | 4 | 4 | 0 |
| Photopsia | 4 | 3 | 1 | Pleurisy | 3 | 3 | 0 |
| Photosensitivity reaction | 3 | 4 | 1 | Pleuritic pain | 4 | 3 | 1 |
| Phototherapy | 3 | 4 | 1 | Pleurodesis | 4 | 4 | 0 |
| Phrenic nerve paralysis | 4 | 4 | 0 | Pleuropericarditis | 4 | 4 | 0 |
| Phyllodes tumour | 4 | 4 | 0 | Pleurothotonus | 3 | 4 | 1 |
| Physical assault | 3 | 3 | 0 | Pneumatosis | 4 | 4 | 0 |
| Physical disability | 4 | 4 | 0 | Pneumatosis intestinalis | 3 | 4 | 1 |
| Pica | 4 | 4 | 0 | Pneumaturia | 4 | 4 | 0 |
| Pickwickian syndrome | 3 | 4 | 1 | Pneumocephalus | 4 | 4 | 0 |
| Pigmentation disorder | 4 | 4 | 0 | Pneumococcal infection | 4 | 4 | 0 |
| Pituitary tumour | 4 | 4 | 0 | Pneumococcal sepsis | 4 | 4 | 0 |
| Pituitary tumour benign | 3 | 4 | 1 | Pneumocystis jirovecii infection | 4 | 4 | 0 |
| Pituitary tumour removal | 4 | 4 | 0 | Pneumocystis jirovecii pneumonia | 4 | 3 | 1 |
| Placenta praevia | 3 | 4 | 1 | Pneumomediastinum | 4 | 4 | 0 |

[Fig. 3-48]

| | | | | | | | |
|---|---|---|---|---|---|---|---|
| Pneumonia | 3 | 3 | 0 | Polyp | 4 | 4 | 0 |
| Pneumonia adenoviral | 4 | 4 | 0 | Polyserositis | 4 | 4 | 0 |
| Pneumonia aspiration | 3 | 3 | 0 | Polyuria | 3 | 3 | 0 |
| Pneumonia bacterial | 3 | 3 | 0 | Poor feeding infant | 3 | 4 | 1 |
| Pneumonia cryptococcal | 4 | 4 | 0 | Poor personal hygiene | 3 | 3 | 0 |
| Pneumonia cytomegaloviral | 4 | 4 | 0 | Poor quality sleep | 3 | 3 | 0 |
| Pneumonia fungal | 4 | 4 | 0 | Poor sucking reflex | 3 | 4 | 1 |
| Pneumonia haemophilus | 4 | 4 | 0 | Poor venous access | 4 | 3 | 1 |
| Pneumonia klebsiella | 4 | 4 | 0 | Poor weight gain neonatal | 4 | 4 | 0 |
| Pneumonia legionella | 3 | 4 | 1 | Poriomania | 3 | 4 | 1 |
| Pneumonia mycoplasmal | 4 | 4 | 0 | Portal hypertension | 3 | 4 | 1 |
| Pneumonia necrotising | 4 | 3 | 1 | Portal vein flow decreased | 4 | 4 | 0 |
| Pneumonia pneumococcal | 4 | 3 | 1 | Portal vein thrombosis | 3 | 4 | 1 |
| Pneumonia pseudomonal | 4 | 4 | 0 | Portal venous gas | 4 | 4 | 0 |
| Pneumonia staphylococcal | 3 | 4 | 1 | Post-traumatic neck syndrome | 4 | 4 | 0 |
| Pneumonia streptococcal | 3 | 4 | 1 | Post-traumatic stress disorder | 3 | 3 | 0 |
| Pneumonia viral | 4 | 4 | 0 | Post concussion syndrome | 4 | 4 | 0 |
| Pneumonitis | 3 | 3 | 0 | Post embolisation syndrome | 4 | 4 | 0 |
| Pneumonitis chemical | 4 | 3 | 1 | Post inflammatory pigmentation change | 4 | 4 | 0 |
| Pneumoperitoneum | 4 | 4 | 0 | Post procedural bile leak | 4 | 4 | 0 |
| Pneumothorax | 3 | 3 | 0 | Post procedural complication | 3 | 3 | 0 |
| Pneumothorax spontaneous | 4 | 4 | 0 | Post procedural haemorrhage | 4 | 4 | 0 |
| PO2 decreased | 3 | 3 | 0 | Post procedural infection | 3 | 4 | 1 |
| Poisoning | 3 | 3 | 0 | Post procedural inflammation | 4 | 4 | 0 |
| Poisoning deliberate | 3 | 4 | 1 | Post procedural pneumonia | 4 | 4 | 0 |
| Pollakiuria | 3 | 3 | 0 | Post procedural sepsis | 4 | 4 | 0 |
| Polyarteritis nodosa | 4 | 4 | 0 | Post procedural swelling | 4 | 4 | 0 |
| Polyarthritis | 4 | 4 | 0 | Posterior reversible encephalopathy syndrome | 4 | 4 | 0 |
| Polychromasia | 4 | 3 | 1 | Postictal state | 3 | 3 | 0 |
| Polycystic ovaries | 3 | 4 | 1 | Postmenopausal haemorrhage | 4 | 4 | 0 |
| Polycythaemia | 3 | 3 | 0 | Postoperative delirium | 4 | 4 | 0 |
| Polycythaemia vera | 4 | 4 | 0 | Postoperative ileus | 4 | 3 | 1 |
| Polydactyly | 3 | 4 | 1 | Postoperative wound infection | 3 | 4 | 1 |
| Polydipsia | 3 | 3 | 0 | Postpartum haemorrhage | 3 | 4 | 1 |
| Polydipsia psychogenic | 3 | 4 | 1 | Postural reflex impairment | 4 | 4 | 0 |
| Polyglandular disorder | 4 | 4 | 0 | Postural tremor | 3 | 4 | 1 |
| Polyhydramnios | 3 | 4 | 1 | Posture abnormal | 3 | 3 | 0 |
| Polymenorrhoea | 3 | 4 | 1 | Posturing | 3 | 4 | 1 |
| Polymyalgia rheumatica | 4 | 4 | 0 | | | | |
| Polyneuropathy | 3 | 3 | 0 | | | | |

[Fig. 3-49]

| | | | |
|---|---|---|---|
| Potentiating drug interaction | 3 | 3 | 0 |
| Poverty of speech | 4 | 4 | 0 |
| Poverty of thought content | 3 | 4 | 1 |
| Pre-eclampsia | 3 | 3 | 0 |
| Pre-existing condition improved | 3 | 4 | 1 |
| Pre-existing disease | 4 | 4 | 0 |
| Precancerous cells present | 4 | 4 | 0 |
| Pregnancy | 3 | 4 | 1 |
| Pregnancy on contraceptive | 3 | 4 | 1 |
| Pregnancy on oral contraceptive | 3 | 4 | 1 |
| Pregnancy with advanced maternal age | 4 | 4 | 0 |
| Premature baby | 3 | 3 | 0 |
| Premature delivery | 3 | 4 | 1 |
| Premature labour | 3 | 4 | 1 |
| Premature menopause | 4 | 4 | 0 |
| Premature rupture of membranes | 3 | 4 | 1 |
| Premature separation of placenta | 3 | 4 | 1 |
| Prerenal failure | 4 | 4 | 0 |
| Presbyacusis | 4 | 4 | 0 |
| Presbyopia | 4 | 4 | 0 |
| Prescribed overdose | 3 | 3 | 0 |
| Prescribed underdose | 3 | 4 | 1 |
| Prescription drug used without a prescription | 4 | 4 | 0 |
| Pressure of speech | 3 | 4 | 1 |
| Presyncope | 3 | 3 | 0 |
| Preterm premature rupture of membranes | 3 | 4 | 1 |
| Priapism | 3 | 3 | 0 |
| Primary effusion lymphoma | 4 | 4 | 0 |
| Primitive neuroectodermal tumour | 4 | 4 | 0 |
| Prinzmetal angina | 4 | 4 | 0 |
| Procalcitonin abnormal | 4 | 4 | 0 |
| Procalcitonin increased | 4 | 3 | 1 |
| Procedural complication | 3 | 3 | 0 |
| Procedural haemorrhage | 4 | 3 | 1 |
| Procedural nausea | 4 | 4 | 0 |
| Procedural pain | 3 | 3 | 0 |
| Procedural site reaction | 4 | 4 | 0 |
| Procedural vomiting | 4 | 4 | 0 |
| Proctalgia | 3 | 3 | 0 |
| Proctitis | 4 | 4 | 0 |
| Product adhesion issue | 3 | 3 | 0 |
| Product availability issue | 4 | 4 | 0 |
| Product closure issue | 3 | 4 | 1 |
| Product colour issue | 3 | 4 | 1 |
| Product communication issue | 3 | 4 | 1 |
| Product container issue | 3 | 4 | 1 |
| Product container seal issue | 4 | 4 | 0 |
| Product contamination microbial | 3 | 4 | 1 |
| Product contamination physical | 4 | 4 | 0 |
| Product label confusion | 3 | 4 | 1 |
| Product label issue | 3 | 3 | 0 |
| Product name confusion | 4 | 4 | 0 |
| Product outer packaging issue | 4 | 4 | 0 |
| Product packaging quantity issue | 3 | 4 | 1 |
| Product physical issue | 3 | 4 | 1 |
| Product preparation error | 3 | 4 | 1 |
| Product quality issue | 3 | 3 | 0 |
| Product reconstitution quality issue | 3 | 4 | 1 |
| Product storage error | 3 | 4 | 1 |
| Product substitution issue | 3 | 4 | 1 |
| Product use in unapproved indication | 3 | 3 | 0 |
| Productive cough | 3 | 3 | 0 |
| Progressive multifocal leukoencephalopathy | 3 | 4 | 1 |
| Progressive multiple sclerosis | 3 | 4 | 1 |
| Prolactin-producing pituitary tumour | 4 | 4 | 0 |
| Prolonged expiration | 4 | 4 | 0 |
| Prolonged labour | 3 | 4 | 1 |
| Prolonged rupture of membranes | 4 | 4 | 0 |
| Prosopagnosia | 4 | 4 | 0 |
| Prostate cancer | 4 | 3 | 1 |
| Prostate cancer stage I | 4 | 4 | 0 |
| Prostatic pain | 3 | 4 | 1 |
| Prostatic specific antigen increased | 3 | 3 | 0 |
| Prostatitis | 4 | 3 | 1 |
| Prostatitis Escherichia coli | 4 | 4 | 0 |
| Prostatomegaly | 3 | 4 | 1 |

[Fig. 3-50]

| | | | | | | | |
|---|---|---|---|---|---|---|---|
| Protein-losing gastroenteropathy | 4 | 4 | 0 | Psychogenic seizure | 4 | 4 | 0 |
| Protein C increased | 4 | 4 | 0 | Psychomotor hyperactivity | 3 | 3 | 0 |
| Protein S decreased | 4 | 4 | 0 | Psychomotor retardation | 3 | 3 | 0 |
| Protein total abnormal | 3 | 4 | 1 | Psychomotor skills impaired | 3 | 3 | 0 |
| Protein total decreased | 3 | 3 | 0 | Psychosocial support | 4 | 4 | 0 |
| Protein total increased | 4 | 4 | 0 | Psychotic behaviour | 3 | 4 | 1 |
| Protein urine | 4 | 4 | 0 | Psychotic disorder | 3 | 3 | 0 |
| Protein urine present | 3 | 4 | 1 | Psychotic disorder due to a general medical condition | 3 | 4 | 1 |
| Proteinuria | 3 | 3 | 0 | Psychotic symptom | 3 | 4 | 1 |
| Proteus infection | 4 | 3 | 1 | Pubis fracture | 3 | 3 | 0 |
| Prothrombin level decreased | 3 | 4 | 1 | Pulmonary alveolar haemorrhage | 4 | 3 | 1 |
| Prothrombin level increased | 4 | 4 | 0 | Pulmonary arterial hypertension | 3 | 4 | 1 |
| Prothrombin time prolonged | 4 | 3 | 1 | Pulmonary arterial pressure increased | 4 | 4 | 0 |
| Prothrombin time ratio abnormal | 4 | 4 | 0 | Pulmonary arterial wedge pressure increased | 3 | 4 | 1 |
| Prothrombin time ratio decreased | 4 | 4 | 0 | | | | |
| Prothrombin time ratio increased | 4 | 4 | 0 | | | | |
| Prothrombin time shortened | 4 | 4 | 0 | Pulmonary arteriovenous fistula | 4 | 4 | 0 |
| Protrusion tongue | 3 | 4 | 1 | Pulmonary artery stenosis | 3 | 4 | 1 |
| Pruritus generalised | 3 | 4 | 1 | Pulmonary artery thrombosis | 4 | 4 | 0 |
| Pruritus genital | 4 | 4 | 0 | Pulmonary cavitation | 4 | 3 | 1 |
| Pseudo-Bartter syndrome | 4 | 4 | 0 | Pulmonary congestion | 3 | 3 | 0 |
| Pseudobulbar palsy | 3 | 4 | 1 | Pulmonary contusion | 4 | 4 | 0 |
| Pseudocellulitis | 4 | 4 | 0 | Pulmonary eosinophilia | 4 | 4 | 0 |
| Pseudocholinesterase deficiency | 3 | 4 | 1 | Pulmonary fibrosis | 4 | 3 | 1 |
| Pseudodementia | 3 | 4 | 1 | Pulmonary fistula | 4 | 4 | 0 |
| Pseudologia | 3 | 4 | 1 | Pulmonary function test abnormal | 4 | 4 | 0 |
| Pseudolymphoma | 3 | 4 | 1 | Pulmonary function test decreased | 3 | 4 | 1 |
| Pseudomembranous colitis | 4 | 4 | 0 | Pulmonary haemorrhage | 4 | 4 | 0 |
| Pseudomonal bacteraemia | 3 | 4 | 1 | Pulmonary hilum mass | 4 | 3 | 1 |
| Pseudomonal sepsis | 4 | 4 | 0 | Pulmonary hypertension | 3 | 3 | 0 |
| Pseudomonas bronchitis | 4 | 4 | 0 | Pulmonary hypoperfusion | 3 | 4 | 1 |
| Pseudomonas infection | 4 | 4 | 0 | Pulmonary infarction | 4 | 3 | 1 |
| Pseudomonas test positive | 4 | 4 | 0 | Pulmonary mass | 3 | 3 | 0 |
| Pseudophaeochromocytoma | 4 | 4 | 0 | Pulmonary necrosis | 4 | 4 | 0 |
| Psoas abscess | 4 | 4 | 0 | Pulmonary oedema | 3 | 3 | 0 |
| Psoriasis | 3 | 3 | 0 | Pulmonary sepsis | 3 | 3 | 0 |
| Psoriatic arthropathy | 3 | 4 | 1 | Pulmonary thrombosis | 3 | 4 | 1 |
| Psychiatric decompensation | 3 | 4 | 1 | Pulmonary toxicity | 3 | 4 | 1 |
| Psychiatric evaluation | 3 | 4 | 1 | Pulmonary tuberculosis | 4 | 3 | 1 |
| Psychiatric symptom | 3 | 4 | 1 | | | | |

[Fig. 3-51]

| | | | | | | | |
|---|---|---|---|---|---|---|---|
| Pulmonary valve incompetence | 3 | 4 | 1 | Radical hysterectomy | 4 | 4 | 0 |
| Pulmonary vasculitis | 4 | 4 | 0 | Radiculopathy | 3 | 4 | 1 |
| Pulmonary veno-occlusive disease | 4 | 4 | 0 | Radius fracture | 4 | 3 | 1 |
| Pulse abnormal | 3 | 3 | 0 | Rales | 3 | 3 | 0 |
| Pulse absent | 3 | 3 | 0 | Rapid eye movements sleep abnormal | 4 | 4 | 0 |
| Pulse pressure increased | 4 | 4 | 0 | | | | |
| Pulseless electrical activity | 3 | 3 | 0 | Rash erythematous | 3 | 3 | 0 |
| Punctate keratitis | 4 | 4 | 0 | Rash generalised | 3 | 3 | 0 |
| Pupillary disorder | 3 | 4 | 1 | Rash macular | 3 | 4 | 1 |
| Pupillary reflex impaired | 4 | 4 | 0 | Rash maculo-papular | 3 | 3 | 0 |
| Purpura | 3 | 3 | 0 | Rash morbilliform | 4 | 4 | 0 |
| Purulence | 4 | 4 | 0 | Rash papular | 3 | 4 | 1 |
| Purulent discharge | 3 | 3 | 0 | Rash pruritic | 3 | 3 | 0 |
| Purulent pericarditis | 4 | 4 | 0 | Rash pustular | 3 | 4 | 1 |
| Pyelocaliectasis | 4 | 4 | 0 | Rash vesicular | 3 | 4 | 1 |
| Pyelonephritis | 3 | 3 | 0 | Raynaud's phenomenon | 3 | 4 | 1 |
| Pyelonephritis acute | 3 | 4 | 1 | Reaction to colouring | 3 | 4 | 1 |
| Pyloric stenosis | 4 | 4 | 0 | Reaction to drug excipients | 3 | 4 | 1 |
| Pyoderma | 4 | 3 | 1 | Reaction to preservatives | 4 | 4 | 0 |
| Pyoderma gangrenosum | 4 | 4 | 0 | Reactive psychosis | 3 | 4 | 1 |
| Pyometra | 4 | 4 | 0 | Reading disorder | 4 | 4 | 0 |
| Pyopneumothorax | 4 | 4 | 0 | Rebound effect | 3 | 3 | 0 |
| Pyuria | 3 | 4 | 1 | Rebound psychosis | 3 | 4 | 1 |
| QRS axis abnormal | 3 | 4 | 1 | Rebound tachycardia | 4 | 4 | 0 |
| Quadrantanopia | 3 | 4 | 1 | Recall phenomenon | 4 | 4 | 0 |
| Quadriparesis | 4 | 4 | 0 | Rectal abscess | 4 | 4 | 0 |
| Quadriplegia | 4 | 4 | 0 | Rectal adenocarcinoma | 4 | 4 | 0 |
| Quality of life decreased | 3 | 3 | 0 | Rectal cancer | 4 | 3 | 1 |
| Rabbit syndrome | 3 | 4 | 1 | Rectal haemorrhage | 3 | 3 | 0 |
| Radial nerve palsy | 3 | 4 | 1 | Rectal perforation | 4 | 3 | 1 |
| Radiation associated haemorrhage | 4 | 4 | 0 | Rectal polyp | 4 | 4 | 0 |
| Radiation associated pain | 4 | 4 | 0 | Rectal prolapse | 3 | 4 | 1 |
| Radiation dysphagia | 4 | 4 | 0 | Rectal stenosis | 4 | 4 | 0 |
| Radiation injury | 4 | 4 | 0 | Rectal tenesmus | 4 | 4 | 0 |
| Radiation interaction | 4 | 4 | 0 | Rectal ulcer | 4 | 4 | 0 |
| Radiation mucositis | 4 | 4 | 0 | Rectal ulcer haemorrhage | 4 | 4 | 0 |
| Radiation oesophagitis | 4 | 4 | 0 | Recurrent cancer | 4 | 4 | 0 |
| Radiation pneumonitis | 4 | 4 | 0 | Red blood cell abnormality | 4 | 4 | 0 |
| Radiation sickness syndrome | 4 | 4 | 0 | Red blood cell count abnormal | 4 | 4 | 0 |
| Radiation skin injury | 4 | 4 | 0 | Red blood cell count decreased | 3 | 3 | 0 |

[Fig. 3-52]

| | | | |
|---|---|---|---|
| Red blood cell count increased | 4 | 3 | 1 |
| Red blood cell sedimentation rate | 4 | 4 | 0 |
| Red blood cell sedimentation rate increased | 3 | 3 | 0 |
| Red blood cells urine positive | 3 | 4 | 1 |
| Red cell distribution width decreased | 3 | 4 | 1 |
| Red cell distribution width increased | 3 | 3 | 0 |
| Reduced bladder capacity | 4 | 4 | 0 |
| Reduced facial expression | 4 | 4 | 0 |
| Refeeding syndrome | 4 | 4 | 0 |
| Reflexes abnormal | 4 | 4 | 0 |
| Refractory anaemia with an excess of blasts | 4 | 4 | 0 |
| Refractory cancer | 4 | 4 | 0 |
| Refractory cytopenia with multilineage dysplasia | 4 | 4 | 0 |
| Refractory cytopenia with unilineage dysplasia | 3 | 4 | 1 |
| Refusal of examination | 4 | 4 | 0 |
| Refusal of treatment by patient | 3 | 3 | 0 |
| Regressive behaviour | 3 | 4 | 1 |
| Regurgitation | 3 | 4 | 1 |
| Rehabilitation therapy | 4 | 4 | 0 |
| Relapsing fever | 4 | 4 | 0 |
| Remission not achieved | 3 | 4 | 1 |
| Renal aneurysm | 4 | 4 | 0 |
| Renal artery occlusion | 4 | 4 | 0 |
| Renal artery thrombosis | 4 | 4 | 0 |
| Renal atrophy | 3 | 4 | 1 |
| Renal cancer | 3 | 3 | 0 |
| Renal cancer recurrent | 4 | 4 | 0 |
| Renal cell carcinoma | 3 | 4 | 1 |
| Renal colic | 4 | 4 | 0 |
| Renal cyst | 3 | 3 | 0 |
| Renal disorder | 3 | 3 | 0 |
| Renal embolism | 4 | 4 | 0 |
| Renal failure | 3 | 3 | 0 |
| Renal failure acute | 3 | 3 | 0 |
| Renal failure chronic | 3 | 3 | 0 |
| Renal function test abnormal | 4 | 4 | 0 |

| | | | |
|---|---|---|---|
| Renal hypertension | 4 | 4 | 0 |
| Renal hypertrophy | 4 | 4 | 0 |
| Renal infarct | 4 | 4 | 0 |
| Renal injury | 4 | 4 | 0 |
| Renal ischaemia | 4 | 4 | 0 |
| Renal mass | 4 | 4 | 0 |
| Renal pain | 3 | 3 | 0 |
| Renal salt-wasting syndrome | 4 | 4 | 0 |
| Renal surgery | 4 | 4 | 0 |
| Renal transplant | 3 | 3 | 0 |
| Renal tubular atrophy | 4 | 4 | 0 |
| Renal tubular disorder | 4 | 4 | 0 |
| Renal tubular necrosis | 3 | 3 | 0 |
| Renal vein thrombosis | 4 | 3 | 1 |
| Renin increased | 4 | 4 | 0 |
| Reperfusion arrhythmia | 4 | 4 | 0 |
| Reproductive toxicity | 4 | 4 | 0 |
| Respiration abnormal | 3 | 4 | 1 |
| Respiratory acidosis | 3 | 3 | 0 |
| Respiratory alkalosis | 4 | 3 | 1 |
| Respiratory arrest | 3 | 3 | 0 |
| Respiratory depression | 3 | 3 | 0 |
| Respiratory disorder | 3 | 3 | 0 |
| Respiratory disorder neonatal | 4 | 4 | 0 |
| Respiratory distress | 3 | 3 | 0 |
| Respiratory dyskinesia | 3 | 4 | 1 |
| Respiratory failure | 3 | 3 | 0 |
| Respiratory fume inhalation disorder | 4 | 4 | 0 |
| Respiratory moniliasis | 4 | 4 | 0 |
| Respiratory paralysis | 4 | 4 | 0 |
| Respiratory rate decreased | 3 | 3 | 0 |
| Respiratory rate increased | 3 | 3 | 0 |
| Respiratory symptom | 4 | 4 | 0 |
| Respiratory syncytial virus infection | 3 | 4 | 1 |
| Respiratory syncytial virus test positive | 4 | 4 | 0 |
| Respiratory tract congestion | 3 | 3 | 0 |
| Respiratory tract haemorrhage | 4 | 4 | 0 |
| Respiratory tract infection | 3 | 3 | 0 |
| Respiratory tract infection bacterial | 4 | 4 | 0 |

[Fig. 3-53]

| | | | |
|---|---|---|---|
| Respiratory tract infection fungal | 4 | 4 | 0 |
| Respiratory tract oedema | 4 | 4 | 0 |
| Resting tremor | 3 | 4 | 1 |
| Restless legs syndrome | 3 | 3 | 0 |
| Restlessness | 3 | 3 | 0 |
| Restrictive pulmonary disease | 4 | 4 | 0 |
| Resuscitation | 4 | 3 | 1 |
| Retching | 3 | 3 | 0 |
| Reticulocyte count decreased | 4 | 4 | 0 |
| Reticulocytosis | 4 | 4 | 0 |
| Retinal artery occlusion | 4 | 4 | 0 |
| Retinal coloboma | 3 | 4 | 1 |
| Retinal degeneration | 3 | 4 | 1 |
| Retinal depigmentation | 4 | 4 | 0 |
| Retinal detachment | 3 | 4 | 1 |
| Retinal exudates | 4 | 4 | 0 |
| Retinal haemorrhage | 4 | 4 | 0 |
| Retinal infiltrates | 4 | 4 | 0 |
| Retinal ischaemia | 4 | 4 | 0 |
| Retinal neovascularisation | 4 | 4 | 0 |
| Retinal tear | 4 | 4 | 0 |
| Retinal toxicity | 4 | 4 | 0 |
| Retinal vasculitis | 4 | 4 | 0 |
| Retinal vein occlusion | 4 | 4 | 0 |
| Retinitis | 4 | 4 | 0 |
| Retinitis pigmentosa | 4 | 3 | 1 |
| Retinopathy | 4 | 3 | 1 |
| Retrograde ejaculation | 4 | 4 | 0 |
| Retroperitoneal abscess | 4 | 4 | 0 |
| Retroperitoneal fibrosis | 4 | 4 | 0 |
| Retroperitoneal lymphadenopathy | 4 | 4 | 0 |
| Retroperitoneal mass | 4 | 4 | 0 |
| Retroperitoneal neoplasm | 4 | 4 | 0 |
| Reversible cerebral vasoconstriction syndrome | 3 | 4 | 1 |
| Rhabdoid tumour | 4 | 4 | 0 |
| Rhabdomyolysis | 3 | 3 | 0 |
| Rheumatic disorder | 4 | 4 | 0 |
| Rheumatoid arthritis | 3 | 3 | 0 |
| Rhinitis | 3 | 3 | 0 |

| | | | |
|---|---|---|---|
| Rhinitis allergic | 4 | 3 | 1 |
| Rhinorrhoea | 3 | 3 | 0 |
| Rhinovirus infection | 4 | 4 | 0 |
| Rhonchi | 4 | 3 | 1 |
| Rib fracture | 3 | 3 | 0 |
| Richter's syndrome | 4 | 4 | 0 |
| Right ventricular dilatation | 4 | 4 | 0 |
| Right ventricular dysfunction | 4 | 4 | 0 |
| Right ventricular failure | 3 | 3 | 0 |
| Right ventricular hypertrophy | 4 | 4 | 0 |
| Road traffic accident | 3 | 3 | 0 |
| Roseolovirus test positive | 4 | 4 | 0 |
| Rotator cuff syndrome | 3 | 3 | 0 |
| Rubber sensitivity | 3 | 4 | 1 |
| Saccadic eye movement | 3 | 4 | 1 |
| Sacroiliitis | 4 | 4 | 0 |
| Saliva altered | 4 | 3 | 1 |
| Salivary gland atrophy | 4 | 4 | 0 |
| Salivary gland cancer | 4 | 3 | 1 |
| Salivary gland cancer recurrent | 4 | 4 | 0 |
| Salivary gland cancer stage IV | 4 | 4 | 0 |
| Salivary gland disorder | 4 | 4 | 0 |
| Salivary gland mucocoele | 4 | 4 | 0 |
| Salivary gland neoplasm | 4 | 4 | 0 |
| Salivary hypersecretion | 3 | 3 | 0 |
| Salmonella bacteraemia | 4 | 4 | 0 |
| Salmonella test positive | 4 | 4 | 0 |
| Salpingitis | 4 | 4 | 0 |
| Sarcoidosis | 4 | 3 | 1 |
| Sarcoma | 4 | 4 | 0 |
| Sarcoma metastatic | 4 | 4 | 0 |
| Sarcomatosis | 4 | 4 | 0 |
| Scab | 3 | 4 | 1 |
| Scapula fracture | 3 | 4 | 1 |
| Scar | 4 | 3 | 1 |
| Scedosporium infection | 4 | 4 | 0 |
| Schizoaffective disorder | 3 | 4 | 1 |
| Schizoaffective disorder bipolar type | 4 | 4 | 0 |
| Schizoaffective disorder depressive type | 3 | 4 | 1 |

[Fig. 3-54]

| | | | | | | | |
|---|---|---|---|---|---|---|---|
| Schizophrenia | 3 | 3 | 0 | Self esteem inflated | 3 | 4 | 1 |
| Schizophrenia, catatonic type | 3 | 4 | 1 | Self injurious behaviour | 3 | 4 | 1 |
| Schizophrenia, disorganised type | 4 | 4 | 0 | Semen analysis abnormal | 4 | 4 | 0 |
| Schizophrenia, paranoid type | 3 | 4 | 1 | Seminoma | 4 | 3 | 1 |
| Schizophrenia, residual type | 4 | 4 | 0 | Senile psychosis | 4 | 4 | 0 |
| Schizophreniform disorder | 3 | 4 | 1 | Sensation of foreign body | 3 | 4 | 1 |
| Schizotypal personality disorder | 4 | 4 | 0 | Sense of oppression | 4 | 4 | 0 |
| Sciatica | 3 | 4 | 1 | Sensorimotor disorder | 4 | 4 | 0 |
| Scleral disorder | 4 | 4 | 0 | Sensory disturbance | 3 | 3 | 0 |
| Scleroderma | 3 | 4 | 1 | Sensory loss | 3 | 3 | 0 |
| Scleroderma-like reaction | 4 | 4 | 0 | Sepsis | 3 | 3 | 0 |
| Scoliosis | 3 | 4 | 1 | Sepsis syndrome | 4 | 4 | 0 |
| Scratch | 3 | 4 | 1 | Septic arthritis streptococcal | 4 | 4 | 0 |
| Screaming | 3 | 4 | 1 | Septic embolus | 4 | 3 | 1 |
| Scrotal abscess | 4 | 4 | 0 | Septic encephalopathy | 4 | 4 | 0 |
| Scrotal haematoma | 3 | 4 | 1 | Septic shock | 3 | 3 | 0 |
| Scrotal mass | 4 | 4 | 0 | Seroconversion test positive | 4 | 4 | 0 |
| Scrotal oedema | 4 | 4 | 0 | Seroma | 4 | 4 | 0 |
| Scrotal swelling | 4 | 4 | 0 | Serositis | 4 | 4 | 0 |
| Seasonal affective disorder | 4 | 4 | 0 | Serotonin syndrome | 3 | 3 | 0 |
| Seasonal allergy | 4 | 3 | 1 | Serum ferritin decreased | 3 | 4 | 1 |
| Seborrhoea | 3 | 4 | 1 | Serum ferritin increased | 4 | 4 | 0 |
| Seborrhoeic dermatitis | 4 | 3 | 1 | Serum procollagen type I N-terminal propeptide increased | 4 | 4 | 0 |
| Seborrhoeic keratosis | 4 | 4 | 0 |
| Second primary malignancy | 4 | 4 | 0 | Serum sickness | 4 | 4 | 0 |
| Secondary adrenocortical insufficiency | 4 | 4 | 0 | Sever's disease | 3 | 4 | 1 |
| | | | | Severe invasive streptococcal infection | 4 | 4 | 0 |
| Secondary hypogonadism | 4 | 4 | 0 |
| Secondary immunodeficiency | 4 | 4 | 0 | Sexual abuse | 4 | 4 | 0 |
| Secretion discharge | 3 | 3 | 0 | Sexual activity increased | 3 | 4 | 1 |
| Sedation | 3 | 3 | 0 | Sexual dysfunction | 3 | 3 | 0 |
| Sedation complication | 3 | 3 | 0 | Sexual inhibition | 3 | 4 | 1 |
| Seizure | 3 | 3 | 0 | Sexually inappropriate behaviour | 3 | 4 | 1 |
| Seizure like phenomena | 3 | 3 | 0 | Shock | 3 | 3 | 0 |
| Selective eating disorder | 3 | 4 | 1 | Shock haemorrhagic | 3 | 3 | 0 |
| Selective mutism | 4 | 4 | 0 | Shock hypoglycaemic | 4 | 4 | 0 |
| Self-induced vomiting | 4 | 4 | 0 | Shock symptom | 4 | 4 | 0 |
| Self-injurious ideation | 3 | 4 | 1 | Short-bowel syndrome | 4 | 4 | 0 |
| Self-medication | 3 | 4 | 1 | Shoulder operation | 3 | 4 | 1 |
| Self esteem decreased | 3 | 4 | 1 | Shwachman-Diamond syndrome | 3 | 4 | 1 |

[Fig. 3-55]

| | | | | | | | |
|---|---|---|---|---|---|---|---|
| Sick sinus syndrome | 4 | 4 | 0 | Skin injury | 3 | 4 | 1 |
| Sickle cell anaemia | 4 | 4 | 0 | Skin irritation | 4 | 3 | 1 |
| Sickle cell anaemia with crisis | 3 | 4 | 1 | Skin lesion | 3 | 3 | 0 |
| Sideroblastic anaemia | 4 | 4 | 0 | Skin mass | 3 | 4 | 1 |
| Silent myocardial infarction | 4 | 4 | 0 | Skin necrosis | 3 | 4 | 1 |
| Simple partial seizures | 4 | 4 | 0 | Skin odour abnormal | 3 | 3 | 0 |
| Sinus arrest | 4 | 4 | 0 | Skin oedema | 4 | 4 | 0 |
| Sinus arrhythmia | 3 | 4 | 1 | Skin papilloma | 3 | 4 | 1 |
| Sinus bradycardia | 3 | 3 | 0 | Skin plaque | 3 | 4 | 1 |
| Sinus congestion | 3 | 3 | 0 | Skin reaction | 3 | 4 | 1 |
| Sinus disorder | 3 | 3 | 0 | Skin striae | 3 | 4 | 1 |
| Sinus headache | 4 | 4 | 0 | Skin test positive | 4 | 3 | 1 |
| Sinus node dysfunction | 4 | 4 | 0 | Skin tightness | 4 | 4 | 0 |
| Sinus pain | 3 | 4 | 1 | Skin toxicity | 4 | 4 | 0 |
| Sinus rhythm | 4 | 4 | 0 | Skin turgor decreased | 3 | 3 | 0 |
| Sinus tachycardia | 3 | 3 | 0 | Skin ulcer | 3 | 3 | 0 |
| Sinusitis | 3 | 3 | 0 | Skin warm | 4 | 4 | 0 |
| Sjogren's syndrome | 3 | 4 | 1 | Skin wound | 4 | 3 | 1 |
| Skeletal injury | 4 | 4 | 0 | Skin wrinkling | 3 | 4 | 1 |
| Skin abrasion | 3 | 4 | 1 | Skull fracture | 4 | 4 | 0 |
| Skin atrophy | 4 | 4 | 0 | Sleep-related eating disorder | 3 | 4 | 1 |
| Skin bacterial infection | 3 | 4 | 1 | Sleep apnoea syndrome | 3 | 3 | 0 |
| Skin burning sensation | 3 | 3 | 0 | Sleep attacks | 3 | 4 | 1 |
| Skin cancer | 3 | 4 | 1 | Sleep disorder | 3 | 3 | 0 |
| Skin candida | 4 | 4 | 0 | Sleep disorder due to a general medical condition | 4 | 4 | 0 |
| Skin depigmentation | 4 | 4 | 0 | Sleep paralysis | 3 | 4 | 1 |
| Skin discolouration | 3 | 3 | 0 | Sleep phase rhythm disturbance | 3 | 4 | 1 |
| Skin disorder | 4 | 3 | 1 | Sleep talking | 4 | 4 | 0 |
| Skin erosion | 3 | 4 | 1 | Sleep terror | 3 | 4 | 1 |
| Skin exfoliation | 3 | 3 | 0 | Slow response to stimuli | 3 | 3 | 0 |
| Skin fibrosis | 4 | 4 | 0 | Slow speech | 3 | 3 | 0 |
| Skin fissures | 4 | 4 | 0 | Sluggishness | 3 | 4 | 1 |
| Skin flap necrosis | 4 | 4 | 0 | Small cell carcinoma | 4 | 3 | 1 |
| Skin graft | 4 | 4 | 0 | Small cell lung cancer | 4 | 3 | 1 |
| Skin graft failure | 4 | 4 | 0 | Small cell lung cancer metastatic | 4 | 4 | 0 |
| Skin haemorrhage | 3 | 4 | 1 | Small for dates baby | 4 | 3 | 1 |
| Skin hyperpigmentation | 4 | 4 | 0 | Small intestinal haemorrhage | 4 | 4 | 0 |
| Skin hypertrophy | 3 | 4 | 1 | Small intestinal obstruction | 3 | 3 | 0 |
| Skin induration | 3 | 4 | 1 | Small intestinal perforation | 4 | 4 | 0 |
| Skin infection | 3 | 3 | 0 | | | | |

[Fig. 3-56]

| | | | | | | | |
|---|---|---|---|---|---|---|---|
| Small intestinal resection | 3 | 4 | 1 | Spinal disorder | 3 | 4 | 1 |
| Small intestine carcinoma | 4 | 4 | 0 | Spinal fracture | 3 | 4 | 1 |
| Small intestine ulcer | 4 | 4 | 0 | Spinal fusion surgery | 3 | 4 | 1 |
| Smoking cessation therapy | 4 | 4 | 0 | Spinal operation | 3 | 4 | 1 |
| Sneezing | 3 | 4 | 1 | Spinal osteoarthritis | 3 | 4 | 1 |
| Snoring | 4 | 3 | 1 | Spinal pain | 4 | 3 | 1 |
| Social (pragmatic) communication disorder | 4 | 4 | 0 | Spleen congestion | 3 | 4 | 1 |
| | | | | Spleen disorder | 4 | 3 | 1 |
| Social anxiety disorder | 3 | 4 | 1 | Splenectomy | 4 | 4 | 0 |
| Social avoidant behaviour | 3 | 4 | 1 | Splenic abscess | 4 | 4 | 0 |
| Social phobia | 3 | 4 | 1 | Splenic haematoma | 4 | 4 | 0 |
| Social problem | 3 | 4 | 1 | Splenic haemorrhage | 4 | 4 | 0 |
| Social stay hospitalisation | 3 | 4 | 1 | Splenic infarction | 4 | 4 | 0 |
| Soft tissue disorder | 4 | 4 | 0 | Splenic lesion | 4 | 4 | 0 |
| Soft tissue infection | 4 | 4 | 0 | Splenic rupture | 3 | 4 | 1 |
| Soft tissue mass | 4 | 4 | 0 | Splenic vein thrombosis | 3 | 4 | 1 |
| Soft tissue necrosis | 4 | 4 | 0 | Splenomegaly | 3 | 3 | 0 |
| Soliloquy | 3 | 4 | 1 | Spondylitis | 4 | 4 | 0 |
| Somatic delusion | 3 | 4 | 1 | Spondyloarthropathy | 4 | 4 | 0 |
| Somatic dysfunction | 4 | 4 | 0 | Spondylolisthesis | 3 | 4 | 1 |
| Somatic hallucination | 3 | 4 | 1 | Spontaneous ejaculation | 3 | 4 | 1 |
| Somatic symptom disorder | 3 | 4 | 1 | Spontaneous haematoma | 4 | 4 | 0 |
| Somatisation disorder | 4 | 4 | 0 | Spontaneous penile erection | 4 | 4 | 0 |
| Somatoform disorder | 3 | 4 | 1 | Sputum abnormal | 4 | 4 | 0 |
| Somnambulism | 3 | 4 | 1 | Sputum discoloured | 3 | 3 | 0 |
| Somnolence neonatal | 4 | 4 | 0 | Sputum purulent | 3 | 4 | 1 |
| Sopor | 3 | 3 | 0 | Sputum retention | 4 | 4 | 0 |
| Spasmodic dysphonia | 4 | 4 | 0 | Squamous cell carcinoma | 4 | 3 | 1 |
| Speech disorder | 3 | 3 | 0 | Squamous cell carcinoma of head and neck | 4 | 4 | 0 |
| Speech disorder developmental | 4 | 4 | 0 | Squamous cell carcinoma of lung | 4 | 4 | 0 |
| Spinal column injury | 4 | 4 | 0 | Squamous cell carcinoma of skin | 4 | 4 | 0 |
| Spinal column stenosis | 3 | 4 | 1 | Squamous cell carcinoma of the cervix | 4 | 4 | 0 |
| Spinal compression fracture | 4 | 4 | 0 | | | | |
| Spinal cord compression | 4 | 4 | 0 | Squamous cell carcinoma of the oral cavity | 4 | 4 | 0 |
| Spinal cord infarction | 4 | 4 | 0 | | | | |
| Spinal cord infection | 4 | 4 | 0 | Squamous cell carcinoma of the tongue | 4 | 4 | 0 |
| Spinal cord injury | 4 | 4 | 0 | | | | |
| Spinal cord ischaemia | 4 | 4 | 0 | Stab wound | 4 | 4 | 0 |
| Spinal cord neoplasm | 4 | 4 | 0 | Staphylococcal bacteraemia | 4 | 3 | 1 |
| Spinal cord oedema | 4 | 4 | 0 | | | | |

[Fig. 3-57]

| | | | | | | | |
|---|---|---|---|---|---|---|---|
| Staphylococcal infection | 3 | 3 | 0 | Streptococcal sepsis | 4 | 4 | 0 |
| Staphylococcal sepsis | 3 | 3 | 0 | Streptococcal urinary tract infection | 4 | 4 | 0 |
| Staphylococcal skin infection | 4 | 4 | 0 | Streptococcus test positive | 3 | 4 | 1 |
| Staphylococcus test positive | 4 | 3 | 1 | Stress cardiomyopathy | 3 | 3 | 0 |
| Staring | 3 | 3 | 0 | Stress urinary incontinence | 3 | 4 | 1 |
| Starvation | 3 | 3 | 0 | Stridor | 3 | 4 | 1 |
| Stasis dermatitis | 4 | 4 | 0 | Strongyloidiasis | 4 | 4 | 0 |
| Status asthmaticus | 3 | 4 | 1 | Stubbornness | 3 | 4 | 1 |
| Status epilepticus | 3 | 3 | 0 | Stupor | 3 | 3 | 0 |
| Steatohepatitis | 3 | 4 | 1 | Subacute cutaneous lupus erythematosus | 4 | 4 | 0 |
| Steatorrhoea | 4 | 4 | 0 | Subarachnoid haemorrhage | 3 | 3 | 0 |
| Stem cell transplant | 4 | 4 | 0 | Subclavian artery stenosis | 4 | 4 | 0 |
| Stenosis | 4 | 4 | 0 | Subclavian artery thrombosis | 4 | 4 | 0 |
| Stenotrophomonas infection | 4 | 4 | 0 | Subclavian steal syndrome | 4 | 4 | 0 |
| Stenotrophomonas sepsis | 4 | 4 | 0 | Subclavian vein thrombosis | 4 | 4 | 0 |
| Stenotrophomonas test positive | 4 | 4 | 0 | Subcutaneous abscess | 4 | 3 | 1 |
| Stent malfunction | 4 | 4 | 0 | Subcutaneous emphysema | 4 | 4 | 0 |
| Stent placement | 3 | 4 | 1 | Subcutaneous haematoma | 4 | 4 | 0 |
| Stereotypy | 3 | 4 | 1 | Subdiaphragmatic abscess | 4 | 4 | 0 |
| Sternal fracture | 4 | 4 | 0 | Subdural haematoma | 3 | 3 | 0 |
| Steroid withdrawal syndrome | 4 | 4 | 0 | Subdural haemorrhage | 3 | 3 | 0 |
| Stevens-Johnson syndrome | 3 | 3 | 0 | Subdural hygroma | 4 | 4 | 0 |
| Stillbirth | 3 | 4 | 1 | Subgaleal haematoma | 4 | 4 | 0 |
| Stoma complication | 4 | 4 | 0 | Subileus | 3 | 3 | 0 |
| Stoma site discharge | 4 | 4 | 0 | Subretinal fibrosis | 4 | 4 | 0 |
| Stoma site discomfort | 4 | 4 | 0 | Substance-induced mood disorder | 3 | 4 | 1 |
| Stoma site erythema | 4 | 4 | 0 | Substance-induced psychotic disorder | 3 | 4 | 1 |
| Stoma site extravasation | 4 | 3 | 1 | Substance abuse | 3 | 4 | 1 |
| Stoma site haemorrhage | 4 | 3 | 1 | Substance use | 4 | 4 | 0 |
| Stoma site hypergranulation | 4 | 4 | 0 | Substance use disorder | 3 | 4 | 1 |
| Stoma site infection | 4 | 3 | 1 | Sudden cardiac death | 3 | 3 | 0 |
| Stoma site inflammation | 4 | 4 | 0 | Sudden death | 3 | 3 | 0 |
| Stoma site irritation | 4 | 4 | 0 | Sudden hearing loss | 4 | 4 | 0 |
| Stoma site odour | 4 | 4 | 0 | Sudden onset of sleep | 3 | 4 | 1 |
| Stoma site pain | 4 | 4 | 0 | Sudden unexplained death in epilepsy | 4 | 4 | 0 |
| Stoma site reaction | 4 | 4 | 0 | | | | |
| Stomatitis | 3 | 3 | 0 | | | | |
| Strangulated hernia | 4 | 4 | 0 | | | | |
| Streptococcal bacteraemia | 4 | 4 | 0 | Suffocation feeling | 4 | 3 | 1 |
| Streptococcal infection | 3 | 4 | 1 | Suicidal behaviour | 3 | 4 | 1 |

[Fig. 3-58]

| | | | |
|---|---|---|---|
| Suicidal ideation | 3 | 3 | 0 |
| Suicide attempt | 3 | 3 | 0 |
| Suicide threat | 4 | 4 | 0 |
| Sunburn | 3 | 4 | 1 |
| Superinfection | 4 | 4 | 0 |
| Superinfection bacterial | 4 | 4 | 0 |
| Superior mesenteric artery syndrome | 4 | 4 | 0 |
| Superior sagittal sinus thrombosis | 4 | 4 | 0 |
| Superior vena cava occlusion | 4 | 4 | 0 |
| Superior vena cava syndrome | 4 | 4 | 0 |
| Suppressed lactation | 3 | 4 | 1 |
| Suprapubic pain | 4 | 4 | 0 |
| Supraventricular extrasystoles | 3 | 3 | 0 |
| Supraventricular tachycardia | 3 | 3 | 0 |
| Surgery | 3 | 3 | 0 |
| Suspiciousness | 3 | 4 | 1 |
| Suture related complication | 4 | 4 | 0 |
| Suture rupture | 4 | 4 | 0 |
| Sweat gland disorder | 3 | 4 | 1 |
| Swelling face | 3 | 3 | 0 |
| Swollen tongue | 3 | 3 | 0 |
| Sycosis barbae | 4 | 4 | 0 |
| Symptom masked | 4 | 4 | 0 |
| Synovial sarcoma | 4 | 4 | 0 |
| Syphilis | 3 | 4 | 1 |
| Syringe issue | 3 | 4 | 1 |
| Systemic candida | 4 | 4 | 0 |
| Systemic infection | 4 | 4 | 0 |
| Systemic inflammatory response syndrome | 4 | 3 | 1 |
| Systemic lupus erythematosus | 3 | 4 | 1 |
| Systemic mycosis | 4 | 4 | 0 |
| Systolic dysfunction | 3 | 3 | 0 |
| Tachyarrhythmia | 3 | 4 | 1 |
| Tachycardia | 3 | 3 | 0 |
| Tachycardia foetal | 3 | 4 | 1 |
| Tachycardia paroxysmal | 3 | 4 | 1 |
| Tachyphrenia | 3 | 4 | 1 |
| Tachypnoea | 3 | 3 | 0 |
| Talipes | 3 | 4 | 1 |
| Tangentiality | 3 | 4 | 1 |
| Tardive dyskinesia | 3 | 4 | 1 |
| Tearfulness | 3 | 3 | 0 |
| Teeth brittle | 4 | 4 | 0 |
| Telangiectasia | 4 | 4 | 0 |
| Temperature intolerance | 4 | 4 | 0 |
| Temperature regulation disorder | 3 | 4 | 1 |
| Temporal lobe epilepsy | 4 | 4 | 0 |
| Temporomandibular joint syndrome | 4 | 4 | 0 |
| Tenderness | 3 | 3 | 0 |
| Tendon disorder | 3 | 4 | 1 |
| Tendon injury | 4 | 3 | 1 |
| Tendon pain | 3 | 3 | 0 |
| Tendon rupture | 3 | 3 | 0 |
| Tendonitis | 3 | 3 | 0 |
| Tension | 3 | 4 | 1 |
| Teratoma | 4 | 4 | 0 |
| Teratoma benign | 4 | 4 | 0 |
| Terminal insomnia | 3 | 4 | 1 |
| Terminal state | 3 | 3 | 0 |
| Testicular cancer metastatic | 4 | 3 | 1 |
| Testicular choriocarcinoma stage III | 4 | 4 | 0 |
| Testicular disorder | 4 | 4 | 0 |
| Testicular failure | 4 | 4 | 0 |
| Testicular germ cell cancer | 4 | 4 | 0 |
| Testicular germ cell cancer metastatic | 4 | 3 | 1 |
| Testicular germ cell tumour mixed stage III | 4 | 4 | 0 |
| Testicular infarction | 4 | 4 | 0 |
| Testicular injury | 4 | 4 | 0 |
| Testicular malignant teratoma | 4 | 4 | 0 |
| Testicular pain | 3 | 4 | 1 |
| Testis cancer | 4 | 3 | 1 |
| Tetany | 4 | 4 | 0 |
| Thalamic infarction | 4 | 4 | 0 |
| Thalamus haemorrhage | 4 | 4 | 0 |
| Thanatophobia | 4 | 4 | 0 |
| Therapeutic aspiration | 3 | 4 | 1 |
| Therapeutic procedure | 4 | 4 | 0 |
| Therapeutic product cross-reactivity | 4 | 4 | 0 |

[Fig. 3-59]

| | | | | | | | |
|---|---|---|---|---|---|---|---|
| Therapeutic product ineffective | 3 | 3 | 0 | Thymoma malignant recurrent | 4 | 4 | 0 |
| Therapeutic response changed | 3 | 3 | 0 | Thyroid adenoma | 4 | 4 | 0 |
| Therapeutic response decreased | 3 | 3 | 0 | Thyroid cancer | 4 | 3 | 1 |
| Therapeutic response delayed | 4 | 4 | 0 | Thyroid cancer metastatic | 4 | 4 | 0 |
| Therapeutic response increased | 4 | 4 | 0 | Thyroid disorder | 3 | 3 | 0 |
| Therapeutic response shortened | 3 | 4 | 1 | Thyroid function test abnormal | 4 | 4 | 0 |
| Therapeutic response unexpected | 3 | 3 | 0 | Thyroid hormones increased | 4 | 4 | 0 |
| Therapy change | 3 | 3 | 0 | Thyroid mass | 3 | 4 | 1 |
| Therapy non-responder | 3 | 3 | 0 | Thyroid neoplasm | 4 | 3 | 1 |
| Therapy partial responder | 4 | 4 | 0 | Thyroidectomy | 3 | 4 | 1 |
| Therapy responder | 4 | 3 | 1 | Thyroiditis | 4 | 4 | 0 |
| Thermal burn | 3 | 3 | 0 | Thyroxine free decreased | 4 | 4 | 0 |
| Thermohyperaesthesia | 4 | 4 | 0 | Thyroxine free increased | 4 | 4 | 0 |
| Thinking abnormal | 3 | 4 | 1 | Tibia fracture | 4 | 3 | 1 |
| Thirst | 3 | 3 | 0 | Tic | 3 | 4 | 1 |
| Thirst decreased | 4 | 4 | 0 | Time perception altered | 4 | 4 | 0 |
| Thoracic vertebral fracture | 4 | 4 | 0 | Tinea pedis | 3 | 4 | 1 |
| Thought blocking | 3 | 3 | 0 | Tinea versicolour | 3 | 4 | 1 |
| Throat irritation | 3 | 3 | 0 | Tinnitus | 3 | 3 | 0 |
| Throat tightness | 3 | 3 | 0 | Tobacco abuse | 4 | 4 | 0 |
| Thrombectomy | 3 | 4 | 1 | Tobacco interaction | 4 | 4 | 0 |
| Thromboangiitis obliterans | 4 | 4 | 0 | Tobacco user | 3 | 4 | 1 |
| Thrombocytopenia | 3 | 3 | 0 | Tobacco withdrawal symptoms | 3 | 4 | 1 |
| Thrombocytopenia neonatal | 4 | 4 | 0 | Toe amputation | 3 | 3 | 0 |
| Thrombocytopenic purpura | 4 | 4 | 0 | Tongue abscess | 4 | 4 | 0 |
| Thrombocytosis | 4 | 3 | 1 | Tongue biting | 3 | 4 | 1 |
| Thrombolysis | 3 | 4 | 1 | Tongue discolouration | 3 | 4 | 1 |
| Thrombophlebitis | 3 | 3 | 0 | Tongue discomfort | 4 | 4 | 0 |
| Thrombophlebitis septic | 4 | 4 | 0 | Tongue disorder | 3 | 3 | 0 |
| Thrombophlebitis superficial | 3 | 4 | 1 | Tongue haemorrhage | 3 | 4 | 1 |
| Thrombosis | 3 | 3 | 0 | Tongue injury | 4 | 4 | 0 |
| Thrombosis in device | 3 | 4 | 1 | Tongue movement disturbance | 4 | 4 | 0 |
| Thrombosis mesenteric vessel | 3 | 4 | 1 | Tongue neoplasm | 4 | 4 | 0 |
| Thrombotic microangiopathy | 3 | 4 | 1 | Tongue neoplasm malignant stage unspecified | 4 | 4 | 0 |
| Thrombotic stroke | 4 | 4 | 0 | Tongue oedema | 3 | 3 | 0 |
| Thrombotic thrombocytopenic purpura | 4 | 4 | 0 | Tongue paralysis | 4 | 4 | 0 |
| Thymic cancer metastatic | 4 | 4 | 0 | Tongue ulceration | 3 | 4 | 1 |
| Thymoma | 4 | 4 | 0 | Tonic clonic movements | 4 | 3 | 1 |
| Thymoma malignant | 4 | 4 | 0 | Tonic convulsion | 3 | 4 | 1 |

[Fig. 3-60]

| | | | | | | | |
|---|---|---|---|---|---|---|---|
| Tonsil cancer | 4 | 4 | 0 | Tracheitis | 4 | 4 | 0 |
| Tonsillar disorder | 4 | 4 | 0 | Tracheo-oesophageal fistula | 4 | 4 | 0 |
| Tonsillar hypertrophy | 4 | 4 | 0 | Tracheobronchitis | 3 | 4 | 1 |
| Tonsillar ulcer | 4 | 4 | 0 | Tracheostomy | 4 | 4 | 0 |
| Tonsillitis | 3 | 4 | 1 | Tracheostomy malfunction | 4 | 4 | 0 |
| Tooth abscess | 3 | 3 | 0 | Transaminases | 4 | 4 | 0 |
| Tooth crowding | 4 | 4 | 0 | Transaminases abnormal | 4 | 4 | 0 |
| Tooth discolouration | 4 | 3 | 1 | Transaminases increased | 3 | 3 | 0 |
| Tooth disorder | 3 | 4 | 1 | Transferrin decreased | 4 | 4 | 0 |
| Tooth erosion | 4 | 4 | 0 | Transferrin saturation decreased | 4 | 4 | 0 |
| Tooth extraction | 3 | 4 | 1 | Transfusion | 3 | 4 | 1 |
| Tooth fracture | 3 | 3 | 0 | Transfusion reaction | 4 | 4 | 0 |
| Tooth hypoplasia | 4 | 4 | 0 | Transfusion related complication | 4 | 4 | 0 |
| Tooth infection | 3 | 4 | 1 | Transient ischaemic attack | 3 | 3 | 0 |
| Tooth injury | 4 | 4 | 0 | Transient tachypnoea of the newborn | 4 | 4 | 0 |
| Tooth loss | 3 | 3 | 0 | Transitional cell cancer of the renal pelvis and ureter | 4 | 4 | 0 |
| Tooth malformation | 4 | 4 | 0 | Transitional cell carcinoma | 4 | 4 | 0 |
| Tooth repair | 3 | 4 | 1 | Transitional cell carcinoma recurrent | 4 | 4 | 0 |
| Tooth socket haemorrhage | 4 | 4 | 0 | Transplant evaluation | 4 | 4 | 0 |
| Toothache | 3 | 3 | 0 | Transplant failure | 4 | 4 | 0 |
| Torsade de pointes | 3 | 3 | 0 | Transposition of the great vessels | 3 | 4 | 1 |
| Torticollis | 3 | 4 | 1 | Transverse sinus thrombosis | 4 | 4 | 0 |
| Torulopsis infection | 4 | 4 | 0 | Traumatic arthropathy | 4 | 4 | 0 |
| Total cholesterol/HDL ratio increased | 4 | 4 | 0 | Traumatic haemothorax | 4 | 4 | 0 |
| Tourette's disorder | 3 | 4 | 1 | Traumatic intracranial haemorrhage | 4 | 4 | 0 |
| Toxic encephalopathy | 4 | 3 | 1 | Traumatic lung injury | 4 | 4 | 0 |
| Toxic epidermal necrolysis | 3 | 3 | 0 | Treatment failure | 3 | 3 | 0 |
| Toxic neuropathy | 4 | 4 | 0 | Treatment noncompliance | 3 | 3 | 0 |
| Toxic shock syndrome | 4 | 4 | 0 | Tremor | 3 | 3 | 0 |
| Toxic shock syndrome streptococcal | 4 | 4 | 0 | Tremor neonatal | 3 | 4 | 1 |
| Toxic skin eruption | 3 | 3 | 0 | Tri-iodothyronine free increased | 4 | 4 | 0 |
| Toxicity to various agents | 3 | 3 | 0 | Trichoglossia | 3 | 4 | 1 |
| Toxicologic test abnormal | 4 | 4 | 0 | Trichomegaly | 4 | 4 | 0 |
| Toxoplasmosis | 4 | 4 | 0 | Trichomoniasis | 4 | 4 | 0 |
| Tracheal disorder | 4 | 4 | 0 | Trichophytic granuloma | 4 | 4 | 0 |
| Tracheal fistula | 4 | 4 | 0 | Trichosporon infection | 4 | 4 | 0 |
| Tracheal haemorrhage | 4 | 4 | 0 | Trichotillomania | 3 | 4 | 1 |
| Tracheal obstruction | 4 | 4 | 0 | Tricuspid valve incompetence | 3 | 3 | 0 |
| Tracheal pain | 4 | 4 | 0 | Trifascicular block | 4 | 4 | 0 |
| Tracheal stenosis | 3 | 4 | 1 | | | | |

[Fig. 3-61]

| | | | |
|---|---|---|---|
| Trigeminal nerve paresis | 4 | 4 | 0 |
| Trigeminal palsy | 4 | 4 | 0 |
| Trigger finger | 3 | 4 | 1 |
| Trimethylaminuria | 3 | 4 | 1 |
| Trismus | 3 | 3 | 0 |
| Trisomy 8 | 4 | 4 | 0 |
| Troponin I increased | 3 | 3 | 0 |
| Troponin increased | 3 | 3 | 0 |
| Troponin T increased | 3 | 3 | 0 |
| Trousseau's syndrome | 4 | 4 | 0 |
| Truncus coeliacus thrombosis | 4 | 4 | 0 |
| Tuberculoid leprosy | 4 | 4 | 0 |
| Tuberculosis | 3 | 3 | 0 |
| Tuberculous pleurisy | 4 | 4 | 0 |
| Tubular breast carcinoma | 3 | 4 | 1 |
| Tubulointerstitial nephritis | 3 | 3 | 0 |
| Tumour embolism | 4 | 4 | 0 |
| Tumour excision | 4 | 4 | 0 |
| Tumour flare | 4 | 4 | 0 |
| Tumour haemorrhage | 4 | 4 | 0 |
| Tumour invasion | 4 | 4 | 0 |
| Tumour lysis syndrome | 4 | 4 | 0 |
| Tumour marker abnormal | 4 | 4 | 0 |
| Tumour marker increased | 3 | 4 | 1 |
| Tumour necrosis | 4 | 4 | 0 |
| Tumour pain | 4 | 4 | 0 |
| Tumour perforation | 4 | 4 | 0 |
| Tumour rupture | 4 | 4 | 0 |
| Tumour thrombosis | 4 | 4 | 0 |
| Tumour ulceration | 4 | 4 | 0 |
| Tunnel vision | 3 | 4 | 1 |
| Twin pregnancy | 3 | 4 | 1 |
| Tympanic membrane disorder | 4 | 4 | 0 |
| Type 1 diabetes mellitus | 3 | 3 | 0 |
| Type 1 lepra reaction | 4 | 4 | 0 |
| Type 2 diabetes mellitus | 3 | 3 | 0 |
| Type I hypersensitivity | 4 | 3 | 1 |
| Type II hypersensitivity | 4 | 4 | 0 |
| Type IV hypersensitivity reaction | 4 | 4 | 0 |
| Type V hyperlipidaemia | 4 | 4 | 0 |

| | | | |
|---|---|---|---|
| Ulcer | 4 | 3 | 1 |
| Ulcer haemorrhage | 4 | 4 | 0 |
| Ulcerative keratitis | 4 | 4 | 0 |
| Ulna fracture | 4 | 4 | 0 |
| Ultrasound abdomen abnormal | 4 | 4 | 0 |
| Ultrasound scan abnormal | 4 | 4 | 0 |
| Umbilical cord around neck | 3 | 4 | 1 |
| Umbilical hernia | 3 | 4 | 1 |
| Umbilical hernia repair | 3 | 4 | 1 |
| Underdose | 3 | 3 | 0 |
| Underweight | 3 | 4 | 1 |
| Unevaluable event | 3 | 3 | 0 |
| Unintentional medical device removal | 4 | 3 | 1 |
| Unresponsive to stimuli | 3 | 3 | 0 |
| Upper-airway cough syndrome | 4 | 3 | 1 |
| Upper airway necrosis | 4 | 4 | 0 |
| Upper airway obstruction | 3 | 4 | 1 |
| Upper extremity mass | 4 | 4 | 0 |
| Upper gastrointestinal haemorrhage | 3 | 3 | 0 |
| Upper limb fracture | 3 | 3 | 0 |
| Upper respiratory tract infection | 3 | 3 | 0 |
| Upper respiratory tract inflammation | 3 | 4 | 1 |
| Urachal abnormality | 4 | 4 | 0 |
| Uraemic encephalopathy | 4 | 4 | 0 |
| Ureteral disorder | 4 | 4 | 0 |
| Ureteric obstruction | 4 | 3 | 1 |
| Ureteric rupture | 4 | 4 | 0 |
| Ureteric stenosis | 4 | 4 | 0 |
| Ureteritis | 4 | 4 | 0 |
| Ureterolithiasis | 4 | 4 | 0 |
| Urethral cancer | 4 | 4 | 0 |
| Urethral cancer metastatic | 4 | 4 | 0 |
| Urethral pain | 4 | 4 | 0 |
| Urethral stenosis | 4 | 4 | 0 |
| Urge incontinence | 4 | 4 | 0 |
| Urinary bladder haemorrhage | 4 | 4 | 0 |
| Urinary bladder rupture | 3 | 4 | 1 |
| Urinary bladder suspension | 4 | 4 | 0 |
| Urinary bladder toxicity | 4 | 4 | 0 |

[Fig. 3-62]

| | | | | | | | | |
|---|---|---|---|---|---|---|---|---|
| Urinary fistula | 4 | 4 | 0 | | Uterine haemorrhage | 4 | 4 | 0 |
| Urinary hesitation | 3 | 3 | 0 | | Uterine leiomyoma | 3 | 4 | 1 |
| Urinary incontinence | 3 | 3 | 0 | | Uterine perforation | 4 | 4 | 0 |
| Urinary retention | 3 | 3 | 0 | | Uterine polyp | 4 | 4 | 0 |
| Urinary straining | 4 | 4 | 0 | | Uterine spasm | 3 | 4 | 1 |
| Urinary tract disorder | 3 | 4 | 1 | | Uveitis | 4 | 4 | 0 |
| Urinary tract infection | 3 | 3 | 0 | | Vaccine virus shedding | 4 | 4 | 0 |
| Urinary tract infection bacterial | 4 | 4 | 0 | | Vaginal discharge | 4 | 4 | 0 |
| Urinary tract infection enterococcal | 3 | 4 | 1 | | Vaginal disorder | 4 | 4 | 0 |
| Urinary tract infection pseudomonal | 3 | 4 | 1 | | Vaginal haematoma | 4 | 4 | 0 |
| Urinary tract malformation | 3 | 4 | 1 | | Vaginal haemorrhage | 3 | 3 | 0 |
| Urinary tract obstruction | 4 | 3 | 1 | | Vaginal infection | 4 | 4 | 0 |
| Urinary tract pain | 4 | 4 | 0 | | Vaginal inflammation | 4 | 4 | 0 |
| Urinary tract stoma complication | 4 | 4 | 0 | | Vaginal perforation | 4 | 4 | 0 |
| Urine abnormality | 4 | 4 | 0 | | Vanishing bile duct syndrome | 3 | 4 | 1 |
| Urine analysis abnormal | 4 | 4 | 0 | | Varicella | 3 | 4 | 1 |
| Urine electrolytes increased | 4 | 4 | 0 | | Varicella post vaccine | 4 | 4 | 0 |
| Urine flow decreased | 4 | 4 | 0 | | Varicella virus test positive | 4 | 4 | 0 |
| Urine ketone body | 4 | 4 | 0 | | Varicella zoster virus infection | 4 | 4 | 0 |
| Urine ketone body absent | 4 | 4 | 0 | | Varices oesophageal | 4 | 4 | 0 |
| Urine ketone body present | 3 | 3 | 0 | | Varicose ulceration | 4 | 4 | 0 |
| Urine leukocyte esterase positive | 4 | 4 | 0 | | Varicose vein | 3 | 4 | 1 |
| Urine odour abnormal | 4 | 4 | 0 | | Vascular access complication | 4 | 4 | 0 |
| Urine osmolarity increased | 4 | 3 | 1 | | Vascular calcification | 4 | 4 | 0 |
| Urine output decreased | 3 | 3 | 0 | | Vascular dissection | 4 | 4 | 0 |
| Urine output increased | 3 | 4 | 1 | | Vascular graft | 3 | 4 | 1 |
| Urine sodium increased | 4 | 4 | 0 | | Vascular headache | 3 | 4 | 1 |
| Urobilinogen urine increased | 4 | 4 | 0 | | Vascular injury | 4 | 4 | 0 |
| Urogenital disorder | 4 | 4 | 0 | | Vascular occlusion | 4 | 4 | 0 |
| Urogenital fistula | 4 | 4 | 0 | | Vascular pain | 4 | 4 | 0 |
| Urogenital haemorrhage | 4 | 4 | 0 | | Vascular parkinsonism | 3 | 4 | 1 |
| Urogenital infection bacterial | 4 | 4 | 0 | | Vascular pseudoaneurysm | 4 | 4 | 0 |
| Urosepsis | 3 | 3 | 0 | | Vascular resistance pulmonary increased | 4 | 4 | 0 |
| Urticaria | 3 | 3 | 0 | | | | | |
| Uterine cancer | 4 | 4 | 0 | | Vascular stent stenosis | 4 | 4 | 0 |
| Uterine contractions during pregnancy | 3 | 4 | 1 | | Vasculitis | 3 | 3 | 0 |
| | | | | | Vasculitis cerebral | 4 | 4 | 0 |
| Uterine dilation and curettage | 3 | 4 | 1 | | Vasculitis necrotising | 4 | 4 | 0 |
| Uterine disorder | 4 | 4 | 0 | | Vasoconstriction | 4 | 4 | 0 |
| Uterine enlargement | 3 | 4 | 1 | | Vasodilatation | 4 | 4 | 0 |

[Fig. 3-63]

| | | | | | | | |
|---|---|---|---|---|---|---|---|
| Vasospasm | 4 | 4 | 0 | VIIth nerve paralysis | 3 | 3 | 0 |
| Veillonella infection | 4 | 4 | 0 | Violence-related symptom | 3 | 4 | 1 |
| Vein disorder | 4 | 4 | 0 | Viraemia | 4 | 4 | 0 |
| Vena cava embolism | 4 | 4 | 0 | Viral infection | 3 | 3 | 0 |
| Vena cava thrombosis | 4 | 4 | 0 | Viral load increased | 4 | 4 | 0 |
| Venoocclusive disease | 4 | 4 | 0 | Viral mutation identified | 4 | 4 | 0 |
| Venoocclusive liver disease | 4 | 3 | 1 | Viral myocarditis | 4 | 3 | 1 |
| Venous aneurysm | 4 | 4 | 0 | Viral pericarditis | 4 | 3 | 1 |
| Venous occlusion | 4 | 4 | 0 | Viral rash | 4 | 4 | 0 |
| Venous oxygen partial pressure decreased | 4 | 4 | 0 | Viral upper respiratory tract infection | 3 | 3 | 0 |
| Venous stenosis | 4 | 4 | 0 | Virologic failure | 4 | 4 | 0 |
| Venous thrombosis | 3 | 4 | 1 | Visceral arterial ischaemia | 4 | 4 | 0 |
| Venous thrombosis limb | 4 | 3 | 1 | Visceral congestion | 3 | 4 | 1 |
| Ventricular arrhythmia | 3 | 3 | 0 | Visceral oedema | 3 | 4 | 1 |
| Ventricular dysfunction | 4 | 3 | 1 | Visceral venous thrombosis | 4 | 4 | 0 |
| Ventricular dyskinesia | 3 | 4 | 1 | Vision blurred | 3 | 3 | 0 |
| Ventricular extrasystoles | 3 | 3 | 0 | Visual acuity reduced | 3 | 3 | 0 |
| Ventricular failure | 4 | 4 | 0 | Visual acuity reduced transiently | 4 | 4 | 0 |
| Ventricular fibrillation | 3 | 4 | 1 | Visual field defect | 3 | 4 | 1 |
| Ventricular hypertrophy | 3 | 4 | 1 | Visual impairment | 3 | 3 | 0 |
| Ventricular hypokinesia | 3 | 3 | 0 | Vital capacity decreased | 4 | 4 | 0 |
| Ventricular septal defect | 3 | 3 | 0 | Vitamin B complex deficiency | 4 | 4 | 0 |
| Ventricular tachyarrhythmia | 3 | 4 | 1 | Vitamin B1 decreased | 4 | 4 | 0 |
| Ventricular tachycardia | 3 | 3 | 0 | Vitamin B12 decreased | 3 | 4 | 1 |
| Verbal abuse | 3 | 4 | 1 | Vitamin B12 deficiency | 3 | 4 | 1 |
| Verbigeration | 4 | 4 | 0 | Vitamin B12 increased | 4 | 4 | 0 |
| Vertebral lesion | 4 | 4 | 0 | Vitamin D abnormal | 4 | 4 | 0 |
| Vertebral osteophyte | 4 | 4 | 0 | Vitamin D decreased | 3 | 4 | 1 |
| Vertebroplasty | 4 | 4 | 0 | Vitamin D deficiency | 3 | 4 | 1 |
| Vertigo | 3 | 3 | 0 | Vitamin D increased | 4 | 4 | 0 |
| Vertigo positional | 4 | 4 | 0 | Vitamin K deficiency | 4 | 4 | 0 |
| Very low density lipoprotein increased | 3 | 4 | 1 | Vitello-intestinal duct remnant | 4 | 4 | 0 |
| | | | | VIth nerve paralysis | 4 | 4 | 0 |
| Vesical fistula | 4 | 4 | 0 | Vitiligo | 3 | 4 | 1 |
| Vessel puncture site haemorrhage | 3 | 4 | 1 | Vitreous haemorrhage | 4 | 4 | 0 |
| Vestibular disorder | 4 | 4 | 0 | Vitritis | 4 | 4 | 0 |
| Victim of abuse | 4 | 4 | 0 | Vocal cord disorder | 4 | 4 | 0 |
| Victim of crime | 3 | 4 | 1 | Vocal cord inflammation | 4 | 4 | 0 |
| | | | | Vocal cord paralysis | 4 | 4 | 0 |
| Victim of homicide | 4 | 4 | 0 | Volume blood decreased | 3 | 4 | 1 |

[Fig. 3-64]

| | | | |
|---|---|---|---|
| Volvulus | 3 | 3 | 0 |
| Volvulus of small bowel | 4 | 4 | 0 |
| Vomiting in pregnancy | 3 | 4 | 1 |
| Vomiting projectile | 3 | 4 | 1 |
| Vulval cancer recurrent | 4 | 4 | 0 |
| Vulval disorder | 3 | 4 | 1 |
| Vulval ulceration | 4 | 4 | 0 |
| Vulvovaginal adhesion | 4 | 4 | 0 |
| Vulvovaginal candidiasis | 4 | 4 | 0 |
| Vulvovaginal discomfort | 4 | 4 | 0 |
| Vulvovaginal erythema | 4 | 4 | 0 |
| Vulvovaginal inflammation | 4 | 4 | 0 |
| Vulvovaginal mycotic infection | 4 | 4 | 0 |
| Vulvovaginal pain | 4 | 4 | 0 |
| Vulvovaginal swelling | 3 | 4 | 1 |
| Waist circumference increased | 4 | 4 | 0 |
| Walking aid user | 4 | 4 | 0 |
| Walking disability | 4 | 3 | 1 |
| Water intoxication | 3 | 3 | 0 |
| Waxy flexibility | 3 | 4 | 1 |
| Weaning failure | 4 | 3 | 1 |
| Weight abnormal | 3 | 4 | 1 |
| Weight bearing difficulty | 4 | 4 | 0 |
| Weight decrease neonatal | 3 | 4 | 1 |
| Weight fluctuation | 3 | 3 | 0 |
| Weight gain poor | 3 | 4 | 1 |
| Weight loss poor | 3 | 4 | 1 |
| Wernicke's encephalopathy | 4 | 4 | 0 |
| Wheelchair user | 4 | 3 | 1 |
| Wheezing | 3 | 3 | 0 |
| Whipple's disease | 4 | 4 | 0 |
| White blood cell analysis abnormal | 4 | 4 | 0 |
| White blood cell count | 4 | 4 | 0 |
| White blood cell count abnormal | 3 | 3 | 0 |
| White blood cell count decreased | 3 | 3 | 0 |
| White blood cell count increased | 3 | 3 | 0 |

| | | | |
|---|---|---|---|
| White blood cell disorder | 4 | 3 | 1 |
| White blood cells urine positive | 3 | 4 | 1 |
| White matter lesion | 3 | 4 | 1 |
| Wisdom teeth removal | 3 | 4 | 1 |
| Withdrawal syndrome | 3 | 3 | 0 |
| Wolff-Parkinson-White syndrome | 3 | 3 | 0 |
| Wound | 3 | 3 | 0 |
| Wound abscess | 4 | 4 | 0 |
| Wound complication | 4 | 4 | 0 |
| Wound decomposition | 4 | 4 | 0 |
| Wound dehiscence | 3 | 4 | 1 |
| Wound drainage | 4 | 4 | 0 |
| Wound evisceration | 4 | 4 | 0 |
| Wound haemorrhage | 3 | 4 | 1 |
| Wound infection | 3 | 3 | 0 |
| Wound infection bacterial | 4 | 4 | 0 |
| Wound infection pseudomonas | 3 | 4 | 1 |
| Wound infection staphylococcal | 3 | 4 | 1 |
| Wound secretion | 4 | 4 | 0 |
| Wrist fracture | 4 | 3 | 1 |
| Wrong drug administered | 3 | 3 | 0 |
| Wrong patient received medication | 3 | 4 | 1 |
| Wrong technique in device usage process | 3 | 4 | 1 |
| Wrong technique in drug usage process | 3 | 3 | 0 |
| Wrong technique in product usage process | 3 | 3 | 0 |
| X-ray abnormal | 3 | 4 | 1 |
| Xanthelasma | 4 | 4 | 0 |
| Xanthogranuloma | 4 | 4 | 0 |
| Xanthoma | 4 | 4 | 0 |
| Xeroderma | 4 | 4 | 0 |
| Xerophthalmia | 3 | 4 | 1 |
| Yellow skin | 3 | 4 | 1 |
| Zygomycosis | 4 | 4 | 0 |

[Fig. 4]

| Pharmacokinetic label | Unit |
|---|---|
| bioavailability | % |
| volume of Distribution | L/kg |
| half life | h |
| clearance | L/h |
| protein binding | % |

[Fig. 5]

| | Heart_Alas2 | Heart_Apod | Heart_Cd74 | Heart_Col15a1 | Heart_Fmo2 | Paroti dG_Alas2 | Paroti dG_Apod | Paroti dG_Cd74 | Paroti dG_Col15a1 | Paroti dG_Fmo2 | Pituit aryG_Alas2 | Pituit aryG_Apod | Pituit aryG_Cd74 | Pituit aryG_Col15a1 | Pituit aryG_Fmo2 | Skin_Alas2 | Skin_Apod | Skin_Cd74 | Skin_Col15a1 | Skin_Fmo2 | WAT_Alas2 | WAT_Apod | WAT_Cd74 | WAT_Col15a1 | WAT_Fmo2 |
|---|---|---|---|---|---|---|---|---|---|---|---|---|---|---|---|---|---|---|---|---|---|---|---|---|---|
| Aripiprazole | -0.20 | -0.39 | 0.16 | 0.07 | 0.40 | -1.13 | 0.26 | -0.08 | -0.12 | -0.23 | 0.32 | -0.19 | 0.02 | 0.16 | 0.19 | -0.28 | -0.13 | -0.28 | 0.35 | -0.02 | -0.58 | 1.56 | 0.21 | -0.24 | 0.46 |
| EMPA | -0.10 | -0.04 | -0.75 | -0.08 | 0.10 | -0.29 | -0.31 | -0.27 | -0.14 | -0.36 | 0.76 | -0.04 | -0.20 | -0.02 | -0.26 | 0.13 | 0.15 | -0.21 | -0.17 | -0.04 | 0.25 | -0.69 | -0.32 | 0.07 | -0.00 |

| Drug name | bioavailability | Half life (h) |
|---|---|---|
| Aripiprazole | 87 | 75 |
| EMPA | 78 | 12.4 |

B

| Drug name | sleepiness | Low blood sugar |
|---|---|---|
| Aripiprazole | 1 | 4 |
| EMPA | 3 | 2 |

C

| Matrix R | Schizophrenia | cardiovascular death |
|---|---|---|
| Aripiprazole | 1 | 0 |
| EMPA | 0 | 1 |

[Fig. 7]
A
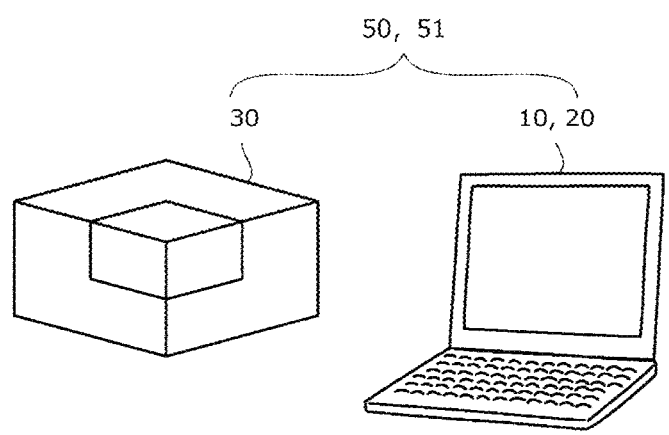
B
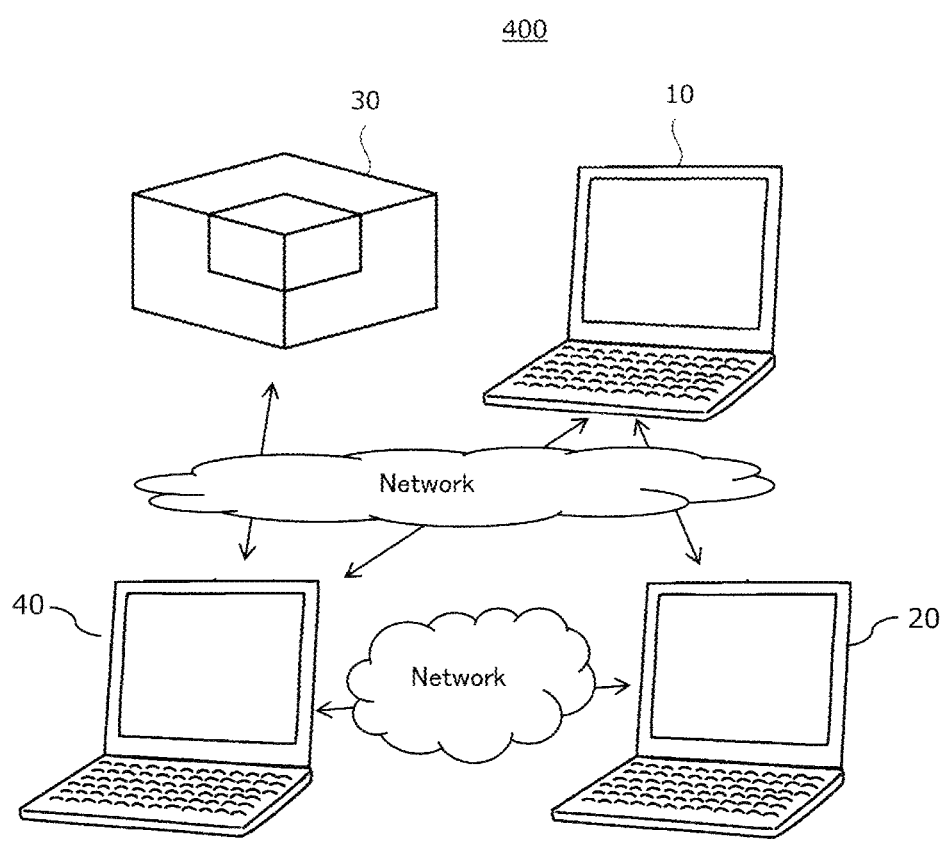

[Fig. 8]
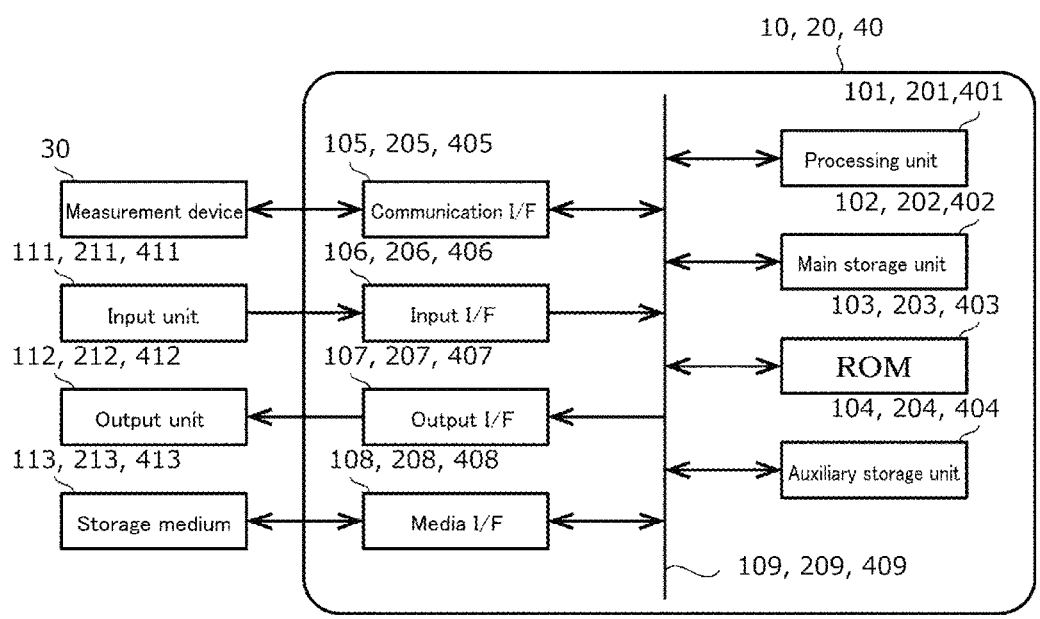

[Fig. 9]
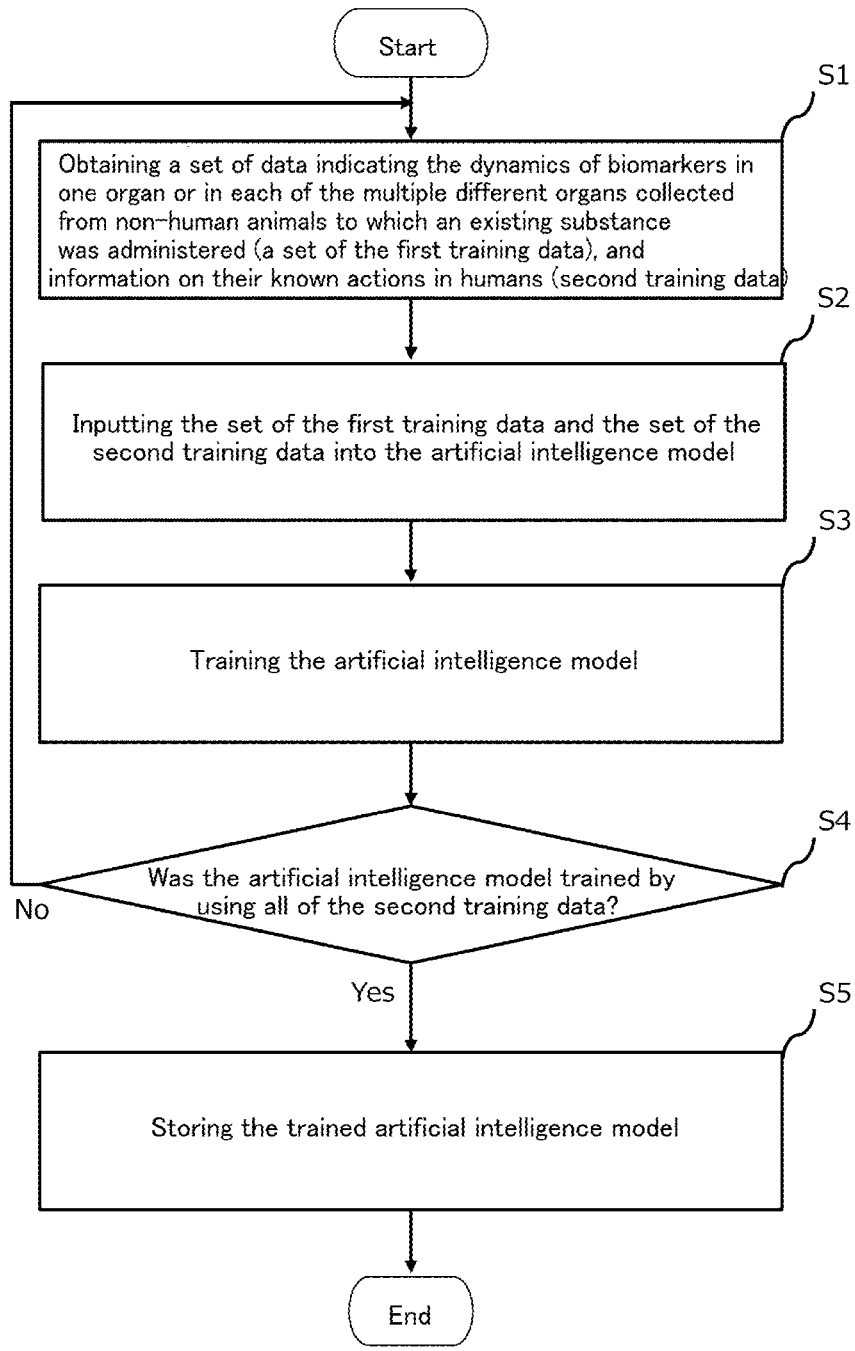

[Fig. 10]
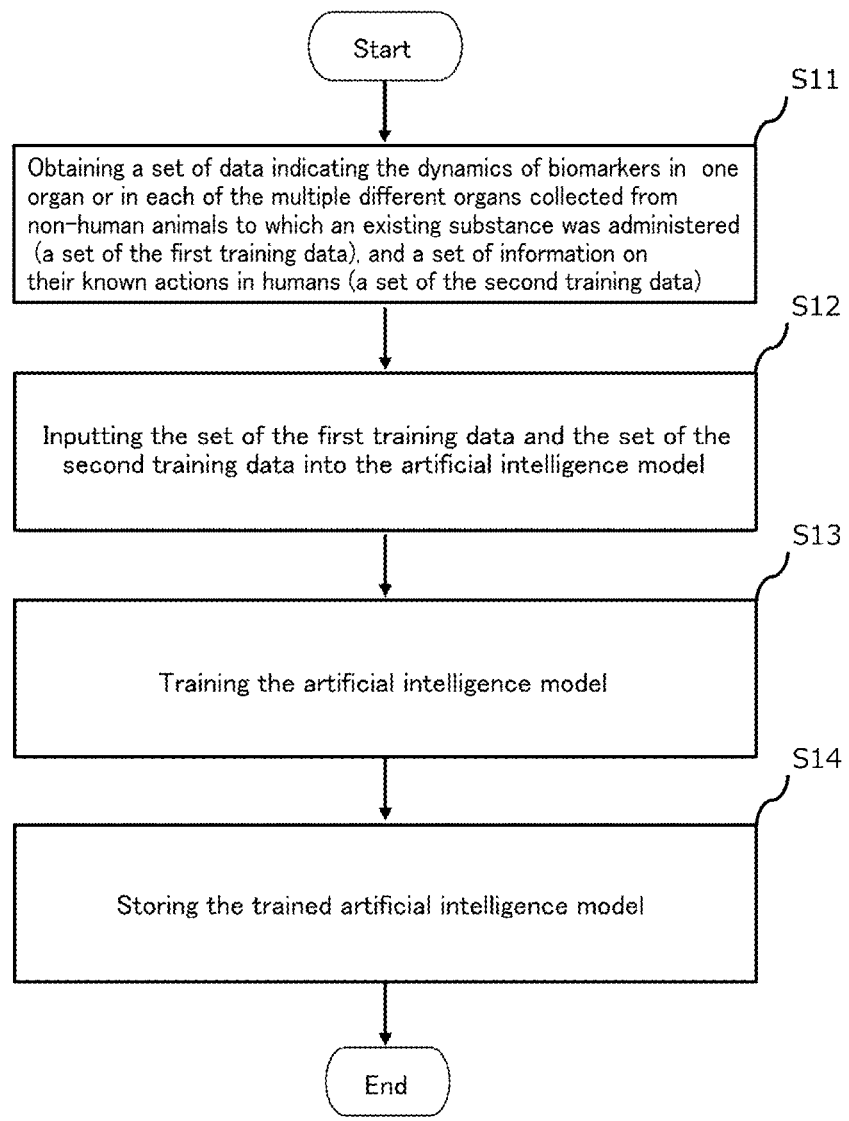

[Fig. 11]
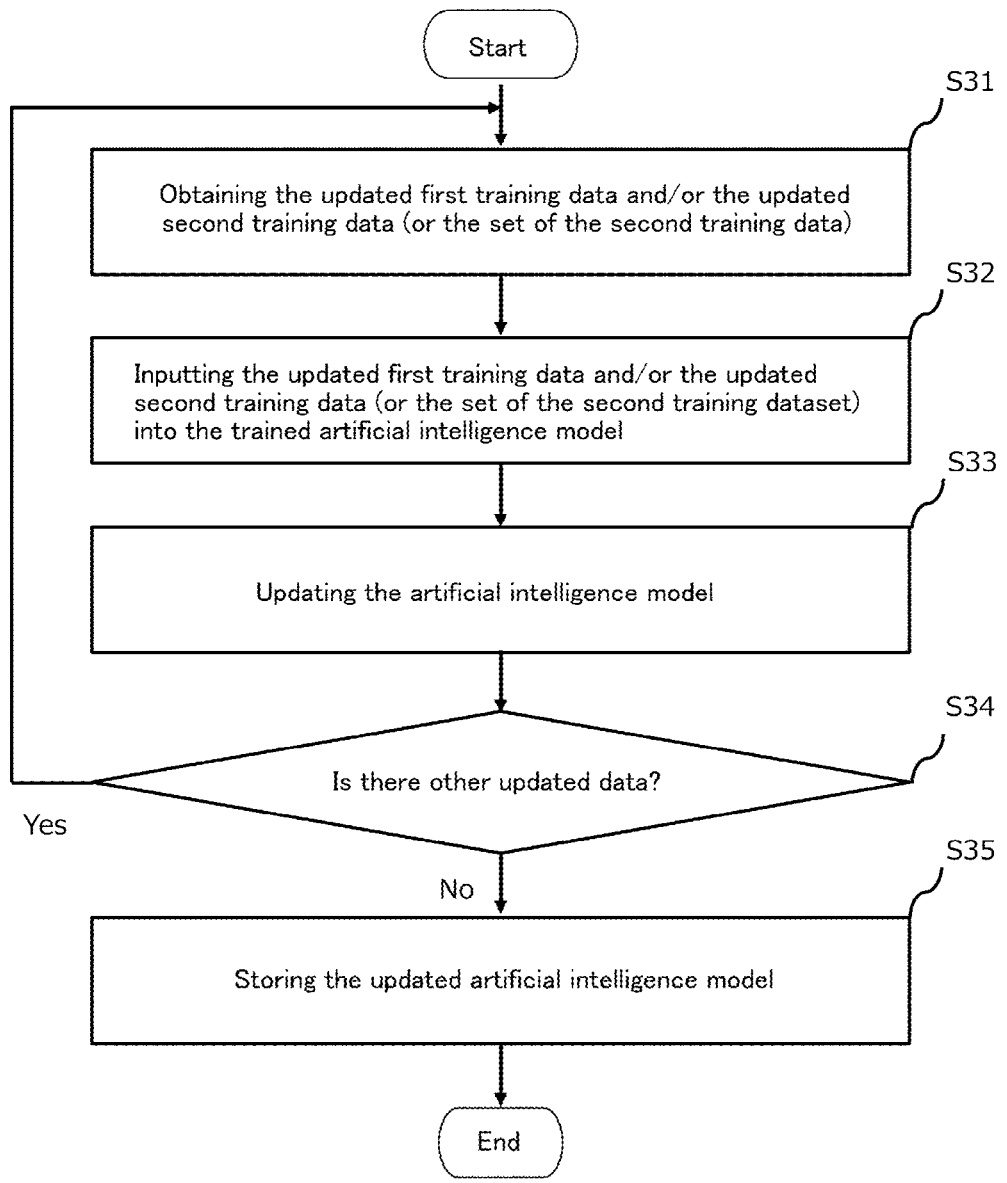

[Fig. 12]
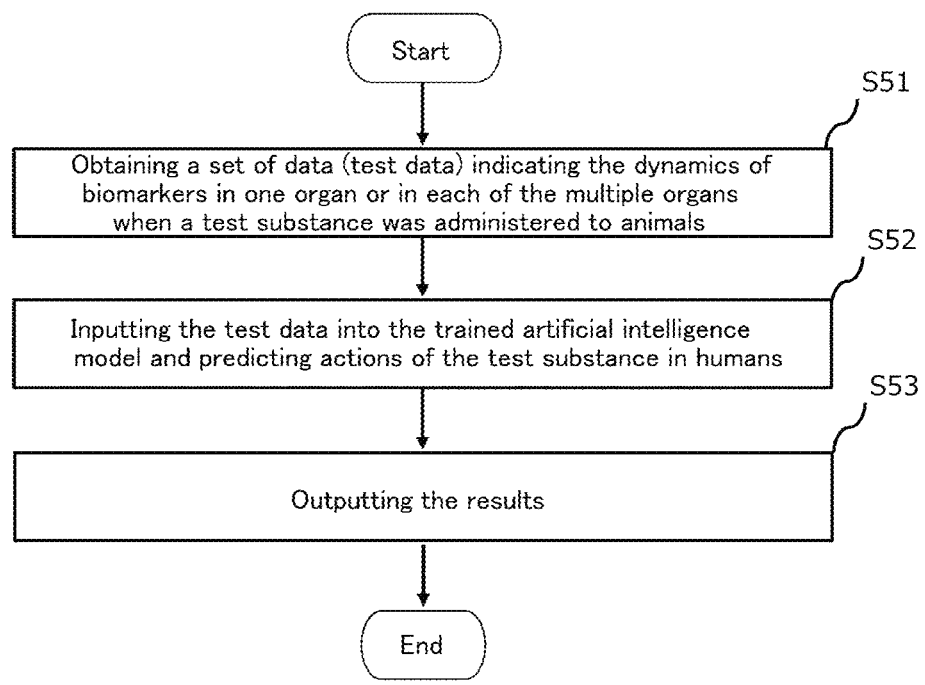

[Fig. 13]
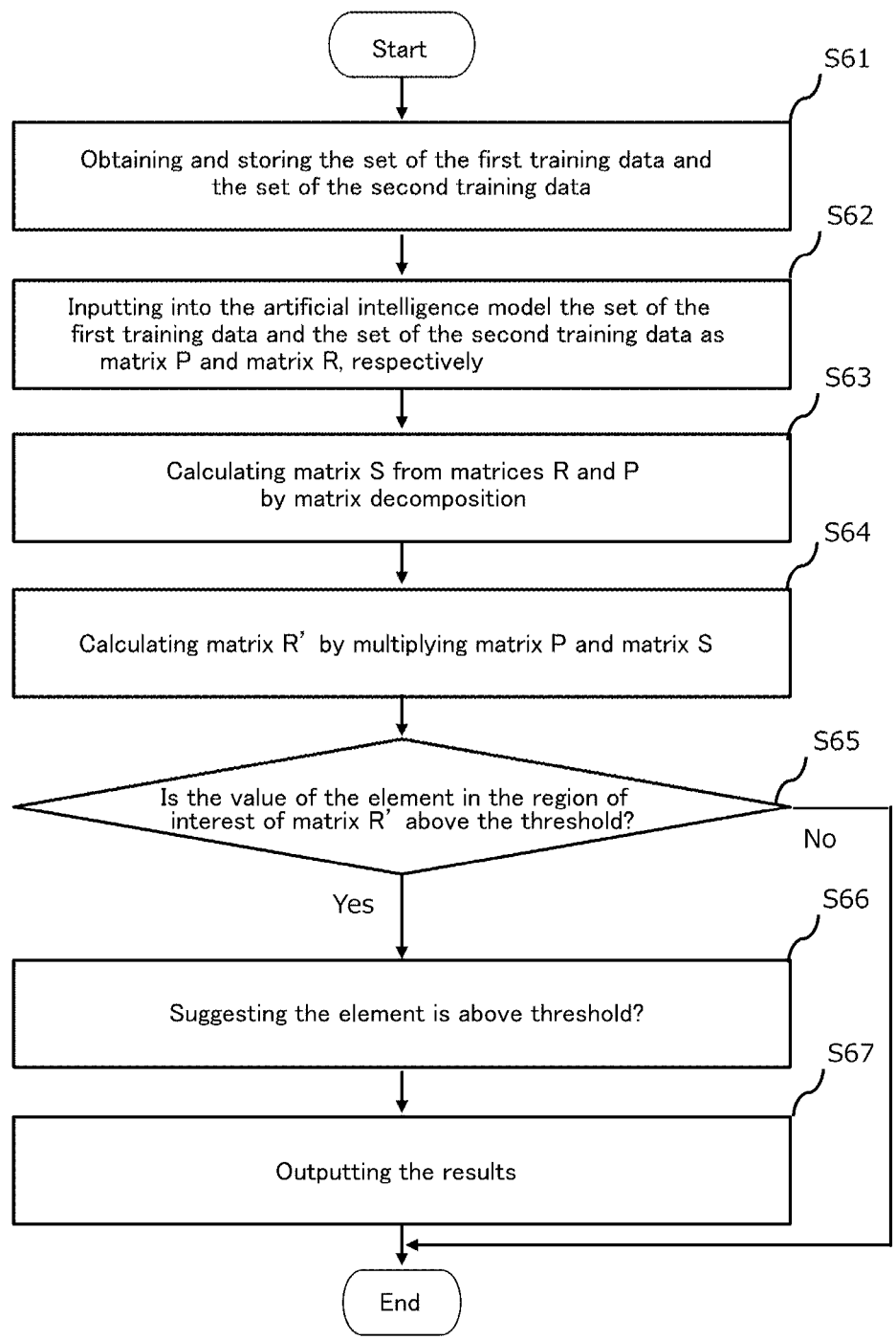

[Fig. 14]
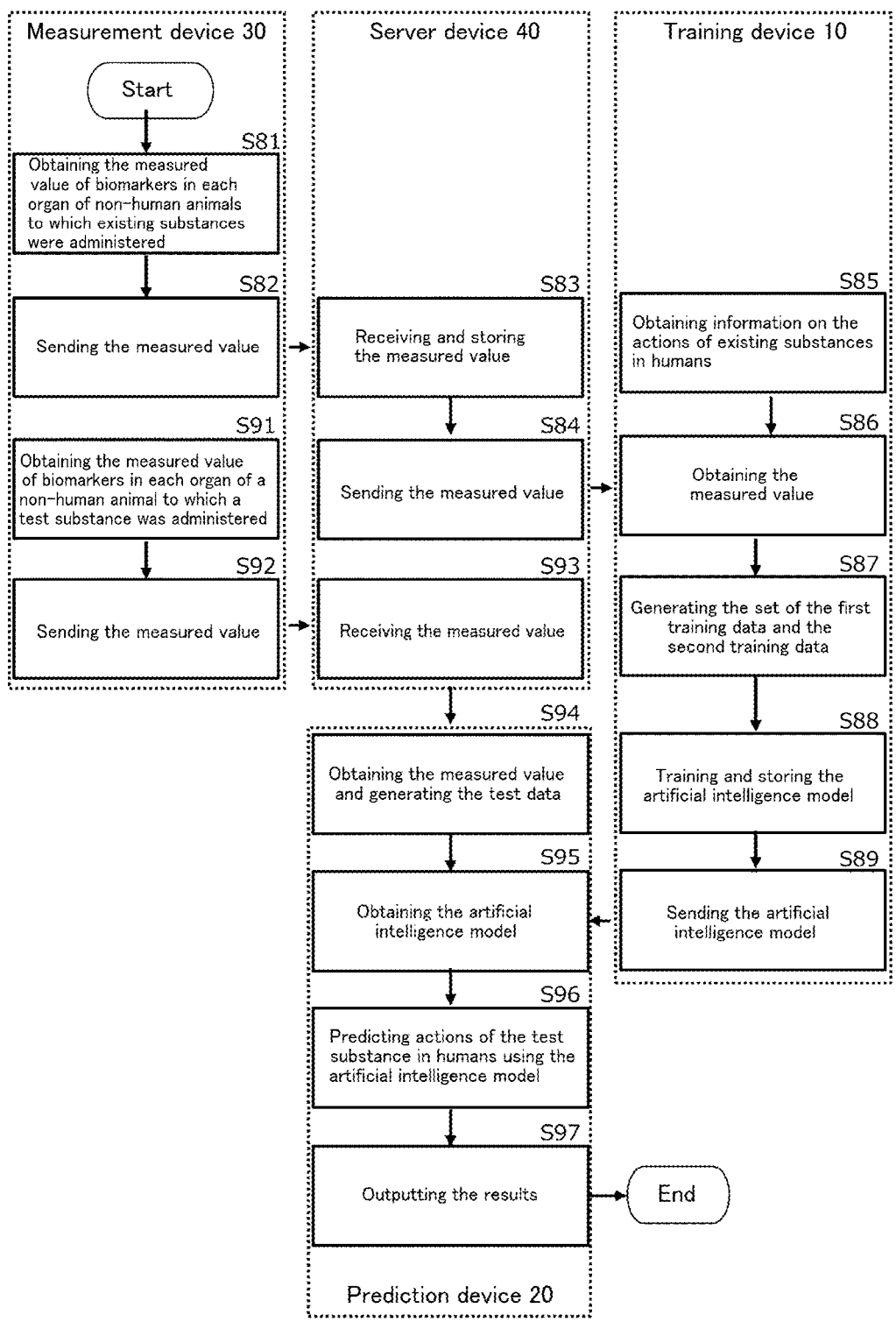

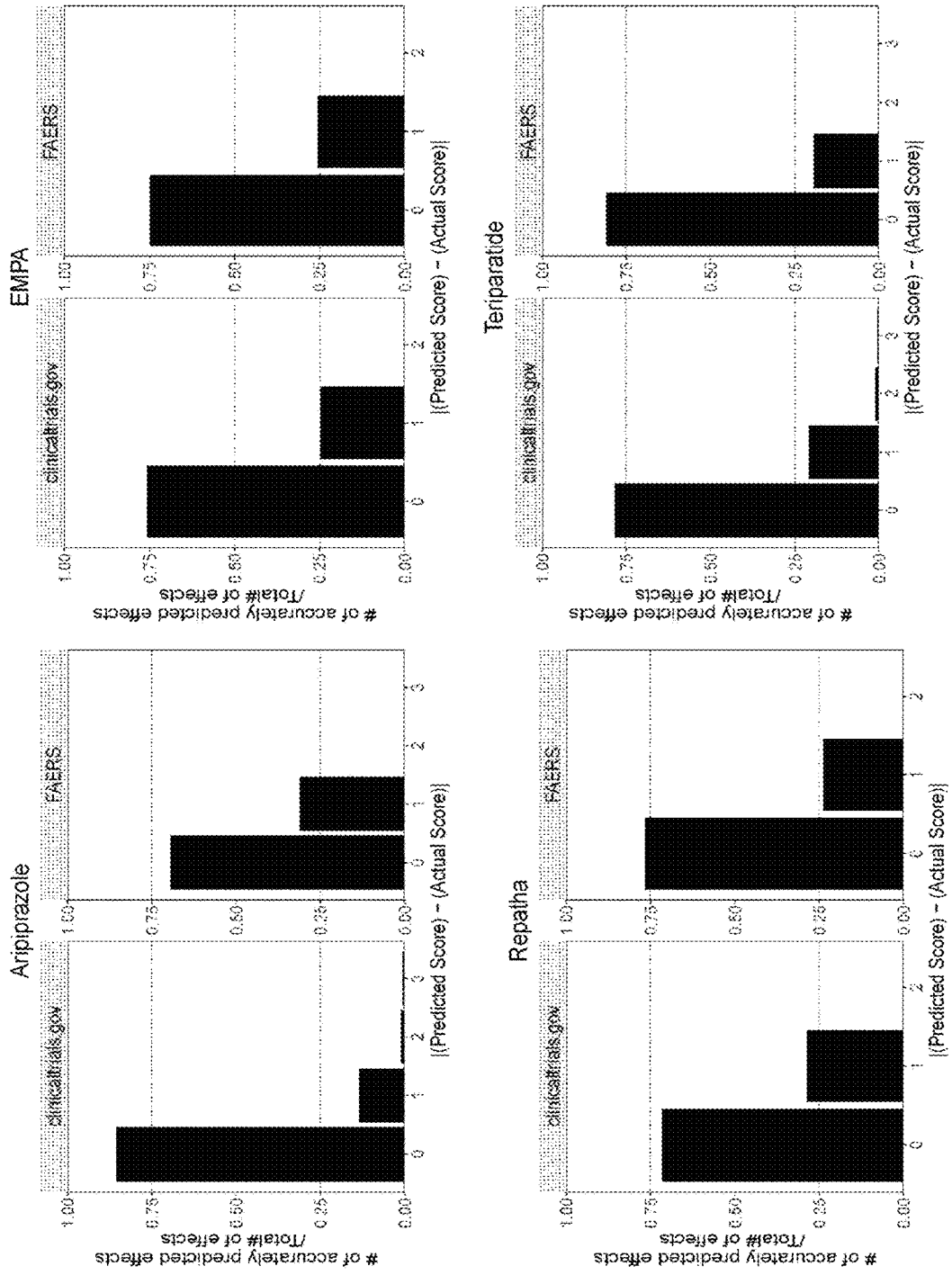
[Fig. 15]

[Fig. 16]
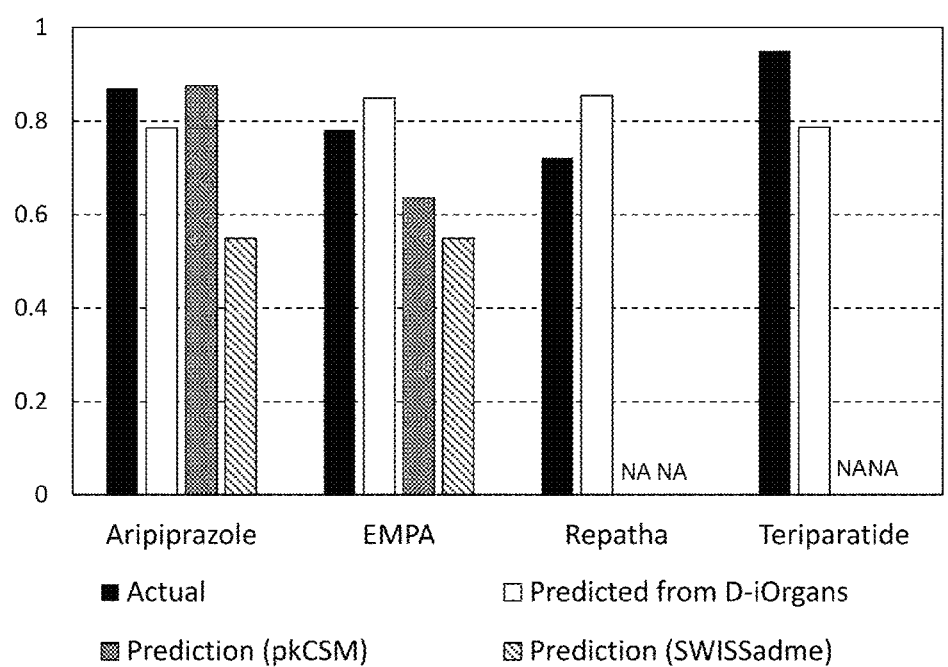

[Fig. 17]
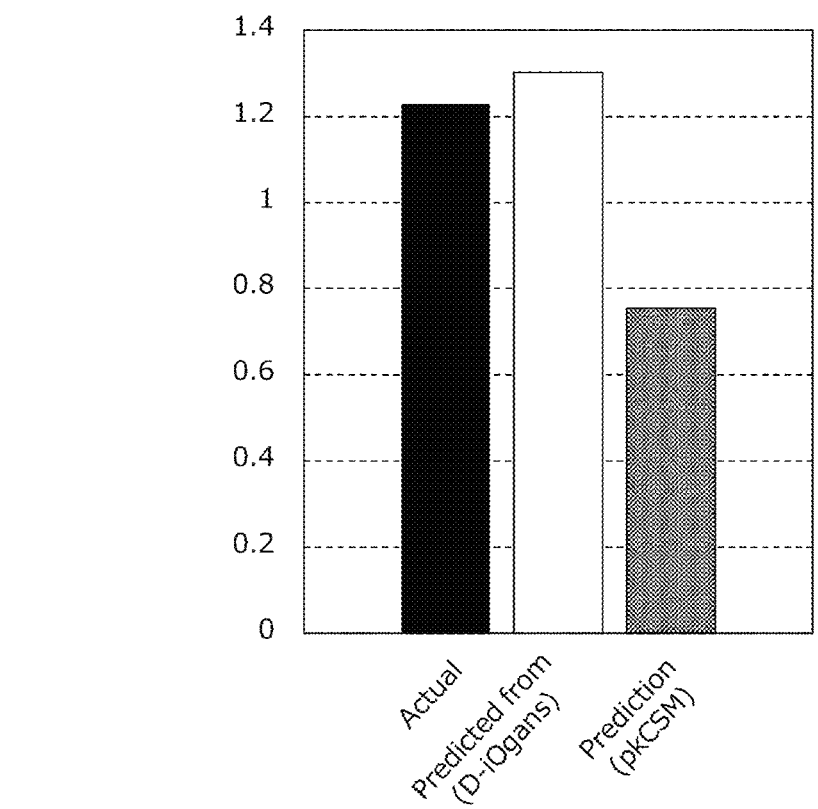

|  | Schizophrenia | bipolar disorder | major depressive disorder | autistic disorder | Tourette's disorder | cancer | recurrent suicidal behavior | suicidal behavior | schizoaffective disorders | cardiovascular death | adults with type 2 diabetes mellitus | establish cardiovascular disease | hyperlipidemia | mixed dyslipidemia | homozygous familial hypercholesterolemia | osteoporosis |
|---|---|---|---|---|---|---|---|---|---|---|---|---|---|---|---|---|
| Aripiprazole |  |  |  |  |  |  |  |  |  | 0 | 0 | 0 | 0 | 0 | 0 | 0 |
| Cisplatin | 0 | 0 | 0 | 0 | 0 |  | 0 | 0 | 0 | 0 | 0 | 0 | 0 | 0 | 0 | 0 |
| Clozapine |  | 0 | 0 | 0 | 0 | 0 | 0 | 0 |  | 0 | 0 | 0 | 0 | 0 | 0 | 0 |
| EMPA | 0 | 0 | 0 | 0 | 0 | 0 | 0 | 0 | 0 | 0 |  |  | 0 | 0 | 0 | 0 |
| Repatha | 0 | 0 | 0 | 0 | 0 | 0 | 0 | 0 | 0 | 0 | 0 | 0 |  |  |  | 0 |
| Teriparatide | 0 | 0 | 0 | 0 | 0 | 0 | 0 | 0 | 0 | 0 | 0 | 0 | 0 | 0 | 0 |  |

B

|  | Schizophrenia | bipolar disorder | major depressive disorder | autistic disorder | Tourette's disorder | cancer | recurrent suicidal behavior | suicidal behavior | schizoaffective disorders | cardiovascular death | adults with type 2 diabetes mellitus | establish cardiovascular disease | hyperlipidemia | mixed dyslipidemia | homozygous familial hypercholesterolemia | osteoporosis |
|---|---|---|---|---|---|---|---|---|---|---|---|---|---|---|---|---|
| Aripiprazole |  |  |  |  |  | -0.19 |  |  |  | -0.43 | -0.43 | -0.43 | -0.24 | -0.24 | -0.24 | -0.13 |
| Cisplatin | -0.59 | -0.27 | -0.27 | -0.27 | -0.27 |  | -0.66 | -0.66 | -0.66 | -0.22 | -0.22 | -0.22 | -0.19 | -0.19 | -0.19 | -0.19 |
| Clozapine |  | 0.34 | 0.34 | 0.34 | 0.34 | -0.18 |  |  |  | 0.13 | 0.13 | 0.13 | -0.11 | -0.11 | -0.11 | -0.31 |
| EMPA | 0.17 | -0.51 | -0.51 | -0.51 | -0.51 | -0.19 | 0.41 | 0.41 | 0.41 |  |  |  | -0.23 | -0.23 | -0.23 | -0.15 |
| Repatha | -0.40 | -0.33 | -0.33 | -0.33 | -0.33 | -0.19 | -0.39 | -0.39 | -0.39 | -0.26 | -0.26 | -0.26 |  |  |  | -0.18 |
| Teriparatide | -0.89 | -0.17 | -0.17 | -0.17 | -0.17 | -0.19 | -1.09 | -1.09 | -1.09 | -0.17 | -0.16 | -0.17 | -0.18 | -0.18 | -0.18 |  |

[Fig. 19]
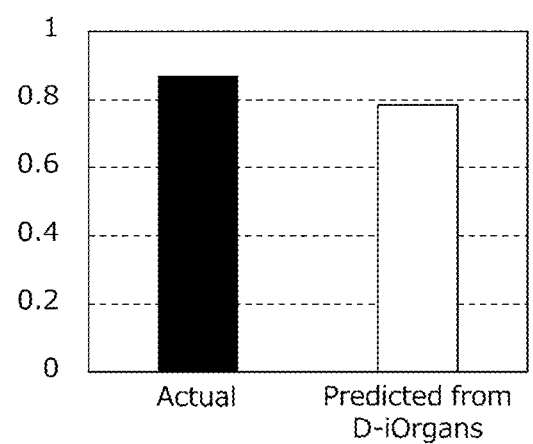

[Fig. 20-1]

| drug | name of adverse effect | number | organs |
|---|---|---|---|
| A | nausea | 1 | 18 |
| A | psychiatric decompensation | 1 | 15 |
| A | haemoglobin decreased | 1 | 19 |
| A | hypomagnesaemia | 1 | 19 |
| A | oesophagitis | 1 | 19 |
| A | diarrhea | 2 | 11, 12 |
| A | acute prerenal failure | 2 | 3, 22 |
| A | aphasia | 2 | 3, 22 |
| A | carbohydrate antigen-9 increased | 2 | 3, 22 |
| A | death | 2 | 3, 22 |
| A | dry eye | 2 | 3, 22 |
| A | enterocolitis | 2 | 3, 22 |
| A | micturition urgency | 2 | 3, 22 |
| A | oral herpes | 2 | 3, 22 |
| A | petechiae | 2 | 3, 22 |
| A | rash pruritic | 2 | 3, 22 |
| A | right ventricular failure | 2 | 3, 22 |
| A | staphylococcal infection | 2 | 3, 22 |
| A | thrombocytopenia | 2 | 3, 22 |
| A | extrapyramidal disorder | 3 | 22, 10, 1 |
| A | irritability | 3 | 22, 10, 1 |
| A | akathisia | 4 | 1, 9, 11, 16 |
| A | apathy | 4 | 1, 9, 11, 16 |
| A | decreased libido | 4 | 1, 9, 11, 16 |
| A | nervousness | 4 | 1, 9, 11, 16 |
| A | seborrhoeic dermatitis | 4 | 1, 9, 11, 16 |
| A | skin rash | 4 | 1, 9, 11, 16 |
| A | slurred speech | 4 | 1, 9, 11, 16 |
| A | hypothyroidism | 4 | 6, 24, 13, 5 |
| A | arthritis | 4 | 9, 18, 14, 22 |
| A | blood creatinine increased | 4 | 9, 18, 14, 22 |
| A | cardiac tamponade | 4 | 9, 18, 14, 22 |
| A | cerebral ischaemia | 4 | 9, 18, 14, 22 |
| A | chronic kidney disease | 4 | 9, 18, 14, 22 |
| A | deafness | 4 | 9, 18, 14, 22 |
| A | dysphonia | 4 | 9, 18, 14, 22 |
| A | dysuria | 4 | 9, 18, 14, 22 |
| A | electrolyte imbalance | 4 | 9, 18, 14, 22 |
| A | febrile neutropenia | 4 | 9, 18, 14, 22 |
| A | haemoptysis | 4 | 9, 18, 14, 22 |
| A | hepatic function abnormal | 4 | 9, 18, 14, 22 |
| A | hypersensitivity | 4 | 9, 18, 14, 22 |
| A | left ventricular failure | 4 | 9, 18, 14, 22 |
| A | melaena | 4 | 9, 18, 14, 22 |
| A | metabolic acidosis | 4 | 9, 18, 14, 22 |
| A | myositis | 4 | 9, 18, 14, 22 |
| A | pancytopenia | 4 | 9, 18, 14, 22 |
| A | pathological fracture | 4 | 9, 18, 14, 22 |
| A | peripheral artery thrombosis | 4 | 9, 18, 14, 22 |
| A | phlebitis | 4 | 9, 18, 14, 22 |
| A | rash erythematous | 4 | 9, 18, 14, 22 |
| A | seizure | 4 | 9, 18, 14, 22 |
| A | visual acuity reduced | 4 | 9, 18, 14, 22 |
| A | acute prerenal failure | 4 | 5, 4, 8, 15 |
| A | aphasia | 4 | 5, 4, 8, 15 |
| A | carbohydrate antigen-9 increased | 4 | 5, 4, 8, 15 |
| A | death | 4 | 5, 4, 8, 15 |
| A | dry eye | 4 | 5, 4, 8, 15 |
| A | enterocolitis | 4 | 5, 4, 8, 15 |
| A | micturition urgency | 4 | 5, 4, 8, 15 |
| A | oral herpes | 4 | 5, 4, 8, 15 |
| A | petechiae | 4 | 5, 4, 8, 15 |
| A | rash pruritic | 4 | 5, 4, 8, 15 |
| A | right ventricular failure | 4 | 5, 4, 8, 15 |
| A | staphylococcal infection | 4 | 5, 4, 8, 15 |
| A | thrombocytopenia | 4 | 5, 4, 8, 15 |

[Fig. 20-2]

| A | aortic thrombosis | 4 | 8, 10, 6, 9 |
|---|---|---|---|
| A | breast pain | 4 | 8, 10, 6, 9 |
| A | device leakage | 4 | 8, 10, 6, 9 |
| A | ejection fraction decreased | 4 | 8, 10, 6, 9 |
| A | haematochezia | 4 | 8, 10, 6, 9 |
| A | hyperuricaemia | 4 | 8, 10, 6, 9 |
| A | joint range of motion decreased | 4 | 8, 10, 6, 9 |
| A | laryngitis | 4 | 8, 10, 6, 9 |
| A | nephropathy toxic | 4 | 8, 10, 6, 9 |
| A | neuropathy peripheral | 4 | 8, 10, 6, 9 |
| A | pain of skin | 4 | 8, 10, 6, 9 |
| A | peripheral embolism | 4 | 8, 10, 6, 9 |
| A | peripheral motor neuropathy | 4 | 8, 10, 6, 9 |
| A | peripheral venous disease | 4 | 8, 10, 6, 9 |
| A | pneumonitis | 4 | 8, 10, 6, 9 |
| A | productive cough | 4 | 8, 10, 6, 9 |
| A | pruritus generalised | 4 | 8, 10, 6, 9 |
| A | sinus congestion | 4 | 8, 10, 6, 9 |
| A | skin exfoliation | 4 | 8, 10, 6, 9 |
| A | skin lesion | 4 | 8, 10, 6, 9 |
| A | superior vena cava syndrome | 4 | 8, 10, 6, 9 |
| A | troponin i increased | 4 | 8, 10, 6, 9 |
| A | upper-airway cough syndrome | 4 | 8, 10, 6, 9 |
| A | urinary tract infection bacterial | 4 | 8, 10, 6, 9 |
| A | abdominal wall abscess | 4 | 1, 6, 2, 11 |
| A | abscess of eyelid | 4 | 1, 6, 2, 11 |
| A | accelerated hypertension | 4 | 1, 6, 2, 11 |
| A | adenocarcinoma gastric | 4 | 1, 6, 2, 11 |
| A | adenocarcinoma pancreas | 4 | 1, 6, 2, 11 |
| A | altered state of consciousness | 4 | 1, 6, 2, 11 |
| A | amoebic dysentery | 4 | 1, 6, 2, 11 |
| A | anal fissure | 4 | 1, 6, 2, 11 |
| A | anaphylactic reaction | 4 | 1, 6, 2, 11 |
| A | anaphylactic shock | 4 | 1, 6, 2, 11 |
| A | angioedema | 4 | 1, 6, 2, 11 |
| A | angle closure glaucoma | 4 | 1, 6, 2, 11 |
| A | aortic valve disease | 4 | 1, 6, 2, 11 |
| A | aortic valve stenosis | 4 | 1, 6, 2, 11 |
| A | arrhythmia prophylaxis | 4 | 1, 6, 2, 11 |
| A | arteriogram coronary | 4 | 1, 6, 2, 11 |
| A | atrial thrombosis | 4 | 1, 6, 2, 11 |
| A | atrioventricular block first degree | 4 | 1, 6, 2, 11 |
| A | atrioventricular block second degree | 4 | 1, 6, 2, 11 |
| A | bacteraemia | 4 | 1, 6, 2, 11 |
| A | bacterial sepsis | 4 | 1, 6, 2, 11 |
| A | basosquamous carcinoma | 4 | 1, 6, 2, 11 |
| A | benign pancreatic neoplasm | 4 | 1, 6, 2, 11 |
| A | bile duct cancer | 4 | 1, 6, 2, 11 |
| A | bile duct obstruction | 4 | 1, 6, 2, 11 |
| A | biliary adenoma | 4 | 1, 6, 2, 11 |
| A | bladder cancer recurrent | 4 | 1, 6, 2, 11 |
| A | bladder prolapse | 4 | 1, 6, 2, 11 |
| A | bladder transitional cell carcinoma | 4 | 1, 6, 2, 11 |
| A | bundle branch block right | 4 | 1, 6, 2, 11 |
| A | cardiac asthma | 4 | 1, 6, 2, 11 |
| A | cardiac failure chronic | 4 | 1, 6, 2, 11 |
| A | cardiac stress test abnormal | 4 | 1, 6, 2, 11 |
| A | cardiogenic shock | 4 | 1, 6, 2, 11 |
| A | cardiopulmonary failure | 4 | 1, 6, 2, 11 |
| A | carotid artery disease | 4 | 1, 6, 2, 11 |
| A | carotid artery occlusion | 4 | 1, 6, 2, 11 |
| A | cerebellar infarction | 4 | 1, 6, 2, 11 |
| A | cerebral artery occlusion | 4 | 1, 6, 2, 11 |
| A | cerebral artery stenosis | 4 | 1, 6, 2, 11 |
| A | cerebrovascular disorder | 4 | 1, 6, 2, 11 |
| A | cerebrovascular insufficiency | 4 | 1, 6, 2, 11 |
| A | cervical radiculopathy | 4 | 1, 6, 2, 11 |

[Fig. 20-3]

| A | cervical spinal stenosis | 4 | 1, 6, 2, 11 |
|---|---|---|---|
| A | chemical poisoning | 4 | 1, 6, 2, 11 |
| A | chest discomfort | 4 | 1, 6, 2, 11 |
| A | chronic gastritis | 4 | 1, 6, 2, 11 |
| A | chronic lymphocytic leukaemia | 4 | 1, 6, 2, 11 |
| A | circulatory collapse | 4 | 1, 6, 2, 11 |
| A | clear cell renal cell carcinoma | 4 | 1, 6, 2, 11 |
| A | colitis ischaemic | 4 | 1, 6, 2, 11 |
| A | colon cancer metastatic | 4 | 1, 6, 2, 11 |
| A | colorectal adenocarcinoma | 4 | 1, 6, 2, 11 |
| A | colorectal cancer | 4 | 1, 6, 2, 11 |
| A | comminuted fracture | 4 | 1, 6, 2, 11 |
| A | congestive cardiomyopathy | 4 | 1, 6, 2, 11 |
| A | coronary artery restenosis | 4 | 1, 6, 2, 11 |
| A | coronary artery stenosis | 4 | 1, 6, 2, 11 |
| A | coronary revascularisation | 4 | 1, 6, 2, 11 |
| A | cystitis escherichia | 4 | 1, 6, 2, 11 |
| A | diabetic foot | 4 | 1, 6, 2, 11 |
| A | diabetic foot infection | 4 | 1, 6, 2, 11 |
| A | diabetic gangrene | 4 | 1, 6, 2, 11 |
| A | diabetic metabolic decompensation | 4 | 1, 6, 2, 11 |
| A | diabetic nephropathy | 4 | 1, 6, 2, 11 |
| A | diabetic neuropathy | 4 | 1, 6, 2, 11 |
| A | diabetic retinopathy | 4 | 1, 6, 2, 11 |
| A | diarrhoea infectious | 4 | 1, 6, 2, 11 |
| A | diffuse large b-cell lymphoma | 4 | 1, 6, 2, 11 |
| A | duodenal ulcer haemorrhage | 4 | 1, 6, 2, 11 |
| A | dupuytren's contracture | 4 | 1, 6, 2, 11 |
| A | electrocardiogram abnormal | 4 | 1, 6, 2, 11 |
| A | endometrial adenocarcinoma | 4 | 1, 6, 2, 11 |
| A | endometrial hyperplasia | 4 | 1, 6, 2, 11 |
| A | erosive duodenitis | 4 | 1, 6, 2, 11 |
| A | extremity necrosis | 4 | 1, 6, 2, 11 |
| A | facial bones fracture | 4 | 1, 6, 2, 11 |
| A | febrile infection | 4 | 1, 6, 2, 11 |
| A | follicular thyroid cancer | 4 | 1, 6, 2, 11 |
| A | food poisoning | 4 | 1, 6, 2, 11 |
| A | fracture displacement | 4 | 1, 6, 2, 11 |
| A | gastric ulcer perforation | 4 | 1, 6, 2, 11 |
| A | gastrointestinal angiodysplasia | 4 | 1, 6, 2, 11 |
| A | generalised tonic-clonic seizure | 4 | 1, 6, 2, 11 |
| A | glioblastoma | 4 | 1, 6, 2, 11 |
| A | gouty arthritis | 4 | 1, 6, 2, 11 |
| A | grand mal convulsion | 4 | 1, 6, 2, 11 |
| A | haemorrhoids thrombosed | 4 | 1, 6, 2, 11 |
| A | hepatic cancer | 4 | 1, 6, 2, 11 |
| A | hepatic cirrhosis | 4 | 1, 6, 2, 11 |
| A | hepatic failure | 4 | 1, 6, 2, 11 |
| A | hepatic neoplasm | 4 | 1, 6, 2, 11 |
| A | hepatitis e | 4 | 1, 6, 2, 11 |
| A | hyperparathyroidism | 4 | 1, 6, 2, 11 |
| A | hyperparathyroidism primary | 4 | 1, 6, 2, 11 |
| A | hypertensive cardiomyopathy | 4 | 1, 6, 2, 11 |
| A | iliac artery occlusion | 4 | 1, 6, 2, 11 |
| A | incarcerated inguinal hernia | 4 | 1, 6, 2, 11 |
| A | incarcerated umbilical hernia | 4 | 1, 6, 2, 11 |
| A | incision site infection | 4 | 1, 6, 2, 11 |
| A | infected skin ulcer | 4 | 1, 6, 2, 11 |
| A | infectious pleural effusion | 4 | 1, 6, 2, 11 |
| A | intervertebral disc disorder | 4 | 1, 6, 2, 11 |
| A | intestinal polyp | 4 | 1, 6, 2, 11 |
| A | intraductal proliferative breast lesion | 4 | 1, 6, 2, 11 |
| A | ischaemic cardiomyopathy | 4 | 1, 6, 2, 11 |
| A | ischaemic cerebral infarction | 4 | 1, 6, 2, 11 |
| A | laryngeal squamous cell carcinoma | 4 | 1, 6, 2, 11 |
| A | left ventricular dysfunction | 4 | 1, 6, 2, 11 |
| A | limb crushing injury | 4 | 1, 6, 2, 11 |

[Fig. 20-4]

| A | lipoma | 4 | 1, 6, 2, 11 |
|---|---|---|---|
| A | liver abscess | 4 | 1, 6, 2, 11 |
| A | liver injury | 4 | 1, 6, 2, 11 |
| A | lumbar radiculopathy | 4 | 1, 6, 2, 11 |
| A | macular fibrosis | 4 | 1, 6, 2, 11 |
| A | malignant hypertension | 4 | 1, 6, 2, 11 |
| A | malignant peritoneal neoplasm | 4 | 1, 6, 2, 11 |
| A | mediastinitis | 4 | 1, 6, 2, 11 |
| A | meningioma | 4 | 1, 6, 2, 11 |
| A | meningitis bacterial | 4 | 1, 6, 2, 11 |
| A | mental disorder | 4 | 1, 6, 2, 11 |
| A | metabolic encephalopathy | 4 | 1, 6, 2, 11 |
| A | metastases to lung | 4 | 1, 6, 2, 11 |
| A | metastases to lymph nodes | 4 | 1, 6, 2, 11 |
| A | metrorrhagia | 4 | 1, 6, 2, 11 |
| A | microvascular coronary artery disease | 4 | 1, 6, 2, 11 |
| A | muscle abscess | 4 | 1, 6, 2, 11 |
| A | myelopathy | 4 | 1, 6, 2, 11 |
| A | nasal obstruction | 4 | 1, 6, 2, 11 |
| A | nasal polyps | 4 | 1, 6, 2, 11 |
| A | neck injury | 4 | 1, 6, 2, 11 |
| A | neuroendocrine carcinoma | 4 | 1, 6, 2, 11 |
| A | neuropathic arthropathy | 4 | 1, 6, 2, 11 |
| A | normochromic normocytic anaemia | 4 | 1, 6, 2, 11 |
| A | oesophageal adenocarcinoma | 4 | 1, 6, 2, 11 |
| A | oesophageal carcinoma | 4 | 1, 6, 2, 11 |
| A | paraparesis | 4 | 1, 6, 2, 11 |
| A | percutaneous coronary intervention | 4 | 1, 6, 2, 11 |
| A | peripheral artery restenosis | 4 | 1, 6, 2, 11 |
| A | peripheral artery stenosis | 4 | 1, 6, 2, 11 |
| A | peripheral ischaemia | 4 | 1, 6, 2, 11 |
| A | perirenal haematoma | 4 | 1, 6, 2, 11 |
| A | petit mal epilepsy | 4 | 1, 6, 2, 11 |
| A | physical assault | 4 | 1, 6, 2, 11 |
| A | pneumonia influenzal | 4 | 1, 6, 2, 11 |
| A | pneumonia legionella | 4 | 1, 6, 2, 11 |
| A | polyarthritis | 4 | 1, 6, 2, 11 |
| A | post procedural haematuria | 4 | 1, 6, 2, 11 |
| A | post procedural haemorrhage | 4 | 1, 6, 2, 11 |
| A | post procedural sepsis | 4 | 1, 6, 2, 11 |
| A | prostatic abscess | 4 | 1, 6, 2, 11 |
| A | psoriasis | 4 | 1, 6, 2, 11 |
| A | pterygium | 4 | 1, 6, 2, 11 |
| A | pulmonary congestion | 4 | 1, 6, 2, 11 |
| A | pulmonary hypertension | 4 | 1, 6, 2, 11 |
| A | rectal adenocarcinoma | 4 | 1, 6, 2, 11 |
| A | renal cell carcinoma stage i | 4 | 1, 6, 2, 11 |
| A | renal colic | 4 | 1, 6, 2, 11 |
| A | renal infarct | 4 | 1, 6, 2, 11 |
| A | retinal artery occlusion | 4 | 1, 6, 2, 11 |
| A | retinal tear | 4 | 1, 6, 2, 11 |
| A | salmonellosis | 4 | 1, 6, 2, 11 |
| A | sarcoma | 4 | 1, 6, 2, 11 |
| A | scrotal abscess | 4 | 1, 6, 2, 11 |
| A | silent myocardial infarction | 4 | 1, 6, 2, 11 |
| A | sinus node dysfunction | 4 | 1, 6, 2, 11 |
| A | skeletal injury | 4 | 1, 6, 2, 11 |
| A | skin abrasion | 4 | 1, 6, 2, 11 |
| A | skin cancer | 4 | 1, 6, 2, 11 |
| A | small cell lung cancer | 4 | 1, 6, 2, 11 |
| A | spinal column injury | 4 | 1, 6, 2, 11 |
| A | squamous cell carcinoma of lung | 4 | 1, 6, 2, 11 |
| A | stab wound | 4 | 1, 6, 2, 11 |
| A | staphylococcal sepsis | 4 | 1, 6, 2, 11 |
| A | stent placement | 4 | 1, 6, 2, 11 |
| A | strangulated hernia | 4 | 1, 6, 2, 11 |
| A | subarachnoid haemorrhage | 4 | 1, 6, 2, 11 |

[Fig. 20-5]

| | | | |
|---|---|---|---|
| A | subclavian artery stenosis | 4 | 1, 6, 2, 11 |
| A | tendon injury | 4 | 1, 6, 2, 11 |
| A | tendonitis | 4 | 1, 6, 2, 11 |
| A | thrombosis mesenteric vessel | 4 | 1, 6, 2, 11 |
| A | transaminases increased | 4 | 1, 6, 2, 11 |
| A | transitional cell carcinoma | 4 | 1, 6, 2, 11 |
| A | troponin increased | 4 | 1, 6, 2, 11 |
| A | tuberculosis | 4 | 1, 6, 2, 11 |
| A | urethral stenosis | 4 | 1, 6, 2, 11 |
| A | urinary tract obstruction | 4 | 1, 6, 2, 11 |
| A | varices oesophageal | 4 | 1, 6, 2, 11 |
| A | varicose vein | 4 | 1, 6, 2, 11 |
| A | vascular graft occlusion | 4 | 1, 6, 2, 11 |
| A | vascular graft thrombosis | 4 | 1, 6, 2, 11 |
| A | vascular insufficiency | 4 | 1, 6, 2, 11 |
| A | vascular pseudoaneurysm | 4 | 1, 6, 2, 11 |
| A | venous thrombosis limb | 4 | 1, 6, 2, 11 |
| A | ventricular extrasystoles | 4 | 1, 6, 2, 11 |
| A | vertebrobasilar insufficiency | 4 | 1, 6, 2, 11 |
| A | vestibular neuronitis | 4 | 1, 6, 2, 11 |
| A | vitreous haemorrhage | 4 | 1, 6, 2, 11 |
| A | wound dehiscence | 4 | 1, 6, 2, 11 |
| A | cold/flu virus/symptoms | 4 | 5, 24, 4, 16 |
| A | debonded crown | 4 | 5, 24, 4, 16 |
| A | dermatologic | 4 | 5, 24, 4, 16 |
| A | gastrointestinal | 4 | 5, 24, 4, 16 |
| A | implant failure | 4 | 5, 24, 4, 16 |
| A | injection site ecchymoses, bruising, erythema | 4 | 5, 24, 4, 16 |
| A | musculoskeletal irritability | 4 | 5, 24, 4, 16 |
| A | neurologic | 4 | 5, 24, 4, 16 |
| A | akathisia | 5 | 12, 10, 5, 19, 2 |
| A | apathy | 5 | 12, 10, 5, 19, 2 |
| A | decreased libido | 5 | 12, 10, 5, 19, 2 |
| A | nervousness | 5 | 12, 10, 5, 19, 2 |
| A | seborrhoeic dermatitis | 5 | 12, 10, 5, 19, 2 |
| A | skin rash | 5 | 12, 10, 5, 19, 2 |
| A | slurred speech | 5 | 12, 10, 5, 19, 2 |
| A | lymphocele | 5 | 5, 4, 3, 21, 17 |
| A | abnormal white blood count | 5 | 6, 9, 16, 20, 22 |
| A | akathesia | 5 | 6, 9, 16, 20, 22 |
| A | difficulty concentrating | 5 | 6, 9, 16, 20, 22 |
| A | gastrointestinal disorders – other, specify: hypersalivation | 5 | 6, 9, 16, 20, 22 |
| A | migraine headache | 5 | 6, 9, 16, 20, 22 |
| A | salivation | 5 | 6, 9, 16, 20, 22 |
| A | stiffness | 5 | 6, 9, 16, 20, 22 |
| A | somnolence | 6 | 22, 14, 1, 19, 24, 7 |
| A | tremor | 6 | 22, 19, 14, 16, 3, 4 |
| A | suicide attempt | 6 | 14, 13, 19, 3, 7, 9 |
| A | abdominal injury | 6 | 1, 17, 21, 20, 5, 16 |
| A | abdominal wall haematoma | 6 | 1, 17, 21, 20, 5, 16 |
| A | abnormal loss of weight | 6 | 1, 17, 21, 20, 5, 16 |
| A | abscess drainage | 6 | 1, 17, 21, 20, 5, 16 |
| A | abscess of salivary gland | 6 | 1, 17, 21, 20, 5, 16 |
| A | abscess soft tissue | 6 | 1, 17, 21, 20, 5, 16 |
| A | acute hepatic failure | 6 | 1, 17, 21, 20, 5, 16 |
| A | acute leukaemia | 6 | 1, 17, 21, 20, 5, 16 |
| A | acute vestibular syndrome | 6 | 1, 17, 21, 20, 5, 16 |
| A | adenomatous polyposis coli | 6 | 1, 17, 21, 20, 5, 16 |
| A | adnexa uteri mass | 6 | 1, 17, 21, 20, 5, 16 |
| A | adrenal adenoma | 6 | 1, 17, 21, 20, 5, 16 |
| A | adrenal mass | 6 | 1, 17, 21, 20, 5, 16 |
| A | affective disorder | 6 | 1, 17, 21, 20, 5, 16 |
| A | allergy to arthropod sting | 6 | 1, 17, 21, 20, 5, 16 |
| A | amputation stump pain | 6 | 1, 17, 21, 20, 5, 16 |
| A | anal incontinence | 6 | 1, 17, 21, 20, 5, 16 |
| A | anal neoplasm | 6 | 1, 17, 21, 20, 5, 16 |
| A | anastomotic fistula | 6 | 1, 17, 21, 20, 5, 16 |

[Fig. 20-6]

| A | angiosclerosis | 6 | 1, 17, 21, 20, 5, 16 |
|---|---|---|---|
| A | animal scratch | 6 | 1, 17, 21, 20, 5, 16 |
| A | anxiety disorder | 6 | 1, 17, 21, 20, 5, 16 |
| A | aortic aneurysm rupture | 6 | 1, 17, 21, 20, 5, 16 |
| A | aortic injury | 6 | 1, 17, 21, 20, 5, 16 |
| A | aortic occlusion | 6 | 1, 17, 21, 20, 5, 16 |
| A | apnoea | 6 | 1, 17, 21, 20, 5, 16 |
| A | arrhythmia supraventricular | 6 | 1, 17, 21, 20, 5, 16 |
| A | arterial bypass occlusion | 6 | 1, 17, 21, 20, 5, 16 |
| A | arterial bypass thrombosis | 6 | 1, 17, 21, 20, 5, 16 |
| A | arteriogram coronary abnormal | 6 | 1, 17, 21, 20, 5, 16 |
| A | arteriogram coronary normal | 6 | 1, 17, 21, 20, 5, 16 |
| A | arteriovenous fistula operation | 6 | 1, 17, 21, 20, 5, 16 |
| A | arteriovenous fistula site complication | 6 | 1, 17, 21, 20, 5, 16 |
| A | arteriovenous malformation | 6 | 1, 17, 21, 20, 5, 16 |
| A | arthropathy | 6 | 1, 17, 21, 20, 5, 16 |
| A | asthma-chronic obstructive pulmonary disease overlap syndrome | 6 | 1, 17, 21, 20, 5, 16 |
| A | autoimmune hepatitis | 6 | 1, 17, 21, 20, 5, 16 |
| A | b-cell lymphoma | 6 | 1, 17, 21, 20, 5, 16 |
| A | b-cell lymphoma stage i | 6 | 1, 17, 21, 20, 5, 16 |
| A | b-cell prolymphocytic leukaemia | 6 | 1, 17, 21, 20, 5, 16 |
| A | bacterial pericarditis | 6 | 1, 17, 21, 20, 5, 16 |
| A | bacterial pyelonephritis | 6 | 1, 17, 21, 20, 5, 16 |
| A | barrett's oesophagus | 6 | 1, 17, 21, 20, 5, 16 |
| A | basal ganglia infarction | 6 | 1, 17, 21, 20, 5, 16 |
| A | basilar artery aneurysm | 6 | 1, 17, 21, 20, 5, 16 |
| A | benign gastric neoplasm | 6 | 1, 17, 21, 20, 5, 16 |
| A | benign lung neoplasm | 6 | 1, 17, 21, 20, 5, 16 |
| A | benign renal neoplasm | 6 | 1, 17, 21, 20, 5, 16 |
| A | biliary tract disorder | 6 | 1, 17, 21, 20, 5, 16 |
| A | bladder adenocarcinoma stage unspecified | 6 | 1, 17, 21, 20, 5, 16 |
| A | bladder cancer stage i, with cancer in situ | 6 | 1, 17, 21, 20, 5, 16 |
| A | bladder cancer stage iii | 6 | 1, 17, 21, 20, 5, 16 |
| A | bladder cancer stage, with cancer in situ | 6 | 1, 17, 21, 20, 5, 16 |
| A | bladder diverticulum | 6 | 1, 17, 21, 20, 5, 16 |
| A | bladder neck obstruction | 6 | 1, 17, 21, 20, 5, 16 |
| A | bladder neoplasm | 6 | 1, 17, 21, 20, 5, 16 |
| A | bladder obstruction | 6 | 1, 17, 21, 20, 5, 16 |
| A | bladder papilloma | 6 | 1, 17, 21, 20, 5, 16 |
| A | bladder tamponade | 6 | 1, 17, 21, 20, 5, 16 |
| A | bladder transitional cell carcinoma recurrent | 6 | 1, 17, 21, 20, 5, 16 |
| A | bladder transitional cell carcinoma stage i | 6 | 1, 17, 21, 20, 5, 16 |
| A | bladder transitional cell carcinoma stage iii | 6 | 1, 17, 21, 20, 5, 16 |
| A | blood pressure fluctuation | 6 | 1, 17, 21, 20, 5, 16 |
| A | bone abscess | 6 | 1, 17, 21, 20, 5, 16 |
| A | brain abscess | 6 | 1, 17, 21, 20, 5, 16 |
| A | breast abscess | 6 | 1, 17, 21, 20, 5, 16 |
| A | breast dysplasia | 6 | 1, 17, 21, 20, 5, 16 |
| A | breast prosthesis implantation | 6 | 1, 17, 21, 20, 5, 16 |
| A | burkholderia pseudomallei infection | 6 | 1, 17, 21, 20, 5, 16 |
| A | bursitis infective | 6 | 1, 17, 21, 20, 5, 16 |
| A | calculus urethral | 6 | 1, 17, 21, 20, 5, 16 |
| A | campylobacter gastroenteritis | 6 | 1, 17, 21, 20, 5, 16 |
| A | campylobacter infection | 6 | 1, 17, 21, 20, 5, 16 |
| A | carcinoid tumour of the caecum | 6 | 1, 17, 21, 20, 5, 16 |
| A | carcinoid tumour pulmonary | 6 | 1, 17, 21, 20, 5, 16 |
| A | cardiac ablation | 6 | 1, 17, 21, 20, 5, 16 |
| A | cardiac flutter | 6 | 1, 17, 21, 20, 5, 16 |
| A | cardiac pacemaker insertion | 6 | 1, 17, 21, 20, 5, 16 |
| A | cardiac resynchronisation therapy | 6 | 1, 17, 21, 20, 5, 16 |
| A | cardiovascular disorder | 6 | 1, 17, 21, 20, 5, 16 |
| A | carotid arteriosclerosis | 6 | 1, 17, 21, 20, 5, 16 |
| A | carotid artery restenosis | 6 | 1, 17, 21, 20, 5, 16 |
| A | cartilage graft | 6 | 1, 17, 21, 20, 5, 16 |
| A | cauda equina syndrome | 6 | 1, 17, 21, 20, 5, 16 |
| A | cerebellar ataxia | 6 | 1, 17, 21, 20, 5, 16 |

[Fig. 20-7]

| A | cerebral atrophy | 6 | 1, 17, 21, 20, 5, 16 |
|---|---|---|---|
| A | cerebral thrombosis | 6 | 1, 17, 21, 20, 5, 16 |
| A | cerebral vasoconstriction | 6 | 1, 17, 21, 20, 5, 16 |
| A | cervical cord compression | 6 | 1, 17, 21, 20, 5, 16 |
| A | cervical polyp | 6 | 1, 17, 21, 20, 5, 16 |
| A | cervicitis | 6 | 1, 17, 21, 20, 5, 16 |
| A | cervicobrachial syndrome | 6 | 1, 17, 21, 20, 5, 16 |
| A | cervicogenic headache | 6 | 1, 17, 21, 20, 5, 16 |
| A | cervix carcinoma stage | 6 | 1, 17, 21, 20, 5, 16 |
| A | cholangiocarcinoma | 6 | 1, 17, 21, 20, 5, 16 |
| A | cholelithiasis obstructive | 6 | 1, 17, 21, 20, 5, 16 |
| A | cholesteatoma | 6 | 1, 17, 21, 20, 5, 16 |
| A | colon adenoma | 6 | 1, 17, 21, 20, 5, 16 |
| A | colon cancer stage i | 6 | 1, 17, 21, 20, 5, 16 |
| A | colon cancer stage iii | 6 | 1, 17, 21, 20, 5, 16 |
| A | colonic abscess | 6 | 1, 17, 21, 20, 5, 16 |
| A | colonoscopy abnormal | 6 | 1, 17, 21, 20, 5, 16 |
| A | coma | 6 | 1, 17, 21, 20, 5, 16 |
| A | combined pulmonary fibrosis and emphysema | 6 | 1, 17, 21, 20, 5, 16 |
| A | complication associated with device | 6 | 1, 17, 21, 20, 5, 16 |
| A | corneal dystrophy | 6 | 1, 17, 21, 20, 5, 16 |
| A | coronary artery dissection | 6 | 1, 17, 21, 20, 5, 16 |
| A | coronary artery thrombosis | 6 | 1, 17, 21, 20, 5, 16 |
| A | cranial nerve injury | 6 | 1, 17, 21, 20, 5, 16 |
| A | cyst rupture | 6 | 1, 17, 21, 20, 5, 16 |
| A | deafness neurosensory | 6 | 1, 17, 21, 20, 5, 16 |
| A | delirium tremens | 6 | 1, 17, 21, 20, 5, 16 |
| A | demyelinating polyneuropathy | 6 | 1, 17, 21, 20, 5, 16 |
| A | dermal cyst | 6 | 1, 17, 21, 20, 5, 16 |
| A | dermatitis exfoliative | 6 | 1, 17, 21, 20, 5, 16 |
| A | dermatofibrosarcoma protuberans | 6 | 1, 17, 21, 20, 5, 16 |
| A | device ineffective | 6 | 1, 17, 21, 20, 5, 16 |
| A | device loosening | 6 | 1, 17, 21, 20, 5, 16 |
| A | device related sepsis | 6 | 1, 17, 21, 20, 5, 16 |
| A | diabetic vascular disorder | 6 | 1, 17, 21, 20, 5, 16 |
| A | diffuse axonal injury | 6 | 1, 17, 21, 20, 5, 16 |
| A | dislocation of sternum | 6 | 1, 17, 21, 20, 5, 16 |
| A | dislocation of vertebra | 6 | 1, 17, 21, 20, 5, 16 |
| A | diverticulitis intestinal haemorrhagic | 6 | 1, 17, 21, 20, 5, 16 |
| A | diverticulum intestinal haemorrhagic | 6 | 1, 17, 21, 20, 5, 16 |
| A | dressler's syndrome | 6 | 1, 17, 21, 20, 5, 16 |
| A | drug intolerance | 6 | 1, 17, 21, 20, 5, 16 |
| A | drug withdrawal syndrome | 6 | 1, 17, 21, 20, 5, 16 |
| A | dry gangrene | 6 | 1, 17, 21, 20, 5, 16 |
| A | dyspnoea at rest | 6 | 1, 17, 21, 20, 5, 16 |
| A | eczema nummular | 6 | 1, 17, 21, 20, 5, 16 |
| A | electrocardiogram st segment depression | 6 | 1, 17, 21, 20, 5, 16 |
| A | embolic pneumonia | 6 | 1, 17, 21, 20, 5, 16 |
| A | end stage renal disease | 6 | 1, 17, 21, 20, 5, 16 |
| A | endometrial adenoma | 6 | 1, 17, 21, 20, 5, 16 |
| A | endometrial thickening | 6 | 1, 17, 21, 20, 5, 16 |
| A | endophthalmitis | 6 | 1, 17, 21, 20, 5, 16 |
| A | endoscopy gastrointestinal abnormal | 6 | 1, 17, 21, 20, 5, 16 |
| A | endotracheal intubation complication | 6 | 1, 17, 21, 20, 5, 16 |
| A | enterobacter bacteraemia | 6 | 1, 17, 21, 20, 5, 16 |
| A | enterococcal bacteraemia | 6 | 1, 17, 21, 20, 5, 16 |
| A | enterococcal sepsis | 6 | 1, 17, 21, 20, 5, 16 |
| A | enterostomy | 6 | 1, 17, 21, 20, 5, 16 |
| A | epididymitis | 6 | 1, 17, 21, 20, 5, 16 |
| A | epiploic appendagitis | 6 | 1, 17, 21, 20, 5, 16 |
| A | erosive oesophagitis | 6 | 1, 17, 21, 20, 5, 16 |
| A | erysipeloid | 6 | 1, 17, 21, 20, 5, 16 |
| A | escherichia sepsis | 6 | 1, 17, 21, 20, 5, 16 |
| A | exercise electrocardiogram abnormal | 6 | 1, 17, 21, 20, 5, 16 |
| A | exercise tolerance decreased | 6 | 1, 17, 21, 20, 5, 16 |
| A | exomphalos | 6 | 1, 17, 21, 20, 5, 16 |
| A | exostosis of external ear canal | 6 | 1, 17, 21, 20, 5, 16 |

[Fig. 20-8]

| A | extrasystoles | 6 | 1, 17, 21, 20, 5, 16 |
|---|---|---|---|
| A | eye injury | 6 | 1, 17, 21, 20, 5, 16 |
| A | eye operation complication | 6 | 1, 17, 21, 20, 5, 16 |
| A | eyelid ptosis | 6 | 1, 17, 21, 20, 5, 16 |
| A | facial paresis | 6 | 1, 17, 21, 20, 5, 16 |
| A | fallopian tube cancer | 6 | 1, 17, 21, 20, 5, 16 |
| A | false positive investigation result | 6 | 1, 17, 21, 20, 5, 16 |
| A | fat necrosis | 6 | 1, 17, 21, 20, 5, 16 |
| A | fibroma | 6 | 1, 17, 21, 20, 5, 16 |
| A | finger amputation | 6 | 1, 17, 21, 20, 5, 16 |
| A | fractured ischium | 6 | 1, 17, 21, 20, 5, 16 |
| A | fungal peritonitis | 6 | 1, 17, 21, 20, 5, 16 |
| A | gallbladder perforation | 6 | 1, 17, 21, 20, 5, 16 |
| A | gallbladder polyp | 6 | 1, 17, 21, 20, 5, 16 |
| A | gastric cancer stage iv | 6 | 1, 17, 21, 20, 5, 16 |
| A | gastric disorder | 6 | 1, 17, 21, 20, 5, 16 |
| A | gastritis alcoholic | 6 | 1, 17, 21, 20, 5, 16 |
| A | gastritis viral | 6 | 1, 17, 21, 20, 5, 16 |
| A | gastroduodenal haemorrhage | 6 | 1, 17, 21, 20, 5, 16 |
| A | gastroduodenitis | 6 | 1, 17, 21, 20, 5, 16 |
| A | gastroenteritis adenovirus | 6 | 1, 17, 21, 20, 5, 16 |
| A | gastroenteritis bacterial | 6 | 1, 17, 21, 20, 5, 16 |
| A | gastroenteritis clostridial | 6 | 1, 17, 21, 20, 5, 16 |
| A | gastroenteritis rotavirus | 6 | 1, 17, 21, 20, 5, 16 |
| A | gastrointestinal motility disorder | 6 | 1, 17, 21, 20, 5, 16 |
| A | genital haemorrhage | 6 | 1, 17, 21, 20, 5, 16 |
| A | glioblastoma multiforme | 6 | 1, 17, 21, 20, 5, 16 |
| A | glomerulonephritis membranous | 6 | 1, 17, 21, 20, 5, 16 |
| A | glomerulonephritis minimal lesion | 6 | 1, 17, 21, 20, 5, 16 |
| A | graft infection | 6 | 1, 17, 21, 20, 5, 16 |
| A | groin abscess | 6 | 1, 17, 21, 20, 5, 16 |
| A | haemangiopericytoma | 6 | 1, 17, 21, 20, 5, 16 |
| A | haemorrhagic erosive gastritis | 6 | 1, 17, 21, 20, 5, 16 |
| A | heat stroke | 6 | 1, 17, 21, 20, 5, 16 |
| A | hemiplegic migraine | 6 | 1, 17, 21, 20, 5, 16 |
| A | henoch-schonlein purpura | 6 | 1, 17, 21, 20, 5, 16 |
| A | hepatic cyst | 6 | 1, 17, 21, 20, 5, 16 |
| A | hepatic pain | 6 | 1, 17, 21, 20, 5, 16 |
| A | hepatitis a antibody positive | 6 | 1, 17, 21, 20, 5, 16 |
| A | hepatitis a virus test positive | 6 | 1, 17, 21, 20, 5, 16 |
| A | hepatitis alcoholic | 6 | 1, 17, 21, 20, 5, 16 |
| A | hepatitis b | 6 | 1, 17, 21, 20, 5, 16 |
| A | hepatitis c | 6 | 1, 17, 21, 20, 5, 16 |
| A | hepatitis c virus test positive | 6 | 1, 17, 21, 20, 5, 16 |
| A | hepatitis toxic | 6 | 1, 17, 21, 20, 5, 16 |
| A | hepatorenal syndrome | 6 | 1, 17, 21, 20, 5, 16 |
| A | hepatotoxicity | 6 | 1, 17, 21, 20, 5, 16 |
| A | hereditary motor and sensory neuropathy | 6 | 1, 17, 21, 20, 5, 16 |
| A | hernial eventration | 6 | 1, 17, 21, 20, 5, 16 |
| A | herpes simplex meningoencephalitis | 6 | 1, 17, 21, 20, 5, 16 |
| A | hodgkin's disease | 6 | 1, 17, 21, 20, 5, 16 |
| A | hospitalisation | 6 | 1, 17, 21, 20, 5, 16 |
| A | hydrocele | 6 | 1, 17, 21, 20, 5, 16 |
| A | hyperinsulinaemic hypoglycaemia | 6 | 1, 17, 21, 20, 5, 16 |
| A | hyperosmolar hyperglycaemic state | 6 | 1, 17, 21, 20, 5, 16 |
| A | hyperthyroidism | 6 | 1, 17, 21, 20, 5, 16 |
| A | hypertransaminasaemia | 6 | 1, 17, 21, 20, 5, 16 |
| A | hypertrophic cardiomyopathy | 6 | 1, 17, 21, 20, 5, 16 |
| A | hypochromic anaemia | 6 | 1, 17, 21, 20, 5, 16 |
| A | hypovitaminosis | 6 | 1, 17, 21, 20, 5, 16 |
| A | iga nephropathy | 6 | 1, 17, 21, 20, 5, 16 |
| A | ilium fracture | 6 | 1, 17, 21, 20, 5, 16 |
| A | implant site infection | 6 | 1, 17, 21, 20, 5, 16 |
| A | implant site inflammation | 6 | 1, 17, 21, 20, 5, 16 |
| A | incarcerated hernia | 6 | 1, 17, 21, 20, 5, 16 |
| A | incisional hernia repair | 6 | 1, 17, 21, 20, 5, 16 |
| A | incomplete spinal fusion | 6 | 1, 17, 21, 20, 5, 16 |

[Fig. 20-9]

| A | infected bite | 6 | 1, 17, 21, 20, 5, 16 |
|---|---|---|---|
| A | infective exacerbation of chronic obstructive airways disease | 6 | 1, 17, 21, 20, 5, 16 |
| A | infective tenosynovitis | 6 | 1, 17, 21, 20, 5, 16 |
| A | influenza a virus test positive | 6 | 1, 17, 21, 20, 5, 16 |
| A | influenza b virus test positive | 6 | 1, 17, 21, 20, 5, 16 |
| A | inguinal hernia repair | 6 | 1, 17, 21, 20, 5, 16 |
| A | injection site induration | 6 | 1, 17, 21, 20, 5, 16 |
| A | inner ear inflammation | 6 | 1, 17, 21, 20, 5, 16 |
| A | international normalised ratio abnormal | 6 | 1, 17, 21, 20, 5, 16 |
| A | intervertebral disc displacement | 6 | 1, 17, 21, 20, 5, 16 |
| A | intestinal fistula | 6 | 1, 17, 21, 20, 5, 16 |
| A | intestinal prolapse | 6 | 1, 17, 21, 20, 5, 16 |
| A | intracardiac thrombus | 6 | 1, 17, 21, 20, 5, 16 |
| A | intracranial mass | 6 | 1, 17, 21, 20, 5, 16 |
| A | intussusception | 6 | 1, 17, 21, 20, 5, 16 |
| A | investigation | 6 | 1, 17, 21, 20, 5, 16 |
| A | iridocyclitis | 6 | 1, 17, 21, 20, 5, 16 |
| A | jaundice | 6 | 1, 17, 21, 20, 5, 16 |
| A | jaw cyst | 6 | 1, 17, 21, 20, 5, 16 |
| A | joint dislocation postoperative | 6 | 1, 17, 21, 20, 5, 16 |
| A | joint effusion | 6 | 1, 17, 21, 20, 5, 16 |
| A | large cell lung cancer stage iii | 6 | 1, 17, 21, 20, 5, 16 |
| A | large intestinal haemorrhage | 6 | 1, 17, 21, 20, 5, 16 |
| A | large intestinal obstruction | 6 | 1, 17, 21, 20, 5, 16 |
| A | large intestinal polypectomy | 6 | 1, 17, 21, 20, 5, 16 |
| A | laryngeal cancer metastatic | 6 | 1, 17, 21, 20, 5, 16 |
| A | laryngeal cancer stage iv | 6 | 1, 17, 21, 20, 5, 16 |
| A | leriche syndrome | 6 | 1, 17, 21, 20, 5, 16 |
| A | limb discomfort | 6 | 1, 17, 21, 20, 5, 16 |
| A | limb traumatic amputation | 6 | 1, 17, 21, 20, 5, 16 |
| A | lip and/or oral cavity cancer | 6 | 1, 17, 21, 20, 5, 16 |
| A | lip and/or oral cavity cancer stage iii | 6 | 1, 17, 21, 20, 5, 16 |
| A | lipoma excision | 6 | 1, 17, 21, 20, 5, 16 |
| A | liposarcoma | 6 | 1, 17, 21, 20, 5, 16 |
| A | lower respiratory tract infection viral | 6 | 1, 17, 21, 20, 5, 16 |
| A | lung adenocarcinoma metastatic | 6 | 1, 17, 21, 20, 5, 16 |
| A | lung adenocarcinoma stage i | 6 | 1, 17, 21, 20, 5, 16 |
| A | lung adenocarcinoma stage iii | 6 | 1, 17, 21, 20, 5, 16 |
| A | lung carcinoma cell type unspecified stage i | 6 | 1, 17, 21, 20, 5, 16 |
| A | lung carcinoma cell type unspecified stage ii | 6 | 1, 17, 21, 20, 5, 16 |
| A | lung carcinoma cell type unspecified stage iii | 6 | 1, 17, 21, 20, 5, 16 |
| A | lung carcinoma cell type unspecified stage iv | 6 | 1, 17, 21, 20, 5, 16 |
| A | lung squamous cell carcinoma metastatic | 6 | 1, 17, 21, 20, 5, 16 |
| A | lung squamous cell carcinoma stage iii | 6 | 1, 17, 21, 20, 5, 16 |
| A | lymphadenopathy | 6 | 1, 17, 21, 20, 5, 16 |
| A | male genital tract fistula | 6 | 1, 17, 21, 20, 5, 16 |
| A | malignant ascites | 6 | 1, 17, 21, 20, 5, 16 |
| A | malignant melanoma of sites other than skin | 6 | 1, 17, 21, 20, 5, 16 |
| A | malignant mesenteric neoplasm | 6 | 1, 17, 21, 20, 5, 16 |
| A | malignant neoplasm of renal pelvis | 6 | 1, 17, 21, 20, 5, 16 |
| A | mammoplasty | 6 | 1, 17, 21, 20, 5, 16 |
| A | mass | 6 | 1, 17, 21, 20, 5, 16 |
| A | mastitis | 6 | 1, 17, 21, 20, 5, 16 |
| A | mastoiditis | 6 | 1, 17, 21, 20, 5, 16 |
| A | medical device discomfort | 6 | 1, 17, 21, 20, 5, 16 |
| A | medical observation | 6 | 1, 17, 21, 20, 5, 16 |
| A | meniere's disease | 6 | 1, 17, 21, 20, 5, 16 |
| A | meningitis viral | 6 | 1, 17, 21, 20, 5, 16 |
| A | menopause | 6 | 1, 17, 21, 20, 5, 16 |
| A | mesenteric artery stenosis | 6 | 1, 17, 21, 20, 5, 16 |
| A | mesothelioma | 6 | 1, 17, 21, 20, 5, 16 |
| A | metastases to adrenals | 6 | 1, 17, 21, 20, 5, 16 |
| A | metastases to pleura | 6 | 1, 17, 21, 20, 5, 16 |
| A | metastases to spine | 6 | 1, 17, 21, 20, 5, 16 |
| A | metastatic bronchial carcinoma | 6 | 1, 17, 21, 20, 5, 16 |
| A | mite allergy | 6 | 1, 17, 21, 20, 5, 16 |

[Fig. 20-10]

| A | mobility decreased | 6 | 1, 17, 21, 20, 5, 16 |
|---|---|---|---|
| A | mood disorder due to a general medical condition | 6 | 1, 17, 21, 20, 5, 16 |
| A | multiple organ dysfunction syndrome | 6 | 1, 17, 21, 20, 5, 16 |
| A | muscle fatigue | 6 | 1, 17, 21, 20, 5, 16 |
| A | myalgia intercostal | 6 | 1, 17, 21, 20, 5, 16 |
| A | myocardial necrosis | 6 | 1, 17, 21, 20, 5, 16 |
| A | myocardial necrosis marker increased | 6 | 1, 17, 21, 20, 5, 16 |
| A | myocarditis | 6 | 1, 17, 21, 20, 5, 16 |
| A | necrotising fasciitis | 6 | 1, 17, 21, 20, 5, 16 |
| A | neoplasm | 6 | 1, 17, 21, 20, 5, 16 |
| A | neoplasm malignant | 6 | 1, 17, 21, 20, 5, 16 |
| A | nervous system disorder | 6 | 1, 17, 21, 20, 5, 16 |
| A | neuroendocrine carcinoma metastatic | 6 | 1, 17, 21, 20, 5, 16 |
| A | neuroendocrine tumour | 6 | 1, 17, 21, 20, 5, 16 |
| A | neurogenic bladder | 6 | 1, 17, 21, 20, 5, 16 |
| A | neuroglycopenia | 6 | 1, 17, 21, 20, 5, 16 |
| A | neurological symptom | 6 | 1, 17, 21, 20, 5, 16 |
| A | neurosis | 6 | 1, 17, 21, 20, 5, 16 |
| A | neurosyphilis | 6 | 1, 17, 21, 20, 5, 16 |
| A | nocturnal dyspnoea | 6 | 1, 17, 21, 20, 5, 16 |
| A | ocular myasthenia | 6 | 1, 17, 21, 20, 5, 16 |
| A | oesophageal adenocarcinoma metastatic | 6 | 1, 17, 21, 20, 5, 16 |
| A | oesophageal obstruction | 6 | 1, 17, 21, 20, 5, 16 |
| A | oesophageal spasm | 6 | 1, 17, 21, 20, 5, 16 |
| A | oesophageal ulcer | 6 | 1, 17, 21, 20, 5, 16 |
| A | open globe injury | 6 | 1, 17, 21, 20, 5, 16 |
| A | open reduction of fracture | 6 | 1, 17, 21, 20, 5, 16 |
| A | ophthalmic herpes zoster | 6 | 1, 17, 21, 20, 5, 16 |
| A | ophthalmoplegia | 6 | 1, 17, 21, 20, 5, 16 |
| A | oral neoplasm | 6 | 1, 17, 21, 20, 5, 16 |
| A | orchitis | 6 | 1, 17, 21, 20, 5, 16 |
| A | orthopnoea | 6 | 1, 17, 21, 20, 5, 16 |
| A | osteochondrosis | 6 | 1, 17, 21, 20, 5, 16 |
| A | osteoporotic fracture | 6 | 1, 17, 21, 20, 5, 16 |
| A | osteotomy | 6 | 1, 17, 21, 20, 5, 16 |
| A | otitis externa bacterial | 6 | 1, 17, 21, 20, 5, 16 |
| A | otorrhoea | 6 | 1, 17, 21, 20, 5, 16 |
| A | ovarian adenoma | 6 | 1, 17, 21, 20, 5, 16 |
| A | ovarian cancer metastatic | 6 | 1, 17, 21, 20, 5, 16 |
| A | ovarian cancer stage ii | 6 | 1, 17, 21, 20, 5, 16 |
| A | pancreas infection | 6 | 1, 17, 21, 20, 5, 16 |
| A | pancreatic pseudocyst | 6 | 1, 17, 21, 20, 5, 16 |
| A | pancreatitis chronic | 6 | 1, 17, 21, 20, 5, 16 |
| A | pancreatitis necrotising | 6 | 1, 17, 21, 20, 5, 16 |
| A | pancreatolithiasis | 6 | 1, 17, 21, 20, 5, 16 |
| A | panic attack | 6 | 1, 17, 21, 20, 5, 16 |
| A | papillary cystadenoma lymphomatosum | 6 | 1, 17, 21, 20, 5, 16 |
| A | papulopustular rosacea | 6 | 1, 17, 21, 20, 5, 16 |
| A | paresis | 6 | 1, 17, 21, 20, 5, 16 |
| A | pemphigoid | 6 | 1, 17, 21, 20, 5, 16 |
| A | penile haemorrhage | 6 | 1, 17, 21, 20, 5, 16 |
| A | peptic ulcer haemorrhage | 6 | 1, 17, 21, 20, 5, 16 |
| A | periodontal disease | 6 | 1, 17, 21, 20, 5, 16 |
| A | periodontitis | 6 | 1, 17, 21, 20, 5, 16 |
| A | peripheral arterial reocclusion | 6 | 1, 17, 21, 20, 5, 16 |
| A | peripheral artery aneurysm | 6 | 1, 17, 21, 20, 5, 16 |
| A | perirectal abscess | 6 | 1, 17, 21, 20, 5, 16 |
| A | peritoneal haematoma | 6 | 1, 17, 21, 20, 5, 16 |
| A | peroneal nerve palsy | 6 | 1, 17, 21, 20, 5, 16 |
| A | peroneal nerve palsy postoperative | 6 | 1, 17, 21, 20, 5, 16 |
| A | personality disorder | 6 | 1, 17, 21, 20, 5, 16 |
| A | phaeochromocytoma | 6 | 1, 17, 21, 20, 5, 16 |
| A | pharyngeal cancer stage iv | 6 | 1, 17, 21, 20, 5, 16 |
| A | pickwickian syndrome | 6 | 1, 17, 21, 20, 5, 16 |
| A | plasmacytoma | 6 | 1, 17, 21, 20, 5, 16 |
| A | pleomorphic adenoma | 6 | 1, 17, 21, 20, 5, 16 |
| A | pleural adhesion | 6 | 1, 17, 21, 20, 5, 16 |

[Fig. 20-11]

| | | | |
|---|---|---|---|
| A | pleural disorder | 6 | 1, 17, 21, 20, 5, 16 |
| A | pleural mesothelioma malignant | 6 | 1, 17, 21, 20, 5, 16 |
| A | pneumococcal sepsis | 6 | 1, 17, 21, 20, 5, 16 |
| A | pneumoconiosis | 6 | 1, 17, 21, 20, 5, 16 |
| A | pneumonia adenoviral | 6 | 1, 17, 21, 20, 5, 16 |
| A | pneumonia mycoplasmal | 6 | 1, 17, 21, 20, 5, 16 |
| A | pneumonia viral | 6 | 1, 17, 21, 20, 5, 16 |
| A | pneumonitis chemical | 6 | 1, 17, 21, 20, 5, 16 |
| A | pneumothorax traumatic | 6 | 1, 17, 21, 20, 5, 16 |
| A | polycythaemia | 6 | 1, 17, 21, 20, 5, 16 |
| A | polycythaemia vera | 6 | 1, 17, 21, 20, 5, 16 |
| A | polymyalgia rheumatica | 6 | 1, 17, 21, 20, 5, 16 |
| A | polymyositis | 6 | 1, 17, 21, 20, 5, 16 |
| A | portal vein thrombosis | 6 | 1, 17, 21, 20, 5, 16 |
| A | post-traumatic pain | 6 | 1, 17, 21, 20, 5, 16 |
| A | post concussion syndrome | 6 | 1, 17, 21, 20, 5, 16 |
| A | post procedural complication | 6 | 1, 17, 21, 20, 5, 16 |
| A | post procedural swelling | 6 | 1, 17, 21, 20, 5, 16 |
| A | postoperative respiratory failure | 6 | 1, 17, 21, 20, 5, 16 |
| A | prerenal failure | 6 | 1, 17, 21, 20, 5, 16 |
| A | procedural dizziness | 6 | 1, 17, 21, 20, 5, 16 |
| A | procedural haemorrhage | 6 | 1, 17, 21, 20, 5, 16 |
| A | prostate cancer metastatic | 6 | 1, 17, 21, 20, 5, 16 |
| A | prostate cancer stage ii | 6 | 1, 17, 21, 20, 5, 16 |
| A | prostate cancer stage iv | 6 | 1, 17, 21, 20, 5, 16 |
| A | prostate infection | 6 | 1, 17, 21, 20, 5, 16 |
| A | prostatomegaly | 6 | 1, 17, 21, 20, 5, 16 |
| A | psychogenic seizure | 6 | 1, 17, 21, 20, 5, 16 |
| A | pulmonary alveolar haemorrhage | 6 | 1, 17, 21, 20, 5, 16 |
| A | pulmonary pain | 6 | 1, 17, 21, 20, 5, 16 |
| A | pulseless electrical activity | 6 | 1, 17, 21, 20, 5, 16 |
| A | puncture site haemorrhage | 6 | 1, 17, 21, 20, 5, 16 |
| A | pyelonephritis chronic | 6 | 1, 17, 21, 20, 5, 16 |
| A | quadriplegia | 6 | 1, 17, 21, 20, 5, 16 |
| A | radiation mucositis | 6 | 1, 17, 21, 20, 5, 16 |
| A | rectal abscess | 6 | 1, 17, 21, 20, 5, 16 |
| A | rectal cancer stage iii | 6 | 1, 17, 21, 20, 5, 16 |
| A | rectal cancer stage iv | 6 | 1, 17, 21, 20, 5, 16 |
| A | reflux gastritis | 6 | 1, 17, 21, 20, 5, 16 |
| A | rehabilitation therapy | 6 | 1, 17, 21, 20, 5, 16 |
| A | renal adenoma | 6 | 1, 17, 21, 20, 5, 16 |
| A | renal cyst haemorrhage | 6 | 1, 17, 21, 20, 5, 16 |
| A | renal pain | 6 | 1, 17, 21, 20, 5, 16 |
| A | reproductive tract disorder | 6 | 1, 17, 21, 20, 5, 16 |
| A | respiratory tract infection bacterial | 6 | 1, 17, 21, 20, 5, 16 |
| A | restless legs syndrome | 6 | 1, 17, 21, 20, 5, 16 |
| A | retinal vein occlusion | 6 | 1, 17, 21, 20, 5, 16 |
| A | retroperitoneal neoplasm | 6 | 1, 17, 21, 20, 5, 16 |
| A | rhinovirus infection | 6 | 1, 17, 21, 20, 5, 16 |
| A | rhythm idioventricular | 6 | 1, 17, 21, 20, 5, 16 |
| A | sacroiliac fracture | 6 | 1, 17, 21, 20, 5, 16 |
| A | salivary gland enlargement | 6 | 1, 17, 21, 20, 5, 16 |
| A | salpingitis | 6 | 1, 17, 21, 20, 5, 16 |
| A | scar pain | 6 | 1, 17, 21, 20, 5, 16 |
| A | shock haemorrhagic | 6 | 1, 17, 21, 20, 5, 16 |
| A | sinoatrial block | 6 | 1, 17, 21, 20, 5, 16 |
| A | sinus arrest | 6 | 1, 17, 21, 20, 5, 16 |
| A | skin bacterial infection | 6 | 1, 17, 21, 20, 5, 16 |
| A | skull fracture | 6 | 1, 17, 21, 20, 5, 16 |
| A | small cell lung cancer limited stage | 6 | 1, 17, 21, 20, 5, 16 |
| A | small cell lung cancer metastatic | 6 | 1, 17, 21, 20, 5, 16 |
| A | small intestinal haemorrhage | 6 | 1, 17, 21, 20, 5, 16 |
| A | snake bite | 6 | 1, 17, 21, 20, 5, 16 |
| A | soft tissue inflammation | 6 | 1, 17, 21, 20, 5, 16 |
| A | soft tissue sarcoma | 6 | 1, 17, 21, 20, 5, 16 |
| A | somatic symptom disorder | 6 | 1, 17, 21, 20, 5, 16 |
| A | spermatic cord funiculitis | 6 | 1, 17, 21, 20, 5, 16 |

[Fig. 20-12]

| | | | |
|---|---|---|---|
| A | spinal anaesthesia | 6 | 1, 17, 21, 20, 5, 16 |
| A | spinal cord injury lumbar | 6 | 1, 17, 21, 20, 5, 16 |
| A | spinal decompression | 6 | 1, 17, 21, 20, 5, 16 |
| A | spinal instability | 6 | 1, 17, 21, 20, 5, 16 |
| A | strangulated umbilical hernia | 6 | 1, 17, 21, 20, 5, 16 |
| A | streptococcal sepsis | 6 | 1, 17, 21, 20, 5, 16 |
| A | stress cardiomyopathy | 6 | 1, 17, 21, 20, 5, 16 |
| A | stress echocardiogram | 6 | 1, 17, 21, 20, 5, 16 |
| A | stroke in evolution | 6 | 1, 17, 21, 20, 5, 16 |
| A | subacute hepatic failure | 6 | 1, 17, 21, 20, 5, 16 |
| A | subclavian steal syndrome | 6 | 1, 17, 21, 20, 5, 16 |
| A | subcutaneous emphysema | 6 | 1, 17, 21, 20, 5, 16 |
| A | subdural effusion | 6 | 1, 17, 21, 20, 5, 16 |
| A | subdural haemorrhage | 6 | 1, 17, 21, 20, 5, 16 |
| A | sympathetic posterior cervical syndrome | 6 | 1, 17, 21, 20, 5, 16 |
| A | symphysiolysis | 6 | 1, 17, 21, 20, 5, 16 |
| A | takayasu's arteritis | 6 | 1, 17, 21, 20, 5, 16 |
| A | testicular abscess | 6 | 1, 17, 21, 20, 5, 16 |
| A | thrombophlebitis superficial | 6 | 1, 17, 21, 20, 5, 16 |
| A | thyroid function test abnormal | 6 | 1, 17, 21, 20, 5, 16 |
| A | thyroid mass | 6 | 1, 17, 21, 20, 5, 16 |
| A | toe amputation | 6 | 1, 17, 21, 20, 5, 16 |
| A | tongue cyst | 6 | 1, 17, 21, 20, 5, 16 |
| A | tongue oedema | 6 | 1, 17, 21, 20, 5, 16 |
| A | tooth impacted | 6 | 1, 17, 21, 20, 5, 16 |
| A | torsade de pointes | 6 | 1, 17, 21, 20, 5, 16 |
| A | toxic encephalopathy | 6 | 1, 17, 21, 20, 5, 16 |
| A | tracheitis | 6 | 1, 17, 21, 20, 5, 16 |
| A | transient global amnesia | 6 | 1, 17, 21, 20, 5, 16 |
| A | transitional cell cancer of the renal pelvis and ureter | 6 | 1, 17, 21, 20, 5, 16 |
| A | transplant rejection | 6 | 1, 17, 21, 20, 5, 16 |
| A | traumatic arthritis | 6 | 1, 17, 21, 20, 5, 16 |
| A | traumatic intracranial haemorrhage | 6 | 1, 17, 21, 20, 5, 16 |
| A | traumatic shock | 6 | 1, 17, 21, 20, 5, 16 |
| A | traumatic ulcer | 6 | 1, 17, 21, 20, 5, 16 |
| A | troponin t increased | 6 | 1, 17, 21, 20, 5, 16 |
| A | umbilical hernia repair | 6 | 1, 17, 21, 20, 5, 16 |
| A | undifferentiated sarcoma | 6 | 1, 17, 21, 20, 5, 16 |
| A | unresponsive to stimuli | 6 | 1, 17, 21, 20, 5, 16 |
| A | ureteric rupture | 6 | 1, 17, 21, 20, 5, 16 |
| A | ureteric stenosis | 6 | 1, 17, 21, 20, 5, 16 |
| A | ureteritis | 6 | 1, 17, 21, 20, 5, 16 |
| A | urethral stricture postoperative | 6 | 1, 17, 21, 20, 5, 16 |
| A | uterine atony | 6 | 1, 17, 21, 20, 5, 16 |
| A | uterine enlargement | 6 | 1, 17, 21, 20, 5, 16 |
| A | vascular bypass dysfunction | 6 | 1, 17, 21, 20, 5, 16 |
| A | vascular occlusion | 6 | 1, 17, 21, 20, 5, 16 |
| A | vascular stenosis | 6 | 1, 17, 21, 20, 5, 16 |
| A | vascular stent occlusion | 6 | 1, 17, 21, 20, 5, 16 |
| A | vascular stent restenosis | 6 | 1, 17, 21, 20, 5, 16 |
| A | vascular stent stenosis | 6 | 1, 17, 21, 20, 5, 16 |
| A | vasoconstriction | 6 | 1, 17, 21, 20, 5, 16 |
| A | vasodilatation | 6 | 1, 17, 21, 20, 5, 16 |
| A | ventricular hypertrophy | 6 | 1, 17, 21, 20, 5, 16 |
| A | ventricular tachyarrhythmia | 6 | 1, 17, 21, 20, 5, 16 |
| A | vertebral artery occlusion | 6 | 1, 17, 21, 20, 5, 16 |
| A | vertigo cns origin | 6 | 1, 17, 21, 20, 5, 16 |
| A | vessel perforation | 6 | 1, 17, 21, 20, 5, 16 |
| A | vessel puncture site haemorrhage | 6 | 1, 17, 21, 20, 5, 16 |
| A | vessel puncture site pain | 6 | 1, 17, 21, 20, 5, 16 |
| A | vestibular ischaemia | 6 | 1, 17, 21, 20, 5, 16 |
| A | viral pericarditis | 6 | 1, 17, 21, 20, 5, 16 |
| A | vitamin b12 deficiency | 6 | 1, 17, 21, 20, 5, 16 |
| A | vocal cord neoplasm | 6 | 1, 17, 21, 20, 5, 16 |
| A | vocal cord paralysis | 6 | 1, 17, 21, 20, 5, 16 |
| A | vulval abscess | 6 | 1, 17, 21, 20, 5, 16 |
| A | wound abscess | 6 | 1, 17, 21, 20, 5, 16 |

[Fig. 20-13]

| A | wound evisceration | 6 | 1, 17, 21, 20, 5, 16 |
|---|---|---|---|
| A | wound necrosis | 6 | 1, 17, 21, 20, 5, 16 |
| A | wound secretion | 6 | 1, 17, 21, 20, 5, 16 |
| A | anxiety/irritabilty/stress | 6 | 24, 5, 13, 3, 2, 1 |
| A | bleeding, bruising or irritation at injection site | 6 | 24, 5, 13, 3, 2, 1 |
| A | bruising at injection site | 6 | 24, 5, 13, 3, 2, 1 |
| A | confusion\disorientation | 6 | 24, 5, 13, 3, 2, 1 |
| A | cysts | 6 | 24, 5, 13, 3, 2, 1 |
| A | decrease in urination | 6 | 24, 5, 13, 3, 2, 1 |
| A | elevated serum calcium | 6 | 24, 5, 13, 3, 2, 1 |
| A | elevatedhr urine calcium | 6 | 24, 5, 13, 3, 2, 1 |
| A | flu-like symptoms | 6 | 24, 5, 13, 3, 2, 1 |
| A | hospitalization or exacerbation | 6 | 24, 5, 13, 3, 2, 1 |
| A | hypercalciuria | 6 | 24, 5, 13, 3, 2, 1 |
| A | increased thirst | 6 | 24, 5, 13, 3, 2, 1 |
| A | increased urination | 6 | 24, 5, 13, 3, 2, 1 |
| A | injection site irritation | 6 | 24, 5, 13, 3, 2, 1 |
| A | kidney stone/kidney pain | 6 | 24, 5, 13, 3, 2, 1 |
| A | mild | 6 | 24, 5, 13, 3, 2, 1 |
| A | muscle pain/spasm | 6 | 24, 5, 13, 3, 2, 1 |
| A | musculoskeletal | 6 | 24, 5, 13, 3, 2, 1 |
| A | nausea/vomitting | 6 | 24, 5, 13, 3, 2, 1 |
| A | opthalmological irritability/visual impairment | 6 | 24, 5, 13, 3, 2, 1 |
| A | psychological | 6 | 24, 5, 13, 3, 2, 1 |
| A | temperature sensitivity | 6 | 24, 5, 13, 3, 2, 1 |
| A | thigh pain | 6 | 24, 5, 13, 3, 2, 1 |
| A | weight fluctuations | 6 | 24, 5, 13, 3, 2, 1 |
| A | anxiety/irritabilty/stress | 6 | 18, 1, 13, 6, 17, 21 |
| A | bleeding, bruising or irritation at injection site | 6 | 18, 1, 13, 6, 17, 21 |
| A | bruising at injection site | 6 | 18, 1, 13, 6, 17, 21 |
| A | confusion\disorientation | 6 | 18, 1, 13, 6, 17, 21 |
| A | cysts | 6 | 18, 1, 13, 6, 17, 21 |
| A | decrease in urination | 6 | 18, 1, 13, 6, 17, 21 |
| A | elevated serum calcium | 6 | 18, 1, 13, 6, 17, 21 |
| A | elevatedhr urine calcium | 6 | 18, 1, 13, 6, 17, 21 |
| A | flu-like symptoms | 6 | 18, 1, 13, 6, 17, 21 |
| A | hospitalization or exacerbation | 6 | 18, 1, 13, 6, 17, 21 |
| A | hypercalciuria | 6 | 18, 1, 13, 6, 17, 21 |
| A | increased thirst | 6 | 18, 1, 13, 6, 17, 21 |
| A | increased urination | 6 | 18, 1, 13, 6, 17, 21 |
| A | injection site irritation | 6 | 18, 1, 13, 6, 17, 21 |
| A | kidney stone/kidney pain | 6 | 18, 1, 13, 6, 17, 21 |
| A | mild | 6 | 18, 1, 13, 6, 17, 21 |
| A | muscle pain/spasm | 6 | 18, 1, 13, 6, 17, 21 |
| A | musculoskeletal | 6 | 18, 1, 13, 6, 17, 21 |
| A | nausea/vomitting | 6 | 18, 1, 13, 6, 17, 21 |
| A | opthalmological irritability/visual impairment | 6 | 18, 1, 13, 6, 17, 21 |
| A | psychological | 6 | 18, 1, 13, 6, 17, 21 |
| A | temperature sensitivity | 6 | 18, 1, 13, 6, 17, 21 |
| A | thigh pain | 6 | 18, 1, 13, 6, 17, 21 |
| A | weight fluctuations | 6 | 18, 1, 13, 6, 17, 21 |
| A | genitourinary tract infection | 7 | 2, 24, 20, 6, 9, 3, 4 |
| A | abdominal wall abscess | 7 | 7, 18, 5, 24, 11, 13, 12 |
| A | abscess of eyelid | 7 | 7, 18, 5, 24, 11, 13, 12 |
| A | accelerated hypertension | 7 | 7, 18, 5, 24, 11, 13, 12 |
| A | adenocarcinoma gastric | 7 | 7, 18, 5, 24, 11, 13, 12 |
| A | adenocarcinoma pancreas | 7 | 7, 18, 5, 24, 11, 13, 12 |
| A | altered state of consciousness | 7 | 7, 18, 5, 24, 11, 13, 12 |
| A | amoebic dysentery | 7 | 7, 18, 5, 24, 11, 13, 12 |
| A | anal fissure | 7 | 7, 18, 5, 24, 11, 13, 12 |
| A | anaphylactic reaction | 7 | 7, 18, 5, 24, 11, 13, 12 |
| A | anaphylactic shock | 7 | 7, 18, 5, 24, 11, 13, 12 |
| A | angioedema | 7 | 7, 18, 5, 24, 11, 13, 12 |
| A | angle closure glaucoma | 7 | 7, 18, 5, 24, 11, 13, 12 |
| A | aortic valve disease | 7 | 7, 18, 5, 24, 11, 13, 12 |
| A | aortic valve stenosis | 7 | 7, 18, 5, 24, 11, 13, 12 |
| A | arrhythmia prophylaxis | 7 | 7, 18, 5, 24, 11, 13, 12 |

[Fig. 20-14]

| A | arteriogram coronary | 7 | 7, 18, 5, 24, 11, 13, 12 |
|---|---|---|---|
| A | atrial thrombosis | 7 | 7, 18, 5, 24, 11, 13, 12 |
| A | atrioventricular block first degree | 7 | 7, 18, 5, 24, 11, 13, 12 |
| A | atrioventricular block second degree | 7 | 7, 18, 5, 24, 11, 13, 12 |
| A | bacteraemia | 7 | 7, 18, 5, 24, 11, 13, 12 |
| A | bacterial sepsis | 7 | 7, 18, 5, 24, 11, 13, 12 |
| A | basosquamous carcinoma | 7 | 7, 18, 5, 24, 11, 13, 12 |
| A | benign pancreatic neoplasm | 7 | 7, 18, 5, 24, 11, 13, 12 |
| A | bile duct cancer | 7 | 7, 18, 5, 24, 11, 13, 12 |
| A | bile duct obstruction | 7 | 7, 18, 5, 24, 11, 13, 12 |
| A | biliary adenoma | 7 | 7, 18, 5, 24, 11, 13, 12 |
| A | bladder cancer recurrent | 7 | 7, 18, 5, 24, 11, 13, 12 |
| A | bladder prolapse | 7 | 7, 18, 5, 24, 11, 13, 12 |
| A | bladder transitional cell carcinoma | 7 | 7, 18, 5, 24, 11, 13, 12 |
| A | bundle branch block right | 7 | 7, 18, 5, 24, 11, 13, 12 |
| A | cardiac asthma | 7 | 7, 18, 5, 24, 11, 13, 12 |
| A | cardiac failure chronic | 7 | 7, 18, 5, 24, 11, 13, 12 |
| A | cardiac stress test abnormal | 7 | 7, 18, 5, 24, 11, 13, 12 |
| A | cardiogenic shock | 7 | 7, 18, 5, 24, 11, 13, 12 |
| A | cardiopulmonary failure | 7 | 7, 18, 5, 24, 11, 13, 12 |
| A | carotid artery disease | 7 | 7, 18, 5, 24, 11, 13, 12 |
| A | carotid artery occlusion | 7 | 7, 18, 5, 24, 11, 13, 12 |
| A | cerebellar infarction | 7 | 7, 18, 5, 24, 11, 13, 12 |
| A | cerebral artery occlusion | 7 | 7, 18, 5, 24, 11, 13, 12 |
| A | cerebral artery stenosis | 7 | 7, 18, 5, 24, 11, 13, 12 |
| A | cerebrovascular disorder | 7 | 7, 18, 5, 24, 11, 13, 12 |
| A | cerebrovascular insufficiency | 7 | 7, 18, 5, 24, 11, 13, 12 |
| A | cervical radiculopathy | 7 | 7, 18, 5, 24, 11, 13, 12 |
| A | cervical spinal stenosis | 7 | 7, 18, 5, 24, 11, 13, 12 |
| A | chemical poisoning | 7 | 7, 18, 5, 24, 11, 13, 12 |
| A | chest discomfort | 7 | 7, 18, 5, 24, 11, 13, 12 |
| A | chronic gastritis | 7 | 7, 18, 5, 24, 11, 13, 12 |
| A | chronic lymphocytic leukaemia | 7 | 7, 18, 5, 24, 11, 13, 12 |
| A | circulatory collapse | 7 | 7, 18, 5, 24, 11, 13, 12 |
| A | clear cell renal cell carcinoma | 7 | 7, 18, 5, 24, 11, 13, 12 |
| A | colitis ischaemic | 7 | 7, 18, 5, 24, 11, 13, 12 |
| A | colon cancer metastatic | 7 | 7, 18, 5, 24, 11, 13, 12 |
| A | colorectal adenocarcinoma | 7 | 7, 18, 5, 24, 11, 13, 12 |
| A | colorectal cancer | 7 | 7, 18, 5, 24, 11, 13, 12 |
| A | comminuted fracture | 7 | 7, 18, 5, 24, 11, 13, 12 |
| A | congestive cardiomyopathy | 7 | 7, 18, 5, 24, 11, 13, 12 |
| A | coronary artery restenosis | 7 | 7, 18, 5, 24, 11, 13, 12 |
| A | coronary artery stenosis | 7 | 7, 18, 5, 24, 11, 13, 12 |
| A | coronary revascularisation | 7 | 7, 18, 5, 24, 11, 13, 12 |
| A | cystitis escherichia | 7 | 7, 18, 5, 24, 11, 13, 12 |
| A | diabetic foot | 7 | 7, 18, 5, 24, 11, 13, 12 |
| A | diabetic foot infection | 7 | 7, 18, 5, 24, 11, 13, 12 |
| A | diabetic gangrene | 7 | 7, 18, 5, 24, 11, 13, 12 |
| A | diabetic metabolic decompensation | 7 | 7, 18, 5, 24, 11, 13, 12 |
| A | diabetic nephropathy | 7 | 7, 18, 5, 24, 11, 13, 12 |
| A | diabetic neuropathy | 7 | 7, 18, 5, 24, 11, 13, 12 |
| A | diabetic retinopathy | 7 | 7, 18, 5, 24, 11, 13, 12 |
| A | diarrhoea infectious | 7 | 7, 18, 5, 24, 11, 13, 12 |
| A | diffuse large b-cell lymphoma | 7 | 7, 18, 5, 24, 11, 13, 12 |
| A | duodenal ulcer haemorrhage | 7 | 7, 18, 5, 24, 11, 13, 12 |
| A | dupuytren's contracture | 7 | 7, 18, 5, 24, 11, 13, 12 |
| A | electrocardiogram abnormal | 7 | 7, 18, 5, 24, 11, 13, 12 |
| A | endometrial adenocarcinoma | 7 | 7, 18, 5, 24, 11, 13, 12 |
| A | endometrial hyperplasia | 7 | 7, 18, 5, 24, 11, 13, 12 |
| A | erosive duodenitis | 7 | 7, 18, 5, 24, 11, 13, 12 |
| A | extremity necrosis | 7 | 7, 18, 5, 24, 11, 13, 12 |
| A | facial bones fracture | 7 | 7, 18, 5, 24, 11, 13, 12 |
| A | febrile infection | 7 | 7, 18, 5, 24, 11, 13, 12 |
| A | follicular thyroid cancer | 7 | 7, 18, 5, 24, 11, 13, 12 |
| A | food poisoning | 7 | 7, 18, 5, 24, 11, 13, 12 |
| A | fracture displacement | 7 | 7, 18, 5, 24, 11, 13, 12 |
| A | gastric ulcer perforation | 7 | 7, 18, 5, 24, 11, 13, 12 |

[Fig. 20-15]

| | | | |
|---|---|---|---|
| A | gastrointestinal angiodysplasia | 7 | 7, 18, 5, 24, 11, 13, 12 |
| A | generalised tonic-clonic seizure | 7 | 7, 18, 5, 24, 11, 13, 12 |
| A | glioblastoma | 7 | 7, 18, 5, 24, 11, 13, 12 |
| A | gouty arthritis | 7 | 7, 18, 5, 24, 11, 13, 12 |
| A | grand mal convulsion | 7 | 7, 18, 5, 24, 11, 13, 12 |
| A | haemorrhoids thrombosed | 7 | 7, 18, 5, 24, 11, 13, 12 |
| A | hepatic cancer | 7 | 7, 18, 5, 24, 11, 13, 12 |
| A | hepatic cirrhosis | 7 | 7, 18, 5, 24, 11, 13, 12 |
| A | hepatic failure | 7 | 7, 18, 5, 24, 11, 13, 12 |
| A | hepatic neoplasm | 7 | 7, 18, 5, 24, 11, 13, 12 |
| A | hepatitis e | 7 | 7, 18, 5, 24, 11, 13, 12 |
| A | hyperparathyroidism | 7 | 7, 18, 5, 24, 11, 13, 12 |
| A | hyperparathyroidism primary | 7 | 7, 18, 5, 24, 11, 13, 12 |
| A | hypertensive cardiomyopathy | 7 | 7, 18, 5, 24, 11, 13, 12 |
| A | iliac artery occlusion | 7 | 7, 18, 5, 24, 11, 13, 12 |
| A | incarcerated inguinal hernia | 7 | 7, 18, 5, 24, 11, 13, 12 |
| A | incarcerated umbilical hernia | 7 | 7, 18, 5, 24, 11, 13, 12 |
| A | incision site infection | 7 | 7, 18, 5, 24, 11, 13, 12 |
| A | infected skin ulcer | 7 | 7, 18, 5, 24, 11, 13, 12 |
| A | infectious pleural effusion | 7 | 7, 18, 5, 24, 11, 13, 12 |
| A | intervertebral disc disorder | 7 | 7, 18, 5, 24, 11, 13, 12 |
| A | intestinal polyp | 7 | 7, 18, 5, 24, 11, 13, 12 |
| A | intraductal proliferative breast lesion | 7 | 7, 18, 5, 24, 11, 13, 12 |
| A | ischaemic cardiomyopathy | 7 | 7, 18, 5, 24, 11, 13, 12 |
| A | ischaemic cerebral infarction | 7 | 7, 18, 5, 24, 11, 13, 12 |
| A | laryngeal squamous cell carcinoma | 7 | 7, 18, 5, 24, 11, 13, 12 |
| A | left ventricular dysfunction | 7 | 7, 18, 5, 24, 11, 13, 12 |
| A | limb crushing injury | 7 | 7, 18, 5, 24, 11, 13, 12 |
| A | lipoma | 7 | 7, 18, 5, 24, 11, 13, 12 |
| A | liver abscess | 7 | 7, 18, 5, 24, 11, 13, 12 |
| A | liver injury | 7 | 7, 18, 5, 24, 11, 13, 12 |
| A | lumbar radiculopathy | 7 | 7, 18, 5, 24, 11, 13, 12 |
| A | macular fibrosis | 7 | 7, 18, 5, 24, 11, 13, 12 |
| A | malignant hypertension | 7 | 7, 18, 5, 24, 11, 13, 12 |
| A | malignant peritoneal neoplasm | 7 | 7, 18, 5, 24, 11, 13, 12 |
| A | mediastinitis | 7 | 7, 18, 5, 24, 11, 13, 12 |
| A | meningioma | 7 | 7, 18, 5, 24, 11, 13, 12 |
| A | meningitis bacterial | 7 | 7, 18, 5, 24, 11, 13, 12 |
| A | mental disorder | 7 | 7, 18, 5, 24, 11, 13, 12 |
| A | metabolic encephalopathy | 7 | 7, 18, 5, 24, 11, 13, 12 |
| A | metastases to lung | 7 | 7, 18, 5, 24, 11, 13, 12 |
| A | metastases to lymph nodes | 7 | 7, 18, 5, 24, 11, 13, 12 |
| A | metrorrhagia | 7 | 7, 18, 5, 24, 11, 13, 12 |
| A | microvascular coronary artery disease | 7 | 7, 18, 5, 24, 11, 13, 12 |
| A | muscle abscess | 7 | 7, 18, 5, 24, 11, 13, 12 |
| A | myelopathy | 7 | 7, 18, 5, 24, 11, 13, 12 |
| A | nasal obstruction | 7 | 7, 18, 5, 24, 11, 13, 12 |
| A | nasal polyps | 7 | 7, 18, 5, 24, 11, 13, 12 |
| A | neck injury | 7 | 7, 18, 5, 24, 11, 13, 12 |
| A | neuroendocrine carcinoma | 7 | 7, 18, 5, 24, 11, 13, 12 |
| A | neuropathic arthropathy | 7 | 7, 18, 5, 24, 11, 13, 12 |
| A | normochromic normocytic anaemia | 7 | 7, 18, 5, 24, 11, 13, 12 |
| A | oesophageal adenocarcinoma | 7 | 7, 18, 5, 24, 11, 13, 12 |
| A | oesophageal carcinoma | 7 | 7, 18, 5, 24, 11, 13, 12 |
| A | paraparesis | 7 | 7, 18, 5, 24, 11, 13, 12 |
| A | percutaneous coronary intervention | 7 | 7, 18, 5, 24, 11, 13, 12 |
| A | peripheral artery restenosis | 7 | 7, 18, 5, 24, 11, 13, 12 |
| A | peripheral artery stenosis | 7 | 7, 18, 5, 24, 11, 13, 12 |
| A | peripheral ischaemia | 7 | 7, 18, 5, 24, 11, 13, 12 |
| A | perirenal haematoma | 7 | 7, 18, 5, 24, 11, 13, 12 |
| A | petit mal epilepsy | 7 | 7, 18, 5, 24, 11, 13, 12 |
| A | physical assault | 7 | 7, 18, 5, 24, 11, 13, 12 |
| A | pneumonia influenzal | 7 | 7, 18, 5, 24, 11, 13, 12 |
| A | pneumonia legionella | 7 | 7, 18, 5, 24, 11, 13, 12 |
| A | polyarthritis | 7 | 7, 18, 5, 24, 11, 13, 12 |
| A | post procedural haematuria | 7 | 7, 18, 5, 24, 11, 13, 12 |
| A | post procedural haemorrhage | 7 | 7, 18, 5, 24, 11, 13, 12 |

[Fig. 20-16]

| | | | |
|---|---|---|---|
| A | post procedural sepsis | 7 | 7, 18, 5, 24, 11, 13, 12 |
| A | prostatic abscess | 7 | 7, 18, 5, 24, 11, 13, 12 |
| A | psoriasis | 7 | 7, 18, 5, 24, 11, 13, 12 |
| A | pterygium | 7 | 7, 18, 5, 24, 11, 13, 12 |
| A | pulmonary congestion | 7 | 7, 18, 5, 24, 11, 13, 12 |
| A | pulmonary hypertension | 7 | 7, 18, 5, 24, 11, 13, 12 |
| A | rectal adenocarcinoma | 7 | 7, 18, 5, 24, 11, 13, 12 |
| A | renal cell carcinoma stage i | 7 | 7, 18, 5, 24, 11, 13, 12 |
| A | renal colic | 7 | 7, 18, 5, 24, 11, 13, 12 |
| A | renal infarct | 7 | 7, 18, 5, 24, 11, 13, 12 |
| A | retinal artery occlusion | 7 | 7, 18, 5, 24, 11, 13, 12 |
| A | retinal tear | 7 | 7, 18, 5, 24, 11, 13, 12 |
| A | salmonellosis | 7 | 7, 18, 5, 24, 11, 13, 12 |
| A | sarcoma | 7 | 7, 18, 5, 24, 11, 13, 12 |
| A | scrotal abscess | 7 | 7, 18, 5, 24, 11, 13, 12 |
| A | silent myocardial infarction | 7 | 7, 18, 5, 24, 11, 13, 12 |
| A | sinus node dysfunction | 7 | 7, 18, 5, 24, 11, 13, 12 |
| A | skeletal injury | 7 | 7, 18, 5, 24, 11, 13, 12 |
| A | skin abrasion | 7 | 7, 18, 5, 24, 11, 13, 12 |
| A | skin cancer | 7 | 7, 18, 5, 24, 11, 13, 12 |
| A | small cell lung cancer | 7 | 7, 18, 5, 24, 11, 13, 12 |
| A | spinal column injury | 7 | 7, 18, 5, 24, 11, 13, 12 |
| A | squamous cell carcinoma of lung | 7 | 7, 18, 5, 24, 11, 13, 12 |
| A | stab wound | 7 | 7, 18, 5, 24, 11, 13, 12 |
| A | staphylococcal sepsis | 7 | 7, 18, 5, 24, 11, 13, 12 |
| A | stent placement | 7 | 7, 18, 5, 24, 11, 13, 12 |
| A | strangulated hernia | 7 | 7, 18, 5, 24, 11, 13, 12 |
| A | subarachnoid haemorrhage | 7 | 7, 18, 5, 24, 11, 13, 12 |
| A | subclavian artery stenosis | 7 | 7, 18, 5, 24, 11, 13, 12 |
| A | tendon injury | 7 | 7, 18, 5, 24, 11, 13, 12 |
| A | tendonitis | 7 | 7, 18, 5, 24, 11, 13, 12 |
| A | thrombosis mesenteric vessel | 7 | 7, 18, 5, 24, 11, 13, 12 |
| A | transaminases increased | 7 | 7, 18, 5, 24, 11, 13, 12 |
| A | transitional cell carcinoma | 7 | 7, 18, 5, 24, 11, 13, 12 |
| A | troponin increased | 7 | 7, 18, 5, 24, 11, 13, 12 |
| A | tuberculosis | 7 | 7, 18, 5, 24, 11, 13, 12 |
| A | urethral stenosis | 7 | 7, 18, 5, 24, 11, 13, 12 |
| A | urinary tract obstruction | 7 | 7, 18, 5, 24, 11, 13, 12 |
| A | varices oesophageal | 7 | 7, 18, 5, 24, 11, 13, 12 |
| A | varicose vein | 7 | 7, 18, 5, 24, 11, 13, 12 |
| A | vascular graft occlusion | 7 | 7, 18, 5, 24, 11, 13, 12 |
| A | vascular graft thrombosis | 7 | 7, 18, 5, 24, 11, 13, 12 |
| A | vascular insufficiency | 7 | 7, 18, 5, 24, 11, 13, 12 |
| A | vascular pseudoaneurysm | 7 | 7, 18, 5, 24, 11, 13, 12 |
| A | venous thrombosis limb | 7 | 7, 18, 5, 24, 11, 13, 12 |
| A | ventricular extrasystoles | 7 | 7, 18, 5, 24, 11, 13, 12 |
| A | vertebrobasilar insufficiency | 7 | 7, 18, 5, 24, 11, 13, 12 |
| A | vestibular neuronitis | 7 | 7, 18, 5, 24, 11, 13, 12 |
| A | vitreous haemorrhage | 7 | 7, 18, 5, 24, 11, 13, 12 |
| A | wound dehiscence | 7 | 7, 18, 5, 24, 11, 13, 12 |
| A | fatigue | 8 | 23, 15, 6, 16, 5, 24, 9, 2 |
| A | abdominal tenderness | 8 | 15, 7, 14, 6, 21, 24, 5, 20 |
| A | balance disorder | 8 | 15, 7, 14, 6, 21, 24, 5, 20 |
| A | diaphragmatic paralysis | 8 | 15, 7, 14, 6, 21, 24, 5, 20 |
| A | mood swings | 8 | 15, 7, 14, 6, 21, 24, 5, 20 |
| A | paronychia | 8 | 15, 7, 14, 6, 21, 24, 5, 20 |
| A | psoas abscess | 8 | 15, 7, 14, 6, 21, 24, 5, 20 |
| A | abdominal distension | 8 | 20, 17, 24, 7, 3, 14, 10, 19 |
| A | acute kidney injury | 8 | 20, 17, 24, 7, 3, 14, 10, 19 |
| A | anal fistula | 8 | 20, 17, 24, 7, 3, 14, 10, 19 |
| A | arrhythmia | 8 | 20, 17, 24, 7, 3, 14, 10, 19 |
| A | ascites | 8 | 20, 17, 24, 7, 3, 14, 10, 19 |
| A | atelectasis | 8 | 20, 17, 24, 7, 3, 14, 10, 19 |
| A | atrial tachycardia | 8 | 20, 17, 24, 7, 3, 14, 10, 19 |
| A | benign prostatic hyperplasia | 8 | 20, 17, 24, 7, 3, 14, 10, 19 |
| A | bradycardia | 8 | 20, 17, 24, 7, 3, 14, 10, 19 |
| A | catheter site infection | 8 | 20, 17, 24, 7, 3, 14, 10, 19 |

[Fig. 20-17]

| | | | |
|---|---|---|---|
| A | cerebral haemorrhage | 8 | 20, 17, 24, 7, 3, 14, 10, 19 |
| A | cerebrovascular accident | 8 | 20, 17, 24, 7, 3, 14, 10, 19 |
| A | colitis | 8 | 20, 17, 24, 7, 3, 14, 10, 19 |
| A | deep vein thrombosis | 8 | 20, 17, 24, 7, 3, 14, 10, 19 |
| A | dermatitis | 8 | 20, 17, 24, 7, 3, 14, 10, 19 |
| A | diverticulitis | 8 | 20, 17, 24, 7, 3, 14, 10, 19 |
| A | drug hypersensitivity | 8 | 20, 17, 24, 7, 3, 14, 10, 19 |
| A | duodenal ulcer | 8 | 20, 17, 24, 7, 3, 14, 10, 19 |
| A | dysarthria | 8 | 20, 17, 24, 7, 3, 14, 10, 19 |
| A | dyspnoea exertional | 8 | 20, 17, 24, 7, 3, 14, 10, 19 |
| A | erysipelas | 8 | 20, 17, 24, 7, 3, 14, 10, 19 |
| A | erythema | 8 | 20, 17, 24, 7, 3, 14, 10, 19 |
| A | general physical health deterioration | 8 | 20, 17, 24, 7, 3, 14, 10, 19 |
| A | haematoma | 8 | 20, 17, 24, 7, 3, 14, 10, 19 |
| A | haematuria | 8 | 20, 17, 24, 7, 3, 14, 10, 19 |
| A | haemorrhoids | 8 | 20, 17, 24, 7, 3, 14, 10, 19 |
| A | herpes zoster | 8 | 20, 17, 24, 7, 3, 14, 10, 19 |
| A | hip fracture | 8 | 20, 17, 24, 7, 3, 14, 10, 19 |
| A | hydronephrosis | 8 | 20, 17, 24, 7, 3, 14, 10, 19 |
| A | hyperkalaemia | 8 | 20, 17, 24, 7, 3, 14, 10, 19 |
| A | hypokalaemia | 8 | 20, 17, 24, 7, 3, 14, 10, 19 |
| A | hypoxia | 8 | 20, 17, 24, 7, 3, 14, 10, 19 |
| A | ileus | 8 | 20, 17, 24, 7, 3, 14, 10, 19 |
| A | intestinal obstruction | 8 | 20, 17, 24, 7, 3, 14, 10, 19 |
| A | iron deficiency anaemia | 8 | 20, 17, 24, 7, 3, 14, 10, 19 |
| A | ischaemic stroke | 8 | 20, 17, 24, 7, 3, 14, 10, 19 |
| A | lung infection | 8 | 20, 17, 24, 7, 3, 14, 10, 19 |
| A | mental status changes | 8 | 20, 17, 24, 7, 3, 14, 10, 19 |
| A | musculoskeletal chest pain | 8 | 20, 17, 24, 7, 3, 14, 10, 19 |
| A | obesity | 8 | 20, 17, 24, 7, 3, 14, 10, 19 |
| A | osteoporosis | 8 | 20, 17, 24, 7, 3, 14, 10, 19 |
| A | pericardial effusion | 8 | 20, 17, 24, 7, 3, 14, 10, 19 |
| A | peritonitis | 8 | 20, 17, 24, 7, 3, 14, 10, 19 |
| A | peritonitis bacterial | 8 | 20, 17, 24, 7, 3, 14, 10, 19 |
| A | pleural effusion | 8 | 20, 17, 24, 7, 3, 14, 10, 19 |
| A | pneumonia aspiration | 8 | 20, 17, 24, 7, 3, 14, 10, 19 |
| A | post procedural infection | 8 | 20, 17, 24, 7, 3, 14, 10, 19 |
| A | postoperative wound infection | 8 | 20, 17, 24, 7, 3, 14, 10, 19 |
| A | pulmonary embolism | 8 | 20, 17, 24, 7, 3, 14, 10, 19 |
| A | pulmonary fibrosis | 8 | 20, 17, 24, 7, 3, 14, 10, 19 |
| A | rectal haemorrhage | 8 | 20, 17, 24, 7, 3, 14, 10, 19 |
| A | renal failure | 8 | 20, 17, 24, 7, 3, 14, 10, 19 |
| A | renal failure acute | 8 | 20, 17, 24, 7, 3, 14, 10, 19 |
| A | respiratory distress | 8 | 20, 17, 24, 7, 3, 14, 10, 19 |
| A | sciatica | 8 | 20, 17, 24, 7, 3, 14, 10, 19 |
| A | septic shock | 8 | 20, 17, 24, 7, 3, 14, 10, 19 |
| A | sinus bradycardia | 8 | 20, 17, 24, 7, 3, 14, 10, 19 |
| A | skin ulcer | 8 | 20, 17, 24, 7, 3, 14, 10, 19 |
| A | small intestinal obstruction | 8 | 20, 17, 24, 7, 3, 14, 10, 19 |
| A | spinal compression fracture | 8 | 20, 17, 24, 7, 3, 14, 10, 19 |
| A | spinal fracture | 8 | 20, 17, 24, 7, 3, 14, 10, 19 |
| A | supraventricular tachycardia | 8 | 20, 17, 24, 7, 3, 14, 10, 19 |
| A | thrombosis | 8 | 20, 17, 24, 7, 3, 14, 10, 19 |
| A | upper gastrointestinal haemorrhage | 8 | 20, 17, 24, 7, 3, 14, 10, 19 |
| A | ureteric obstruction | 8 | 20, 17, 24, 7, 3, 14, 10, 19 |
| A | urinary tract infection | 8 | 20, 17, 24, 7, 3, 14, 10, 19 |
| A | urosepsis | 8 | 20, 17, 24, 7, 3, 14, 10, 19 |
| A | ventricular fibrillation | 8 | 20, 17, 24, 7, 3, 14, 10, 19 |
| A | ventricular tachycardia | 8 | 20, 17, 24, 7, 3, 14, 10, 19 |
| A | wound infection | 8 | 20, 17, 24, 7, 3, 14, 10, 19 |
| A | pharyngotonsillitis | 9 | 1, 6, 24, 18, 10, 2, 7, 22, 13 |
| A | psychiatric decompensation | 10 | 23, 9, 2, 14, 3, 22, 17, 10, 15, 6 |
| A | amnesia | 10 | 6, 20, 10, 5, 2, 14, 3, 13, 15, 23 |
| A | arteriosclerosis coronary artery | 10 | 6, 20, 10, 5, 2, 14, 3, 13, 15, 23 |
| A | cystitis | 10 | 6, 20, 10, 5, 2, 14, 3, 13, 15, 23 |
| A | spinal osteoarthritis | 10 | 6, 20, 10, 5, 2, 14, 3, 13, 15, 23 |
| A | blood bilirubin increased | 10 | 15, 17, 7, 21, 16, 6, 23, 19, 2, 18 |

[Fig. 20-18]

| A | blood potassium increased | 10 | 15, 17, 7, 21, 16, 6, 23, 19, 2, 18 |
|---|---|---|---|
| A | blood urea increased | 10 | 15, 17, 7, 21, 16, 6, 23, 19, 2, 18 |
| A | cardiovascular insufficiency | 10 | 15, 17, 7, 21, 16, 6, 23, 19, 2, 18 |
| A | cerumen impaction | 10 | 15, 17, 7, 21, 16, 6, 23, 19, 2, 18 |
| A | duodenal perforation | 10 | 15, 17, 7, 21, 16, 6, 23, 19, 2, 18 |
| A | embolism | 10 | 15, 17, 7, 21, 16, 6, 23, 19, 2, 18 |
| A | flank pain | 10 | 15, 17, 7, 21, 16, 6, 23, 19, 2, 18 |
| A | gastric perforation | 10 | 15, 17, 7, 21, 16, 6, 23, 19, 2, 18 |
| A | genital infection fungal | 10 | 15, 17, 7, 21, 16, 6, 23, 19, 2, 18 |
| A | herpes virus infection | 10 | 15, 17, 7, 21, 16, 6, 23, 19, 2, 18 |
| A | hyperbilirubinaemia | 10 | 15, 17, 7, 21, 16, 6, 23, 19, 2, 18 |
| A | ingrowing nail | 10 | 15, 17, 7, 21, 16, 6, 23, 19, 2, 18 |
| A | intestinal ischaemia | 10 | 15, 17, 7, 21, 16, 6, 23, 19, 2, 18 |
| A | malignant neoplasm progression | 10 | 15, 17, 7, 21, 16, 6, 23, 19, 2, 18 |
| A | mallory-weiss syndrome | 10 | 15, 17, 7, 21, 16, 6, 23, 19, 2, 18 |
| A | metastases to central nervous system | 10 | 15, 17, 7, 21, 16, 6, 23, 19, 2, 18 |
| A | nocturia | 10 | 15, 17, 7, 21, 16, 6, 23, 19, 2, 18 |
| A | oesophageal stenosis | 10 | 15, 17, 7, 21, 16, 6, 23, 19, 2, 18 |
| A | sinus disorder | 10 | 15, 17, 7, 21, 16, 6, 23, 19, 2, 18 |
| A | tumour haemorrhage | 10 | 15, 17, 7, 21, 16, 6, 23, 19, 2, 18 |
| A | white blood cell count increased | 10 | 15, 17, 7, 21, 16, 6, 23, 19, 2, 18 |
| A | nerve compression | 10 | 17, 9, 20, 2, 16, 24, 18, 12, 21, 6 |
| A | diarrhea | 15 | 16, 5, 14, 3, 9, 6, 18, 19, 23, 10, 17, 22, 11, 15, 13 |
| A | amnesia | 15 | 4, 21, 13, 3, 23, 10, 18, 16, 8, 1, 7, 5, 14, 11, 2 |
| A | arteriosclerosis coronary artery | 15 | 4, 21, 13, 3, 23, 10, 18, 16, 8, 1, 7, 5, 14, 11, 2 |
| A | cystitis | 15 | 4, 21, 13, 3, 23, 10, 18, 16, 8, 1, 7, 5, 14, 11, 2 |
| A | spinal osteoarthritis | 15 | 4, 21, 13, 3, 23, 10, 18, 16, 8, 1, 7, 5, 14, 11, 2 |
| A | ataxia | 15 | 4, 23, 19, 8, 21, 15, 3, 2, 16, 10, 9, 20, 1, 17, 14 |
| A | bronchospasm | 15 | 4, 23, 19, 8, 21, 15, 3, 2, 16, 10, 9, 20, 1, 17, 14 |
| A | clostridium difficile infection | 15 | 4, 23, 19, 8, 21, 15, 3, 2, 16, 10, 9, 20, 1, 17, 14 |
| A | decubitus ulcer | 15 | 4, 23, 19, 8, 21, 15, 3, 2, 16, 10, 9, 20, 1, 17, 14 |
| A | device related infection | 15 | 4, 23, 19, 8, 21, 15, 3, 2, 16, 10, 9, 20, 1, 17, 14 |
| A | encephalopathy | 15 | 4, 23, 19, 8, 21, 15, 3, 2, 16, 10, 9, 20, 1, 17, 14 |
| A | fracture | 15 | 4, 23, 19, 8, 21, 15, 3, 2, 16, 10, 9, 20, 1, 17, 14 |
| A | hypercalcaemia | 15 | 4, 23, 19, 8, 21, 15, 3, 2, 16, 10, 9, 20, 1, 17, 14 |
| A | hypocalcaemia | 15 | 4, 23, 19, 8, 21, 15, 3, 2, 16, 10, 9, 20, 1, 17, 14 |
| A | injection site reaction | 15 | 4, 23, 19, 8, 21, 15, 3, 2, 16, 10, 9, 20, 1, 17, 14 |
| A | international normalised ratio increased | 15 | 4, 23, 19, 8, 21, 15, 3, 2, 16, 10, 9, 20, 1, 17, 14 |
| A | lower gastrointestinal haemorrhage | 15 | 4, 23, 19, 8, 21, 15, 3, 2, 16, 10, 9, 20, 1, 17, 14 |
| A | neuralgia | 15 | 4, 23, 19, 8, 21, 15, 3, 2, 16, 10, 9, 20, 1, 17, 14 |
| A | pseudomembranous colitis | 15 | 4, 23, 19, 8, 21, 15, 3, 2, 16, 10, 9, 20, 1, 17, 14 |
| A | respiratory disorder | 15 | 4, 23, 19, 8, 21, 15, 3, 2, 16, 10, 9, 20, 1, 17, 14 |
| A | tooth infection | 15 | 4, 23, 19, 8, 21, 15, 3, 2, 16, 10, 9, 20, 1, 17, 14 |
| E | nausea/vomiting | 1 | 19 |
| E | decreased appetite | 1 | 21 |
| E | rash | 1 | 21 |
| E | accidental overdose | 1 | 10 |
| E | drug-induced liver injury | 1 | 10 |
| E | flatulence | 1 | 10 |
| E | gait disturbance | 1 | 10 |
| E | wound | 1 | 10 |
| E | abdominal discomfort | 2 | 22, 16 |
| E | hyperhidrosis | 2 | 22, 16 |
| E | lethargy | 2 | 22, 16 |
| E | leukocytosis | 2 | 22, 16 |
| E | procedural pain | 2 | 22, 16 |
| E | sinus tachycardia | 2 | 22, 16 |
| E | skin infection | 2 | 22, 16 |
| E | thermal burn | 2 | 22, 16 |
| E | weight increased | 2 | 22, 16 |
| E | nausea/vomiting | 3 | 7, 22, 23 |
| E | blood prolactin decreased | 3 | 23, 8, 5 |
| E | daytime sleepiness | 3 | 23, 8, 5 |
| E | decreased energy | 3 | 23, 8, 5 |
| E | difficulty sleeping | 3 | 23, 8, 5 |
| E | frequent urination | 3 | 23, 8, 5 |
| E | general malaise | 3 | 23, 8, 5 |

[Fig. 20-19]

| E | head aches | 3 | 23, 8, 5 |
|---|---|---|---|
| E | increase perspiraton | 3 | 23, 8, 5 |
| E | increased perspiration | 3 | 23, 8, 5 |
| E | loss of sexual desire | 3 | 23, 8, 5 |
| E | poor coordination | 3 | 23, 8, 5 |
| E | ringing in the ears | 3 | 23, 8, 5 |
| E | sleeping too much | 3 | 23, 8, 5 |
| E | tiredness | 3 | 23, 8, 5 |
| E | extrapyramidal disorder | 3 | 19, 12, 23 |
| E | irritability | 3 | 19, 12, 23 |
| E | acute prerenal failure | 3 | 16, 17, 5 |
| E | aphasia | 3 | 16, 17, 5 |
| E | carbohydrate antigen-9 increased | 3 | 16, 17, 5 |
| E | death | 3 | 16, 17, 5 |
| E | dry eye | 3 | 16, 17, 5 |
| E | enterocolitis | 3 | 16, 17, 5 |
| E | micturition urgency | 3 | 16, 17, 5 |
| E | oral herpes | 3 | 16, 17, 5 |
| E | petechiae | 3 | 16, 17, 5 |
| E | rash pruritic | 3 | 16, 17, 5 |
| E | right ventricular failure | 3 | 16, 17, 5 |
| E | staphylococcal infection | 3 | 16, 17, 5 |
| E | thrombocytopenia | 3 | 16, 17, 5 |
| E | abnormal ecg | 3 | 12, 14, 4 |
| E | ademia | 3 | 12, 14, 4 |
| E | bleeding | 3 | 12, 14, 4 |
| E | dysmenorthoea | 3 | 12, 14, 4 |
| E | ear and labyrinth disorder other: ear canal blockage | 3 | 12, 14, 4 |
| E | extreme sedation | 3 | 12, 14, 4 |
| E | eye irritation/swelling | 3 | 12, 14, 4 |
| E | forgetfulness | 3 | 12, 14, 4 |
| E | fracture of distal clavicle, lt. | 3 | 12, 14, 4 |
| E | halucinations | 3 | 12, 14, 4 |
| E | hospitalization | 3 | 12, 14, 4 |
| E | hyper glycemia | 3 | 12, 14, 4 |
| E | increased auditory hallucinations | 3 | 12, 14, 4 |
| E | injury, poisoning and procedural complications, other: sprain | 3 | 12, 14, 4 |
| E | investigations other - increased liver function tests | 3 | 12, 14, 4 |
| E | lactation | 3 | 12, 14, 4 |
| E | libido decreased | 3 | 12, 14, 4 |
| E | menstrual distubances | 3 | 12, 14, 4 |
| E | metabolism & nutrition disorders, other: increased appetite | 3 | 12, 14, 4 |
| E | musculo-skeletal connective tissue disorder-other, muscle twitch | 3 | 12, 14, 4 |
| E | musculoskeletal and connective tissue disorder - other: muscle spasms | 3 | 12, 14, 4 |
| E | musculoskeletal other: ankle pain | 3 | 12, 14, 4 |
| E | musculoskeletal other: knee and foot pain | 3 | 12, 14, 4 |
| E | nervous sytem disorder - other: unusual dream activity | 3 | 12, 14, 4 |
| E | ocular discomfort | 3 | 12, 14, 4 |
| E | psychiatric disorder - other: accidental overdose | 3 | 12, 14, 4 |
| E | qtc prolongation | 3 | 12, 14, 4 |
| E | severe eps | 3 | 12, 14, 4 |
| E | skin and subcutaneous tissue disorders, other: acne | 3 | 12, 14, 4 |
| E | tachycardia >120 beats/min (supine) | 3 | 12, 14, 4 |
| E | uri | 3 | 12, 14, 4 |
| E | urinary uregency | 3 | 12, 14, 4 |
| E | aortic thrombosis | 4 | 9, 21, 11, 3 |
| E | breast pain | 4 | 9, 21, 11, 3 |
| E | device leakage | 4 | 9, 21, 11, 3 |
| E | ejection fraction decreased | 4 | 9, 21, 11, 3 |
| E | haematochezia | 4 | 9, 21, 11, 3 |
| E | hyperuricaemia | 4 | 9, 21, 11, 3 |
| E | joint range of motion decreased | 4 | 9, 21, 11, 3 |
| E | laryngitis | 4 | 9, 21, 11, 3 |

[Fig. 20-20]

| E | nephropathy toxic | 4 | 9, 21, 11, 3 |
|---|---|---|---|
| E | neuropathy peripheral | 4 | 9, 21, 11, 3 |
| E | pain of skin | 4 | 9, 21, 11, 3 |
| E | peripheral embolism | 4 | 9, 21, 11, 3 |
| E | peripheral motor neuropathy | 4 | 9, 21, 11, 3 |
| E | peripheral venous disease | 4 | 9, 21, 11, 3 |
| E | pneumonitis | 4 | 9, 21, 11, 3 |
| E | productive cough | 4 | 9, 21, 11, 3 |
| E | pruritus generalised | 4 | 9, 21, 11, 3 |
| E | sinus congestion | 4 | 9, 21, 11, 3 |
| E | skin exfoliation | 4 | 9, 21, 11, 3 |
| E | skin lesion | 4 | 9, 21, 11, 3 |
| E | superior vena cava syndrome | 4 | 9, 21, 11, 3 |
| E | troponin i increased | 4 | 9, 21, 11, 3 |
| E | upper-airway cough syndrome | 4 | 9, 21, 11, 3 |
| E | urinary tract infection bacterial | 4 | 9, 21, 11, 3 |
| E | rhinorrhea | 5 | 8, 22, 18, 2, 10 |
| E | nausea | 5 | 3, 13, 16, 11, 14 |
| E | anemia | 5 | 18, 5, 22, 13, 15 |
| E | anorexia | 5 | 18, 5, 22, 13, 15 |
| E | feeling hot | 5 | 18, 5, 22, 13, 15 |
| E | vision blurred | 5 | 18, 5, 22, 13, 15 |
| E | flu like symptoms | 5 | 24, 9, 16, 5, 11 |
| E | abnormal ecg | 5 | 10, 17, 2, 21, 15 |
| E | ademia | 5 | 10, 17, 2, 21, 15 |
| E | bleeding | 5 | 10, 17, 2, 21, 15 |
| E | dysmenorthoea | 5 | 10, 17, 2, 21, 15 |
| E | ear and labyrinth disorder other: ear canal blockage | 5 | 10, 17, 2, 21, 15 |
| E | extreme sedation | 5 | 10, 17, 2, 21, 15 |
| E | eye irritation/swelling | 5 | 10, 17, 2, 21, 15 |
| E | forgetfulness | 5 | 10, 17, 2, 21, 15 |
| E | fracture of distal clavicle, lt. | 5 | 10, 17, 2, 21, 15 |
| E | halucinations | 5 | 10, 17, 2, 21, 15 |
| E | hospitalization | 5 | 10, 17, 2, 21, 15 |
| E | hyper glycemia | 5 | 10, 17, 2, 21, 15 |
| E | increased auditory hallucinations | 5 | 10, 17, 2, 21, 15 |
| E | injury, poisoning and procedural complications, other: sprain | 5 | 10, 17, 2, 21, 15 |
| E | investigations other - increased liver function tests | 5 | 10, 17, 2, 21, 15 |
| E | lactation | 5 | 10, 17, 2, 21, 15 |
| E | libido decreased | 5 | 10, 17, 2, 21, 15 |
| E | menstrual disturbances | 5 | 10, 17, 2, 21, 15 |
| E | metabolism & nutrition disorders, other: increased appetite | 5 | 10, 17, 2, 21, 15 |
| E | musculo-skeletal connective tissue disorder-other, muscle twitch | 5 | 10, 17, 2, 21, 15 |
| E | musculoskeletal and connective tissue disorder - other: muscle spasms | 5 | 10, 17, 2, 21, 15 |
| E | musculoskeletal other: ankle pain | 5 | 10, 17, 2, 21, 15 |
| E | musculoskeletal other: knee and foot pain | 5 | 10, 17, 2, 21, 15 |
| E | nervous sytem disorder - other: unusual dream activity | 5 | 10, 17, 2, 21, 15 |
| E | ocular discomfort | 5 | 10, 17, 2, 21, 15 |
| E | psychiatric disorder – other: accidental overdose | 5 | 10, 17, 2, 21, 15 |
| E | qtc prolongation | 5 | 10, 17, 2, 21, 15 |
| E | severe eps | 5 | 10, 17, 2, 21, 15 |
| E | skin and subcutaneous tissue disorders, other: acne | 5 | 10, 17, 2, 21, 15 |
| E | tachycardia >120 beats/min (supine) | 5 | 10, 17, 2, 21, 15 |
| E | uri | 5 | 10, 17, 2, 21, 15 |
| E | urinary uregency | 5 | 10, 17, 2, 21, 15 |
| E | tremors | 6 | 18, 11, 21, 6, 13, 23 |
| E | anorgasmia | 7 | 21, 7, 18, 8, 5, 11, 23 |
| E | appetite increased | 7 | 21, 7, 18, 8, 5, 11, 23 |
| E | blurry vision | 7 | 21, 7, 18, 8, 5, 11, 23 |
| E | body aches | 7 | 21, 7, 18, 8, 5, 11, 23 |
| E | body pain | 7 | 21, 7, 18, 8, 5, 11, 23 |
| E | cold extremity | 7 | 21, 7, 18, 8, 5, 11, 23 |
| E | coughing | 7 | 21, 7, 18, 8, 5, 11, 23 |

[Fig. 20-21]

| E | cramps | 7 | 21, 7, 18, 8, 5, 11, 23 |
|---|---|---|---|
| E | decreased interest in sex | 7 | 21, 7, 18, 8, 5, 11, 23 |
| E | decreased motor activity | 7 | 21, 7, 18, 8, 5, 11, 23 |
| E | dizziness on standing | 7 | 21, 7, 18, 8, 5, 11, 23 |
| E | emesis | 7 | 21, 7, 18, 8, 5, 11, 23 |
| E | gastrointestinal distress | 7 | 21, 7, 18, 8, 5, 11, 23 |
| E | impaired sexual performance | 7 | 21, 7, 18, 8, 5, 11, 23 |
| E | increased alanine transaminase (alt) | 7 | 21, 7, 18, 8, 5, 11, 23 |
| E | increased anxiety | 7 | 21, 7, 18, 8, 5, 11, 23 |
| E | increased aspartate transaminase (ast) | 7 | 21, 7, 18, 8, 5, 11, 23 |
| E | increased fatigue | 7 | 21, 7, 18, 8, 5, 11, 23 |
| E | increased sleep | 7 | 21, 7, 18, 8, 5, 11, 23 |
| E | join pain/stiffness | 7 | 21, 7, 18, 8, 5, 11, 23 |
| E | joint pain/stiffness | 7 | 21, 7, 18, 8, 5, 11, 23 |
| E | low energy | 7 | 21, 7, 18, 8, 5, 11, 23 |
| E | menstrual irregularity | 7 | 21, 7, 18, 8, 5, 11, 23 |
| E | poor concentration | 7 | 21, 7, 18, 8, 5, 11, 23 |
| E | stomach ache | 7 | 21, 7, 18, 8, 5, 11, 23 |
| E | trouble achieving orgasm | 7 | 21, 7, 18, 8, 5, 11, 23 |
| E | trouble concentrating | 7 | 21, 7, 18, 8, 5, 11, 23 |
| E | trouble sleeping | 7 | 21, 7, 18, 8, 5, 11, 23 |
| E | upper respiratory infection (uri) | 7 | 21, 7, 18, 8, 5, 11, 23 |
| E | insomnia | 7 | 13, 20, 12, 6, 2, 3, 9 |
| E | blood alkaline phosphatase increased | 7 | 13, 15, 7, 5, 11, 18, 23 |
| E | blood cholesterol increased | 7 | 13, 15, 7, 5, 11, 18, 23 |
| E | scoliosis | 7 | 13, 15, 7, 5, 11, 18, 23 |
| E | thrush | 7 | 13, 15, 7, 5, 11, 18, 23 |
| E | vaginal discharge | 7 | 13, 15, 7, 5, 11, 18, 23 |
| E | abcess | 7 | 12, 4, 1, 18, 13, 20, 16 |
| E | activated partial thromboplastin time prolonged | 7 | 12, 4, 1, 18, 13, 20, 16 |
| E | acute renal failure | 7 | 12, 4, 1, 18, 13, 20, 16 |
| E | ageusia | 7 | 12, 4, 1, 18, 13, 20, 16 |
| E | airway edema | 7 | 12, 4, 1, 18, 13, 20, 16 |
| E | alanine aminotransferase (alt) | 7 | 12, 4, 1, 18, 13, 20, 16 |
| E | albumin, low (hypoalbuminemia) | 7 | 12, 4, 1, 18, 13, 20, 16 |
| E | albumin, serum-low (hypoalbuminemia) | 7 | 12, 4, 1, 18, 13, 20, 16 |
| E | alkaline phosphatase increased | 7 | 12, 4, 1, 18, 13, 20, 16 |
| E | alt, sgpt (serum glutamic pyruvic transaminase) | 7 | 12, 4, 1, 18, 13, 20, 16 |
| E | anorexia (loss of appetite) | 7 | 12, 4, 1, 18, 13, 20, 16 |
| E | anoxeria | 7 | 12, 4, 1, 18, 13, 20, 16 |
| E | ascites (accumulation of fluid in the abdomen) | 7 | 12, 4, 1, 18, 13, 20, 16 |
| E | aspartate aminotransferase increase | 7 | 12, 4, 1, 18, 13, 20, 16 |
| E | ast, sgot(serum glutamic oxaloacetic transaminase) | 7 | 12, 4, 1, 18, 13, 20, 16 |
| E | bilirubin (hyperbilirubinemia) | 7 | 12, 4, 1, 18, 13, 20, 16 |
| E | blood albumin decreased | 7 | 12, 4, 1, 18, 13, 20, 16 |
| E | blood fibrinogen increased | 7 | 12, 4, 1, 18, 13, 20, 16 |
| E | blood magnesium decreased | 7 | 12, 4, 1, 18, 13, 20, 16 |
| E | blood phosphorus decreased | 7 | 12, 4, 1, 18, 13, 20, 16 |
| E | blood sodium decreased | 7 | 12, 4, 1, 18, 13, 20, 16 |
| E | blood/bone marrow-other (specify,____) | 7 | 12, 4, 1, 18, 13, 20, 16 |
| E | breath sounds abnormal | 7 | 12, 4, 1, 18, 13, 20, 16 |
| E | calcium, serum-high (hypercalcemia) | 7 | 12, 4, 1, 18, 13, 20, 16 |
| E | calcium, serum-low (hypocalcemia) | 7 | 12, 4, 1, 18, 13, 20, 16 |
| E | catatonia | 7 | 12, 4, 1, 18, 13, 20, 16 |
| E | creatinine | 7 | 12, 4, 1, 18, 13, 20, 16 |
| E | creatinine increased | 7 | 12, 4, 1, 18, 13, 20, 16 |
| E | death nos | 7 | 12, 4, 1, 18, 13, 20, 16 |
| E | dermatitis - radiation | 7 | 12, 4, 1, 18, 13, 20, 16 |
| E | dermatitis acneiform | 7 | 12, 4, 1, 18, 13, 20, 16 |
| E | dermatology/skin-other (specify,____) | 7 | 12, 4, 1, 18, 13, 20, 16 |
| E | dermatology/skin - other (specify) | 7 | 12, 4, 1, 18, 13, 20, 16 |
| E | dermatology/skin - other (specify, ___) | 7 | 12, 4, 1, 18, 13, 20, 16 |
| E | desquamating rash | 7 | 12, 4, 1, 18, 13, 20, 16 |
| E | diarrhea patients without colostomy | 7 | 12, 4, 1, 18, 13, 20, 16 |
| E | diarrhea w/o prior colostomy | 7 | 12, 4, 1, 18, 13, 20, 16 |
| E | dyspepsia/heartburn | 7 | 12, 4, 1, 18, 13, 20, 16 |
| E | dyspnea | 7 | 12, 4, 1, 18, 13, 20, 16 |

[Fig. 20-22]

| | | | |
|---|---|---|---|
| E | dyspnea (shortness of breath) | 7 | 12, 4, 1, 18, 13, 20, 16 |
| E | edema | 7 | 12, 4, 1, 18, 13, 20, 16 |
| E | edema limb | 7 | 12, 4, 1, 18, 13, 20, 16 |
| E | edema limbs | 7 | 12, 4, 1, 18, 13, 20, 16 |
| E | edema: limbs | 7 | 12, 4, 1, 18, 13, 20, 16 |
| E | electrocardiogram st segment elevation | 7 | 12, 4, 1, 18, 13, 20, 16 |
| E | elevated alt | 7 | 12, 4, 1, 18, 13, 20, 16 |
| E | elevated ast | 7 | 12, 4, 1, 18, 13, 20, 16 |
| E | exfoliative rash | 7 | 12, 4, 1, 18, 13, 20, 16 |
| E | eye discharge | 7 | 12, 4, 1, 18, 13, 20, 16 |
| E | eye disorders - other, specify: decreased visual acuity | 7 | 12, 4, 1, 18, 13, 20, 16 |
| E | febrile neutropenia (fever of unknown origin without clinically or microbiologically documented infe | 7 | 12, 4, 1, 18, 13, 20, 16 |
| E | fever w/o neutropenia | 7 | 12, 4, 1, 18, 13, 20, 16 |
| E | gastrointestinal-other (specify,___) | 7 | 12, 4, 1, 18, 13, 20, 16 |
| E | gastrointestinal - other (specify,___) | 7 | 12, 4, 1, 18, 13, 20, 16 |
| E | gastrointestinal disorders - other, specify: feeling of stomach fullness | 7 | 12, 4, 1, 18, 13, 20, 16 |
| E | general disorders and admin site conditions | 7 | 12, 4, 1, 18, 13, 20, 16 |
| E | gerd | 7 | 12, 4, 1, 18, 13, 20, 16 |
| E | glucose, serum-low (hypoglycemia) | 7 | 12, 4, 1, 18, 13, 20, 16 |
| E | hair loss/alopecia (scalp or body) | 7 | 12, 4, 1, 18, 13, 20, 16 |
| E | heartburn/dyspepsia | 7 | 12, 4, 1, 18, 13, 20, 16 |
| E | hemolysis (red blood cell destruction) | 7 | 12, 4, 1, 18, 13, 20, 16 |
| E | hemorrhage | 7 | 12, 4, 1, 18, 13, 20, 16 |
| E | hyperbilirubinemia (high level of bilirubin) | 7 | 12, 4, 1, 18, 13, 20, 16 |
| E | hyperglycemia | 7 | 12, 4, 1, 18, 13, 20, 16 |
| E | hypoalbuminemia | 7 | 12, 4, 1, 18, 13, 20, 16 |
| E | hypoalbuminemia (low level of albumin in blood) | 7 | 12, 4, 1, 18, 13, 20, 16 |
| E | hypokalemia | 7 | 12, 4, 1, 18, 13, 20, 16 |
| E | hypomagnesemia | 7 | 12, 4, 1, 18, 13, 20, 16 |
| E | hyponatremia | 7 | 12, 4, 1, 18, 13, 20, 16 |
| E | hyponatremia (low sodium level in blood) | 7 | 12, 4, 1, 18, 13, 20, 16 |
| E | hypophosphatemia | 7 | 12, 4, 1, 18, 13, 20, 16 |
| E | increased creatinine | 7 | 12, 4, 1, 18, 13, 20, 16 |
| E | increased upper airway secretion | 7 | 12, 4, 1, 18, 13, 20, 16 |
| E | infection - other (specify,___) | 7 | 12, 4, 1, 18, 13, 20, 16 |
| E | infection with normal anc or grade or neutrophils | 7 | 12, 4, 1, 18, 13, 20, 16 |
| E | infusion reaction (cetuximab) | 7 | 12, 4, 1, 18, 13, 20, 16 |
| E | leukocytes (total wbc) | 7 | 12, 4, 1, 18, 13, 20, 16 |
| E | lymphatics - other (specify,___) | 7 | 12, 4, 1, 18, 13, 20, 16 |
| E | lymphopenia | 7 | 12, 4, 1, 18, 13, 20, 16 |
| E | magnesium, low (hypomagnesemia) | 7 | 12, 4, 1, 18, 13, 20, 16 |
| E | magnesium, serum-high (hypermagnesemia) | 7 | 12, 4, 1, 18, 13, 20, 16 |
| E | magnesium, serum-low (hypomagnesemia) | 7 | 12, 4, 1, 18, 13, 20, 16 |
| E | metabolic/laboratory - other (specify,___) | 7 | 12, 4, 1, 18, 13, 20, 16 |
| E | monocyte count increased | 7 | 12, 4, 1, 18, 13, 20, 16 |
| E | mood alteration | 7 | 12, 4, 1, 18, 13, 20, 16 |
| E | mood alteration-anxiety, agitation | 7 | 12, 4, 1, 18, 13, 20, 16 |
| E | mood alteration-depression | 7 | 12, 4, 1, 18, 13, 20, 16 |
| E | muco/stomatitis by exam, oral cavity | 7 | 12, 4, 1, 18, 13, 20, 16 |
| E | mucosal edema (laryngeal and hypopharyngeal) | 7 | 12, 4, 1, 18, 13, 20, 16 |
| E | mucositis-oral | 7 | 12, 4, 1, 18, 13, 20, 16 |
| E | mucositis oral | 7 | 12, 4, 1, 18, 13, 20, 16 |
| E | mucositis/stomatitis (clinical exam) | 7 | 12, 4, 1, 18, 13, 20, 16 |
| E | mucositis/stomatitis (clinical exam), oral cavity | 7 | 12, 4, 1, 18, 13, 20, 16 |
| E | mucositis/stomatitis (functional/symptomatic), oral cavity | 7 | 12, 4, 1, 18, 13, 20, 16 |
| E | muscle, pain | 7 | 12, 4, 1, 18, 13, 20, 16 |
| E | musculoskeletal/soft tissue - other | 7 | 12, 4, 1, 18, 13, 20, 16 |
| E | nervous system disorders | 7 | 12, 4, 1, 18, 13, 20, 16 |
| E | neuropathy | 7 | 12, 4, 1, 18, 13, 20, 16 |
| E | neuropathy-sensory | 7 | 12, 4, 1, 18, 13, 20, 16 |
| E | neuropathy: sensory | 7 | 12, 4, 1, 18, 13, 20, 16 |
| E | neutropenia/neutrophil count | 7 | 12, 4, 1, 18, 13, 20, 16 |
| E | neutrophil count increased | 7 | 12, 4, 1, 18, 13, 20, 16 |
| E | neutrophils | 7 | 12, 4, 1, 18, 13, 20, 16 |

[Fig. 20-23]

| E | oropharyngeal candidiasis | 7 | 12, 4, 1, 18, 13, 20, 16 |
|---|---|---|---|
| E | other-skin | 7 | 12, 4, 1, 18, 13, 20, 16 |
| E | pain-other (specify,___) | 7 | 12, 4, 1, 18, 13, 20, 16 |
| E | pain - abdomen nos | 7 | 12, 4, 1, 18, 13, 20, 16 |
| E | pain - joint | 7 | 12, 4, 1, 18, 13, 20, 16 |
| E | pain (abdominal/pelvic) | 7 | 12, 4, 1, 18, 13, 20, 16 |
| E | pain (back) | 7 | 12, 4, 1, 18, 13, 20, 16 |
| E | pain (joint) | 7 | 12, 4, 1, 18, 13, 20, 16 |
| E | pain: abdominal pain nos | 7 | 12, 4, 1, 18, 13, 20, 16 |
| E | pain: extremity-limb | 7 | 12, 4, 1, 18, 13, 20, 16 |
| E | pain: head/headache | 7 | 12, 4, 1, 18, 13, 20, 16 |
| E | pallor | 7 | 12, 4, 1, 18, 13, 20, 16 |
| E | palmar-plantar erythrodysaesthesia syndrome | 7 | 12, 4, 1, 18, 13, 20, 16 |
| E | palmar -- plantar erythrodysaesthesia syndrome | 7 | 12, 4, 1, 18, 13, 20, 16 |
| E | paranasal sinus hypersecretion | 7 | 12, 4, 1, 18, 13, 20, 16 |
| E | peripheral sensory neuropathy | 7 | 12, 4, 1, 18, 13, 20, 16 |
| E | phosphate, serum-low (hypophosphatemia) | 7 | 12, 4, 1, 18, 13, 20, 16 |
| E | pigmentation disorder | 7 | 12, 4, 1, 18, 13, 20, 16 |
| E | platelets | 7 | 12, 4, 1, 18, 13, 20, 16 |
| E | platelets decreased | 7 | 12, 4, 1, 18, 13, 20, 16 |
| E | potassium, high (hyperkalemia) | 7 | 12, 4, 1, 18, 13, 20, 16 |
| E | potassium, serum-high (hyperkalemia) | 7 | 12, 4, 1, 18, 13, 20, 16 |
| E | protein total decreased | 7 | 12, 4, 1, 18, 13, 20, 16 |
| E | pruritus/itching | 7 | 12, 4, 1, 18, 13, 20, 16 |
| E | pulmonary | 7 | 12, 4, 1, 18, 13, 20, 16 |
| E | pulmonary-other (specify,___) | 7 | 12, 4, 1, 18, 13, 20, 16 |
| E | radiation skin injury | 7 | 12, 4, 1, 18, 13, 20, 16 |
| E | rash-hand foot skin reaction | 7 | 12, 4, 1, 18, 13, 20, 16 |
| E | rash maculopapular | 7 | 12, 4, 1, 18, 13, 20, 16 |
| E | rash/desquamation | 7 | 12, 4, 1, 18, 13, 20, 16 |
| E | rash: acne/acneiform | 7 | 12, 4, 1, 18, 13, 20, 16 |
| E | rash: dermatitis associated with radiation, chemoradiation | 7 | 12, 4, 1, 18, 13, 20, 16 |
| E | rash: dermatitis associated with radiation, radiation | 7 | 12, 4, 1, 18, 13, 20, 16 |
| E | rhinitis (runny nose) | 7 | 12, 4, 1, 18, 13, 20, 16 |
| E | rigors | 7 | 12, 4, 1, 18, 13, 20, 16 |
| E | salivary gland changes/saliva | 7 | 12, 4, 1, 18, 13, 20, 16 |
| E | serum amylase increased | 7 | 12, 4, 1, 18, 13, 20, 16 |
| E | shortness of breath | 7 | 12, 4, 1, 18, 13, 20, 16 |
| E | skin fissures | 7 | 12, 4, 1, 18, 13, 20, 16 |
| E | skin hyperpigmentation | 7 | 12, 4, 1, 18, 13, 20, 16 |
| E | sodium, serum-low (hyponatremia) | 7 | 12, 4, 1, 18, 13, 20, 16 |
| E | stomatitis/pharyngitis (oral/pharyngeal mucositis) | 7 | 12, 4, 1, 18, 13, 20, 16 |
| E | streptococcal bacteraemia | 7 | 12, 4, 1, 18, 13, 20, 16 |
| E | tachypnoea | 7 | 12, 4, 1, 18, 13, 20, 16 |
| E | taste alteration | 7 | 12, 4, 1, 18, 13, 20, 16 |
| E | taste alteration (dysgeusia) | 7 | 12, 4, 1, 18, 13, 20, 16 |
| E | taste disturbance | 7 | 12, 4, 1, 18, 13, 20, 16 |
| E | thromboembolic event | 7 | 12, 4, 1, 18, 13, 20, 16 |
| E | thrombotic events | 7 | 12, 4, 1, 18, 13, 20, 16 |
| E | thyroid function, low (hypothyroidism) | 7 | 12, 4, 1, 18, 13, 20, 16 |
| E | vision disturbance | 7 | 12, 4, 1, 18, 13, 20, 16 |
| E | voice changes/dysarthria (e.g., hoarseness, loss or alteration in voice, laryngitis) | 7 | 12, 4, 1, 18, 13, 20, 16 |
| E | weakness | 7 | 12, 4, 1, 18, 13, 20, 16 |
| E | lightheadedness | 8 | 8, 2, 12, 20, 5, 17, 13, 3 |
| E | blurred vision | 9 | 15, 11, 10, 24, 6, 21, 2, 22, 23 |
| E | cognitive disorder | 9 | 22, 19, 10, 20, 16, 8, 11, 17, 5 |
| E | convulsion | 9 | 22, 19, 10, 20, 16, 8, 11, 17, 5 |
| E | musculoskeletal stiffness | 9 | 22, 19, 10, 20, 16, 8, 11, 17, 5 |
| E | acne | 9 | 17, 1, 9, 2, 6, 10, 7, 22, 19 |
| E | axillary pain | 9 | 17, 1, 9, 2, 6, 10, 7, 22, 19 |
| E | blood magnesium increased | 9 | 17, 1, 9, 2, 6, 10, 7, 22, 19 |
| E | blood potassium decreased | 9 | 17, 1, 9, 2, 6, 10, 7, 22, 19 |
| E | depressed mood | 9 | 17, 1, 9, 2, 6, 10, 7, 22, 19 |
| E | facial pain | 9 | 17, 1, 9, 2, 6, 10, 7, 22, 19 |

[Fig. 20-24]

| E | fever | 9 | 17, 1, 9, 2, 6, 10, 7, 22, 19 |
|---|---|---|---|
| E | flushing | 9 | 17, 1, 9, 2, 6, 10, 7, 22, 19 |
| E | gingival pain | 9 | 17, 1, 9, 2, 6, 10, 7, 22, 19 |
| E | hiccups | 9 | 17, 1, 9, 2, 6, 10, 7, 22, 19 |
| E | hypernatremia | 9 | 17, 1, 9, 2, 6, 10, 7, 22, 19 |
| E | lip dry | 9 | 17, 1, 9, 2, 6, 10, 7, 22, 19 |
| E | multiple allergies | 9 | 17, 1, 9, 2, 6, 10, 7, 22, 19 |
| E | paresthesia | 9 | 17, 1, 9, 2, 6, 10, 7, 22, 19 |
| E | pharyngolaryngeal pain | 9 | 17, 1, 9, 2, 6, 10, 7, 22, 19 |
| E | protein urine present | 9 | 17, 1, 9, 2, 6, 10, 7, 22, 19 |
| E | proteinuria | 9 | 17, 1, 9, 2, 6, 10, 7, 22, 19 |
| E | retching | 9 | 17, 1, 9, 2, 6, 10, 7, 22, 19 |
| E | salivary hypersecretion | 9 | 17, 1, 9, 2, 6, 10, 7, 22, 19 |
| E | vaginal infection | 9 | 17, 1, 9, 2, 6, 10, 7, 22, 19 |
| E | abdominal hernia | 9 | 9, 17, 24, 23, 18, 13, 6, 2, 3 |
| E | angina pectoris | 9 | 9, 17, 24, 23, 18, 13, 6, 2, 3 |
| E | ankle fracture | 9 | 9, 17, 24, 23, 18, 13, 6, 2, 3 |
| E | appendicitis perforated | 9 | 9, 17, 24, 23, 18, 13, 6, 2, 3 |
| E | bile duct stone | 9 | 9, 17, 24, 23, 18, 13, 6, 2, 3 |
| E | breast cancer | 9 | 9, 17, 24, 23, 18, 13, 6, 2, 3 |
| E | bronchitis chronic | 9 | 9, 17, 24, 23, 18, 13, 6, 2, 3 |
| E | cardiac failure | 9 | 9, 17, 24, 23, 18, 13, 6, 2, 3 |
| E | cardiac failure congestive | 9 | 9, 17, 24, 23, 18, 13, 6, 2, 3 |
| E | cardiac murmur | 9 | 9, 17, 24, 23, 18, 13, 6, 2, 3 |
| E | cardio-respiratory arrest | 9 | 9, 17, 24, 23, 18, 13, 6, 2, 3 |
| E | carpal tunnel syndrome | 9 | 9, 17, 24, 23, 18, 13, 6, 2, 3 |
| E | cholecystitis | 9 | 9, 17, 24, 23, 18, 13, 6, 2, 3 |
| E | cholelithiasis | 9 | 9, 17, 24, 23, 18, 13, 6, 2, 3 |
| E | colon cancer | 9 | 9, 17, 24, 23, 18, 13, 6, 2, 3 |
| E | concussion | 9 | 9, 17, 24, 23, 18, 13, 6, 2, 3 |
| E | costochondritis | 9 | 9, 17, 24, 23, 18, 13, 6, 2, 3 |
| E | craniocerebral injury | 9 | 9, 17, 24, 23, 18, 13, 6, 2, 3 |
| E | ear infection | 9 | 9, 17, 24, 23, 18, 13, 6, 2, 3 |
| E | eczema | 9 | 9, 17, 24, 23, 18, 13, 6, 2, 3 |
| E | gastric ulcer haemorrhage | 9 | 9, 17, 24, 23, 18, 13, 6, 2, 3 |
| E | gastroenteritis viral | 9 | 9, 17, 24, 23, 18, 13, 6, 2, 3 |
| E | glaucoma | 9 | 9, 17, 24, 23, 18, 13, 6, 2, 3 |
| E | hand fracture | 9 | 9, 17, 24, 23, 18, 13, 6, 2, 3 |
| E | head injury | 9 | 9, 17, 24, 23, 18, 13, 6, 2, 3 |
| E | hernia | 9 | 9, 17, 24, 23, 18, 13, 6, 2, 3 |
| E | hypovolaemia | 9 | 9, 17, 24, 23, 18, 13, 6, 2, 3 |
| E | inguinal hernia | 9 | 9, 17, 24, 23, 18, 13, 6, 2, 3 |
| E | injury | 9 | 9, 17, 24, 23, 18, 13, 6, 2, 3 |
| E | ligament rupture | 9 | 9, 17, 24, 23, 18, 13, 6, 2, 3 |
| E | ligament sprain | 9 | 9, 17, 24, 23, 18, 13, 6, 2, 3 |
| E | localised infection | 9 | 9, 17, 24, 23, 18, 13, 6, 2, 3 |
| E | loss of consciousness | 9 | 9, 17, 24, 23, 18, 13, 6, 2, 3 |
| E | lower respiratory tract infection | 9 | 9, 17, 24, 23, 18, 13, 6, 2, 3 |
| E | malignant melanoma | 9 | 9, 17, 24, 23, 18, 13, 6, 2, 3 |
| E | metastases to liver | 9 | 9, 17, 24, 23, 18, 13, 6, 2, 3 |
| E | migraine | 9 | 9, 17, 24, 23, 18, 13, 6, 2, 3 |
| E | osteoarthritis | 9 | 9, 17, 24, 23, 18, 13, 6, 2, 3 |
| E | ovarian cyst | 9 | 9, 17, 24, 23, 18, 13, 6, 2, 3 |
| E | pancreatic carcinoma | 9 | 9, 17, 24, 23, 18, 13, 6, 2, 3 |
| E | pancreatitis acute | 9 | 9, 17, 24, 23, 18, 13, 6, 2, 3 |
| E | radius fracture | 9 | 9, 17, 24, 23, 18, 13, 6, 2, 3 |
| E | renal cell carcinoma | 9 | 9, 17, 24, 23, 18, 13, 6, 2, 3 |
| E | rhabdomyolysis | 9 | 9, 17, 24, 23, 18, 13, 6, 2, 3 |
| E | rib fracture | 9 | 9, 17, 24, 23, 18, 13, 6, 2, 3 |
| E | sudden death | 9 | 9, 17, 24, 23, 18, 13, 6, 2, 3 |
| E | suicidal ideation | 9 | 9, 17, 24, 23, 18, 13, 6, 2, 3 |
| E | type diabetes mellitus | 9 | 9, 17, 24, 23, 18, 13, 6, 2, 3 |
| E | umbilical hernia | 9 | 9, 17, 24, 23, 18, 13, 6, 2, 3 |
| E | wrist fracture | 9 | 9, 17, 24, 23, 18, 13, 6, 2, 3 |
| E | abdominal hernia | 9 | 20, 17, 5, 9, 13, 22, 7, 14, 2 |
| E | angina pectoris | 9 | 20, 17, 5, 9, 13, 22, 7, 14, 2 |
| E | ankle fracture | 9 | 20, 17, 5, 9, 13, 22, 7, 14, 2 |

[Fig. 20-25]

| | | | |
|---|---|---|---|
| E | appendicitis perforated | 9 | 20, 17, 5, 9, 13, 22, 7, 14, 2 |
| E | bile duct stone | 9 | 20, 17, 5, 9, 13, 22, 7, 14, 2 |
| E | breast cancer | 9 | 20, 17, 5, 9, 13, 22, 7, 14, 2 |
| E | bronchitis chronic | 9 | 20, 17, 5, 9, 13, 22, 7, 14, 2 |
| E | cardiac failure | 9 | 20, 17, 5, 9, 13, 22, 7, 14, 2 |
| E | cardiac failure congestive | 9 | 20, 17, 5, 9, 13, 22, 7, 14, 2 |
| E | cardiac murmur | 9 | 20, 17, 5, 9, 13, 22, 7, 14, 2 |
| E | cardio-respiratory arrest | 9 | 20, 17, 5, 9, 13, 22, 7, 14, 2 |
| E | carpal tunnel syndrome | 9 | 20, 17, 5, 9, 13, 22, 7, 14, 2 |
| E | cholecystitis | 9 | 20, 17, 5, 9, 13, 22, 7, 14, 2 |
| E | cholelithiasis | 9 | 20, 17, 5, 9, 13, 22, 7, 14, 2 |
| E | colon cancer | 9 | 20, 17, 5, 9, 13, 22, 7, 14, 2 |
| E | concussion | 9 | 20, 17, 5, 9, 13, 22, 7, 14, 2 |
| E | costochondritis | 9 | 20, 17, 5, 9, 13, 22, 7, 14, 2 |
| E | craniocerebral injury | 9 | 20, 17, 5, 9, 13, 22, 7, 14, 2 |
| E | ear infection | 9 | 20, 17, 5, 9, 13, 22, 7, 14, 2 |
| E | eczema | 9 | 20, 17, 5, 9, 13, 22, 7, 14, 2 |
| E | gastric ulcer haemorrhage | 9 | 20, 17, 5, 9, 13, 22, 7, 14, 2 |
| E | gastroenteritis viral | 9 | 20, 17, 5, 9, 13, 22, 7, 14, 2 |
| E | glaucoma | 9 | 20, 17, 5, 9, 13, 22, 7, 14, 2 |
| E | hand fracture | 9 | 20, 17, 5, 9, 13, 22, 7, 14, 2 |
| E | head injury | 9 | 20, 17, 5, 9, 13, 22, 7, 14, 2 |
| E | hernia | 9 | 20, 17, 5, 9, 13, 22, 7, 14, 2 |
| E | hypovolaemia | 9 | 20, 17, 5, 9, 13, 22, 7, 14, 2 |
| E | inguinal hernia | 9 | 20, 17, 5, 9, 13, 22, 7, 14, 2 |
| E | injury | 9 | 20, 17, 5, 9, 13, 22, 7, 14, 2 |
| E | ligament rupture | 9 | 20, 17, 5, 9, 13, 22, 7, 14, 2 |
| E | ligament sprain | 9 | 20, 17, 5, 9, 13, 22, 7, 14, 2 |
| E | localised infection | 9 | 20, 17, 5, 9, 13, 22, 7, 14, 2 |
| E | loss of consciousness | 9 | 20, 17, 5, 9, 13, 22, 7, 14, 2 |
| E | lower respiratory tract infection | 9 | 20, 17, 5, 9, 13, 22, 7, 14, 2 |
| E | malignant melanoma | 9 | 20, 17, 5, 9, 13, 22, 7, 14, 2 |
| E | metastases to liver | 9 | 20, 17, 5, 9, 13, 22, 7, 14, 2 |
| E | migraine | 9 | 20, 17, 5, 9, 13, 22, 7, 14, 2 |
| E | osteoarthritis | 9 | 20, 17, 5, 9, 13, 22, 7, 14, 2 |
| E | ovarian cyst | 9 | 20, 17, 5, 9, 13, 22, 7, 14, 2 |
| E | pancreatic carcinoma | 9 | 20, 17, 5, 9, 13, 22, 7, 14, 2 |
| E | pancreatitis acute | 9 | 20, 17, 5, 9, 13, 22, 7, 14, 2 |
| E | radius fracture | 9 | 20, 17, 5, 9, 13, 22, 7, 14, 2 |
| E | renal cell carcinoma | 9 | 20, 17, 5, 9, 13, 22, 7, 14, 2 |
| E | rhabdomyolysis | 9 | 20, 17, 5, 9, 13, 22, 7, 14, 2 |
| E | rib fracture | 9 | 20, 17, 5, 9, 13, 22, 7, 14, 2 |
| E | sudden death | 9 | 20, 17, 5, 9, 13, 22, 7, 14, 2 |
| E | suicidal ideation | 9 | 20, 17, 5, 9, 13, 22, 7, 14, 2 |
| E | type diabetes mellitus | 9 | 20, 17, 5, 9, 13, 22, 7, 14, 2 |
| E | umbilical hernia | 9 | 20, 17, 5, 9, 13, 22, 7, 14, 2 |
| E | wrist fracture | 9 | 20, 17, 5, 9, 13, 22, 7, 14, 2 |
| E | amnesia | 9 | 8, 21, 14, 16, 1, 15, 2, 20, 9 |
| E | arteriosclerosis coronary artery | 9 | 8, 21, 14, 16, 1, 15, 2, 20, 9 |
| E | cystitis | 9 | 8, 21, 14, 16, 1, 15, 2, 20, 9 |
| E | spinal osteoarthritis | 9 | 8, 21, 14, 16, 1, 15, 2, 20, 9 |
| E | abdominal tenderness | 9 | 1, 18, 20, 15, 17, 16, 9, 14, 24 |
| E | balance disorder | 9 | 1, 18, 20, 15, 17, 16, 9, 14, 24 |
| E | diaphragmatic paralysis | 9 | 1, 18, 20, 15, 17, 16, 9, 14, 24 |
| E | mood swings | 9 | 1, 18, 20, 15, 17, 16, 9, 14, 24 |
| E | paronychia | 9 | 1, 18, 20, 15, 17, 16, 9, 14, 24 |
| E | psoas abscess | 9 | 1, 18, 20, 15, 17, 16, 9, 14, 24 |
| E | abdominal pain upper | 10 | 17, 6, 9, 16, 20, 22, 23, 3, 12, 7 |
| E | acute myocardial infarction | 10 | 17, 6, 9, 16, 20, 22, 23, 3, 12, 7 |
| E | acute respiratory failure | 10 | 17, 6, 9, 16, 20, 22, 23, 3, 12, 7 |
| E | appendicitis | 10 | 17, 6, 9, 16, 20, 22, 23, 3, 12, 7 |
| E | arthralgia | 10 | 17, 6, 9, 16, 20, 22, 23, 3, 12, 7 |
| E | asthma | 10 | 17, 6, 9, 16, 20, 22, 23, 3, 12, 7 |
| E | atrial fibrillation | 10 | 17, 6, 9, 16, 20, 22, 23, 3, 12, 7 |
| E | atrial flutter | 10 | 17, 6, 9, 16, 20, 22, 23, 3, 12, 7 |
| E | back pain | 10 | 17, 6, 9, 16, 20, 22, 23, 3, 12, 7 |
| E | bronchitis | 10 | 17, 6, 9, 16, 20, 22, 23, 3, 12, 7 |

[Fig. 20-26]

| E | cardiac arrest | 10 | 17, 6, 9, 16, 20, 22, 23, 3, 12, 7 |
|---|---|---|---|
| E | cataract | 10 | 17, 6, 9, 16, 20, 22, 23, 3, 12, 7 |
| E | cellulitis | 10 | 17, 6, 9, 16, 20, 22, 23, 3, 12, 7 |
| E | chest pain | 10 | 17, 6, 9, 16, 20, 22, 23, 3, 12, 7 |
| E | chronic obstructive pulmonary disease | 10 | 17, 6, 9, 16, 20, 22, 23, 3, 12, 7 |
| E | confusional state | 10 | 17, 6, 9, 16, 20, 22, 23, 3, 12, 7 |
| E | contusion | 10 | 17, 6, 9, 16, 20, 22, 23, 3, 12, 7 |
| E | dehydration | 10 | 17, 6, 9, 16, 20, 22, 23, 3, 12, 7 |
| E | diabetes mellitus | 10 | 17, 6, 9, 16, 20, 22, 23, 3, 12, 7 |
| E | epistaxis | 10 | 17, 6, 9, 16, 20, 22, 23, 3, 12, 7 |
| E | fall | 10 | 17, 6, 9, 16, 20, 22, 23, 3, 12, 7 |
| E | femur fracture | 10 | 17, 6, 9, 16, 20, 22, 23, 3, 12, 7 |
| E | gastritis | 10 | 17, 6, 9, 16, 20, 22, 23, 3, 12, 7 |
| E | gastroenteritis | 10 | 17, 6, 9, 16, 20, 22, 23, 3, 12, 7 |
| E | gastrointestinal haemorrhage | 10 | 17, 6, 9, 16, 20, 22, 23, 3, 12, 7 |
| E | gastrooesophageal reflux disease | 10 | 17, 6, 9, 16, 20, 22, 23, 3, 12, 7 |
| E | hyponatraemia | 10 | 17, 6, 9, 16, 20, 22, 23, 3, 12, 7 |
| E | influenza | 10 | 17, 6, 9, 16, 20, 22, 23, 3, 12, 7 |
| E | laceration | 10 | 17, 6, 9, 16, 20, 22, 23, 3, 12, 7 |
| E | muscle spasms | 10 | 17, 6, 9, 16, 20, 22, 23, 3, 12, 7 |
| E | muscular weakness | 10 | 17, 6, 9, 16, 20, 22, 23, 3, 12, 7 |
| E | musculoskeletal pain | 10 | 17, 6, 9, 16, 20, 22, 23, 3, 12, 7 |
| E | myalgia | 10 | 17, 6, 9, 16, 20, 22, 23, 3, 12, 7 |
| E | myocardial infarction | 10 | 17, 6, 9, 16, 20, 22, 23, 3, 12, 7 |
| E | myocardial ischaemia | 10 | 17, 6, 9, 16, 20, 22, 23, 3, 12, 7 |
| E | neck pain | 10 | 17, 6, 9, 16, 20, 22, 23, 3, 12, 7 |
| E | oropharyngeal pain | 10 | 17, 6, 9, 16, 20, 22, 23, 3, 12, 7 |
| E | orthostatic hypotension | 10 | 17, 6, 9, 16, 20, 22, 23, 3, 12, 7 |
| E | overdose | 10 | 17, 6, 9, 16, 20, 22, 23, 3, 12, 7 |
| E | pain in extremity | 10 | 17, 6, 9, 16, 20, 22, 23, 3, 12, 7 |
| E | paraesthesia | 10 | 17, 6, 9, 16, 20, 22, 23, 3, 12, 7 |
| E | pharyngitis | 10 | 17, 6, 9, 16, 20, 22, 23, 3, 12, 7 |
| E | pneumonia | 10 | 17, 6, 9, 16, 20, 22, 23, 3, 12, 7 |
| E | pneumothorax | 10 | 17, 6, 9, 16, 20, 22, 23, 3, 12, 7 |
| E | presyncope | 10 | 17, 6, 9, 16, 20, 22, 23, 3, 12, 7 |
| E | pruritus | 10 | 17, 6, 9, 16, 20, 22, 23, 3, 12, 7 |
| E | respiratory failure | 10 | 17, 6, 9, 16, 20, 22, 23, 3, 12, 7 |
| E | respiratory tract infection | 10 | 17, 6, 9, 16, 20, 22, 23, 3, 12, 7 |
| E | rhinitis | 10 | 17, 6, 9, 16, 20, 22, 23, 3, 12, 7 |
| E | sepsis | 10 | 17, 6, 9, 16, 20, 22, 23, 3, 12, 7 |
| E | sinusitis | 10 | 17, 6, 9, 16, 20, 22, 23, 3, 12, 7 |
| E | syncope | 10 | 17, 6, 9, 16, 20, 22, 23, 3, 12, 7 |
| E | tachycardia | 10 | 17, 6, 9, 16, 20, 22, 23, 3, 12, 7 |
| E | upper respiratory tract infection | 10 | 17, 6, 9, 16, 20, 22, 23, 3, 12, 7 |
| E | vertigo | 10 | 17, 6, 9, 16, 20, 22, 23, 3, 12, 7 |
| E | viral infection | 10 | 17, 6, 9, 16, 20, 22, 23, 3, 12, 7 |
| E | sedation | 10 | 14, 5, 21, 4, 19, 12, 1, 16, 3, 2 |
| E | psychosis | 10 | 23, 13, 12, 14, 15, 2, 11, 5, 8, 24 |
| E | gastrointestinal disorder - other: hypersalivation | 10 | 16, 15, 24, 11, 4, 3, 10, 20, 17, 18 |
| E | hypersalivation | 10 | 16, 15, 24, 11, 4, 3, 10, 20, 17, 18 |
| E | tachycardia >100 beats/min (supine) | 10 | 16, 15, 24, 11, 4, 3, 10, 20, 17, 18 |
| E | weight decreased | 15 | 24, 20, 3, 10, 7, 22, 9, 4, 23, 19, 21, 13, 5, 8, 15 |
| E | otitis media | 15 | 13, 18, 15, 14, 5, 20, 12, 8, 21, 2, 11, 4, 3, 17, 24 |
| E | psychotic disorder | 15 | 13, 18, 15, 14, 5, 20, 12, 8, 21, 2, 11, 4, 3, 17, 24 |
| E | rhinitis allergic | 15 | 13, 18, 15, 14, 5, 20, 12, 8, 21, 2, 11, 4, 3, 17, 24 |
| E | acne | 15 | 17, 18, 16, 9, 21, 5, 1, 15, 20, 7, 22, 23, 13, 6, 24 |
| E | axillary pain | 15 | 17, 18, 16, 9, 21, 5, 1, 15, 20, 7, 22, 23, 13, 6, 24 |
| E | blood magnesium increased | 15 | 17, 18, 16, 9, 21, 5, 1, 15, 20, 7, 22, 23, 13, 6, 24 |
| E | blood potassium decreased | 15 | 17, 18, 16, 9, 21, 5, 1, 15, 20, 7, 22, 23, 13, 6, 24 |
| E | depressed mood | 15 | 17, 18, 16, 9, 21, 5, 1, 15, 20, 7, 22, 23, 13, 6, 24 |
| E | facial pain | 15 | 17, 18, 16, 9, 21, 5, 1, 15, 20, 7, 22, 23, 13, 6, 24 |
| E | fever | 15 | 17, 18, 16, 9, 21, 5, 1, 15, 20, 7, 22, 23, 13, 6, 24 |
| E | flushing | 15 | 17, 18, 16, 9, 21, 5, 1, 15, 20, 7, 22, 23, 13, 6, 24 |
| E | gingival pain | 15 | 17, 18, 16, 9, 21, 5, 1, 15, 20, 7, 22, 23, 13, 6, 24 |
| E | hiccups | 15 | 17, 18, 16, 9, 21, 5, 1, 15, 20, 7, 22, 23, 13, 6, 24 |
| E | hypernatremia | 15 | 17, 18, 16, 9, 21, 5, 1, 15, 20, 7, 22, 23, 13, 6, 24 |
| E | lip dry | 15 | 17, 18, 16, 9, 21, 5, 1, 15, 20, 7, 22, 23, 13, 6, 24 |

[Fig. 20-27]

| | | | |
|---|---|---|---|
| E | multiple allergies | 15 | 17, 18, 16, 9, 21, 5, 1, 15, 20, 7, 22, 23, 13, 6, 24 |
| E | paresthesia | 15 | 17, 18, 16, 9, 21, 5, 1, 15, 20, 7, 22, 23, 13, 6, 24 |
| E | pharyngolaryngeal pain | 15 | 17, 18, 16, 9, 21, 5, 1, 15, 20, 7, 22, 23, 13, 6, 24 |
| E | protein urine present | 15 | 17, 18, 16, 9, 21, 5, 1, 15, 20, 7, 22, 23, 13, 6, 24 |
| E | proteinuria | 15 | 17, 18, 16, 9, 21, 5, 1, 15, 20, 7, 22, 23, 13, 6, 24 |
| E | retching | 15 | 17, 18, 16, 9, 21, 5, 1, 15, 20, 7, 22, 23, 13, 6, 24 |
| E | salivary hypersecretion | 15 | 17, 18, 16, 9, 21, 5, 1, 15, 20, 7, 22, 23, 13, 6, 24 |
| E | vaginal infection | 15 | 17, 18, 16, 9, 21, 5, 1, 15, 20, 7, 22, 23, 13, 6, 24 |
| E | abdominal adhesions | 15 | 24, 1, 18, 19, 16, 21, 22, 3, 14, 20, 11, 7, 13, 8, 2 |
| E | abdominal sepsis | 15 | 24, 1, 18, 19, 16, 21, 22, 3, 14, 20, 11, 7, 13, 8, 2 |
| E | abscess bacterial | 15 | 24, 1, 18, 19, 16, 21, 22, 3, 14, 20, 11, 7, 13, 8, 2 |
| E | adrenal insufficiency | 15 | 24, 1, 18, 19, 16, 21, 22, 3, 14, 20, 11, 7, 13, 8, 2 |
| E | alcohol withdrawal syndrome | 15 | 24, 1, 18, 19, 16, 21, 22, 3, 14, 20, 11, 7, 13, 8, 2 |
| E | amyotrophic lateral sclerosis | 15 | 24, 1, 18, 19, 16, 21, 22, 3, 14, 20, 11, 7, 13, 8, 2 |
| E | anaemia postoperative | 15 | 24, 1, 18, 19, 16, 21, 22, 3, 14, 20, 11, 7, 13, 8, 2 |
| E | aortic valve incompetence | 15 | 24, 1, 18, 19, 16, 21, 22, 3, 14, 20, 11, 7, 13, 8, 2 |
| E | back injury | 15 | 24, 1, 18, 19, 16, 21, 22, 3, 14, 20, 11, 7, 13, 8, 2 |
| E | bile duct stenosis | 15 | 24, 1, 18, 19, 16, 21, 22, 3, 14, 20, 11, 7, 13, 8, 2 |
| E | biliary colic | 15 | 24, 1, 18, 19, 16, 21, 22, 3, 14, 20, 11, 7, 13, 8, 2 |
| E | breast cancer in situ | 15 | 24, 1, 18, 19, 16, 21, 22, 3, 14, 20, 11, 7, 13, 8, 2 |
| E | bronchitis bacterial | 15 | 24, 1, 18, 19, 16, 21, 22, 3, 14, 20, 11, 7, 13, 8, 2 |
| E | bundle branch block left | 15 | 24, 1, 18, 19, 16, 21, 22, 3, 14, 20, 11, 7, 13, 8, 2 |
| E | cervical vertebral fracture | 15 | 24, 1, 18, 19, 16, 21, 22, 3, 14, 20, 11, 7, 13, 8, 2 |
| E | chondropathy | 15 | 24, 1, 18, 19, 16, 21, 22, 3, 14, 20, 11, 7, 13, 8, 2 |
| E | chronic respiratory failure | 15 | 24, 1, 18, 19, 16, 21, 22, 3, 14, 20, 11, 7, 13, 8, 2 |
| E | colitis ulcerative | 15 | 24, 1, 18, 19, 16, 21, 22, 3, 14, 20, 11, 7, 13, 8, 2 |
| E | coronary artery perforation | 15 | 24, 1, 18, 19, 16, 21, 22, 3, 14, 20, 11, 7, 13, 8, 2 |
| E | device breakage | 15 | 24, 1, 18, 19, 16, 21, 22, 3, 14, 20, 11, 7, 13, 8, 2 |
| E | device malfunction | 15 | 24, 1, 18, 19, 16, 21, 22, 3, 14, 20, 11, 7, 13, 8, 2 |
| E | drug eruption | 15 | 24, 1, 18, 19, 16, 21, 22, 3, 14, 20, 11, 7, 13, 8, 2 |
| E | ecchymosis | 15 | 24, 1, 18, 19, 16, 21, 22, 3, 14, 20, 11, 7, 13, 8, 2 |
| E | exostosis | 15 | 24, 1, 18, 19, 16, 21, 22, 3, 14, 20, 11, 7, 13, 8, 2 |
| E | facet joint syndrome | 15 | 24, 1, 18, 19, 16, 21, 22, 3, 14, 20, 11, 7, 13, 8, 2 |
| E | foot fracture | 15 | 24, 1, 18, 19, 16, 21, 22, 3, 14, 20, 11, 7, 13, 8, 2 |
| E | forearm fracture | 15 | 24, 1, 18, 19, 16, 21, 22, 3, 14, 20, 11, 7, 13, 8, 2 |
| E | gastrointestinal ulcer haemorrhage | 15 | 24, 1, 18, 19, 16, 21, 22, 3, 14, 20, 11, 7, 13, 8, 2 |
| E | guillain-barre syndrome | 15 | 24, 1, 18, 19, 16, 21, 22, 3, 14, 20, 11, 7, 13, 8, 2 |
| E | haemorrhage | 15 | 24, 1, 18, 19, 16, 21, 22, 3, 14, 20, 11, 7, 13, 8, 2 |
| E | haemothorax | 15 | 24, 1, 18, 19, 16, 21, 22, 3, 14, 20, 11, 7, 13, 8, 2 |
| E | immune thrombocytopenic purpura | 15 | 24, 1, 18, 19, 16, 21, 22, 3, 14, 20, 11, 7, 13, 8, 2 |
| E | inappropriate antidiuretic hormone secretion | 15 | 24, 1, 18, 19, 16, 21, 22, 3, 14, 20, 11, 7, 13, 8, 2 |
| E | injection site erythema | 15 | 24, 1, 18, 19, 16, 21, 22, 3, 14, 20, 11, 7, 13, 8, 2 |
| E | injection site haematoma | 15 | 24, 1, 18, 19, 16, 21, 22, 3, 14, 20, 11, 7, 13, 8, 2 |
| E | injection site haemorrhage | 15 | 24, 1, 18, 19, 16, 21, 22, 3, 14, 20, 11, 7, 13, 8, 2 |
| E | intervertebral discitis | 15 | 24, 1, 18, 19, 16, 21, 22, 3, 14, 20, 11, 7, 13, 8, 2 |
| E | intracranial aneurysm | 15 | 24, 1, 18, 19, 16, 21, 22, 3, 14, 20, 11, 7, 13, 8, 2 |
| E | invasive breast carcinoma | 15 | 24, 1, 18, 19, 16, 21, 22, 3, 14, 20, 11, 7, 13, 8, 2 |
| E | joint instability | 15 | 24, 1, 18, 19, 16, 21, 22, 3, 14, 20, 11, 7, 13, 8, 2 |
| E | lung neoplasm | 15 | 24, 1, 18, 19, 16, 21, 22, 3, 14, 20, 11, 7, 13, 8, 2 |
| E | meningioma benign | 15 | 24, 1, 18, 19, 16, 21, 22, 3, 14, 20, 11, 7, 13, 8, 2 |
| E | mitral valve incompetence | 15 | 24, 1, 18, 19, 16, 21, 22, 3, 14, 20, 11, 7, 13, 8, 2 |
| E | mitral valve stenosis | 15 | 24, 1, 18, 19, 16, 21, 22, 3, 14, 20, 11, 7, 13, 8, 2 |
| E | multiple fractures | 15 | 24, 1, 18, 19, 16, 21, 22, 3, 14, 20, 11, 7, 13, 8, 2 |
| E | myelodysplastic syndrome | 15 | 24, 1, 18, 19, 16, 21, 22, 3, 14, 20, 11, 7, 13, 8, 2 |
| E | non-hodgkin's lymphoma | 15 | 24, 1, 18, 19, 16, 21, 22, 3, 14, 20, 11, 7, 13, 8, 2 |
| E | oesophageal achalasia | 15 | 24, 1, 18, 19, 16, 21, 22, 3, 14, 20, 11, 7, 13, 8, 2 |
| E | osteitis | 15 | 24, 1, 18, 19, 16, 21, 22, 3, 14, 20, 11, 7, 13, 8, 2 |
| E | papillary thyroid cancer | 15 | 24, 1, 18, 19, 16, 21, 22, 3, 14, 20, 11, 7, 13, 8, 2 |
| E | peripheral artery occlusion | 15 | 24, 1, 18, 19, 16, 21, 22, 3, 14, 20, 11, 7, 13, 8, 2 |
| E | pernicious anaemia | 15 | 24, 1, 18, 19, 16, 21, 22, 3, 14, 20, 11, 7, 13, 8, 2 |
| E | post procedural haematoma | 15 | 24, 1, 18, 19, 16, 21, 22, 3, 14, 20, 11, 7, 13, 8, 2 |
| E | pulmonary arterial hypertension | 15 | 24, 1, 18, 19, 16, 21, 22, 3, 14, 20, 11, 7, 13, 8, 2 |
| E | pyonephrosis | 15 | 24, 1, 18, 19, 16, 21, 22, 3, 14, 20, 11, 7, 13, 8, 2 |
| E | radicular syndrome | 15 | 24, 1, 18, 19, 16, 21, 22, 3, 14, 20, 11, 7, 13, 8, 2 |
| E | retroperitoneal haematoma | 15 | 24, 1, 18, 19, 16, 21, 22, 3, 14, 20, 11, 7, 13, 8, 2 |
| E | rheumatoid arthritis | 15 | 24, 1, 18, 19, 16, 21, 22, 3, 14, 20, 11, 7, 13, 8, 2 |
| E | scapula fracture | 15 | 24, 1, 18, 19, 16, 21, 22, 3, 14, 20, 11, 7, 13, 8, 2 |

[Fig. 20-28]

| | | | |
|---|---|---|---|
| E | shock | 15 | 24, 1, 18, 19, 16, 21, 22, 3, 14, 20, 11, 7, 13, 8, 2 |
| E | staphylococcal bacteraemia | 15 | 24, 1, 18, 19, 16, 21, 22, 3, 14, 20, 11, 7, 13, 8, 2 |
| E | sternal fracture | 15 | 24, 1, 18, 19, 16, 21, 22, 3, 14, 20, 11, 7, 13, 8, 2 |
| E | stress urinary incontinence | 15 | 24, 1, 18, 19, 16, 21, 22, 3, 14, 20, 11, 7, 13, 8, 2 |
| E | subclavian artery occlusion | 15 | 24, 1, 18, 19, 16, 21, 22, 3, 14, 20, 11, 7, 13, 8, 2 |
| E | subcutaneous haematoma | 15 | 24, 1, 18, 19, 16, 21, 22, 3, 14, 20, 11, 7, 13, 8, 2 |
| E | temporal arteritis | 15 | 24, 1, 18, 19, 16, 21, 22, 3, 14, 20, 11, 7, 13, 8, 2 |
| E | temporomandibular joint syndrome | 15 | 24, 1, 18, 19, 16, 21, 22, 3, 14, 20, 11, 7, 13, 8, 2 |
| E | tension headache | 15 | 24, 1, 18, 19, 16, 21, 22, 3, 14, 20, 11, 7, 13, 8, 2 |
| E | thoracic vertebral fracture | 15 | 24, 1, 18, 19, 16, 21, 22, 3, 14, 20, 11, 7, 13, 8, 2 |
| E | traumatic haematoma | 15 | 24, 1, 18, 19, 16, 21, 22, 3, 14, 20, 11, 7, 13, 8, 2 |
| E | ureterolithiasis | 15 | 24, 1, 18, 19, 16, 21, 22, 3, 14, 20, 11, 7, 13, 8, 2 |
| E | vaginal haemorrhage | 15 | 24, 1, 18, 19, 16, 21, 22, 3, 14, 20, 11, 7, 13, 8, 2 |
| E | vascular encephalopathy | 15 | 24, 1, 18, 19, 16, 21, 22, 3, 14, 20, 11, 7, 13, 8, 2 |
| E | vena cava thrombosis | 15 | 24, 1, 18, 19, 16, 21, 22, 3, 14, 20, 11, 7, 13, 8, 2 |
| E | ventricular arrhythmia | 15 | 24, 1, 18, 19, 16, 21, 22, 3, 14, 20, 11, 7, 13, 8, 2 |
| E | vertebral foraminal stenosis | 15 | 24, 1, 18, 19, 16, 21, 22, 3, 14, 20, 11, 7, 13, 8, 2 |
| E | viral upper respiratory tract infection | 15 | 24, 1, 18, 19, 16, 21, 22, 3, 14, 20, 11, 7, 13, 8, 2 |
| E | wound infection staphylococcal | 15 | 24, 1, 18, 19, 16, 21, 22, 3, 14, 20, 11, 7, 13, 8, 2 |
| R | abnormal ecg | 1 | 6 |
| R | ademia | 1 | 6 |
| R | bleeding | 1 | 6 |
| R | dysmenorthoea | 1 | 6 |
| R | ear and labyrinth disorder other: ear canal blockage | 1 | 6 |
| R | extreme sedation | 1 | 6 |
| R | eye irritation/swelling | 1 | 6 |
| R | forgetfulness | 1 | 6 |
| R | fracture of distal clavicle, lt. | 1 | 6 |
| R | halucinations | 1 | 6 |
| R | hospitalization | 1 | 6 |
| R | hyper glycemia | 1 | 6 |
| R | increased auditory hallucinations | 1 | 6 |
| R | injury, poisoning and procedural complications, other: sprain | 1 | 6 |
| R | investigations other - increased liver function tests | 1 | 6 |
| R | lactation | 1 | 6 |
| R | libido decreased | 1 | 6 |
| R | menstrual distubances | 1 | 6 |
| R | metabolism & nutrition disorders, other: increased appetite | 1 | 6 |
| R | musculo-skeletal connective tissue disorder-other, muscle twitch | 1 | 6 |
| R | musculoskeletal and connective tissue disorder - other: muscle spasms | 1 | 6 |
| R | musculoskeletal other: ankle pain | 1 | 6 |
| R | musculoskeletal other: knee and foot pain | 1 | 6 |
| R | nervous sytem disorder - other: unusual dream activity | 1 | 6 |
| R | ocular discomfort | 1 | 6 |
| R | psychiatric disorder - other: accidental overdose | 1 | 6 |
| R | qtc prolongation | 1 | 6 |
| R | severe eps | 1 | 6 |
| R | skin and subcutaneous tissue disorders, other: acne | 1 | 6 |
| R | tachycardia >120 beats/min (supine) | 1 | 6 |
| R | uri | 1 | 6 |
| R | urinary uregency | 1 | 6 |
| R | weight loss | 2 | 9, 14 |
| R | clavicle fracture | 2 | 24, 11 |
| R | headache/migraine | 3 | 7, 16, 1 |
| R | dry skin | 3 | 8, 22, 1 |
| R | neutropenia | 3 | 8, 22, 1 |
| R | adjustment disorder | 3 | 1, 10, 13 |
| R | bilirubin conjugated increased | 3 | 1, 10, 13 |
| R | blood triglycerides increased | 3 | 1, 10, 13 |
| R | completed suicide | 3 | 1, 10, 13 |
| R | coronary artery insufficiency | 3 | 1, 10, 13 |
| R | foreign body | 3 | 1, 10, 13 |
| R | gun shot wound | 3 | 1, 10, 13 |

[Fig. 20-29]

| R | hepatitis | 3 | 1, 10, 13 |
|---|---|---|---|
| R | hepatitis acute | 3 | 1, 10, 13 |
| R | infectious mononucleosis | 3 | 1, 10, 13 |
| R | muscle twitching | 3 | 1, 10, 13 |
| R | nasopharyngeal cancer | 3 | 1, 10, 13 |
| R | oesophageal varices haemorrhage | 3 | 1, 10, 13 |
| R | open angle glaucoma | 3 | 1, 10, 13 |
| R | salivary gland pain | 3 | 1, 10, 13 |
| R | schizophrenia | 3 | 1, 10, 13 |
| R | sick sinus syndrome | 3 | 1, 10, 13 |
| R | tonsillitis | 3 | 1, 10, 13 |
| R | toothache | 3 | 1, 10, 13 |
| R | toxicity to various agents | 3 | 1, 10, 13 |
| R | tremors | 4 | 23, 10, 14, 21 |
| R | alanine aminotransferase increased | 4 | 24, 22, 23, 4 |
| R | anaemia | 4 | 24, 22, 23, 4 |
| R | aspartate aminotransferase increased | 4 | 24, 22, 23, 4 |
| R | blood creatine phosphokinase increased | 4 | 24, 22, 23, 4 |
| R | cough | 4 | 24, 22, 23, 4 |
| R | diarrhoea | 4 | 24, 22, 23, 4 |
| R | dysgeusia | 4 | 24, 22, 23, 4 |
| R | dyspnoea | 4 | 24, 22, 23, 4 |
| R | hyperglycaemia | 4 | 24, 22, 23, 4 |
| R | hypoaesthesia | 4 | 24, 22, 23, 4 |
| R | abdominal discomfort | 4 | 2, 19, 14, 18 |
| R | hyperhidrosis | 4 | 2, 19, 14, 18 |
| R | lethargy | 4 | 2, 19, 14, 18 |
| R | leukocytosis | 4 | 2, 19, 14, 18 |
| R | procedural pain | 4 | 2, 19, 14, 18 |
| R | sinus tachycardia | 4 | 2, 19, 14, 18 |
| R | skin infection | 4 | 2, 19, 14, 18 |
| R | thermal burn | 4 | 2, 19, 14, 18 |
| R | weight increased | 4 | 2, 19, 14, 18 |
| R | genitourinary tract infection | 4 | 12, 19, 5, 11 |
| R | cold/flu virus/symptoms | 4 | 2, 11, 15, 13 |
| R | debonded crown | 4 | 2, 11, 15, 13 |
| R | dermatologic | 4 | 2, 11, 15, 13 |
| R | gastrointestinal | 4 | 2, 11, 15, 13 |
| R | implant failure | 4 | 2, 11, 15, 13 |
| R | injection site ecchymoses, bruising, erythema | 4 | 2, 11, 15, 13 |
| R | musculoskeletal irritability | 4 | 2, 11, 15, 13 |
| R | neurologic | 4 | 2, 11, 15, 13 |
| R | anxiety/irritabilty/stress | 4 | 18, 15, 1, 23 |
| R | bleeding, bruising or irritation at injection site | 4 | 18, 15, 1, 23 |
| R | bruising at injection site | 4 | 18, 15, 1, 23 |
| R | confusion\disorientation | 4 | 18, 15, 1, 23 |
| R | cysts | 4 | 18, 15, 1, 23 |
| R | decrease in urination | 4 | 18, 15, 1, 23 |
| R | elevated serum calcium | 4 | 18, 15, 1, 23 |
| R | elevatedhr urine calcium | 4 | 18, 15, 1, 23 |
| R | flu-like symptoms | 4 | 18, 15, 1, 23 |
| R | hospitalization or exacerbation | 4 | 18, 15, 1, 23 |
| R | hypercalciuria | 4 | 18, 15, 1, 23 |
| R | increased thirst | 4 | 18, 15, 1, 23 |
| R | increased urination | 4 | 18, 15, 1, 23 |
| R | injection site irritation | 4 | 18, 15, 1, 23 |
| R | kidney stone/kidney pain | 4 | 18, 15, 1, 23 |
| R | mild | 4 | 18, 15, 1, 23 |
| R | muscle pain/spasm | 4 | 18, 15, 1, 23 |
| R | musculoskeletal | 4 | 18, 15, 1, 23 |
| R | nausea/vomitting | 4 | 18, 15, 1, 23 |
| R | opthalmological irritability/visual impairment | 4 | 18, 15, 1, 23 |
| R | psychological | 4 | 18, 15, 1, 23 |
| R | temperature sensitivity | 4 | 18, 15, 1, 23 |
| R | thigh pain | 4 | 18, 15, 1, 23 |
| R | weight fluctuations | 4 | 18, 15, 1, 23 |
| R | aspiration pneumonia | 5 | 21, 2, 20, 6, 15 |

[Fig. 20-30]

| R | electrocardiogram qt corrected interval prolonged | 5 | 21, 2, 20, 6, 15 |
|---|---|---|---|
| R | hypocalcemia | 5 | 21, 2, 20, 6, 15 |
| R | mouth sores | 5 | 21, 2, 20, 6, 15 |
| R | white blood cell count decreased | 5 | 21, 2, 20, 6, 15 |
| R | accidental overdose | 5 | 14, 9, 21, 7, 16 |
| R | drug-induced liver injury | 5 | 14, 9, 21, 7, 16 |
| R | flatulence | 5 | 14, 9, 21, 7, 16 |
| R | gait disturbance | 5 | 14, 9, 21, 7, 16 |
| R | wound | 5 | 14, 9, 21, 7, 16 |
| R | abscess | 5 | 21, 4, 15, 7, 6 |
| R | cyst | 5 | 21, 4, 15, 7, 6 |
| R | dental caries | 5 | 21, 4, 15, 7, 6 |
| R | hallucination | 5 | 21, 4, 15, 7, 6 |
| R | lobar pneumonia | 5 | 21, 4, 15, 7, 6 |
| R | pulmonary thrombosis | 5 | 21, 4, 15, 7, 6 |
| R | status asthmaticus | 5 | 21, 4, 15, 7, 6 |
| R | thirst | 5 | 21, 4, 15, 7, 6 |
| R | thrombophlebitis | 5 | 21, 4, 15, 7, 6 |
| R | upper respiratory tract inflammation | 5 | 21, 4, 15, 7, 6 |
| R | allergic rhinitis | 5 | 9, 10, 19, 7, 21 |
| R | aspiration | 5 | 9, 10, 19, 7, 21 |
| R | bladder spasm | 5 | 9, 10, 19, 7, 21 |
| R | blepharitis | 5 | 9, 10, 19, 7, 21 |
| R | blood uric acid increased | 5 | 9, 10, 19, 7, 21 |
| R | bone pain | 5 | 9, 10, 19, 7, 21 |
| R | cachexia | 5 | 9, 10, 19, 7, 21 |
| R | conjunctivitis | 5 | 9, 10, 19, 7, 21 |
| R | duodenal obstruction | 5 | 9, 10, 19, 7, 21 |
| R | enteritis | 5 | 9, 10, 19, 7, 21 |
| R | eye infection | 5 | 9, 10, 19, 7, 21 |
| R | failure to thrive | 5 | 9, 10, 19, 7, 21 |
| R | gastric haemorrhage | 5 | 9, 10, 19, 7, 21 |
| R | groin pain | 5 | 9, 10, 19, 7, 21 |
| R | haemorrhage intracranial | 5 | 9, 10, 19, 7, 21 |
| R | hematoma | 5 | 9, 10, 19, 7, 21 |
| R | hypercalcemia | 5 | 9, 10, 19, 7, 21 |
| R | hypertriglyceridemia | 5 | 9, 10, 19, 7, 21 |
| R | implant site irritation | 5 | 9, 10, 19, 7, 21 |
| R | infusion related reaction | 5 | 9, 10, 19, 7, 21 |
| R | lip disorder | 5 | 9, 10, 19, 7, 21 |
| R | malnutrition | 5 | 9, 10, 19, 7, 21 |
| R | mouth ulceration | 5 | 9, 10, 19, 7, 21 |
| R | nail infection | 5 | 9, 10, 19, 7, 21 |
| R | oral candidiasis | 5 | 9, 10, 19, 7, 21 |
| R | panniculitis | 5 | 9, 10, 19, 7, 21 |
| R | platelet count increased | 5 | 9, 10, 19, 7, 21 |
| R | pleuritic pain | 5 | 9, 10, 19, 7, 21 |
| R | pneumonia haemophilus | 5 | 9, 10, 19, 7, 21 |
| R | raynaud's phenomenon | 5 | 9, 10, 19, 7, 21 |
| R | soft tissue infection | 5 | 9, 10, 19, 7, 21 |
| R | stomach pain | 5 | 9, 10, 19, 7, 21 |
| R | streptococcal infection | 5 | 9, 10, 19, 7, 21 |
| R | stridor | 5 | 9, 10, 19, 7, 21 |
| R | swelling face | 5 | 9, 10, 19, 7, 21 |
| R | visual impairment | 5 | 9, 10, 19, 7, 21 |
| R | gastrointestinal disorder - other: hypersalivation | 5 | 14, 24, 3, 23, 21 |
| R | hypersalivation | 5 | 14, 24, 3, 23, 21 |
| R | tachycardia >100 beats/min (supine) | 5 | 14, 24, 3, 23, 21 |
| R | anxiety/irribilty/stress | 5 | 8, 5, 20, 16, 3 |
| R | bleeding, bruising or irritation at injection site | 5 | 8, 5, 20, 16, 3 |
| R | bruising at injection site | 5 | 8, 5, 20, 16, 3 |
| R | confusion\disorientation | 5 | 8, 5, 20, 16, 3 |
| R | cysts | 5 | 8, 5, 20, 16, 3 |
| R | decrease in urination | 5 | 8, 5, 20, 16, 3 |
| R | elevated serum calcium | 5 | 8, 5, 20, 16, 3 |
| R | elevatedhr urine calcium | 5 | 8, 5, 20, 16, 3 |
| R | flu-like symptoms | 5 | 8, 5, 20, 16, 3 |

[Fig. 20-31]

| R | hospitalization or exacerbation | 5 | 8, 5, 20, 16, 3 |
|---|---|---|---|
| R | hypercalciuria | 5 | 8, 5, 20, 16, 3 |
| R | increased thirst | 5 | 8, 5, 20, 16, 3 |
| R | increased urination | 5 | 8, 5, 20, 16, 3 |
| R | injection site irritation | 5 | 8, 5, 20, 16, 3 |
| R | kidney stone/kidney pain | 5 | 8, 5, 20, 16, 3 |
| R | mild | 5 | 8, 5, 20, 16, 3 |
| R | muscle pain/spasm | 5 | 8, 5, 20, 16, 3 |
| R | musculoskeletal | 5 | 8, 5, 20, 16, 3 |
| R | nausea/vomitting | 5 | 8, 5, 20, 16, 3 |
| R | opthalmological irritability/visual impairment | 5 | 8, 5, 20, 16, 3 |
| R | psychological | 5 | 8, 5, 20, 16, 3 |
| R | temperature sensitivity | 5 | 8, 5, 20, 16, 3 |
| R | thigh pain | 5 | 8, 5, 20, 16, 3 |
| R | weight fluctuations | 5 | 8, 5, 20, 16, 3 |
| R | blood prolactin decreased | 6 | 2, 5, 11, 21, 15, 23 |
| R | daytime sleepiness | 6 | 2, 5, 11, 21, 15, 23 |
| R | decreased energy | 6 | 2, 5, 11, 21, 15, 23 |
| R | difficulty sleeping | 6 | 2, 5, 11, 21, 15, 23 |
| R | frequent urination | 6 | 2, 5, 11, 21, 15, 23 |
| R | general malaise | 6 | 2, 5, 11, 21, 15, 23 |
| R | head aches | 6 | 2, 5, 11, 21, 15, 23 |
| R | increase perspiraton | 6 | 2, 5, 11, 21, 15, 23 |
| R | increased perspiration | 6 | 2, 5, 11, 21, 15, 23 |
| R | loss of sexual desire | 6 | 2, 5, 11, 21, 15, 23 |
| R | poor coordination | 6 | 2, 5, 11, 21, 15, 23 |
| R | ringing in the ears | 6 | 2, 5, 11, 21, 15, 23 |
| R | sleeping too much | 6 | 2, 5, 11, 21, 15, 23 |
| R | tiredness | 6 | 2, 5, 11, 21, 15, 23 |
| R | oedema peripheral | 6 | 14, 8, 2, 18, 12, 3 |
| R | nasal congestion | 6 | 1, 8, 24, 6, 20, 15 |
| R | abdominal pain upper | 6 | 16, 10, 24, 1, 17, 7 |
| R | acute myocardial infarction | 6 | 16, 10, 24, 1, 17, 7 |
| R | acute respiratory failure | 6 | 16, 10, 24, 1, 17, 7 |
| R | appendicitis | 6 | 16, 10, 24, 1, 17, 7 |
| R | arthralgia | 6 | 16, 10, 24, 1, 17, 7 |
| R | asthma | 6 | 16, 10, 24, 1, 17, 7 |
| R | atrial fibrillation | 6 | 16, 10, 24, 1, 17, 7 |
| R | atrial flutter | 6 | 16, 10, 24, 1, 17, 7 |
| R | back pain | 6 | 16, 10, 24, 1, 17, 7 |
| R | bronchitis | 6 | 16, 10, 24, 1, 17, 7 |
| R | cardiac arrest | 6 | 16, 10, 24, 1, 17, 7 |
| R | cataract | 6 | 16, 10, 24, 1, 17, 7 |
| R | cellulitis | 6 | 16, 10, 24, 1, 17, 7 |
| R | chest pain | 6 | 16, 10, 24, 1, 17, 7 |
| R | chronic obstructive pulmonary disease | 6 | 16, 10, 24, 1, 17, 7 |
| R | confusional state | 6 | 16, 10, 24, 1, 17, 7 |
| R | contusion | 6 | 16, 10, 24, 1, 17, 7 |
| R | dehydration | 6 | 16, 10, 24, 1, 17, 7 |
| R | diabetes mellitus | 6 | 16, 10, 24, 1, 17, 7 |
| R | epistaxis | 6 | 16, 10, 24, 1, 17, 7 |
| R | fall | 6 | 16, 10, 24, 1, 17, 7 |
| R | femur fracture | 6 | 16, 10, 24, 1, 17, 7 |
| R | gastritis | 6 | 16, 10, 24, 1, 17, 7 |
| R | gastroenteritis | 6 | 16, 10, 24, 1, 17, 7 |
| R | gastrointestinal haemorrhage | 6 | 16, 10, 24, 1, 17, 7 |
| R | gastrooesophageal reflux disease | 6 | 16, 10, 24, 1, 17, 7 |
| R | hyponatraemia | 6 | 16, 10, 24, 1, 17, 7 |
| R | influenza | 6 | 16, 10, 24, 1, 17, 7 |
| R | laceration | 6 | 16, 10, 24, 1, 17, 7 |
| R | muscle spasms | 6 | 16, 10, 24, 1, 17, 7 |
| R | muscular weakness | 6 | 16, 10, 24, 1, 17, 7 |
| R | musculoskeletal pain | 6 | 16, 10, 24, 1, 17, 7 |
| R | myalgia | 6 | 16, 10, 24, 1, 17, 7 |
| R | myocardial infarction | 6 | 16, 10, 24, 1, 17, 7 |
| R | myocardial ischaemia | 6 | 16, 10, 24, 1, 17, 7 |
| R | neck pain | 6 | 16, 10, 24, 1, 17, 7 |

[Fig. 20-32]

| R | oropharyngeal pain | 6 | 16, 10, 24, 1, 17, 7 |
|---|---|---|---|
| R | orthostatic hypotension | 6 | 16, 10, 24, 1, 17, 7 |
| R | overdose | 6 | 16, 10, 24, 1, 17, 7 |
| R | pain in extremity | 6 | 16, 10, 24, 1, 17, 7 |
| R | paraesthesia | 6 | 16, 10, 24, 1, 17, 7 |
| R | pharyngitis | 6 | 16, 10, 24, 1, 17, 7 |
| R | pneumonia | 6 | 16, 10, 24, 1, 17, 7 |
| R | pneumothorax | 6 | 16, 10, 24, 1, 17, 7 |
| R | presyncope | 6 | 16, 10, 24, 1, 17, 7 |
| R | pruritus | 6 | 16, 10, 24, 1, 17, 7 |
| R | respiratory failure | 6 | 16, 10, 24, 1, 17, 7 |
| R | respiratory tract infection | 6 | 16, 10, 24, 1, 17, 7 |
| R | rhinitis | 6 | 16, 10, 24, 1, 17, 7 |
| R | sepsis | 6 | 16, 10, 24, 1, 17, 7 |
| R | sinusitis | 6 | 16, 10, 24, 1, 17, 7 |
| R | syncope | 6 | 16, 10, 24, 1, 17, 7 |
| R | tachycardia | 6 | 16, 10, 24, 1, 17, 7 |
| R | upper respiratory tract infection | 6 | 16, 10, 24, 1, 17, 7 |
| R | vertigo | 6 | 16, 10, 24, 1, 17, 7 |
| R | viral infection | 6 | 16, 10, 24, 1, 17, 7 |
| R | sedation | 6 | 20, 5, 15, 14, 17, 19 |
| R | dry skin | 7 | 22, 16, 23, 9, 20, 7, 4 |
| R | neutropenia | 7 | 22, 16, 23, 9, 20, 7, 4 |
| R | abdominal pain | 7 | 7, 12, 8, 16, 4, 15, 10 |
| R | asthenia | 7 | 7, 12, 8, 16, 4, 15, 10 |
| R | dizziness | 7 | 7, 12, 8, 16, 4, 15, 10 |
| R | dyspepsia | 7 | 7, 12, 8, 16, 4, 15, 10 |
| R | headache | 7 | 7, 12, 8, 16, 4, 15, 10 |
| R | hypertension | 7 | 7, 12, 8, 16, 4, 15, 10 |
| R | malaise | 7 | 7, 12, 8, 16, 4, 15, 10 |
| R | accidental overdose | 7 | 4, 6, 5, 11, 17, 15, 19 |
| R | drug-induced liver injury | 7 | 4, 6, 5, 11, 17, 15, 19 |
| R | flatulence | 7 | 4, 6, 5, 11, 17, 15, 19 |
| R | gait disturbance | 7 | 4, 6, 5, 11, 17, 15, 19 |
| R | wound | 7 | 4, 6, 5, 11, 17, 15, 19 |
| R | abnormal behaviour | 7 | 2, 8, 20, 7, 11, 4, 15 |
| R | abortion spontaneous | 7 | 2, 8, 20, 7, 11, 4, 15 |
| R | abrasions | 7 | 2, 8, 20, 7, 11, 4, 15 |
| R | acute psychosis | 7 | 2, 8, 20, 7, 11, 4, 15 |
| R | adenoidal hypertrophy | 7 | 2, 8, 20, 7, 11, 4, 15 |
| R | aggression | 7 | 2, 8, 20, 7, 11, 4, 15 |
| R | agression | 7 | 2, 8, 20, 7, 11, 4, 15 |
| R | allergies | 7 | 2, 8, 20, 7, 11, 4, 15 |
| R | anger | 7 | 2, 8, 20, 7, 11, 4, 15 |
| R | aphthous stomatitis | 7 | 2, 8, 20, 7, 11, 4, 15 |
| R | appetite decreased | 7 | 2, 8, 20, 7, 11, 4, 15 |
| R | athletes foot | 7 | 2, 8, 20, 7, 11, 4, 15 |
| R | attention deficit / hyperactivity disorder | 7 | 2, 8, 20, 7, 11, 4, 15 |
| R | attention deficit/hyperactivity disorder | 7 | 2, 8, 20, 7, 11, 4, 15 |
| R | autism | 7 | 2, 8, 20, 7, 11, 4, 15 |
| R | bartholin's cyst | 7 | 2, 8, 20, 7, 11, 4, 15 |
| R | bed bug infestation | 7 | 2, 8, 20, 7, 11, 4, 15 |
| R | birth of a baby (deception by subject) | 7 | 2, 8, 20, 7, 11, 4, 15 |
| R | blood creatinine phosphokinase increased | 7 | 2, 8, 20, 7, 11, 4, 15 |
| R | blood thyroid stimulating hormone increased | 7 | 2, 8, 20, 7, 11, 4, 15 |
| R | blunted affect | 7 | 2, 8, 20, 7, 11, 4, 15 |
| R | bradykinesia | 7 | 2, 8, 20, 7, 11, 4, 15 |
| R | bronchitis acute | 7 | 2, 8, 20, 7, 11, 4, 15 |
| R | bruxism | 7 | 2, 8, 20, 7, 11, 4, 15 |
| R | chest pain with inspiration | 7 | 2, 8, 20, 7, 11, 4, 15 |
| R | cold symptoms | 7 | 2, 8, 20, 7, 11, 4, 15 |
| R | conjunctivitis allergic | 7 | 2, 8, 20, 7, 11, 4, 15 |
| R | decreased activity | 7 | 2, 8, 20, 7, 11, 4, 15 |
| R | depressive symptom | 7 | 2, 8, 20, 7, 11, 4, 15 |
| R | difficulty urinating | 7 | 2, 8, 20, 7, 11, 4, 15 |
| R | disturbance in attention | 7 | 2, 8, 20, 7, 11, 4, 15 |
| R | drooling | 7 | 2, 8, 20, 7, 11, 4, 15 |

[Fig. 20-33]

| R | drowsiness | 7 | 2, 8, 20, 7, 11, 4, 15 |
|---|---|---|---|
| R | drug abuse | 7 | 2, 8, 20, 7, 11, 4, 15 |
| R | drug toxicity | 7 | 2, 8, 20, 7, 11, 4, 15 |
| R | duodenal ulcer perforation | 7 | 2, 8, 20, 7, 11, 4, 15 |
| R | dyskinesia | 7 | 2, 8, 20, 7, 11, 4, 15 |
| R | dysphoria | 7 | 2, 8, 20, 7, 11, 4, 15 |
| R | dystonia | 7 | 2, 8, 20, 7, 11, 4, 15 |
| R | electrocution | 7 | 2, 8, 20, 7, 11, 4, 15 |
| R | emotional disorder | 7 | 2, 8, 20, 7, 11, 4, 15 |
| R | emotional poverty | 7 | 2, 8, 20, 7, 11, 4, 15 |
| R | encopresis | 7 | 2, 8, 20, 7, 11, 4, 15 |
| R | enteritis infectious | 7 | 2, 8, 20, 7, 11, 4, 15 |
| R | erectile dysfunction | 7 | 2, 8, 20, 7, 11, 4, 15 |
| R | eructation | 7 | 2, 8, 20, 7, 11, 4, 15 |
| R | excessive eye blinking | 7 | 2, 8, 20, 7, 11, 4, 15 |
| R | eye inflammation | 7 | 2, 8, 20, 7, 11, 4, 15 |
| R | feeling depressed | 7 | 2, 8, 20, 7, 11, 4, 15 |
| R | flat affect | 7 | 2, 8, 20, 7, 11, 4, 15 |
| R | furuncle | 7 | 2, 8, 20, 7, 11, 4, 15 |
| R | gastrointestinal viral infection | 7 | 2, 8, 20, 7, 11, 4, 15 |
| R | genital candidiasis | 7 | 2, 8, 20, 7, 11, 4, 15 |
| R | hallucination, auditory | 7 | 2, 8, 20, 7, 11, 4, 15 |
| R | head banging | 7 | 2, 8, 20, 7, 11, 4, 15 |
| R | hepatitis a | 7 | 2, 8, 20, 7, 11, 4, 15 |
| R | hepatitis viral | 7 | 2, 8, 20, 7, 11, 4, 15 |
| R | homicidal ideation | 7 | 2, 8, 20, 7, 11, 4, 15 |
| R | homicide | 7 | 2, 8, 20, 7, 11, 4, 15 |
| R | hordeolum | 7 | 2, 8, 20, 7, 11, 4, 15 |
| R | house dust allergy | 7 | 2, 8, 20, 7, 11, 4, 15 |
| R | hyperbilirubinemia | 7 | 2, 8, 20, 7, 11, 4, 15 |
| R | hyperinsulinaemia | 7 | 2, 8, 20, 7, 11, 4, 15 |
| R | hypomania | 7 | 2, 8, 20, 7, 11, 4, 15 |
| R | illusion | 7 | 2, 8, 20, 7, 11, 4, 15 |
| R | impatience | 7 | 2, 8, 20, 7, 11, 4, 15 |
| R | impulsive behavior | 7 | 2, 8, 20, 7, 11, 4, 15 |
| R | impulsive behaviour | 7 | 2, 8, 20, 7, 11, 4, 15 |
| R | inadequate housing | 7 | 2, 8, 20, 7, 11, 4, 15 |
| R | increased libido | 7 | 2, 8, 20, 7, 11, 4, 15 |
| R | increased sweating | 7 | 2, 8, 20, 7, 11, 4, 15 |
| R | infected insect bite | 7 | 2, 8, 20, 7, 11, 4, 15 |
| R | initial insomnia | 7 | 2, 8, 20, 7, 11, 4, 15 |
| R | injection site discomfort | 7 | 2, 8, 20, 7, 11, 4, 15 |
| R | injection site rash | 7 | 2, 8, 20, 7, 11, 4, 15 |
| R | insulin resistance | 7 | 2, 8, 20, 7, 11, 4, 15 |
| R | intentional self-injury | 7 | 2, 8, 20, 7, 11, 4, 15 |
| R | intentional self injury | 7 | 2, 8, 20, 7, 11, 4, 15 |
| R | iron deficiency | 7 | 2, 8, 20, 7, 11, 4, 15 |
| R | itching | 7 | 2, 8, 20, 7, 11, 4, 15 |
| R | large intestine carcinoma | 7 | 2, 8, 20, 7, 11, 4, 15 |
| R | left ankle swelling (injury) | 7 | 2, 8, 20, 7, 11, 4, 15 |
| R | lymphadenitis bacterial | 7 | 2, 8, 20, 7, 11, 4, 15 |
| R | middle ear effusion | 7 | 2, 8, 20, 7, 11, 4, 15 |
| R | miliaria | 7 | 2, 8, 20, 7, 11, 4, 15 |
| R | mood altered | 7 | 2, 8, 20, 7, 11, 4, 15 |
| R | movement disorder | 7 | 2, 8, 20, 7, 11, 4, 15 |
| R | muscle rigidity | 7 | 2, 8, 20, 7, 11, 4, 15 |
| R | neuroleptic malignant syndrome | 7 | 2, 8, 20, 7, 11, 4, 15 |
| R | nightmare | 7 | 2, 8, 20, 7, 11, 4, 15 |
| R | nightmares | 7 | 2, 8, 20, 7, 11, 4, 15 |
| R | non-small cell lung cancer metastatic | 7 | 2, 8, 20, 7, 11, 4, 15 |
| R | obsessive-compulsive disorder | 7 | 2, 8, 20, 7, 11, 4, 15 |
| R | organising pneumonia | 7 | 2, 8, 20, 7, 11, 4, 15 |
| R | otitis media acute | 7 | 2, 8, 20, 7, 11, 4, 15 |
| R | ovarian fibroma | 7 | 2, 8, 20, 7, 11, 4, 15 |
| R | painful urination | 7 | 2, 8, 20, 7, 11, 4, 15 |
| R | penile oedema | 7 | 2, 8, 20, 7, 11, 4, 15 |
| R | persecutory delusion | 7 | 2, 8, 20, 7, 11, 4, 15 |

[Fig. 20-34]

| R | pilonidal cyst | 7 | 2, 8, 20, 7, 11, 4, 15 |
|---|---|---|---|
| R | pregnancy | 7 | 2, 8, 20, 7, 11, 4, 15 |
| R | prostatic disorder | 7 | 2, 8, 20, 7, 11, 4, 15 |
| R | pruritis | 7 | 2, 8, 20, 7, 11, 4, 15 |
| R | psychiatric symptom | 7 | 2, 8, 20, 7, 11, 4, 15 |
| R | psychomotor hyperactivity | 7 | 2, 8, 20, 7, 11, 4, 15 |
| R | psychosocial support | 7 | 2, 8, 20, 7, 11, 4, 15 |
| R | psychotic behaviour | 7 | 2, 8, 20, 7, 11, 4, 15 |
| R | rectal cancer metastatic | 7 | 2, 8, 20, 7, 11, 4, 15 |
| R | respite care | 7 | 2, 8, 20, 7, 11, 4, 15 |
| R | ruptured cerebral aneurysm | 7 | 2, 8, 20, 7, 11, 4, 15 |
| R | schizoaffective disorder | 7 | 2, 8, 20, 7, 11, 4, 15 |
| R | schizophrenia, paranoid type | 7 | 2, 8, 20, 7, 11, 4, 15 |
| R | schizophrenia, undifferentiated type | 7 | 2, 8, 20, 7, 11, 4, 15 |
| R | seborrhoea | 7 | 2, 8, 20, 7, 11, 4, 15 |
| R | sexual abuse | 7 | 2, 8, 20, 7, 11, 4, 15 |
| R | skin and soft tissue infection | 7 | 2, 8, 20, 7, 11, 4, 15 |
| R | skin discolouration | 7 | 2, 8, 20, 7, 11, 4, 15 |
| R | skin nodule | 7 | 2, 8, 20, 7, 11, 4, 15 |
| R | sleep disturbance | 7 | 2, 8, 20, 7, 11, 4, 15 |
| R | somnambulism | 7 | 2, 8, 20, 7, 11, 4, 15 |
| R | sputum discoloured | 7 | 2, 8, 20, 7, 11, 4, 15 |
| R | stomach mass | 7 | 2, 8, 20, 7, 11, 4, 15 |
| R | stomachache | 7 | 2, 8, 20, 7, 11, 4, 15 |
| R | substance use | 7 | 2, 8, 20, 7, 11, 4, 15 |
| R | suicidal attempt | 7 | 2, 8, 20, 7, 11, 4, 15 |
| R | suividal ideation | 7 | 2, 8, 20, 7, 11, 4, 15 |
| R | syphilis | 7 | 2, 8, 20, 7, 11, 4, 15 |
| R | tic | 7 | 2, 8, 20, 7, 11, 4, 15 |
| R | tongue neoplasm | 7 | 2, 8, 20, 7, 11, 4, 15 |
| R | tonsillar hypertrophy | 7 | 2, 8, 20, 7, 11, 4, 15 |
| R | tourette's disorder | 7 | 2, 8, 20, 7, 11, 4, 15 |
| R | transient ischemic attack | 7 | 2, 8, 20, 7, 11, 4, 15 |
| R | traumatic liver injury | 7 | 2, 8, 20, 7, 11, 4, 15 |
| R | treatment noncompliance | 7 | 2, 8, 20, 7, 11, 4, 15 |
| R | trouble with erections | 7 | 2, 8, 20, 7, 11, 4, 15 |
| R | tympanic membrane perforation | 7 | 2, 8, 20, 7, 11, 4, 15 |
| R | type diabetis mellitus | 7 | 2, 8, 20, 7, 11, 4, 15 |
| R | urinary hesitation | 7 | 2, 8, 20, 7, 11, 4, 15 |
| R | urination | 7 | 2, 8, 20, 7, 11, 4, 15 |
| R | uveitis | 7 | 2, 8, 20, 7, 11, 4, 15 |
| R | varicella | 7 | 2, 8, 20, 7, 11, 4, 15 |
| R | viral rash | 7 | 2, 8, 20, 7, 11, 4, 15 |
| R | viral syndrome | 7 | 2, 8, 20, 7, 11, 4, 15 |
| R | vivid dreaming | 7 | 2, 8, 20, 7, 11, 4, 15 |
| R | vocal cord disorder | 7 | 2, 8, 20, 7, 11, 4, 15 |
| R | worsening of major depression with psychotic features | 7 | 2, 8, 20, 7, 11, 4, 15 |
| R | flu like symptoms | 7 | 2, 5, 14, 1, 11, 22, 17 |
| R | nausea | 8 | 17, 1, 8, 16, 3, 2, 21, 18 |
| R | adjustment disorder | 8 | 8, 23, 5, 6, 17, 12, 10, 1 |
| R | bilirubin conjugated increased | 8 | 8, 23, 5, 6, 17, 12, 10, 1 |
| R | blood triglycerides increased | 8 | 8, 23, 5, 6, 17, 12, 10, 1 |
| R | completed suicide | 8 | 8, 23, 5, 6, 17, 12, 10, 1 |
| R | coronary artery insufficiency | 8 | 8, 23, 5, 6, 17, 12, 10, 1 |
| R | foreign body | 8 | 8, 23, 5, 6, 17, 12, 10, 1 |
| R | gun shot wound | 8 | 8, 23, 5, 6, 17, 12, 10, 1 |
| R | hepatitis | 8 | 8, 23, 5, 6, 17, 12, 10, 1 |
| R | hepatitis acute | 8 | 8, 23, 5, 6, 17, 12, 10, 1 |
| R | infectious mononucleosis | 8 | 8, 23, 5, 6, 17, 12, 10, 1 |
| R | muscle twitching | 8 | 8, 23, 5, 6, 17, 12, 10, 1 |
| R | nasopharyngeal cancer | 8 | 8, 23, 5, 6, 17, 12, 10, 1 |
| R | oesophageal varices haemorrhage | 8 | 8, 23, 5, 6, 17, 12, 10, 1 |
| R | open angle glaucoma | 8 | 8, 23, 5, 6, 17, 12, 10, 1 |
| R | salivary gland pain | 8 | 8, 23, 5, 6, 17, 12, 10, 1 |
| R | schizophrenia | 8 | 8, 23, 5, 6, 17, 12, 10, 1 |
| R | sick sinus syndrome | 8 | 8, 23, 5, 6, 17, 12, 10, 1 |
| R | tonsillitis | 8 | 8, 23, 5, 6, 17, 12, 10, 1 |

[Fig. 20-35]

| R | toothache | 8 | 8, 23, 5, 6, 17, 12, 10, 1 |
|---|---|---|---|
| R | toxicity to various agents | 8 | 8, 23, 5, 6, 17, 12, 10, 1 |
| R | weight loss | 8 | 21, 12, 18, 8, 20, 16, 19, 10 |
| R | abnormal behaviour | 9 | 19, 1, 18, 6, 5, 9, 21, 24, 16 |
| R | abortion spontaneous | 9 | 19, 1, 18, 6, 5, 9, 21, 24, 16 |
| R | abrasions | 9 | 19, 1, 18, 6, 5, 9, 21, 24, 16 |
| R | acute psychosis | 9 | 19, 1, 18, 6, 5, 9, 21, 24, 16 |
| R | adenoidal hypertrophy | 9 | 19, 1, 18, 6, 5, 9, 21, 24, 16 |
| R | aggression | 9 | 19, 1, 18, 6, 5, 9, 21, 24, 16 |
| R | agression | 9 | 19, 1, 18, 6, 5, 9, 21, 24, 16 |
| R | allergies | 9 | 19, 1, 18, 6, 5, 9, 21, 24, 16 |
| R | anger | 9 | 19, 1, 18, 6, 5, 9, 21, 24, 16 |
| R | aphthous stomatitis | 9 | 19, 1, 18, 6, 5, 9, 21, 24, 16 |
| R | appetite decreased | 9 | 19, 1, 18, 6, 5, 9, 21, 24, 16 |
| R | athletes foot | 9 | 19, 1, 18, 6, 5, 9, 21, 24, 16 |
| R | attention deficit / hyperactivity disorder | 9 | 19, 1, 18, 6, 5, 9, 21, 24, 16 |
| R | attention deficit/hyperactivity disorder | 9 | 19, 1, 18, 6, 5, 9, 21, 24, 16 |
| R | autism | 9 | 19, 1, 18, 6, 5, 9, 21, 24, 16 |
| R | bartholin's cyst | 9 | 19, 1, 18, 6, 5, 9, 21, 24, 16 |
| R | bed bug infestation | 9 | 19, 1, 18, 6, 5, 9, 21, 24, 16 |
| R | birth of a baby (deception by subject) | 9 | 19, 1, 18, 6, 5, 9, 21, 24, 16 |
| R | blood creatinine phosphokinase increased | 9 | 19, 1, 18, 6, 5, 9, 21, 24, 16 |
| R | blood thyroid stimulating hormone increased | 9 | 19, 1, 18, 6, 5, 9, 21, 24, 16 |
| R | blunted affect | 9 | 19, 1, 18, 6, 5, 9, 21, 24, 16 |
| R | bradykinesia | 9 | 19, 1, 18, 6, 5, 9, 21, 24, 16 |
| R | bronchitis acute | 9 | 19, 1, 18, 6, 5, 9, 21, 24, 16 |
| R | bruxism | 9 | 19, 1, 18, 6, 5, 9, 21, 24, 16 |
| R | chest pain with inspiration | 9 | 19, 1, 18, 6, 5, 9, 21, 24, 16 |
| R | cold symptoms | 9 | 19, 1, 18, 6, 5, 9, 21, 24, 16 |
| R | conjunctivitis allergic | 9 | 19, 1, 18, 6, 5, 9, 21, 24, 16 |
| R | decreased activity | 9 | 19, 1, 18, 6, 5, 9, 21, 24, 16 |
| R | depressive symptom | 9 | 19, 1, 18, 6, 5, 9, 21, 24, 16 |
| R | difficulty urinating | 9 | 19, 1, 18, 6, 5, 9, 21, 24, 16 |
| R | disturbance in attention | 9 | 19, 1, 18, 6, 5, 9, 21, 24, 16 |
| R | drooling | 9 | 19, 1, 18, 6, 5, 9, 21, 24, 16 |
| R | drowsiness | 9 | 19, 1, 18, 6, 5, 9, 21, 24, 16 |
| R | drug abuse | 9 | 19, 1, 18, 6, 5, 9, 21, 24, 16 |
| R | drug toxicity | 9 | 19, 1, 18, 6, 5, 9, 21, 24, 16 |
| R | duodenal ulcer perforation | 9 | 19, 1, 18, 6, 5, 9, 21, 24, 16 |
| R | dyskinesia | 9 | 19, 1, 18, 6, 5, 9, 21, 24, 16 |
| R | dysphoria | 9 | 19, 1, 18, 6, 5, 9, 21, 24, 16 |
| R | dystonia | 9 | 19, 1, 18, 6, 5, 9, 21, 24, 16 |
| R | electrocution | 9 | 19, 1, 18, 6, 5, 9, 21, 24, 16 |
| R | emotional disorder | 9 | 19, 1, 18, 6, 5, 9, 21, 24, 16 |
| R | emotional poverty | 9 | 19, 1, 18, 6, 5, 9, 21, 24, 16 |
| R | encopresis | 9 | 19, 1, 18, 6, 5, 9, 21, 24, 16 |
| R | enteritis infectious | 9 | 19, 1, 18, 6, 5, 9, 21, 24, 16 |
| R | erectile dysfunction | 9 | 19, 1, 18, 6, 5, 9, 21, 24, 16 |
| R | eructation | 9 | 19, 1, 18, 6, 5, 9, 21, 24, 16 |
| R | excessive eye blinking | 9 | 19, 1, 18, 6, 5, 9, 21, 24, 16 |
| R | eye inflammation | 9 | 19, 1, 18, 6, 5, 9, 21, 24, 16 |
| R | feeling depressed | 9 | 19, 1, 18, 6, 5, 9, 21, 24, 16 |
| R | flat affect | 9 | 19, 1, 18, 6, 5, 9, 21, 24, 16 |
| R | furuncle | 9 | 19, 1, 18, 6, 5, 9, 21, 24, 16 |
| R | gastrointestinal viral infection | 9 | 19, 1, 18, 6, 5, 9, 21, 24, 16 |
| R | genital candidiasis | 9 | 19, 1, 18, 6, 5, 9, 21, 24, 16 |
| R | hallucination, auditory | 9 | 19, 1, 18, 6, 5, 9, 21, 24, 16 |
| R | head banging | 9 | 19, 1, 18, 6, 5, 9, 21, 24, 16 |
| R | hepatitis a | 9 | 19, 1, 18, 6, 5, 9, 21, 24, 16 |
| R | hepatitis viral | 9 | 19, 1, 18, 6, 5, 9, 21, 24, 16 |
| R | homicidal ideation | 9 | 19, 1, 18, 6, 5, 9, 21, 24, 16 |
| R | homicide | 9 | 19, 1, 18, 6, 5, 9, 21, 24, 16 |
| R | hordeolum | 9 | 19, 1, 18, 6, 5, 9, 21, 24, 16 |
| R | house dust allergy | 9 | 19, 1, 18, 6, 5, 9, 21, 24, 16 |
| R | hyperbilirubinemia | 9 | 19, 1, 18, 6, 5, 9, 21, 24, 16 |
| R | hyperinsulinaemia | 9 | 19, 1, 18, 6, 5, 9, 21, 24, 16 |
| R | hypomania | 9 | 19, 1, 18, 6, 5, 9, 21, 24, 16 |

[Fig. 20-36]

| R | illusion | 9 | 19, 1, 18, 6, 5, 9, 21, 24, 16 |
|---|---|---|---|
| R | impatience | 9 | 19, 1, 18, 6, 5, 9, 21, 24, 16 |
| R | impulsive behavior | 9 | 19, 1, 18, 6, 5, 9, 21, 24, 16 |
| R | impulsive behaviour | 9 | 19, 1, 18, 6, 5, 9, 21, 24, 16 |
| R | inadequate housing | 9 | 19, 1, 18, 6, 5, 9, 21, 24, 16 |
| R | increased libido | 9 | 19, 1, 18, 6, 5, 9, 21, 24, 16 |
| R | increased sweating | 9 | 19, 1, 18, 6, 5, 9, 21, 24, 16 |
| R | infected insect bite | 9 | 19, 1, 18, 6, 5, 9, 21, 24, 16 |
| R | initial insomnia | 9 | 19, 1, 18, 6, 5, 9, 21, 24, 16 |
| R | injection site discomfort | 9 | 19, 1, 18, 6, 5, 9, 21, 24, 16 |
| R | injection site rash | 9 | 19, 1, 18, 6, 5, 9, 21, 24, 16 |
| R | insulin resistance | 9 | 19, 1, 18, 6, 5, 9, 21, 24, 16 |
| R | intentional self-injury | 9 | 19, 1, 18, 6, 5, 9, 21, 24, 16 |
| R | intentional self injury | 9 | 19, 1, 18, 6, 5, 9, 21, 24, 16 |
| R | iron deficiency | 9 | 19, 1, 18, 6, 5, 9, 21, 24, 16 |
| R | itching | 9 | 19, 1, 18, 6, 5, 9, 21, 24, 16 |
| R | large intestine carcinoma | 9 | 19, 1, 18, 6, 5, 9, 21, 24, 16 |
| R | left ankle swelling (injury) | 9 | 19, 1, 18, 6, 5, 9, 21, 24, 16 |
| R | lymphadenitis bacterial | 9 | 19, 1, 18, 6, 5, 9, 21, 24, 16 |
| R | middle ear effusion | 9 | 19, 1, 18, 6, 5, 9, 21, 24, 16 |
| R | miliaria | 9 | 19, 1, 18, 6, 5, 9, 21, 24, 16 |
| R | mood altered | 9 | 19, 1, 18, 6, 5, 9, 21, 24, 16 |
| R | movement disorder | 9 | 19, 1, 18, 6, 5, 9, 21, 24, 16 |
| R | muscle rigidity | 9 | 19, 1, 18, 6, 5, 9, 21, 24, 16 |
| R | neuroleptic malignant syndrome | 9 | 19, 1, 18, 6, 5, 9, 21, 24, 16 |
| R | nightmare | 9 | 19, 1, 18, 6, 5, 9, 21, 24, 16 |
| R | nightmares | 9 | 19, 1, 18, 6, 5, 9, 21, 24, 16 |
| R | non-small cell lung cancer metastatic | 9 | 19, 1, 18, 6, 5, 9, 21, 24, 16 |
| R | obsessive-compulsive disorder | 9 | 19, 1, 18, 6, 5, 9, 21, 24, 16 |
| R | organising pneumonia | 9 | 19, 1, 18, 6, 5, 9, 21, 24, 16 |
| R | otitis media acute | 9 | 19, 1, 18, 6, 5, 9, 21, 24, 16 |
| R | ovarian fibroma | 9 | 19, 1, 18, 6, 5, 9, 21, 24, 16 |
| R | painful urination | 9 | 19, 1, 18, 6, 5, 9, 21, 24, 16 |
| R | penile oedema | 9 | 19, 1, 18, 6, 5, 9, 21, 24, 16 |
| R | persecutory delusion | 9 | 19, 1, 18, 6, 5, 9, 21, 24, 16 |
| R | pilonidal cyst | 9 | 19, 1, 18, 6, 5, 9, 21, 24, 16 |
| R | pregnancy | 9 | 19, 1, 18, 6, 5, 9, 21, 24, 16 |
| R | prostatic disorder | 9 | 19, 1, 18, 6, 5, 9, 21, 24, 16 |
| R | pruritis | 9 | 19, 1, 18, 6, 5, 9, 21, 24, 16 |
| R | psychiatric symptom | 9 | 19, 1, 18, 6, 5, 9, 21, 24, 16 |
| R | psychomotor hyperactivity | 9 | 19, 1, 18, 6, 5, 9, 21, 24, 16 |
| R | psychosocial support | 9 | 19, 1, 18, 6, 5, 9, 21, 24, 16 |
| R | psychotic behaviour | 9 | 19, 1, 18, 6, 5, 9, 21, 24, 16 |
| R | rectal cancer metastatic | 9 | 19, 1, 18, 6, 5, 9, 21, 24, 16 |
| R | respite care | 9 | 19, 1, 18, 6, 5, 9, 21, 24, 16 |
| R | ruptured cerebral aneurysm | 9 | 19, 1, 18, 6, 5, 9, 21, 24, 16 |
| R | schizoaffective disorder | 9 | 19, 1, 18, 6, 5, 9, 21, 24, 16 |
| R | schizophrenia, paranoid type | 9 | 19, 1, 18, 6, 5, 9, 21, 24, 16 |
| R | schizophrenia, undifferentiated type | 9 | 19, 1, 18, 6, 5, 9, 21, 24, 16 |
| R | seborrhoea | 9 | 19, 1, 18, 6, 5, 9, 21, 24, 16 |
| R | sexual abuse | 9 | 19, 1, 18, 6, 5, 9, 21, 24, 16 |
| R | skin and soft tissue infection | 9 | 19, 1, 18, 6, 5, 9, 21, 24, 16 |
| R | skin discolouration | 9 | 19, 1, 18, 6, 5, 9, 21, 24, 16 |
| R | skin nodule | 9 | 19, 1, 18, 6, 5, 9, 21, 24, 16 |
| R | sleep disturbance | 9 | 19, 1, 18, 6, 5, 9, 21, 24, 16 |
| R | somnambulism | 9 | 19, 1, 18, 6, 5, 9, 21, 24, 16 |
| R | sputum discoloured | 9 | 19, 1, 18, 6, 5, 9, 21, 24, 16 |
| R | stomach mass | 9 | 19, 1, 18, 6, 5, 9, 21, 24, 16 |
| R | stomachache | 9 | 19, 1, 18, 6, 5, 9, 21, 24, 16 |
| R | substance use | 9 | 19, 1, 18, 6, 5, 9, 21, 24, 16 |
| R | suicidal attempt | 9 | 19, 1, 18, 6, 5, 9, 21, 24, 16 |
| R | suividal ideation | 9 | 19, 1, 18, 6, 5, 9, 21, 24, 16 |
| R | syphilis | 9 | 19, 1, 18, 6, 5, 9, 21, 24, 16 |
| R | tic | 9 | 19, 1, 18, 6, 5, 9, 21, 24, 16 |
| R | tongue neoplasm | 9 | 19, 1, 18, 6, 5, 9, 21, 24, 16 |
| R | tonsillar hypertrophy | 9 | 19, 1, 18, 6, 5, 9, 21, 24, 16 |
| R | tourette's disorder | 9 | 19, 1, 18, 6, 5, 9, 21, 24, 16 |

[Fig. 20-37]

| R | transient ischemic attack | 9 | 19, 1, 18, 6, 5, 9, 21, 24, 16 |
|---|---|---|---|
| R | traumatic liver injury | 9 | 19, 1, 18, 6, 5, 9, 21, 24, 16 |
| R | treatment noncompliance | 9 | 19, 1, 18, 6, 5, 9, 21, 24, 16 |
| R | trouble with erections | 9 | 19, 1, 18, 6, 5, 9, 21, 24, 16 |
| R | tympanic membrane perforation | 9 | 19, 1, 18, 6, 5, 9, 21, 24, 16 |
| R | type diabetis mellitus | 9 | 19, 1, 18, 6, 5, 9, 21, 24, 16 |
| R | urinary hesitation | 9 | 19, 1, 18, 6, 5, 9, 21, 24, 16 |
| R | urination | 9 | 19, 1, 18, 6, 5, 9, 21, 24, 16 |
| R | uveitis | 9 | 19, 1, 18, 6, 5, 9, 21, 24, 16 |
| R | varicella | 9 | 19, 1, 18, 6, 5, 9, 21, 24, 16 |
| R | viral rash | 9 | 19, 1, 18, 6, 5, 9, 21, 24, 16 |
| R | viral syndrome | 9 | 19, 1, 18, 6, 5, 9, 21, 24, 16 |
| R | vivid dreaming | 9 | 19, 1, 18, 6, 5, 9, 21, 24, 16 |
| R | vocal cord disorder | 9 | 19, 1, 18, 6, 5, 9, 21, 24, 16 |
| R | worsening of major depression with psychotic features | 9 | 19, 1, 18, 6, 5, 9, 21, 24, 16 |
| R | blood alkaline phosphatase increased | 9 | 12, 15, 24, 21, 11, 19, 23, 16, 7 |
| R | blood cholesterol increased | 9 | 12, 15, 24, 21, 11, 19, 23, 16, 7 |
| R | scoliosis | 9 | 12, 15, 24, 21, 11, 19, 23, 16, 7 |
| R | thrush | 9 | 12, 15, 24, 21, 11, 19, 23, 16, 7 |
| R | vaginal discharge | 9 | 12, 15, 24, 21, 11, 19, 23, 16, 7 |
| R | blood bilirubin increased | 9 | 23, 7, 22, 24, 20, 11, 4, 3, 5 |
| R | blood potassium increased | 9 | 23, 7, 22, 24, 20, 11, 4, 3, 5 |
| R | blood urea increased | 9 | 23, 7, 22, 24, 20, 11, 4, 3, 5 |
| R | cardiovascular insufficiency | 9 | 23, 7, 22, 24, 20, 11, 4, 3, 5 |
| R | cerumen impaction | 9 | 23, 7, 22, 24, 20, 11, 4, 3, 5 |
| R | duodenal perforation | 9 | 23, 7, 22, 24, 20, 11, 4, 3, 5 |
| R | embolism | 9 | 23, 7, 22, 24, 20, 11, 4, 3, 5 |
| R | flank pain | 9 | 23, 7, 22, 24, 20, 11, 4, 3, 5 |
| R | gastric perforation | 9 | 23, 7, 22, 24, 20, 11, 4, 3, 5 |
| R | genital infection fungal | 9 | 23, 7, 22, 24, 20, 11, 4, 3, 5 |
| R | herpes virus infection | 9 | 23, 7, 22, 24, 20, 11, 4, 3, 5 |
| R | hyperbilirubinaemia | 9 | 23, 7, 22, 24, 20, 11, 4, 3, 5 |
| R | ingrowing nail | 9 | 23, 7, 22, 24, 20, 11, 4, 3, 5 |
| R | intestinal ischaemia | 9 | 23, 7, 22, 24, 20, 11, 4, 3, 5 |
| R | malignant neoplasm progression | 9 | 23, 7, 22, 24, 20, 11, 4, 3, 5 |
| R | mallory-weiss syndrome | 9 | 23, 7, 22, 24, 20, 11, 4, 3, 5 |
| R | metastases to central nervous system | 9 | 23, 7, 22, 24, 20, 11, 4, 3, 5 |
| R | nocturia | 9 | 23, 7, 22, 24, 20, 11, 4, 3, 5 |
| R | oesophageal stenosis | 9 | 23, 7, 22, 24, 20, 11, 4, 3, 5 |
| R | sinus disorder | 9 | 23, 7, 22, 24, 20, 11, 4, 3, 5 |
| R | tumour haemorrhage | 9 | 23, 7, 22, 24, 20, 11, 4, 3, 5 |
| R | white blood cell count increased | 9 | 23, 7, 22, 24, 20, 11, 4, 3, 5 |
| R | difficulty breathing | 9 | 22, 4, 17, 1, 8, 6, 12, 21, 23 |
| R | blood prolactin decreased | 10 | 6, 14, 9, 12, 17, 11, 19, 8, 13, 2 |
| R | daytime sleepiness | 10 | 6, 14, 9, 12, 17, 11, 19, 8, 13, 2 |
| R | decreased energy | 10 | 6, 14, 9, 12, 17, 11, 19, 8, 13, 2 |
| R | difficulty sleeping | 10 | 6, 14, 9, 12, 17, 11, 19, 8, 13, 2 |
| R | frequent urination | 10 | 6, 14, 9, 12, 17, 11, 19, 8, 13, 2 |
| R | general malaise | 10 | 6, 14, 9, 12, 17, 11, 19, 8, 13, 2 |
| R | head aches | 10 | 6, 14, 9, 12, 17, 11, 19, 8, 13, 2 |
| R | increase perspiraton | 10 | 6, 14, 9, 12, 17, 11, 19, 8, 13, 2 |
| R | increased perspiration | 10 | 6, 14, 9, 12, 17, 11, 19, 8, 13, 2 |
| R | loss of sexual desire | 10 | 6, 14, 9, 12, 17, 11, 19, 8, 13, 2 |
| R | poor coordination | 10 | 6, 14, 9, 12, 17, 11, 19, 8, 13, 2 |
| R | ringing in the ears | 10 | 6, 14, 9, 12, 17, 11, 19, 8, 13, 2 |
| R | sleeping too much | 10 | 6, 14, 9, 12, 17, 11, 19, 8, 13, 2 |
| R | tiredness | 10 | 6, 14, 9, 12, 17, 11, 19, 8, 13, 2 |
| R | rhinorrhea | 10 | 17, 20, 14, 18, 7, 2, 11, 21, 8, 4 |
| R | alanine aminotransferase increased | 10 | 22, 3, 21, 20, 15, 12, 1, 14, 2, 10 |
| R | anaemia | 10 | 22, 3, 21, 20, 15, 12, 1, 14, 2, 10 |
| R | aspartate aminotransferase increased | 10 | 22, 3, 21, 20, 15, 12, 1, 14, 2, 10 |
| R | blood creatine phosphokinase increased | 10 | 22, 3, 21, 20, 15, 12, 1, 14, 2, 10 |
| R | cough | 10 | 22, 3, 21, 20, 15, 12, 1, 14, 2, 10 |
| R | diarrhoea | 10 | 22, 3, 21, 20, 15, 12, 1, 14, 2, 10 |
| R | dysgeusia | 10 | 22, 3, 21, 20, 15, 12, 1, 14, 2, 10 |
| R | dyspnoea | 10 | 22, 3, 21, 20, 15, 12, 1, 14, 2, 10 |
| R | hyperglycaemia | 10 | 22, 3, 21, 20, 15, 12, 1, 14, 2, 10 |

[Fig. 20-38]

| R | hypoaesthesia | 10 | 22, 3, 21, 20, 15, 12, 1, 14, 2, 10 |
|---|---|---|---|
| R | blood alkaline phosphatase increased | 10 | 15, 19, 1, 7, 13, 12, 22, 16, 6, 18 |
| R | blood cholesterol increased | 10 | 15, 19, 1, 7, 13, 12, 22, 16, 6, 18 |
| R | scoliosis | 10 | 15, 19, 1, 7, 13, 12, 22, 16, 6, 18 |
| R | thrush | 10 | 15, 19, 1, 7, 13, 12, 22, 16, 6, 18 |
| R | vaginal discharge | 10 | 15, 19, 1, 7, 13, 12, 22, 16, 6, 18 |
| R | tremors | 15 | 6, 10, 22, 21, 13, 1, 7, 19, 9, 14, 16, 4, 15, 20, 24 |
| R | aspiration pneumonia | 15 | 17, 20, 23, 10, 13, 15, 11, 9, 21, 4, 14, 8, 16, 18, 3 |
| R | electrocardiogram qt corrected interval prolonged | 15 | 17, 20, 23, 10, 13, 15, 11, 9, 21, 4, 14, 8, 16, 18, 3 |
| R | hypocalcemia | 15 | 17, 20, 23, 10, 13, 15, 11, 9, 21, 4, 14, 8, 16, 18, 3 |
| R | mouth sores | 15 | 17, 20, 23, 10, 13, 15, 11, 9, 21, 4, 14, 8, 16, 18, 3 |
| R | white blood cell count decreased | 15 | 17, 20, 23, 10, 13, 15, 11, 9, 21, 4, 14, 8, 16, 18, 3 |
| R | enuresis | 15 | 21, 19, 2, 9, 6, 1, 12, 17, 22, 18, 3, 13, 14, 5, 24 |
| R | increased appetite | 15 | 21, 19, 2, 9, 6, 1, 12, 17, 22, 18, 3, 13, 14, 5, 24 |
| R | anxiety/irritabilty/stress | 15 | 21, 2, 11, 8, 13, 16, 18, 22, 17, 1, 10, 14, 9, 24, 4 |
| R | bleeding, bruising or irritation at injection site | 15 | 21, 2, 11, 8, 13, 16, 18, 22, 17, 1, 10, 14, 9, 24, 4 |
| R | bruising at injection site | 15 | 21, 2, 11, 8, 13, 16, 18, 22, 17, 1, 10, 14, 9, 24, 4 |
| R | confusion\disorientation | 15 | 21, 2, 11, 8, 13, 16, 18, 22, 17, 1, 10, 14, 9, 24, 4 |
| R | cysts | 15 | 21, 2, 11, 8, 13, 16, 18, 22, 17, 1, 10, 14, 9, 24, 4 |
| R | decrease in urination | 15 | 21, 2, 11, 8, 13, 16, 18, 22, 17, 1, 10, 14, 9, 24, 4 |
| R | elevated serum calcium | 15 | 21, 2, 11, 8, 13, 16, 18, 22, 17, 1, 10, 14, 9, 24, 4 |
| R | elevatedhr urine calcium | 15 | 21, 2, 11, 8, 13, 16, 18, 22, 17, 1, 10, 14, 9, 24, 4 |
| R | flu-like symptoms | 15 | 21, 2, 11, 8, 13, 16, 18, 22, 17, 1, 10, 14, 9, 24, 4 |
| R | hospitalization or exacerbation | 15 | 21, 2, 11, 8, 13, 16, 18, 22, 17, 1, 10, 14, 9, 24, 4 |
| R | hypercalciuria | 15 | 21, 2, 11, 8, 13, 16, 18, 22, 17, 1, 10, 14, 9, 24, 4 |
| R | increased thirst | 15 | 21, 2, 11, 8, 13, 16, 18, 22, 17, 1, 10, 14, 9, 24, 4 |
| R | increased urination | 15 | 21, 2, 11, 8, 13, 16, 18, 22, 17, 1, 10, 14, 9, 24, 4 |
| R | injection site irritation | 15 | 21, 2, 11, 8, 13, 16, 18, 22, 17, 1, 10, 14, 9, 24, 4 |
| R | kidney stone/kidney pain | 15 | 21, 2, 11, 8, 13, 16, 18, 22, 17, 1, 10, 14, 9, 24, 4 |
| R | mild | 15 | 21, 2, 11, 8, 13, 16, 18, 22, 17, 1, 10, 14, 9, 24, 4 |
| R | muscle pain/spasm | 15 | 21, 2, 11, 8, 13, 16, 18, 22, 17, 1, 10, 14, 9, 24, 4 |
| R | musculoskeletal | 15 | 21, 2, 11, 8, 13, 16, 18, 22, 17, 1, 10, 14, 9, 24, 4 |
| R | nausea/vomitting | 15 | 21, 2, 11, 8, 13, 16, 18, 22, 17, 1, 10, 14, 9, 24, 4 |
| R | opthalmological irritability/visual impairment | 15 | 21, 2, 11, 8, 13, 16, 18, 22, 17, 1, 10, 14, 9, 24, 4 |
| R | psychological | 15 | 21, 2, 11, 8, 13, 16, 18, 22, 17, 1, 10, 14, 9, 24, 4 |
| R | temperature sensitivity | 15 | 21, 2, 11, 8, 13, 16, 18, 22, 17, 1, 10, 14, 9, 24, 4 |
| R | thigh pain | 15 | 21, 2, 11, 8, 13, 16, 18, 22, 17, 1, 10, 14, 9, 24, 4 |
| R | weight fluctuations | 15 | 21, 2, 11, 8, 13, 16, 18, 22, 17, 1, 10, 14, 9, 24, 4 |
| T | suicide attempt | 1 | 4 |
| T | abscess | 1 | 24 |
| T | cyst | 1 | 24 |
| T | dental caries | 1 | 24 |
| T | hallucination | 1 | 24 |
| T | lobar pneumonia | 1 | 24 |
| T | pulmonary thrombosis | 1 | 24 |
| T | status asthmaticus | 1 | 24 |
| T | thirst | 1 | 24 |
| T | thrombophlebitis | 1 | 24 |
| T | upper respiratory tract inflammation | 1 | 24 |
| T | abscess | 1 | 20 |
| T | cyst | 1 | 20 |
| T | dental caries | 1 | 20 |
| T | hallucination | 1 | 20 |
| T | lobar pneumonia | 1 | 20 |
| T | pulmonary thrombosis | 1 | 20 |
| T | status asthmaticus | 1 | 20 |
| T | thirst | 1 | 20 |
| T | thrombophlebitis | 1 | 20 |
| T | upper respiratory tract inflammation | 1 | 20 |
| T | nausea | 2 | 5, 8 |
| T | extrapyramidal disorder | 3 | 7, 19, 9 |
| T | irritability | 3 | 7, 19, 9 |
| T | abnormal behaviour | 3 | 15, 19, 2 |
| T | abortion spontaneous | 3 | 15, 19, 2 |
| T | abrasions | 3 | 15, 19, 2 |
| T | acute psychosis | 3 | 15, 19, 2 |
| T | adenoidal hypertrophy | 3 | 15, 19, 2 |

[Fig. 20-39]

| T | aggression | 3 | 15, 19, 2 |
|---|---|---|---|
| T | agression | 3 | 15, 19, 2 |
| T | allergies | 3 | 15, 19, 2 |
| T | anger | 3 | 15, 19, 2 |
| T | aphthous stomatitis | 3 | 15, 19, 2 |
| T | appetite decreased | 3 | 15, 19, 2 |
| T | athletes foot | 3 | 15, 19, 2 |
| T | attention deficit / hyperactivity disorder | 3 | 15, 19, 2 |
| T | attention deficit/hyperactivity disorder | 3 | 15, 19, 2 |
| T | autism | 3 | 15, 19, 2 |
| T | bartholin's cyst | 3 | 15, 19, 2 |
| T | bed bug infestation | 3 | 15, 19, 2 |
| T | birth of a baby (deception by subject) | 3 | 15, 19, 2 |
| T | blood creatinine phosphokinase increased | 3 | 15, 19, 2 |
| T | blood thyroid stimulating hormone increased | 3 | 15, 19, 2 |
| T | blunted affect | 3 | 15, 19, 2 |
| T | bradykinesia | 3 | 15, 19, 2 |
| T | bronchitis acute | 3 | 15, 19, 2 |
| T | bruxism | 3 | 15, 19, 2 |
| T | chest pain with inspiration | 3 | 15, 19, 2 |
| T | cold symptoms | 3 | 15, 19, 2 |
| T | conjunctivitis allergic | 3 | 15, 19, 2 |
| T | decreased activity | 3 | 15, 19, 2 |
| T | depressive symptom | 3 | 15, 19, 2 |
| T | difficulty urinating | 3 | 15, 19, 2 |
| T | disturbance in attention | 3 | 15, 19, 2 |
| T | drooling | 3 | 15, 19, 2 |
| T | drowsiness | 3 | 15, 19, 2 |
| T | drug abuse | 3 | 15, 19, 2 |
| T | drug toxicity | 3 | 15, 19, 2 |
| T | duodenal ulcer perforation | 3 | 15, 19, 2 |
| T | dyskinesia | 3 | 15, 19, 2 |
| T | dysphoria | 3 | 15, 19, 2 |
| T | dystonia | 3 | 15, 19, 2 |
| T | electrocution | 3 | 15, 19, 2 |
| T | emotional disorder | 3 | 15, 19, 2 |
| T | emotional poverty | 3 | 15, 19, 2 |
| T | encopresis | 3 | 15, 19, 2 |
| T | enteritis infectious | 3 | 15, 19, 2 |
| T | erectile dysfunction | 3 | 15, 19, 2 |
| T | eructation | 3 | 15, 19, 2 |
| T | excessive eye blinking | 3 | 15, 19, 2 |
| T | eye inflammation | 3 | 15, 19, 2 |
| T | feeling depressed | 3 | 15, 19, 2 |
| T | flat affect | 3 | 15, 19, 2 |
| T | furuncle | 3 | 15, 19, 2 |
| T | gastrointestinal viral infection | 3 | 15, 19, 2 |
| T | genital candidiasis | 3 | 15, 19, 2 |
| T | hallucination, auditory | 3 | 15, 19, 2 |
| T | head banging | 3 | 15, 19, 2 |
| T | hepatitis a | 3 | 15, 19, 2 |
| T | hepatitis viral | 3 | 15, 19, 2 |
| T | homicidal ideation | 3 | 15, 19, 2 |
| T | homicide | 3 | 15, 19, 2 |
| T | hordeolum | 3 | 15, 19, 2 |
| T | house dust allergy | 3 | 15, 19, 2 |
| T | hyperbilirubinemia | 3 | 15, 19, 2 |
| T | hyperinsulinaemia | 3 | 15, 19, 2 |
| T | hypomania | 3 | 15, 19, 2 |
| T | illusion | 3 | 15, 19, 2 |
| T | impatience | 3 | 15, 19, 2 |
| T | impulsive behavior | 3 | 15, 19, 2 |
| T | impulsive behaviour | 3 | 15, 19, 2 |
| T | inadequate housing | 3 | 15, 19, 2 |
| T | increased libido | 3 | 15, 19, 2 |
| T | increased sweating | 3 | 15, 19, 2 |
| T | infected insect bite | 3 | 15, 19, 2 |

[Fig. 20-40]

| T | initial insomnia | 3 | 15, 19, 2 |
|---|---|---|---|
| T | injection site discomfort | 3 | 15, 19, 2 |
| T | injection site rash | 3 | 15, 19, 2 |
| T | insulin resistance | 3 | 15, 19, 2 |
| T | intentional self-injury | 3 | 15, 19, 2 |
| T | intentional self injury | 3 | 15, 19, 2 |
| T | iron deficiency | 3 | 15, 19, 2 |
| T | itching | 3 | 15, 19, 2 |
| T | large intestine carcinoma | 3 | 15, 19, 2 |
| T | left ankle swelling (injury) | 3 | 15, 19, 2 |
| T | lymphadenitis bacterial | 3 | 15, 19, 2 |
| T | middle ear effusion | 3 | 15, 19, 2 |
| T | miliaria | 3 | 15, 19, 2 |
| T | mood altered | 3 | 15, 19, 2 |
| T | movement disorder | 3 | 15, 19, 2 |
| T | muscle rigidity | 3 | 15, 19, 2 |
| T | neuroleptic malignant syndrome | 3 | 15, 19, 2 |
| T | nightmare | 3 | 15, 19, 2 |
| T | nightmares | 3 | 15, 19, 2 |
| T | non-small cell lung cancer metastatic | 3 | 15, 19, 2 |
| T | obsessive-compulsive disorder | 3 | 15, 19, 2 |
| T | organising pneumonia | 3 | 15, 19, 2 |
| T | otitis media acute | 3 | 15, 19, 2 |
| T | ovarian fibroma | 3 | 15, 19, 2 |
| T | painful urination | 3 | 15, 19, 2 |
| T | penile oedema | 3 | 15, 19, 2 |
| T | persecutory delusion | 3 | 15, 19, 2 |
| T | pilonidal cyst | 3 | 15, 19, 2 |
| T | pregnancy | 3 | 15, 19, 2 |
| T | prostatic disorder | 3 | 15, 19, 2 |
| T | pruritis | 3 | 15, 19, 2 |
| T | psychiatric symptom | 3 | 15, 19, 2 |
| T | psychomotor hyperactivity | 3 | 15, 19, 2 |
| T | psychosocial support | 3 | 15, 19, 2 |
| T | psychotic behaviour | 3 | 15, 19, 2 |
| T | rectal cancer metastatic | 3 | 15, 19, 2 |
| T | respite care | 3 | 15, 19, 2 |
| T | ruptured cerebral aneurysm | 3 | 15, 19, 2 |
| T | schizoaffective disorder | 3 | 15, 19, 2 |
| T | schizophrenia, paranoid type | 3 | 15, 19, 2 |
| T | schizophrenia, undifferentiated type | 3 | 15, 19, 2 |
| T | seborrhoea | 3 | 15, 19, 2 |
| T | sexual abuse | 3 | 15, 19, 2 |
| T | skin and soft tissue infection | 3 | 15, 19, 2 |
| T | skin discolouration | 3 | 15, 19, 2 |
| T | skin nodule | 3 | 15, 19, 2 |
| T | sleep disturbance | 3 | 15, 19, 2 |
| T | somnambulism | 3 | 15, 19, 2 |
| T | sputum discoloured | 3 | 15, 19, 2 |
| T | stomach mass | 3 | 15, 19, 2 |
| T | stomachache | 3 | 15, 19, 2 |
| T | substance use | 3 | 15, 19, 2 |
| T | suicidal attempt | 3 | 15, 19, 2 |
| T | suividal ideation | 3 | 15, 19, 2 |
| T | syphilis | 3 | 15, 19, 2 |
| T | tic | 3 | 15, 19, 2 |
| T | tongue neoplasm | 3 | 15, 19, 2 |
| T | tonsillar hypertrophy | 3 | 15, 19, 2 |
| T | tourette's disorder | 3 | 15, 19, 2 |
| T | transient ischemic attack | 3 | 15, 19, 2 |
| T | traumatic liver injury | 3 | 15, 19, 2 |
| T | treatment noncompliance | 3 | 15, 19, 2 |
| T | trouble with erections | 3 | 15, 19, 2 |
| T | tympanic membrane perforation | 3 | 15, 19, 2 |
| T | type diabetis mellitus | 3 | 15, 19, 2 |
| T | urinary hesitation | 3 | 15, 19, 2 |
| T | urination | 3 | 15, 19, 2 |

[Fig. 20-41]

| T | uveitis | 3 | 15, 19, 2 |
|---|---|---|---|
| T | varicella | 3 | 15, 19, 2 |
| T | viral rash | 3 | 15, 19, 2 |
| T | viral syndrome | 3 | 15, 19, 2 |
| T | vivid dreaming | 3 | 15, 19, 2 |
| T | vocal cord disorder | 3 | 15, 19, 2 |
| T | worsening of major depression with psychotic features | 3 | 15, 19, 2 |
| T | abdominal distension | 3 | 21, 2, 8 |
| T | acute kidney injury | 3 | 21, 2, 8 |
| T | anal fistula | 3 | 21, 2, 8 |
| T | arrhythmia | 3 | 21, 2, 8 |
| T | ascites | 3 | 21, 2, 8 |
| T | atelectasis | 3 | 21, 2, 8 |
| T | atrial tachycardia | 3 | 21, 2, 8 |
| T | benign prostatic hyperplasia | 3 | 21, 2, 8 |
| T | bradycardia | 3 | 21, 2, 8 |
| T | catheter site infection | 3 | 21, 2, 8 |
| T | cerebral haemorrhage | 3 | 21, 2, 8 |
| T | cerebrovascular accident | 3 | 21, 2, 8 |
| T | colitis | 3 | 21, 2, 8 |
| T | deep vein thrombosis | 3 | 21, 2, 8 |
| T | dermatitis | 3 | 21, 2, 8 |
| T | diverticulitis | 3 | 21, 2, 8 |
| T | drug hypersensitivity | 3 | 21, 2, 8 |
| T | duodenal ulcer | 3 | 21, 2, 8 |
| T | dysarthria | 3 | 21, 2, 8 |
| T | dyspnoea exertional | 3 | 21, 2, 8 |
| T | erysipelas | 3 | 21, 2, 8 |
| T | erythema | 3 | 21, 2, 8 |
| T | general physical health deterioration | 3 | 21, 2, 8 |
| T | haematoma | 3 | 21, 2, 8 |
| T | haematuria | 3 | 21, 2, 8 |
| T | haemorrhoids | 3 | 21, 2, 8 |
| T | herpes zoster | 3 | 21, 2, 8 |
| T | hip fracture | 3 | 21, 2, 8 |
| T | hydronephrosis | 3 | 21, 2, 8 |
| T | hyperkalaemia | 3 | 21, 2, 8 |
| T | hypokalaemia | 3 | 21, 2, 8 |
| T | hypoxia | 3 | 21, 2, 8 |
| T | ileus | 3 | 21, 2, 8 |
| T | intestinal obstruction | 3 | 21, 2, 8 |
| T | iron deficiency anaemia | 3 | 21, 2, 8 |
| T | ischaemic stroke | 3 | 21, 2, 8 |
| T | lung infection | 3 | 21, 2, 8 |
| T | mental status changes | 3 | 21, 2, 8 |
| T | musculoskeletal chest pain | 3 | 21, 2, 8 |
| T | obesity | 3 | 21, 2, 8 |
| T | osteoporosis | 3 | 21, 2, 8 |
| T | pericardial effusion | 3 | 21, 2, 8 |
| T | peritonitis | 3 | 21, 2, 8 |
| T | peritonitis bacterial | 3 | 21, 2, 8 |
| T | pleural effusion | 3 | 21, 2, 8 |
| T | pneumonia aspiration | 3 | 21, 2, 8 |
| T | post procedural infection | 3 | 21, 2, 8 |
| T | postoperative wound infection | 3 | 21, 2, 8 |
| T | pulmonary embolism | 3 | 21, 2, 8 |
| T | pulmonary fibrosis | 3 | 21, 2, 8 |
| T | rectal haemorrhage | 3 | 21, 2, 8 |
| T | renal failure | 3 | 21, 2, 8 |
| T | renal failure acute | 3 | 21, 2, 8 |
| T | respiratory distress | 3 | 21, 2, 8 |
| T | sciatica | 3 | 21, 2, 8 |
| T | septic shock | 3 | 21, 2, 8 |
| T | sinus bradycardia | 3 | 21, 2, 8 |
| T | skin ulcer | 3 | 21, 2, 8 |
| T | small intestinal obstruction | 3 | 21, 2, 8 |
| T | spinal compression fracture | 3 | 21, 2, 8 |

[Fig. 20-42]

| T | spinal fracture | 3 | 21, 2, 8 |
|---|---|---|---|
| T | supraventricular tachycardia | 3 | 21, 2, 8 |
| T | thrombosis | 3 | 21, 2, 8 |
| T | upper gastrointestinal haemorrhage | 3 | 21, 2, 8 |
| T | ureteric obstruction | 3 | 21, 2, 8 |
| T | urinary tract infection | 3 | 21, 2, 8 |
| T | urosepsis | 3 | 21, 2, 8 |
| T | ventricular fibrillation | 3 | 21, 2, 8 |
| T | ventricular tachycardia | 3 | 21, 2, 8 |
| T | wound infection | 3 | 21, 2, 8 |
| T | gastrointestinal disorder - other: hypersalivation | 3 | 4, 15, 13 |
| T | hypersalivation | 3 | 4, 15, 13 |
| T | tachycardia >100 beats/min (supine) | 3 | 4, 15, 13 |
| T | abdominal injury | 3 | 3, 7, 8 |
| T | abdominal wall haematoma | 3 | 3, 7, 8 |
| T | abnormal loss of weight | 3 | 3, 7, 8 |
| T | abscess drainage | 3 | 3, 7, 8 |
| T | abscess of salivary gland | 3 | 3, 7, 8 |
| T | abscess soft tissue | 3 | 3, 7, 8 |
| T | acute hepatic failure | 3 | 3, 7, 8 |
| T | acute leukaemia | 3 | 3, 7, 8 |
| T | acute vestibular syndrome | 3 | 3, 7, 8 |
| T | adenomatous polyposis coli | 3 | 3, 7, 8 |
| T | adnexa uteri mass | 3 | 3, 7, 8 |
| T | adrenal adenoma | 3 | 3, 7, 8 |
| T | adrenal mass | 3 | 3, 7, 8 |
| T | affective disorder | 3 | 3, 7, 8 |
| T | allergy to arthropod sting | 3 | 3, 7, 8 |
| T | amputation stump pain | 3 | 3, 7, 8 |
| T | anal incontinence | 3 | 3, 7, 8 |
| T | anal neoplasm | 3 | 3, 7, 8 |
| T | anastomotic fistula | 3 | 3, 7, 8 |
| T | angiosclerosis | 3 | 3, 7, 8 |
| T | animal scratch | 3 | 3, 7, 8 |
| T | anxiety disorder | 3 | 3, 7, 8 |
| T | aortic aneurysm rupture | 3 | 3, 7, 8 |
| T | aortic injury | 3 | 3, 7, 8 |
| T | aortic occlusion | 3 | 3, 7, 8 |
| T | apnoea | 3 | 3, 7, 8 |
| T | arrhythmia supraventricular | 3 | 3, 7, 8 |
| T | arterial bypass occlusion | 3 | 3, 7, 8 |
| T | arterial bypass thrombosis | 3 | 3, 7, 8 |
| T | arteriogram coronary abnormal | 3 | 3, 7, 8 |
| T | arteriogram coronary normal | 3 | 3, 7, 8 |
| T | arteriovenous fistula operation | 3 | 3, 7, 8 |
| T | arteriovenous fistula site complication | 3 | 3, 7, 8 |
| T | arteriovenous malformation | 3 | 3, 7, 8 |
| T | arthropathy | 3 | 3, 7, 8 |
| T | asthma-chronic obstructive pulmonary disease overlap syndrome | 3 | 3, 7, 8 |
| T | autoimmune hepatitis | 3 | 3, 7, 8 |
| T | b-cell lymphoma | 3 | 3, 7, 8 |
| T | b-cell lymphoma stage i | 3 | 3, 7, 8 |
| T | b-cell prolymphocytic leukaemia | 3 | 3, 7, 8 |
| T | bacterial pericarditis | 3 | 3, 7, 8 |
| T | bacterial pyelonephritis | 3 | 3, 7, 8 |
| T | barrett's oesophagus | 3 | 3, 7, 8 |
| T | basal ganglia infarction | 3 | 3, 7, 8 |
| T | basilar artery aneurysm | 3 | 3, 7, 8 |
| T | benign gastric neoplasm | 3 | 3, 7, 8 |
| T | benign lung neoplasm | 3 | 3, 7, 8 |
| T | benign renal neoplasm | 3 | 3, 7, 8 |
| T | biliary tract disorder | 3 | 3, 7, 8 |
| T | bladder adenocarcinoma stage unspecified | 3 | 3, 7, 8 |
| T | bladder cancer stage i, with cancer in situ | 3 | 3, 7, 8 |
| T | bladder cancer stage iii | 3 | 3, 7, 8 |
| T | bladder cancer stage, with cancer in situ | 3 | 3, 7, 8 |

[Fig. 20-43]

| T | bladder diverticulum | 3 | 3, 7, 8 |
|---|---|---|---|
| T | bladder neck obstruction | 3 | 3, 7, 8 |
| T | bladder neoplasm | 3 | 3, 7, 8 |
| T | bladder obstruction | 3 | 3, 7, 8 |
| T | bladder papilloma | 3 | 3, 7, 8 |
| T | bladder tamponade | 3 | 3, 7, 8 |
| T | bladder transitional cell carcinoma recurrent | 3 | 3, 7, 8 |
| T | bladder transitional cell carcinoma stage i | 3 | 3, 7, 8 |
| T | bladder transitional cell carcinoma stage iii | 3 | 3, 7, 8 |
| T | blood pressure fluctuation | 3 | 3, 7, 8 |
| T | bone abscess | 3 | 3, 7, 8 |
| T | brain abscess | 3 | 3, 7, 8 |
| T | breast abscess | 3 | 3, 7, 8 |
| T | breast dysplasia | 3 | 3, 7, 8 |
| T | breast prosthesis implantation | 3 | 3, 7, 8 |
| T | burkholderia pseudomallei infection | 3 | 3, 7, 8 |
| T | bursitis infective | 3 | 3, 7, 8 |
| T | calculus urethral | 3 | 3, 7, 8 |
| T | campylobacter gastroenteritis | 3 | 3, 7, 8 |
| T | campylobacter infection | 3 | 3, 7, 8 |
| T | carcinoid tumour of the caecum | 3 | 3, 7, 8 |
| T | carcinoid tumour pulmonary | 3 | 3, 7, 8 |
| T | cardiac ablation | 3 | 3, 7, 8 |
| T | cardiac flutter | 3 | 3, 7, 8 |
| T | cardiac pacemaker insertion | 3 | 3, 7, 8 |
| T | cardiac resynchronisation therapy | 3 | 3, 7, 8 |
| T | cardiovascular disorder | 3 | 3, 7, 8 |
| T | carotid arteriosclerosis | 3 | 3, 7, 8 |
| T | carotid artery restenosis | 3 | 3, 7, 8 |
| T | cartilage graft | 3 | 3, 7, 8 |
| T | cauda equina syndrome | 3 | 3, 7, 8 |
| T | cerebellar ataxia | 3 | 3, 7, 8 |
| T | cerebral atrophy | 3 | 3, 7, 8 |
| T | cerebral thrombosis | 3 | 3, 7, 8 |
| T | cerebral vasoconstriction | 3 | 3, 7, 8 |
| T | cervical cord compression | 3 | 3, 7, 8 |
| T | cervical polyp | 3 | 3, 7, 8 |
| T | cervicitis | 3 | 3, 7, 8 |
| T | cervicobrachial syndrome | 3 | 3, 7, 8 |
| T | cervicogenic headache | 3 | 3, 7, 8 |
| T | cervix carcinoma stage | 3 | 3, 7, 8 |
| T | cholangiocarcinoma | 3 | 3, 7, 8 |
| T | cholelithiasis obstructive | 3 | 3, 7, 8 |
| T | cholesteatoma | 3 | 3, 7, 8 |
| T | colon adenoma | 3 | 3, 7, 8 |
| T | colon cancer stage i | 3 | 3, 7, 8 |
| T | colon cancer stage iii | 3 | 3, 7, 8 |
| T | colonic abscess | 3 | 3, 7, 8 |
| T | colonoscopy abnormal | 3 | 3, 7, 8 |
| T | coma | 3 | 3, 7, 8 |
| T | combined pulmonary fibrosis and emphysema | 3 | 3, 7, 8 |
| T | complication associated with device | 3 | 3, 7, 8 |
| T | corneal dystrophy | 3 | 3, 7, 8 |
| T | coronary artery dissection | 3 | 3, 7, 8 |
| T | coronary artery thrombosis | 3 | 3, 7, 8 |
| T | cranial nerve injury | 3 | 3, 7, 8 |
| T | cyst rupture | 3 | 3, 7, 8 |
| T | deafness neurosensory | 3 | 3, 7, 8 |
| T | delirium tremens | 3 | 3, 7, 8 |
| T | demyelinating polyneuropathy | 3 | 3, 7, 8 |
| T | dermal cyst | 3 | 3, 7, 8 |
| T | dermatitis exfoliative | 3 | 3, 7, 8 |
| T | dermatofibrosarcoma protuberans | 3 | 3, 7, 8 |
| T | device ineffective | 3 | 3, 7, 8 |
| T | device loosening | 3 | 3, 7, 8 |
| T | device related sepsis | 3 | 3, 7, 8 |

[Fig. 20-44]

| T | diabetic vascular disorder | 3 | 3, 7, 8 |
|---|---|---|---|
| T | diffuse axonal injury | 3 | 3, 7, 8 |
| T | dislocation of sternum | 3 | 3, 7, 8 |
| T | dislocation of vertebra | 3 | 3, 7, 8 |
| T | diverticulitis intestinal haemorrhagic | 3 | 3, 7, 8 |
| T | diverticulum intestinal haemorrhagic | 3 | 3, 7, 8 |
| T | dressler's syndrome | 3 | 3, 7, 8 |
| T | drug intolerance | 3 | 3, 7, 8 |
| T | drug withdrawal syndrome | 3 | 3, 7, 8 |
| T | dry gangrene | 3 | 3, 7, 8 |
| T | dyspnoea at rest | 3 | 3, 7, 8 |
| T | eczema nummular | 3 | 3, 7, 8 |
| T | electrocardiogram st segment depression | 3 | 3, 7, 8 |
| T | embolic pneumonia | 3 | 3, 7, 8 |
| T | end stage renal disease | 3 | 3, 7, 8 |
| T | endometrial adenoma | 3 | 3, 7, 8 |
| T | endometrial thickening | 3 | 3, 7, 8 |
| T | endophthalmitis | 3 | 3, 7, 8 |
| T | endoscopy gastrointestinal abnormal | 3 | 3, 7, 8 |
| T | endotracheal intubation complication | 3 | 3, 7, 8 |
| T | enterobacter bacteraemia | 3 | 3, 7, 8 |
| T | enterococcal bacteraemia | 3 | 3, 7, 8 |
| T | enterococcal sepsis | 3 | 3, 7, 8 |
| T | enterostomy | 3 | 3, 7, 8 |
| T | epididymitis | 3 | 3, 7, 8 |
| T | epiploic appendagitis | 3 | 3, 7, 8 |
| T | erosive oesophagitis | 3 | 3, 7, 8 |
| T | erysipeloid | 3 | 3, 7, 8 |
| T | escherichia sepsis | 3 | 3, 7, 8 |
| T | exercise electrocardiogram abnormal | 3 | 3, 7, 8 |
| T | exercise tolerance decreased | 3 | 3, 7, 8 |
| T | exomphalos | 3 | 3, 7, 8 |
| T | exostosis of external ear canal | 3 | 3, 7, 8 |
| T | extrasystoles | 3 | 3, 7, 8 |
| T | eye injury | 3 | 3, 7, 8 |
| T | eye operation complication | 3 | 3, 7, 8 |
| T | eyelid ptosis | 3 | 3, 7, 8 |
| T | facial paresis | 3 | 3, 7, 8 |
| T | fallopian tube cancer | 3 | 3, 7, 8 |
| T | false positive investigation result | 3 | 3, 7, 8 |
| T | fat necrosis | 3 | 3, 7, 8 |
| T | fibroma | 3 | 3, 7, 8 |
| T | finger amputation | 3 | 3, 7, 8 |
| T | fractured ischium | 3 | 3, 7, 8 |
| T | fungal peritonitis | 3 | 3, 7, 8 |
| T | gallbladder perforation | 3 | 3, 7, 8 |
| T | gallbladder polyp | 3 | 3, 7, 8 |
| T | gastric cancer stage iv | 3 | 3, 7, 8 |
| T | gastric disorder | 3 | 3, 7, 8 |
| T | gastritis alcoholic | 3 | 3, 7, 8 |
| T | gastritis viral | 3 | 3, 7, 8 |
| T | gastroduodenal haemorrhage | 3 | 3, 7, 8 |
| T | gastroduodenitis | 3 | 3, 7, 8 |
| T | gastroenteritis adenovirus | 3 | 3, 7, 8 |
| T | gastroenteritis bacterial | 3 | 3, 7, 8 |
| T | gastroenteritis clostridial | 3 | 3, 7, 8 |
| T | gastroenteritis rotavirus | 3 | 3, 7, 8 |
| T | gastrointestinal motility disorder | 3 | 3, 7, 8 |
| T | genital haemorrhage | 3 | 3, 7, 8 |
| T | glioblastoma multiforme | 3 | 3, 7, 8 |
| T | glomerulonephritis membranous | 3 | 3, 7, 8 |
| T | glomerulonephritis minimal lesion | 3 | 3, 7, 8 |
| T | graft infection | 3 | 3, 7, 8 |
| T | groin abscess | 3 | 3, 7, 8 |
| T | haemangiopericytoma | 3 | 3, 7, 8 |
| T | haemorrhagic erosive gastritis | 3 | 3, 7, 8 |
| T | heat stroke | 3 | 3, 7, 8 |

[Fig. 20-45]

| T | hemiplegic migraine | 3 | 3, 7, 8 |
|---|---|---|---|
| T | henoch-schonlein purpura | 3 | 3, 7, 8 |
| T | hepatic cyst | 3 | 3, 7, 8 |
| T | hepatic pain | 3 | 3, 7, 8 |
| T | hepatitis a antibody positive | 3 | 3, 7, 8 |
| T | hepatitis a virus test positive | 3 | 3, 7, 8 |
| T | hepatitis alcoholic | 3 | 3, 7, 8 |
| T | hepatitis b | 3 | 3, 7, 8 |
| T | hepatitis c | 3 | 3, 7, 8 |
| T | hepatitis c virus test positive | 3 | 3, 7, 8 |
| T | hepatitis toxic | 3 | 3, 7, 8 |
| T | hepatorenal syndrome | 3 | 3, 7, 8 |
| T | hepatotoxicity | 3 | 3, 7, 8 |
| T | hereditary motor and sensory neuropathy | 3 | 3, 7, 8 |
| T | hernial eventration | 3 | 3, 7, 8 |
| T | herpes simplex meningoencephalitis | 3 | 3, 7, 8 |
| T | hodgkin's disease | 3 | 3, 7, 8 |
| T | hospitalisation | 3 | 3, 7, 8 |
| T | hydrocele | 3 | 3, 7, 8 |
| T | hyperinsulinaemic hypoglycaemia | 3 | 3, 7, 8 |
| T | hyperosmolar hyperglycaemic state | 3 | 3, 7, 8 |
| T | hyperthyroidism | 3 | 3, 7, 8 |
| T | hypertransaminasaemia | 3 | 3, 7, 8 |
| T | hypertrophic cardiomyopathy | 3 | 3, 7, 8 |
| T | hypochromic anaemia | 3 | 3, 7, 8 |
| T | hypovitaminosis | 3 | 3, 7, 8 |
| T | iga nephropathy | 3 | 3, 7, 8 |
| T | ilium fracture | 3 | 3, 7, 8 |
| T | implant site infection | 3 | 3, 7, 8 |
| T | implant site inflammation | 3 | 3, 7, 8 |
| T | incarcerated hernia | 3 | 3, 7, 8 |
| T | incisional hernia repair | 3 | 3, 7, 8 |
| T | incomplete spinal fusion | 3 | 3, 7, 8 |
| T | infected bite | 3 | 3, 7, 8 |
| T | infective exacerbation of chronic obstructive airways disease | 3 | 3, 7, 8 |
| T | infective tenosynovitis | 3 | 3, 7, 8 |
| T | influenza a virus test positive | 3 | 3, 7, 8 |
| T | influenza b virus test positive | 3 | 3, 7, 8 |
| T | inguinal hernia repair | 3 | 3, 7, 8 |
| T | injection site induration | 3 | 3, 7, 8 |
| T | inner ear inflammation | 3 | 3, 7, 8 |
| T | international normalised ratio abnormal | 3 | 3, 7, 8 |
| T | intervertebral disc displacement | 3 | 3, 7, 8 |
| T | intestinal fistula | 3 | 3, 7, 8 |
| T | intestinal prolapse | 3 | 3, 7, 8 |
| T | intracardiac thrombus | 3 | 3, 7, 8 |
| T | intracranial mass | 3 | 3, 7, 8 |
| T | intussusception | 3 | 3, 7, 8 |
| T | investigation | 3 | 3, 7, 8 |
| T | iridocyclitis | 3 | 3, 7, 8 |
| T | jaundice | 3 | 3, 7, 8 |
| T | jaw cyst | 3 | 3, 7, 8 |
| T | joint dislocation postoperative | 3 | 3, 7, 8 |
| T | joint effusion | 3 | 3, 7, 8 |
| T | large cell lung cancer stage iii | 3 | 3, 7, 8 |
| T | large intestinal haemorrhage | 3 | 3, 7, 8 |
| T | large intestinal obstruction | 3 | 3, 7, 8 |
| T | large intestinal polypectomy | 3 | 3, 7, 8 |
| T | laryngeal cancer metastatic | 3 | 3, 7, 8 |
| T | laryngeal cancer stage iv | 3 | 3, 7, 8 |
| T | leriche syndrome | 3 | 3, 7, 8 |
| T | limb discomfort | 3 | 3, 7, 8 |
| T | limb traumatic amputation | 3 | 3, 7, 8 |
| T | lip and/or oral cavity cancer | 3 | 3, 7, 8 |
| T | lip and/or oral cavity cancer stage iii | 3 | 3, 7, 8 |
| T | lipoma excision | 3 | 3, 7, 8 |

[Fig. 20-46]

| T | liposarcoma | 3 | 3, 7, 8 |
|---|---|---|---|
| T | lower respiratory tract infection viral | 3 | 3, 7, 8 |
| T | lung adenocarcinoma metastatic | 3 | 3, 7, 8 |
| T | lung adenocarcinoma stage i | 3 | 3, 7, 8 |
| T | lung adenocarcinoma stage iii | 3 | 3, 7, 8 |
| T | lung carcinoma cell type unspecified stage i | 3 | 3, 7, 8 |
| T | lung carcinoma cell type unspecified stage ii | 3 | 3, 7, 8 |
| T | lung carcinoma cell type unspecified stage iii | 3 | 3, 7, 8 |
| T | lung carcinoma cell type unspecified stage iv | 3 | 3, 7, 8 |
| T | lung squamous cell carcinoma metastatic | 3 | 3, 7, 8 |
| T | lung squamous cell carcinoma stage iii | 3 | 3, 7, 8 |
| T | lymphadenopathy | 3 | 3, 7, 8 |
| T | male genital tract fistula | 3 | 3, 7, 8 |
| T | malignant ascites | 3 | 3, 7, 8 |
| T | malignant melanoma of sites other than skin | 3 | 3, 7, 8 |
| T | malignant mesenteric neoplasm | 3 | 3, 7, 8 |
| T | malignant neoplasm of renal pelvis | 3 | 3, 7, 8 |
| T | mammoplasty | 3 | 3, 7, 8 |
| T | mass | 3 | 3, 7, 8 |
| T | mastitis | 3 | 3, 7, 8 |
| T | mastoiditis | 3 | 3, 7, 8 |
| T | medical device discomfort | 3 | 3, 7, 8 |
| T | medical observation | 3 | 3, 7, 8 |
| T | meniere's disease | 3 | 3, 7, 8 |
| T | meningitis viral | 3 | 3, 7, 8 |
| T | menopause | 3 | 3, 7, 8 |
| T | mesenteric artery stenosis | 3 | 3, 7, 8 |
| T | mesothelioma | 3 | 3, 7, 8 |
| T | metastases to adrenals | 3 | 3, 7, 8 |
| T | metastases to pleura | 3 | 3, 7, 8 |
| T | metastases to spine | 3 | 3, 7, 8 |
| T | metastatic bronchial carcinoma | 3 | 3, 7, 8 |
| T | mite allergy | 3 | 3, 7, 8 |
| T | mobility decreased | 3 | 3, 7, 8 |
| T | mood disorder due to a general medical condition | 3 | 3, 7, 8 |
| T | multiple organ dysfunction syndrome | 3 | 3, 7, 8 |
| T | muscle fatigue | 3 | 3, 7, 8 |
| T | myalgia intercostal | 3 | 3, 7, 8 |
| T | myocardial necrosis | 3 | 3, 7, 8 |
| T | myocardial necrosis marker increased | 3 | 3, 7, 8 |
| T | myocarditis | 3 | 3, 7, 8 |
| T | necrotising fasciitis | 3 | 3, 7, 8 |
| T | neoplasm | 3 | 3, 7, 8 |
| T | neoplasm malignant | 3 | 3, 7, 8 |
| T | nervous system disorder | 3 | 3, 7, 8 |
| T | neuroendocrine carcinoma metastatic | 3 | 3, 7, 8 |
| T | neuroendocrine tumour | 3 | 3, 7, 8 |
| T | neurogenic bladder | 3 | 3, 7, 8 |
| T | neuroglycopenia | 3 | 3, 7, 8 |
| T | neurological symptom | 3 | 3, 7, 8 |
| T | neurosis | 3 | 3, 7, 8 |
| T | neurosyphilis | 3 | 3, 7, 8 |
| T | nocturnal dyspnoea | 3 | 3, 7, 8 |
| T | ocular myasthenia | 3 | 3, 7, 8 |
| T | oesophageal adenocarcinoma metastatic | 3 | 3, 7, 8 |
| T | oesophageal obstruction | 3 | 3, 7, 8 |
| T | oesophageal spasm | 3 | 3, 7, 8 |
| T | oesophageal ulcer | 3 | 3, 7, 8 |
| T | open globe injury | 3 | 3, 7, 8 |
| T | open reduction of fracture | 3 | 3, 7, 8 |
| T | ophthalmic herpes zoster | 3 | 3, 7, 8 |
| T | ophthalmoplegia | 3 | 3, 7, 8 |
| T | oral neoplasm | 3 | 3, 7, 8 |
| T | orchitis | 3 | 3, 7, 8 |
| T | orthopnoea | 3 | 3, 7, 8 |
| T | osteochondrosis | 3 | 3, 7, 8 |
| T | osteoporotic fracture | 3 | 3, 7, 8 |

[Fig. 20-47]

| T | osteotomy | 3 | 3, 7, 8 |
|---|---|---|---|
| T | otitis externa bacterial | 3 | 3, 7, 8 |
| T | otorrhoea | 3 | 3, 7, 8 |
| T | ovarian adenoma | 3 | 3, 7, 8 |
| T | ovarian cancer metastatic | 3 | 3, 7, 8 |
| T | ovarian cancer stage ii | 3 | 3, 7, 8 |
| T | pancreas infection | 3 | 3, 7, 8 |
| T | pancreatic pseudocyst | 3 | 3, 7, 8 |
| T | pancreatitis chronic | 3 | 3, 7, 8 |
| T | pancreatitis necrotising | 3 | 3, 7, 8 |
| T | pancreatolithiasis | 3 | 3, 7, 8 |
| T | panic attack | 3 | 3, 7, 8 |
| T | papillary cystadenoma lymphomatosum | 3 | 3, 7, 8 |
| T | papulopustular rosacea | 3 | 3, 7, 8 |
| T | paresis | 3 | 3, 7, 8 |
| T | pemphigoid | 3 | 3, 7, 8 |
| T | penile haemorrhage | 3 | 3, 7, 8 |
| T | peptic ulcer haemorrhage | 3 | 3, 7, 8 |
| T | periodontal disease | 3 | 3, 7, 8 |
| T | periodontitis | 3 | 3, 7, 8 |
| T | peripheral arterial reocclusion | 3 | 3, 7, 8 |
| T | peripheral artery aneurysm | 3 | 3, 7, 8 |
| T | perirectal abscess | 3 | 3, 7, 8 |
| T | peritoneal haematoma | 3 | 3, 7, 8 |
| T | peroneal nerve palsy | 3 | 3, 7, 8 |
| T | peroneal nerve palsy postoperative | 3 | 3, 7, 8 |
| T | personality disorder | 3 | 3, 7, 8 |
| T | phaeochromocytoma | 3 | 3, 7, 8 |
| T | pharyngeal cancer stage iv | 3 | 3, 7, 8 |
| T | pickwickian syndrome | 3 | 3, 7, 8 |
| T | plasmacytoma | 3 | 3, 7, 8 |
| T | pleomorphic adenoma | 3 | 3, 7, 8 |
| T | pleural adhesion | 3 | 3, 7, 8 |
| T | pleural disorder | 3 | 3, 7, 8 |
| T | pleural mesothelioma malignant | 3 | 3, 7, 8 |
| T | pneumococcal sepsis | 3 | 3, 7, 8 |
| T | pneumoconiosis | 3 | 3, 7, 8 |
| T | pneumonia adenoviral | 3 | 3, 7, 8 |
| T | pneumonia mycoplasmal | 3 | 3, 7, 8 |
| T | pneumonia viral | 3 | 3, 7, 8 |
| T | pneumonitis chemical | 3 | 3, 7, 8 |
| T | pneumothorax traumatic | 3 | 3, 7, 8 |
| T | polycythaemia | 3 | 3, 7, 8 |
| T | polycythaemia vera | 3 | 3, 7, 8 |
| T | polymyalgia rheumatica | 3 | 3, 7, 8 |
| T | polymyositis | 3 | 3, 7, 8 |
| T | portal vein thrombosis | 3 | 3, 7, 8 |
| T | post-traumatic pain | 3 | 3, 7, 8 |
| T | post concussion syndrome | 3 | 3, 7, 8 |
| T | post procedural complication | 3 | 3, 7, 8 |
| T | post procedural swelling | 3 | 3, 7, 8 |
| T | postoperative respiratory failure | 3 | 3, 7, 8 |
| T | prerenal failure | 3 | 3, 7, 8 |
| T | procedural dizziness | 3 | 3, 7, 8 |
| T | procedural haemorrhage | 3 | 3, 7, 8 |
| T | prostate cancer metastatic | 3 | 3, 7, 8 |
| T | prostate cancer stage ii | 3 | 3, 7, 8 |
| T | prostate cancer stage iv | 3 | 3, 7, 8 |
| T | prostate infection | 3 | 3, 7, 8 |
| T | prostatomegaly | 3 | 3, 7, 8 |
| T | psychogenic seizure | 3 | 3, 7, 8 |
| T | pulmonary alveolar haemorrhage | 3 | 3, 7, 8 |
| T | pulmonary pain | 3 | 3, 7, 8 |
| T | pulseless electrical activity | 3 | 3, 7, 8 |
| T | puncture site haemorrhage | 3 | 3, 7, 8 |
| T | pyelonephritis chronic | 3 | 3, 7, 8 |
| T | quadriplegia | 3 | 3, 7, 8 |

[Fig. 20-48]

| T | radiation mucositis | 3 | 3, 7, 8 |
|---|---|---|---|
| T | rectal abscess | 3 | 3, 7, 8 |
| T | rectal cancer stage iii | 3 | 3, 7, 8 |
| T | rectal cancer stage iv | 3 | 3, 7, 8 |
| T | reflux gastritis | 3 | 3, 7, 8 |
| T | rehabilitation therapy | 3 | 3, 7, 8 |
| T | renal adenoma | 3 | 3, 7, 8 |
| T | renal cyst haemorrhage | 3 | 3, 7, 8 |
| T | renal pain | 3 | 3, 7, 8 |
| T | reproductive tract disorder | 3 | 3, 7, 8 |
| T | respiratory tract infection bacterial | 3 | 3, 7, 8 |
| T | restless legs syndrome | 3 | 3, 7, 8 |
| T | retinal vein occlusion | 3 | 3, 7, 8 |
| T | retroperitoneal neoplasm | 3 | 3, 7, 8 |
| T | rhinovirus infection | 3 | 3, 7, 8 |
| T | rhythm idioventricular | 3 | 3, 7, 8 |
| T | sacroiliac fracture | 3 | 3, 7, 8 |
| T | salivary gland enlargement | 3 | 3, 7, 8 |
| T | salpingitis | 3 | 3, 7, 8 |
| T | scar pain | 3 | 3, 7, 8 |
| T | shock haemorrhagic | 3 | 3, 7, 8 |
| T | sinoatrial block | 3 | 3, 7, 8 |
| T | sinus arrest | 3 | 3, 7, 8 |
| T | skin bacterial infection | 3 | 3, 7, 8 |
| T | skull fracture | 3 | 3, 7, 8 |
| T | small cell lung cancer limited stage | 3 | 3, 7, 8 |
| T | small cell lung cancer metastatic | 3 | 3, 7, 8 |
| T | small intestinal haemorrhage | 3 | 3, 7, 8 |
| T | snake bite | 3 | 3, 7, 8 |
| T | soft tissue inflammation | 3 | 3, 7, 8 |
| T | soft tissue sarcoma | 3 | 3, 7, 8 |
| T | somatic symptom disorder | 3 | 3, 7, 8 |
| T | spermatic cord funiculitis | 3 | 3, 7, 8 |
| T | spinal anaesthesia | 3 | 3, 7, 8 |
| T | spinal cord injury lumbar | 3 | 3, 7, 8 |
| T | spinal decompression | 3 | 3, 7, 8 |
| T | spinal instability | 3 | 3, 7, 8 |
| T | strangulated umbilical hernia | 3 | 3, 7, 8 |
| T | streptococcal sepsis | 3 | 3, 7, 8 |
| T | stress cardiomyopathy | 3 | 3, 7, 8 |
| T | stress echocardiogram | 3 | 3, 7, 8 |
| T | stroke in evolution | 3 | 3, 7, 8 |
| T | subacute hepatic failure | 3 | 3, 7, 8 |
| T | subclavian steal syndrome | 3 | 3, 7, 8 |
| T | subcutaneous emphysema | 3 | 3, 7, 8 |
| T | subdural effusion | 3 | 3, 7, 8 |
| T | subdural haemorrhage | 3 | 3, 7, 8 |
| T | sympathetic posterior cervical syndrome | 3 | 3, 7, 8 |
| T | symphysiolysis | 3 | 3, 7, 8 |
| T | takayasu's arteritis | 3 | 3, 7, 8 |
| T | testicular abscess | 3 | 3, 7, 8 |
| T | thrombophlebitis superficial | 3 | 3, 7, 8 |
| T | thyroid function test abnormal | 3 | 3, 7, 8 |
| T | thyroid mass | 3 | 3, 7, 8 |
| T | toe amputation | 3 | 3, 7, 8 |
| T | tongue cyst | 3 | 3, 7, 8 |
| T | tongue oedema | 3 | 3, 7, 8 |
| T | tooth impacted | 3 | 3, 7, 8 |
| T | torsade de pointes | 3 | 3, 7, 8 |
| T | toxic encephalopathy | 3 | 3, 7, 8 |
| T | tracheitis | 3 | 3, 7, 8 |
| T | transient global amnesia | 3 | 3, 7, 8 |
| T | transitional cell cancer of the renal pelvis and ureter | 3 | 3, 7, 8 |
| T | transplant rejection | 3 | 3, 7, 8 |
| T | traumatic arthritis | 3 | 3, 7, 8 |
| T | traumatic intracranial haemorrhage | 3 | 3, 7, 8 |
| T | traumatic shock | 3 | 3, 7, 8 |

[Fig. 20-49]

| T | traumatic ulcer | 3 | 3, 7, 8 |
|---|---|---|---|
| T | troponin t increased | 3 | 3, 7, 8 |
| T | umbilical hernia repair | 3 | 3, 7, 8 |
| T | undifferentiated sarcoma | 3 | 3, 7, 8 |
| T | unresponsive to stimuli | 3 | 3, 7, 8 |
| T | ureteric rupture | 3 | 3, 7, 8 |
| T | ureteric stenosis | 3 | 3, 7, 8 |
| T | ureteritis | 3 | 3, 7, 8 |
| T | urethral stricture postoperative | 3 | 3, 7, 8 |
| T | uterine atony | 3 | 3, 7, 8 |
| T | uterine enlargement | 3 | 3, 7, 8 |
| T | vascular bypass dysfunction | 3 | 3, 7, 8 |
| T | vascular occlusion | 3 | 3, 7, 8 |
| T | vascular stenosis | 3 | 3, 7, 8 |
| T | vascular stent occlusion | 3 | 3, 7, 8 |
| T | vascular stent restenosis | 3 | 3, 7, 8 |
| T | vascular stent stenosis | 3 | 3, 7, 8 |
| T | vasoconstriction | 3 | 3, 7, 8 |
| T | vasodilatation | 3 | 3, 7, 8 |
| T | ventricular hypertrophy | 3 | 3, 7, 8 |
| T | ventricular tachyarrhythmia | 3 | 3, 7, 8 |
| T | vertebral artery occlusion | 3 | 3, 7, 8 |
| T | vertigo cns origin | 3 | 3, 7, 8 |
| T | vessel perforation | 3 | 3, 7, 8 |
| T | vessel puncture site haemorrhage | 3 | 3, 7, 8 |
| T | vessel puncture site pain | 3 | 3, 7, 8 |
| T | vestibular ischaemia | 3 | 3, 7, 8 |
| T | viral pericarditis | 3 | 3, 7, 8 |
| T | vitamin b12 deficiency | 3 | 3, 7, 8 |
| T | vocal cord neoplasm | 3 | 3, 7, 8 |
| T | vocal cord paralysis | 3 | 3, 7, 8 |
| T | vulval abscess | 3 | 3, 7, 8 |
| T | wound abscess | 3 | 3, 7, 8 |
| T | wound evisceration | 3 | 3, 7, 8 |
| T | wound necrosis | 3 | 3, 7, 8 |
| T | wound secretion | 3 | 3, 7, 8 |
| T | acute respiratory distress syndrome | 4 | 16, 5, 23, 17 |
| T | alcohol poisoning | 4 | 16, 5, 23, 17 |
| T | alcoholism | 4 | 16, 5, 23, 17 |
| T | cirrhosis alcoholic | 4 | 16, 5, 23, 17 |
| T | conversion disorder | 4 | 16, 5, 23, 17 |
| T | dizziness postural | 4 | 16, 5, 23, 17 |
| T | drug dependence | 4 | 16, 5, 23, 17 |
| T | dysmenorrhoea | 4 | 16, 5, 23, 17 |
| T | escherichia urinary tract infection | 4 | 16, 5, 23, 17 |
| T | glomerulonephritis acute | 4 | 16, 5, 23, 17 |
| T | hallucination, visual | 4 | 16, 5, 23, 17 |
| T | infected bites | 4 | 16, 5, 23, 17 |
| T | injection site pain | 4 | 16, 5, 23, 17 |
| T | intestinal haemorrhage | 4 | 16, 5, 23, 17 |
| T | mania | 4 | 16, 5, 23, 17 |
| T | myopathy | 4 | 16, 5, 23, 17 |
| T | otitis externa | 4 | 16, 5, 23, 17 |
| T | paranoia | 4 | 16, 5, 23, 17 |
| T | pharyngitis streptococcal | 4 | 16, 5, 23, 17 |
| T | scrotal oedema | 4 | 16, 5, 23, 17 |
| T | social stay hospitalisation | 4 | 16, 5, 23, 17 |
| T | strabismus | 4 | 16, 5, 23, 17 |
| T | tooth abscess | 4 | 16, 5, 23, 17 |
| T | abnormal ecg | 4 | 15, 19, 6, 2 |
| T | ademia | 4 | 15, 19, 6, 2 |
| T | bleeding | 4 | 15, 19, 6, 2 |
| T | dysmenorthoea | 4 | 15, 19, 6, 2 |
| T | ear and labyrinth disorder other: ear canal blockage | 4 | 15, 19, 6, 2 |
| T | extreme sedation | 4 | 15, 19, 6, 2 |
| T | eye irritation/swelling | 4 | 15, 19, 6, 2 |
| T | forgetfulness | 4 | 15, 19, 6, 2 |

[Fig. 20-50]

| T | fracture of distal clavicle, lt. | 4 | 15, 19, 6, 2 |
|---|---|---|---|
| T | halucinations | 4 | 15, 19, 6, 2 |
| T | hospitalization | 4 | 15, 19, 6, 2 |
| T | hyper glycemia | 4 | 15, 19, 6, 2 |
| T | increased auditory hallucinations | 4 | 15, 19, 6, 2 |
| T | injury, poisoning and procedural complications, other: sprain | 4 | 15, 19, 6, 2 |
| T | investigations other - increased liver function tests | 4 | 15, 19, 6, 2 |
| T | lactation | 4 | 15, 19, 6, 2 |
| T | libido decreased | 4 | 15, 19, 6, 2 |
| T | menstrual distubances | 4 | 15, 19, 6, 2 |
| T | metabolism & nutrition disorders, other: increased appetite | 4 | 15, 19, 6, 2 |
| T | musculo-skeletal connective tissue disorder-other, muscle twitch | 4 | 15, 19, 6, 2 |
| T | musculoskeletal and connective tissue disorder - other: muscle spasms | 4 | 15, 19, 6, 2 |
| T | musculoskeletal other: ankle pain | 4 | 15, 19, 6, 2 |
| T | musculoskeletal other: knee and foot pain | 4 | 15, 19, 6, 2 |
| T | nervous sytem disorder - other: unusual dream activity | 4 | 15, 19, 6, 2 |
| T | ocular discomfort | 4 | 15, 19, 6, 2 |
| T | psychiatric disorder - other: accidental overdose | 4 | 15, 19, 6, 2 |
| T | qtc prolongation | 4 | 15, 19, 6, 2 |
| T | severe eps | 4 | 15, 19, 6, 2 |
| T | skin and subcutaneous tissue disorders, other: acne | 4 | 15, 19, 6, 2 |
| T | tachycardia >120 beats/min (supine) | 4 | 15, 19, 6, 2 |
| T | uri | 4 | 15, 19, 6, 2 |
| T | urinary uregency | 4 | 15, 19, 6, 2 |
| T | nausea/vomiting | 5 | 4, 6, 15, 13, 17 |
| T | extrapyramidal disorder | 5 | 15, 12, 2, 24, 1 |
| T | irritability | 5 | 15, 12, 2, 24, 1 |
| T | psychiatric decompensation | 5 | 9, 16, 21, 20, 11 |
| T | delirium | 5 | 18, 23, 3, 21, 17 |
| T | pancreatitis | 5 | 18, 23, 3, 21, 17 |
| T | urticaria | 5 | 18, 23, 3, 21, 17 |
| T | delirium | 5 | 4, 19, 12, 2, 3 |
| T | pancreatitis | 5 | 4, 19, 12, 2, 3 |
| T | urticaria | 5 | 4, 19, 12, 2, 3 |
| T | suicide attempt | 6 | 1, 22, 13, 9, 16, 7 |
| T | psychosis | 6 | 5, 22, 14, 20, 12, 17 |
| T | nausea | 7 | 3, 15, 1, 19, 14, 8, 18 |
| T | abdominal pain upper | 7 | 21, 8, 19, 7, 20, 16, 6 |
| T | acute myocardial infarction | 7 | 21, 8, 19, 7, 20, 16, 6 |
| T | acute respiratory failure | 7 | 21, 8, 19, 7, 20, 16, 6 |
| T | appendicitis | 7 | 21, 8, 19, 7, 20, 16, 6 |
| T | arthralgia | 7 | 21, 8, 19, 7, 20, 16, 6 |
| T | asthma | 7 | 21, 8, 19, 7, 20, 16, 6 |
| T | atrial fibrillation | 7 | 21, 8, 19, 7, 20, 16, 6 |
| T | atrial flutter | 7 | 21, 8, 19, 7, 20, 16, 6 |
| T | back pain | 7 | 21, 8, 19, 7, 20, 16, 6 |
| T | bronchitis | 7 | 21, 8, 19, 7, 20, 16, 6 |
| T | cardiac arrest | 7 | 21, 8, 19, 7, 20, 16, 6 |
| T | cataract | 7 | 21, 8, 19, 7, 20, 16, 6 |
| T | cellulitis | 7 | 21, 8, 19, 7, 20, 16, 6 |
| T | chest pain | 7 | 21, 8, 19, 7, 20, 16, 6 |
| T | chronic obstructive pulmonary disease | 7 | 21, 8, 19, 7, 20, 16, 6 |
| T | confusional state | 7 | 21, 8, 19, 7, 20, 16, 6 |
| T | contusion | 7 | 21, 8, 19, 7, 20, 16, 6 |
| T | dehydration | 7 | 21, 8, 19, 7, 20, 16, 6 |
| T | diabetes mellitus | 7 | 21, 8, 19, 7, 20, 16, 6 |
| T | epistaxis | 7 | 21, 8, 19, 7, 20, 16, 6 |
| T | fall | 7 | 21, 8, 19, 7, 20, 16, 6 |
| T | femur fracture | 7 | 21, 8, 19, 7, 20, 16, 6 |
| T | gastritis | 7 | 21, 8, 19, 7, 20, 16, 6 |
| T | gastroenteritis | 7 | 21, 8, 19, 7, 20, 16, 6 |
| T | gastrointestinal haemorrhage | 7 | 21, 8, 19, 7, 20, 16, 6 |
| T | gastrooesophageal reflux disease | 7 | 21, 8, 19, 7, 20, 16, 6 |

[Fig. 20-51]

| | | | |
|---|---|---|---|
| T | hyponatraemia | 7 | 21, 8, 19, 7, 20, 16, 6 |
| T | influenza | 7 | 21, 8, 19, 7, 20, 16, 6 |
| T | laceration | 7 | 21, 8, 19, 7, 20, 16, 6 |
| T | muscle spasms | 7 | 21, 8, 19, 7, 20, 16, 6 |
| T | muscular weakness | 7 | 21, 8, 19, 7, 20, 16, 6 |
| T | musculoskeletal pain | 7 | 21, 8, 19, 7, 20, 16, 6 |
| T | myalgia | 7 | 21, 8, 19, 7, 20, 16, 6 |
| T | myocardial infarction | 7 | 21, 8, 19, 7, 20, 16, 6 |
| T | myocardial ischaemia | 7 | 21, 8, 19, 7, 20, 16, 6 |
| T | neck pain | 7 | 21, 8, 19, 7, 20, 16, 6 |
| T | oropharyngeal pain | 7 | 21, 8, 19, 7, 20, 16, 6 |
| T | orthostatic hypotension | 7 | 21, 8, 19, 7, 20, 16, 6 |
| T | overdose | 7 | 21, 8, 19, 7, 20, 16, 6 |
| T | pain in extremity | 7 | 21, 8, 19, 7, 20, 16, 6 |
| T | paraesthesia | 7 | 21, 8, 19, 7, 20, 16, 6 |
| T | pharyngitis | 7 | 21, 8, 19, 7, 20, 16, 6 |
| T | pneumonia | 7 | 21, 8, 19, 7, 20, 16, 6 |
| T | pneumothorax | 7 | 21, 8, 19, 7, 20, 16, 6 |
| T | presyncope | 7 | 21, 8, 19, 7, 20, 16, 6 |
| T | pruritus | 7 | 21, 8, 19, 7, 20, 16, 6 |
| T | respiratory failure | 7 | 21, 8, 19, 7, 20, 16, 6 |
| T | respiratory tract infection | 7 | 21, 8, 19, 7, 20, 16, 6 |
| T | rhinitis | 7 | 21, 8, 19, 7, 20, 16, 6 |
| T | sepsis | 7 | 21, 8, 19, 7, 20, 16, 6 |
| T | sinusitis | 7 | 21, 8, 19, 7, 20, 16, 6 |
| T | syncope | 7 | 21, 8, 19, 7, 20, 16, 6 |
| T | tachycardia | 7 | 21, 8, 19, 7, 20, 16, 6 |
| T | upper respiratory tract infection | 7 | 21, 8, 19, 7, 20, 16, 6 |
| T | vertigo | 7 | 21, 8, 19, 7, 20, 16, 6 |
| T | viral infection | 7 | 21, 8, 19, 7, 20, 16, 6 |
| T | acne | 7 | 7, 9, 3, 18, 22, 19, 11 |
| T | axillary pain | 7 | 7, 9, 3, 18, 22, 19, 11 |
| T | blood magnesium increased | 7 | 7, 9, 3, 18, 22, 19, 11 |
| T | blood potassium decreased | 7 | 7, 9, 3, 18, 22, 19, 11 |
| T | depressed mood | 7 | 7, 9, 3, 18, 22, 19, 11 |
| T | facial pain | 7 | 7, 9, 3, 18, 22, 19, 11 |
| T | fever | 7 | 7, 9, 3, 18, 22, 19, 11 |
| T | flushing | 7 | 7, 9, 3, 18, 22, 19, 11 |
| T | gingival pain | 7 | 7, 9, 3, 18, 22, 19, 11 |
| T | hiccups | 7 | 7, 9, 3, 18, 22, 19, 11 |
| T | hypernatremia | 7 | 7, 9, 3, 18, 22, 19, 11 |
| T | lip dry | 7 | 7, 9, 3, 18, 22, 19, 11 |
| T | multiple allergies | 7 | 7, 9, 3, 18, 22, 19, 11 |
| T | paresthesia | 7 | 7, 9, 3, 18, 22, 19, 11 |
| T | pharyngolaryngeal pain | 7 | 7, 9, 3, 18, 22, 19, 11 |
| T | protein urine present | 7 | 7, 9, 3, 18, 22, 19, 11 |
| T | proteinuria | 7 | 7, 9, 3, 18, 22, 19, 11 |
| T | retching | 7 | 7, 9, 3, 18, 22, 19, 11 |
| T | salivary hypersecretion | 7 | 7, 9, 3, 18, 22, 19, 11 |
| T | vaginal infection | 7 | 7, 9, 3, 18, 22, 19, 11 |
| T | abdominal hernia | 7 | 10, 9, 8, 21, 14, 23, 12 |
| T | angina pectoris | 7 | 10, 9, 8, 21, 14, 23, 12 |
| T | ankle fracture | 7 | 10, 9, 8, 21, 14, 23, 12 |
| T | appendicitis perforated | 7 | 10, 9, 8, 21, 14, 23, 12 |
| T | bile duct stone | 7 | 10, 9, 8, 21, 14, 23, 12 |
| T | breast cancer | 7 | 10, 9, 8, 21, 14, 23, 12 |
| T | bronchitis chronic | 7 | 10, 9, 8, 21, 14, 23, 12 |
| T | cardiac failure | 7 | 10, 9, 8, 21, 14, 23, 12 |
| T | cardiac failure congestive | 7 | 10, 9, 8, 21, 14, 23, 12 |
| T | cardiac murmur | 7 | 10, 9, 8, 21, 14, 23, 12 |
| T | cardio-respiratory arrest | 7 | 10, 9, 8, 21, 14, 23, 12 |
| T | carpal tunnel syndrome | 7 | 10, 9, 8, 21, 14, 23, 12 |
| T | cholecystitis | 7 | 10, 9, 8, 21, 14, 23, 12 |
| T | cholelithiasis | 7 | 10, 9, 8, 21, 14, 23, 12 |
| T | colon cancer | 7 | 10, 9, 8, 21, 14, 23, 12 |
| T | concussion | 7 | 10, 9, 8, 21, 14, 23, 12 |
| T | costochondritis | 7 | 10, 9, 8, 21, 14, 23, 12 |

[Fig. 20-52]

| T | craniocerebral injury | 7 | 10, 9, 8, 21, 14, 23, 12 |
|---|---|---|---|
| T | ear infection | 7 | 10, 9, 8, 21, 14, 23, 12 |
| T | eczema | 7 | 10, 9, 8, 21, 14, 23, 12 |
| T | gastric ulcer haemorrhage | 7 | 10, 9, 8, 21, 14, 23, 12 |
| T | gastroenteritis viral | 7 | 10, 9, 8, 21, 14, 23, 12 |
| T | glaucoma | 7 | 10, 9, 8, 21, 14, 23, 12 |
| T | hand fracture | 7 | 10, 9, 8, 21, 14, 23, 12 |
| T | head injury | 7 | 10, 9, 8, 21, 14, 23, 12 |
| T | hernia | 7 | 10, 9, 8, 21, 14, 23, 12 |
| T | hypovolaemia | 7 | 10, 9, 8, 21, 14, 23, 12 |
| T | inguinal hernia | 7 | 10, 9, 8, 21, 14, 23, 12 |
| T | injury | 7 | 10, 9, 8, 21, 14, 23, 12 |
| T | ligament rupture | 7 | 10, 9, 8, 21, 14, 23, 12 |
| T | ligament sprain | 7 | 10, 9, 8, 21, 14, 23, 12 |
| T | localised infection | 7 | 10, 9, 8, 21, 14, 23, 12 |
| T | loss of consciousness | 7 | 10, 9, 8, 21, 14, 23, 12 |
| T | lower respiratory tract infection | 7 | 10, 9, 8, 21, 14, 23, 12 |
| T | malignant melanoma | 7 | 10, 9, 8, 21, 14, 23, 12 |
| T | metastases to liver | 7 | 10, 9, 8, 21, 14, 23, 12 |
| T | migraine | 7 | 10, 9, 8, 21, 14, 23, 12 |
| T | osteoarthritis | 7 | 10, 9, 8, 21, 14, 23, 12 |
| T | ovarian cyst | 7 | 10, 9, 8, 21, 14, 23, 12 |
| T | pancreatic carcinoma | 7 | 10, 9, 8, 21, 14, 23, 12 |
| T | pancreatitis acute | 7 | 10, 9, 8, 21, 14, 23, 12 |
| T | radius fracture | 7 | 10, 9, 8, 21, 14, 23, 12 |
| T | renal cell carcinoma | 7 | 10, 9, 8, 21, 14, 23, 12 |
| T | rhabdomyolysis | 7 | 10, 9, 8, 21, 14, 23, 12 |
| T | rib fracture | 7 | 10, 9, 8, 21, 14, 23, 12 |
| T | sudden death | 7 | 10, 9, 8, 21, 14, 23, 12 |
| T | suicidal ideation | 7 | 10, 9, 8, 21, 14, 23, 12 |
| T | type diabetes mellitus | 7 | 10, 9, 8, 21, 14, 23, 12 |
| T | umbilical hernia | 7 | 10, 9, 8, 21, 14, 23, 12 |
| T | wrist fracture | 7 | 10, 9, 8, 21, 14, 23, 12 |
| T | blood lactate dehydrogenase increased | 7 | 14, 9, 13, 15, 23, 5, 1 |
| T | cold sweat | 7 | 14, 9, 13, 15, 23, 5, 1 |
| T | lipase increased | 7 | 14, 9, 13, 15, 23, 5, 1 |
| T | trigeminal neuralgia | 7 | 14, 9, 13, 15, 23, 5, 1 |
| T | abnormal white blood count | 7 | 5, 6, 22, 21, 8, 23, 2 |
| T | akathesia | 7 | 5, 6, 22, 21, 8, 23, 2 |
| T | difficulty concentrating | 7 | 5, 6, 22, 21, 8, 23, 2 |
| T | gastointestinal disorders - other, specify: hypersalivation | 7 | 5, 6, 22, 21, 8, 23, 2 |
| T | migraine headache | 7 | 5, 6, 22, 21, 8, 23, 2 |
| T | salivation | 7 | 5, 6, 22, 21, 8, 23, 2 |
| T | stiffness | 7 | 5, 6, 22, 21, 8, 23, 2 |
| T | anorgasmia | 8 | 22, 21, 5, 16, 23, 10, 3, 2 |
| T | appetite increased | 8 | 22, 21, 5, 16, 23, 10, 3, 2 |
| T | blurry vision | 8 | 22, 21, 5, 16, 23, 10, 3, 2 |
| T | body aches | 8 | 22, 21, 5, 16, 23, 10, 3, 2 |
| T | body pain | 8 | 22, 21, 5, 16, 23, 10, 3, 2 |
| T | cold extremity | 8 | 22, 21, 5, 16, 23, 10, 3, 2 |
| T | coughing | 8 | 22, 21, 5, 16, 23, 10, 3, 2 |
| T | cramps | 8 | 22, 21, 5, 16, 23, 10, 3, 2 |
| T | decreased interest in sex | 8 | 22, 21, 5, 16, 23, 10, 3, 2 |
| T | decreased motor activity | 8 | 22, 21, 5, 16, 23, 10, 3, 2 |
| T | dizziness on standing | 8 | 22, 21, 5, 16, 23, 10, 3, 2 |
| T | emesis | 8 | 22, 21, 5, 16, 23, 10, 3, 2 |
| T | gastrointestinal distress | 8 | 22, 21, 5, 16, 23, 10, 3, 2 |
| T | impaired sexual performance | 8 | 22, 21, 5, 16, 23, 10, 3, 2 |
| T | increased alanine transaminase (alt) | 8 | 22, 21, 5, 16, 23, 10, 3, 2 |
| T | increased anxiety | 8 | 22, 21, 5, 16, 23, 10, 3, 2 |
| T | increased aspartate transaminase (ast) | 8 | 22, 21, 5, 16, 23, 10, 3, 2 |
| T | increased fatigue | 8 | 22, 21, 5, 16, 23, 10, 3, 2 |
| T | increased sleep | 8 | 22, 21, 5, 16, 23, 10, 3, 2 |
| T | join pain/stiffness | 8 | 22, 21, 5, 16, 23, 10, 3, 2 |
| T | joint pain/stiffness | 8 | 22, 21, 5, 16, 23, 10, 3, 2 |
| T | low energy | 8 | 22, 21, 5, 16, 23, 10, 3, 2 |
| T | menstrual irregularity | 8 | 22, 21, 5, 16, 23, 10, 3, 2 |

[Fig. 20-53]

| | | | |
|---|---|---|---|
| T | poor concentration | 8 | 22, 21, 5, 16, 23, 10, 3, 2 |
| T | stomach ache | 8 | 22, 21, 5, 16, 23, 10, 3, 2 |
| T | trouble achieving orgasm | 8 | 22, 21, 5, 16, 23, 10, 3, 2 |
| T | trouble concentrating | 8 | 22, 21, 5, 16, 23, 10, 3, 2 |
| T | trouble sleeping | 8 | 22, 21, 5, 16, 23, 10, 3, 2 |
| T | upper respiratory infection (uri) | 8 | 22, 21, 5, 16, 23, 10, 3, 2 |
| T | weight decreased | 9 | 13, 7, 3, 16, 4, 9, 15, 14, 19 |
| T | stomatitis | 9 | 2, 9, 10, 7, 13, 1, 4, 19, 24 |
| T | abcess | 9 | 6, 11, 16, 22, 7, 19, 1, 17, 2 |
| T | activated partial thromboplastin time prolonged | 9 | 6, 11, 16, 22, 7, 19, 1, 17, 2 |
| T | acute renal failure | 9 | 6, 11, 16, 22, 7, 19, 1, 17, 2 |
| T | ageusia | 9 | 6, 11, 16, 22, 7, 19, 1, 17, 2 |
| T | airway edema | 9 | 6, 11, 16, 22, 7, 19, 1, 17, 2 |
| T | alanine aminotransferase (alt) | 9 | 6, 11, 16, 22, 7, 19, 1, 17, 2 |
| T | albumin, low (hypoalbuminemia) | 9 | 6, 11, 16, 22, 7, 19, 1, 17, 2 |
| T | albumin, serum-low (hypoalbuminemia) | 9 | 6, 11, 16, 22, 7, 19, 1, 17, 2 |
| T | alkaline phosphatase increased | 9 | 6, 11, 16, 22, 7, 19, 1, 17, 2 |
| T | alt, sgpt (serum glutamic pyruvic transaminase) | 9 | 6, 11, 16, 22, 7, 19, 1, 17, 2 |
| T | anorexia (loss of appetite) | 9 | 6, 11, 16, 22, 7, 19, 1, 17, 2 |
| T | anoxeria | 9 | 6, 11, 16, 22, 7, 19, 1, 17, 2 |
| T | ascites (accumulation of fluid in the abdomen) | 9 | 6, 11, 16, 22, 7, 19, 1, 17, 2 |
| T | aspartate aminotransferase increase | 9 | 6, 11, 16, 22, 7, 19, 1, 17, 2 |
| T | ast, sgot(serum glutamic oxaloacetic transaminase) | 9 | 6, 11, 16, 22, 7, 19, 1, 17, 2 |
| T | bilirubin (hyperbilirubinemia) | 9 | 6, 11, 16, 22, 7, 19, 1, 17, 2 |
| T | blood albumin decreased | 9 | 6, 11, 16, 22, 7, 19, 1, 17, 2 |
| T | blood fibrinogen increased | 9 | 6, 11, 16, 22, 7, 19, 1, 17, 2 |
| T | blood magnesium decreased | 9 | 6, 11, 16, 22, 7, 19, 1, 17, 2 |
| T | blood phosphorus decreased | 9 | 6, 11, 16, 22, 7, 19, 1, 17, 2 |
| T | blood sodium decreased | 9 | 6, 11, 16, 22, 7, 19, 1, 17, 2 |
| T | blood/bone marrow-other (specify,___) | 9 | 6, 11, 16, 22, 7, 19, 1, 17, 2 |
| T | breath sounds abnormal | 9 | 6, 11, 16, 22, 7, 19, 1, 17, 2 |
| T | calcium, serum-high (hypercalcemia) | 9 | 6, 11, 16, 22, 7, 19, 1, 17, 2 |
| T | calcium, serum-low (hypocalcemia) | 9 | 6, 11, 16, 22, 7, 19, 1, 17, 2 |
| T | catatonia | 9 | 6, 11, 16, 22, 7, 19, 1, 17, 2 |
| T | creatinine | 9 | 6, 11, 16, 22, 7, 19, 1, 17, 2 |
| T | creatinine increased | 9 | 6, 11, 16, 22, 7, 19, 1, 17, 2 |
| T | death nos | 9 | 6, 11, 16, 22, 7, 19, 1, 17, 2 |
| T | dermatitis - radiation | 9 | 6, 11, 16, 22, 7, 19, 1, 17, 2 |
| T | dermatitis acneiform | 9 | 6, 11, 16, 22, 7, 19, 1, 17, 2 |
| T | dermatology/skin-other (specify,___) | 9 | 6, 11, 16, 22, 7, 19, 1, 17, 2 |
| T | dermatology/skin - other (specify) | 9 | 6, 11, 16, 22, 7, 19, 1, 17, 2 |
| T | dermatology/skin - other (specify,__) | 9 | 6, 11, 16, 22, 7, 19, 1, 17, 2 |
| T | desquamating rash | 9 | 6, 11, 16, 22, 7, 19, 1, 17, 2 |
| T | diarrhea patients without colostomy | 9 | 6, 11, 16, 22, 7, 19, 1, 17, 2 |
| T | diarrhea w/o prior colostomy | 9 | 6, 11, 16, 22, 7, 19, 1, 17, 2 |
| T | dyspepsia/heartburn | 9 | 6, 11, 16, 22, 7, 19, 1, 17, 2 |
| T | dyspnea | 9 | 6, 11, 16, 22, 7, 19, 1, 17, 2 |
| T | dyspnea (shortness of breath) | 9 | 6, 11, 16, 22, 7, 19, 1, 17, 2 |
| T | edema | 9 | 6, 11, 16, 22, 7, 19, 1, 17, 2 |
| T | edema limb | 9 | 6, 11, 16, 22, 7, 19, 1, 17, 2 |
| T | edema limbs | 9 | 6, 11, 16, 22, 7, 19, 1, 17, 2 |
| T | edema: limbs | 9 | 6, 11, 16, 22, 7, 19, 1, 17, 2 |
| T | electrocardiogram st segment elevation | 9 | 6, 11, 16, 22, 7, 19, 1, 17, 2 |
| T | elevated alt | 9 | 6, 11, 16, 22, 7, 19, 1, 17, 2 |
| T | elevated ast | 9 | 6, 11, 16, 22, 7, 19, 1, 17, 2 |
| T | exfoliative rash | 9 | 6, 11, 16, 22, 7, 19, 1, 17, 2 |
| T | eye discharge | 9 | 6, 11, 16, 22, 7, 19, 1, 17, 2 |
| T | eye disorders - other, specify: decreased visual acuity | 9 | 6, 11, 16, 22, 7, 19, 1, 17, 2 |
| T | febrile neutropenia (fever of unknown origin without clinically or microbiologically documented infe | 9 | 6, 11, 16, 22, 7, 19, 1, 17, 2 |
| T | fever w/o neutropenia | 9 | 6, 11, 16, 22, 7, 19, 1, 17, 2 |
| T | gastrointestinal-other (specify,___) | 9 | 6, 11, 16, 22, 7, 19, 1, 17, 2 |
| T | gastrointestinal - other (specify,__) | 9 | 6, 11, 16, 22, 7, 19, 1, 17, 2 |

[Fig. 20-54]

| | | | |
|---|---|---|---|
| T | gastrointestinal disorders - other, specify: feeling of stomach fullness | 9 | 6, 11, 16, 22, 7, 19, 1, 17, 2 |
| T | general disorders and admin site conditions | 9 | 6, 11, 16, 22, 7, 19, 1, 17, 2 |
| T | gerd | 9 | 6, 11, 16, 22, 7, 19, 1, 17, 2 |
| T | glucose, serum-low (hypoglycemia) | 9 | 6, 11, 16, 22, 7, 19, 1, 17, 2 |
| T | hair loss/alopecia (scalp or body) | 9 | 6, 11, 16, 22, 7, 19, 1, 17, 2 |
| T | heartburn/dyspepsia | 9 | 6, 11, 16, 22, 7, 19, 1, 17, 2 |
| T | hemolysis (red blood cell destruction) | 9 | 6, 11, 16, 22, 7, 19, 1, 17, 2 |
| T | hemorrhage | 9 | 6, 11, 16, 22, 7, 19, 1, 17, 2 |
| T | hyperbilirubinemia (high level of bilirubin) | 9 | 6, 11, 16, 22, 7, 19, 1, 17, 2 |
| T | hyperglycemia | 9 | 6, 11, 16, 22, 7, 19, 1, 17, 2 |
| T | hypoalbuminemia | 9 | 6, 11, 16, 22, 7, 19, 1, 17, 2 |
| T | hypoalbuminemia (low level of albumin in blood) | 9 | 6, 11, 16, 22, 7, 19, 1, 17, 2 |
| T | hypokalemia | 9 | 6, 11, 16, 22, 7, 19, 1, 17, 2 |
| T | hypomagnesemia | 9 | 6, 11, 16, 22, 7, 19, 1, 17, 2 |
| T | hyponatremia | 9 | 6, 11, 16, 22, 7, 19, 1, 17, 2 |
| T | hyponatremia (low sodium level in blood) | 9 | 6, 11, 16, 22, 7, 19, 1, 17, 2 |
| T | hypophosphatemia | 9 | 6, 11, 16, 22, 7, 19, 1, 17, 2 |
| T | increased creatinine | 9 | 6, 11, 16, 22, 7, 19, 1, 17, 2 |
| T | increased upper airway secretion | 9 | 6, 11, 16, 22, 7, 19, 1, 17, 2 |
| T | infection - other (specify,__) | 9 | 6, 11, 16, 22, 7, 19, 1, 17, 2 |
| T | infection with normal anc or grade or neutrophils | 9 | 6, 11, 16, 22, 7, 19, 1, 17, 2 |
| T | infusion reaction (cetuximab) | 9 | 6, 11, 16, 22, 7, 19, 1, 17, 2 |
| T | leukocytes (total wbc) | 9 | 6, 11, 16, 22, 7, 19, 1, 17, 2 |
| T | lymphatics - other (specify,__) | 9 | 6, 11, 16, 22, 7, 19, 1, 17, 2 |
| T | lymphopenia | 9 | 6, 11, 16, 22, 7, 19, 1, 17, 2 |
| T | magnesium, low (hypomagnesemia) | 9 | 6, 11, 16, 22, 7, 19, 1, 17, 2 |
| T | magnesium, serum-high (hypermagnesemia) | 9 | 6, 11, 16, 22, 7, 19, 1, 17, 2 |
| T | magnesium, serum-low (hypomagnesemia) | 9 | 6, 11, 16, 22, 7, 19, 1, 17, 2 |
| T | metabolic/laboratory - other (specify,__) | 9 | 6, 11, 16, 22, 7, 19, 1, 17, 2 |
| T | monocyte count increased | 9 | 6, 11, 16, 22, 7, 19, 1, 17, 2 |
| T | mood alteration | 9 | 6, 11, 16, 22, 7, 19, 1, 17, 2 |
| T | mood alteration-anxiety, agitation | 9 | 6, 11, 16, 22, 7, 19, 1, 17, 2 |
| T | mood alteration-depression | 9 | 6, 11, 16, 22, 7, 19, 1, 17, 2 |
| T | muco/stomatitis by exam, oral cavity | 9 | 6, 11, 16, 22, 7, 19, 1, 17, 2 |
| T | mucosal edema (laryngeal and hypopharyngeal) | 9 | 6, 11, 16, 22, 7, 19, 1, 17, 2 |
| T | mucositis-oral | 9 | 6, 11, 16, 22, 7, 19, 1, 17, 2 |
| T | mucositis oral | 9 | 6, 11, 16, 22, 7, 19, 1, 17, 2 |
| T | mucositis/stomatitis (clinical exam) | 9 | 6, 11, 16, 22, 7, 19, 1, 17, 2 |
| T | mucositis/stomatitis (clinical exam), oral cavity | 9 | 6, 11, 16, 22, 7, 19, 1, 17, 2 |
| T | mucositis/stomatitis (functional/symptomatic), oral cavity | 9 | 6, 11, 16, 22, 7, 19, 1, 17, 2 |
| T | muscle, pain | 9 | 6, 11, 16, 22, 7, 19, 1, 17, 2 |
| T | musculoskeletal/soft tissue - other | 9 | 6, 11, 16, 22, 7, 19, 1, 17, 2 |
| T | nervous system disorders | 9 | 6, 11, 16, 22, 7, 19, 1, 17, 2 |
| T | neuropathy | 9 | 6, 11, 16, 22, 7, 19, 1, 17, 2 |
| T | neuropathy-sensory | 9 | 6, 11, 16, 22, 7, 19, 1, 17, 2 |
| T | neuropathy: sensory | 9 | 6, 11, 16, 22, 7, 19, 1, 17, 2 |
| T | neutropenia/neutrophil count | 9 | 6, 11, 16, 22, 7, 19, 1, 17, 2 |
| T | neutrophil count increased | 9 | 6, 11, 16, 22, 7, 19, 1, 17, 2 |
| T | neutrophils | 9 | 6, 11, 16, 22, 7, 19, 1, 17, 2 |
| T | oropharyngeal candidiasis | 9 | 6, 11, 16, 22, 7, 19, 1, 17, 2 |
| T | other-skin | 9 | 6, 11, 16, 22, 7, 19, 1, 17, 2 |
| T | pain-other (specify,__) | 9 | 6, 11, 16, 22, 7, 19, 1, 17, 2 |
| T | pain - abdomen nos | 9 | 6, 11, 16, 22, 7, 19, 1, 17, 2 |
| T | pain - joint | 9 | 6, 11, 16, 22, 7, 19, 1, 17, 2 |
| T | pain (abdominal/pelvic) | 9 | 6, 11, 16, 22, 7, 19, 1, 17, 2 |
| T | pain (back) | 9 | 6, 11, 16, 22, 7, 19, 1, 17, 2 |
| T | pain (joint) | 9 | 6, 11, 16, 22, 7, 19, 1, 17, 2 |
| T | pain: abdominal pain nos | 9 | 6, 11, 16, 22, 7, 19, 1, 17, 2 |
| T | pain: extremity-limb | 9 | 6, 11, 16, 22, 7, 19, 1, 17, 2 |
| T | pain: head/headache | 9 | 6, 11, 16, 22, 7, 19, 1, 17, 2 |
| T | pallor | 9 | 6, 11, 16, 22, 7, 19, 1, 17, 2 |
| T | palmar-plantar erythrodysaesthesia syndrome | 9 | 6, 11, 16, 22, 7, 19, 1, 17, 2 |
| T | palmar-plantar erythrodysaesthesia syndrome | 9 | 6, 11, 16, 22, 7, 19, 1, 17, 2 |
| T | paranasal sinus hypersecretion | 9 | 6, 11, 16, 22, 7, 19, 1, 17, 2 |
| T | peripheral sensory neuropathy | 9 | 6, 11, 16, 22, 7, 19, 1, 17, 2 |

[Fig. 20-55]

| | | | |
|---|---|---|---|
| T | phosphate, serum-low (hypophosphatemia) | 9 | 6, 11, 16, 22, 7, 19, 1, 17, 2 |
| T | pigmentation disorder | 9 | 6, 11, 16, 22, 7, 19, 1, 17, 2 |
| T | platelets | 9 | 6, 11, 16, 22, 7, 19, 1, 17, 2 |
| T | platelets decreased | 9 | 6, 11, 16, 22, 7, 19, 1, 17, 2 |
| T | potassium, high (hyperkalemia) | 9 | 6, 11, 16, 22, 7, 19, 1, 17, 2 |
| T | potassium, serum-high (hyperkalemia) | 9 | 6, 11, 16, 22, 7, 19, 1, 17, 2 |
| T | protein total decreased | 9 | 6, 11, 16, 22, 7, 19, 1, 17, 2 |
| T | pruritus/itching | 9 | 6, 11, 16, 22, 7, 19, 1, 17, 2 |
| T | pulmonary | 9 | 6, 11, 16, 22, 7, 19, 1, 17, 2 |
| T | pulmonary-other (specify,___) | 9 | 6, 11, 16, 22, 7, 19, 1, 17, 2 |
| T | radiation skin injury | 9 | 6, 11, 16, 22, 7, 19, 1, 17, 2 |
| T | rash-hand foot skin reaction | 9 | 6, 11, 16, 22, 7, 19, 1, 17, 2 |
| T | rash maculopapular | 9 | 6, 11, 16, 22, 7, 19, 1, 17, 2 |
| T | rash/desquamation | 9 | 6, 11, 16, 22, 7, 19, 1, 17, 2 |
| T | rash: acne/acneiform | 9 | 6, 11, 16, 22, 7, 19, 1, 17, 2 |
| T | rash: dermatitis associated with radiation, chemoradiation | 9 | 6, 11, 16, 22, 7, 19, 1, 17, 2 |
| T | rash: dermatitis associated with radiation, radiation | 9 | 6, 11, 16, 22, 7, 19, 1, 17, 2 |
| T | rhinitis (runny nose) | 9 | 6, 11, 16, 22, 7, 19, 1, 17, 2 |
| T | rigors | 9 | 6, 11, 16, 22, 7, 19, 1, 17, 2 |
| T | salivary gland changes/saliva | 9 | 6, 11, 16, 22, 7, 19, 1, 17, 2 |
| T | serum amylase increased | 9 | 6, 11, 16, 22, 7, 19, 1, 17, 2 |
| T | shortness of breath | 9 | 6, 11, 16, 22, 7, 19, 1, 17, 2 |
| T | skin fissures | 9 | 6, 11, 16, 22, 7, 19, 1, 17, 2 |
| T | skin hyperpigmentation | 9 | 6, 11, 16, 22, 7, 19, 1, 17, 2 |
| T | sodium, serum-low (hyponatremia) | 9 | 6, 11, 16, 22, 7, 19, 1, 17, 2 |
| T | stomatitis/pharyngitis (oral/pharyngeal mucositis) | 9 | 6, 11, 16, 22, 7, 19, 1, 17, 2 |
| T | streptococcal bacteraemia | 9 | 6, 11, 16, 22, 7, 19, 1, 17, 2 |
| T | tachypnoea | 9 | 6, 11, 16, 22, 7, 19, 1, 17, 2 |
| T | taste alteration | 9 | 6, 11, 16, 22, 7, 19, 1, 17, 2 |
| T | taste alteration (dysgeusia) | 9 | 6, 11, 16, 22, 7, 19, 1, 17, 2 |
| T | taste disturbance | 9 | 6, 11, 16, 22, 7, 19, 1, 17, 2 |
| T | thromboembolic event | 9 | 6, 11, 16, 22, 7, 19, 1, 17, 2 |
| T | thrombotic events | 9 | 6, 11, 16, 22, 7, 19, 1, 17, 2 |
| T | thyroid function, low (hypothyroidism) | 9 | 6, 11, 16, 22, 7, 19, 1, 17, 2 |
| T | vision disturbance | 9 | 6, 11, 16, 22, 7, 19, 1, 17, 2 |
| T | voice changes/dysarthria (e.g., hoarseness, loss or alteration in voice, laryngitis) | 9 | 6, 11, 16, 22, 7, 19, 1, 17, 2 |
| T | weakness | 9 | 6, 11, 16, 22, 7, 19, 1, 17, 2 |
| T | genitourinary tract infection | 9 | 22, 5, 19, 17, 20, 12, 24, 15, 9 |
| T | fatigue | 10 | 19, 5, 4, 21, 10, 6, 3, 11, 18, 14 |
| T | weight decreased | 10 | 2, 4, 15, 9, 1, 10, 7, 8, 19, 16 |
| T | restlessness | 10 | 21, 11, 14, 18, 1, 19, 5, 6, 13, 8 |
| T | suicide attempt | 10 | 18, 7, 21, 3, 15, 22, 14, 16, 1, 9 |
| T | akathisia | 10 | 24, 16, 18, 10, 7, 14, 22, 23, 19, 11 |
| T | apathy | 10 | 24, 16, 18, 10, 7, 14, 22, 23, 19, 11 |
| T | decreased libido | 10 | 24, 16, 18, 10, 7, 14, 22, 23, 19, 11 |
| T | nervousness | 10 | 24, 16, 18, 10, 7, 14, 22, 23, 19, 11 |
| T | seborrhoeic dermatitis | 10 | 24, 16, 18, 10, 7, 14, 22, 23, 19, 11 |
| T | skin rash | 10 | 24, 16, 18, 10, 7, 14, 22, 23, 19, 11 |
| T | slurred speech | 10 | 24, 16, 18, 10, 7, 14, 22, 23, 19, 11 |
| T | abdomen, pain | 10 | 6, 19, 17, 14, 9, 7, 3, 5, 20, 13 |
| T | abdomial pain | 10 | 6, 19, 17, 14, 9, 7, 3, 5, 20, 13 |
| T | abdominal distention | 10 | 6, 19, 17, 14, 9, 7, 3, 5, 20, 13 |
| T | abdominal pain and dehydration | 10 | 6, 19, 17, 14, 9, 7, 3, 5, 20, 13 |
| T | abscess neck | 10 | 6, 19, 17, 14, 9, 7, 3, 5, 20, 13 |
| T | abscess oral | 10 | 6, 19, 17, 14, 9, 7, 3, 5, 20, 13 |
| T | acidosis | 10 | 6, 19, 17, 14, 9, 7, 3, 5, 20, 13 |
| T | acoustic nerve disorder nos | 10 | 6, 19, 17, 14, 9, 7, 3, 5, 20, 13 |
| T | acute interstitial pneumonitis | 10 | 6, 19, 17, 14, 9, 7, 3, 5, 20, 13 |
| T | acute vascular leak, gi other, hypotension, anorexia, hypothermia,inr | 10 | 6, 19, 17, 14, 9, 7, 3, 5, 20, 13 |
| T | adenoviral conjunctivitis | 10 | 6, 19, 17, 14, 9, 7, 3, 5, 20, 13 |
| T | alanine aminotransferase decreased | 10 | 6, 19, 17, 14, 9, 7, 3, 5, 20, 13 |

[Fig. 20-56]

| | | | |
|---|---|---|---|
| T | alanine aminotransferase increase | 10 | 6, 19, 17, 14, 9, 7, 3, 5, 20, 13 |
| T | alanine amiotransferase (alt) | 10 | 6, 19, 17, 14, 9, 7, 3, 5, 20, 13 |
| T | alkaline phosphatase | 10 | 6, 19, 17, 14, 9, 7, 3, 5, 20, 13 |
| T | alkalosis | 10 | 6, 19, 17, 14, 9, 7, 3, 5, 20, 13 |
| T | allergic reaction | 10 | 6, 19, 17, 14, 9, 7, 3, 5, 20, 13 |
| T | allergic reaction/hypersensitivity | 10 | 6, 19, 17, 14, 9, 7, 3, 5, 20, 13 |
| T | allergic reaction/hypersensitivity (including drug fever) | 10 | 6, 19, 17, 14, 9, 7, 3, 5, 20, 13 |
| T | allergic rhinitis (including sneezing, nasal stuffiness, postnasal drip) | 10 | 6, 19, 17, 14, 9, 7, 3, 5, 20, 13 |
| T | allergy | 10 | 6, 19, 17, 14, 9, 7, 3, 5, 20, 13 |
| T | allergy/immunology - other | 10 | 6, 19, 17, 14, 9, 7, 3, 5, 20, 13 |
| T | alopecia (hair loss) | 10 | 6, 19, 17, 14, 9, 7, 3, 5, 20, 13 |
| T | alt | 10 | 6, 19, 17, 14, 9, 7, 3, 5, 20, 13 |
| T | alt increased | 10 | 6, 19, 17, 14, 9, 7, 3, 5, 20, 13 |
| T | alt, sgpt | 10 | 6, 19, 17, 14, 9, 7, 3, 5, 20, 13 |
| T | amylase | 10 | 6, 19, 17, 14, 9, 7, 3, 5, 20, 13 |
| T | anal pain | 10 | 6, 19, 17, 14, 9, 7, 3, 5, 20, 13 |
| T | anal ulcer | 10 | 6, 19, 17, 14, 9, 7, 3, 5, 20, 13 |
| T | anisocytosis | 10 | 6, 19, 17, 14, 9, 7, 3, 5, 20, 13 |
| T | aortic thrombus | 10 | 6, 19, 17, 14, 9, 7, 3, 5, 20, 13 |
| T | aphonia | 10 | 6, 19, 17, 14, 9, 7, 3, 5, 20, 13 |
| T | ards | 10 | 6, 19, 17, 14, 9, 7, 3, 5, 20, 13 |
| T | arterial thrombosis limb | 10 | 6, 19, 17, 14, 9, 7, 3, 5, 20, 13 |
| T | artery injury - aorta | 10 | 6, 19, 17, 14, 9, 7, 3, 5, 20, 13 |
| T | aspartate aminotransferase (ast) | 10 | 6, 19, 17, 14, 9, 7, 3, 5, 20, 13 |
| T | ast | 10 | 6, 19, 17, 14, 9, 7, 3, 5, 20, 13 |
| T | ast increased | 10 | 6, 19, 17, 14, 9, 7, 3, 5, 20, 13 |
| T | ast, sgot | 10 | 6, 19, 17, 14, 9, 7, 3, 5, 20, 13 |
| T | asthenopia | 10 | 6, 19, 17, 14, 9, 7, 3, 5, 20, 13 |
| T | ataxia (incoordination) | 10 | 6, 19, 17, 14, 9, 7, 3, 5, 20, 13 |
| T | auditory/ear - other | 10 | 6, 19, 17, 14, 9, 7, 3, 5, 20, 13 |
| T | auditory/ear - other (specify, __) | 10 | 6, 19, 17, 14, 9, 7, 3, 5, 20, 13 |
| T | back, pain | 10 | 6, 19, 17, 14, 9, 7, 3, 5, 20, 13 |
| T | bacteremia | 10 | 6, 19, 17, 14, 9, 7, 3, 5, 20, 13 |
| T | belching | 10 | 6, 19, 17, 14, 9, 7, 3, 5, 20, 13 |
| T | benign neoplasm | 10 | 6, 19, 17, 14, 9, 7, 3, 5, 20, 13 |
| T | bicarbonate, serum-low | 10 | 6, 19, 17, 14, 9, 7, 3, 5, 20, 13 |
| T | bilirubin | 10 | 6, 19, 17, 14, 9, 7, 3, 5, 20, 13 |
| T | bilirubin increased | 10 | 6, 19, 17, 14, 9, 7, 3, 5, 20, 13 |
| T | bleeding varicose vein | 10 | 6, 19, 17, 14, 9, 7, 3, 5, 20, 13 |
| T | bloating | 10 | 6, 19, 17, 14, 9, 7, 3, 5, 20, 13 |
| T | blood amylase increased | 10 | 6, 19, 17, 14, 9, 7, 3, 5, 20, 13 |
| T | blood and lymphatic system disorders - other, specify | 10 | 6, 19, 17, 14, 9, 7, 3, 5, 20, 13 |
| T | blood bicarbonate | 10 | 6, 19, 17, 14, 9, 7, 3, 5, 20, 13 |
| T | blood bicarbonate decreased | 10 | 6, 19, 17, 14, 9, 7, 3, 5, 20, 13 |
| T | blood calcium decreased | 10 | 6, 19, 17, 14, 9, 7, 3, 5, 20, 13 |
| T | blood calcium increased | 10 | 6, 19, 17, 14, 9, 7, 3, 5, 20, 13 |
| T | blood chloride decreased | 10 | 6, 19, 17, 14, 9, 7, 3, 5, 20, 13 |
| T | blood disorder | 10 | 6, 19, 17, 14, 9, 7, 3, 5, 20, 13 |
| T | blood sodium increased | 10 | 6, 19, 17, 14, 9, 7, 3, 5, 20, 13 |
| T | blood urine present | 10 | 6, 19, 17, 14, 9, 7, 3, 5, 20, 13 |
| T | blood/bone marrow - other | 10 | 6, 19, 17, 14, 9, 7, 3, 5, 20, 13 |
| T | bone marrow failure | 10 | 6, 19, 17, 14, 9, 7, 3, 5, 20, 13 |
| T | bronchial infection | 10 | 6, 19, 17, 14, 9, 7, 3, 5, 20, 13 |
| T | bronchopulmonary hemorrhage | 10 | 6, 19, 17, 14, 9, 7, 3, 5, 20, 13 |
| T | bruising | 10 | 6, 19, 17, 14, 9, 7, 3, 5, 20, 13 |
| T | burn | 10 | 6, 19, 17, 14, 9, 7, 3, 5, 20, 13 |
| T | cardiac arrest | 10 | 6, 19, 17, 14, 9, 7, 3, 5, 20, 13 |
| T | cancer pain | 10 | 6, 19, 17, 14, 9, 7, 3, 5, 20, 13 |
| T | candida infection | 10 | 6, 19, 17, 14, 9, 7, 3, 5, 20, 13 |
| T | candidiasis | 10 | 6, 19, 17, 14, 9, 7, 3, 5, 20, 13 |
| T | carbohydrate antigen increased | 10 | 6, 19, 17, 14, 9, 7, 3, 5, 20, 13 |
| T | carcinoembryonic antigen increased | 10 | 6, 19, 17, 14, 9, 7, 3, 5, 20, 13 |
| T | cardiac | 10 | 6, 19, 17, 14, 9, 7, 3, 5, 20, 13 |
| T | cardiac disorders - other, specify: tachycardia | 10 | 6, 19, 17, 14, 9, 7, 3, 5, 20, 13 |

[Fig. 20-57]

| T | cardiac general - other | 10 | 6, 19, 17, 14, 9, 7, 3, 5, 20, 13 |
|---|---|---|---|
| T | cardiac ischemia/infarction | 10 | 6, 19, 17, 14, 9, 7, 3, 5, 20, 13 |
| T | cardiac troponin i increased | 10 | 6, 19, 17, 14, 9, 7, 3, 5, 20, 13 |
| T | cardiac troponin t (ctnt) | 10 | 6, 19, 17, 14, 9, 7, 3, 5, 20, 13 |
| T | catarrh | 10 | 6, 19, 17, 14, 9, 7, 3, 5, 20, 13 |
| T | catheter related infection | 10 | 6, 19, 17, 14, 9, 7, 3, 5, 20, 13 |
| T | catheter site abscess | 10 | 6, 19, 17, 14, 9, 7, 3, 5, 20, 13 |
| T | catheter site haemorrhage | 10 | 6, 19, 17, 14, 9, 7, 3, 5, 20, 13 |
| T | catheter site pain | 10 | 6, 19, 17, 14, 9, 7, 3, 5, 20, 13 |
| T | cellulitis orbital | 10 | 6, 19, 17, 14, 9, 7, 3, 5, 20, 13 |
| T | central line infection | 10 | 6, 19, 17, 14, 9, 7, 3, 5, 20, 13 |
| T | cheilitis | 10 | 6, 19, 17, 14, 9, 7, 3, 5, 20, 13 |
| T | chest pain-cardiac | 10 | 6, 19, 17, 14, 9, 7, 3, 5, 20, 13 |
| T | chest pain - cardiac | 10 | 6, 19, 17, 14, 9, 7, 3, 5, 20, 13 |
| T | chest wall pain | 10 | 6, 19, 17, 14, 9, 7, 3, 5, 20, 13 |
| T | cholesterol high | 10 | 6, 19, 17, 14, 9, 7, 3, 5, 20, 13 |
| T | chronic obstructive pulmonary exacerbation | 10 | 6, 19, 17, 14, 9, 7, 3, 5, 20, 13 |
| T | chylothorax | 10 | 6, 19, 17, 14, 9, 7, 3, 5, 20, 13 |
| T | cleatinine clearance decreased | 10 | 6, 19, 17, 14, 9, 7, 3, 5, 20, 13 |
| T | cns cerebrovascular ischemia | 10 | 6, 19, 17, 14, 9, 7, 3, 5, 20, 13 |
| T | cognitive disturbance | 10 | 6, 19, 17, 14, 9, 7, 3, 5, 20, 13 |
| T | colitis, infectious | 10 | 6, 19, 17, 14, 9, 7, 3, 5, 20, 13 |
| T | colitis, infectious (e.g., clostridium difficile) | 10 | 6, 19, 17, 14, 9, 7, 3, 5, 20, 13 |
| T | coma hepatic | 10 | 6, 19, 17, 14, 9, 7, 3, 5, 20, 13 |
| T | concentration impairment | 10 | 6, 19, 17, 14, 9, 7, 3, 5, 20, 13 |
| T | conduct disorder | 10 | 6, 19, 17, 14, 9, 7, 3, 5, 20, 13 |
| T | conduction | 10 | 6, 19, 17, 14, 9, 7, 3, 5, 20, 13 |
| T | confusion | 10 | 6, 19, 17, 14, 9, 7, 3, 5, 20, 13 |
| T | conjunctivitis infective | 10 | 6, 19, 17, 14, 9, 7, 3, 5, 20, 13 |
| T | constitutional symptoms - other | 10 | 6, 19, 17, 14, 9, 7, 3, 5, 20, 13 |
| T | cranial neuropathy/ hearing and balance | 10 | 6, 19, 17, 14, 9, 7, 3, 5, 20, 13 |
| T | cystitis noninfective | 10 | 6, 19, 17, 14, 9, 7, 3, 5, 20, 13 |
| T | cytokine release syndrome | 10 | 6, 19, 17, 14, 9, 7, 3, 5, 20, 13 |
| T | death-disease progression | 10 | 6, 19, 17, 14, 9, 7, 3, 5, 20, 13 |
| T | death no ctcae term - death nos | 10 | 6, 19, 17, 14, 9, 7, 3, 5, 20, 13 |
| T | death no ctcae term - multi-organ failure | 10 | 6, 19, 17, 14, 9, 7, 3, 5, 20, 13 |
| T | death no ctcae term - sudden death | 10 | 6, 19, 17, 14, 9, 7, 3, 5, 20, 13 |
| T | death not assoc w ctcae term-disease prog nos | 10 | 6, 19, 17, 14, 9, 7, 3, 5, 20, 13 |
| T | death not associated with ctcae term | 10 | 6, 19, 17, 14, 9, 7, 3, 5, 20, 13 |
| T | decreased apetite | 10 | 6, 19, 17, 14, 9, 7, 3, 5, 20, 13 |
| T | decubitus | 10 | 6, 19, 17, 14, 9, 7, 3, 5, 20, 13 |
| T | dental: teeth | 10 | 6, 19, 17, 14, 9, 7, 3, 5, 20, 13 |
| T | dermatitis - chemoradiation | 10 | 6, 19, 17, 14, 9, 7, 3, 5, 20, 13 |
| T | dermatologic effect | 10 | 6, 19, 17, 14, 9, 7, 3, 5, 20, 13 |
| T | dermatology/skin - other | 10 | 6, 19, 17, 14, 9, 7, 3, 5, 20, 13 |
| T | dermatophytosis of nail | 10 | 6, 19, 17, 14, 9, 7, 3, 5, 20, 13 |
| T | device deployment issue | 10 | 6, 19, 17, 14, 9, 7, 3, 5, 20, 13 |
| T | difficulty speaking | 10 | 6, 19, 17, 14, 9, 7, 3, 5, 20, 13 |
| T | diplopia | 10 | 6, 19, 17, 14, 9, 7, 3, 5, 20, 13 |
| T | distention | 10 | 6, 19, 17, 14, 9, 7, 3, 5, 20, 13 |
| T | dizziness/lightheadedness | 10 | 6, 19, 17, 14, 9, 7, 3, 5, 20, 13 |
| T | dlco | 10 | 6, 19, 17, 14, 9, 7, 3, 5, 20, 13 |
| T | dry mouth/salivary gland (xerostomia) | 10 | 6, 19, 17, 14, 9, 7, 3, 5, 20, 13 |
| T | dvt | 10 | 6, 19, 17, 14, 9, 7, 3, 5, 20, 13 |
| T | dysaesthesia | 10 | 6, 19, 17, 14, 9, 7, 3, 5, 20, 13 |
| T | dysphagia, dizziness, dehydration | 10 | 6, 19, 17, 14, 9, 7, 3, 5, 20, 13 |
| T | dyspnoae | 10 | 6, 19, 17, 14, 9, 7, 3, 5, 20, 13 |
| T | ear and labyrinth disorders - other | 10 | 6, 19, 17, 14, 9, 7, 3, 5, 20, 13 |
| T | ear and labyrinth disorders - other, specify | 10 | 6, 19, 17, 14, 9, 7, 3, 5, 20, 13 |
| T | ear and labyrinth disorders - other, specify: vibrations and muffling | 10 | 6, 19, 17, 14, 9, 7, 3, 5, 20, 13 |
| T | ear, nose and throat examination abnormal | 10 | 6, 19, 17, 14, 9, 7, 3, 5, 20, 13 |
| T | edema face | 10 | 6, 19, 17, 14, 9, 7, 3, 5, 20, 13 |
| T | edema trunk | 10 | 6, 19, 17, 14, 9, 7, 3, 5, 20, 13 |
| T | edema: head and neck | 10 | 6, 19, 17, 14, 9, 7, 3, 5, 20, 13 |

[Fig. 20-58]

| T | edema: limb | 10 | 6, 19, 17, 14, 9, 7, 3, 5, 20, 13 |
|---|---|---|---|
| T | edema: trunk/genital | 10 | 6, 19, 17, 14, 9, 7, 3, 5, 20, 13 |
| T | elevated serum glutamic oxaloacetic transaminase (sgot) | 10 | 6, 19, 17, 14, 9, 7, 3, 5, 20, 13 |
| T | elevated troponin | 10 | 6, 19, 17, 14, 9, 7, 3, 5, 20, 13 |
| T | enterocolitis infectious | 10 | 6, 19, 17, 14, 9, 7, 3, 5, 20, 13 |
| T | epistaxis (nosebleed) | 10 | 6, 19, 17, 14, 9, 7, 3, 5, 20, 13 |
| T | erythema multiforme | 10 | 6, 19, 17, 14, 9, 7, 3, 5, 20, 13 |
| T | esophageal pain | 10 | 6, 19, 17, 14, 9, 7, 3, 5, 20, 13 |
| T | esophageal perforation | 10 | 6, 19, 17, 14, 9, 7, 3, 5, 20, 13 |
| T | esophagitis | 10 | 6, 19, 17, 14, 9, 7, 3, 5, 20, 13 |
| T | esophagitis, nauseam dehydration, electrolyte imbalance, potassium and mood alteration | 10 | 6, 19, 17, 14, 9, 7, 3, 5, 20, 13 |
| T | esophagus, hemorrhage | 10 | 6, 19, 17, 14, 9, 7, 3, 5, 20, 13 |
| T | esophagus, pain | 10 | 6, 19, 17, 14, 9, 7, 3, 5, 20, 13 |
| T | extremity-limb, pain | 10 | 6, 19, 17, 14, 9, 7, 3, 5, 20, 13 |
| T | extremity - limb pain | 10 | 6, 19, 17, 14, 9, 7, 3, 5, 20, 13 |
| T | eye disorders - other, specify | 10 | 6, 19, 17, 14, 9, 7, 3, 5, 20, 13 |
| T | eye irritation | 10 | 6, 19, 17, 14, 9, 7, 3, 5, 20, 13 |
| T | eye pain | 10 | 6, 19, 17, 14, 9, 7, 3, 5, 20, 13 |
| T | face oedema | 10 | 6, 19, 17, 14, 9, 7, 3, 5, 20, 13 |
| T | febrile bone marrow aplasia | 10 | 6, 19, 17, 14, 9, 7, 3, 5, 20, 13 |
| T | febrile neutropenia (fever of unknown origin without documented infection) | 10 | 6, 19, 17, 14, 9, 7, 3, 5, 20, 13 |
| T | fecal incontinence | 10 | 6, 19, 17, 14, 9, 7, 3, 5, 20, 13 |
| T | feeling cold | 10 | 6, 19, 17, 14, 9, 7, 3, 5, 20, 13 |
| T | fever (in the absence of neutropenia) | 10 | 6, 19, 17, 14, 9, 7, 3, 5, 20, 13 |
| T | fever (in the absence of neutropenia, where neutropenia is defined as agc<1.0 xe9/l) | 10 | 6, 19, 17, 14, 9, 7, 3, 5, 20, 13 |
| T | fever (in the absence of neutropenia, where neutropenia is defined as anc <1.0 xe9/l) | 10 | 6, 19, 17, 14, 9, 7, 3, 5, 20, 13 |
| T | fever neutropenia | 10 | 6, 19, 17, 14, 9, 7, 3, 5, 20, 13 |
| T | fibrin d dimer increased | 10 | 6, 19, 17, 14, 9, 7, 3, 5, 20, 13 |
| T | fistula, gi - colon/cecum/appendix | 10 | 6, 19, 17, 14, 9, 7, 3, 5, 20, 13 |
| T | fistula, gi - small bowel nos | 10 | 6, 19, 17, 14, 9, 7, 3, 5, 20, 13 |
| T | fistula, gu - vagina | 10 | 6, 19, 17, 14, 9, 7, 3, 5, 20, 13 |
| T | fistula, rectum | 10 | 6, 19, 17, 14, 9, 7, 3, 5, 20, 13 |
| T | flashing lights | 10 | 6, 19, 17, 14, 9, 7, 3, 5, 20, 13 |
| T | flashing lights/floaters | 10 | 6, 19, 17, 14, 9, 7, 3, 5, 20, 13 |
| T | floaters | 10 | 6, 19, 17, 14, 9, 7, 3, 5, 20, 13 |
| T | folliculitis | 10 | 6, 19, 17, 14, 9, 7, 3, 5, 20, 13 |
| T | fungal skin infection | 10 | 6, 19, 17, 14, 9, 7, 3, 5, 20, 13 |
| T | gallbladder obstruction | 10 | 6, 19, 17, 14, 9, 7, 3, 5, 20, 13 |
| T | gamma - glutamyltransferase increased | 10 | 6, 19, 17, 14, 9, 7, 3, 5, 20, 13 |
| T | gastritis (stomach lining inflammation) | 10 | 6, 19, 17, 14, 9, 7, 3, 5, 20, 13 |
| T | gastroesophageal reflux disease | 10 | 6, 19, 17, 14, 9, 7, 3, 5, 20, 13 |
| T | gastrointestinal - other | 10 | 6, 19, 17, 14, 9, 7, 3, 5, 20, 13 |
| T | gastrointestinal disorders - other | 10 | 6, 19, 17, 14, 9, 7, 3, 5, 20, 13 |
| T | gastrointestinal disorders - other, specify | 10 | 6, 19, 17, 14, 9, 7, 3, 5, 20, 13 |
| T | gastrointestinal, other | 10 | 6, 19, 17, 14, 9, 7, 3, 5, 20, 13 |
| T | gastrostomy failure | 10 | 6, 19, 17, 14, 9, 7, 3, 5, 20, 13 |
| T | general disorders and administration site conditions-other, specify | 10 | 6, 19, 17, 14, 9, 7, 3, 5, 20, 13 |
| T | general disorders and administration site conditions - other, specify | 10 | 6, 19, 17, 14, 9, 7, 3, 5, 20, 13 |
| T | general disorders and administration site conditions - other, specify: smell alteration | 10 | 6, 19, 17, 14, 9, 7, 3, 5, 20, 13 |
| T | general symptom | 10 | 6, 19, 17, 14, 9, 7, 3, 5, 20, 13 |
| T | generalized muscle weakness | 10 | 6, 19, 17, 14, 9, 7, 3, 5, 20, 13 |
| T | gfr | 10 | 6, 19, 17, 14, 9, 7, 3, 5, 20, 13 |
| T | ggt | 10 | 6, 19, 17, 14, 9, 7, 3, 5, 20, 13 |
| T | ggt increased | 10 | 6, 19, 17, 14, 9, 7, 3, 5, 20, 13 |
| T | gi hemorrage | 10 | 6, 19, 17, 14, 9, 7, 3, 5, 20, 13 |
| T | gingival bleeding | 10 | 6, 19, 17, 14, 9, 7, 3, 5, 20, 13 |
| T | glomerular filtration rate increased | 10 | 6, 19, 17, 14, 9, 7, 3, 5, 20, 13 |

[Fig. 20-59]

| T | | | |
|---|---|---|---|
| T | glossodynia | 10 | 6, 19, 17, 14, 9, 7, 3, 5, 20, 13 |
| T | growth of eyelashes | 10 | 6, 19, 17, 14, 9, 7, 3, 5, 20, 13 |
| T | gum infection | 10 | 6, 19, 17, 14, 9, 7, 3, 5, 20, 13 |
| T | haematocrit decreased | 10 | 6, 19, 17, 14, 9, 7, 3, 5, 20, 13 |
| T | hair colour changes | 10 | 6, 19, 17, 14, 9, 7, 3, 5, 20, 13 |
| T | hair disorder | 10 | 6, 19, 17, 14, 9, 7, 3, 5, 20, 13 |
| T | hair loss/alopecia | 10 | 6, 19, 17, 14, 9, 7, 3, 5, 20, 13 |
| T | hand-foot-and-mouth disease | 10 | 6, 19, 17, 14, 9, 7, 3, 5, 20, 13 |
| T | hand and foot syndrome | 10 | 6, 19, 17, 14, 9, 7, 3, 5, 20, 13 |
| T | head/headache | 10 | 6, 19, 17, 14, 9, 7, 3, 5, 20, 13 |
| T | hearing (monitoring program) | 10 | 6, 19, 17, 14, 9, 7, 3, 5, 20, 13 |
| T | hearing (without monitoring program) | 10 | 6, 19, 17, 14, 9, 7, 3, 5, 20, 13 |
| T | hearing effect | 10 | 6, 19, 17, 14, 9, 7, 3, 5, 20, 13 |
| T | hearing impaired | 10 | 6, 19, 17, 14, 9, 7, 3, 5, 20, 13 |
| T | hearing loss | 10 | 6, 19, 17, 14, 9, 7, 3, 5, 20, 13 |
| T | hematuria | 10 | 6, 19, 17, 14, 9, 7, 3, 5, 20, 13 |
| T | hemetemesis | 10 | 6, 19, 17, 14, 9, 7, 3, 5, 20, 13 |
| T | hemoglobin decreased | 10 | 6, 19, 17, 14, 9, 7, 3, 5, 20, 13 |
| T | hemoglobin increased | 10 | 6, 19, 17, 14, 9, 7, 3, 5, 20, 13 |
| T | hemoglobinuria | 10 | 6, 19, 17, 14, 9, 7, 3, 5, 20, 13 |
| T | hemoptysis | 10 | 6, 19, 17, 14, 9, 7, 3, 5, 20, 13 |
| T | hemorrhage-other | 10 | 6, 19, 17, 14, 9, 7, 3, 5, 20, 13 |
| T | hemorrhage, abdomen nos | 10 | 6, 19, 17, 14, 9, 7, 3, 5, 20, 13 |
| T | hemorrhage, gi | 10 | 6, 19, 17, 14, 9, 7, 3, 5, 20, 13 |
| T | hemorrhage, gi - abdomen nos | 10 | 6, 19, 17, 14, 9, 7, 3, 5, 20, 13 |
| T | hemorrhage, gi - anus | 10 | 6, 19, 17, 14, 9, 7, 3, 5, 20, 13 |
| T | hemorrhage, gi - oral cavity | 10 | 6, 19, 17, 14, 9, 7, 3, 5, 20, 13 |
| T | hemorrhage, gi - rectum | 10 | 6, 19, 17, 14, 9, 7, 3, 5, 20, 13 |
| T | hemorrhage, gi - stomach | 10 | 6, 19, 17, 14, 9, 7, 3, 5, 20, 13 |
| T | hemorrhage, gu | 10 | 6, 19, 17, 14, 9, 7, 3, 5, 20, 13 |
| T | hemorrhage, gu - bladder | 10 | 6, 19, 17, 14, 9, 7, 3, 5, 20, 13 |
| T | hemorrhage, gu - kidney | 10 | 6, 19, 17, 14, 9, 7, 3, 5, 20, 13 |
| T | hemorrhage, gu - urinary nos | 10 | 6, 19, 17, 14, 9, 7, 3, 5, 20, 13 |
| T | hemorrhage, gu - uterus | 10 | 6, 19, 17, 14, 9, 7, 3, 5, 20, 13 |
| T | hemorrhage, gu - vagina | 10 | 6, 19, 17, 14, 9, 7, 3, 5, 20, 13 |
| T | hemorrhage, pulmonary/upper respiratory | 10 | 6, 19, 17, 14, 9, 7, 3, 5, 20, 13 |
| T | hemorrhage/bleeding - other | 10 | 6, 19, 17, 14, 9, 7, 3, 5, 20, 13 |
| T | hemorrhage/bleeding, other | 10 | 6, 19, 17, 14, 9, 7, 3, 5, 20, 13 |
| T | hemorrhage/pulmonary - nose | 10 | 6, 19, 17, 14, 9, 7, 3, 5, 20, 13 |
| T | hemorrhagic stroke | 10 | 6, 19, 17, 14, 9, 7, 3, 5, 20, 13 |
| T | hemorrhoidal hemorrhage | 10 | 6, 19, 17, 14, 9, 7, 3, 5, 20, 13 |
| T | hemorrhoids | 10 | 6, 19, 17, 14, 9, 7, 3, 5, 20, 13 |
| T | hepatobiliary/pancreas - other | 10 | 6, 19, 17, 14, 9, 7, 3, 5, 20, 13 |
| T | hiccoughs | 10 | 6, 19, 17, 14, 9, 7, 3, 5, 20, 13 |
| T | hiccoughs (hiccups, singultus) | 10 | 6, 19, 17, 14, 9, 7, 3, 5, 20, 13 |
| T | hirsutism | 10 | 6, 19, 17, 14, 9, 7, 3, 5, 20, 13 |
| T | hoarseness | 10 | 6, 19, 17, 14, 9, 7, 3, 5, 20, 13 |
| T | hot flashes | 10 | 6, 19, 17, 14, 9, 7, 3, 5, 20, 13 |
| T | hyperglycemia (high glucose level in blood) | 10 | 6, 19, 17, 14, 9, 7, 3, 5, 20, 13 |
| T | hyperglycemia, dehydration | 10 | 6, 19, 17, 14, 9, 7, 3, 5, 20, 13 |
| T | hyperkalemia | 10 | 6, 19, 17, 14, 9, 7, 3, 5, 20, 13 |
| T | hypermagnesaemia | 10 | 6, 19, 17, 14, 9, 7, 3, 5, 20, 13 |
| T | hypermagnesemia | 10 | 6, 19, 17, 14, 9, 7, 3, 5, 20, 13 |
| T | hypernatraemia | 10 | 6, 19, 17, 14, 9, 7, 3, 5, 20, 13 |
| T | hyperpigmentation | 10 | 6, 19, 17, 14, 9, 7, 3, 5, 20, 13 |
| T | hypersensitivity reaction | 10 | 6, 19, 17, 14, 9, 7, 3, 5, 20, 13 |
| T | hypertrichosis | 10 | 6, 19, 17, 14, 9, 7, 3, 5, 20, 13 |
| T | hyperuricemia | 10 | 6, 19, 17, 14, 9, 7, 3, 5, 20, 13 |
| T | hypoacusis | 10 | 6, 19, 17, 14, 9, 7, 3, 5, 20, 13 |
| T | hypoalbuminaemia | 10 | 6, 19, 17, 14, 9, 7, 3, 5, 20, 13 |
| T | hypocalcemia (low calcium level in blood) | 10 | 6, 19, 17, 14, 9, 7, 3, 5, 20, 13 |
| T | hypochloraemia | 10 | 6, 19, 17, 14, 9, 7, 3, 5, 20, 13 |
| T | hypoglycemia | 10 | 6, 19, 17, 14, 9, 7, 3, 5, 20, 13 |
| T | hypokalemia (low potassium level in blood) | 10 | 6, 19, 17, 14, 9, 7, 3, 5, 20, 13 |
| T | hypokalemia, hypomagnesemia, weakness, anorexia, opportunistic infection | 10 | 6, 19, 17, 14, 9, 7, 3, 5, 20, 13 |
| T | hypomagnesemia (low magnesium level in blood) | 10 | 6, 19, 17, 14, 9, 7, 3, 5, 20, 13 |

[Fig. 20-60]

| | | | |
|---|---|---|---|
| T | hypophosphataemia | 10 | 6, 19, 17, 14, 9, 7, 3, 5, 20, 13 |
| T | hypopigmentation | 10 | 6, 19, 17, 14, 9, 7, 3, 5, 20, 13 |
| T | hypoxemia | 10 | 6, 19, 17, 14, 9, 7, 3, 5, 20, 13 |
| T | ill-defined disorder | 10 | 6, 19, 17, 14, 9, 7, 3, 5, 20, 13 |
| T | immune system disorder | 10 | 6, 19, 17, 14, 9, 7, 3, 5, 20, 13 |
| T | immune system disorders - other, specify: hives | 10 | 6, 19, 17, 14, 9, 7, 3, 5, 20, 13 |
| T | impetigo | 10 | 6, 19, 17, 14, 9, 7, 3, 5, 20, 13 |
| T | implant site cellulitis | 10 | 6, 19, 17, 14, 9, 7, 3, 5, 20, 13 |
| T | implant site erythema | 10 | 6, 19, 17, 14, 9, 7, 3, 5, 20, 13 |
| T | incontinence, anal | 10 | 6, 19, 17, 14, 9, 7, 3, 5, 20, 13 |
| T | incontinence, urinary | 10 | 6, 19, 17, 14, 9, 7, 3, 5, 20, 13 |
| T | inf unknown anc: bladder (urinary) | 10 | 6, 19, 17, 14, 9, 7, 3, 5, 20, 13 |
| T | inf unknown anc: bronchus | 10 | 6, 19, 17, 14, 9, 7, 3, 5, 20, 13 |
| T | inf unknown anc: nerve-peripheral | 10 | 6, 19, 17, 14, 9, 7, 3, 5, 20, 13 |
| T | inf unknown anc: rectum | 10 | 6, 19, 17, 14, 9, 7, 3, 5, 20, 13 |
| T | inf unknown anc: salivary gland | 10 | 6, 19, 17, 14, 9, 7, 3, 5, 20, 13 |
| T | inf unknown anc: skin (cellulitis) | 10 | 6, 19, 17, 14, 9, 7, 3, 5, 20, 13 |
| T | inf unknown anc: urinary tract nos | 10 | 6, 19, 17, 14, 9, 7, 3, 5, 20, 13 |
| T | inf unknown anc: vagina | 10 | 6, 19, 17, 14, 9, 7, 3, 5, 20, 13 |
| T | inf w/gr or anc: bladder (urinary) | 10 | 6, 19, 17, 14, 9, 7, 3, 5, 20, 13 |
| T | inf w/gr or anc: blood | 10 | 6, 19, 17, 14, 9, 7, 3, 5, 20, 13 |
| T | inf w/gr or anc: lung (pneumonia) | 10 | 6, 19, 17, 14, 9, 7, 3, 5, 20, 13 |
| T | inf w/gr or anc: oral cavity-gums | 10 | 6, 19, 17, 14, 9, 7, 3, 5, 20, 13 |
| T | inf w/gr or anc: skin (cellulitis) | 10 | 6, 19, 17, 14, 9, 7, 3, 5, 20, 13 |
| T | inf w/gr or anc: urinary tract nos | 10 | 6, 19, 17, 14, 9, 7, 3, 5, 20, 13 |
| T | inf w/nml or gr or anc: abdomen nos | 10 | 6, 19, 17, 14, 9, 7, 3, 5, 20, 13 |
| T | inf w/nml or gr or anc: anal/perianal | 10 | 6, 19, 17, 14, 9, 7, 3, 5, 20, 13 |
| T | inf w/nml or gr or anc: artery | 10 | 6, 19, 17, 14, 9, 7, 3, 5, 20, 13 |
| T | inf w/nml or gr or anc: bladder | 10 | 6, 19, 17, 14, 9, 7, 3, 5, 20, 13 |
| T | inf w/nml or gr or anc: blood | 10 | 6, 19, 17, 14, 9, 7, 3, 5, 20, 13 |
| T | inf w/nml or gr or anc: bronchus | 10 | 6, 19, 17, 14, 9, 7, 3, 5, 20, 13 |
| T | inf w/nml or gr or anc: catheter-related | 10 | 6, 19, 17, 14, 9, 7, 3, 5, 20, 13 |
| T | inf w/nml or gr or anc: cervix | 10 | 6, 19, 17, 14, 9, 7, 3, 5, 20, 13 |
| T | inf w/nml or gr or anc: colon | 10 | 6, 19, 17, 14, 9, 7, 3, 5, 20, 13 |
| T | inf w/nml or gr or anc: kidney | 10 | 6, 19, 17, 14, 9, 7, 3, 5, 20, 13 |
| T | inf w/nml or gr or anc: lung(pneumonia) | 10 | 6, 19, 17, 14, 9, 7, 3, 5, 20, 13 |
| T | inf w/nml or gr or anc: nerve-peripheral | 10 | 6, 19, 17, 14, 9, 7, 3, 5, 20, 13 |
| T | inf w/nml or gr or anc: oral cavity-gums | 10 | 6, 19, 17, 14, 9, 7, 3, 5, 20, 13 |
| T | inf w/nml or gr or anc: pelvis nos | 10 | 6, 19, 17, 14, 9, 7, 3, 5, 20, 13 |
| T | inf w/nml or gr or anc: pharynx | 10 | 6, 19, 17, 14, 9, 7, 3, 5, 20, 13 |
| T | inf w/nml or gr or anc: salivary gland | 10 | 6, 19, 17, 14, 9, 7, 3, 5, 20, 13 |
| T | inf w/nml or gr or anc: sinus | 10 | 6, 19, 17, 14, 9, 7, 3, 5, 20, 13 |
| T | inf w/nml or gr or anc: skin(cellulitis) | 10 | 6, 19, 17, 14, 9, 7, 3, 5, 20, 13 |
| T | inf w/nml or gr or anc: soft tissue nos | 10 | 6, 19, 17, 14, 9, 7, 3, 5, 20, 13 |
| T | inf w/nml or gr or anc: urinary tract nos | 10 | 6, 19, 17, 14, 9, 7, 3, 5, 20, 13 |
| T | inf w/nml or gr or anc: vagina | 10 | 6, 19, 17, 14, 9, 7, 3, 5, 20, 13 |
| T | inf w/nml or gr or anc: vulva | 10 | 6, 19, 17, 14, 9, 7, 3, 5, 20, 13 |
| T | inf w/nml or gr or anc: wound | 10 | 6, 19, 17, 14, 9, 7, 3, 5, 20, 13 |
| T | inf w/nml or gr or anc:peritoneal cavity | 10 | 6, 19, 17, 14, 9, 7, 3, 5, 20, 13 |
| T | infection- abdomen | 10 | 6, 19, 17, 14, 9, 7, 3, 5, 20, 13 |
| T | infection - other | 10 | 6, 19, 17, 14, 9, 7, 3, 5, 20, 13 |
| T | infection (documented clinically or microbiologically) with grade or neutrophils | 10 | 6, 19, 17, 14, 9, 7, 3, 5, 20, 13 |
| T | infection gr0-2 neut, blood | 10 | 6, 19, 17, 14, 9, 7, 3, 5, 20, 13 |
| T | infection gr0-2 neut, foreign body | 10 | 6, 19, 17, 14, 9, 7, 3, 5, 20, 13 |
| T | infection of gallbladder with normal anc | 10 | 6, 19, 17, 14, 9, 7, 3, 5, 20, 13 |
| T | infection w/ gr3-4 neut, blood | 10 | 6, 19, 17, 14, 9, 7, 3, 5, 20, 13 |
| T | infection w/ gr3-4 neut, catheter relate | 10 | 6, 19, 17, 14, 9, 7, 3, 5, 20, 13 |
| T | infection w/ gr3-4 neut, urinary tract | 10 | 6, 19, 17, 14, 9, 7, 3, 5, 20, 13 |
| T | infection with normal anc (cellulitis) and albumin | 10 | 6, 19, 17, 14, 9, 7, 3, 5, 20, 13 |
| T | infection with normal anc or grade or neutrophils, trachea | 10 | 6, 19, 17, 14, 9, 7, 3, 5, 20, 13 |
| T | infection with unknown anc | 10 | 6, 19, 17, 14, 9, 7, 3, 5, 20, 13 |
| T | infection without neutropenia | 10 | 6, 19, 17, 14, 9, 7, 3, 5, 20, 13 |
| T | infection, other | 10 | 6, 19, 17, 14, 9, 7, 3, 5, 20, 13 |

[Fig. 20-61]

| T | infections and infestations - infection with grade or neutrophils : abdomen nos | 10 | 6, 19, 17, 14, 9, 7, 3, 5, 20, 13 |
|---|---|---|---|
| T | infections and infestations - infection with grade or neutrophils: blood | 10 | 6, 19, 17, 14, 9, 7, 3, 5, 20, 13 |
| T | infections and infestations - infection with grade or neutrophils: lung (pneumonia) | 10 | 6, 19, 17, 14, 9, 7, 3, 5, 20, 13 |
| T | infections and infestations - other | 10 | 6, 19, 17, 14, 9, 7, 3, 5, 20, 13 |
| T | infections and infestations - other, folliculitis, axilla right | 10 | 6, 19, 17, 14, 9, 7, 3, 5, 20, 13 |
| T | infections and infestations - other, meningoencephylitis | 10 | 6, 19, 17, 14, 9, 7, 3, 5, 20, 13 |
| T | infections and infestations - other, pseudomonas bacteremia | 10 | 6, 19, 17, 14, 9, 7, 3, 5, 20, 13 |
| T | infections and infestations - other, specify | 10 | 6, 19, 17, 14, 9, 7, 3, 5, 20, 13 |
| T | infections and infestations - other, specify (oral thrush) | 10 | 6, 19, 17, 14, 9, 7, 3, 5, 20, 13 |
| T | infections and infestations - other, specify: infected cyst on neck | 10 | 6, 19, 17, 14, 9, 7, 3, 5, 20, 13 |
| T | infections and infestations - other, west nile virus | 10 | 6, 19, 17, 14, 9, 7, 3, 5, 20, 13 |
| T | infective spondylitis | 10 | 6, 19, 17, 14, 9, 7, 3, 5, 20, 13 |
| T | infusion site cellulitis | 10 | 6, 19, 17, 14, 9, 7, 3, 5, 20, 13 |
| T | infusion site extravasation | 10 | 6, 19, 17, 14, 9, 7, 3, 5, 20, 13 |
| T | infusion site pain | 10 | 6, 19, 17, 14, 9, 7, 3, 5, 20, 13 |
| T | infusion site reaction | 10 | 6, 19, 17, 14, 9, 7, 3, 5, 20, 13 |
| T | infusion site urticaria | 10 | 6, 19, 17, 14, 9, 7, 3, 5, 20, 13 |
| T | inr | 10 | 6, 19, 17, 14, 9, 7, 3, 5, 20, 13 |
| T | inr increased | 10 | 6, 19, 17, 14, 9, 7, 3, 5, 20, 13 |
| T | intracranial hemorrhage | 10 | 6, 19, 17, 14, 9, 7, 3, 5, 20, 13 |
| T | involuntary movement | 10 | 6, 19, 17, 14, 9, 7, 3, 5, 20, 13 |
| T | irregular menstruation | 10 | 6, 19, 17, 14, 9, 7, 3, 5, 20, 13 |
| T | ischemia cerebrovascular | 10 | 6, 19, 17, 14, 9, 7, 3, 5, 20, 13 |
| T | ischemic stroke | 10 | 6, 19, 17, 14, 9, 7, 3, 5, 20, 13 |
| T | joint-function | 10 | 6, 19, 17, 14, 9, 7, 3, 5, 20, 13 |
| T | joint infection | 10 | 6, 19, 17, 14, 9, 7, 3, 5, 20, 13 |
| T | jugular vein distension | 10 | 6, 19, 17, 14, 9, 7, 3, 5, 20, 13 |
| T | jugular vein thrombosis | 10 | 6, 19, 17, 14, 9, 7, 3, 5, 20, 13 |
| T | keratoconjunctivitis sicca | 10 | 6, 19, 17, 14, 9, 7, 3, 5, 20, 13 |
| T | lacrimation increased | 10 | 6, 19, 17, 14, 9, 7, 3, 5, 20, 13 |
| T | laryngeal hemorrhage | 10 | 6, 19, 17, 14, 9, 7, 3, 5, 20, 13 |
| T | leak, gu - vagina | 10 | 6, 19, 17, 14, 9, 7, 3, 5, 20, 13 |
| T | leukopenia, esophagitis, dehydration, nausea, vomiting, neutropenia, hypotension | 10 | 6, 19, 17, 14, 9, 7, 3, 5, 20, 13 |
| T | lipase | 10 | 6, 19, 17, 14, 9, 7, 3, 5, 20, 13 |
| T | liver dysfunction | 10 | 6, 19, 17, 14, 9, 7, 3, 5, 20, 13 |
| T | localised oedema | 10 | 6, 19, 17, 14, 9, 7, 3, 5, 20, 13 |
| T | localized edema | 10 | 6, 19, 17, 14, 9, 7, 3, 5, 20, 13 |
| T | lower gastrointestinal hemorrhage | 10 | 6, 19, 17, 14, 9, 7, 3, 5, 20, 13 |
| T | lymph gland infection | 10 | 6, 19, 17, 14, 9, 7, 3, 5, 20, 13 |
| T | lymphatic duct injury | 10 | 6, 19, 17, 14, 9, 7, 3, 5, 20, 13 |
| T | lymphedema | 10 | 6, 19, 17, 14, 9, 7, 3, 5, 20, 13 |
| T | lymphocyte count increased | 10 | 6, 19, 17, 14, 9, 7, 3, 5, 20, 13 |
| T | macrocytosis | 10 | 6, 19, 17, 14, 9, 7, 3, 5, 20, 13 |
| T | memory impairment | 10 | 6, 19, 17, 14, 9, 7, 3, 5, 20, 13 |
| T | metabolic/laboratory - other | 10 | 6, 19, 17, 14, 9, 7, 3, 5, 20, 13 |
| T | metabolism and nutrition disorders - other, specify (amylase) | 10 | 6, 19, 17, 14, 9, 7, 3, 5, 20, 13 |
| T | microcytosis | 10 | 6, 19, 17, 14, 9, 7, 3, 5, 20, 13 |
| T | micturition frequency decreased | 10 | 6, 19, 17, 14, 9, 7, 3, 5, 20, 13 |
| T | monocyte count decreased | 10 | 6, 19, 17, 14, 9, 7, 3, 5, 20, 13 |
| T | mood alteration - agitation | 10 | 6, 19, 17, 14, 9, 7, 3, 5, 20, 13 |
| T | mood alteration - anxiety | 10 | 6, 19, 17, 14, 9, 7, 3, 5, 20, 13 |
| T | mood alteration - depression | 10 | 6, 19, 17, 14, 9, 7, 3, 5, 20, 13 |
| T | mortality | 10 | 6, 19, 17, 14, 9, 7, 3, 5, 20, 13 |

[Fig. 20-62]

| | | | |
|---|---|---|---|
| T | mucosal dryness | 10 | 6, 19, 17, 14, 9, 7, 3, 5, 20, 13 |
| T | mucosal infection | 10 | 6, 19, 17, 14, 9, 7, 3, 5, 20, 13 |
| T | mucosal inflamation | 10 | 6, 19, 17, 14, 9, 7, 3, 5, 20, 13 |
| T | mucosal inflammation | 10 | 6, 19, 17, 14, 9, 7, 3, 5, 20, 13 |
| T | mucositis (clinical exam) - esophagus | 10 | 6, 19, 17, 14, 9, 7, 3, 5, 20, 13 |
| T | mucositis (clinical exam) - oral cavity | 10 | 6, 19, 17, 14, 9, 7, 3, 5, 20, 13 |
| T | mucositis (functional/sympt) - anus | 10 | 6, 19, 17, 14, 9, 7, 3, 5, 20, 13 |
| T | mucositis (functional/sympt) - oral cavity | 10 | 6, 19, 17, 14, 9, 7, 3, 5, 20, 13 |
| T | mucositis (functional/sympt) - rectum | 10 | 6, 19, 17, 14, 9, 7, 3, 5, 20, 13 |
| T | mucositis/stomatitis (functional/symptomatic) | 10 | 6, 19, 17, 14, 9, 7, 3, 5, 20, 13 |
| T | multiorgan failure | 10 | 6, 19, 17, 14, 9, 7, 3, 5, 20, 13 |
| T | muscle weakness - extremity-lower | 10 | 6, 19, 17, 14, 9, 7, 3, 5, 20, 13 |
| T | muscle weakness - extremity-upper | 10 | 6, 19, 17, 14, 9, 7, 3, 5, 20, 13 |
| T | muscle weakness - whole body/generalized | 10 | 6, 19, 17, 14, 9, 7, 3, 5, 20, 13 |
| T | muscle weakness left-sided | 10 | 6, 19, 17, 14, 9, 7, 3, 5, 20, 13 |
| T | muscle weakness lower limb | 10 | 6, 19, 17, 14, 9, 7, 3, 5, 20, 13 |
| T | muscle weakness, generalized or specific area (not due to neuropathy) | 10 | 6, 19, 17, 14, 9, 7, 3, 5, 20, 13 |
| T | muscle weakness, generalized or specific area (not due to neuropathy) - extremity-lower | 10 | 6, 19, 17, 14, 9, 7, 3, 5, 20, 13 |
| T | musculoskeletal and connective tissue disorder - other | 10 | 6, 19, 17, 14, 9, 7, 3, 5, 20, 13 |
| T | musculoskeletal and connective tissue disorder - other, specify | 10 | 6, 19, 17, 14, 9, 7, 3, 5, 20, 13 |
| T | musculoskeletal and connective tissue disorder - other, specify: leg cramp | 10 | 6, 19, 17, 14, 9, 7, 3, 5, 20, 13 |
| T | musculoskeletal/st: other | 10 | 6, 19, 17, 14, 9, 7, 3, 5, 20, 13 |
| T | myalgia (muscle pain) | 10 | 6, 19, 17, 14, 9, 7, 3, 5, 20, 13 |
| T | nail changes | 10 | 6, 19, 17, 14, 9, 7, 3, 5, 20, 13 |
| T | nail discoloration | 10 | 6, 19, 17, 14, 9, 7, 3, 5, 20, 13 |
| T | nail disorder | 10 | 6, 19, 17, 14, 9, 7, 3, 5, 20, 13 |
| T | nail dystrophy | 10 | 6, 19, 17, 14, 9, 7, 3, 5, 20, 13 |
| T | nail loss | 10 | 6, 19, 17, 14, 9, 7, 3, 5, 20, 13 |
| T | nasal dryness | 10 | 6, 19, 17, 14, 9, 7, 3, 5, 20, 13 |
| T | nausea, dehydration, esophagitis, death | 10 | 6, 19, 17, 14, 9, 7, 3, 5, 20, 13 |
| T | nausea, vomiting, weakness, ischemic colitis | 10 | 6, 19, 17, 14, 9, 7, 3, 5, 20, 13 |
| T | neck edema | 10 | 6, 19, 17, 14, 9, 7, 3, 5, 20, 13 |
| T | necrosis, gi- small bowel nos | 10 | 6, 19, 17, 14, 9, 7, 3, 5, 20, 13 |
| T | necrosis, gi - rectum | 10 | 6, 19, 17, 14, 9, 7, 3, 5, 20, 13 |
| T | necrosis, gi - stoma | 10 | 6, 19, 17, 14, 9, 7, 3, 5, 20, 13 |
| T | neoplasms benign, malignant and unspecified (incl cysts and polyps) - other, death | 10 | 6, 19, 17, 14, 9, 7, 3, 5, 20, 13 |
| T | neoplasms benign, malignant and unspecified (incl cysts and polyps) - other, specify | 10 | 6, 19, 17, 14, 9, 7, 3, 5, 20, 13 |
| T | neoplasms benign, malignant and unspecified (incl cysts and polyps) - other, basal cell carcinoma | 10 | 6, 19, 17, 14, 9, 7, 3, 5, 20, 13 |
| T | nervous system disorders - other, specify: left interal carotid artery stenosis | 10 | 6, 19, 17, 14, 9, 7, 3, 5, 20, 13 |
| T | neurology - other | 10 | 6, 19, 17, 14, 9, 7, 3, 5, 20, 13 |
| T | neuropathy-motor | 10 | 6, 19, 17, 14, 9, 7, 3, 5, 20, 13 |
| T | neuropathy - motor | 10 | 6, 19, 17, 14, 9, 7, 3, 5, 20, 13 |
| T | neuropathy,cranial - cn i smell | 10 | 6, 19, 17, 14, 9, 7, 3, 5, 20, 13 |
| T | neuropathy,cranial - cn x motor-palate | 10 | 6, 19, 17, 14, 9, 7, 3, 5, 20, 13 |
| T | neuropathy: motor | 10 | 6, 19, 17, 14, 9, 7, 3, 5, 20, 13 |
| T | neuropothy | 10 | 6, 19, 17, 14, 9, 7, 3, 5, 20, 13 |
| T | neurotoxicity | 10 | 6, 19, 17, 14, 9, 7, 3, 5, 20, 13 |
| T | neutropenic infection | 10 | 6, 19, 17, 14, 9, 7, 3, 5, 20, 13 |
| T | neutropenic sepsis | 10 | 6, 19, 17, 14, 9, 7, 3, 5, 20, 13 |
| T | neutrophil count decrease | 10 | 6, 19, 17, 14, 9, 7, 3, 5, 20, 13 |
| T | night sweats | 10 | 6, 19, 17, 14, 9, 7, 3, 5, 20, 13 |
| T | nonmalignant ascites | 10 | 6, 19, 17, 14, 9, 7, 3, 5, 20, 13 |

[Fig. 20-63]

| T | obstruction gastric | 10 | 6, 19, 17, 14, 9, 7, 3, 5, 20, 13 |
|---|---|---|---|
| T | obstruction, gi | 10 | 6, 19, 17, 14, 9, 7, 3, 5, 20, 13 |
| T | obstruction, gi - small bowel nos | 10 | 6, 19, 17, 14, 9, 7, 3, 5, 20, 13 |
| T | obstruction, gi - ileum | 10 | 6, 19, 17, 14, 9, 7, 3, 5, 20, 13 |
| T | obstruction, gi - small bowel nos | 10 | 6, 19, 17, 14, 9, 7, 3, 5, 20, 13 |
| T | obstruction, gu | 10 | 6, 19, 17, 14, 9, 7, 3, 5, 20, 13 |
| T | obstruction, gu - bladder | 10 | 6, 19, 17, 14, 9, 7, 3, 5, 20, 13 |
| T | obstruction, gu - ureter | 10 | 6, 19, 17, 14, 9, 7, 3, 5, 20, 13 |
| T | obstruction, gu - urethra | 10 | 6, 19, 17, 14, 9, 7, 3, 5, 20, 13 |
| T | ocular/visual-other (specify,___) | 10 | 6, 19, 17, 14, 9, 7, 3, 5, 20, 13 |
| T | ocular/visual - other | 10 | 6, 19, 17, 14, 9, 7, 3, 5, 20, 13 |
| T | odynophagia | 10 | 6, 19, 17, 14, 9, 7, 3, 5, 20, 13 |
| T | oedema | 10 | 6, 19, 17, 14, 9, 7, 3, 5, 20, 13 |
| T | oesophageal disorder | 10 | 6, 19, 17, 14, 9, 7, 3, 5, 20, 13 |
| T | oesophageal haemorrhage | 10 | 6, 19, 17, 14, 9, 7, 3, 5, 20, 13 |
| T | oesophageal pain | 10 | 6, 19, 17, 14, 9, 7, 3, 5, 20, 13 |
| T | onycholysis | 10 | 6, 19, 17, 14, 9, 7, 3, 5, 20, 13 |
| T | onychomadesis | 10 | 6, 19, 17, 14, 9, 7, 3, 5, 20, 13 |
| T | opportunistic infection | 10 | 6, 19, 17, 14, 9, 7, 3, 5, 20, 13 |
| T | oral dysesthesia | 10 | 6, 19, 17, 14, 9, 7, 3, 5, 20, 13 |
| T | oral pain | 10 | 6, 19, 17, 14, 9, 7, 3, 5, 20, 13 |
| T | oropharyngeal discomfort | 10 | 6, 19, 17, 14, 9, 7, 3, 5, 20, 13 |
| T | osteolysis | 10 | 6, 19, 17, 14, 9, 7, 3, 5, 20, 13 |
| T | ototoxicity | 10 | 6, 19, 17, 14, 9, 7, 3, 5, 20, 13 |
| T | oxygen saturation decreased | 10 | 6, 19, 17, 14, 9, 7, 3, 5, 20, 13 |
| T | pain-not otherwise specified (nos) | 10 | 6, 19, 17, 14, 9, 7, 3, 5, 20, 13 |
| T | pain-other | 10 | 6, 19, 17, 14, 9, 7, 3, 5, 20, 13 |
| T | pain - back | 10 | 6, 19, 17, 14, 9, 7, 3, 5, 20, 13 |
| T | pain - head/headache | 10 | 6, 19, 17, 14, 9, 7, 3, 5, 20, 13 |
| T | pain - other | 10 | 6, 19, 17, 14, 9, 7, 3, 5, 20, 13 |
| T | pain - tumor pain | 10 | 6, 19, 17, 14, 9, 7, 3, 5, 20, 13 |
| T | pain (bladder) | 10 | 6, 19, 17, 14, 9, 7, 3, 5, 20, 13 |
| T | pain (extremity) | 10 | 6, 19, 17, 14, 9, 7, 3, 5, 20, 13 |
| T | pain (neck) | 10 | 6, 19, 17, 14, 9, 7, 3, 5, 20, 13 |
| T | pain, chest/thorax nos | 10 | 6, 19, 17, 14, 9, 7, 3, 5, 20, 13 |
| T | pain: anus | 10 | 6, 19, 17, 14, 9, 7, 3, 5, 20, 13 |
| T | pain: back | 10 | 6, 19, 17, 14, 9, 7, 3, 5, 20, 13 |
| T | pain: bladder | 10 | 6, 19, 17, 14, 9, 7, 3, 5, 20, 13 |
| T | pain: bone | 10 | 6, 19, 17, 14, 9, 7, 3, 5, 20, 13 |
| T | pain: buttock | 10 | 6, 19, 17, 14, 9, 7, 3, 5, 20, 13 |
| T | pain: cardiac/ heart | 10 | 6, 19, 17, 14, 9, 7, 3, 5, 20, 13 |
| T | pain: chest /thorax nos | 10 | 6, 19, 17, 14, 9, 7, 3, 5, 20, 13 |
| T | pain: chest wall | 10 | 6, 19, 17, 14, 9, 7, 3, 5, 20, 13 |
| T | pain: dental/teeth/peridontal | 10 | 6, 19, 17, 14, 9, 7, 3, 5, 20, 13 |
| T | pain: esophagus | 10 | 6, 19, 17, 14, 9, 7, 3, 5, 20, 13 |
| T | pain: external ear | 10 | 6, 19, 17, 14, 9, 7, 3, 5, 20, 13 |
| T | pain: joint | 10 | 6, 19, 17, 14, 9, 7, 3, 5, 20, 13 |
| T | pain: kidney | 10 | 6, 19, 17, 14, 9, 7, 3, 5, 20, 13 |
| T | pain: lymph node | 10 | 6, 19, 17, 14, 9, 7, 3, 5, 20, 13 |
| T | pain: middle ear | 10 | 6, 19, 17, 14, 9, 7, 3, 5, 20, 13 |
| T | pain: muscle | 10 | 6, 19, 17, 14, 9, 7, 3, 5, 20, 13 |
| T | pain: neck | 10 | 6, 19, 17, 14, 9, 7, 3, 5, 20, 13 |
| T | pain: neuralgia | 10 | 6, 19, 17, 14, 9, 7, 3, 5, 20, 13 |
| T | pain: oral - gums | 10 | 6, 19, 17, 14, 9, 7, 3, 5, 20, 13 |
| T | pain: oral cavity | 10 | 6, 19, 17, 14, 9, 7, 3, 5, 20, 13 |
| T | pain: pain nos | 10 | 6, 19, 17, 14, 9, 7, 3, 5, 20, 13 |
| T | pain: pelvis | 10 | 6, 19, 17, 14, 9, 7, 3, 5, 20, 13 |
| T | pain: perineum | 10 | 6, 19, 17, 14, 9, 7, 3, 5, 20, 13 |
| T | pain: peritoneum | 10 | 6, 19, 17, 14, 9, 7, 3, 5, 20, 13 |
| T | pain: rectum | 10 | 6, 19, 17, 14, 9, 7, 3, 5, 20, 13 |
| T | pain: stomach | 10 | 6, 19, 17, 14, 9, 7, 3, 5, 20, 13 |
| T | pain: throat/pharynx/larynx | 10 | 6, 19, 17, 14, 9, 7, 3, 5, 20, 13 |
| T | pain: tumor | 10 | 6, 19, 17, 14, 9, 7, 3, 5, 20, 13 |
| T | pain: urethra | 10 | 6, 19, 17, 14, 9, 7, 3, 5, 20, 13 |
| T | pain: uterus | 10 | 6, 19, 17, 14, 9, 7, 3, 5, 20, 13 |
| T | pain: vagina | 10 | 6, 19, 17, 14, 9, 7, 3, 5, 20, 13 |

[Fig. 20-64]

| T | palmar-plantar erythrodysesthesia syndrome | 10 | 6, 19, 17, 14, 9, 7, 3, 5, 20, 13 |
|---|---|---|---|
| T | papulopustular rash | 10 | 6, 19, 17, 14, 9, 7, 3, 5, 20, 13 |
| T | partial thromboplastin time (ptt) | 10 | 6, 19, 17, 14, 9, 7, 3, 5, 20, 13 |
| T | peg tube infection | 10 | 6, 19, 17, 14, 9, 7, 3, 5, 20, 13 |
| T | pelvic pain | 10 | 6, 19, 17, 14, 9, 7, 3, 5, 20, 13 |
| T | penile ulceration | 10 | 6, 19, 17, 14, 9, 7, 3, 5, 20, 13 |
| T | perforation, gi- colon | 10 | 6, 19, 17, 14, 9, 7, 3, 5, 20, 13 |
| T | perforation, gi - appendix | 10 | 6, 19, 17, 14, 9, 7, 3, 5, 20, 13 |
| T | perforation, gi - colon | 10 | 6, 19, 17, 14, 9, 7, 3, 5, 20, 13 |
| T | perforation, gi - rectum | 10 | 6, 19, 17, 14, 9, 7, 3, 5, 20, 13 |
| T | pericardial effusion with tamponade | 10 | 6, 19, 17, 14, 9, 7, 3, 5, 20, 13 |
| T | periorbital oedema | 10 | 6, 19, 17, 14, 9, 7, 3, 5, 20, 13 |
| T | peripheral arterial ischemia | 10 | 6, 19, 17, 14, 9, 7, 3, 5, 20, 13 |
| T | personality | 10 | 6, 19, 17, 14, 9, 7, 3, 5, 20, 13 |
| T | pharyngeal inflammation | 10 | 6, 19, 17, 14, 9, 7, 3, 5, 20, 13 |
| T | pharyngeal mucositis | 10 | 6, 19, 17, 14, 9, 7, 3, 5, 20, 13 |
| T | pharyngitis bacterial | 10 | 6, 19, 17, 14, 9, 7, 3, 5, 20, 13 |
| T | photophobia | 10 | 6, 19, 17, 14, 9, 7, 3, 5, 20, 13 |
| T | photopsia | 10 | 6, 19, 17, 14, 9, 7, 3, 5, 20, 13 |
| T | photosensitivity | 10 | 6, 19, 17, 14, 9, 7, 3, 5, 20, 13 |
| T | platelet count decrease | 10 | 6, 19, 17, 14, 9, 7, 3, 5, 20, 13 |
| T | pneumonitis/pulmonary infiltrates | 10 | 6, 19, 17, 14, 9, 7, 3, 5, 20, 13 |
| T | postnasal drip | 10 | 6, 19, 17, 14, 9, 7, 3, 5, 20, 13 |
| T | postoperative hemorrhage | 10 | 6, 19, 17, 14, 9, 7, 3, 5, 20, 13 |
| T | potassium, low (hypokalemia) | 10 | 6, 19, 17, 14, 9, 7, 3, 5, 20, 13 |
| T | proctalgia | 10 | 6, 19, 17, 14, 9, 7, 3, 5, 20, 13 |
| T | proctitis | 10 | 6, 19, 17, 14, 9, 7, 3, 5, 20, 13 |
| T | progression of disease | 10 | 6, 19, 17, 14, 9, 7, 3, 5, 20, 13 |
| T | prothrombin time international normalized ratio (inr) | 10 | 6, 19, 17, 14, 9, 7, 3, 5, 20, 13 |
| T | prothrombin time prolonged | 10 | 6, 19, 17, 14, 9, 7, 3, 5, 20, 13 |
| T | psychosis (hallucinations/delusions) | 10 | 6, 19, 17, 14, 9, 7, 3, 5, 20, 13 |
| T | ptt | 10 | 6, 19, 17, 14, 9, 7, 3, 5, 20, 13 |
| T | pulmonary-other (specify, respiratory distress) | 10 | 6, 19, 17, 14, 9, 7, 3, 5, 20, 13 |
| T | pulmonary-other (specify, rll pneumonia) | 10 | 6, 19, 17, 14, 9, 7, 3, 5, 20, 13 |
| T | pulmonary edema | 10 | 6, 19, 17, 14, 9, 7, 3, 5, 20, 13 |
| T | pulmonary embolus | 10 | 6, 19, 17, 14, 9, 7, 3, 5, 20, 13 |
| T | pulmonary haemorrhage | 10 | 6, 19, 17, 14, 9, 7, 3, 5, 20, 13 |
| T | pulmonary hemorrhage | 10 | 6, 19, 17, 14, 9, 7, 3, 5, 20, 13 |
| T | pulmonary radiation injury | 10 | 6, 19, 17, 14, 9, 7, 3, 5, 20, 13 |
| T | pulmonary/upper respiratory - other (specify) | 10 | 6, 19, 17, 14, 9, 7, 3, 5, 20, 13 |
| T | pulmonary: other | 10 | 6, 19, 17, 14, 9, 7, 3, 5, 20, 13 |
| T | radiation pneumonitis | 10 | 6, 19, 17, 14, 9, 7, 3, 5, 20, 13 |
| T | rash - maculopapular | 10 | 6, 19, 17, 14, 9, 7, 3, 5, 20, 13 |
| T | rash acneiform | 10 | 6, 19, 17, 14, 9, 7, 3, 5, 20, 13 |
| T | rash generalised | 10 | 6, 19, 17, 14, 9, 7, 3, 5, 20, 13 |
| T | rash macular | 10 | 6, 19, 17, 14, 9, 7, 3, 5, 20, 13 |
| T | rash maculo-papular | 10 | 6, 19, 17, 14, 9, 7, 3, 5, 20, 13 |
| T | rash papular | 10 | 6, 19, 17, 14, 9, 7, 3, 5, 20, 13 |
| T | rash pustular | 10 | 6, 19, 17, 14, 9, 7, 3, 5, 20, 13 |
| T | rash vesicular | 10 | 6, 19, 17, 14, 9, 7, 3, 5, 20, 13 |
| T | rash: erythema multiforme | 10 | 6, 19, 17, 14, 9, 7, 3, 5, 20, 13 |
| T | rash: hand-foot skin reaction | 10 | 6, 19, 17, 14, 9, 7, 3, 5, 20, 13 |
| T | rectal bleeding | 10 | 6, 19, 17, 14, 9, 7, 3, 5, 20, 13 |
| T | rectal hemorrhage | 10 | 6, 19, 17, 14, 9, 7, 3, 5, 20, 13 |
| T | rectal obstruction | 10 | 6, 19, 17, 14, 9, 7, 3, 5, 20, 13 |
| T | red blood cell count decreased | 10 | 6, 19, 17, 14, 9, 7, 3, 5, 20, 13 |
| T | renal and urinary disorders - other, specify | 10 | 6, 19, 17, 14, 9, 7, 3, 5, 20, 13 |
| T | renal artery thrombosis | 10 | 6, 19, 17, 14, 9, 7, 3, 5, 20, 13 |
| T | renal insufficiency | 10 | 6, 19, 17, 14, 9, 7, 3, 5, 20, 13 |
| T | renal/genitourinary-other (specify,___) | 10 | 6, 19, 17, 14, 9, 7, 3, 5, 20, 13 |
| T | renal/genitourinary - other | 10 | 6, 19, 17, 14, 9, 7, 3, 5, 20, 13 |
| T | respiratory rate increased | 10 | 6, 19, 17, 14, 9, 7, 3, 5, 20, 13 |

[Fig. 20-65]

| | | | |
|---|---|---|---|
| T | respiratory tract haemorrhage | 10 | 6, 19, 17, 14, 9, 7, 3, 5, 20, 13 |
| T | respiratory, thoracic and mediastinal disorders - other, specify: left base crackle/pleural rub | 10 | 6, 19, 17, 14, 9, 7, 3, 5, 20, 13 |
| T | rigors/chills | 10 | 6, 19, 17, 14, 9, 7, 3, 5, 20, 13 |
| T | s/n arrhythmia: atrial fibrillation | 10 | 6, 19, 17, 14, 9, 7, 3, 5, 20, 13 |
| T | s/n arrhythmia: atrial tachycardia | 10 | 6, 19, 17, 14, 9, 7, 3, 5, 20, 13 |
| T | s/n arrhythmia: sinus bradycardia | 10 | 6, 19, 17, 14, 9, 7, 3, 5, 20, 13 |
| T | s/n arrhythmia: sinus tachycardia | 10 | 6, 19, 17, 14, 9, 7, 3, 5, 20, 13 |
| T | s/n arrhythmia:supraventricular nos | 10 | 6, 19, 17, 14, 9, 7, 3, 5, 20, 13 |
| T | scab | 10 | 6, 19, 17, 14, 9, 7, 3, 5, 20, 13 |
| T | scalp pain | 10 | 6, 19, 17, 14, 9, 7, 3, 5, 20, 13 |
| T | scalp, pain | 10 | 6, 19, 17, 14, 9, 7, 3, 5, 20, 13 |
| T | scrotal infection | 10 | 6, 19, 17, 14, 9, 7, 3, 5, 20, 13 |
| T | seizure(s) | 10 | 6, 19, 17, 14, 9, 7, 3, 5, 20, 13 |
| T | sensation of foreign body | 10 | 6, 19, 17, 14, 9, 7, 3, 5, 20, 13 |
| T | sensitivity of teeth | 10 | 6, 19, 17, 14, 9, 7, 3, 5, 20, 13 |
| T | sexual/reproductive function: other | 10 | 6, 19, 17, 14, 9, 7, 3, 5, 20, 13 |
| T | sinus headache | 10 | 6, 19, 17, 14, 9, 7, 3, 5, 20, 13 |
| T | skin and subcutaneous tissue disorders - other, basal cell carcinoma per biopsy | 10 | 6, 19, 17, 14, 9, 7, 3, 5, 20, 13 |
| T | skin and subcutaneous tissue disorders - other, ecchymotic nod l arm | 10 | 6, 19, 17, 14, 9, 7, 3, 5, 20, 13 |
| T | skin and subcutaneous tissue disorders - other, skin lesion | 10 | 6, 19, 17, 14, 9, 7, 3, 5, 20, 13 |
| T | skin and subcutaneous tissue disorders - other, specify | 10 | 6, 19, 17, 14, 9, 7, 3, 5, 20, 13 |
| T | skin and subcutaneous tissue disorders - other, specify: chapped lips | 10 | 6, 19, 17, 14, 9, 7, 3, 5, 20, 13 |
| T | skin erosion | 10 | 6, 19, 17, 14, 9, 7, 3, 5, 20, 13 |
| T | skin hypopigmentation | 10 | 6, 19, 17, 14, 9, 7, 3, 5, 20, 13 |
| T | skin irritation | 10 | 6, 19, 17, 14, 9, 7, 3, 5, 20, 13 |
| T | skin reaction | 10 | 6, 19, 17, 14, 9, 7, 3, 5, 20, 13 |
| T | skin toxicity | 10 | 6, 19, 17, 14, 9, 7, 3, 5, 20, 13 |
| T | skin ulceration | 10 | 6, 19, 17, 14, 9, 7, 3, 5, 20, 13 |
| T | small bowel obstruction | 10 | 6, 19, 17, 14, 9, 7, 3, 5, 20, 13 |
| T | sodium, low (hyponatremia) | 10 | 6, 19, 17, 14, 9, 7, 3, 5, 20, 13 |
| T | sodium, serum-high (hypernatremia) | 10 | 6, 19, 17, 14, 9, 7, 3, 5, 20, 13 |
| T | soft tissue necrosis | 10 | 6, 19, 17, 14, 9, 7, 3, 5, 20, 13 |
| T | stenosis (incl anastomotic) esophagus | 10 | 6, 19, 17, 14, 9, 7, 3, 5, 20, 13 |
| T | stomatitis necrotising | 10 | 6, 19, 17, 14, 9, 7, 3, 5, 20, 13 |
| T | stricture, anastomotic, gu - ureter | 10 | 6, 19, 17, 14, 9, 7, 3, 5, 20, 13 |
| T | stricture, anastomotic, gu - urethra | 10 | 6, 19, 17, 14, 9, 7, 3, 5, 20, 13 |
| T | stricture, gi - rectum | 10 | 6, 19, 17, 14, 9, 7, 3, 5, 20, 13 |
| T | stroke | 10 | 6, 19, 17, 14, 9, 7, 3, 5, 20, 13 |
| T | superficial thrombophlebitis | 10 | 6, 19, 17, 14, 9, 7, 3, 5, 20, 13 |
| T | supraventricular and nodal arrhythmia | 10 | 6, 19, 17, 14, 9, 7, 3, 5, 20, 13 |
| T | supraventricular arrhythmias (svt/atrial fibrillation/flutter | 10 | 6, 19, 17, 14, 9, 7, 3, 5, 20, 13 |
| T | supraventricular extrasystoles | 10 | 6, 19, 17, 14, 9, 7, 3, 5, 20, 13 |
| T | sweating | 10 | 6, 19, 17, 14, 9, 7, 3, 5, 20, 13 |
| T | syncope (fainting) | 10 | 6, 19, 17, 14, 9, 7, 3, 5, 20, 13 |
| T | syndromes - other | 10 | 6, 19, 17, 14, 9, 7, 3, 5, 20, 13 |
| T | tachyarrhythmia | 10 | 6, 19, 17, 14, 9, 7, 3, 5, 20, 13 |
| T | tearing | 10 | 6, 19, 17, 14, 9, 7, 3, 5, 20, 13 |
| T | tearing (watery eyes) | 10 | 6, 19, 17, 14, 9, 7, 3, 5, 20, 13 |
| T | tenderness | 10 | 6, 19, 17, 14, 9, 7, 3, 5, 20, 13 |
| T | testicular pain | 10 | 6, 19, 17, 14, 9, 7, 3, 5, 20, 13 |
| T | thrombosis, hematoma, hypomagnesemia, extrapyramidal/restless | 10 | 6, 19, 17, 14, 9, 7, 3, 5, 20, 13 |
| T | thrombosis/embolism | 10 | 6, 19, 17, 14, 9, 7, 3, 5, 20, 13 |
| T | thrombosis/embolism - pulmonary embolism | 10 | 6, 19, 17, 14, 9, 7, 3, 5, 20, 13 |

[Fig. 20-66]

| | | | |
|---|---|---|---|
| T | thrombosis/embolism (vascular access-related) | 10 | 6, 19, 17, 14, 9, 7, 3, 5, 20, 13 |
| T | thrombosis/thrombus/embolism | 10 | 6, 19, 17, 14, 9, 7, 3, 5, 20, 13 |
| T | tinea pedis | 10 | 6, 19, 17, 14, 9, 7, 3, 5, 20, 13 |
| T | trichiasis | 10 | 6, 19, 17, 14, 9, 7, 3, 5, 20, 13 |
| T | trichomegaly | 10 | 6, 19, 17, 14, 9, 7, 3, 5, 20, 13 |
| T | trismus | 10 | 6, 19, 17, 14, 9, 7, 3, 5, 20, 13 |
| T | trousseau's syndrome | 10 | 6, 19, 17, 14, 9, 7, 3, 5, 20, 13 |
| T | tumor lysis syndrome | 10 | 6, 19, 17, 14, 9, 7, 3, 5, 20, 13 |
| T | tumor pain | 10 | 6, 19, 17, 14, 9, 7, 3, 5, 20, 13 |
| T | tumour associated fever | 10 | 6, 19, 17, 14, 9, 7, 3, 5, 20, 13 |
| T | tumour pain | 10 | 6, 19, 17, 14, 9, 7, 3, 5, 20, 13 |
| T | typhlitis (cecal inflammation) | 10 | 6, 19, 17, 14, 9, 7, 3, 5, 20, 13 |
| T | ulcer, gi | 10 | 6, 19, 17, 14, 9, 7, 3, 5, 20, 13 |
| T | ulcer,gi - esophagus | 10 | 6, 19, 17, 14, 9, 7, 3, 5, 20, 13 |
| T | ulceration | 10 | 6, 19, 17, 14, 9, 7, 3, 5, 20, 13 |
| T | unevaluable event | 10 | 6, 19, 17, 14, 9, 7, 3, 5, 20, 13 |
| T | unknown hospitalization not required | 10 | 6, 19, 17, 14, 9, 7, 3, 5, 20, 13 |
| T | upper gastrointestinal hemorrhage | 10 | 6, 19, 17, 14, 9, 7, 3, 5, 20, 13 |
| T | upper gi hemorrage | 10 | 6, 19, 17, 14, 9, 7, 3, 5, 20, 13 |
| T | upper respiratory | 10 | 6, 19, 17, 14, 9, 7, 3, 5, 20, 13 |
| T | urinary color change | 10 | 6, 19, 17, 14, 9, 7, 3, 5, 20, 13 |
| T | urinary frequency | 10 | 6, 19, 17, 14, 9, 7, 3, 5, 20, 13 |
| T | urinary frequency/urgency | 10 | 6, 19, 17, 14, 9, 7, 3, 5, 20, 13 |
| T | urinary retention (including neurogenic bladder) | 10 | 6, 19, 17, 14, 9, 7, 3, 5, 20, 13 |
| T | urinary tract pain | 10 | 6, 19, 17, 14, 9, 7, 3, 5, 20, 13 |
| T | urine discoloration | 10 | 6, 19, 17, 14, 9, 7, 3, 5, 20, 13 |
| T | urine leukocyte esterase | 10 | 6, 19, 17, 14, 9, 7, 3, 5, 20, 13 |
| T | urogenital disorder | 10 | 6, 19, 17, 14, 9, 7, 3, 5, 20, 13 |
| T | vaginal dryness | 10 | 6, 19, 17, 14, 9, 7, 3, 5, 20, 13 |
| T | vascular - other | 10 | 6, 19, 17, 14, 9, 7, 3, 5, 20, 13 |
| T | vascular access complication | 10 | 6, 19, 17, 14, 9, 7, 3, 5, 20, 13 |
| T | vasovagal episode | 10 | 6, 19, 17, 14, 9, 7, 3, 5, 20, 13 |
| T | vein injury - extremity-upper | 10 | 6, 19, 17, 14, 9, 7, 3, 5, 20, 13 |
| T | ventricular arrhythmia - fibrillation | 10 | 6, 19, 17, 14, 9, 7, 3, 5, 20, 13 |
| T | ventricular arrhythmia - pvcs | 10 | 6, 19, 17, 14, 9, 7, 3, 5, 20, 13 |
| T | ventricular arrhythmia - tachycardia | 10 | 6, 19, 17, 14, 9, 7, 3, 5, 20, 13 |
| T | ventricular arrhythmia - trigeminny | 10 | 6, 19, 17, 14, 9, 7, 3, 5, 20, 13 |
| T | vision-blurred vision | 10 | 6, 19, 17, 14, 9, 7, 3, 5, 20, 13 |
| T | vitreous floaters | 10 | 6, 19, 17, 14, 9, 7, 3, 5, 20, 13 |
| T | voice alteration | 10 | 6, 19, 17, 14, 9, 7, 3, 5, 20, 13 |
| T | voice changes | 10 | 6, 19, 17, 14, 9, 7, 3, 5, 20, 13 |
| T | watering eyes | 10 | 6, 19, 17, 14, 9, 7, 3, 5, 20, 13 |
| T | watery eye | 10 | 6, 19, 17, 14, 9, 7, 3, 5, 20, 13 |
| T | wound complication, non-infectious | 10 | 6, 19, 17, 14, 9, 7, 3, 5, 20, 13 |
| T | xeroderma | 10 | 6, 19, 17, 14, 9, 7, 3, 5, 20, 13 |
| T | ypocalcemia (low calcium level in blood) | 10 | 6, 19, 17, 14, 9, 7, 3, 5, 20, 13 |
| T | extrapyramidal disorder | 15 | 3, 15, 8, 17, 13, 14, 12, 1, 18, 16, 9, 22, 5, 19, 6 |
| T | irritability | 15 | 3, 15, 8, 17, 13, 14, 12, 1, 18, 16, 9, 22, 5, 19, 6 |
| T | psychosis | 15 | 13, 2, 14, 11, 19, 3, 7, 1, 24, 23, 17, 10, 16, 20, 4 |
| T | somnolence | 16 | 4, 9, 1, 5, 8, 6, 3, 12, 14, 2, 7, 22, 21, 23, 24, 20 |
| T | fatigue | 16 | 5, 6, 17, 23, 3, 22, 15, 16, 4, 21, 14, 11, 8, 24, 2, 19 |
| T | abdominal hernia | 16 | 16, 5, 20, 3, 17, 13, 2, 7, 14, 22, 19, 10, 24, 8, 11, 9 |
| T | angina pectoris | 16 | 16, 5, 20, 3, 17, 13, 2, 7, 14, 22, 19, 10, 24, 8, 11, 9 |
| T | ankle fracture | 16 | 16, 5, 20, 3, 17, 13, 2, 7, 14, 22, 19, 10, 24, 8, 11, 9 |
| T | appendicitis perforated | 16 | 16, 5, 20, 3, 17, 13, 2, 7, 14, 22, 19, 10, 24, 8, 11, 9 |
| T | bile duct stone | 16 | 16, 5, 20, 3, 17, 13, 2, 7, 14, 22, 19, 10, 24, 8, 11, 9 |
| T | breast cancer | 16 | 16, 5, 20, 3, 17, 13, 2, 7, 14, 22, 19, 10, 24, 8, 11, 9 |
| T | bronchitis chronic | 16 | 16, 5, 20, 3, 17, 13, 2, 7, 14, 22, 19, 10, 24, 8, 11, 9 |
| T | cardiac failure | 16 | 16, 5, 20, 3, 17, 13, 2, 7, 14, 22, 19, 10, 24, 8, 11, 9 |
| T | cardiac failure congestive | 16 | 16, 5, 20, 3, 17, 13, 2, 7, 14, 22, 19, 10, 24, 8, 11, 9 |
| T | cardiac murmur | 16 | 16, 5, 20, 3, 17, 13, 2, 7, 14, 22, 19, 10, 24, 8, 11, 9 |
| T | cardio-respiratory arrest | 16 | 16, 5, 20, 3, 17, 13, 2, 7, 14, 22, 19, 10, 24, 8, 11, 9 |
| T | carpal tunnel syndrome | 16 | 16, 5, 20, 3, 17, 13, 2, 7, 14, 22, 19, 10, 24, 8, 11, 9 |
| T | cholecystitis | 16 | 16, 5, 20, 3, 17, 13, 2, 7, 14, 22, 19, 10, 24, 8, 11, 9 |
| T | cholelithiasis | 16 | 16, 5, 20, 3, 17, 13, 2, 7, 14, 22, 19, 10, 24, 8, 11, 9 |

[Fig. 20-67]

| | | | |
|---|---|---|---|
| T | colon cancer | 16 | 16, 5, 20, 3, 17, 13, 2, 7, 14, 22, 19, 10, 24, 8, 11, 9 |
| T | concussion | 16 | 16, 5, 20, 3, 17, 13, 2, 7, 14, 22, 19, 10, 24, 8, 11, 9 |
| T | costochondritis | 16 | 16, 5, 20, 3, 17, 13, 2, 7, 14, 22, 19, 10, 24, 8, 11, 9 |
| T | craniocerebral injury | 16 | 16, 5, 20, 3, 17, 13, 2, 7, 14, 22, 19, 10, 24, 8, 11, 9 |
| T | ear infection | 16 | 16, 5, 20, 3, 17, 13, 2, 7, 14, 22, 19, 10, 24, 8, 11, 9 |
| T | eczema | 16 | 16, 5, 20, 3, 17, 13, 2, 7, 14, 22, 19, 10, 24, 8, 11, 9 |
| T | gastric ulcer haemorrhage | 16 | 16, 5, 20, 3, 17, 13, 2, 7, 14, 22, 19, 10, 24, 8, 11, 9 |
| T | gastroenteritis viral | 16 | 16, 5, 20, 3, 17, 13, 2, 7, 14, 22, 19, 10, 24, 8, 11, 9 |
| T | glaucoma | 16 | 16, 5, 20, 3, 17, 13, 2, 7, 14, 22, 19, 10, 24, 8, 11, 9 |
| T | hand fracture | 16 | 16, 5, 20, 3, 17, 13, 2, 7, 14, 22, 19, 10, 24, 8, 11, 9 |
| T | head injury | 16 | 16, 5, 20, 3, 17, 13, 2, 7, 14, 22, 19, 10, 24, 8, 11, 9 |
| T | hernia | 16 | 16, 5, 20, 3, 17, 13, 2, 7, 14, 22, 19, 10, 24, 8, 11, 9 |
| T | hypovolaemia | 16 | 16, 5, 20, 3, 17, 13, 2, 7, 14, 22, 19, 10, 24, 8, 11, 9 |
| T | inguinal hernia | 16 | 16, 5, 20, 3, 17, 13, 2, 7, 14, 22, 19, 10, 24, 8, 11, 9 |
| T | injury | 16 | 16, 5, 20, 3, 17, 13, 2, 7, 14, 22, 19, 10, 24, 8, 11, 9 |
| T | ligament rupture | 16 | 16, 5, 20, 3, 17, 13, 2, 7, 14, 22, 19, 10, 24, 8, 11, 9 |
| T | ligament sprain | 16 | 16, 5, 20, 3, 17, 13, 2, 7, 14, 22, 19, 10, 24, 8, 11, 9 |
| T | localised infection | 16 | 16, 5, 20, 3, 17, 13, 2, 7, 14, 22, 19, 10, 24, 8, 11, 9 |
| T | loss of consciousness | 16 | 16, 5, 20, 3, 17, 13, 2, 7, 14, 22, 19, 10, 24, 8, 11, 9 |
| T | lower respiratory tract infection | 16 | 16, 5, 20, 3, 17, 13, 2, 7, 14, 22, 19, 10, 24, 8, 11, 9 |
| T | malignant melanoma | 16 | 16, 5, 20, 3, 17, 13, 2, 7, 14, 22, 19, 10, 24, 8, 11, 9 |
| T | metastases to liver | 16 | 16, 5, 20, 3, 17, 13, 2, 7, 14, 22, 19, 10, 24, 8, 11, 9 |
| T | migraine | 16 | 16, 5, 20, 3, 17, 13, 2, 7, 14, 22, 19, 10, 24, 8, 11, 9 |
| T | osteoarthritis | 16 | 16, 5, 20, 3, 17, 13, 2, 7, 14, 22, 19, 10, 24, 8, 11, 9 |
| T | ovarian cyst | 16 | 16, 5, 20, 3, 17, 13, 2, 7, 14, 22, 19, 10, 24, 8, 11, 9 |
| T | pancreatic carcinoma | 16 | 16, 5, 20, 3, 17, 13, 2, 7, 14, 22, 19, 10, 24, 8, 11, 9 |
| T | pancreatitis acute | 16 | 16, 5, 20, 3, 17, 13, 2, 7, 14, 22, 19, 10, 24, 8, 11, 9 |
| T | radius fracture | 16 | 16, 5, 20, 3, 17, 13, 2, 7, 14, 22, 19, 10, 24, 8, 11, 9 |
| T | renal cell carcinoma | 16 | 16, 5, 20, 3, 17, 13, 2, 7, 14, 22, 19, 10, 24, 8, 11, 9 |
| T | rhabdomyolysis | 16 | 16, 5, 20, 3, 17, 13, 2, 7, 14, 22, 19, 10, 24, 8, 11, 9 |
| T | rib fracture | 16 | 16, 5, 20, 3, 17, 13, 2, 7, 14, 22, 19, 10, 24, 8, 11, 9 |
| T | sudden death | 16 | 16, 5, 20, 3, 17, 13, 2, 7, 14, 22, 19, 10, 24, 8, 11, 9 |
| T | suicidal ideation | 16 | 16, 5, 20, 3, 17, 13, 2, 7, 14, 22, 19, 10, 24, 8, 11, 9 |
| T | type diabetes mellitus | 16 | 16, 5, 20, 3, 17, 13, 2, 7, 14, 22, 19, 10, 24, 8, 11, 9 |
| T | umbilical hernia | 16 | 16, 5, 20, 3, 17, 13, 2, 7, 14, 22, 19, 10, 24, 8, 11, 9 |
| T | wrist fracture | 16 | 16, 5, 20, 3, 17, 13, 2, 7, 14, 22, 19, 10, 24, 8, 11, 9 |
| T | lymphocele | 16 | 6, 14, 9, 10, 18, 21, 5, 20, 16, 3, 17, 22, 24, 8, 23, 4 |
| T | abdominal distension | 16 | 8, 2, 6, 22, 1, 15, 10, 13, 14, 5, 21, 18, 9, 23, 12, 11 |
| T | acute kidney injury | 16 | 8, 2, 6, 22, 1, 15, 10, 13, 14, 5, 21, 18, 9, 23, 12, 11 |
| T | anal fistula | 16 | 8, 2, 6, 22, 1, 15, 10, 13, 14, 5, 21, 18, 9, 23, 12, 11 |
| T | arrhythmia | 16 | 8, 2, 6, 22, 1, 15, 10, 13, 14, 5, 21, 18, 9, 23, 12, 11 |
| T | ascites | 16 | 8, 2, 6, 22, 1, 15, 10, 13, 14, 5, 21, 18, 9, 23, 12, 11 |
| T | atelectasis | 16 | 8, 2, 6, 22, 1, 15, 10, 13, 14, 5, 21, 18, 9, 23, 12, 11 |
| T | atrial tachycardia | 16 | 8, 2, 6, 22, 1, 15, 10, 13, 14, 5, 21, 18, 9, 23, 12, 11 |
| T | benign prostatic hyperplasia | 16 | 8, 2, 6, 22, 1, 15, 10, 13, 14, 5, 21, 18, 9, 23, 12, 11 |
| T | bradycardia | 16 | 8, 2, 6, 22, 1, 15, 10, 13, 14, 5, 21, 18, 9, 23, 12, 11 |
| T | catheter site infection | 16 | 8, 2, 6, 22, 1, 15, 10, 13, 14, 5, 21, 18, 9, 23, 12, 11 |
| T | cerebral haemorrhage | 16 | 8, 2, 6, 22, 1, 15, 10, 13, 14, 5, 21, 18, 9, 23, 12, 11 |
| T | cerebrovascular accident | 16 | 8, 2, 6, 22, 1, 15, 10, 13, 14, 5, 21, 18, 9, 23, 12, 11 |
| T | colitis | 16 | 8, 2, 6, 22, 1, 15, 10, 13, 14, 5, 21, 18, 9, 23, 12, 11 |
| T | deep vein thrombosis | 16 | 8, 2, 6, 22, 1, 15, 10, 13, 14, 5, 21, 18, 9, 23, 12, 11 |
| T | dermatitis | 16 | 8, 2, 6, 22, 1, 15, 10, 13, 14, 5, 21, 18, 9, 23, 12, 11 |
| T | diverticulitis | 16 | 8, 2, 6, 22, 1, 15, 10, 13, 14, 5, 21, 18, 9, 23, 12, 11 |
| T | drug hypersensitivity | 16 | 8, 2, 6, 22, 1, 15, 10, 13, 14, 5, 21, 18, 9, 23, 12, 11 |
| T | duodenal ulcer | 16 | 8, 2, 6, 22, 1, 15, 10, 13, 14, 5, 21, 18, 9, 23, 12, 11 |
| T | dysarthria | 16 | 8, 2, 6, 22, 1, 15, 10, 13, 14, 5, 21, 18, 9, 23, 12, 11 |
| T | dyspnoea exertional | 16 | 8, 2, 6, 22, 1, 15, 10, 13, 14, 5, 21, 18, 9, 23, 12, 11 |
| T | erysipelas | 16 | 8, 2, 6, 22, 1, 15, 10, 13, 14, 5, 21, 18, 9, 23, 12, 11 |
| T | erythema | 16 | 8, 2, 6, 22, 1, 15, 10, 13, 14, 5, 21, 18, 9, 23, 12, 11 |
| T | general physical health deterioration | 16 | 8, 2, 6, 22, 1, 15, 10, 13, 14, 5, 21, 18, 9, 23, 12, 11 |
| T | haematoma | 16 | 8, 2, 6, 22, 1, 15, 10, 13, 14, 5, 21, 18, 9, 23, 12, 11 |
| T | haematuria | 16 | 8, 2, 6, 22, 1, 15, 10, 13, 14, 5, 21, 18, 9, 23, 12, 11 |
| T | haemorrhoids | 16 | 8, 2, 6, 22, 1, 15, 10, 13, 14, 5, 21, 18, 9, 23, 12, 11 |
| T | herpes zoster | 16 | 8, 2, 6, 22, 1, 15, 10, 13, 14, 5, 21, 18, 9, 23, 12, 11 |
| T | hip fracture | 16 | 8, 2, 6, 22, 1, 15, 10, 13, 14, 5, 21, 18, 9, 23, 12, 11 |
| T | hydronephrosis | 16 | 8, 2, 6, 22, 1, 15, 10, 13, 14, 5, 21, 18, 9, 23, 12, 11 |
| T | hyperkalaemia | 16 | 8, 2, 6, 22, 1, 15, 10, 13, 14, 5, 21, 18, 9, 23, 12, 11 |

[Fig. 20-68]

| T | hypokalaemia | 16 | 8, 2, 6, 22, 1, 15, 10, 13, 14, 5, 21, 18, 9, 23, 12, 11 |
|---|---|---|---|
| T | hypoxia | 16 | 8, 2, 6, 22, 1, 15, 10, 13, 14, 5, 21, 18, 9, 23, 12, 11 |
| T | ileus | 16 | 8, 2, 6, 22, 1, 15, 10, 13, 14, 5, 21, 18, 9, 23, 12, 11 |
| T | intestinal obstruction | 16 | 8, 2, 6, 22, 1, 15, 10, 13, 14, 5, 21, 18, 9, 23, 12, 11 |
| T | iron deficiency anaemia | 16 | 8, 2, 6, 22, 1, 15, 10, 13, 14, 5, 21, 18, 9, 23, 12, 11 |
| T | ischaemic stroke | 16 | 8, 2, 6, 22, 1, 15, 10, 13, 14, 5, 21, 18, 9, 23, 12, 11 |
| T | lung infection | 16 | 8, 2, 6, 22, 1, 15, 10, 13, 14, 5, 21, 18, 9, 23, 12, 11 |
| T | mental status changes | 16 | 8, 2, 6, 22, 1, 15, 10, 13, 14, 5, 21, 18, 9, 23, 12, 11 |
| T | musculoskeletal chest pain | 16 | 8, 2, 6, 22, 1, 15, 10, 13, 14, 5, 21, 18, 9, 23, 12, 11 |
| T | obesity | 16 | 8, 2, 6, 22, 1, 15, 10, 13, 14, 5, 21, 18, 9, 23, 12, 11 |
| T | osteoporosis | 16 | 8, 2, 6, 22, 1, 15, 10, 13, 14, 5, 21, 18, 9, 23, 12, 11 |
| T | pericardial effusion | 16 | 8, 2, 6, 22, 1, 15, 10, 13, 14, 5, 21, 18, 9, 23, 12, 11 |
| T | peritonitis | 16 | 8, 2, 6, 22, 1, 15, 10, 13, 14, 5, 21, 18, 9, 23, 12, 11 |
| T | peritonitis bacterial | 16 | 8, 2, 6, 22, 1, 15, 10, 13, 14, 5, 21, 18, 9, 23, 12, 11 |
| T | pleural effusion | 16 | 8, 2, 6, 22, 1, 15, 10, 13, 14, 5, 21, 18, 9, 23, 12, 11 |
| T | pneumonia aspiration | 16 | 8, 2, 6, 22, 1, 15, 10, 13, 14, 5, 21, 18, 9, 23, 12, 11 |
| T | post procedural infection | 16 | 8, 2, 6, 22, 1, 15, 10, 13, 14, 5, 21, 18, 9, 23, 12, 11 |
| T | postoperative wound infection | 16 | 8, 2, 6, 22, 1, 15, 10, 13, 14, 5, 21, 18, 9, 23, 12, 11 |
| T | pulmonary embolism | 16 | 8, 2, 6, 22, 1, 15, 10, 13, 14, 5, 21, 18, 9, 23, 12, 11 |
| T | pulmonary fibrosis | 16 | 8, 2, 6, 22, 1, 15, 10, 13, 14, 5, 21, 18, 9, 23, 12, 11 |
| T | rectal haemorrhage | 16 | 8, 2, 6, 22, 1, 15, 10, 13, 14, 5, 21, 18, 9, 23, 12, 11 |
| T | renal failure | 16 | 8, 2, 6, 22, 1, 15, 10, 13, 14, 5, 21, 18, 9, 23, 12, 11 |
| T | renal failure acute | 16 | 8, 2, 6, 22, 1, 15, 10, 13, 14, 5, 21, 18, 9, 23, 12, 11 |
| T | respiratory distress | 16 | 8, 2, 6, 22, 1, 15, 10, 13, 14, 5, 21, 18, 9, 23, 12, 11 |
| T | sciatica | 16 | 8, 2, 6, 22, 1, 15, 10, 13, 14, 5, 21, 18, 9, 23, 12, 11 |
| T | septic shock | 16 | 8, 2, 6, 22, 1, 15, 10, 13, 14, 5, 21, 18, 9, 23, 12, 11 |
| T | sinus bradycardia | 16 | 8, 2, 6, 22, 1, 15, 10, 13, 14, 5, 21, 18, 9, 23, 12, 11 |
| T | skin ulcer | 16 | 8, 2, 6, 22, 1, 15, 10, 13, 14, 5, 21, 18, 9, 23, 12, 11 |
| T | small intestinal obstruction | 16 | 8, 2, 6, 22, 1, 15, 10, 13, 14, 5, 21, 18, 9, 23, 12, 11 |
| T | spinal compression fracture | 16 | 8, 2, 6, 22, 1, 15, 10, 13, 14, 5, 21, 18, 9, 23, 12, 11 |
| T | spinal fracture | 16 | 8, 2, 6, 22, 1, 15, 10, 13, 14, 5, 21, 18, 9, 23, 12, 11 |
| T | supraventricular tachycardia | 16 | 8, 2, 6, 22, 1, 15, 10, 13, 14, 5, 21, 18, 9, 23, 12, 11 |
| T | thrombosis | 16 | 8, 2, 6, 22, 1, 15, 10, 13, 14, 5, 21, 18, 9, 23, 12, 11 |
| T | upper gastrointestinal haemorrhage | 16 | 8, 2, 6, 22, 1, 15, 10, 13, 14, 5, 21, 18, 9, 23, 12, 11 |
| T | ureteric obstruction | 16 | 8, 2, 6, 22, 1, 15, 10, 13, 14, 5, 21, 18, 9, 23, 12, 11 |
| T | urinary tract infection | 16 | 8, 2, 6, 22, 1, 15, 10, 13, 14, 5, 21, 18, 9, 23, 12, 11 |
| T | urosepsis | 16 | 8, 2, 6, 22, 1, 15, 10, 13, 14, 5, 21, 18, 9, 23, 12, 11 |
| T | ventricular fibrillation | 16 | 8, 2, 6, 22, 1, 15, 10, 13, 14, 5, 21, 18, 9, 23, 12, 11 |
| T | ventricular tachycardia | 16 | 8, 2, 6, 22, 1, 15, 10, 13, 14, 5, 21, 18, 9, 23, 12, 11 |
| T | wound infection | 16 | 8, 2, 6, 22, 1, 15, 10, 13, 14, 5, 21, 18, 9, 23, 12, 11 |
| T | gastrointestinal disorder - other: hypersalivation | 16 | 19, 24, 14, 8, 18, 16, 5, 22, 11, 9, 10, 3, 4, 13, 15, 7 |
| T | hypersalivation | 16 | 19, 24, 14, 8, 18, 16, 5, 22, 11, 9, 10, 3, 4, 13, 15, 7 |
| T | tachycardia >100 beats/min (supine) | 16 | 19, 24, 14, 8, 18, 16, 5, 22, 11, 9, 10, 3, 4, 13, 15, 7 |

[Fig. 21-1]
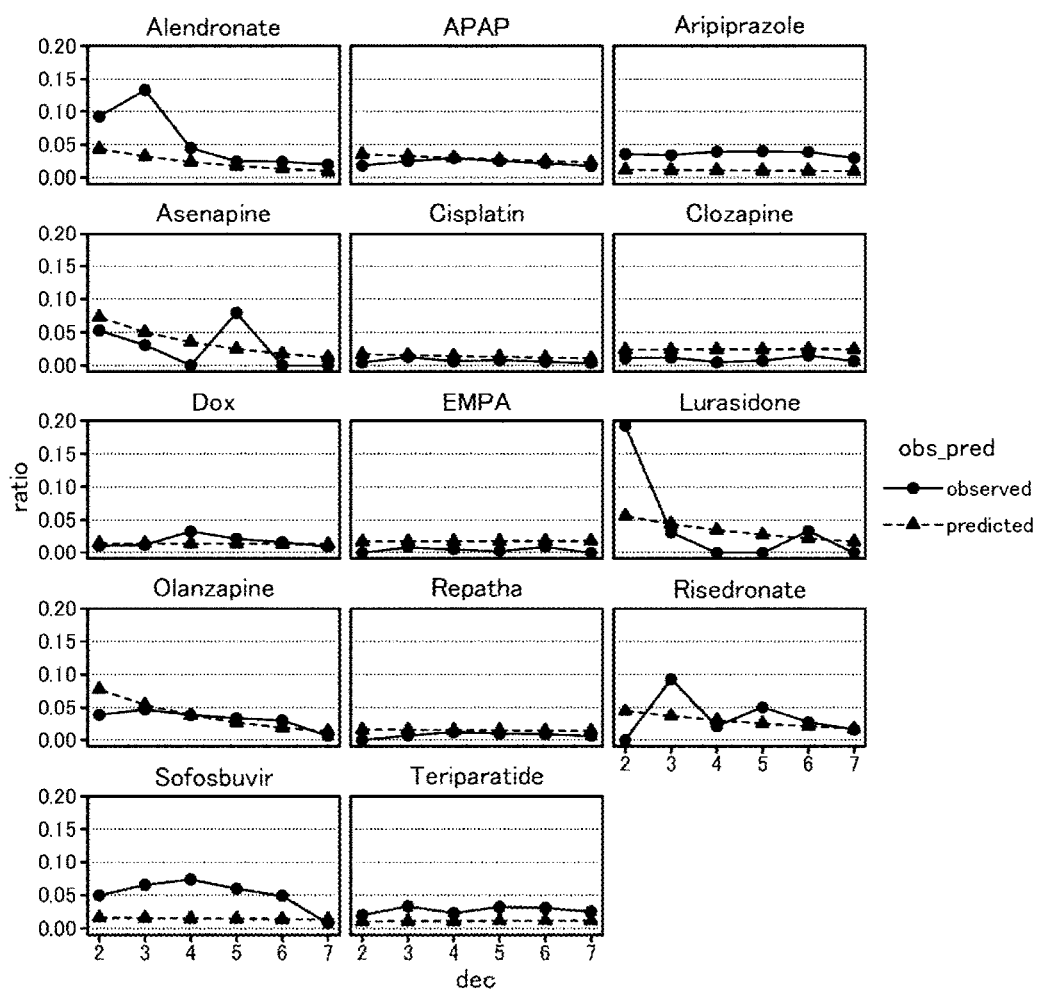

[Fig. 21-2]
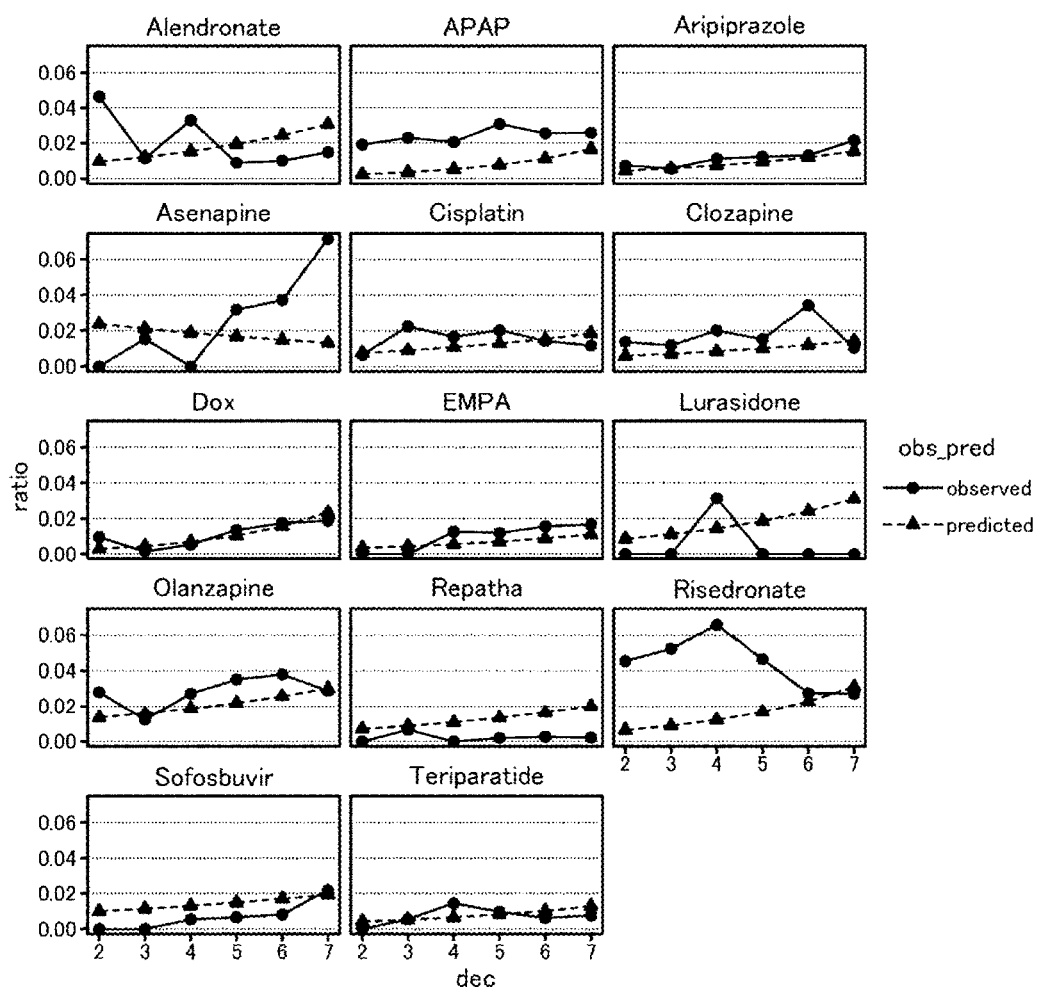

[Fig. 21-3]
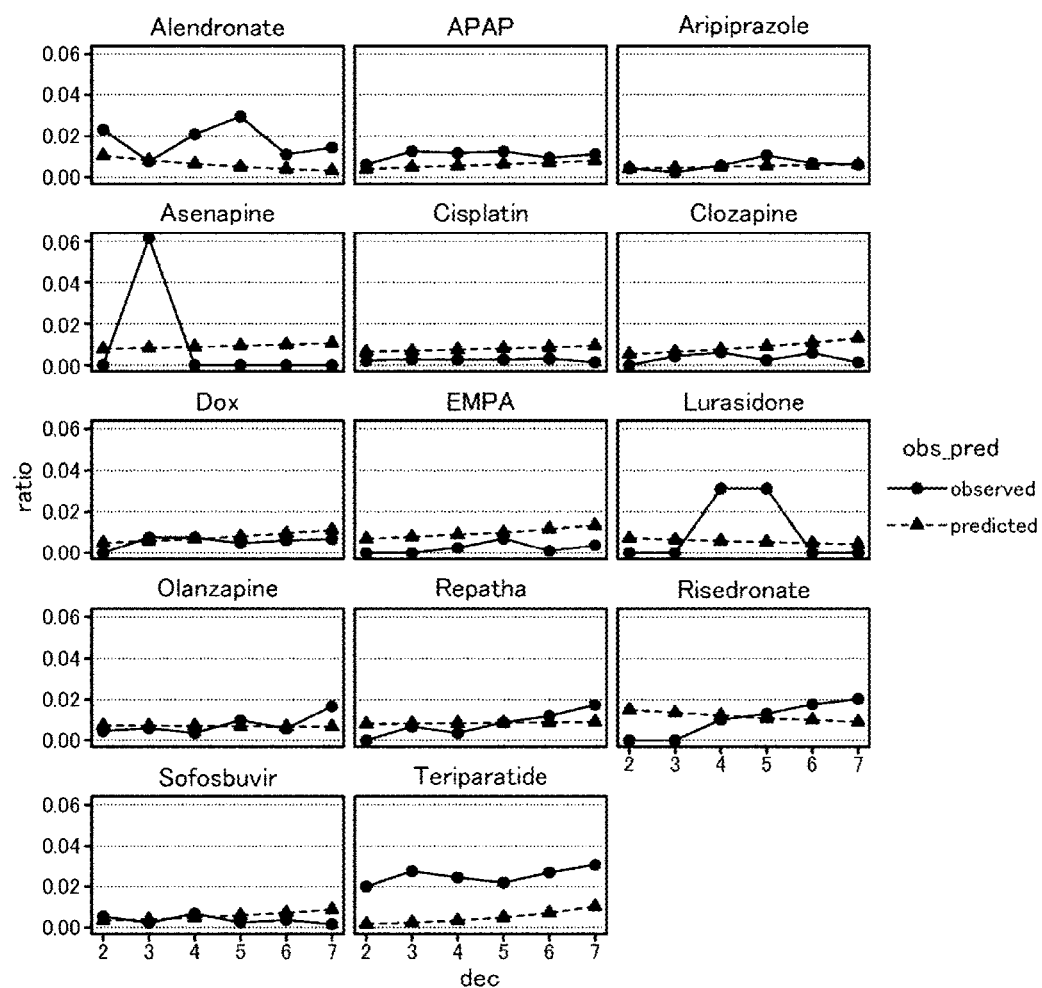

[Fig. 21-4]
Pollakiuria
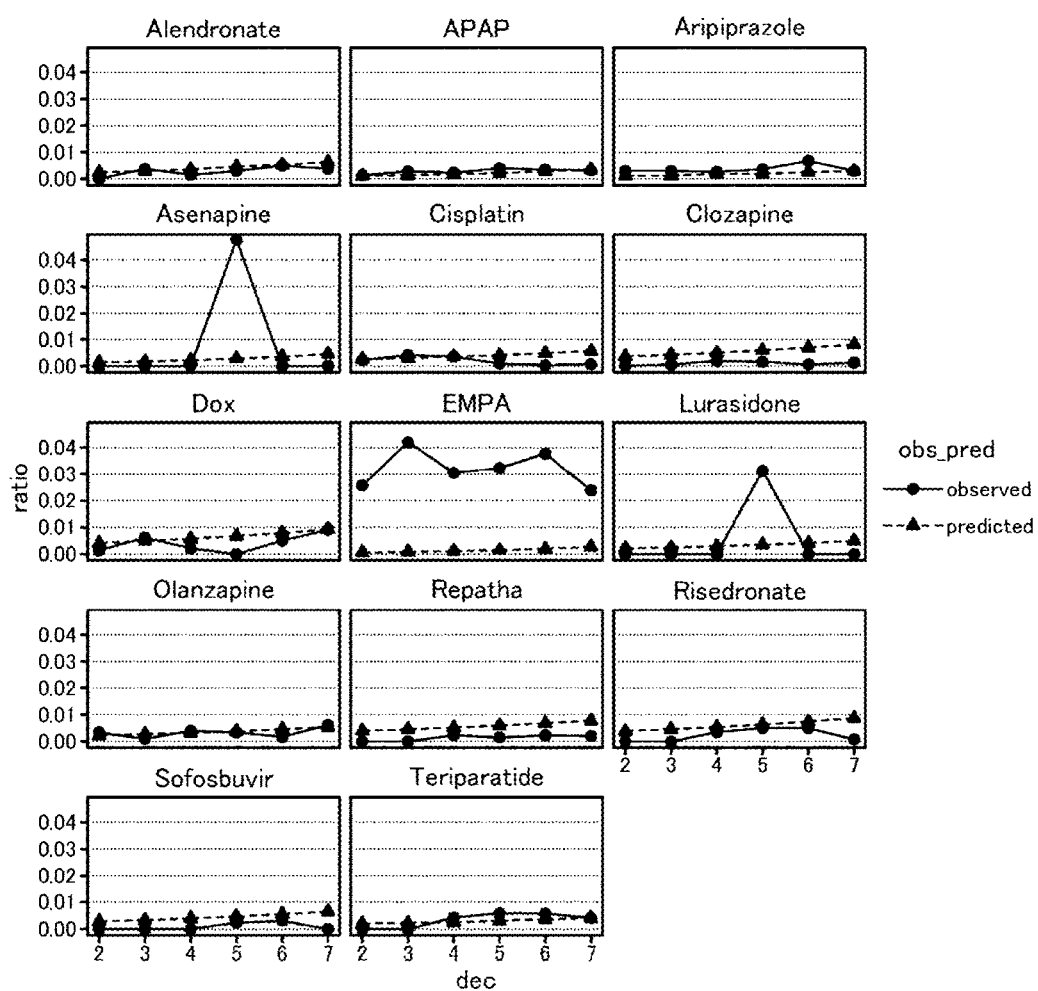

[Fig. 21-5]
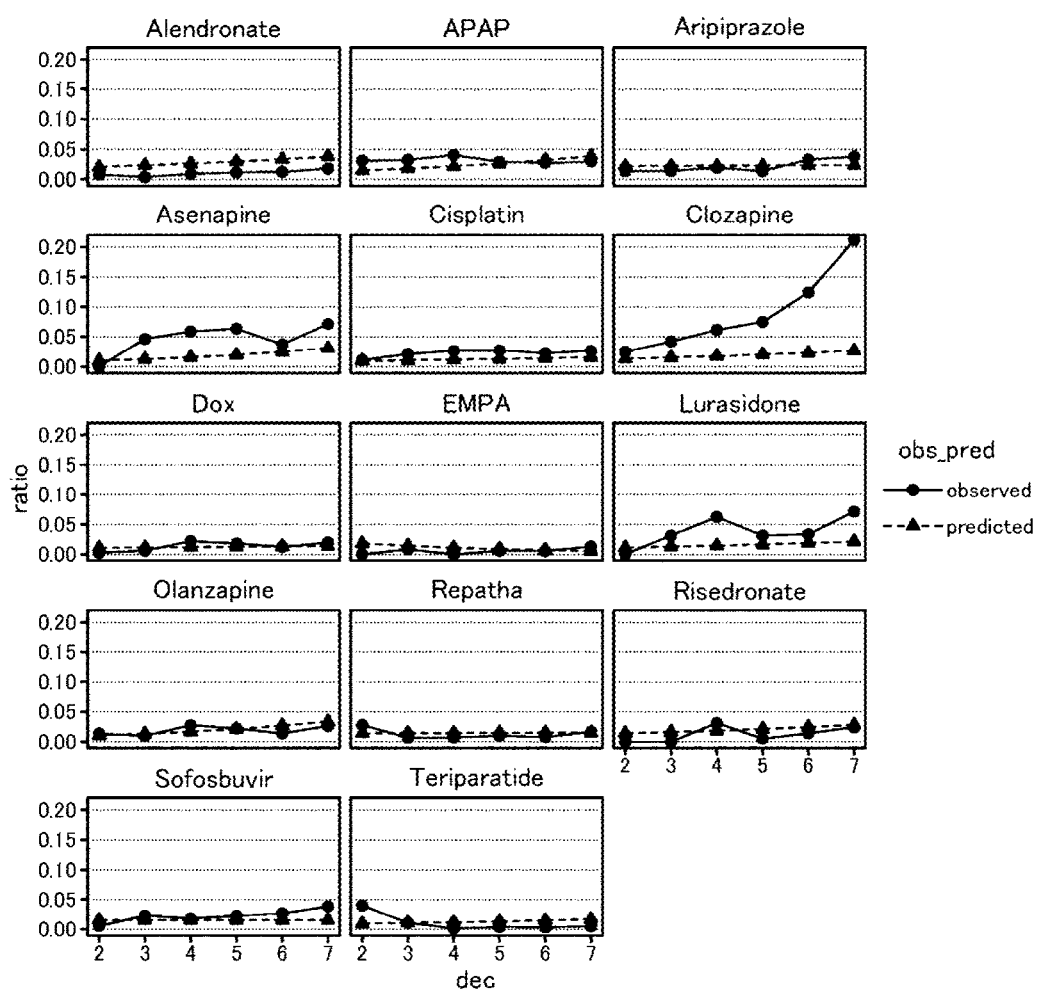

ARTIFICIAL INTELLIGENCE MODEL FOR PREDICTING ACTIONS OF TEST SUBSTANCE IN HUMANS

TECHNICAL FIELD

The present disclosure relates to a method for training an artificial intelligence model for predicting one or more actions of a test substance in humans using a set of data indicating the dynamics of one or more biomarkers in one organ or in each of multiple different organs collected from non-human animals to which multiple existing substances with known actions in humans have been individually administered, and also relates to a training device, a training program, a method for predicting one or more actions of a test substance in humans, a prediction device, a prediction program, and a prediction system.

BACKGROUND ART

PTL 1 discloses a method for predicting the efficacy or side effects of a test substance, including the steps of obtaining similarity of patterns for calculating similarity of patterns of inter-organ cross talk indicators between subject data and reference data by comparing the subject data regarding an inter-organ cross talk indicator in one or more organs of an individual to which the test substance has been administered with predetermined reference data on the corresponding inter-organ cross talk indicator, the subject data being derived from cells or tissue originating from the one or more organs; and predicting the efficacy or side effects of the test substance in the one or more organs and/or one or more organs other than the one or more organs by using the similarity of patterns of the inter-organ cross talk indicators as a measure.

New drug development begins with drug discovery research to find candidate substances for new drugs (discovery phase), followed by preclinical studies using animals and cultured cells (phase 0). Then, clinical trials in humans including phases I to III are conducted, after which only substances that have passed the clinical trials are allowed to apply for authorization to receive approval for manufacturing and marketing the substances as pharmaceutical products from the Ministry of Health, Labor and Welfare. Even after the substances have been approved as pharmaceutical products through review and are marketed, an observation period is set in order to monitor adverse-events and other efficacy that could not be expected at the development and approval review stages. Thus, launching a new drug takes an enormous amount of time and money. Nonetheless, the probability that a substance found in the discovery phase will be ultimately approved for manufacture and marketing is about 1.6%. Additionally, merely 13.8% of the substances that pass the preclinical trials show an effect during clinical trials (after preclinical trials until phase III) without showing adverse-events, and are allowed to apply for authorization. In other words, more than 80% of candidate substances drop out during phases I to III of clinical trials. The loss due to this dropout is thought to be 150 million dollars to 200 million dollars per substance, which is enormous.

CITATION LIST

Patent Literature

PTL 1: WO2016/208776

SUMMARY OF INVENTION

Technical Problem

If actions such as effects and adverse-events of a candidate substance in humans can be predicted as early as possible in new drug development, such loss can be reduced. As shown in FIG. 2A, shown later, in the conventional method, the effects of a test substance in humans have been predicted by speculating the mechanism of biological reaction, for example, based on databases such as of mice, previously reported pathological mechanisms and previously reported clinical data; and linking the structure and activity of an existing drug to the speculated mechanism; further followed by linking the result to the structure of the test substance and activity of the test substance on non-human animals or cultured cells. However, this method requires an enormous variety of information because the method predicts a biological mechanism based on a large amount of information. Additionally, the biological reaction mechanism itself is logically constructed based on the prediction; thus, if the predicted biological reaction mechanism is wrong in the first place, the actions of the test substance will be incorrectly predicted. Therefore, it is difficult to efficiently predict actions such as effects and adverse-events of a candidate substance in humans at present.

An object of the present disclosure is to efficiently predict one or more actions of a test substance in humans from actions of the test substance in non-human animals.

Solution to Problem

The present inventor conducted extensive research and found that actions such as effects and adverse-events of a test substance in humans can be efficiently predicted from the dynamics of one or more biomarkers in multiple different organs of non-human animals to which the test substance has been administered, by using an artificial intelligence model trained using, as training data, a set of data indicating the dynamics of one or more biomarkers in multiple different organs collected from non-human animals to which multiple existing substances have been administered and using actions of the multiple existing substances in humans.

The present invention includes the following embodiments.

Item 1

A method for training an artificial intelligence model,
the method comprising inputting into the artificial intelligence model a set of first training data and second training data or a set of the second training data to train the artificial intelligence model,
wherein the set of first training data contains a set of data indicating the dynamics of one or more biomarkers in one organ or in each of the multiple different organs,
the one organ or the multiple different organs are collected from individual non-human animals to which multiple existing substances with known actions in humans have been individually administered,
the second training data contains information on a known action in humans, the information on a known action in humans being obtained from each of the multiple existing substances administered to the non-human animals, and
the artificial intelligence model predicts one or more actions of a test substance in humans from a set of data that indicates the dynamics of one or more biomarkers in one organ or in each of multiple different organs of non-human animals to which the test substance has been administered, the one organ or the multiple different organs respectively corresponding to the one organ or the multiple different organs collected at the time of generating the set of first training data.

Item 2

The method for training an artificial intelligence model according to Item 1, wherein each item of the data indicating the dynamics of one or more biomarkers in the one organ or in each of the multiple different organs is linked to information on the name of one of the multiple existing substances administered to non-human animals, information on the name of one of the collected organs, and information on the name of one of the biomarkers, the information on a known action in humans is linked to the information on the name of one of the multiple existing substances administered to non-human animals, and the set of data indicating the dynamics of one or more biomarkers in the one organ or in each of the multiple organs is linked to the respective information on a known action in humans on the basis of the information on the name of one of the multiple existing substances administered to non-human animals to train the artificial intelligence model.

Item 3

The method for training an artificial intelligence model according to Item 1 or 2, wherein the information on a known action in humans includes information on the rate of occurrence of the action, and the artificial intelligence model outputs a prediction result as a score that corresponds to the degree of association with each action.

Item 4

The method for training an artificial intelligence model according to Item 3, wherein the score is indicated by at least two quantiles.

Item 5

The method for training an artificial intelligence model according to any one of Items 1 to 4, wherein the information on a known action in humans includes information on the demographic profile of individual humans from whom the information on a known action in humans has been obtained, and the second training data is stratified according to each demographic profile of the humans.

Item 6

The method for training an artificial intelligence model according to Item 5, wherein the demographic profile of individual humans is at least one of age group and gender.

Item 7

The method for training an artificial intelligence model according to Item 5 or 6, wherein the artificial intelligence model predicts one or more actions of the test substance in humans according to the demographic profile of individual humans.

Item 8

The method for training an artificial intelligence model according to any one of Items 1 to 7, wherein the one or more actions are at least one member selected from the group consisting of adverse-events of the existing substances, pharmacokinetics of the existing substances, and indications of the existing substances.

Item 9

The method for training an artificial intelligence model according to any one of Items 1 to 8, wherein the test substance does not include the existing substances and substances equivalent to the existing substances.

Item 10

The method for training an artificial intelligence model according to any one of Items 1 to 8, wherein the test substance is one member selected from the group consisting of the existing substances and substances equivalent to the existing substances.

Item 11

The method for training an artificial intelligence model according to any one of Items 1 to 10, wherein the one or more biomarkers are a transcriptome.

Item 12

The method for training an artificial intelligence model according to any one of Items 1 to 11, wherein the artificial intelligence model is support vector machine (SVM), relevance vector machine (RVM), naive Bayes, logistic regression, random forest, feedforward neural network, deep learning, K-nearest neighbor algorithm, AdaBoost, bagging, C4.5, kernel approximation, stochastic gradient descent (SGD) classifier, lasso, ridge regression, elastic net, SGD regression, kernel regression, LOWESS regression, matrix factorization, non-negative matrix factorization, kernel matrix factorization, interpolation, kernel smoother, or collaborative filtering.

Item 13

A method for predicting one or more actions of a test substance in humans, the method comprising the steps of:

obtaining test data, the test data containing a set of data indicating the dynamics of one or more biomarkers in one organ or in multiple organs collected from non-human animals to which the test substance has been administered, and inputting the test data into an artificial intelligence model trained by the method of any one of Items 1 to 12, and predicting one or more actions of the test substance in humans on the basis of the input test data by the trained artificial intelligence model.

Item 14

The method according to Item 13, wherein the test substance is an existing substance or a substance equivalent to the existing substance, and the one or more actions are one or more new indications of the existing substance.

Item 15

A prediction device for predicting one or more actions of a test substance in humans, the device comprising a processing unit, the processing unit configured to:

obtain test data, wherein the test data contains a set of data indicating the dynamics of one or more biomarkers in one organ or in multiple organs collected from non-human animals to which the test substance has been administered, and input a set of the test data into an artificial intelligence model trained by the method of any one of Items 1 to 12, and, predict one or more actions of the test substance in humans on the basis of the input test data by the trained artificial intelligence model.

Item 16

A computer program for predicting one or more actions of a test substance in humans, the computer program causing a computer to execute a process including the steps of:

obtaining test data, the test data containing a set of data indicating the dynamics of one or more biomarkers in one organ or in multiple organs collected from non-human animals to which the test substance has been administered, and inputting the test data into an artificial intelligence model trained by the method of any one of Items 1 to 12, and, predicting one or more actions of the test substance in humans on the basis of the input test data by the trained artificial intelligence model.

Item 17

A system for predicting one or more actions of a test substance in humans, the system comprising a server device for transmitting test data, the test data containing a set of data indicating the dynamics of one or more biomarkers in one organ or in each of the multiple organs collected from non-human animals to which the test substance has been administered, and a prediction device for predicting one or more actions of the test substance in humans, the prediction device being connected to the server device via a network, wherein the server device includes a communication unit for transmitting the test data, the prediction device includes a processing unit and a communication unit, the communication unit of the prediction device receives the test data transmitted from the server device, and the processing unit inputs the test data received by the communication unit of the prediction device into an artificial intelligence model trained by the method of any one of Items 1 to 12, and predicts one or more actions of the test substance in human by the trained artificial intelligence model.

Item 18

A method for constructing a system for predicting one or more actions of a test substance in humans, the method comprising the steps of:

preparing a server device for transmitting test data, the test data containing a set of data indicating the dynamics of one or more biomarkers in one organ or in each of the multiple organs collected from non-human animals to which the test substance has been administered, and preparing a prediction device for predicting one or more actions of the test substance in humans, the prediction device being connected to the server device via a network, wherein the server device includes a communication unit for transmitting the test data, the prediction device includes a processing unit and a communication unit, the communication unit of the prediction device receives the test data transmitted from the server device, the processing unit inputs the test data received by the communication unit of the prediction device into an artificial intelligence model trained by the method of any one of Items 1 to 12, and predicts one or more actions of the test substance in human by the trained artificial intelligence model.

Item 19

A method for supporting in predicting one or more unknown actions of a test substance in humans, the method comprising the steps of:

inputting a set of first training data and a set of second training data into an artificial intelligence model provided with a matrix decomposition function, the first training data containing a set of data indicating the dynamics of one or more biomarkers in one organ or in each of the multiple different organs, the one organ or the multiple different organs being collected from individual non-human animals to which multiple existing substances with known actions in humans have been individually administered, the second training data containing information on a known action in humans, the information on a known action in humans being obtained from each of the multiple existing substances administered to non-human animals;

constructing a new matrix containing values output from the artificial intelligence model as new elements, the values each indicating the degree of association between information on the name of one of the existing substances and information on a known action; and suggesting, when an element equal to or greater than a threshold exists in the region of interest corresponding to the test substance, information on a known action that corresponds to the element equal to or greater than the threshold;

wherein the test substance is one member selected from the group consisting of existing substances and substances equivalent to the existing substances.

Item 20

The method according to Item 19, which is for use in drug repositioning.

Item 21

A device that supports in predicting one or more unknown actions of a test substance in humans, the device comprising a processing unit, wherein the processing unit executes a process of:

inputting a set of first training data and a set of second training data into an artificial intelligence model provided with a matrix decomposition function, the first training data containing a set of data indicating the dynamics of one or more biomarkers in one organ or in each of the multiple different organs, the one organ or the multiple different organs being collected from individual non-human animals to which multiple existing substances with known actions in humans have been individually administered, and the second training data containing information on a known action in humans, the information on a known action in humans being obtained from each of the multiple existing substances administered to non-human animals;

constructing a new matrix containing values output from the artificial intelligence model as new elements, the values each indicating the degree of association between information on the name of one of the existing substances and information on a known action; and suggesting, when an element equal to or greater than a threshold exists in the region of interest corresponding to the test substance, information on a known action that corresponds to the element equal to or greater than the threshold;

wherein the test substance is one member selected from the group consisting of existing substances and substances equivalent to the existing substances.

Item 22

The device according to Item 21, which is for use in drug repositioning.

Item 23

A method for using a database that stores a set of first training data and a database that stores second training data or a set of the second training data in training an artificial intelligence model, wherein the artificial intelligence model predicts one or more actions of a test substance in humans from the dynamics of one or more biomarkers in one organ or in multiple different organs of non-human animals to which the test substance has been administered, the one organ or the multiple different organs respectively corresponding to one or multiple organs collected at the time of generating the training data, the set of first training data is linked to the second training data or the set of the second training data via information on the name of one of multiple existing substances, the set of first training data contains a set of data indicating the dynamics of one or more biomarkers in the one organ or in the multiple different organs, and the one organ or the multiple different organs are collected from individual non-human animals to which the multiple existing substances with known actions in humans have been individually administered, and the second training data contains information on a known action in humans, the information on a known action in humans being obtained from each of the multiple existing substances administered to non-human animals.

Item 24

The method according to any one of Items 1 to 14, 19, and 20, which is executed by a computer.

Item 25

A computer-readable storage medium that stores the prediction program of Item 16.

Advantageous Effects of Invention

The effects of a test substance in humans can be efficiently predicted.

BRIEF DESCRIPTION OF DRAWINGS

FIG. 1 is a diagram explaining an outline of the prediction method according to the present disclosure.

FIG. 2 is a diagram showing a comparison between a conventional method and the prediction method according to the present disclosure. FIG. 2A outlines a conventional method. FIG. 2B outlines the prediction method according to the present disclosure.

FIG. 3 shows an example of adverse-events collectable from FAERS. FIG. 3 also shows the scores of actual rate of occurrence of adverse-event and predicted rate of occurrence of adverse-event, and the difference between them.

FIG. 4 shows an example of pharmacokinetics collectable from Drugs@FDA and DAILYMED.

FIG. 5 shows an example of data on the dynamics of biomarkers.

FIG. 6 shows an example of data on actions in humans. FIG. 6A shows a case where the action is pharmacokinetic, FIG. 6B shows a case where the action is a adverse-event, and FIG. 6C shows a case where the action is an indication.

FIG. 7A illustrates a configuration example of a training device and a configuration example of a prediction device. FIG. 7B shows a configuration example of an artificial intelligence training system.

FIG. 8 illustrates a configuration example of hardware of a training device and a configuration example of hardware of a prediction device.

FIG. 9 is a flowchart showing a flow of a method for training an artificial intelligence model.

FIG. 10 is a flowchart showing a flow of a method for training an artificial intelligence model.

FIG. 11 is a flowchart showing a flow of a method for updating a trained artificial intelligence model.

FIG. 12 is a flowchart showing a flow of a method for predicting one or more actions in humans.

FIG. 13 is a flowchart showing a flow of a method for predicting one or more actions in humans.

FIG. 14 is a flowchart showing a flow of the operation of a prediction system.

FIG. 15 is a graph showing the difference between the prediction results of adverse-events in humans and the actual scores.

FIG. 16 shows the prediction results of bioavailability.

FIG. 17 shows the prediction results of drug distribution using EMPA.

FIG. 18 shows examples of drug repositioning. FIG. 18A shows already known drug efficacy. FIG. 18B shows predicted drug efficacy.

FIG. 19 shows bioavailability prediction results based on the dynamics of a transcriptome of three organs selected using SVM.

FIG. 20 shows the evaluation results of prediction effects depending on the number of organs.

FIG. 21 shows the evaluation results of prediction effects according to stratification.

DESCRIPTION OF EMBODIMENTS

1. Outline of Prediction Method and Explanation of Terms

First, an outline of the prediction method will be described with reference to FIG. 1, and the differences between the conventional method and the prediction method included in the present disclosure will be described with reference to FIG. 2.

The prediction method predicts one or more actions of a test substance in humans. Preferably, the prediction method predicts one or more actions of a test substance in humans on the basis of the dynamics of one or more biomarkers in non-human animals to which individual existing substances with known actions in humans have been administered and on the basis of known actions of the existing substances in humans. More preferably, the prediction method is completed using an artificial intelligence model.

As shown in FIG. 1, for example, drugs A, B, and C are individually administered as existing substances to non-human animals such as mice, and organs or tissues (part of organs) are collected from the non-human animals. The dynamics of one or more biomarkers in the collected organs or tissues are analyzed to generate a set of first training data. Second training data is generated from a human clinical database, such as of adverse-events, efficacy, pharmacokinetics, and indications of existing substances.

The artificial intelligence model is generated by training an artificial intelligence model using the set of first training data and the second training data. The prediction method includes predicting one or more actions of test substance X in humans from the dynamics of one or more biomarkers in one organ or in multiple organs of non-human animals to which test substance X has been administered, by using a trained artificial intelligence model. Specifically, one or multiple organs or parts of organs are individually collected from the non-human animals to which test substance X has been administered, and a set of data indicating the dynamics of the one or more biomarkers in each organ is obtained. Subsequently, the set of data is input into the trained artificial intelligence model to predict one or more actions of test substance X in humans by the artificial intelligence model.

As shown in FIG. 2A, in the conventional method, the efficacy and pharmacokinetics of test substance X have also been predicted from existing substances. However, the conventional method predicts a therapeutic mechanism regarding what kind of drug can treat a target disease, for example, from gene expression databases of mice, pathological mechanisms, clinical data, and existing drug information; and then predicts on the basis of the predicted mechanism what actions are provided when test substance X is administered to non-human animals.

In contrast, as shown in FIG. 2B, the prediction method included in the present disclosure is not bound by the therapeutic mechanism regarding what kind of drug can treat the target disease, and the method predicts the actions of test substance X in humans from the dynamics of one or more biomarkers in non-human animals to which existing substances have been actually administered.

More specifically, in the conventional method, if the predicted mechanism was incorrect, the subsequent prediction for test substance X would also be incorrect. However, the prediction method included in the present disclosure does not require such a mechanism prediction; it is not necessary to consider the risk involved in the prediction of the mechanism.

Additionally, although the working mechanism of an existing drug in such a conventional method is typically predicted on the basis of the chemical structure of the drug using an in silico drug discovery system etc., there is difficulty in predicting the working mechanism of macromolecular drugs, such as antibodies, for example. However, the prediction method included in the present disclosure can make a prediction for macromolecular test substances.

In the present disclosure, the non-human animals are not limited. Examples include mammals, such as mice, rats, dogs, cats, rabbits, cows, horses, goats, sheep, and pigs; and birds, such as chickens. The non-human animals are preferably mammals, such as mice, rats, dogs, cats, cows, horses, and pigs, more preferably mice and rats, and still more preferably mice. The non-human animals also include fetuses and chicks of these animals.

In the present disclosure, the term "substance" includes, for example, compounds; nucleic acids; carbohydrates; lipids; glycoproteins; glycolipids; lipoproteins; amino acids; peptides; proteins; polyphenols; chemokines; at least one metabolite selected from the group consisting of terminal metabolites of these substances, intermediary metabolites of these substances, and synthetic raw materials of these substances; metal ions; and microorganisms. The substance may be a single substance or a mixture of two or more kinds of substances. Preferably, the substance includes pharmaceutical products, quasi-drugs, cosmeceuticals, food, food for specified health use, food with function claims, and candidate products of these products. The substance further includes substances for which testing was stopped or suspended in the preclinical test or clinical test for regulatory approval.

The "existing substance" is not limited as long as the substance is an existing substance. Preferably, it is a substance with one or more known actions in humans. The "substance equivalent to an existing substance" can include substances that are similar to an existing substance in structure and action. "Similar action" in the present specification means having the same kind of action as that of an existing substance, regardless of a difference in intensity of action.

The "action" is not limited as long as the action is an effect that a substance has on humans. Examples of action include efficacy, adverse-events, and pharmacokinetics. The action is preferably efficacy and a adverse-event, and more preferably a adverse-event.

The "adverse-event" is not limited as long as the adverse-event is an effect that is determined to be harmful to humans. Preferable examples of adverse-events include those listed on FAERS (fda.gov/Drugs/GuidanceComplianceRegulatoryInformatio n/Surveillance/AdverseDrugEffects/ucm082193.htm) or clinicaltrials.gov (clinicaltrials.gov/), which are shown in FIG. 3.

The "efficacy" is not limited as long as the efficacy is an action to improve or treat diseases or symptoms in humans, or to stop or prevent the progression of diseases or symptoms in humans. Examples of the diseases and symptoms include those disclosed in all drug labels of DailyMed (dailymed.nlm.nih.gov/dailymed/spl-resources-all-drug-labels.cfm), Medical Subject Headings (nlm.nih.gov/mesh/meshhome.html), Drugs@FDA (accessdata.fda.gov/scripts/cder/daf/), and International Classification of Diseases (who.int/health-topics/international-classification-of-diseases). More specifically, indications include symptoms and diseases associated with ischemic diseases, such as thrombosis, embolism, and stenosis (in particular, heart, brain, lungs, large intestine, etc.); circulatory disorders, such as aneurysms, varicose veins, congestion, and bleeding (aortas, veins, lungs, liver, spleen, retinas, etc.); allergic diseases, such as allergic bronchitis and glomerulonephritis; degenerative diseases (nerves, skeletal muscles, etc.), such as dementia, including Alzheimer's dementia, Parkinson's disease, amyotrophic lateral sclerosis, and myasthenia gravis; tumors (benign epithelial tumors, benign non-epithelial tumors, malignant epithelial tumors, and malignant non-epithelial tumors); metabolic diseases (carbohydrate metabolism disorder, lipid metabolism disorder, and electrolyte imbalance); and autoimmune diseases, such as infectious diseases (bacteria, viruses, rickettsiae, *Chlamydia trachomatis*, fungi, protozoa, parasites, etc.), kidney diseases, systemic lupus erythematosus, and multiple sclerosis.

The rate of occurrence of adverse-events and efficacy can be determined by the following method. In the case of a adverse-event, for example, words indicating the name of a adverse-event are retrieved, for example, by text extraction from a database such as those at clinicaltrials.gov, FAERS, or DAILYMED for all drug labels. A single retrieved word can be counted as one reported adverse-event. For a single existing substance, the rate of occurrence of adverse-event can be calculated using the following equation: the rate of occurrence=(the number of reports on a particular adverse-event)/(the total number of reports on adverse-events for that existing substance). The rate of occurrence of efficacy of a single existing substance can also be determined by retrieving the name of the efficacy instead of a adverse-event from the database, for example, by text extraction, and using the following equation: the rate of occurrence=(the number of reports on a particular efficacy)/(the total number of reports on efficacies of that existing substance). Efficacy and other effects can also be retrieved in the same manner as with adverse-events by retrieving the words indicating efficacy. If a database contains a description of an action registered in sentence form, then syntax analysis, word segmentation, semantic analysis, etc. can be performed on the registered sentence by natural language processing, and then the text that corresponds to the action can be extracted.

The "pharmacokinetics" is not limited as long as it is the dynamics of the substance described above in the body of the mammals or birds described above. Examples include the dynamics illustrated in FIG. 4.

The "organ" is not limited as long as it is an organ present in the body of the mammals or birds described above. The organ, for example, of mammals, is at least one selected from circulatory organs (heart, arteries, veins, lymphatic vessels, etc.); respiratory organs (nasal cavity, nasal sinuses, larynx, trachea, bronchus, lungs, etc.); digestive organs (lips, malar region, palate, teeth, gingiva, tongue, salivary gland, pharynx, esophagus, stomach, duodenum, jejunum, ileum, cecum, appendix, ascending colon, transverse colon, sigmoid colon, rectum, anus, liver, gallbladder, bile duct, biliary tract, pancreas, pancreatic duct, etc.); urinary organs (urethra, bladder, ureter, kidney), nervous system organs (cerebrum, cerebellum, midbrain, brainstem, spinal cord, peripheral nerve, autonomic nerve, etc.); female reproductive organs (ovaries, fallopian tubes, uterus, vagina, etc.), breasts; male reproductive organs (penis, prostate, testis, epididymis, vas deferens); endocrine organs (hypothalamus, pituitary gland, pineal body, thyroid gland, accessory thyroid, adrenal gland, etc.); integumentary organs (skin, hair, nails, etc.); hematopoietic organs (blood, bone marrow, spleen, etc.); immune system organs (lymph nodes, tonsils, thymus, etc.); bone and soft tissue organs (bone, cartilage, skeletal muscle, connective tissue, ligaments, tendons, diaphragm, peritoneum, pleura, adipose tissue (brown adipose, white adipose) etc.); and sensory organs (eyeballs, eyelids, lacrimal glands, outer ear, middle ear, inner ear, cochlea, etc.). The organ is preferably at least one member selected from bone marrow, pancreas, skull, liver, skin, brain, pituitary gland, adrenal gland, thyroid gland, spleen, thymus, heart, lungs, aorta, skeletal muscle, testis, epididymal fat, eyeball, ileum, stomach, jejunum, large intestine, kidney, and parotid gland. Preferably, bone marrow, a pancreas, a skull, a liver, skin, a brain, a pituitary gland, an adrenal gland, a thyroid gland, a spleen, a thymus, a heart, a lung, an aorta, a skeletal muscle, a testis, epididymal fat, an eyeball, an ileum, a stomach, a jejunum, a large intestine, a kidney, and a parotid gland are all used in the prediction according to the present disclosure. The "multiple organs" is not limited as long as the number of organs is two or more. For example, the multiple organs can be selected from 2, 3, 4, 5, 6, 7, 8, 9, 10, 11, 12, 13, 14, 15, 16, 17, 18, 19, 20, 21, 22, 23, or 24 types of organs.

The "biomarker" refers to a biological substance that can change in the cells or tissues of the organs and/or in body fluid dependently on the administration of the substance described above. The biological substance that can be used as a biomarker is, for example, at least one member selected from nucleic acids; carbohydrates; lipids; glycoproteins; glycolipids; lipoproteins; amino acids, peptides; proteins; polyphenols; chemokines; at least one metabolite selected from the group consisting of terminal metabolites of these substances, intermediary metabolites of these substances, and synthetic raw materials of these substances; metal ions; and the like. More preferably, the biological substance that can be used as a biomarker is a nucleic acid. The biomarker is preferably a biological substance group that can change in the cells or tissues of the organs and/or in body fluid dependently on the administration of the substance described above. The biological substance group is, for example, a group of at least one member selected from nucleic acids; carbohydrates; lipids; glycoproteins; glycolipids; lipoproteins; amino acids, peptides; proteins; polyphenols; chemokines; at least one metabolite selected from the group consisting of terminal metabolites of these substances, intermediary metabolites of these substances, and synthetic raw materials of these substances; metal ions; and the like.

The "nucleic acid" is preferably a group of RNAs, such as mRNA, untranslated RNA, and microRNA, contained in a transcriptome; and more preferably a group of mRNAs. The RNA is preferably mRNA, untranslated RNA, and/or microRNA that can be expressed in the cells or tissues of the organs, or in the cells in body fluid; more preferably mRNA, untranslated RNA, and/or microRNA that can be detected, for example, by RNA-Seq (ncbi.nlm.nih.gov/gene?LinkName=genome_gene&from_uid=52, and jp.support.illumina.com/sequencing/sequencing_software/igenome.html). Preferably, all RNAs that can be analyzed using RNA-Seq are used in the prediction according to the present disclosure.

The "set of data indicating the dynamics of one or more biomarkers" refers to a set of data indicating that one or more biomarker have changed or have not changed, depending on the administration of an existing substance. Preferably, the dynamics of one or more biomarkers means that one or more biomarkers have changed in response to the administration of an existing substance. The data can be obtained, for example, by the following method. The amount or concentration of each biomarker in tissues, cells, or body fluid, etc. derived from organs collected from non-human animals to which an existing substance has been administered is measured to obtain a measured value for each organ of the individual non-human animals to which the existing substance has been administered. Additionally, the amount or concentration of each biomarker in tissues, cells, or body fluid, etc. derived from organs of non-human animals to which the existing substance is not administered (the organs correspond to the organs of which the measured values were obtained from the individuals to which the existing substance has been administered) is measured in the same manner to obtain a measured value of the individual non-human animals to which the existing substance is not administered. The measured value of each biomarker derived from each organ of the individuals to which the existing substance has been administered is compared with the measured value of each biomarker derived from each organ that corresponds to each organ of the individual non-human animals to which the existing substance is not administered to obtain a value indicating the difference as data. The term "correspond" as used here means that organs or biomarkers are the same or of same type. Preferably, the difference can be indicated by the ratio of a measured value of a biomarker derived from individuals to which an existing substance has been administered to a measured value of the corresponding biomarker in non-human animals to which the existing substance is not administered (e.g., a division value). For example, the data is a division value obtained by dividing the measured value of biomarker A in organ A derived from individuals to which an existing substance has been administered by the measured value of biomarker A in organ A derived from individuals to which the existing substance is not administered.

When the biomarker is a transcriptome, total RNA, which can be analyzed with RNA-seq, may be used. Alternatively, the expression of the RNA may be analyzed using, for example, WGCNA (labs.genetics.ucla.edu/horvath/CoexpressionNetwork/Rpack ages/WGCNA/), and the results may be divided into subsets (modules) of data indicating the dynamics of each RNA linked with the name of an organ and the name of a gene. For each module divided by WGCNA, the Pearson's correlation coefficient between the 1-of-K representation and each existing substance is calculated, and the module with the highest absolute value of the correlation coefficient is selected for each existing substance. RNA in each organ included in the selected module may be used as a biomarker.

Additionally, when the biomarker is a transcriptome in response to the administration of an existing substance, the change in the transcriptome in each organ of the animals to which an existing substance has been administered compared to that in the animals to which the existing substance is not administered can be measured using DESeq2 analysis. For example, the expression level of RNA in each organ collected from the animals to which the existing substance has been administered and the expression level of the gene in each corresponding organ collected from the animals to which the existing substance has not been administered are quantified by htseq-count to obtain count data for each. The organs and the expression level of the gene in each organ are compared. As a comparison result, the $\log_2$ (fold) value of the change in gene expression level of the animals to which the existing substance has been administered and the p value that serves as an index of the probability of the change in expression level are output for each gene for each organ. Whether the dynamics of the biomarker, such as a transcriptome, is present can be determined based on the $\log_2$ (fold) values.

The phrase "derived from an organ" means, for example, being collected from an organ, or being cultured from cells, tissues, or body fluid of the collected organ.

The "body fluid" includes serum, plasma, urine, spinal fluid, ascites, pleural effusion, saliva, gastric fluid, pancreatic juice, bile, breast fluid, lymph fluid, and interstitial fluid.

The measured value of a biomarker can be obtained by a known method. When the biomarker is a nucleic acid, the measured value can be obtained by sequencing, such as RNA-Seq, quantitative PCR, or the like. When the biomarker is, for example, a carbohydrate, a lipid, a glycolipid, an amino acid, a polyphenol, a chemokine, or at least one metabolite selected from the group consisting of terminal metabolites of these substances, intermediary metabolites of these substances, and synthetic raw materials of these substances, the measured value can be obtained, for example, by mass spectrometry. When the biomarker is a glycoprotein, a lipoprotein, a peptide, a protein, or the like, the measured value can be obtained, for example, by ELISA (enzyme-linked immunosorbent assay). The method for collecting tissues, cells, or body fluid derived from an organ for use in measurement and the pretreatment method for the measurement of a biomarker are also known.

The "test substance" refers to a substance whose action is to be evaluated. The test substance may be an existing substance, a substance equivalent to an existing substance, or a novel substance. The prediction method can predict one or more actions of the test substance in humans even if the relationship between the actions of the test substance and the actions of the existing substance or the substance equivalent to an existing substance is unknown. When the test substance is one member selected from existing substances and substances equivalent to the existing substances, unknown action of an existing substance or a substance equivalent to an existing substance can be found. The unknown action may be one or multiple actions. The unknown action is preferably a new indication. Drug repositioning can also be performed by predicting new indications of a test substance in humans. Administration of a test substance to a non-human animal is known. Data indicating the dynamics of one or more biomarkers in one organ or in multiple organs collected from non-human animals to which a test substance has been administered can be obtained in the same manner as with the data indicating the dynamics of one or more biomarkers in one organ or in multiple organs collected from non-human animals to which existing substances have been administered.

2. Construction of Artificial Intelligence Model 2-1. Generation of Training Data
(1) Generation of a Set of First Training Data The set of first training data may be composed of a set of data indicating the dynamics of one or more biomarkers in one organ or in each of the multiple different organs. The one organ or the multiple different organs can be collected from non-human animals to which multiple existing substances with known actions in humans have been individually administered. The set of first training data may be stored as a database.

Each item of the data indicating the dynamics of one or more biomarkers in each organ can be linked to information on the name of one of the multiple administered existing substances, information on the name of one of the collected organs, information on the name of one of the biomarkers, etc. Information on the name may be the name itself, a label such as an abbreviation, or a label value corresponding to each name.

Each item of data included in the set of data indicating the dynamics of one or more biomarkers serves as an element that constitutes a matrix in the set of first training data for the artificial intelligence model described later. When the biomarker is a transcriptome, the expression level of each RNA corresponds to the data and serves as an element of a matrix that constitutes the set of first training data. For example, when the biomarker is a transcriptome, the $\log_2$ (fold) value of each existing substance obtained by DESeq2 analysis may be used as an element of the set of first training data.

FIG. 5 shows part of an example of the set of first training data in the case of the use of a transcriptome as a biomarker. The data indicating the dynamics of one or more biomarkers is illustrated as a matrix in which labels that each represent a combination of the name of an organ and the name of a gene (which may be expressed as "organ-gene") are arranged in the column direction for each label of the name of an existing substance (row direction). Each element of the matrix shows the expression level of the gene indicated in the column label in the organ indicated in the column label collected from a non-human animal to which the existing substance indicated in the row label has been administered. More specifically, existing substances, "Aripiprazole" and "EMPA," are labels in the row direction. In the column direction, labels such as "Heart_Alas2," "Heart_Apod," "ParotidG_Alas2," and "ParotidG_Apod" are shown. "Heart" and "ParotidG" are labels indicating organs such as the heart and parotid gland. "Alas2" and "Apod" indicate the name of a gene from which RNA is derived. In other words, the label "Heart_Alas2" means "the expression of Alas2 gene in the heart."

The set of data indicating the dynamics of one or more biomarkers may be used as is as the set of first training data; alternatively, the set of data indicating the dynamics of one or more biomarkers may be subjected to normalization, dimensionality reduction, etc., and then used as the set of first training data. Examples of normalization include a method in which data indicating a difference in expression is converted such that the average value is 0, and the variance is 1. The average value in normalization can be the average value of each organ, the average value of each gene, or the average value of all data. Dimensionality reduction can be performed by statistical processing, such as principal component analysis. The population for performing statistical processing may be each organ, each gene, or total data. For example, when the biomarker is a transcriptome, only genes whose p value for the $\log_2$ (fold) value of each existing substance obtained by DESeq2 analysis is a predetermined value or below may be used as the set of first training data. The predetermined value may be, for example, $10^{-3}$ or $10^{-4}$, and preferably, $10^{-4}$.

The set of first training data can be updated by updating existing substances or adding data indicating the dynamics of new biomarkers.

(2) Generation of Second Training Data

The second training data can be composed of information on a known action in humans obtained from each of the multiple existing substances administered to non-human animals when the set of first training data is generated. In the second training data, information on a known action in humans of each existing substance administered to non-human animals when generating the set of first training data corresponds to one action (e.g., "headache"). The second training data can be obtained as a adverse-event, efficacy, pharmacokinetics, or an indication of an existing substance from already known databases. One, two, or more actions can be present in one existing substance. When there are two or more actions in one existing substance, the multiple actions constitute a set of the second training data. In the following description, the part simply described as "second training data" can be replaced with "a set of second training data" as necessary. Information on known actions in humans can be obtained by performing text extraction, natural language processing, digitizing processing, image analysis processing, etc. on the set of data stored in a database. For example, information on the name of each action corresponding to each existing substance administered to non-human animals when generating the set of first training data stored in a database can be extracted as information on a known action in humans, for example, by text extraction. Preferably, information on a known action in humans includes information on the name of an existing substance administered to non-human animals when the set of first training data is generated, with the information on a known action in humans linked with the information on the name of an action that corresponds to an existing substance. When the description regarding an action is registered in sentence form in a database, syntax analysis, word segmentation, semantic analysis, etc. can be performed on the sentence by natural language processing, and then the text that corresponds to the action can be extracted.

Information on a known action in humans can include information on the rate of occurrence of the action. Preferably, when the action is a adverse-event, the information on a known action in humans may include information on the rate of occurrence of the adverse-event that corresponds to an existing substance. When the information on a known action in humans includes information on the rate of occurrence of the action, the second training data can be stratified according to the rate of occurrence of the action. The quantile for stratifying the second training data is not limited as long as it is 2 or more. The quantile of rate of occurrence can be categorized into 2, 3, 4 or 5 stages, depending on the rate of occurrence of each action when an existing substance that has been administered to non-human animals is administered to humans.

Information on a known action in humans may include information on the demographic profile of humans from whom the information on a known action in humans has been obtained. Examples of demographic profile include age group and gender. The second training data can be stratified according to age group or gender. The quantile for stratifying age groups is not limited as long as it is 2 or more. Examples include quantiles of adults and non-adults; quantiles of juveniles, working ages, early elderly, and late elderly; and quantiles by age group such as 20s, 30s, 40s, 50s, 60s, and 70s.

When an artificial intelligence model is trained by stratifying the second training data according to the demographic profile of humans from whom information on a known action in humans of each existing substance has been obtained (e.g., age group and gender), the information on a known action in humans can include the following information.

For example, in the case of a adverse-event, reports on a adverse-event are extracted from a database, such as those at clinicaltrials.gov, FAERS, and all drug labels of DAILYMED on the basis of a word indicating a particular adverse-event described in the report. Subsequently, from the reports extracted on the basis of the word indicating the adverse-event, a report including a word indicating gender, or a number or word indicating age or age group, is extracted. For each existing substance, the rate of occurrence of a adverse-event is determined by gender, age group, and the combination of gender and age group. Subsequently, a polynomial for correspondence between the rate of occurrence and each group, such as an approximated linear function ($y=ax+b$; a and b are a coefficient), a quadratic function ($y=ax^2+bx+c$; a, b, and c are a coefficient), or a cubic function ($y=ax^3+bx^2+cx+d$; a, b, c, and d are a coefficient), is solved. The coefficients of the functions can be used by linking them with the rate of occurrence of a adverse-event. For efficacy instead of adverse-events, the coefficients of functions can also be used in combination with the rate of occurrence of efficacy in the same manner.

FIG. 6A shows an example of data on actions in humans used as the second training data. The examples of actions are pharmacokinetics (bioavailability and half-life (h)). The data on actions in humans are composed of rows each represented by a label of the name of an existing substance as information on the name of an existing substance administered to non-human animals, and columns each represented by a label indicating an pharmacokinetics item as information on an action in humans corresponding to the label of the name of an existing substance. Each cell contains as an example a specific value for bioavailability or half-life, which are elements.

FIG. 6B shows an example of the case in which an action in humans is a adverse-event. In FIG. 6B, adverse-events in humans are scored one by one on a scale of 1 to 4 according to the rate of occurrence illustrated in Table 3 shown later. However, it is not necessarily required to score the rate of occurrence of adverse-events, and a case in which a adverse-event has been confirmed may be expressed as "1," and a case in which no adverse-event has been confirmed may be expressed as "0."

The second training data can be updated by updating existing substances, updating known databases, etc.

2-2. Artificial Intelligence Model

The artificial intelligence model is not limited as long as the model can solve the problem according to the present invention. Examples include techniques similar to support vector machine (SVM), relevance vector machine (RVM), naive Bayes, logistic regression, random forest, feedforward neural network, deep learning, K-nearest neighbor algorithm, AdaBoost, bagging, C4.5, Kernel approximation, stochastic gradient descent (SGD) classifier, lasso, ridge regression, elastic net, SGD regression, kernel regression, LOWESS regression, matrix factorization, non-negative matrix factorization, kernel matrix factorization, interpolation, kernel smoothers, and collaborative filtering.

Examples of preferable artificial intelligence models for predicting adverse-events include SVM, RVM, naive Bayes, logistic regression, random forest, feedforward neural network, deep learning, K-nearest neighbor algorithm, AdaBoost, bagging, C4.5, kernel approximation, and SGD classifier.

Examples of preferable artificial intelligence models for predicting pharmacokinetics include SVM, RVM, naive Bayes, random forest, feedforward neural network, deep learning, lasso, ridge regression, elastic net, SGD regression, kernel regression, and LOWESS regression.

Examples of preferable artificial intelligence models for predicting indications include techniques similar to matrix factorization, non-negative matrix factorization, kernel matrix factorization, interpolation, kernel smoother, and collaborative filtering.

An artificial intelligence model with a function that performs matrix decomposition, such as matrix factorization, non-negative matrix factorization, or kernel matrix factorization, uses matrix R and matrix P to determine matrix S on the assumption that R≈PS. Thus, this matrix S can be considered to be a feature.

Techniques such as feedforward neural networks and deep learning can be described as an artificial intelligence model of the type in which training is performed by deep learning in training.

2-3. Training of Artificial Intelligence Model

An artificial intelligence model is trained using the set of first training data and the second training data or the set of the second training data described above to construct an artificial intelligence model. Constructing an artificial intelligence model may include training an untrained artificial intelligence model and retraining an artificial intelligence model that has been once trained. For retraining, the updated set of first training data and/or second training data described above can be used.

The set of first training data and the second training data or the set of the second training data are combined and input into an artificial intelligence model as training data. In the training data, the set of first training data is linked to the set of the second training data on the basis of the information on the name of each existing substance administered to non-human animals linked to respective item of the data indicating the dynamics of one or more biomarkers in each organ contained in the set of first training data, and the information on the name of each existing substance administered to the non-human animals linked to the information on a known action in humans contained in the second training data or the set of the second training data. The set of data indicating the dynamics of one or more biomarkers in each organ is linked to the respective information on a known action in humans that is "correct" (or true) to the set of data on the basis of the information on the name of one of the existing substances administered to non-human animals to train the artificial intelligence model.

If the artificial intelligence model trained for predicting actions is the type in which the algorithm of a single artificial intelligence model corresponds to one action (e.g., headache), such as SVM, relevance vector machine (RVM), naive Bayes, random forest, AdaBoost, C4.5, stochastic gradient descent (SGD) classifier, lasso, ridge regression, elastic net, SGD regression, or kernel regression, the set of first training data is linked to a single item of the second training data. If the trained artificial intelligence model is of the type in which a single artificial intelligence model can predict multiple actions (e.g., headache, vomiting), such as feedforward neural network, deep learning, or matrix decomposition, the first training data is linked to multiple the second training data items (i.e., a set of the second training data).

Take a look at FIGS. 5 and 6, for example. The rows of FIG. 5 indicated by the label of an existing substance are linked to respective cells shown in FIG. 6A one by one to generate training data to be input into an artificial intelligence model. Specifically, the row of Aripiprazole shown in FIG. 5 is linked to the Aripiprazole-bioavailability shown in FIG. 6A as one set of data. The row of Aripiprazole shown in FIG. 5 is linked to the Aripiprazole-half-life as one set of data. The row of EMPA shown in FIG. 5 is linked to the EMPA-bioavailability as one set of data. The row of EMPA shown in FIG. 5 is linked to the EMPA-half-life as one set of data. A total of 4 sets of data are generated as training data.

Additionally, the use of an artificial intelligence model based on matrix decomposition, such as matrix factorization, can generate training data, for example, with the matrix shown in FIG. 5 as matrix P (the first training data) and matrix R in which the rows indicate the name of existing substances and the columns indicate the name of indications as shown in FIG. 6C (the set of the second training data). For example, in matrix R, an indication reported for an existing substances is labeled "1," and an unreported indication is labeled "0." Using the element "1" of matrix R and matrix P shown in FIG. 5, matrix S that can decompose matrix R such that R≈PS is calculated. Matrix R is reconstructed from the calculated matrix S and matrix P using the formula R≈PS again, and the value of the element that corresponds to an indication not reported on the existing substance of matrix R is estimated. In other words, matrix S, which is a feature, is calculated using the information on the name of an existing substance labeled with element "1" of matrix R and the information on the name of an indication as the set of the second training data, and matrix P as the set of first training data. When an analysis is performed based on matrix decomposition, the test substance may be one member selected from existing substances and substances equivalent to existing substances.

If the artificial intelligence model trained for predicting one or more actions is of such a type that a single artificial intelligence model corresponds to one action (e.g., headache), such as SVM, relevance vector machine (RVM), naive Bayes, random forest, AdaBoost, C4.5, stochastic gradient descent (SGD) classifier, lasso, ridge regression, elastic net, SGD regression, or kernel regression, and stratified second training data is used, it is preferable to train the artificial intelligence model by stratified quantiles each by each.

To make a prediction by scoring the rate of occurrence of an action, an artificial intelligence model is trained, for example, such that the model outputs a score when the rate of occurrence is scored in accordance with the value of the rate of occurrence as shown in Tables 3 and 4 described later, and test data described later is input into the model. An artificial intelligence model that makes a prediction by scoring the rate of occurrence of an action is preferably SVM.

When stratified second training data is used, the coefficients of the polynomials described above may be used. The set of first training data is linked to the coefficients of a polynomial by information on the name of each existing substance administered to non-human animals to generate training data. In other words, the artificial intelligence model is trained such that the coefficients of a polynomial are output when test data described later is input. The artificial intelligence model that predicts the actions of each stratified group is preferably random forest.

2-4. Training Device for Artificial Intelligence Model

The artificial intelligence model described above can be constructed using, for example, the following training device 10. In the description of the device 10 and the operation of the device 10, the explanation of the terms in common with those described in the "Outline of Prediction Method and Explanation of Terms" section and the "Generation of Training Data" section above is incorporated herein.

The training device 10 (which may be referred to as "device 10" below) includes at least a processing unit 101 and a storage unit. The storage unit includes a main storage unit 102 and/or an auxiliary storage unit 104. Preferably, the device 10 may be a device for enabling the training method according to Items 1 to 12.

FIG. 7A illustrates the configuration of the device 10. The device 10 may be connected to an input unit 111, an output unit 112, and a storage medium 113. The device 10 may also be connected to a measurement device 30, such as a next-generation sequencer or a mass spectrometer. Specifically, the device 10 may constitute an artificial intelligence training system 50 that is connected to the measurement device 30 directly or via a network, for example.

FIG. 8 illustrates the configuration of hardware of the device 10. In the device 10, the processing unit 101, the main storage unit 102, a ROM (read-only memory) 103, the auxiliary storage unit 104, a communication interface (I/F) 105, an input interface (I/F) 106, an output interface (I/F) 107, and a media interface (I/F) 108 are communicably connected to each other via a bus 109.

The processing unit 101 includes a CPU, an MPU, or a GPU. The processing unit 101 executes a computer program stored in the auxiliary storage unit 104 or the ROM 103, and processes the obtained data, thereby enabling the device 10 to function. The processing unit 101 obtains as training data the set of data indicating the dynamics of one or more biomarkers in multiple different organs collected from non-human animals to which individual existing substances have been administered, described in section 1 above, and known actions of the existing substances in humans. The processing unit 101 also trains an artificial intelligence model by using these two types of training data.

The ROM 103 includes mask ROM, PROM, EPROM, EEPROM, or the like, and stores a computer program executed by the processing unit 101 and data used for the program. The ROM 103 stores a boot program executed by the processing unit 101 when the device 10 is started up and programs and settings for the operation of hardware of the device 10.

The main storage unit 102 includes RAM (random access memory), such as SRAM or DRAM. The main storage unit 102 is used to read out the computer programs saved in the ROM 103 and in the auxiliary storage unit 104. The main storage unit 102 is used as a workspace when the processing unit 101 executes these computer programs. The main storage unit 102 temporarily stores functions of the artificial intelligence model read from the auxiliary storage unit 104, such as training data obtained via a network.

The auxiliary storage unit 104 includes a semiconductor memory device, such as a hard disk and a flash memory, or an optical disk. The auxiliary storage unit 104 stores various computer programs to be executed by the processing unit 101, such as an operating system and application programs, and various setting data used in executing the computer programs. Specifically, the auxiliary storage unit 104 stores functions and training data for an artificial intelligence model before training, and a trained artificial intelligence model in a non-volatile manner.

The communication I/F 105 includes a serial interface, such as USB, IEEE 1394, or RS-232C; a parallel interface, such as SCSI, IDE, or IEEE 1284; an analog interface composed of a D/A converter or an A/D converter; or a network interface controller (NIC) etc. Under the control of the processing unit 101, the communication I/F 105 receives data from the measurement device 30 or other external device, and transmits or displays the information stored or generated by the device 10 to the measurement device 30 or outside as necessary. The communication I/F 105 may communicate with the measurement device 30 or other external device (not shown; e.g., another computer or a cloud system) via a network.

The input I/F 106 includes, for example, a serial interface such as USB, IEEE 1394, or RS-232C; a parallel interface such as SCSI, IDE, or IEEE 1284; or an analog interface composed of a D/A converter or an A/D converter. The input I/F 106 receives, for example, a character input, a click, or a voice input from the input unit 111. The received input information is stored in the main storage unit 102 or the auxiliary storage unit 104.

The input unit 111 includes, for example, a touchscreen, a keyboard, a mouse, a pen tablet, or a microphone, and performs character input or voice input on the device 10. The input unit 111 may be externally connected to the device 10 or may be integrated with the device 10.

The output I/F 107 includes, for example, the same interface as that of the input I/F 106. The output I/F 107 outputs the information generated by the processing unit 101 to the output unit 112. The output I/F 107 outputs the information that has been generated by the processing unit 101 and that has been stored in the auxiliary storage unit 104 to the output unit 112.

The output unit 112 includes, for example, a display, a printer, or the like, and displays measurement results transmitted from the measurement device 30, various operation windows in the device 10, training data, functions of an artificial intelligence model, and the like.

The media I/F 108 reads, for example, application software stored in the storage medium 113. The read application software, for example, is stored in the main storage unit 102 or the auxiliary storage unit 104. The media I/F 108 writes the information generated by the processing unit 101 on the storage medium 113. The media I/F 108 writes the information that has been generated by the processing unit 101 and that has been stored in the auxiliary storage unit 104 on the storage medium 113.

The storage medium 113 includes, for example, a flexible disk, CD-ROM, DVD-ROM, or the like. The storage medium 113 is connected to the media I/F 108 by a flexible disk drive, a CD-ROM drive, a DVD-ROM drive, or the like. The storage medium 113 may store an application program for the computer to execute an operation.

The processing unit 101 may obtain application software and various settings necessary for control of the device 10 via a network instead of reading them out from the ROM 103 or the auxiliary storage unit 104. The application program may be stored in an auxiliary storage unit of the server computer on the network. The device 10 can access the server computer to download the computer program and store the computer program in the ROM 103 or the auxiliary storage unit 104.

The ROM 103 or the auxiliary storage unit 104 has installed on it an operation system that provides a graphical user interface environment, such as Windows (registered trademark) manufactured and sold by Microsoft Corporation of the United States. The application program according to the second embodiment is assumed to be operated on the operating system. Specifically, the device 10 can be a personal computer or the like.

2-5. Operation 1 of Training Device

The training device 10 enables its function as a training device by allowing a processing unit to execute a computer program described later as application software.

With reference to FIG. 9, the operation of the device 10 is described here. FIG. 9 illustrates the operation in the case in which the set of first training data and the second training data are input into an artificial intelligence model to train the artificial intelligence model, as with SVM.

Receiving the input for process-start from the input unit 111 by the user, the processing unit 100 temporarily invokes, for example, an artificial intelligence model stored in the auxiliary storage unit 104 in the main storage unit 102. Alternatively, the processing unit 100 downloads an artificial intelligence model from, for example, a network via the communication I/F 105, and temporarily stores the downloaded model in the main storage unit 102. In another embodiment, the processing unit 100 may access an artificial intelligence model stored in a cloud.

The processing unit 100 obtains a set of data indicating the dynamics of one or more biomarkers, which is the set of first training data described for the method for training an artificial intelligence model, and information on one or more known actions of existing substances in humans, which is the second training data (step S1). The obtained set of first training data and second training data are stored in the auxiliary storage unit 104 or the main storage unit 102 by the processing unit 100. At this time, the processing unit 100 functions as a training data acquisition unit.

The processing unit 100 links one set of the set of first training data obtained in step S1 and the second training data with the information on the name of each existing substance administered to non-human animals contained in the set of first training data and the information on the name of each existing substance administered to non-human animals contained in the second training data, and inputs the linked data into a single artificial intelligence model (e.g., one set of functions in the case of SVM) (step S2). At this time, the processing unit 100 functions as a training data input unit. When the second training data is stratified, the processing unit 100 associates the set of first training data and each layer of the second training data with respective information on the name of an existing substance administered to non-human animals. For example, when the second training data is stratified into the first quantile and the second quantile, training data obtained by linking the set of first training data to the first quantile of the second training data ("the first quantile training data") is generated, and the first quantile training data is input into a single artificial intelligence model. The processing unit 100 also generates training data ("the second quantile training data") by linking the set of first training data to the set of the second quantile training data, and inputs the second quantile training data into another artificial intelligence model. The artificial intelligence model to which the first quantile training data is input and the artificial intelligence model to which the second quantile training data is input are of the same type, but are trained independently of each other.

Next, the processing unit 100 calculates parameters such as weights of a function of the artificial intelligence model, and trains the artificial intelligence model (step S3). Training an artificial intelligence model may include validation, generalization, etc. Examples of validation and generalization include the holdout method, the cross-validation method, AIC (an information theoretical criterion/Akaike information criterion), MDL (minimum description length), and WAIC (widely applicable information criterion). At this time, the processing unit 100 functions as an artificial intelligence model generation unit.

Next, the processing unit 100 determines whether training has been performed using all the second training data (step S4). If determination has been made on all actions (if "Yes"), the process goes to step 5, followed by storing the trained artificial intelligence model. This stored data is then saved in the auxiliary storage unit 104 of the device 10 or in a cloud. In step S4, if second training data that has not been used for training remains (if "No"), the process returns to step S1 to obtain a new set of first training data and second training data, and repeats steps S1 to S4 until all the second training data are processed.

The artificial intelligence model for use in operation 1 of the training device is preferably SMV or random forest.

2-6. Operation 2 of Training Device

The operation of another training device 10 is shown in FIG. 10. FIG. 10 illustrates the operation in the case in which the set of first training data and the set of the second training data are input into an artificial intelligence model, such as deep learning, to train the model. In the same manner as in the operation illustrated in FIG. 9, the processing unit 100 receives an input for process-start by the user from the input unit 111, and temporarily invokes the artificial intelligence model in the main storage unit 102.

The processing unit 100 obtains a set of data indicating the dynamics of one or more biomarkers, which is the set of first training data described for the method for training an artificial intelligence model, and a set of information on one or more known actions in humans, which is the set of the second training data (step S11). The obtained set of first training data and set of the second training data are stored in the auxiliary storage unit 104 or the main storage unit 102. At this time, the processing unit 100 functions as a training data acquisition unit.

Next, the processing unit 100 inputs the set of first training data and the set of the second training data to a single artificial intelligence model (e.g., a single neural network if the model is deep learning) (step S12). If the artificial intelligence model is a neural network, the set of first training data is input into the input layer, and the set of the second training data is input into the output layer. At this time, the processing unit 100 functions as a training data input unit.

Subsequently, the processing unit 100 calculates parameters such as weights of the functions of an artificial intelligence model, and constructs a trained artificial intelligence model (step S13). Training an artificial intelligence model may include validation, generalization, etc. Examples of validation and generalization include the holdout method, the cross validation method, AIC (an information theoretical criterion/Akaike information criterion), MDL (minimum description length), and WAIC (widely applicable information criterion). Additionally, when the artificial intelligence model includes matrix decomposition in its algorithm, each element of matrix S is calculated so that $R \approx PS$ is satisfied by using matrix P and matrix R described in section 2-2 (1) above. At this time, the processing unit 100 functions as an artificial intelligence model generation unit.

The processing unit 100 then stores the trained artificial intelligence model (step S14). The stored model is saved on the auxiliary storage unit 104 of the device 10 or in a cloud. When the artificial intelligence model includes matrix decomposition in its algorithm, each element of matrix S is stored as an artificial intelligence model.

The artificial intelligence model for use in operation 2 of the training device is preferably SVM or an artificial intelligence model containing a function of matrix decomposition.

2-7. Updating Process for Artificial Intelligence Model

FIG. 11 illustrates an updating process for an artificial intelligence model once trained.

Receiving an input for process-start by the user from the input unit 111, the processing unit 100 temporarily invokes, for example, a trained artificial intelligence model stored in the auxiliary storage unit 104 in the main storage unit 102. Alternatively, the processing unit 100 downloads an artificial intelligence model from, for example, a network via the communication I/F 105, and temporarily stores the downloaded model in the main storage unit 102. In another embodiment, the processing unit 100 may access an artificial intelligence model stored in a cloud.

The processing unit 100 obtains the set of data indicating the dynamics of one or more biomarkers, which is an updated set of first training data described in the Training of Artificial Intelligence Model section, and the information on one or more known actions in humans, which is updated second training data, or a set of information on one or more known actions in humans, which is a set of the second training data (step S31). The updated set of first training data can be composed of a set of data indicating the dynamics of one or more biomarkers in one organ or in each of the multiple different organs collected from non-human animals to which additional different existing substances have been administered. The updated second training data or the updated set of the second training data may be composed of information on one or more known actions in humans.

Next, the processing unit 100 inputs the set of first training data and/or the second training data or the set of the second training data into the trained artificial intelligence model, as in step S2 of FIG. 9 or step 12 of FIG. 10 (step S32).

The processing unit 100 recalculates parameters such as weights of the functions of the artificial intelligence model and updates the artificial intelligence model (step S33). Updating an artificial intelligence model may include validation, generalization, etc. as described above. Steps 32 to 33 may be the retraining of the trained artificial intelligence model using the updated set of first training data and the updated second training data or the updated set of the second training data. Steps 32 to 33 may also be, for example, validation, generalization, etc., using the updated set of first training data and the updated second training data or the updated set of the second training data.

In step S34, the processing unit 100 investigates whether other updated data exist. If there is updated data (Yes), the processing unit 100 returns to step 31 and performs the updating process again. In step S33, if there is no other updated data (No), the process proceeds to step S35, and the updated artificial intelligence model is stored.

3. Prediction of Action of Test Substance in Humans

The one or more actions of a test substance in humans are predicted from a set of data indicating the dynamics of one or more biomarkers in one organ or in each of the multiple different organs of non-human animals to which the test substance has been administered, by using a trained artificial intelligence model.

3-1. Generation of Test Data

Test data is a set of data indicating the dynamics of one or more biomarkers in one organ or in each of the multiple different organs of non-human animals to which a test substance has been administered. The administration of a test substance can be arranged according to individual test substances.

The data indicating the dynamics of one or more biomarkers for generating the test data is obtained from an organ that corresponds to the organ collected at the time of generating the set of first training data. The non-human animals used to generate the set of first training data and the non-human animals for generating the test data are preferably of the same species. The type of the biomarker used to generate the test data is preferably the same as that of the biomarker used to generate the set of first training data. In other words, if a transcriptome is used to generate the set of first training data, it is preferable to use the transcriptome as a biomarker in the test data. The method for obtaining the data indicating the dynamics of one or more biomarkers is preferably the same in both obtaining the test data and obtaining the first training data, or methods capable of obtaining equivalent data are used in obtaining the test data and obtaining the first training data. If a process such as normalization and dimensionality reduction is performed in generating the set of first training data, it is preferable to perform the same process in generating the test data. Additionally, the arrangement of the organ-gene combination in the column direction of the test data is preferably the same as that in the training data.

3-2. Prediction of Action of Test Substance

Prediction of one or more actions of a test substance in humans includes obtaining test data and inputting the test data into an artificial intelligence model trained by the method for training an artificial intelligence model described above to predict, on the basis of the input test data, one or more actions of the test substance from which the test data has been obtained. The test substance may be an existing substance or a substance equivalent to an existing substance. When an existing substance or a substance equivalent to an existing substance is used as a test substance, the prediction method can support predicting an unknown action of the existing substance or the substance equivalent to an existing substance, preferably predicting a new indication (drug repositioning).

If the artificial intelligence model is, for example, SVM, relevance vector machine (RVM), naive Bayes, random forest, AdaBoost, C4.5, stochastic gradient descent (SGD) classifier, lasso, ridge regression, elastic net, SGD regression, or kernel regression, the test data must be input into individual trained artificial intelligence models in order to predict all of the actions; this is because one single trained artificial intelligence model corresponds to one action. If the artificial intelligence model is based on a neural network, deep learning, or matrix decomposition, multiple actions can be predicted by inputting one item of test data to a single trained artificial intelligence model.

To predict the rate of occurrence of an action by scoring, the test data is input into a trained artificial intelligence model, and the score is output from the artificial intelligence model.

When an artificial intelligence model based on matrix decomposition is used, the elements of matrix R, due to the established relationship of matrix R≈PS, can be predicted using matrix S calculated by training, and matrix P, which is the matrix data of the set of data indicating the dynamics of one or more biomarkers in multiple different organs collected from non-human animals to which the test substance has been administered. The predicted matrix R is determined to be matrix R'. An indication with a column label in which the element value in matrix R' is, for example, 0.5 or more, 0.6 or more, 0.7 or more, 0.75 or more, 0.8 or more, 0.85 or more, 0.9 or more, or 0.95 or more, can be estimated as an indication of the test substance.

A specific example of matrix decomposition is described below. Matrix R of the set of the second training data is prepared. For example, if the name of a disease is listed as an indication on the package insert of a pharmaceutical product, the corresponding element is "1", and the other elements are "0." In matrix decomposition, an element that is zero of matrix R is estimated. This suggests that the larger the value of the estimated element of R is, the more likely it is that the existing substance that corresponds to the element is applicable to the disease with a larger value.

To actually estimate element 0 of matrix R, for example, matrix factorization (dtic.mil/docs/citations/ADA439541) can be applied to matrix R. When matrix factorization is applied, matrix P and matrix S that satisfy R≈PS are generated using elements other than element 0 of R. The value of an element of matrix R' in which PS=R' is determined to be a predicted value of element 0 of R. Matrix P is the set of first training data and considered to be a matrix that represents the properties of existing substances, and matrix S is considered to be a matrix that represents the properties of diseases. In typical matrix factorization, matrix P is generated, together with matrix S, from matrix R. Here, however, only matrix S can be generated by using the set of first training data as matrix P. Specifically, if the elements of matrix R, P, S are each described as Rij, Pik, Skj, for the following non-zero element Rij, an element of matrix S (Skj) that minimizes the following objective function:

$$e_{ij} = \left(r_{ij} - \sum_{k=1}^{K} p_{ki}s_{kj}\right)^2 + \frac{\beta}{2}\sum_{k,j}(s_{kj})^2$$

is calculated.

To minimize this function, if the gradient of $S_{kj}$ is taken, the result is the following:

$$\frac{\partial e_{ij}}{\partial s_{kj}} = -2e_{ij}p_{ik} + \beta s_{kj}$$

Thus, matrix S can be generated by updating $s_{kj}^{(0)}$ to $s_{kj}^{(1)}$ until $e_{ij}$ is converged in accordance with the following formula:

$$s_{kj}^{(1)} = s_{kj}^{(0)} + \alpha(2e_{ij}p_{ik} - \beta s_{kj}^{(0)})$$

Additionally, matrix R is reconstructed using matrix P and the generated matrix S in accordance with the following formula:

$$PS = R'$$

The reconstructed new matrix R is defined as matrix R'. Each element of matrix R' is a newly calculated element. The value of each element of matrix R' is the estimated value of element 0 of the corresponding R. Thus, each element of matrix R' is a new value indicating the strength of the association between the information on the name of an existing substance and the information on a known action. Matrix R' can be considered to be a prediction of a new action of a test substance, such as a prediction of an indication.

When performing drag repositioning, it is preferable to use an artificial intelligence model with matrix decomposition as its algorithm. When predicting adverse-events and pharmacokinetics, it is preferable to use SVM.

When stratified actions are predicted, test data may be input into an artificial intelligence model trained layer by layer, and the coefficients of the polynomial described above may be output from the artificial intelligence model.

3-3. Prediction Device

Prediction of actions of a test substance in humans can be performed using, for example, the following prediction device 20 (which may be hereinafter referred to as "device 20"). The device 20 includes at least a processing unit 201 and a storage unit. The storage unit includes a main storage unit 202 and/or an auxiliary storage unit 204. Preferably, the device 20 may be a device for enabling the prediction method according to Item 13. FIG. 7A illustrates the configuration of the device 20. FIG. 8 illustrates the configuration of hardware of the device 20. Because the configuration of the prediction device 20 and the configuration of hardware are the same as those of the training device 10, the description of the training device 10 referring to FIGS. 7A and 8 is incorporated herein. The device 20 and the device 10 may be integrated. The device 20 may constitute a prediction system 51 connected to the measurement device 30 directly or via a network, for example.

In this section, the description of the training device 10 is incorporated herein by reading the device 10 as a device 20, the processing unit 101 as a processing unit 201, the main storage unit 102 as a main storage unit 202, the ROM 103 as a ROM 203, the auxiliary storage unit 104 as an auxiliary storage unit 204, the communication interface (I/F) 105 as a communication interface (I/F) 205, the input interface (I/F) 106 as an input interface (I/F) 206, the output interface (I/F) 107 as an output interface (I/F) 207, the media interface (I/F) 108 as a media interface (I/F) 208, the bus 109 as a bus 209, the input unit 111 as an input unit 211, the output unit 112 as an output unit 212, and the storage medium 113 as a storage medium 213.

3-4. Operation 1 of Prediction Device

The prediction device 20 enables the function as a first prediction device 20 by causing the processing unit to execute a computer program described later, which is application software. With reference to the flowchart of FIG. 12, the first operation of the device 20 for performing prediction will be described.

Receiving the input for process-start by the user from the input unit 211, the processing unit 200, for example, temporarily invokes a trained artificial intelligence model stored in the auxiliary storage unit 204 in the main storage unit 202. Alternatively, the processing unit downloads a trained artificial intelligence model from, for example, a network via the communication I/F 205, and temporarily stores the model in the main storage unit 202. In another embodiment, the processing unit 200 may access a trained artificial intelligence model stored in a cloud.

The processing unit 200 obtains a set of data indicating the change of one or more biomarkers in one organ or in each of the multiple organs observed when a test substance, which is test data, has been administered to animals (step S51). The obtained test data is stored in the auxiliary storage unit 204 or the main storage unit 202. At this time, the processing unit 200 functions as a test data acquisition unit. The test data is obtained beforehand from the measurement device 30 directly or via a network etc., and may be stored, for example, in the auxiliary storage unit 204, the main storage unit 202, or a storage device such as a server in a cloud. The test data may also be obtained from the measurement device 30 directly or via a network etc. at the time of prediction.

The processing unit 200 inputs the test data obtained in step S51 into the trained artificial intelligence model, and the trained artificial intelligence model predicts the actions of the test substance in humans (step S52). At this time, the processing unit 200 functions as an action prediction unit. The prediction method is as described in the prediction of the actions of the test substance above.

The processing unit 200 outputs the prediction result to the output unit 212 in step S53. The processing unit 200 may store the prediction result in, for example, the auxiliary storage unit 204, the main storage unit 202, or a storage device such as a server in a cloud via the communication I/F 205 or via a network.

3-5. Operation 2 of Prediction Device

The prediction device 20 enables a function as a second prediction device 20 for predicting one or more new actions of an existing substance by causing the processing unit to execute a computer program described later as application software. The prediction device 20 can also be considered to be a device for performing drag repositioning. The prediction device 20 also functions as a device for assisting prediction.

Receiving an input for process-start by the user from the input unit 211, the processing unit 200 temporarily invokes, for example, an artificial intelligence model stored in the auxiliary storage unit 204 in the main storage unit 202. Alternatively, the processing unit downloads an artificial intelligence model from a network etc. via the communication I/F 205 and temporarily stores the model in the main storage unit 202. In another embodiment, the processing unit 200 may access an artificial intelligence model stored in a cloud. The artificial intelligence model preferably contains a matrix decomposition function. The artificial intelligence model containing a matrix decomposition function is as described in the "Training of Artificial Intelligence Model" section above.

The processing unit 200 obtains the set of first training data and the set of the second training data (step S61). At this time, the set of first training data includes test data, and the set of the second training data includes information on one or more known actions of test substances in humans. The obtained set of first training data and set of the second training data are stored in the auxiliary storage unit 204 or the main storage unit 202. At this time, the processing unit 200 functions as a data acquisition unit. The processing unit 200 constructs and stores matrix R when storing the set of the second training data. The processing unit 200 also constructs and stores matrix P when storing the set of first training data.

The processing unit 200 receives an input for process-start to the input unit 211 by the user, and inputs matrix R and matrix P stored in step S61 into an artificial intelligence model (step S62). At this time, the processing unit 200 functions as a data input unit.

Next, the processing unit 200 calculates matrix S from matrix R and matrix P by matrix decomposition with the relationship of R≈PS. The array of column labels of matrix S corresponds to the array of column labels of matrix R (step S63). Further, matrix R is reconstructed from matrix P and the calculated matrix S, and this reconstructed new matrix is set as R' (step S64). Each element of matrix R' is a new value that indicates the strength of the association between information on the name of an existing substance and information on a known action. At this time, the processing unit 200 functions as a calculation unit for matrix S and matrix R'.

Next, the processing unit 200 determines whether the value of an element in the region of interest of matrix R' is equal to or greater than a threshold (step S65). The region of interest as used here refers to some or all of matrix R', and includes an element of a substance (test substance), a new action of which the user wants to search for. Preferably, the region of interest refers to a region of matrix R to which "1" is not assigned ("1" meaning that there is an indication). At this time, the processing unit 200 functions as a value determination unit.

In matrix R', the threshold is, for example, 0.5 or more, 0.6 or more, 0.7 or more, 0.75 or more, 0.8 or more, 0.85 or more, 0.9 or more, or 0.95 or more.

If the value of an element is equal to or greater than the threshold in step S65 (if "Yes"), the processing unit 200 proceeds to step S66. In step S66, the processing unit 200 suggests one or more elements that exceed the threshold. The processing unit 200 can suggest the part in which "1" is not assigned in matrix R and in which the element is equal to or greater than the threshold in matrix R', by changing the color of the label, cell, and/or character, such as when displaying R' in the output unit (e.g. display unit), because the array of matrix R' corresponds to the array of matrix R. At this time, the processing unit 200 functions as an element suggestion unit.

Although not shown in figures, the processing unit 200 may output the indication shown in the column label of a cell whose element is in the region of interest and is equal to or greater than the threshold, as a candidate for a new indication of the substance indicated in the row label of the cell.

In step S67, the processing unit 200 may output as a result the information or indication candidate suggested in step S66 to the output unit 212, such as a printer.

The processing unit 200 may end the process in step S65 if the value of the element is not equal to or greater than the threshold (if "No"), or may output the result that there is no element in step S67.

4. Computer Program 4-1. Training Program

The computer program causes a computer to execute a process including steps S1 to S5 in FIG. 9 and/or steps S11 to S14 in FIG. 10 described in the "Training of Artificial Intelligence" section above to cause the computer to function as the training device 10. Alternatively, the computer program causes a computer to execute a process including computer steps S1 to S5 and steps S31 to 35, or steps S11 to S14 and steps S31 to 35, to cause the computer to function as the training device 10.

4-2. Prediction Program

The computer program causes a computer to execute a process including steps S51 to S53 or steps S61 to 67 described in the "Prediction of Action of Test Substance" section above to cause the computer to function as the prediction device 20.

5. Storage Medium that Stores Computer Program

This section relates to a storage medium that stores the computer program. The computer program is stored on a storage medium, such as a hard disk, a semiconductor memory chip including a flash memory, or an optical disc. The computer program may also be stored on a storage medium connectable through a network, such as a cloud server. The computer program may be a downloadable program product or a program product stored on a storage medium.

The storage format of a program on the storage medium is not limited as long as the devices described above can read the program. The storage in the storage medium is preferably non-volatile.

6. Prediction System and its Construction Method

As shown in FIG. 7B, the training device 10 may be communicably connected to a server device 40 that transmits a set of data indicating the dynamics of one or more biomarkers via a network so as to constitute an artificial intelligence training system. The prediction device 20 may also be communicably connected to the server device 40 that transmits a set of data indicating the dynamics of one or more biomarkers via a network as shown in FIG. 7B to constitute a prediction system. The training device 10, the server device 40, and the prediction device 20 may be communicably connected via a network to constitute an artificial intelligence training system. The artificial intelligence training system and the prediction system may be provided with the measurement device 30.

6-1. Server Device

FIG. 8 illustrates the configuration of hardware of the device 40. The server device 40 (which may be hereinafter referred to as "device 40") includes at least a processing unit 401 and a storage unit. The storage unit includes a main storage unit 402 and/or an auxiliary storage unit 404. The device 40 may be a general-purpose computer with a server function. Because the configuration of the server device 40 and the configuration of the hardware are the same as those of the training device 10, the description of the training device 10 referring to FIGS. 7A and 8 is incorporated herein. The device 40 and the device 10, the device 40 and the device 10, or the device 40, the device 10, and the device 20 may be integrated. The device 40 can be connected to the measurement device 30 directly or via a network etc.

In this section, the description of the training device 10 is incorporated herein by reading the device 10 as a device 40, the processing unit 101 as a processing unit 401, the main storage unit 102 as a main storage unit 402, the ROM 103 as a ROM 403, and the auxiliary storage unit 104 as an auxiliary storage unit 404, the communication interface (I/F) 105 as a communication interface (I/F) 405, the input interface (I/F) 106 as an input interface (I/F) 406, the output interface (I/F) 107 as an output interface (I/F) 407, the media interface (I/F) 108 as a media interface (I/F) 408, the bus 109 as a bus 409, the input unit 111 as an input unit 411, the output unit 112 as an output unit 412, and the storage medium 113 as a storage medium 413.

6-2. Measurement Device

Examples of the measurement device 30 include a transcriptome analyzer, such as a next-generation sequencer, and a mass spectrometer.

6-3. System Operation

With reference to FIG. 14, the operation of the system will be described here. This section describes a flow from the acquisition of the measured value of a biomarker by the measurement device 30 through the output of the prediction result.

In step S81, the measurement device 30 obtains the measured value of a biomarker in each organ of non-human animals to which an existing substance has been administered. Acquisition of the measured value by the measurement device 30 can be performed by an input for an instruction for starting measurement by the operator. In step S82, the measurement device 30 transmits the obtained measured value to the server device 40. The transmission process can be performed by an input for an instruction for staring transmission by the operator.

In step S83, the processing unit 401 of the server device 40 obtains the measured value via the communication I/F 405. At this time, the communication I/F 405 functions as a communication unit.

In step S84, the processing unit 100 of the training device 10 transmits a signal for starting the transmission of the measured value to the server device 40 from the communication I/F 105 in response to an instruction to start the acquisition of the measured value, which is input by the operator from the input unit 111 of the training device 10. The processing unit 400 of the server device 40 receives the input for the start of transmission of the measured value via the communication I/F 405, and starts transmitting the measured value from the communication I/F 405. At this time, the communication I/F 105 and the communication I/F 405 function as a communication unit.

In step S85, the processing unit 100 of the training device 10 obtains information on actions in humans of existing substances administered to non-human animals, for example, from a known database via the communication I/F 105. The database may be stored on a server other than the server device 40, or in the storage unit of the server device 40.

In step S84, the processing unit 100 of the training device 10 obtains the measured value transmitted from the server device 40 via the communication I/F 105 (step S86), and stores the obtained value in the storage unit of the training device 10. Step S86 may be performed before step S85.

Next, the processing unit 100 of the training device 10 generates a set of first training data and second training data in step S87 shown in FIG. 14 in accordance with the process shown in step S1 of FIG. 9. The description of step S1 in FIG. 9 is incorporated herein.

Next, the processing unit 100 of the training device 10 inputs the set of first training data and the second training data into an artificial intelligence model in step S88 shown in FIG. 14 in accordance with the process in steps S2 to S5 of FIG. 9, trains the artificial intelligence model, and stores the trained artificial intelligence model in the storage unit. The description of steps S2 to S5 of FIG. 9 is incorporated herein.

After having received an instruction to start transmission of the artificial intelligence model from the prediction device 20, the processing unit 100 of the training device 10 transmits the trained artificial intelligence model to the prediction device 20 via the communication I/F 105 in step S89 of FIG. 14. At this time, the communication I/F 105 functions as a communication unit.

Next, the measurement device 30 obtains the measured value of the biomarker in each organ of non-human animals to which a test substance has been administered in step S91. Acquisition of the measured value in the measurement device 30 can be performed by an input for an instruction to start measurement by the operator. In step S92, the measurement device 30 transmits the obtained measured value to the server device 40. The transmission process can be performed by an input for an instruction to start transmission by the operator.

In step S93, the processing unit 401 of the server device 40 obtains the measured value via the communication I/F 405. At this time, the communication I/F 405 functions as a communication unit.

In step S94, in response to an instruction to start obtaining a measured value input by the operator from the input unit 211 of the prediction device 20, the processing unit 100 of the prediction device 20 transmits a signal for starting the transmission of the measured value to the server device 40 from the communication I/F 205. The processing unit 400 of the server device 40 receives an input for starting the transmission of the measured value via the communication I/F 405, and starts transmitting the measured value from the communication I/F 405. At this time, the communication I/F 205 and the communication I/F 405 function as a communication unit. The processing unit 200 of the prediction device 20 obtains the measured value via the communication I/F 205 and stores the obtained value in the storage unit of the prediction device 20. Subsequently, the processing unit 200 of the prediction device 20 generates test data in accordance with step S51 of FIG. 12. The description of step S51 of FIG. 12 is incorporated herein.

Next, in step S95, the processing unit 200 of the prediction device 20 transmits an instruction to start transmission of an artificial intelligence model to the training device 10 via the communication I/F 205. When the processing unit 100 of the training device 10 receives an instruction for staring transmission of the artificial intelligence model from the prediction device 20, the processing unit 100 transmits the trained artificial intelligence model to the prediction device 20 via the communication I/F 105 of the training device 10. The prediction device 20 obtains the trained artificial intelligence model via the communication I/F 205. Step S95 may be performed before step S94.

Next, in step S96, the processing unit 200 of the prediction device 20 predicts one or more actions of the substance in humans using the test data generated in step S94 and the trained artificial intelligence model obtained in step S95 in accordance with step S52 of FIG. 12. The processing unit 200 of the prediction device 20 outputs the result in step S97. Alternatively, in steps S94 to S97 of FIG. 14, the processing unit 200 of the prediction device 10 may perform steps S62 to S67 described in FIG. 13 to predict a prediction result concerning a new indication of the existing substance.

6-4 System Construction Method

The method for constructing a system, in order to train an artificial intelligence model, may include preparing the server device 40 and preparing the training device 10. The method for constructing a system, in order to predict the actions of a test substance in humans, may include preparing the server device 40 and preparing the prediction device 20. The description in each section regarding the configuration of each device, the configuration of the system, and the operation of each device and system is incorporated herein.

EXAMPLES

The present invention is described in more detail below with reference to examples. The present invention, however, should not be construed as limited to the examples.

Experimental Example I: Gene Expression Analysis in Drug Administration Mice

I-1. Preparation of Drug Administration Mice and Gene Expression Analysis
(1) Administration of Pharmaceutical Product
Administration of Aripiprazole Aripiprazole was purchased from Sigma-Aldrich. 10 mg of aripiprazole was mixed with 200 mL of 0.5 w/v % methyl cellulose (Wako), and the resulting solution was used for administration.

Male C57BL/6N mice at 11 weeks of age received a single intraperitoneal injection of the aripiprazole solution (the dosage was 0.3 mg/kg, and the administration volume was 6 mL/kg). Organs or tissues were harvested 2 hours after the administration.

Administration of Empagliflozin

Empagliflozin (EMPA) was purchased from Toronto Research Chemicals. 50 mg of empagliflozin was mixed with 25 mL of 0.5 w/v % methyl cellulose, and the resulting solution was used for administration.

Male C57BL/6N mice at 10 weeks of age received oral administration of the empagliflozin solution through a feeding needle once a day, every day, for 2 weeks (the dosage was 10 mg/kg, and the administration volume was 10 mL/kg). Organs or tissues were harvested 2 weeks after the first administration.

Administration of Clozapine

Clozapine was purchased from Sigma-Aldrich.

25 mg of clozapine was dissolved in 1 mL of acetic acid. 120 μL of the dissolved clozapine acetic acid solution was mixed with 54 mL of physiological saline, and the pH was adjusted to 6 with 1M NaOH. The resulting solution was used for administration.

Male C57BL/6N mice at 11 weeks of age received a single subcutaneous injection of the clozapine solution (the dosage was 0.3 mg/kg, and the administration volume was 6 mL/kg). Organs or tissues were harvested 2 hours after the administration.

Administration of Cisplatin

Briplatin injection (10 mg/20 mL) was purchased from Bristol-Myers Squibb.

Male C57BL/6N mice at 11 weeks of age received a single intraperitoneal injection of the briplatin injection (the dosage was 20 mg/kg, and the administration volume was 40 mL/kg). Organs or tissues were harvested on the third day after the administration.

Administration of Teriparatide

Parathyroid Hormone Fragment 1-24 Human (Teriparatide) was purchased from Sigma-Aldrich. After 0.2 mg of teriparatide was dissolved in 200 μL of Ultrapure Water (Thermo Fisher Scientific), 5 μL of the resultant was dispensed into a 1.5-mL tube, and stored at −80° C. 5 μL of teriparatide stored at −80° C. was melted at room temperature, and mixed with 995 μL of physiological saline. The resulting solution was used for administration.

Male C57BL/6N mice at 10 weeks of age received subcutaneous injection of the teriparatide solution once a day, every day, for 4 weeks (the dosage was 40 μg/kg, and the administration volume was 8 mL/kg). Organs or tissues were harvested 4 weeks after the first administration.

Administration of Repatha

Repatha subcutaneous injection (140 mg/mL) was purchased from Astellas Pharma Inc. 14.4 μL of repatha subcutaneous injection was mixed with 985.6 μL of physiological saline, and the resulting solution was used for administration.

Male C57BL/6N mice at 11 weeks of age received subcutaneous injection of the repatha solution once every 10 days for 4 weeks (the dosage was 10 mg/kg, and the administration volume was 5 mL/kg). Organs or tissues were harvested 4 weeks after the first administration.

No Pharmaceutical Product Administration (Wild Mouse)

Organs or tissues of male C57BL/6N mice at 11 weeks of age were harvested.

(2) Harvest of Organs or Tissues

Mice whose administration period was completed were euthanized by cervical dislocation without anesthesia, and organs or tissues were harvested according to the following procedure.

70% ethanol was sprayed on each mouse whose euthanasia had been confirmed, and the neck was cut. The skin of the larynx was incised, and the salivary glands were harvested. The sublingual gland and submandibular gland were removed from the salivary glands. The remaining parotid gland was collected in a 1.5-mL tube and frozen in liquid nitrogen.

After the parotid gland was harvested, muscles on the trachea were removed. A pair of left and right thyroid glands was collected in a 1.5-mL tube and frozen in liquid nitrogen.

The skin at the top of the head was incised to expose the skull, and the skull was harvested. After tissue and muscles attached to the harvested skull were cut off, the skull was collected in a 1.5-mL tube and frozen in liquid nitrogen.

After the brain was harvested from the head, the olfactory bulb was removed. The brain was collected in a 1.5-mL tube and frozen in liquid nitrogen.

The pituitary gland remaining on the head was carefully taken out with tweezers so as not to crush the pituitary gland, collected in a 1.5-mL tube, and frozen in liquid nitrogen.

After the left and right eyeballs were taken out, and the optic nerve and muscles were removed, the eyeballs were collected in a 1.5-mL tube and frozen in liquid nitrogen.

After the abdomen was opened, the pancreas was quickly harvested, and the surrounding tissue was removed. Thereafter, the pancreas was collected in a 1.5-mL tube and frozen in liquid nitrogen.

After the left and right adrenal glands were harvested, the surrounding fat was removed. The adrenal glands were collected in a 1.5-mL tube and frozen in liquid nitrogen.

After the left kidney was harvested, the renal arteriovenous vein, surrounding fat, and membrane were removed. The left kidney was collected in a 1.5-mL tube and frozen in liquid nitrogen.

After the spleen was harvested, the surrounding tissue, particularly the pancreas, was carefully removed. Thereafter, the spleen was collected in a 1.5-mL tube and frozen in liquid nitrogen.

After the left lobe (the largest lobe) of the liver was harvested and cut in half, the left lobe was collected in a 1.5-mL tube and frozen in liquid nitrogen.

The stomach was harvested from the cardia and the pylorus, and the surrounding fat and pancreas were carefully removed. Thereafter, the stomach was cut with scissors to expose the inside of the stomach. After the stomach contents were removed by washing with PBS at ordinal temperature three times, the stomach was collected in a 1.5-mL tube and frozen in liquid nitrogen.

The jejunum (7 cm) was harvested from the gastric pylorus, and a 2-cm portion just below the pylorus was removed. The surrounding fat was removed, and the jejunum was cut with scissors to expose the inside of the intestine. After the intestinal contents were removed by washing with PBS at ordinary temperature three times, the jejunum was collected in a 1.5-mL tube and frozen in liquid nitrogen.

The ileum (7 cm) was harvested from the cecum side, and the surrounding fat was removed. The ileum was cut with scissors to expose the inside of the intestine. After the intestinal contents were removed by washing with PBS at ordinal temperature three times, the ileum was collected in a 1.5-mL tube and frozen in liquid nitrogen.

After the large intestine (5 cm) was harvested from the rectal side, the surrounding fat was removed. The large intestine was cut with scissors to expose the inside of the intestine. After the intestinal contents were removed by washing with PBS at ordinal temperature three times, the large intestine was collected in a 1.5-mL tube and frozen in liquid nitrogen.

The chest was opened, and the thymus, heart, and lungs were taken out together. The thymus was harvested, and the blood, surrounding tissue, and fat were removed. Thereafter, the thymus was collected in a 1.5-mL tube and frozen in liquid nitrogen.

The heart and lungs were separated, and the heart was harvested. The pericardium, aorta, vena cava, pulmonary artery, and pulmonary vein were removed so as not to cut the paired atrial appendages. After the heart was vertically cut in half, the atrial appendages and the blood in heart were removed. The heart was then collected in a 1.5-mL tube and frozen in liquid nitrogen.

One left lobe of the lung was harvested, and the trachea, blood vessels, and blood were removed. Thereafter, the left lobe was collected in a 1.5-mL tube, and frozen in liquid nitrogen.

The descending thoracic aorta was harvested, and the surrounding tissue was carefully removed. Thereafter, the descending thoracic aorta was collected in a 1.5-mL tube and frozen in liquid nitrogen.

The quadriceps muscle (skeletal muscle) was harvested from the left femur, collected in a 1.5-mL tube and frozen in liquid nitrogen.

The left femur was taken out, and the muscle was scraped off with a scalpel. Both ends of the femur were cut with scissors.

A cell strainer (pore size: 40 µm, Coring) was set in a 50-mL tube. Using a 5-mL syringe and a 26G needle, bone marrow was flushed from one end of the femur with 3 mL of PBS onto the cell strainer. On completion of the flush of the bone marrow from both ends, the flushed bone marrow was centrifuged in a 1.5 mL tube at 4° C. for 5 minutes. After the centrifugation, the supernatant was removed with a pipette.

500 µL of PBS on ice was added, and the mixture was stirred by pipetting and then centrifuged at 4° C. for 5 minutes at 1,500 rpm. After the centrifugation, the supernatant was removed, and 1 mL of TRIzol Reagent (TRIzol, Thermo Fisher Scientific) was added, followed by stirring. The mixture was then transferred to a 1.5-mL tube and frozen in liquid nitrogen.

The left epididymal fat was collected in a 1.5-mL tube and frozen in liquid nitrogen.

The left testis was harvested, and the surrounding fat was removed. Thereafter, the left testis was collected in a 1.5-mL tube and frozen in liquid nitrogen.

After the back hair (around the scapula) was shaved, the skin was harvested, and fat and muscles were removed. Thereafter, the skin was collected in a 1.5-mL tube and frozen in liquid nitrogen.

After the completion of the harvest, the 24 organs or tissues were stored at −80° C.

(3) Extraction of RNA

RNA was extracted from each cryopreserved organ or tissue according to the following procedure.

i. Grinding of Organs or Tissues

The pancreas, skull, liver, and skin were ground with a pestle and mortar in liquid nitrogen.

Each ground sample was immediately transferred to TRIzol and homogenized with a PT10-35 GT Polytron homogenizer (KINEMATICA). The brain was transferred to TRIzol and homogenized with a Polytron homogenizer.

Table 1 below shows the amount of TRIzol used for grinding and the amount of the sample used for extraction.

TABLE 1

| Name of organ | Amount of TRIzol used for grinding | Amount of sample used for extraction |
| --- | --- | --- |
| Pancreas | 8 mL | 1 mL |
| Skull | 4 mL | 4 mL |
| Liver | 4 mL | 1 mL |
| Skin | 4 mL | 4 mL |
| Brain | 4 mL | 1 mL |

The pituitary gland, adrenal glands, thyroid gland, spleen, thymus, heart, lungs, descending thoracic aorta, skeletal muscle, testis, epididymal fat, eyeballs, ileum, stomach, jejunum, large intestine, kidney, and parotid gland were ground with zirconia beads (Biomedical Science) (see the table below).

For grinding, 1 mL of TRIzol was introduced in a tube for grinding (Biomedical Science) containing one kind of zirconia beads (fifty 1.5-mm beads) or three kinds of zirconia beads (fifty 1.5-mm beads, five 3-mm beads, and two 5-mm beads), and the tube was placed on ice. Each organ was placed in the tube for grinding containing TRIzol and zirconia beads, and homogenized with Cell Destroyer PS2000 (Biomedical Science) (4,260 rpm, 4° C., 45 seconds, twice). After grinding, the TRIzol amount was scaled up to 2 mL in some organs. In each of such organs, the ground sample and beads were transferred to a 1.5-mL tube, and 1 mL of TRIzol was added thereto, followed by stirring.

Table 2 below shows the amount of TRIzol used for grinding and the amount of sample used for extraction.

TABLE 2

| Name of organ | Beads | Scale up | Amount of sample used for extraction |
| --- | --- | --- | --- |
| Pituitary gland | One | No scale up | 1 mL |
| Adrenal glands | One kind | No scale up | 1 mL |
| Thyroid gland | One kind | No scale up | 1 mL |
| Spleen | Three kinds | No scale up | 1 mL |
| Thymus | Three kinds | No scale up | 1 mL |
| Heart | Three kinds | No scale up | 1 mL |
| Lungs | Three kinds | No scale up | 1 mL |
| Aorta | Three kinds | No scale up | 1 mL |
| Skeletal muscle | Three kinds | No scale up | 1 mL |
| Testis | Three kinds | No scale up | 1 mL |
| Epididymal fat | Three kinds | No scale up | 1 mL |
| Eyeballs | Three kinds | No scale up | 1 mL |
| Ileum | Three kinds | No scale up | 1 mL |
| Stomach | Three kinds | Scale up | 1 mL |
| Jejunum | Three kinds | Scale up | 1 mL |
| Large intestine | Three kinds | Scale up | 1 mL |
| Kidney | Three kinds | Scale up | 1 mL |
| Parotid gland | Three kinds | Scale up | 1 mL |

The bone marrow collected in TRIzol was taken out from the −80° C. freezer and brought back to room temperature.

ii. Extraction of RNA

Each sample homogenized in TRIzol was allowed to stand at room temperature for 5 minutes. 0.2 mL of chloroform was added per mL of TRIzol, and the mixture was vortexed vigorously for 15 seconds. After stirring, the mixture was allowed to stand at room temperature for 3 minutes and then centrifuged at 4° C. for 15 minutes at 12,000 g. After centrifugation, 500 µL of the RNA-containing aqueous layer was collected in a fresh tube, and an equal amount (500 µL) of 70% ethanol was added thereto and stirred. RNAs were extracted from each sample using an RNeasy Mini Kit (Qiagen) according to the manual. The concentration, purity, and yield of each of the extracted RNAs were evaluated by using NanoDrop (Thermo Fisher Scientific).

(4) Acquisition of RNA-Seq Data

Using the RNA samples, RNA-Seq data was obtained according to the following procedure. The quality was evaluated by measuring the concentration with Agilent 2100 Bioanalyzer G2939A (Agilent Technologies).

(4)-1. Preparation of Library

Using each Total RNA that passed quality testing as a template, a library for next-generation sequencer 1500 was prepared with a SureSelect Strand-Specific RNA library preparation kit (Agilent Technologies) in the following manner.

(a) Collection of poly (A$^+$)RNA (=mRNA) from total RNA using Oligo
(dT) magnetic beads
(b) Fragmentation of RNA
(c) cDNA synthesis
(d) Double-stranded cDNA synthesis
(e) Terminus repair, phosphorylation, A tail addition
(f) Ligation of adapters with indices
(g) 13-cycle PCR
(h) Purification with magnetic beads (4)-2. Reading Sequence In accordance with the following steps, nucleotide sequence data was obtained using a HiSeq 1500, HiSeq 2000, and HiSeq 2500 (Illumina) by reading 50 bp bases according to the single-read method.

(a) Addition of sequencing reagent
(b) Single-base extension reaction
(c) Removal of unreacted bases
(d) Incorporation of fluorescent signal
(e) Removal of protecting groups and fluorescence Amplification in HiSeq was repeated (e.g., cycle 2, cycle 3 . . . ), and run for 50 cycles.

(4)-3. Primary Data Analysis

Using program CASAVA ver.1.8.2 (illumina), the FASTQ file was created from the obtained reads.

(4)-4. Secondary Analysis of Output Data

The FASTQ file obtained using an Illumina HiSeq 1500, HiSeq 2000, and HiSeq 2500 was uploaded on a local server. Thereafter, an analysis file was obtained using TopHat (ccb.jhu.edu/software/tophat/index.shtml) to map each sequence to mouse genome map information mm10. The BAM file obtained was analyzed using htseq-count (with parameters -r pos and -s no; htseq.readthedocs.io/en/master/count.html) to calculate the number of annotations of each transcript.

(5) Analysis of Difference in Gene Expression Level

In order to quantify the difference in gene expression level, analysis was performed with DESeq2 (Love, M I, Huber, W. and Anders, S.; Genome Biology 15,550, doi: 10.1186/s13059-014-0550-8 (2014)). Using htseq-count output as input for DESeq2, the expression difference was compared between a pharmaceutical product administration mouse (n=1) and wild mice (n=2). Since the output data of htseq-count in the pharmaceutical product administration mice was two, the $\log_2$ (fold) value of the change in gene expression level was obtained with n being 2 as the output of DESeq2.

(6) Selection of Pharmaceutical Product-Specific Organ-Gene Pair

The RNA-Seq data (log 2 (fold) values) of the total genes in all of the organs to which pharmaceutical products were individually administered was analyzed using WGCNA (labs.genetics.ucla.edu/horvath/CoexpressionNetwork/Rpack ages/WGCNA/), and the dataset of the expression difference of each gene was divided into subsets (modules) having a value in which the name of an organ is linked with the name of a gene. In each divided module, the Pearsons's correlation coefficient between the 1-of-K representation and the expression difference of each gene was calculated in each pharmaceutical product. The module with the highest absolute value of the correlation coefficient was selected for each pharmaceutical product. An organ-gene combination included in the selected module was used in the subsequent treatment.

Experimental Example II: Prediction of Data of Actions in Humans Using Pharmaceutical Product Administration Mice II-1. Construction and Prediction of Machine Learning Model Using Mouse RNA-Seq Data and Human Adverse-Event Data (1) Generation of Mouse Data and Division into Data for Training and Data for Testing Data on change in gene expression level ($\log_2$ (fold)) in mice with respect to organ-gene selected by WGCNA was prepared for all of the pharmaceutical products mentioned above (n=2 for each pharmaceutical product). Since each organ has two sets of data (n=2), and a person can freely choose which data to use, the number of data items constituted by 24 organs is $2^{24}=16777216$. Of these, data sampling was performed using just over 200 combinations, and data having dimensions of (just over 200 samples×6 pharmaceutical products)×(tens of thousands of organ-gene combinations selected by WGCNA) was obtained in a matrix format. FIG. 5 shows an example of the matrix. In order to train the artificial intelligence model and quantify its generalization performance, this matrix was divided into two matrices, i.e., data in which a particular pharmaceutical product was administered to mice (data for testing) and data in which the other pharmaceutical products were individually administered to mice (data for training).

(2) Collection of Human Adverse-Event Data (2)-1. Prediction of Adverse-Events Registered at Clinicaltrials.Gov Information on the occurrence of adverse-events of the target pharmaceutical products was collected from the clinical trial data registered at clinicaltrials.gov (clinicaltrials.gov/). Additionally, for each pharmaceutical product administered to mice, the word indicating the name of a adverse-event was extracted from the clinical trial data. A single extracted word was referred to as one reported adverse-event. The rate of occurrence of each adverse-event was calculated by using the following formula: (the number of occurrences of a adverse-event)/(the number of patients receiving the pharmaceutical product), and a score was given as shown in Table 3 based on the obtained value. Each adverse-event was correlated to the score of rate of occurrence and used as data for training.

TABLE 3

| Rate of occurrence | Score |
|---|---|
| 30% or more | 1 |
| 30% to 10% | 2 |
| 10% to 0% | 3 |
| 0% | 4 |

(2)-2. Prediction of Adverse-Events Registered at FAERS

Adverse event reporting data of 2014Q2 to 2018Q1 was downloaded from FAERS (fda.gov/Drugs/GuidanceCompliananceRegulatoryInformatio n/Surveillance/AdverseDrugEffects/ucm082193.htm). Additionally, for each pharmaceutical product administered to the mice, the word indicating the name of an adverse-event was extracted from the reporting data. A single extracted word was referred to as one reported adverse-event. The rate of occurrence of each adverse-event was calculated by using the following formula: (the number of reports on a particular adverse-event)/(the number of reports on all of the adverse-events for the pharmaceutical product), and a score was given as shown in Table 4 based on the obtained value. Each adverse-event was linked to the numerical value of the score and used in training.

TABLE 4

| Rate of occurrence | Score |
|---|---|
| 30% or more | 1 |
| 30% to 10% | 2 |
| 10% to 0% | 3 |
| 0% | 4 |

(3) Preprocessing of Mouse RNA-Seq Data

The data for training obtained in Item (1) was normalized so that the average was 0 and the variance was 1. Normalization was performed according to the following formula: (normalized value)=(x−m)/s, wherein when the value of expression difference of each gene in the pharmaceutical product-administered mice and wild mice was x, the average of all of the expression differences obtained by the administration of pharmaceutical products in one organ-gene combination was m, and the standard deviation was s. All of the normalized values were dimension-reduced by principal component analysis (PCA). The same treatment was performed on the data for testing.

(4) Construction of Artificial Intelligence Model Using SVM and Prediction of Adverse-Events The construction and prediction of artificial intelligence models used "e1071" (rdocumentation.org/packages/e1071/versions/1.6-8), which is a wrapper of R library LibSVM (csie.ntu.edu.tw/~cjlin/libsvm/).

SVM was trained using, as the set of first training data, the data for training pre-processed in Item (3), and as the set of the second training data, human adverse-event data created in Item (2) from the names of adverse-events registered at clinicaltrials.gov or FAERS, thereby constructing the artificial intelligence model. The data for testing that had been pre-processed in Item (3) was input as test data into the trained artificial intelligence model, and the output prediction score and the actual adverse-event score were compared and quantified.

(5) Results

For each adverse-event, a subtracted value was obtained by subtracting the (actual score) from the (predicted score).

FIG. 3 shows a subtracted value of each adverse-event for each pharmaceutical product obtained when FAERS was used as a database for generating the second training data. FIG. 15 shows the ratio of the difference (subtraction value) between the actual adverse-event score and the predicted score of each pharmaceutical product. The graph of FIG. 15 shows the ratio of the number of adverse-events showing the same subtracted value to the number of all of the predicted adverse-events. In all pharmaceutical products, adverse-events having a difference between the (predicted score) and the (actual score) of 1 or less accounted for 95% or more. This indicates that the artificial intelligence model according to the present disclosure can accurately predict the actions of the test substances in humans based on the dynamics of biomarkers in multiple organs of non-human animals to which the test substances have been individually administered.

Accurate prediction was possible for all examined pharmaceutical products; however, as to adverse-events having a relatively high occurrence rate (actual score of 2 or 3), diarrhea, drowsiness, acute myocardial infarction, acute respiratory failure, asthma, bronchitis, dizziness, muscle weakness, etc. can be predicted with high accuracy for aripiprazole; acute kidney injury, atrial fibrillation, heart failure, deep vein thrombosis, hyperglycemia, hypertension, osteoporosis, pancreatitis, etc. can be predicted with high accuracy for EMPA; and cognitive impairment, depression, diabetes, ischemic stroke, mental state change, pulmonary fibrosis, suicidal ideation, suicide attempt, etc. can be predicted with high accuracy for teriparatide.

II-2. Construction and Prediction of Artificial Intelligence Model Using Mouse RNA-Seq Data and Human Pharmacokinetic Data (1) Generation of Mouse Data and Division into Data for Training and Data for Testing Data on change in gene expression level in mice ($\log_2$ (fold)) with respect to organ-gene selected by WGCNA was prepared for all pharmaceutical products (n=2 for each pharmaceutical product). Since each organ has two sets of data (n=2), and a person can freely choose which data to use, the number of data items constituted by 24 organs is $2^{24}$=16777216. Of these, data sampling was performed using just over 200 combinations, and data having dimensions of (just over 200 samples×6 pharmaceutical products)×(tens of thousands of organ-gene combinations selected by WGCNA) was obtained in a matrix format. In order to train the artificial intelligence model and quantify its generalization performance, this matrix was divided into two matrices, i.e., data in which a particular pharmaceutical product was administered to mice (data for testing) and data in which the other pharmaceutical products were individually administered to mice (data for training).

(2) Acquisition of Human Pharmacokinetic Data

The package inserts of pharmaceutical products were obtained from Drugs@FDA (accessdata.fda.gov/scripts/cder/daf/) and DAILYMED (dailymed.nlm.nih.gov/dailymed/). The bioavailability, half-life, and time to maximum blood concentration (Tmax) listed on the package inserts were collected as pharmacokinetic parameters.

(3) Preprocessing of Mouse RNA-Seq Data

According to the method described in the Experimental Example II-1 (3) section, the data for training obtained in Experimental Example II-2 (1) was normalized so that the average was 0 and the variance was 1, and dimension-reduced by PCA. The same treatment was performed on the data for testing.

(4) Construction and Prediction of Artificial Intelligence Model Using SVM

SVM was trained using the data for training created in Experimental Example II-2 (3) as the set of first training data, and the human pharmacokinetic parameters obtained in Experimental Example II-2 (2) as the second training data, thereby constructing an artificial intelligence model. The data for testing obtained in Experimental Example II-2 (3) was input as test data into the trained artificial intelligence model, and the output pharmacokinetic value was compared with the actual value. Moreover, comparisons were made based on the chemical structures of pharmaceutical products using pharmacokinetic parameter prediction methods, such as pkCSM (biosig.unimelb.edu.au/pkcsm/) and SwissADME (swissadme.ch/).

(5) Prediction Results of Artificial Intelligence Model Using SVM

FIG. 16 shows prediction results of bioavailability. The vertical axis shows the value of bioavailability converted to a scale of 0 to 1. The black bar indicates the actually reported bioavailability (Actual). The white bar indicates the prediction results of the present invention (Predicted from D-iOrgans). The hatched bar indicates the prediction results of pkCSM (prediction (pkCSM)). The shaded bar indicates the prediction results of SwissADME (prediction (SWISSadme)). The prediction results of the present invention were almost the same as the results actually reported. For aripiprazole, the results obtained by the conventional prediction method pkCSM were similar to those actually reported; however, for EMPA, the prediction accuracy was reduced. SwissADME showed low prediction accuracy for both aripiprazole and EMPA. This indicates that the prediction method of the present invention has high prediction accuracy compared to the conventional methods, and that the prediction accuracy did not significantly vary depending on the pharmaceutical products. pkCSM and SwissADME both predict pharmacokinetics based on the chemical structure of the main component of a pharmaceutical product. For this reason, it was impossible to predict the pharmacokinetics etc. of a pharmaceutical product having a peptide, such as repatha and teriparatide, as a skeleton. In contrast, this experiment reveals that the prediction method of the present invention can predict pharmacokinetics etc. regardless of the skeleton of the main component of a pharmaceutical product.

FIG. 17 shows the prediction results of drug distribution of EMPA. The vertical axis represents a drug distribution value (L/kg). The black bar indicates actually reported drug distribution (Actual). The white bar indicates the prediction results of the present invention (Predicted from D-iOrgans). The hatched bar indicates the prediction results of pkCSM (Prediction (pkCSM)). The prediction method according to the present disclosure showed nearly the same results as the actual report; however, the prediction results of pkCSM were significantly different from the actual report.

From the results, it was thought that the prediction method of the present invention can predict pharmacokinetics with high accuracy.

II-3. Construction of Machine Learning Model Using Mouse RNA-Seq Data and Human Indication, and Drug Repositioning (1) Preprocessing of RNA-Seq Data Data on change in gene expression level in mice ($\log_2$ (fold)) with respect to organ-gene selected by WGCNA was prepared for all pharmaceutical products (n=2 for each pharmaceutical product), and the average between samples was obtained. Specifically, a matrix having dimensions of (6 pharmaceutical products)×(tens of thousands of organ-gene combinations selected by WGCNA) was obtained. The matrix data was normalized so that the average was 0 and the variance was 1, and dimension-reduced by PCA according to the method described in the Experimental Example II-1 (3) section. The resulting data was used as data for training an artificial intelligence model (matrix factorization).
(2) Acquisition of Indication of Each Pharmaceutical Product
The package inserts of pharmaceutical products that were administered to mice were obtained from Drugs@FDA and DAILYMED. The names of diseases listed as indications were obtained.
(3) Construction of Artificial Intelligence Model, Drug Efficacy Prediction, and Repositioning
Based on the list of indications obtained in Item (2), matrix R (number of pharmaceutical products)×(number of diseases) was prepared according to the method described in the "Training of Artificial Intelligence Model" section and "Prediction of Action of Test Substance" section. In this case, when the name of a disease was listed as an indication on the package insert of the pharmaceutical product, the corresponding element was determined to be "1", and the other elements were determined to be "0". Items defined as "0" were considered to have not been examined for whether the pharmaceutical product was applied to the target disease. The drug repositioning system was constructed by estimating the element that is zero in matrix R. The larger the value of the estimated element of R is, the more likely that the corresponding pharmaceutical product is applicable to the corresponding disease.
To actually estimate element 0 in matrix R, matrix factorization (dtic.mil/docs/citations/ADA439541) was applied to matrix R. When matrix factorization was applied, matrix P and matrix S that satisfy R≈PS were generated using elements other than element 0 of R. The value of an element of matrix R' in which PS=R' was determined to be a predicted value of element 0 of R. Matrix P was considered to be a matrix that represents the properties of pharmaceutical products, and matrix S was considered to be a matrix that represents the properties of diseases. In typical matrix factorization, matrix P is generated, together with matrix S, from matrix R. Here, however, only matrix S was generated by using the input data created in Item (1) as P. Specifically, the matrix was generated according to the method described in the "Prediction of Action of Test Substance" section.
(4) Results
FIG. 18 shows the results. In FIG. 18A, "1" indicates that drug efficacy has already been reported. "0" indicates that drug efficacy has not been confirmed, or, if confirmed, there is no drug efficacy. FIG. 18B shows the prediction results obtained by the prediction method according to the present disclosure. The columns of FIG. 18B corresponding to the columns indicating "1" in FIG. 18A showed a value higher than 0.7. This indicates that the prediction method according to the present disclosure can predict known drug efficacy with high accuracy.
In contrast, the columns of FIG. 18B corresponding to the columns indicating "0" in FIG. 18A showed a value lower than 0.5 with some exceptions. However, with respect to aripiprazole, the columns of recurrent suicidal dynamics, suicidal dynamics, and schizoaffective disorder showed 0.89. This suggests that aripiprazole may be effective for other diseases to which the application of aripiprazole has not been reported so far.

The above indicates that the prediction method of the present invention is useful for selecting candidates for drug repositioning.

Experimental Example III: Selection of Organs Important for Prediction of Each Pharmacokinetic Parameter Organs of non-human animals highly contributing to prediction of actions in humans were selected using SVM.
(1) Duplication of Mouse Samples and Division into Data for Training and Data for Testing
Data on change in gene expression level ($\log_2$(fold)) in mice with respect to organ-gene selected by WGCNA was prepared for all pharmaceutical products (n=2 for each pharmaceutical product). Since each organ has two sets of data (n=2), and a person can freely choose which data to use, the number of data items constituted by 24 organs is $2^{24}$=16777216. Of these, data sampling was performed using just over 200 combinations, and data having dimensions of (just over 200 samples×6 pharmaceutical products)×(tens of thousands of organ-gene combinations selected by WGCNA) was obtained in a matrix format. In order to train the artificial intelligence model and quantify its generalization performance, this matrix was divided into two matrices, i.e., data in which a particular pharmaceutical product was administered to mice (data for testing) and data in which the other pharmaceutical products were individually administered to mice (data for training).
(2) Acquisition of Human Pharmacokinetic Data
The package inserts of pharmaceutical products were obtained from Drugs@FDA (accessdata.fda.gov/scripts/cder/daf/) and DAILYMED (dailymed.nlm.nih.gov/dailymed/). The pharmacokinetic parameters listed on the package inserts were collected.
(3) Selection of Candidate Organs
For data for training and data for testing, only data on one particular organ was extracted.
(4) Preprocessing of Mouse RNA-Seq Data
The data for training extracted in Experimental Example III (3) was normalized so that the average was 0 and the variance was 1, and dimension-reduced by PCA. The resulting data was used as input data for SVM. The same treatment was performed on the data for testing.
(5) Training and Prediction Using SVM
SVM was trained using the data for training that had been pre-processed in Example III (4) as the set of first training data, and human pharmacokinetic parameters created in Example III (2) as the second training data, thereby constructing an artificial intelligence model. The data for testing pre-processed in Example III (4) was input as test data into the trained artificial intelligence model, and the error between the output prediction score and the actual score of the adverse-event was quantified.
(6) Selection of Organ (Group)
Experimental Example III (3) to (5) were repeated for all organs, and the organ having the least error was selected. Subsequently, Experimental Example III (3) to (5) were repeated for the already selected organ and one of the non-selected organs, and the organ having the least error was additionally selected. The above procedure was repeated until the error was not reduced no matter which organ was added. The analysis revealed that organs that most clearly reflect pharmacokinetics were the ileum, testis, and brain.

(7) Construction and Prediction of Artificial Intelligence Model Using Transcriptome in Organs Selected by SVM Data on the ileum, testis, and brain was extracted from the data for training created in Experimental Example III (3). The extracted data for training was pre-processed according to Experimental Example III (4). By using the pre-processed data as the set of first training data, and the human pharmacokinetic parameters created in Experimental Example III (2) as the second training data, SVM was made to learn and construct an artificial intelligence model. Subsequently, data on the ileum, testis, and brain was extracted from data for testing obtained in Item (3). The extracted data for testing was pre-processed according to Experimental Example III (4). The pre-processed data was input as test data into the trained artificial intelligence model, and the bioavailability was predicted. The predicted bioavailability was compared with the actual bioavailability.

As shown in FIG. 19, the actual bioavailability value (Actual) was 0.87, while the predicted bioavailability value (Predicted from D-iOrgans) was 0.785; an excellent predicted value was obtained.

This indicates that organs that are more suitable for prediction can be narrowed down by the analysis of the artificial intelligence model trained for the prediction method according to the present disclosure. The results apparently indicate that it is not always necessary to use all the data of the 24 organs.

Experimental Example IV: Effects of Prediction Depending on the Number of Organs In order to verify that actions can be predicted from a low number of organs, the set of first training data and the set of the second training data were created as in Experimental Example II, using aripiprazole, EMPA, clozapine, cisplatin, teriparatide, and reparser. The number of organs used for creating the set of first training data was set to 1 to 23 as shown in FIG. 20. Organs used for obtaining test data were made to correspond to the organs used for generating the set of first training data.

FIG. 20 shows the number of organs with which prediction was possible and examples of adverse-events (aripiprazole: A, EMPA: E, teriparatide: T, and reparser: R). In FIG. 20, the names of organs were labelled with the following numerals.

Bone marrow: 1, pancreas: 2, skull: 3, liver: 4, skin: 5, brain: 6, pituitary gland: 7, adrenal glands: 8, thyroid gland: 9, spleen: 10, thymus: 11, heart: 12, lungs: 13, aorta: 14, skeletal muscle: 15, testis: 16, left epididymal fat: 17, eyeballs: 18, ileum: 19, stomach: 20, jejunum: 21, large intestine: 22, kidney: 23, and parotid gland: 24.

As is clear from FIG. 20, adverse-events were predicted even when the number of organs was 1 to 10 and 15 or 16. Although it is not shown, adverse-events of clozapine and cisplatin were similarly predicted when the number of organs was 1 to 10 and 15 or 16.

The results indicate that actions of a test substance in humans can be predicted by an artificial intelligence model trained based on the second training data and the dynamics of one or more biomarkers in at least one organ collected from a non-human animal to which an existing substance was administered.

Experimental Example V: Effects of Prediction According to Stratification (1) Mouse RNA-Seq Data According to the method of Experimental Example II, 24 organs were collected from mice to which 14 pharmaceutical products (acetaminophen, alendronate, aripiprazole, asenapine, cisplatin, clozapine, doxycycline, empagliflozin, repatha, lurasidone, olanzapine, risedronate, sofosbuvir, and teriparatide) were individually administered. RNA-Seq data of each organ was obtained. For each pharmaceutical product, two samples were collected (n=2).

(2) Quantification of Change in Gene Expression Level

DESeq2 analysis was performed to quantify change in gene expression level between drug administration mice and wild-type mice. The count data on genes of each mouse quantified by htseq-count was used as the input for DESeq2. The count data was compared between drug administration mice and wild-type mice. As a result, the $\log_2(\text{fold})$ value of the change in gene expression level of drug administration mice, and the p value serving as an index of the probability of each change level were output for each gene. Analysis was performed based on this $\log_2(\text{fold})$ value.

(3) Pre-Processing of Mouse Data

The $\log_2(\text{fold})$ data of each pharmaceutical product (n=14, n=1 for each pharmaceutical product) output by DESeq2 was dimensionally compressed using PCA, and used as the set of first training data.

(4) Collection, Stratification, and Curve Approximation of Human Adverse-Event Data Data was downloaded from FAERS (fda.gov/Drugs/GuidanceComplianceRegulatoryInformation/Surveillance/AdverseDrugEffects/ucm082193.htm), and adverse-event (AE) reporting information on the target pharmaceutical products was obtained on the basis of words indicating adverse-events. Of the information, reports including words of gender or age were extracted. Of the extracted reports, gender-AE combinations and age-AE combinations that were reported more than 25 times were stratified according to gender or age for each pharmaceutical product. For gender, males were extracted, and the age groups were divided into 20s, 30s, 40s, 50s, 60s, and 70s. In each group, words indicating the names of adverse-events were extracted from the reporting data. Taking a single extracted word as one reported adverse-event, the rate of occurrence of each adverse-event was calculated using (the number of reports on a particular adverse-event)/(the total number of reports on adverse-events for the pharmaceutical product). With respect to the correspondence between the adverse-event rate of occurrence and the age group, curve approximation was made using a linear function or a cubic function. The polynomial (linear or cubic) coefficients constituting the approximate curve were used as input data for the artificial intelligence model.

(5) Training and Prediction of Artificial Intelligence Model Using Random Forest Using the data on change in expression in mice obtained in Experimental Example V (3) as the first training data, and the polynomial coefficient data obtained by approximating the rate of occurrence of human adverse-events obtained in Experimental Example (4) as the set of the second training data, an artificial intelligence model was constructed by random forest so that the polynomial coefficients were output when the first training data was input. During this operation, mouse data and human adverse-event data were individually divided into data on one particular pharmaceutical product (test data) and data on pharmaceutical products other than the particular pharmaceutical product (training data). The artificial intelligence model was constructed using training data, and test data was input into the trained artificial intelligence model. The prediction curve of thus-output rate of occurrence of adverse-event was compared with the approximate curve of the actual rate of occurrence of adverse-event, or the actual adverse-event rate of occurrence.

(6) Results

FIG. 21 shows one example of the results. With respect to the adverse-events of insomnia, hypotension, muscular weakness, pollakiuria, and death, FIG. 21 shows the rate of occurrence predicted by the trained artificial intelligence model (predicted) and the actual rate of occurrence (observed) according to the age group. The vertical axis shows the rate of occurrence obtained by inputting, to the corresponding polynomial, coefficients output from the artificial intelligence model to which the test data was input. On the horizontal axis, "2," "3," "4," "5," "6," and "7" respectively represent individuals in their 20s, 30s, 40s, 50s, 60s, and 70s. The solid line indicates the actual rate of occurrence, and the dotted line indicates the predicted rate of occurrence. None of the tested pharmaceutical products showed a significant difference between the rate of occurrence of insomnia, hypotension, muscular weakness, pollakiuria, or death predicted by the trained artificial intelligence model and the actual rate of occurrence. This indicates that the artificial intelligence model of the present invention can predict actions for each stratified group.

EXPLANATION OF SYMBOLS

10 Training device
100 Processing unit
105 Communication I/F
20 Prediction device
200 Processing unit
205 Communication I/F

The invention claimed is:

1. A method for predicting one or more actions of a test substance in humans, the method comprising the steps of:
selecting an artificial intelligence model trained according to (i) a first set of training data measuring dynamics of one or more biomarkers from one or more organs of non-human animals into which multiple existing substances, distinct from the test substance, have been individually administered and (ii) a second set of training data quantifying known actions in humans in response to each of the multiple existing substances;
administering the test substance into a plurality of non-human animals;
measuring an amount or concentration of each of the one or more biomarkers from one or more organs of the plurality of non-human animals, the one or more organs corresponding to the one or more organs of non-human animals into which the multiple existing substances were administered for the first set of training data;
generating test data indicating dynamics of the one or more biomarkers from the amount or concentration of each biomarker in the organs by comparing (a) the measured value of each biomarker in the organs from non-human animals administered the test substance with (b) a measured value of each biomarker corresponding to organs of individual non-human animals into which the test substance has not been administered, thereby obtaining a respective net difference value for each of the one or more biomarkers; and
applying the artificial intelligence model to the test data to compute one or more predicted actions of the test substance in humans.

2. The method according to claim 1, wherein the test substance is an existing substance and a substance equivalent to the existing substance, and the one or more predicted actions are one or more new therapeutic indications of the existing substance.

3. The method according to claim 1,
wherein the one or more biomarkers include a transcriptome.

4. The method according to claim 1,
wherein the artificial intelligence model outputs a prediction result as a score that corresponds to the degree of association with each action.

5. The method according to claim 4, wherein the score is indicated by at least two quantiles.

6. The method according to claim 1,
wherein the artificial intelligence model computes one or more predicted actions of the test substance in humans according to the demographic profile of individual humans.

7. The method according to claim 6, wherein the demographic profile of individual humans includes at least one of age group and gender.

8. The method according to claim 1,
wherein the one or more predicted actions include at least one member selected from the group consisting of adverse-events of the multiple existing substances, pharmacokinetics of the multiple existing substances, and therapeutic indications of the multiple existing substances, wherein the multiple existing substances are substances that have known actions in humans.

9. The method according to claim 1,
wherein the test substance does not include the multiple existing substances or substances equivalent to the multiple existing substances.

10. The method according to claim 1,
wherein the test substance is one member selected from the group consisting of the multiple existing substances and substances equivalent to the multiple existing substances.

11. The method according to claim 1,
wherein the one or more biomarkers include a transcriptome.

12. The method according to claim 1,
wherein the artificial intelligence model is a support vector machine (SVM), a random forest, relevance vector machine (RVM), naive Bayes, logistic regression, a feedforward neural network, deep learning, a K-nearest neighbor algorithm, AdaBoost, bagging, C4.5, kernel approximation, a stochastic gradient descent (SGD) classifier, lasso, ridge regression, elastic net, SGD regression, kernel regression, LOWESS regression, matrix factorization, non-negative matrix factorization, kernel matrix factorization, interpolation, a kernel smoother, or collaborative filtering.

13. A prediction device for predicting one or more actions of a test substance in humans, the device comprising a processing unit, wherein
the processing unit is configured to:
select an artificial intelligence model trained according to (i) a first set of training data measuring dynamics of one or more biomarkers from one or more organs of non-human animals into which multiple existing substances, distinct from the test substance, have been individually administered and (ii) a second set of training data quantifying known actions in humans in response to each of the multiple existing substances;
measure an amount or concentration of each of the one or more biomarkers from one or more organs of a plurality of non-human animals into which the test substance is administered, the one or more organs corresponding to the one or more organs of non-human animals into which the multiple existing substances were administered for the first set of training data;
generate test data indicating dynamics of the one or more biomarkers from the amount or concentration of each biomarker in the organs by comparing (a) the measured value of each biomarker in the organs from non-human animals administered the test substance with (b) a measured value of each biomarker corresponding to organs of individual non-human animals into which the test substance has not been administered, thereby obtaining a respective net difference value for each of the one or more biomarkers; and
apply the artificial intelligence model to the test data to compute one or more predicted actions of the test substance in humans.

14. A method for training an artificial intelligence model, comprising:
selecting an artificial intelligence model trained according to (i) a first set of training data measuring dynamics of one or more biomarkers from one or more organs of non-human animals into which multiple existing substances, distinct from the test substance, have been individually administered and (ii) a second set of training data quantifying known actions in humans in response to each of the multiple existing substances; and
applying the artificial intelligence model to test data to compute one or more predicted actions of the test substance in humans;
wherein the test data is obtained by:
administering the test substance into a plurality of non-human animals;
measuring an amount or concentration of each of the one or more biomarkers from one or more organs of the plurality of non-human animals, the one or more organs corresponding to the one or more organs of non-human animals into which the multiple existing substances were administered for the first set of training data; and
generating the test data indicating dynamics of the one or more biomarkers from the amount or concentration of each biomarker in the organs by comparing (a) the measured value of each biomarker in the organs from non-human animals administered the test substance with (b) a measured value of each biomarker corresponding to organs of individual non-human animals into which the test substance has not been administered, thereby obtaining a respective net difference value for each of the one or more biomarkers.

15. The method for training an artificial intelligence model according to claim 14,
wherein each item of the first set of training data is linked to information on the name of one of the multiple existing substances administered to the non-human animals, information on the name of one of the collected organs, and information on the name of one of the biomarkers,
the second set of training data is linked to the information on the name of one of the multiple existing substances administered to non-human animals, and
the first set of training data is linked to the second set of training data based on the information on the name of one of the multiple existing substances administered to the non-human animals to train the artificial intelligence model.

16. The method for training an artificial intelligence model according to claim 14,
wherein the second set of training data includes information on the rate of occurrence of the action, and
the artificial intelligence model outputs a prediction result as a score that corresponds to the degree of association with each of the one or more predicted actions of the test substance in humans.

17. A device that supports predicting one or more actions of test substances in humans, the device comprising a processing unit, wherein
the processing unit executes a process of:
selecting an artificial intelligence model trained according to (i) a first set of training data measuring dynamics of one or more biomarkers from one or more organs of non-human animals into which multiple existing substances, distinct from the test substance, have been individually administered and (ii) a second set of training data quantifying known actions in humans in response to each of the multiple existing substances;
measuring an amount or concentration of each of the one or more biomarkers from one or more organs of a plurality of non-human animals into which the test substance is administered, the one or more organs corresponding to the one or more organs of non-human animals into which the multiple existing substances were administered for the first set of training data;
generating test data indicating dynamics of the one or more biomarkers from the amount or concentration of each biomarker in the organs by comparing (a) the measured value of each biomarker in the organs from non-human animals administered the test substance with (b) a measured value of each biomarker corresponding to organs of individual non-human animals into which the test substance has not been administered, thereby obtaining a respective net difference value for each of the one or more biomarkers;
applying the artificial intelligence model to the test data to compute one or more predicted actions of the test substance in humans;
constructing a new matrix containing values output from the artificial intelligence model as new elements, each value indicating degree of association between information on the name of one of the existing substances and information on a known action; and
suggesting, when a first element has a value equal to or greater than a threshold in the region of interest corresponding to the test substance, information on a known action that corresponds to the first element, wherein the test substance is one member selected from the group consisting of existing substances and substances equivalent to the existing substances.

18. The device according to claim 17, wherein the information on a known action comprises drug repositioning.

* * * * *